United States Patent
Achab et al.

(10) Patent No.: US 12,180,226 B2
(45) Date of Patent: Dec. 31, 2024

(54) SPIROTRICYCLE RIPK1 INHIBITORS AND METHODS OF USES THEREOF

(71) Applicant: Merck Sharp & Dohme LLC, Rahway, NJ (US)

(72) Inventors: Abdelghani Abe Achab, Melrose, MA (US); Zachary G. Brill, San Francisco, CA (US); Jenny Lorena Rico Duque, Canton, MA (US); Xavier Fradera, Boston, MA (US); Joey L. Methot, Westwood, MA (US); Phieng Siliphaivanh, Newton, MA (US); Jing Su, Scotch Plains, NJ (US); Brandon A. Vara, Boston, MA (US); Erin F. DiMauro, Cambridge, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 18/049,344

(22) Filed: Oct. 25, 2022

(65) Prior Publication Data
US 2023/0159558 A1    May 25, 2023

Related U.S. Application Data

(60) Provisional application No. 63/407,851, filed on Sep. 19, 2022, provisional application No. 63/272,276, filed on Oct. 27, 2021.

(51) Int. Cl.
| | | |
|---|---|---|
| C07D 498/20 | (2006.01) | |
| C07D 513/20 | (2006.01) | |
| C07D 519/00 | (2006.01) | |

(52) U.S. Cl.
CPC ......... *C07D 498/20* (2013.01); *C07D 513/20* (2013.01); *C07D 519/00* (2013.01)

(58) Field of Classification Search
CPC ............................. C07D 498/20; C07D 513/20
See application file for complete search history.

(56) References Cited

FOREIGN PATENT DOCUMENTS
WO    2018107060 A1    6/2018

OTHER PUBLICATIONS

Philip A. Harris, Inhibitors of RIP1 kinase: a patent review (2016-present), Expert Opinion on Therapeutic Patents, 2021, 137-151, 31:2.
Caccamo, Antonella et al., Necroptosis activation in Alzheimer's disease, Nat Neurosci, 2017, 1236-1246, vol. 20 | No. 9.
Degterev, Alexei et al., Chemical inhibitor of nonapoptotic cell death with therapeutic potential for ischemic brain Injury, Nat Chem Biol, 2005, 112-119, vol. 1 | No. 2.
Degterev, Alexei et al., Targeting RIPK1 for the treatment of human diseases, PNAS, 2019, 9714-9722, vol. 116 | No. 20.
Gong, Yitao et al., The role of necroptosis in cancer biology and therapy, Molecular Cancer, 2019, 1-17, 18:100.
Ito, Yasushi et al., RIPK1 mediates axonal degeneration by promoting inflammation and necroptosis in ALS, Science, 2016, 603-608, 353.
Ofengeim, Dimitry et al., Activation of necroptosis in multiple sclerosis, Cell Rep., 2015, 1836-1849, 10(11).
Wang, Jia-Nan et al., RIPK1 inhibitor Cpd-71 attenuates renal dysfunction in cisplatin-treated mice via attenuating hecroptosis, inflammation and oxidative stress, Clin Sci, 2019, 1609-1627, 133(14).

*Primary Examiner* — Susanna Moore
(74) *Attorney, Agent, or Firm* — Daniel Woods; John C. Todaro

(57) ABSTRACT

Described herein are compounds of Formula I:

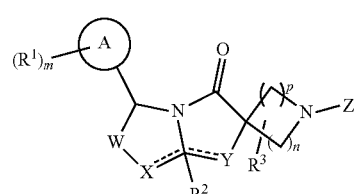

or a pharmaceutically acceptable salt thereof, wherein A, $R^1$, $R^2$, $R^3$, W, X, Y, Z, m, n and p are as defined herein. The compounds of Formula I act as RIPK1 inhibitors and can be useful in preventing, treating or acting as a remedial agent for RIPK1-related diseases.

27 Claims, No Drawings

SPIROTRICYCLE RIPK1 INHIBITORS AND METHODS OF USES THEREOF

CROSS-REFERENCE TO RELATED APPLICATIONS

This application claims the benefit of priority to U.S. Provisional Patent Application No. 63/272,276, filed Oct. 27, 2021 and U.S. Provisional Patent Application No. 63/407,851, filed Sep. 19, 2022.

FIELD OF THE INVENTION

The present invention is directed to RIPK1 inhibitors. Specifically, the RIPK1 inhibitors described herein can be useful in preventing, treating, or acting as a remedial agent for RIPK1-related diseases.

BACKGROUND OF THE INVENTION

Receptor-interacting protein-1 kinase (RIPK1) belongs to the family serine/threonine protein kinase involved in innate immune signaling. RIPK1 has emerged as a promising therapeutic target for the treatment of a wide range of human neurodegenerative, autoimmune, and inflammatory diseases. This is supported by extensive studies which have demonstrated that RIPK1 is a key mediator of apoptotic and necrotic cell death as well as inflammatory pathways.

For example, RIPK1 inhibition has been found to be useful as a treatment of acute kidney injury (AKI), a destructive clinical condition induced by multiple insults including ischemic reperfusion, nephrotoxic drugs, and sepsis. It has been found that RIPK1-mediated necroptosis plays an important role in AKI and a RIPK1 inhibitor may serve as a promising clinical candidate for AKI treatment. Wang J N, et al., *RIPK1 Inhibitor Cpd-71 Attenuates Renal Dysfunction in Cisplatin-Treated Mice via Attenuating Necroptosis, Inflammation and Oxidative Stress*, Clin Sci (Lond.) 2019 Jul. 25; 133(14):1609-1627.

Additionally, human genetic evidence has linked the dysregulation of RIPK1 to the pathogenesis of amyotrophic lateral sclerosis (ALS), Alzheimer's disease and multiple sclerosis, as well as other inflammatory and neurodegenerative diseases. Degterev A., et al., *Targeting RIPK1 for the treatment of human diseases*, Proc. Natl. Acad. Sci. USA, May 14, 2019, 116 (20), 9714-9722; Ito Y, et al., *RIPK1 mediates axonal degeneration by promoting inflammation and necroptosis in ALS*, Science, 2016, 353:603-8; Caccamo A, et al., *Necroptosis activation in Alzheimer's disease*, Nat Neurosci, 2017, 20:1236-46; Ofengeim D, et al., *Activation of necroptosis in multiple sclerosis*, Cell Rep., 2015, 10:1836-49.

It also has been demonstrated that necroptosis is a delayed component of ischemic neuronal injury; thus, RIPK1 inhibition may also play a promising role as a treatment for stroke. Degterev A, et al., *Chemical inhibitor of nonapoptotic cell death with therapeutic potential for ischemic brain injury*, Nat Chem Biol 2005, 1(2):112-119.

Therefore, there is a need for inhibitors of RIPK1 that offer high selectivity which can penetrate the blood-brain barrier, thus offering the possibility to target neuroinflammation and cell death which drive various neurologic conditions including Alzheimer's disease, ALS, and multiple sclerosis as well as acute neurological diseases such as stroke and traumatic brain injuries.

SUMMARY OF THE INVENTION

Described herein are compounds of Formula I:

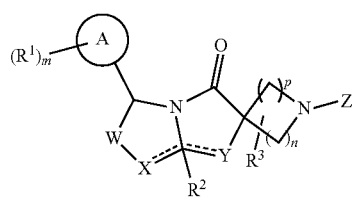

and pharmaceutically acceptable salts thereof, wherein A, W, X, Y, Z, $R^1$, $R^2$, $R^3$, n, m and p are described below.

The compounds described herein are RIPK1 inhibitors, which can be useful in the prevention, treatment or amelioration of neurodegenerative, autoimmune and inflammatory diseases and other RIPK1-related diseases.

Also described herein are methods of treating neurodegenerative, autoimmune, and inflammatory diseases comprising administering to a patient in need thereof a compound described herein, or a pharmaceutically acceptable salt thereof.

Also described herein are uses of a compound described herein, or a pharmaceutically acceptable salt thereof, to treat neurodegenerative, autoimmune, and inflammatory diseases in a patient in need thereof.

Also described herein are pharmaceutical compositions comprising a compound described herein, or a pharmaceutically acceptable salt thereof and a pharmaceutically acceptable carrier.

Also described herein are pharmaceutical compositions comprising a compound described herein and a pharmaceutically acceptable carrier.

Also described herein are methods of treating neurodegenerative, autoimmune, and inflammatory diseases comprising administering to a patient in need thereof a compound described herein, or a pharmaceutically acceptable salt thereof, and at least one additional therapeutic agent.

Also described herein are uses of a compound described herein, or a pharmaceutically acceptable salt thereof, in combination with at least one additional agent, to treat neurodegenerative, autoimmune, and inflammatory diseases in a patient in need thereof.

Also described herein are pharmaceutical compositions comprising a compound described herein, or a pharmaceutically acceptable salt thereof, at least one additional therapeutic agent and a pharmaceutically acceptable carrier.

Also described herein are pharmaceutical compositions comprising a compound described herein, at least one additional therapeutic agent and a pharmaceutically acceptable carrier.

DETAILED DESCRIPTION OF THE INVENTION

Described herein are compounds of Formula I:

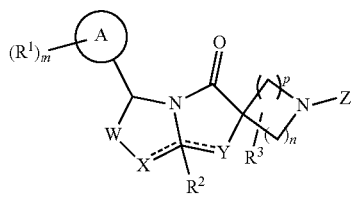

or a pharmaceutically acceptable salt thereof, wherein:

A is aryl, heteroaryl, heterocycloalkyl or $C_3$-$C_6$cycloalkyl;

each occurrence of $R^1$ is independently selected from the group consisting of —OH, $C_1$-$C_6$alkylOH, —CN, $C_1$-$C_6$alkylCN, $C_1$-$C_6$alkyl, halo$C_1$-$C_6$alkyl, halogen, —$NH_2$, —$N(C_1$-$C_6$alkyl$)_2$, —$NH(C_1$-$C_6$alkyl) and $C_1$-$C_6$alkoxy;

W is $CH_2$, N, O or S;

X is $C(R^4)_2$, N, O or S, wherein when X is N, the dashed line connecting to X is present; wherein when X is $C(R^4)_2$, O or S, the dashed line connecting to X is absent; wherein when X is $C(R^4)_2$, Y is N, O, or S, and wherein when X is N, O or S, Y is $CH_2$;

Y is $CH_2$, N, O or S, wherein when Y is N, the dashed line connecting to Y is present; wherein when Y is $CH_2$, O or S the dashed line connecting to Y is absent; and wherein when Y is N, O or S, X is $C(R^4)_2$;

$R^2$ is hydrogen, —OH, $C_1$-$C_6$alkylOH, CN, $C_1$-$C_6$alkylCN, $C_1$-$C_6$alkyl, halo$C_1$-$C_6$alkyl, halogen, —$NH_2$, —$N(C_1$-$C_6$alkyl$)_2$, —$NH(C_1$-$C_6$alkyl) or $C_1$-$C_6$alkoxy, or when X or Y is N, $R^2$ is absent;

$R^3$ is hydrogen, —OH, $C_1$-$C_6$alkylOH, —CN, $C_1$-$C_6$alkylCN, $C_1$-$C_6$alkyl, halo$C_1$-$C_6$alkyl, halogen, —$NH_2$, —$N(C_1$-$C_6$alkyl$)_2$, —$NH(C_1$-$C_6$alkyl) or $C_1$-$C_6$alkoxy;

each occurrence of $R^4$ is independently selected from the group consisting of hydrogen, —OH, $C_1$-$C_6$alkylOH, —CN, $C_1$-$C_6$alkylCN, $C_1$-$C_6$alkyl, halo$C_1$-$C_6$alkyl, halogen, —$NH_2$, —$N(C_1$-$C_6$alkyl$)_2$, —$NH(C_1$-$C_6$alkyl) and $C_1$-$C_6$alkoxy;

Z is —CN, aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —$COC_3$-$C_{10}$cycloalkyl, —$CONHC_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, —CONHheterocycloalkyl, —$SO_2$heterocycloalkyl, —$COOC_1$-$C_6$alkyl, or —$COOC_3$-$C_6$cycloalkyl, wherein the aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —$COC_3$-$C_{10}$cycloalkyl, —$CONHC_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, —CONHheterocycloalkyl or —$SO_2$heterocycloalkyl, is unsubstituted or substituted with one to three substituents independently selected from the group consisting of halogen, —CN, $C_1$-$C_6$alkylCN, $C_1$-$C_6$alkyl, $C_1$-$C_6$alkynyl, $C_1$-$C_6$haloalkyl, $C_1$-$C_6$alkoxy, $C_1$-$C_6$haloalkoxy, —$COOC_1$-$C_6$alkyl, —$SC_1$-$C_6$alkyl, oxo, $C_3$-$C_6$cycloalkyl, aryl, heteroaryl and heterocycloalkyl, wherein the heteroaryl, heterocycloalkyl, $C_3$-$C_6$cycloalkyl, $C_1$-$C_6$alkynyl and $C_1$-$C_6$alkoxy, is unsubstituted or substituted with one to two substituents independently selected from the group consisting of halogen, —CN, $C_1$-$C_6$alkyl, $C_1$-$C_6$haloalkyl, $C_1$-$C_6$alkoxy, —OH and heterocycloalkyl;

m is 0, 1, 2 or 3;

n is 1 or 2; and p is 1 or 2.

Described herein are compounds wherein A is aryl, heteroaryl, heterocycloalkyl or $C_3$-$C_6$cycloalkyl. In certain embodiments, A is aryl, heteroaryl, or $C_3$-$C_6$cycloalkyl. In certain embodiments, A is aryl. In certain embodiments, wherein A is aryl, the aryl is phenyl.

In certain embodiments A is heteroaryl. Suitable heteroaryls include, but are not limited to, pyridyl (pyridinyl), oxazolyl, imidazolyl, triazolyl, furyl, triazinyl, thienyl, pyrimidyl, pyrazinyl, indolizinyl, cinnolinyl, phthalazinyl, quinazolinyl, naphthyridinyl, quinoxalinyl, purinyl, benzimidazolyl, quinolyl, benothiophenyl, isothiazolyl and isoquinolyl. In certain embodiments, wherein A is heteroaryl, the heteroaryl is pyridinyl, pyrazinyl, benothiophenyl, isothiazolyl or thienyl.

In certain embodiments, wherein A is heteroaryl, the heteroaryl is

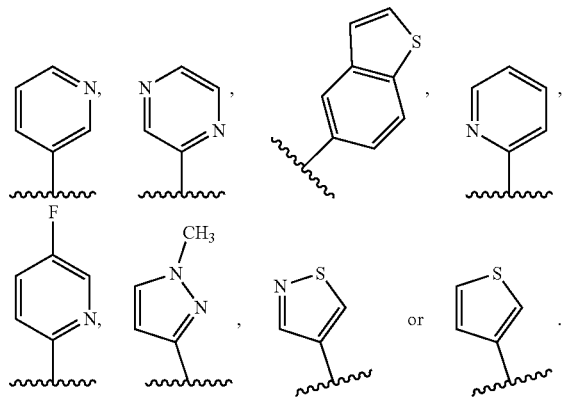

In certain embodiments, A is heterocycloalkyl. Suitable heterocycloalkyls include, but are not limited to, azetidine, tetrahydropyranyl, tetrahydrofuranyl, pyrrolidinyl, piperidinyl, piperazinyl, dioxanyl, imidazolidinyl, 2,3-dihydrofuro[2,3-b]pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl and dihydrocyclopentapyridinyl. In certain embodiments, wherein A is heterocycloalkyl, A is

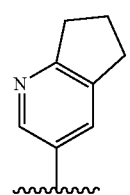

In certain embodiments, A is $C_3$-$C_6$cycloalkyl. Suitable cycloalkyls include, but are not limited to, cyclopropyl, cyclobutyl, cyclopentyl and cyclohexyl. In certain embodiments, wherein A is $C_3$-$C_6$cycloalkyl, the $C_3$-$C_6$cycloalkyl is cyclohexyl or cyclopentyl.

In certain embodiments, A is

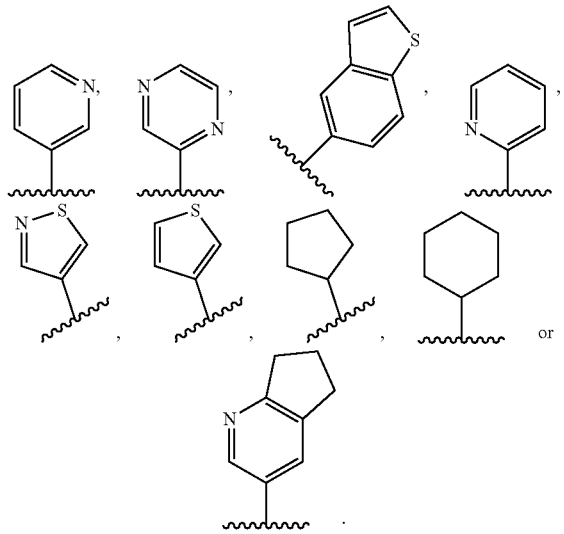

Described herein are compounds, wherein each occurrence of $R^1$ is independently selected from the group of —OH, $C_1$-$C_6$alkylOH, —CN, $C_1$-$C_6$alkylCN, $C_1$-$C_6$alkyl, halo$C_1$-$C_6$alkyl, halogen, —$NH_2$, —$N(C_1$-$C_6$alkyl$)_2$, —NH($C_1$-$C_6$alkyl) and $C_1$-$C_6$alkoxy. In certain embodiments, $R^1$ is —CN, $C_1$-$C_6$alkyl, halogen, or $C_1$-$C_6$alkoxy.

In certain embodiments, $R^1$ is —OH. In certain embodiments, $R^1$ is $C_1$-$C_6$alkylOH. Suitable alcohols include, but are not limited to, methanol, ethanol, propanol, and butanol.

In certain embodiments, $R^1$ is —CN. In certain embodiments, $R^1$ is $C_1$-$C_6$alkylCN. Suitable include, but are not limited to,

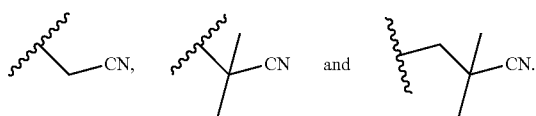

In certain embodiments, $R^1$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^1$ is methyl.

In certain embodiments, $R^1$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl.

In certain embodiments, $R^1$ is halogen. Suitable halogens include, but are not limited to, fluorine, chlorine, bromine, or iodine. In certain embodiments, $R^1$ is fluorine.

In certain embodiments, $R^1$ is —$NH_2$.

In certain embodiments, $R^1$ is —$N(C_1$-$C_6$alkyl$)_2$. In certain embodiments, $R^1$ is —$N(CH_3)_2$.

In certain embodiments, $R^1$ is —NH($C_1$-$C_6$alkyl). In certain embodiments, $R^1$ is —$NH(CH_3)$.

In certain embodiments, $R^1$ is $C_1$-$C_6$alkoxy. Suitable alkoxys include, but are not limited to, methoxy, ethoxy, n-propoxy, isopropoxy and n-butoxy. In certain embodiments, $R^1$ is methoxy.

Described herein are compounds wherein m is 0, 1, 2, or 3. In certain embodiments, m is 0. In certain embodiments, m is 1. In certain embodiments, m is 2. In certain embodiments, m is 3. In certain embodiments, m is 1 or 2.

In certain embodiments of the compounds described herein, A is phenyl, m is 0, 1 or 2 and $R^1$ is fluorine, methoxy, methyl or —CN.

In certain embodiments of the compounds described herein, A is pyridinyl, m is 0, 1 or 2 and $R^1$ is fluorine, methyl, or —CN.

Described herein are compounds wherein W is $CH_2$, N, O or S. In certain embodiments W is $CH_2$. In certain embodiments W is N. In certain embodiments W is O. In certain embodiments W is S. In certain embodiments where W is N, X is $CH_2$ and Y is $CH_2$. In certain embodiments where W is O, X is $CH_2$ and Y is $CH_2$. In certain embodiments where W is S, X is $CH_2$ and Y is $CH_2$.

Described herein are compounds wherein X is $C(R^4)_2$, N, O or S, wherein when X is N, the dashed line connecting to X is present; wherein when X is $C(R^4)_2$, O or S, the dashed line connecting to X is absent; wherein when X is $C(R^4)_2$, Y is N, O, or S, and wherein when X is N, O or S, Y is $CH_2$. In certain embodiments, X is $CH_2$, N, O or S, wherein when X is N, the dashed line connecting to X is present. In certain embodiments, wherein when X is $C(R^4)_2$, O or S, the dashed line connecting to X is absent. In certain embodiments, X is $C(R^4)_2$, wherein $R^4$ is described in detail below. In certain embodiments, X is $CH_2$. In certain embodiments, X is N. In certain embodiments, X is O. In certain embodiments, X is S. In certain embodiments, wherein when X is $C(R^4)_2$, Y is N, O, or S. In certain embodiments, when X is N and Y is $CH_2$ the dashed line connecting to X is present. In other embodiments, wherein when X is N, O or S, Y is $CH_2$.

Described herein are compounds wherein Y is $CH_2$, N, O or S, wherein when Y is N, the dashed line connecting to Y is present; wherein when Y is $CH_2$, O or S the dashed line connecting to Y is absent; and wherein when Y is N, O or S, X is $C(R^4)_2$. In certain embodiments, wherein when Y is N, the dashed line connecting to Y is present. In certain embodiments, wherein when Y is $CH_2$, O or S the dashed line connecting to Y is absent. In certain embodiments, Y is $CH_2$. In certain embodiments, Y is N. In certain embodiments, Y is O. In certain embodiments, Y is S. In other embodiments, wherein when Y is N, O or S, X is $C(R^4)_2$. In other embodiments, wherein when Y is N, O or S, X is $CH_2$.

In certain embodiments, Y is O and X is $CH_2$. In certain embodiments, Y is S and X is $CH_2$. In certain embodiments, Y is $CH_2$ and X is O. In certain embodiments, Y is N and X is $CH_2$, and the dashed line connecting to Y is present.

In certain embodiments, X cannot be $C(R^4)_2$ when Y is $CH_2$. In certain embodiments, W cannot be N, O, or S when X is N, O, or S.

Described herein are compounds wherein, $R^2$ is hydrogen, —OH, $C_1$-$C_6$alkylOH, CN, $C_1$-$C_6$alkylCN, $C_1$-$C_6$alkyl, halo$C_1$-$C_6$alkyl, halogen, —$NH_2$, —$N(C_1$-$C_6$alkyl$)_2$, —NH($C_1$-$C_6$alkyl) or $C_1$-$C_6$alkoxy, or when X or Y is N. $R^2$ is absent.

In certain embodiments, $R^2$ is hydrogen.

In certain embodiments, $R^2$ is —OH. In certain embodiments, $R^2$ is $C_1$-$C_6$alkylOH. Suitable alcohols include, but are not limited to, methanol, ethanol, propanol, and butanol.

In certain embodiments, $R^2$ is —CN. In certain embodiments, $R^2$ is $C_1$-$C_6$alkylCN. Suitable $C_1$-$C_6$alkylCNs include, but are not limited to,

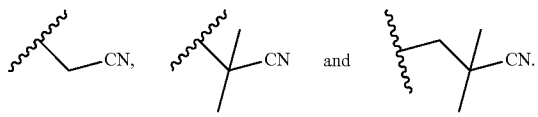

In certain embodiments, $R^2$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^2$ is methyl.

In certain embodiments, $R^2$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl.

In certain embodiments, $R^2$ is halogen. Suitable halogens include, but are not limited to, fluorine, chlorine, bromine, or iodine. In certain embodiments, $R^2$ is fluorine.

In certain embodiments, $R^2$ is —$NH_2$.

In certain embodiments, $R^2$ is —$N(C_1$-$C_6$alkyl$)_2$. In certain embodiments, $R^2$ is —$N(CH_3)_2$.

In certain embodiments, $R^2$ is —$NH(C_1$-$C_6$alkyl). In certain embodiments, $R^2$ is —$NH(CH_3)$.

In certain embodiments, $R^2$ is $C_1$-$C_6$alkoxy. Suitable alkoxys include, but are not limited to, methoxy, ethoxy, n-propoxy, isopropoxy and n-butoxy. In certain embodiments, $R^2$ is methoxy.

In certain embodiments wherein a dashed line is present, $R_2$ is absent. In certain embodiments, when X or Y is N, $R^2$ is absent. For example, in Formula Ic below, and wherein when Y is N, X is $CH_2$, and the dashed line is present, $R^2$ is absent. Also, in certain embodiments, wherein when X is N, Y is $CH_2$ and the dashed line is present, $R^2$ is absent.

In certain embodiments, described herein are compound of Formula Ia, Ib, Ic and Id:

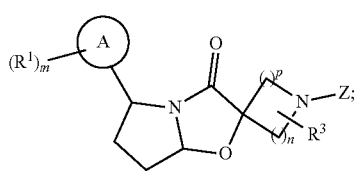

Ia

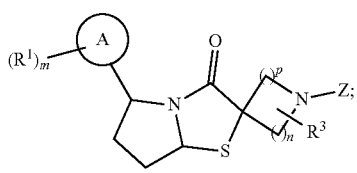

Ib

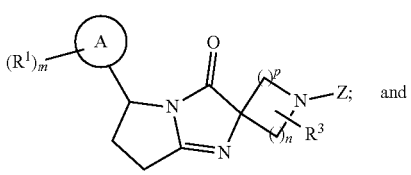

Ic and

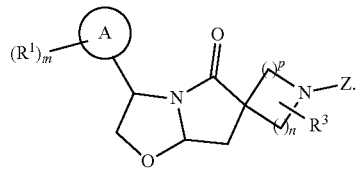

Id

Described herein are compounds wherein n is 1 or 2. In certain embodiments, n is 1. In certain embodiments, n is 2.

Described herein are compounds wherein p is 1 or 2. In certain embodiments, p is 1. In certain embodiments, p is 2.

In certain embodiments, n and p are both 1, as shown in Formula II.

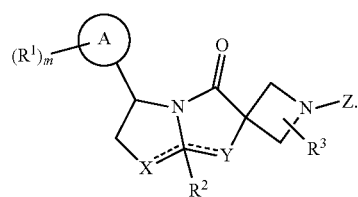

II

In certain embodiments, n and p are both 2, as shown in Formula III.

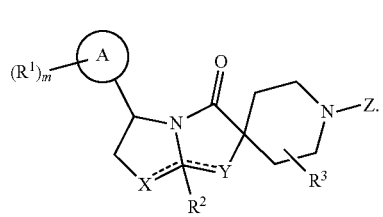

III

Described herein are compounds wherein, $R^3$ is hydrogen, —OH, $C_1$-$C_6$alkylOH, —CN, $C_1$-$C_6$alkylCN, $C_1$-$C_6$alkyl, halo$C_1$-$C_6$alkyl, halogen, —$NH_2$, $N(C_1$-$C_6$alkyl$)_2$, —NH ($C_1$-$C_6$alkyl) or $C_1$-$C_6$alkoxy.

In certain embodiments, $R^3$ is hydrogen.

In certain embodiments, $R^3$ is —OH. In certain embodiments, $R^3$ is $C_1$-$C_6$alkylOH. Suitable alcohols include, but are not limited to, methanol, ethanol, propanol, and butanol.

In certain embodiments, $R^3$ is —CN. In certain embodiments, $R^3$ is $C_1$-$C_6$alkylCN. Suitable $C_1$-$C_6$alkylCNs include, but are not limited to,

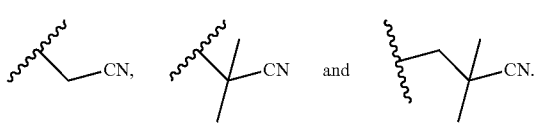

In certain embodiments, $R^3$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^3$ is methyl.

In certain embodiments, $R^3$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl.

In certain embodiments, $R^3$ is halogen. Suitable halogens include, but are not limited to, fluorine, chlorine, bromine, or iodine. In certain embodiments, $R^3$ is fluorine.

In certain embodiments, $R^3$ is —$NH_2$.

In certain embodiments, $R^3$ is —$N(C_1$-$C_6$alkyl$)_2$. In certain embodiments, $R^3$ is —$N(CH_3)_2$.

In certain embodiments, $R^3$ is —$NH(C_1$-$C_6$alkyl). In certain embodiments, $R^3$ is —$NH(CH_3)$.

In certain embodiments, $R^3$ is $C_1$-$C_6$alkoxy. Suitable alkoxys include, but are not limited to, methoxy, ethoxy, n-propoxy, isopropoxy and n-butoxy. In certain embodiments, $R^3$ is methoxy.

Described herein are compounds, wherein each occurrence of $R^4$ is independently selected from the group consisting of hydrogen, —OH, $C_1$-$C_6$alkylOH, —CN, $C_1$-$C_6$alkylCN, $C_1$-$C_6$alkyl, halo$C_1$-$C_6$alkyl, halogen, —$NH_2$, —$N(C_1$-$C_6$alkyl$)_2$, —$NH(C_1$-$C_6$alkyl) and $C_1$-$C_6$alkoxy. In certain embodiments, each occurrence of $R^4$ is hydrogen or —OH.

In certain embodiments, $R^4$ is hydrogen. In certain embodiments, $R^4$ is —OH. In certain embodiments, $R^4$ is $C_1$-$C_6$alkylOH. Suitable alcohols include, but are not limited to, methanol, ethanol, propanol, and butanol.

In certain embodiments, $R^4$ is —CN. In certain embodiments, $R^4$ is $C_1$-$C_6$alkylCN. Suitable $C_1$-$C_6$alkylCNs include, but are not limited to,

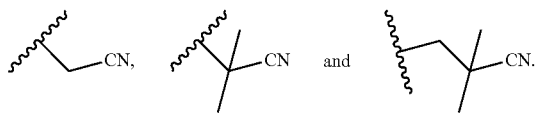

In certain embodiments, $R^4$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^4$ is methyl.

In certain embodiments, $R^4$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl.

In certain embodiments, $R^4$ is halogen. Suitable halogens include, but are not limited to, fluorine, chlorine, bromine, or iodine. In certain embodiments, $R^1$ is fluorine.

In certain embodiments, $R^4$ is —$NH_2$.

In certain embodiments, $R^4$ is —$N(C_1$-$C_6$alkyl$)_2$. In certain embodiments, $R^4$ is —$N(CH_3)_2$.

In certain embodiments, $R^4$ is —$NH(C_1$-$C_6$alkyl). In certain embodiments, $R^4$ is —$NH(CH_3)$.

In certain embodiments, $R^4$ is $C_1$-$C_6$alkoxy. Suitable alkoxys include, but are not limited to, methoxy, ethoxy, n-propoxy, isopropoxy and n-butoxy. In certain embodiments, $R^4$ is methoxy.

Described herein are compounds wherein Z is —CN, aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —CO$C_3$-$C_{10}$cycloalkyl, —CONH$C_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, —CONHheterocycloalkyl, —$SO_2$heterocycloalkyl, —COO$C_1$-$C_6$alkyl, or —COO$C_3$-$C_6$cycloalkyl, wherein the aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —CO$C_3$-$C_{10}$cycloalkyl, —CONH$C_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, —CONHheterocycloalkyl or —$SO_2$heterocycloalkyl, is unsubstituted or substituted with one to three substituents independently selected from the group consisting of halogen, —CN, $C_1$-$C_6$alkylCN, $C_1$-$C_6$alkyl, $C_1$-$C_6$alkynyl, $C_1$-$C_6$haloalkyl, $C_1$-$C_6$alkoxy, $C_1$-$C_6$haloalkoxy, —COO$C_1$-$C_6$alkyl, —S$C_1$-$C_6$alkyl, oxo, $C_3$-$C_6$cycloalkyl, aryl, heteroaryl and heterocycloalkyl, wherein the heteroaryl, heterocycloalkyl, $C_3$-$C_6$cycloalkyl, $C_1$-$C_6$alkynyl and $C_1$-$C_6$alkoxy, is unsubstituted or substituted with one to two substituents independently selected from the group consisting of halogen, —CN, $C_1$-$C_6$alkyl, $C_1$-$C_6$haloalkyl, $C_1$-$C_6$alkoxy, —OH and heterocycloalkyl.

In certain embodiments, Z is —CN, aryl, $C_1$-$C_6$alkylaryl, —COaryl, —CONHaryl, —$SO_2$aryl, $C_3$-$C_{10}$cycloalkyl, $C_1$-$C_6$alkyl$C_3$-$C_{10}$cycloalkyl, —CO$C_3$-$C_{10}$cycloalkyl, —CONH$C_3$-$C_{10}$cycloalkyl, —$SO_2C_3$-$C_{10}$cycloalkyl, heteroaryl, $C_1$-$C_6$alkylheteroaryl, —COheteroaryl, —CONHheteroaryl, —$SO_2$heteroaryl, heterocycloalkyl, $C_1$-$C_6$alkylheterocycloalkyl, —COheterocycloalkyl, —CONHheterocycloalkyl, —$SO_2$heterocycloalkyl, —COO$C_1$-$C_6$alkyl, or —COO$C_3$-$C_6$cycloalkyl.

In certain embodiments, Z is —CN.

In certain embodiments, Z is aryl. In certain embodiments, Z is phenyl.

In certain embodiments, Z is $C_1$-$C_6$alkylaryl. In certain embodiments, Z is $CH_2$phenyl.

In certain embodiments, Z is —COaryl. In certain embodiments, Z is —COphenyl.

In certain embodiments, Z is —CONHaryl. In certain embodiments, Z is —CONHphenyl.

In certain embodiments, Z is —$SO_2$aryl. In certain embodiments, Z is —$SO_2$phenyl.

In certain embodiments, Z is $C_3$-$C_{10}$cycloalkyl. Suitable cycloalkyls include, but are not limited to, cyclopropyl, cyclobutyl, cyclopentyl and cyclohexyl.

In certain embodiments, Z is $C_1$-$C_6$alkyl$C_3$-$C_{10}$cycloalkyl. Suitable cycloalkyls include, but are not limited to, $C_1$-$C_6$alkylcyclopropyl, $C_1$-$C_6$alkylcyclobutyl, $C_1$-$C_6$alkylcyclopentyl and $C_1$-$C_6$alkylcyclohexyl.

In certain embodiments, Z is —CO$C_3$-$C_{10}$cycloalkyl. Suitable cycloalkyls include, but are not limited to, —COcyclopropyl, —COcyclobutyl, —COcyclopentyl and —COcyclohexyl. In certain embodiments, wherein when Z is —CO$C_3$-$C_{10}$cycloalkyl, the —CO$C_3$-$C_{10}$cycloalkyl is —COcyclopropyl, —COcyclobutyl, —COcyclohexane, —COcyclopentane or

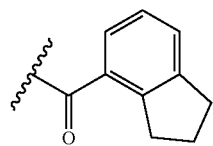

In certain embodiments, Z is —CONHC$_3$-C$_{10}$cycloalkyl. Suitable cycloalkyls include, but are not limited to, —CONHcyclopropyl, —CONHcyclobutyl, —CONHcyclopentyl and —CONHcyclohexyl.

In certain embodiments, Z is —SO$_2$C$_3$-C$_{10}$cycloalkyl. Suitable cycloalkyls include, but are not limited to, —SO$_2$cyclopropyl, —SO$_2$cyclobutyl, —SO$_2$cyclopentyl and —SO$_2$cyclohexyl.

In certain embodiments, Z is heteroaryl. In certain embodiments, wherein Z is heteroaryl, the heteroaryl is

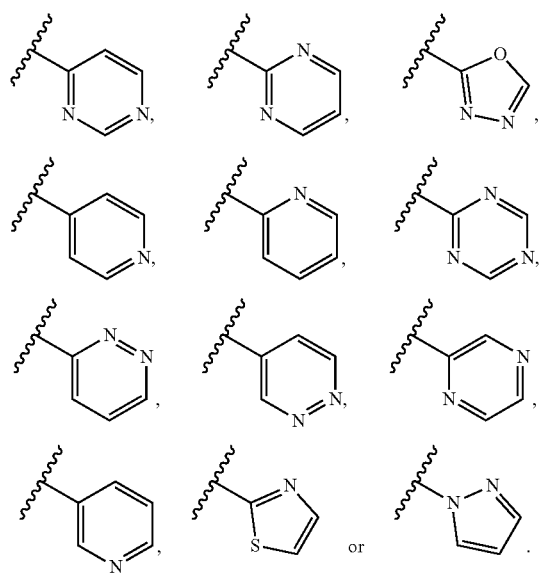

In certain embodiments, Z is heteroaryl. In certain embodiments, wherein Z is heteroaryl, the heteroaryl is

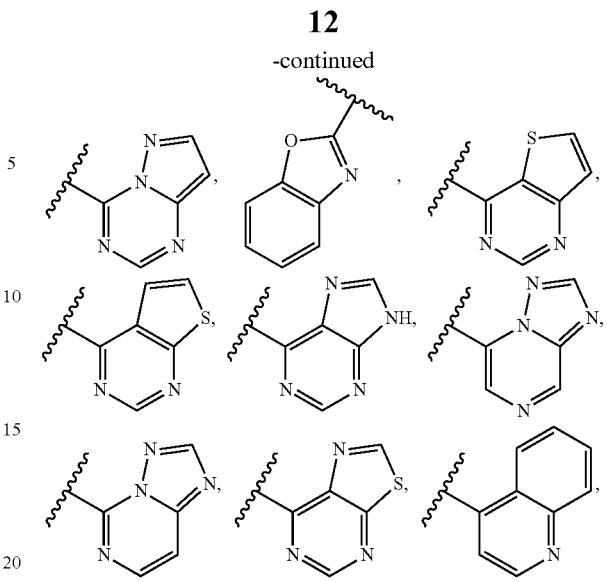

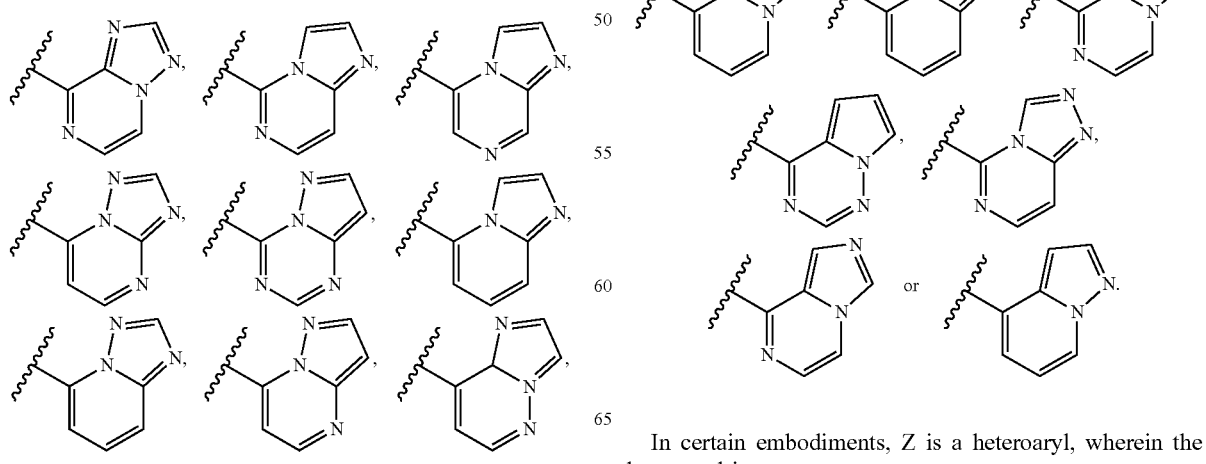

In certain embodiments, Z is a heteroaryl, wherein the heteroaryl is

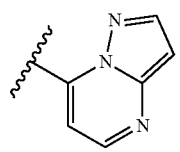
In certain embodiments, Z is $C_1$-$C_6$alkylheteroaryl. In certain embodiments, wherein when Z is $C_1$-$C_6$alkylheteroaryl, the $C_1$-$C_6$alkylheteroaryl is
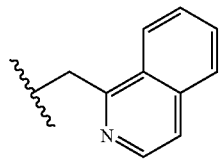
In certain embodiments, Z is —COheteroaryl. In certain embodiments, wherein when Z is —COheteroaryl, the —COheteroaryl is wherein the —COheteroaryl is
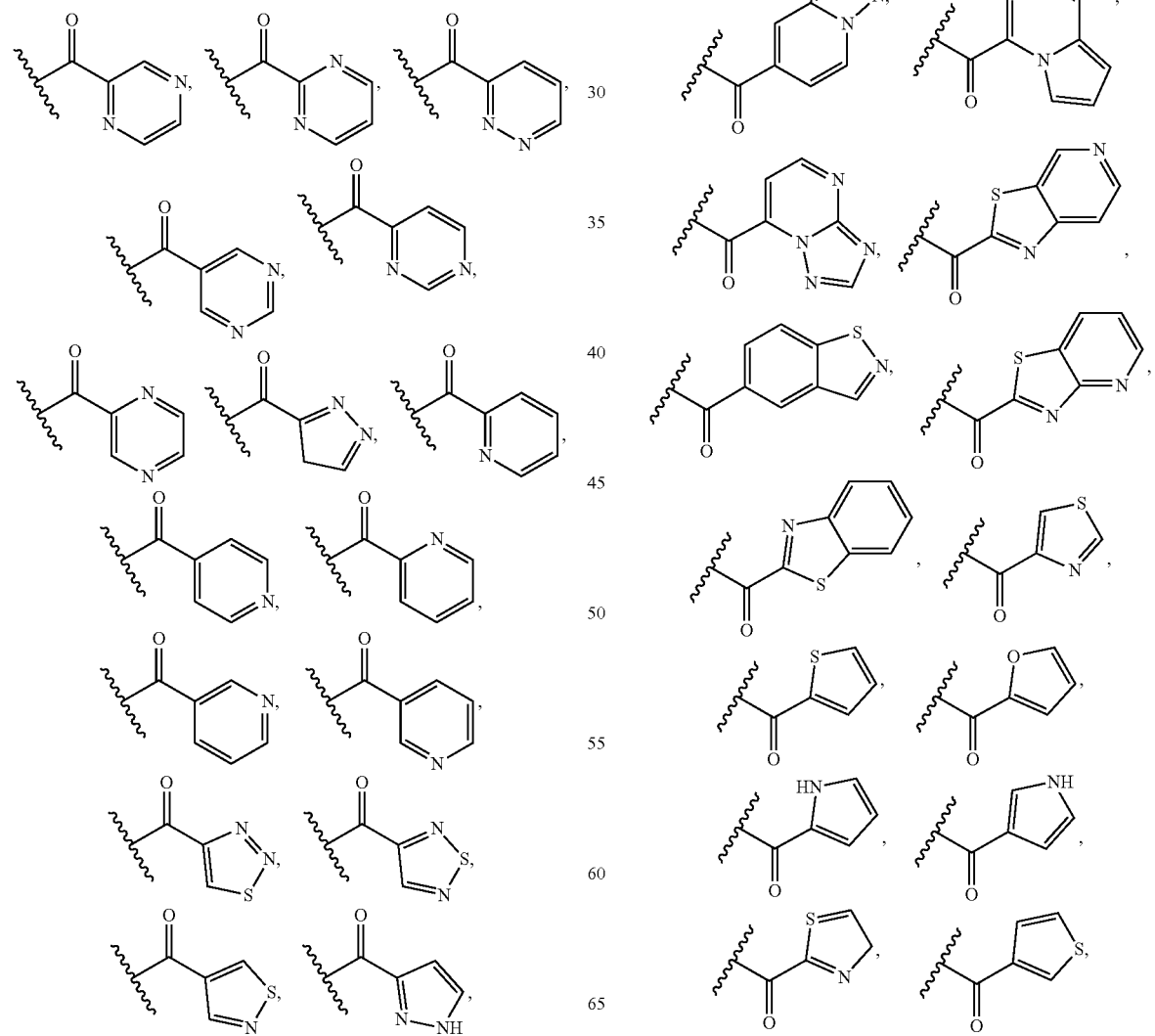

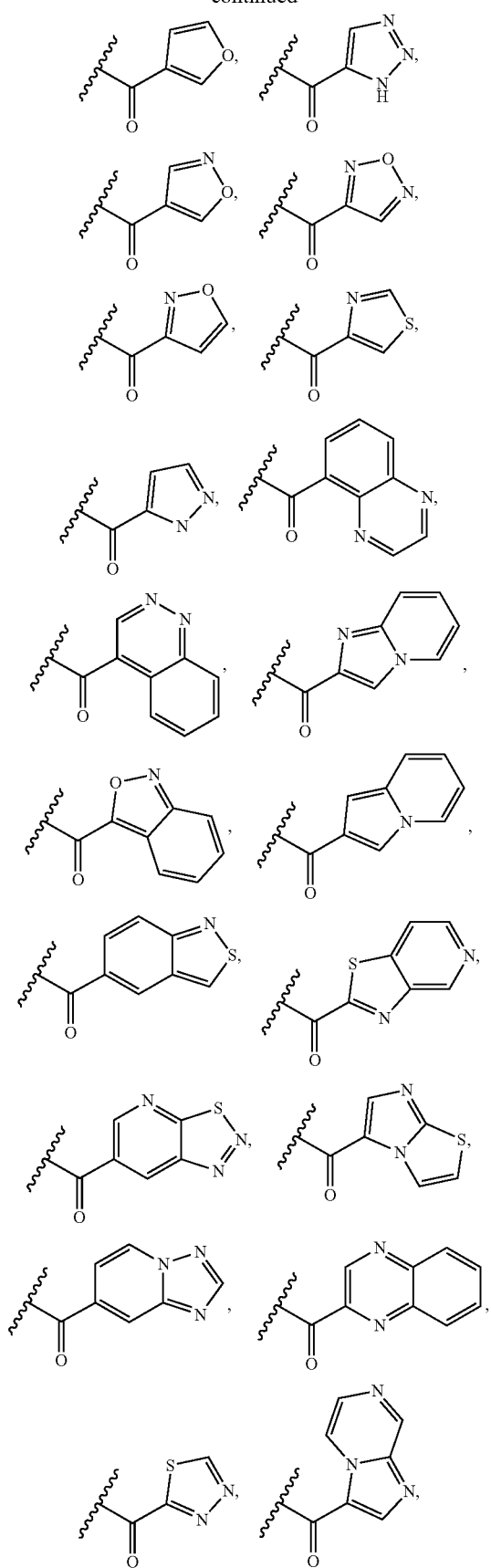
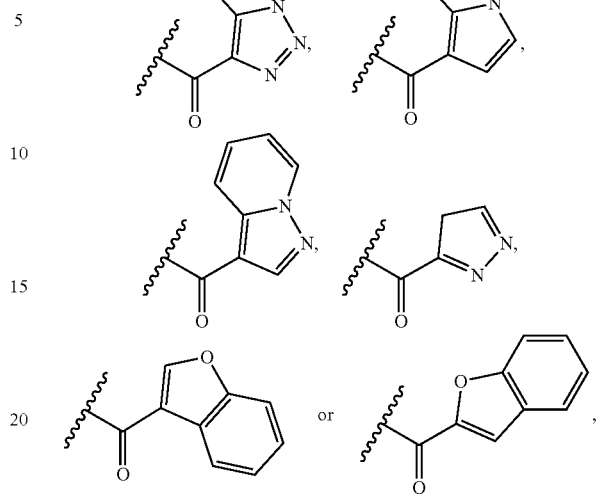

In certain embodiments, Z is —CONHheteroaryl. Suitable —CONHheteroaryls include any of the heteroaryls discussed above attached to a —CONH group.

In certain embodiments, Z is —SO₂heteroaryl. Suitable —SO₂heteroaryls include any of the heteroaryls discussed above attached to a SO₂ group.

In certain embodiments, Z is heterocycloalkyl. Suitable heterocycloalkyls include, but are not limited to, azetidine, tetrahydropyranyl, tetrahydrofuranyl, pyrrolidinyl, piperidinyl, piperazinyl, dioxanyl, imidazolidinyl, 2,3-dihydrofuro (2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl and dihydrocyclopentapyridinyl.

In certain embodiments, Z is C₁-C₆alkylheterocycloalkyl. Suitable C₁-C₆alkylheterocycloalkyls include any of the heterocycloalkyls discussed above attached to an alkyl group.

In certain embodiments, Z is —COheterocycloalkyl. Suitable —COheterocycloalkyls include any of the heterocycloalkyls discussed above attached to a CO group.

In certain embodiments, Z is —CONHheterocycloalkyl. Suitable —CONHheterocycloalkyls include any of the heterocycloalkyls discussed above attached to a CONH group.

In certain embodiments, Z is —SO₂heterocycloalkyl. Suitable —SO₂heterocycloalkyls include any of the heterocycloalkyls discussed above attached to a SO₂ group.

In certain embodiments, Z is —COOC₁-C₆alkyl. In certain embodiments, Z is

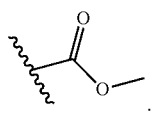

In certain embodiments, Z is —COOC₃-C₆cycloalkyl. In certain embodiments, —COOcyclobutyl.

Described herein are compounds, wherein Z is unsubstituted or substituted. In certain embodiments, Z is unsubstituted. In certain embodiments, Z is substituted. In certain embodiments, Z is substituted with one to three substituents. In certain embodiments, Z is substituted with one substituent. In certain embodiments, Z is substituted with two substituents. In certain embodiments, Z is substituted with three substituents. In certain embodiments, Z is substituted with one to three substituents, wherein the substituents are selected from the group consisting of halogen, —CN, $C_1$-$C_6$alkylCN, $C_1$-$C_6$alkyl, $C_1$-$C_6$alkynyl, $C_1$-$C_6$haloalkyl, $C_1$-$C_6$alkoxy, $C_1$-$C_6$haloalkoxy, —COO$C_1$-$C_6$alkyl, —S$C_1$-$C_6$alkyl, oxo, $C_3$-$C_6$cycloalkyl, aryl, heteroaryl, heterocycloalkyl, wherein the heteroaryl, heterocycloalkyl, $C_3$-$C_6$cycloalkyl, $C_1$-$C_6$alkynyl, $C_1$-$C_6$alkoxy, is unsubstituted or substituted with one to two substituents selected from the group consisting of halogen, —CN, $C_1$-$C_6$alkyl, $C_1$-$C_6$haloalkyl, $C_1$-$C_6$alkoxy, —OH or heterocycloalkyl.

In certain embodiments, wherein Z is aryl, $C_1$-$C_6$alkylaryl, —COaryl, —CONHaryl, —SO$_2$aryl, $C_3$-$C_{10}$cycloalkyl, $C_1$-$C_6$alkyl$C_3$-$C_{10}$cycloalkyl, —CO$C_3$-$C_{10}$cycloalkyl, —CONH$C_3$-$C_{10}$cycloalkyl, —SO$_2$$C_3$-$C_{10}$cycloalkyl, heteroaryl, $C_1$-$C_6$alkylheteroaryl, —COheteroaryl, —CONHheteroaryl, —SO$_2$heteroaryl, heterocycloalkyl, $C_1$-$C_6$alkylheterocycloalkyl, —COheterocycloalkyl, —CONHheterocycloalkyl or —SO$_2$heterocycloalkyl, the aryl, $C_1$-$C_6$alkylaryl, —COaryl, —CONHaryl, —SO$_2$aryl, $C_3$-$C_{10}$cycloalkyl, $C_1$-$C_6$alkyl$C_3$-$C_{10}$cycloalkyl, —CO$C_3$-$C_{10}$cycloalkyl, —CONH$C_3$-$C_{10}$cycloalkyl, —SO$_2$$C_3$-$C_{10}$cycloalkyl, heteroaryl, $C_1$-$C_6$alkylheteroaryl, —COheteroaryl, —CONHheteroaryl, —SO$_2$heteroaryl, heterocycloalkyl, $C_1$-$C_6$alkylheterocycloalkyl, —COheterocycloalkyl, —CONHheterocycloalkyl or —SO$_2$heterocycloalkyl is unsubstituted or substituted with one to three substituents selected from the group consisting of halogen, —CN, $C_1$-$C_6$alkylCN, $C_1$-$C_6$alkyl, $C_1$-$C_6$alkynyl, $C_1$-$C_6$haloalkyl, $C_1$-$C_6$alkoxy, $C_1$-$C_6$haloalkoxy, —COO$C_1$-$C_6$alkyl, —S$C_1$-$C_6$alkyl, oxo, $C_3$-$C_6$cycloalkyl, aryl, heteroaryl, heterocycloalkyl, wherein the heteroaryl, heterocycloalkyl, $C_3$-$C_6$cycloalkyl, $C_1$-$C_6$alkynyl, $C_1$-$C_6$alkoxy, is unsubstituted or substituted with one to two substituents selected from the group consisting of halogen, —CN, $C_1$-$C_6$alkyl, $C_1$-$C_6$haloalkyl, $C_1$-$C_6$alkoxy, —OH or heterocycloalkyl.

In certain embodiments, Z is substituted with halogen. Suitable halogens include, but are not limited to, fluorine, chlorine, bromine, or iodine. In certain embodiments, Z is substituted with fluorine or chlorine.

In certain embodiments, Z is substituted with —CN.

In certain embodiments, Z is substituted with $C_1$-$C_6$alkylCN. Suitable $C_1$-$C_6$alkylCN groups include, but are not limited to,

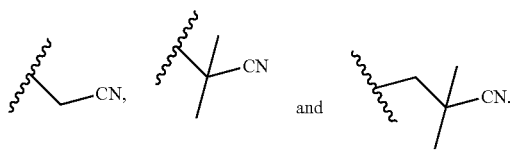

In certain embodiments, Z is substituted with $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, Z is substituted with methyl.

In certain embodiments, Z is substituted with $C_1$-$C_6$alkynyl.

In certain embodiments, Z is substituted with $C_1$-$C_6$haloalkyl. Suitable examples of haloalkyls include, but are not limited to, fluoromethyl, difluoromethyl, trifluoromethyl, 2-fluoroethyl, 1,2-difluoroethyl and 2,2-difluoroethyl.

In certain embodiments, Z is substituted with $C_1$-$C_6$alkoxy. Suitable alkoxys include, but are not limited to, methoxy, ethoxy, n-propoxy, isopropoxy and n-butoxy.

In certain embodiments, Z is substituted with $C_1$-$C_6$haloalkoxy. Suitable alkoxys include, but are not limited to, trifluoromethoxy and difluoroethoxy.

In certain embodiments, Z is substituted with —COO$C_1$-$C_6$alkyl.

In certain embodiments, Z is substituted with —S$C_1$-$C_6$alkyl. Suitable —S$C_1$-$C_6$alkyls include, but are not limited to, —SCH$_3$.

In certain embodiments, Z is substituted with oxo.

In certain embodiments, Z is substituted with $C_3$-$C_6$cycloalkyl. Suitable cycloalkyls include, but are not limited to, cyclopropyl, cyclobutyl, cyclopentyl and cyclohexyl.

In certain embodiments, Z is substituted with aryl. Suitable aryls include phenyl.

In certain embodiments, Z is substituted with heteroaryl. Suitable heteroaryls include, but are not limited to, pyridyl (pyridinyl), oxazolyl, imidazolyl, triazolyl, furyl, triazinyl, thienyl, pyrimidyl, pyrazinyl, indolizinyl, cinnolinyl, phthalazinyl, quinazolinyl, naphthyridinyl, quinoxalinyl, purinyl, benzimidazolyl, quinolyl, benothiophenyl, isothiazolyl and isoquinolyl. In certain embodiments, wherein A is heteroaryl, the heteroaryl is pyridinyl, pyrazinyl, benothiophenyl, isothiazolyl or thienyl.

In certain embodiments, Z is substituted with heterocycloalkyl. Suitable heterocycloalkyls include, but are not limited to, azetidine, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl and dihydrocyclopentapyridinyl.

In certain embodiments, wherein when Z is substituted heteroaryl, heterocycloalkyl, $C_3$-$C_6$cycloalkyl, $C_1$-$C_6$alkynyl, $C_1$-$C_6$alkoxy, the heteroaryl, heterocycloalkyl, $C_3$-$C_6$cycloalkyl, $C_1$-$C_6$alkynyl, $C_1$-$C_6$alkoxy, is unsubstituted or substituted with one to two substituents selected from the group consisting of halogen, —CN, $C_1$-$C_6$alkyl, $C_1$-$C_6$haloalkyl, $C_1$-$C_6$alkoxy, —OH or heterocycloalkyl.

In certain embodiments, wherein Z is aryl, the aryl is unsubstituted or substituted with one, two or three substituents selected from the group consisting of halogen, —CN, —OH, $C_1$-$C_6$alkyl, heterocycloalkyl, $C_3$-$C_6$cycloalkyl, $C_1$-$C_6$alkoxy, $C_1$-$C_6$alkynyl, heteroaryl or $C_1$-$C_6$haloalkoxy, wherein the heterocycloalkyl, $C_1$-$C_6$alkynyl or $C_3$-$C_6$cycloalkyl is unsubstituted or substituted with an oxo group, —CN or —OH.

In certain embodiments, wherein Z is phenyl, the phenyl is unsubstituted or substituted with one, two or three substituents selected from the group consisting of —CN, chlorine, fluorine, or methyl.

In certain embodiments, wherein Z is —COaryl, the aryl is unsubstituted or substituted with one, two or three substituents selected from the group consisting of halogen, CN, —OH, $C_1$-$C_6$alkyl, heterocycloalkyl, $C_3$-$C_6$cycloalkyl, $C_1$-$C_6$alkoxy, $C_1$-$C_6$alkynyl, heteroaryl or $C_1$-$C_6$haloalkoxy, wherein the heterocycloalkyl, $C_1$-$C_6$alkynyl or $C_3$-$C_6$cycloalkyl is unsubstituted or substituted with an oxo group, —CN or —OH.

In certain embodiments, wherein Z is —COphenyl, the —COphenyl is unsubstituted or substituted with one, two or three substituents selected from the group consisting of fluorine, chlorine, iodine, —CN, ethynyl, hydroxymethylbutynl, —OH, triazole, morpholine, oxopyrrolidinyl, difluoromethoxy, oxadiazolyl, ethyl, cyclopropyl and methyl.

In certain embodiments, wherein Z is heteroaryl, the heteroaryl unsubstituted or substituted with one to four substituents selected from the group consisting of —CN, —OH, phenyl, halogen, $C_1$-$C_6$alkylOH, $C_1$-$C_6$alkylCN, $C_1$-$C_6$alkyl, $C_1$-$C_6$haloalkyl, $C_1$-$C_6$alkoxy, $C_1$-$C_6$haloalkoxy, —CO$C_1$-$C_6$alkyl, —COO$C_1$-$C_6$alkyl, —S$C_1$-$C_6$alkyl, oxo, $C_3$-$C_6$cycloalkyl, heterocycloalkyl, —CONH($C_1$-$C_6$alkyl), —CONH$_2$, —CON($C_1$-$C_6$alkyl)$_2$ or heteroaryl, wherein the phenyl, $C_1$-$C_6$alkoxy or heteroaryl is unsubstituted or substituted with halogen, $C_1$-$C_6$haloalkyl, heterocycloalkyl or $C_1$-$C_6$alkyl.

In certain embodiments, wherein Z is heteroaryl, the heteroaryl unsubstituted or substituted with one to four substituents selected from the group consisting of fluorine, bromine, —CN, methyl, methoxy, ethoxy, difluoromethyl, phenyl, methylimidazolyl, —SCH$_2$, chlorine, trifluoromethyl, cyclopropyl, cyclobutyl, propoxy, difluoromethoxy, ethyl, difluoromethylpyrazole, methoxyoxetane, difluoroethoxy and triazolyl.

In certain embodiments, wherein Z is —COheteroaryl, the —COheteroaryl unsubstituted or substituted with one to four substituents selected from the group consisting of —CN, —OH, phenyl, halogen, $C_1$-$C_6$alkylOH, $C_1$-$C_6$alkylCN, $C_1$-$C_6$alkyl, $C_1$-$C_6$haloalkyl, $C_1$-$C_6$alkoxy, $C_1$-$C_6$haloalkoxy, —CO$C_1$-$C_6$alkyl, —COO$C_1$-$C_6$alkyl, —S$C_1$-$C_6$alkyl, oxo, $C_3$-$C_6$cycloalkyl, heterocycloalkyl, —CONH($C_1$-$C_6$alkyl), —CONH$_2$, —CON($C_1$-$C_6$alkyl)$_2$ or heteroaryl, wherein the phenyl, $C_1$-$C_6$alkoxy or heteroaryl is unsubstituted or substituted with halogen, $C_1$-$C_6$haloalkyl, heterocycloalkyl or $C_1$-$C_6$alkyl.

In certain embodiments, wherein Z is —COheteroaryl, the —COheteroaryl unsubstituted or substituted with one to four substituents selected from the group consisting of fluorine, bromine, —CN, methyl, methoxy, difluoromethyl, phenyl, methylimidazolyl, —SCH$_2$, chlorine, trifluoromethyl, cyclopropyl, propoxy, ethoxy, difluoromethoxy, ethyl, CH$_2$CN, pyridinyl, pyrimidinyl, propyl, pyrrole, and triazolyl.

In certain embodiments, wherein Z is —SO$_2$aryl, wherein the —SO$_2$aryl is unsubstituted or substituted with halogen, —CN or $C_1$-$C_6$alkyl.

In certain embodiments, wherein Z is —SO$_2$phenyl, wherein the —SO$_2$phenyl is unsubstituted or substituted with fluorine, —CN, or methyl.

In certain embodiments, Z is unsubstituted or substituted with one to four substituents selected from the group consisting of —CN, —OH, phenyl, halogen, $C_1$-$C_6$alkylOH, $C_1$-$C_6$alkylCN, $C_1$-$C_6$alkyl, $C_1$-$C_6$haloalkyl, $C_1$-$C_6$alkoxy, $C_1$-$C_6$haloalkoxy, —CO$C_1$-$C_6$alkyl, $C_1$-$C_6$alkynyl, —COO$C_1$-$C_6$alkyl, —S$C_1$-$C_6$alkyl, oxo, $C_3$-$C_6$cycloalkyl, heterocycloalkyl, —CONH($C_1$-$C_6$alkyl), —CONH$_2$, —CON($C_1$-$C_6$alkyl)$_2$ or heteroaryl, wherein the phenyl, heterocycloalkyl, $C_1$-$C_6$alkynyl, $C_3$-$C_6$cycloalkyl, $C_1$-$C_6$alkoxy or heteroaryl is unsubstituted or substituted with an oxo group, —CN or —OH, halogen, $C_1$-$C_6$haloalkyl, heterocycloalkyl or $C_1$-$C_6$alkyl.

Also, described herein are compounds of Formula IV:

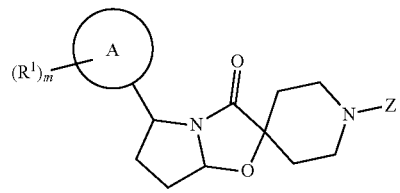

IV or a pharmaceutically acceptable salt thereof, wherein:
A is aryl, heteroaryl, heterocycloalkyl or $C_3$-$C_6$cycloalkyl;
each occurrence of $R^1$ is independently selected from the group consisting of —OH, $C_1$-$C_6$alkylOH, —CN, $C_1$-$C_6$alkylCN, $C_1$-$C_6$alkyl, halo$C_1$-$C_6$alkyl, halogen, —NH$_2$, —N($C_1$-$C_6$alkyl)$_2$, —NH($C_1$-$C_6$alkyl) and $C_1$-$C_6$alkoxy;
Z is —CN, aryl, $C_1$-$C_6$alkylaryl, —COaryl, —CONHaryl, —SO$_2$aryl, $C_3$-$C_{10}$cycloalkyl, $C_1$-$C_6$alkyl$C_3$-$C_{10}$cycloalkyl, —CO$C_3$-$C_{10}$cycloalkyl, —CONH$C_3$-$C_{10}$cycloalkyl, —SO$_2$$C_3$-$C_{10}$cycloalkyl, heteroaryl, $C_1$-$C_6$alkylheteroaryl, —COheteroaryl, —CONHheteroaryl, —SO$_2$heteroaryl, heterocycloalkyl, $C_1$-$C_6$alkylheterocycloalkyl, —COheterocycloalkyl, —CONHheterocycloalkyl, —SO$_2$heterocycloalkyl, —COO$C_1$-$C_6$alkyl or —COO$C_3$-$C_6$cycloalkyl, wherein the aryl, $C_1$-$C_6$alkylaryl, —COaryl, —CONHaryl, —SO$_2$aryl, $C_3$-$C_{10}$cycloalkyl, $C_1$-$C_6$alkyl$C_3$-$C_{10}$cycloalkyl, —CO$C_3$-$C_{10}$cycloalkyl, —CONH$C_3$-$C_{10}$cycloalkyl, —SO$_2$$C_3$-$C_{10}$cycloalkyl, heteroaryl, $C_1$-$C_6$alkylheteroaryl, —COheteroaryl, —CONHheteroaryl, —SO$_2$heteroaryl, heterocycloalkyl, $C_1$-$C_6$alkylheterocycloalkyl, —COheterocycloalkyl, —CONHheterocycloalkyl or —SO$_2$heterocycloalkyl, is unsubstituted or substituted with one to four substituents independently selected from the group consisting of —CN, —OH, halogen, $C_1$-$C_6$alkylCN, $C_1$-$C_6$alkylOH, $C_1$-$C_6$alkyl, $C_1$-$C_6$alkynyl, $C_1$-$C_6$haloalkyl, $C_1$-$C_6$alkoxy, $C_1$-$C_6$haloalkoxy, —COO$C_1$-$C_6$alkyl, —CO$C_1$-$C_6$alkyl, —S$C_1$-$C_6$alkyl, oxo, $C_3$-$C_6$cycloalkyl, aryl, heteroaryl, heterocycloalkyl, —CONH($C_1$-$C_6$alkyl), —CONH$_2$, —CON($C_1$-$C_6$alkyl)$_2$, wherein the heteroaryl, heterocycloalkyl, $C_3$-$C_6$cycloalkyl, $C_1$-$C_6$alkynyl, $C_1$-$C_6$alkoxy, is unsubstituted or substituted with one to two substituents independently selected from the group consisting of halogen, —CN, $C_1$-$C_6$alkyl, $C_1$-$C_6$haloalkyl, $C_1$-$C_6$alkoxy, —OH or heterocycloalkyl; and
m is 0, 1, 2 or 3.

Also, described herein are compounds of Formula V:

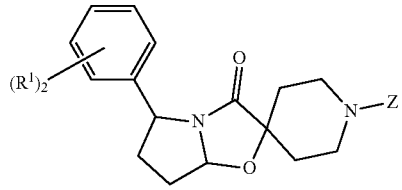

V or a pharmaceutically acceptable salt thereof, wherein:
each occurrence of $R^1$ is independently selected from the group consisting of —OH, $C_1$-$C_6$alkylOH, —CN, $C_1$-$C_6$alkylCN, $C_1$-$C_6$alkyl, halo$C_1$-$C_6$alkyl, halogen and $C_1$-$C_6$alkoxy; and Z is —CN, aryl, $C_1$-$C_6$alkylaryl, —COaryl, CONHaryl, —SO$_2$aryl, $C_3$-$C_{10}$cycloalkyl, $C_1$-$C_6$alkyl$C_3$-$C_{10}$cycloalkyl, —COC$_3$-$C_{10}$cycloalkyl, —CONHC$_3$-$C_{10}$cycloalkyl, —SO$_2$C$_3$-$C_{10}$cycloalkyl, heteroaryl, $C_1$-$C_6$alkylheteroaryl, —COheteroaryl, —CONHheteroaryl, —SO$_2$heteroaryl, heterocycloalkyl, $C_1$-$C_6$alkylheterocycloalkyl, —COheterocycloalkyl, —CONHheterocycloalkyl, —SO$_2$heterocycloalkyl, —COOC$_1$-$C_6$alkyl or —COOC$_3$-$C_6$cycloalkyl, wherein the aryl, $C_1$-$C_6$alkylaryl, —COaryl, —CONHaryl, —SO$_2$aryl, $C_3$-$C_{10}$cycloalkyl, $C_1$-$C_6$alkyl$C_3$-$C_{10}$cycloalkyl, —COC$_3$-$C_{10}$cycloalkyl, —CONHC$_3$-$C_{10}$cycloalkyl, —SO$_2$C$_3$-$C_{10}$cycloalkyl, heteroaryl, $C_1$-$C_6$alkylheteroaryl, —COheteroaryl, —CONHheteroaryl, —SO$_2$heteroaryl, heterocycloalkyl, $C_1$-$C_6$alkylheterocycloalkyl, —COheterocycloalkyl, —CONHheterocycloalkyl or —SO$_2$heterocycloalkyl, is unsubstituted or substituted with one to four substituents independently selected from the group consisting of —CN, —OH, halogen, $C_1$-$C_6$alkylCN, $C_1$-$C_6$alkylOH, $C_1$-$C_6$alkyl, $C_1$-$C_6$alkynyl, $C_1$-$C_6$haloalkyl, $C_1$-$C_6$alkoxy, $C_1$-$C_6$haloalkoxy, —COOC$_1$-$C_6$alkyl, —COC$_1$-$C_6$alkyl, —SC$_1$-$C_6$alkyl, oxo, $C_3$-$C_6$cycloalkyl, aryl, heteroaryl, heterocycloalkyl, —CONH($C_1$-$C_6$alkyl), —CONH$_2$, —CON($C_1$-$C_6$alkyl)$_2$, wherein the heteroaryl, heterocycloalkyl, $C_3$-$C_6$cycloalkyl, $C_1$-$C_6$alkynyl, $C_1$-$C_6$alkoxy, is unsubstituted or substituted with one to two substituents independently selected from the group consisting of halogen, CN, $C_1$-$C_6$alkyl, $C_1$-$C_6$haloalkyl, $C_1$-$C_6$alkoxy, OH or heterocycloalkyl.

Also, described herein are the following compounds:

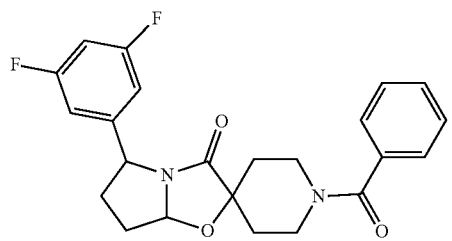

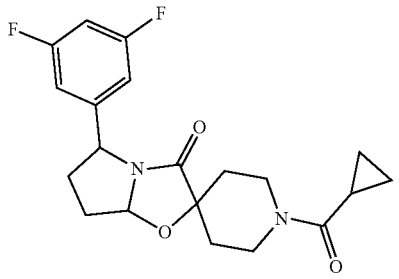

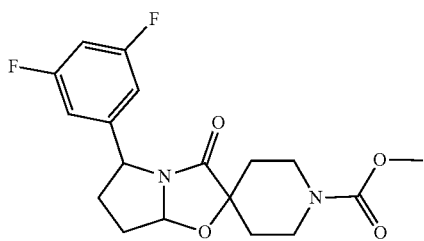

-continued

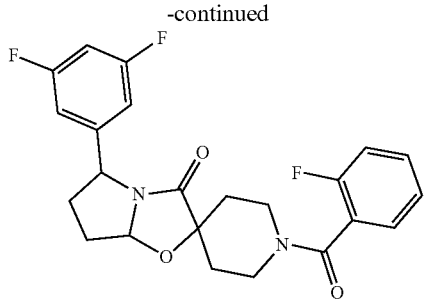

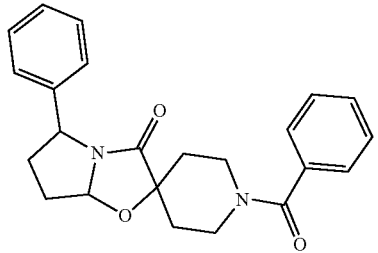

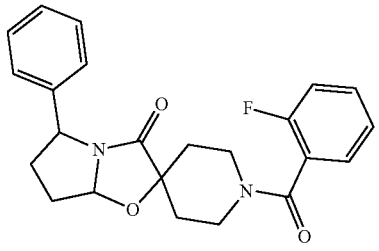

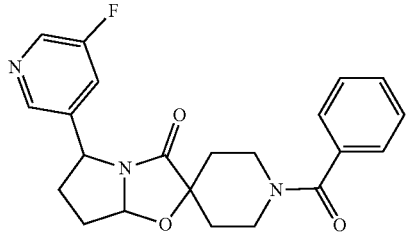

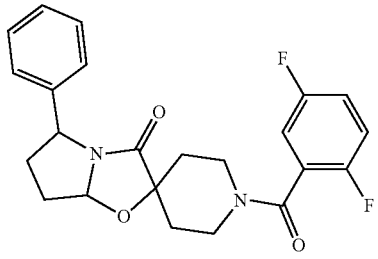

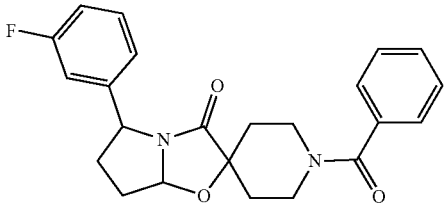

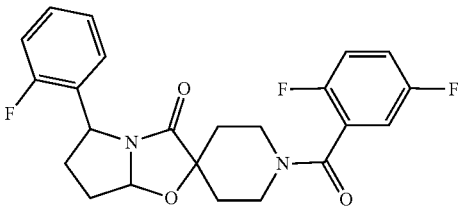

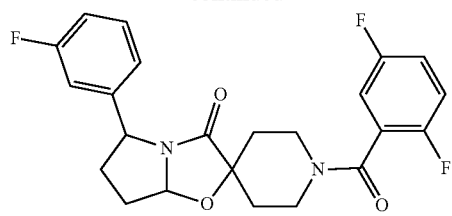
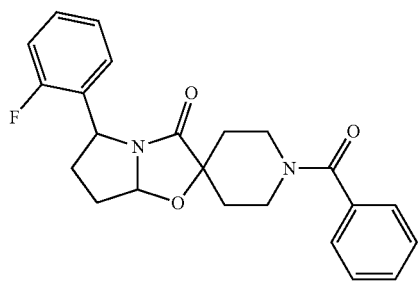
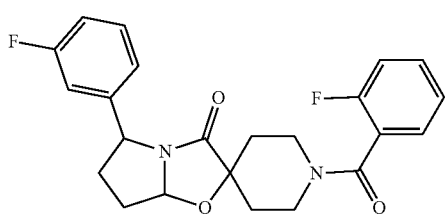
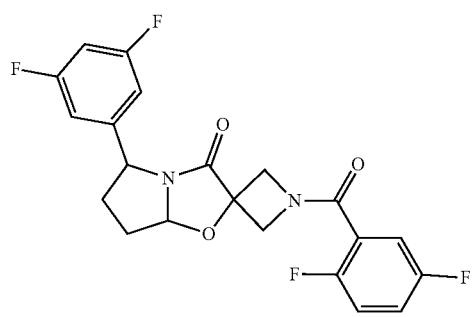
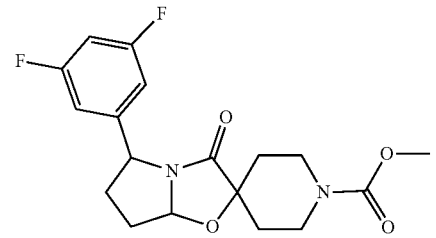
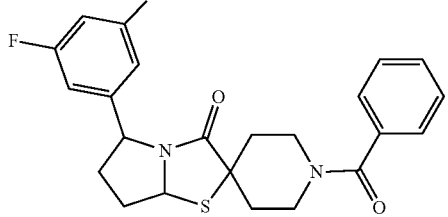
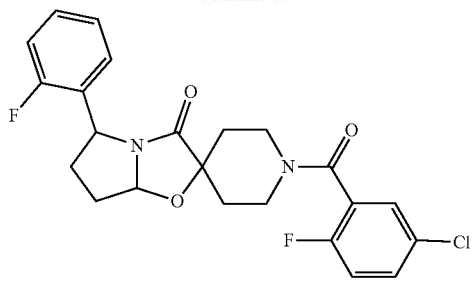
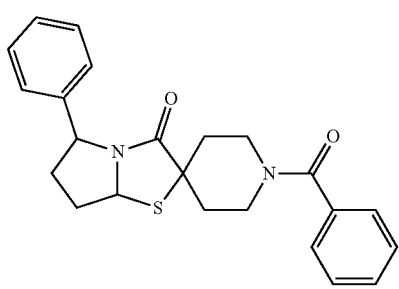
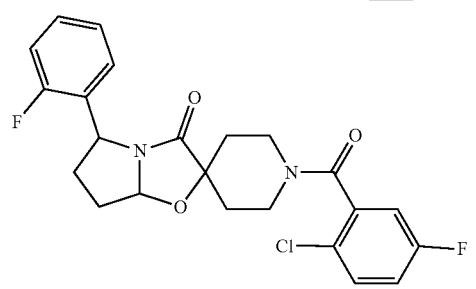
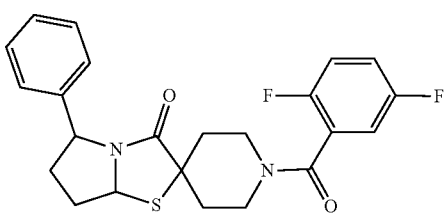
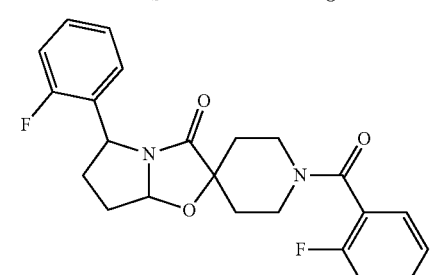
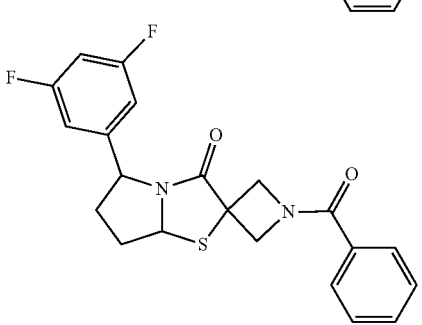

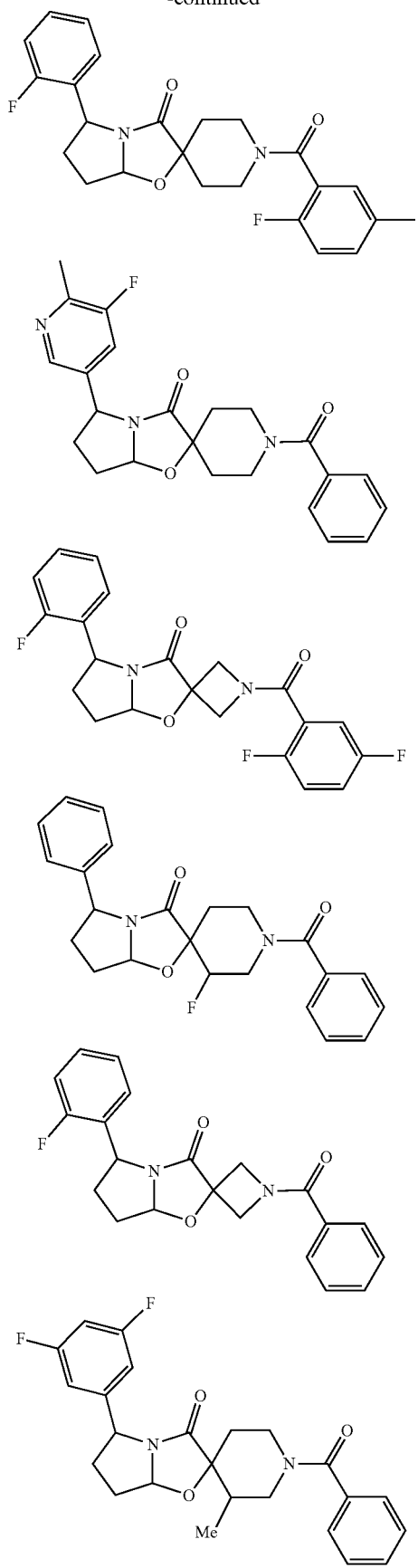
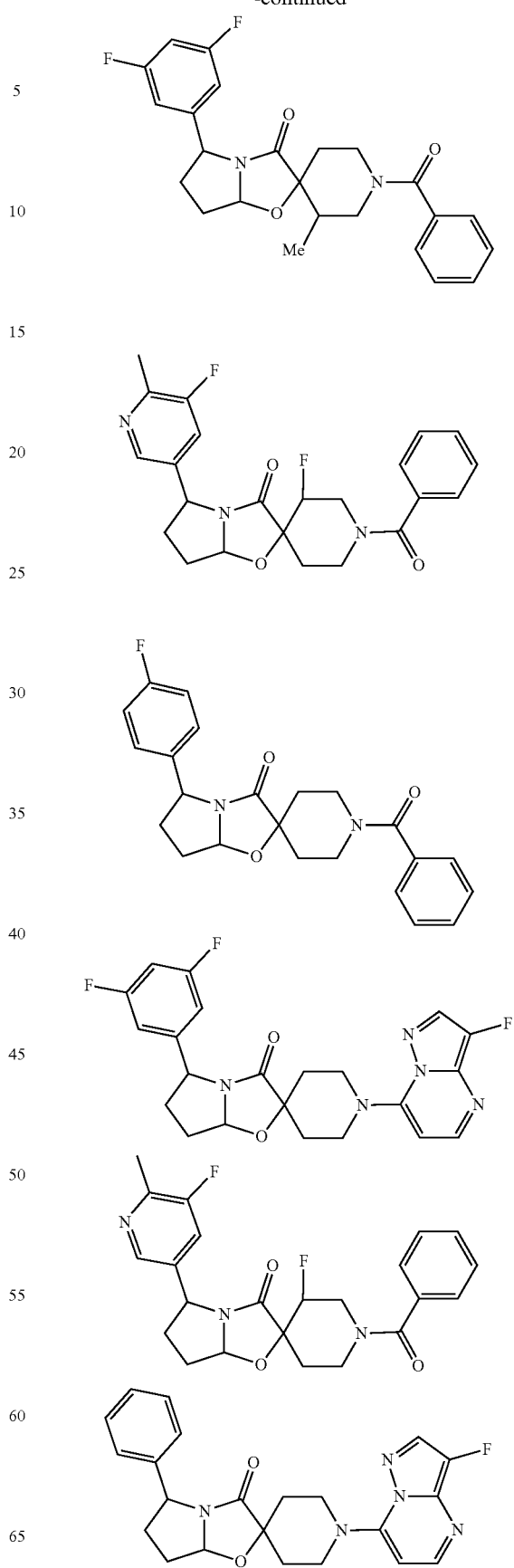

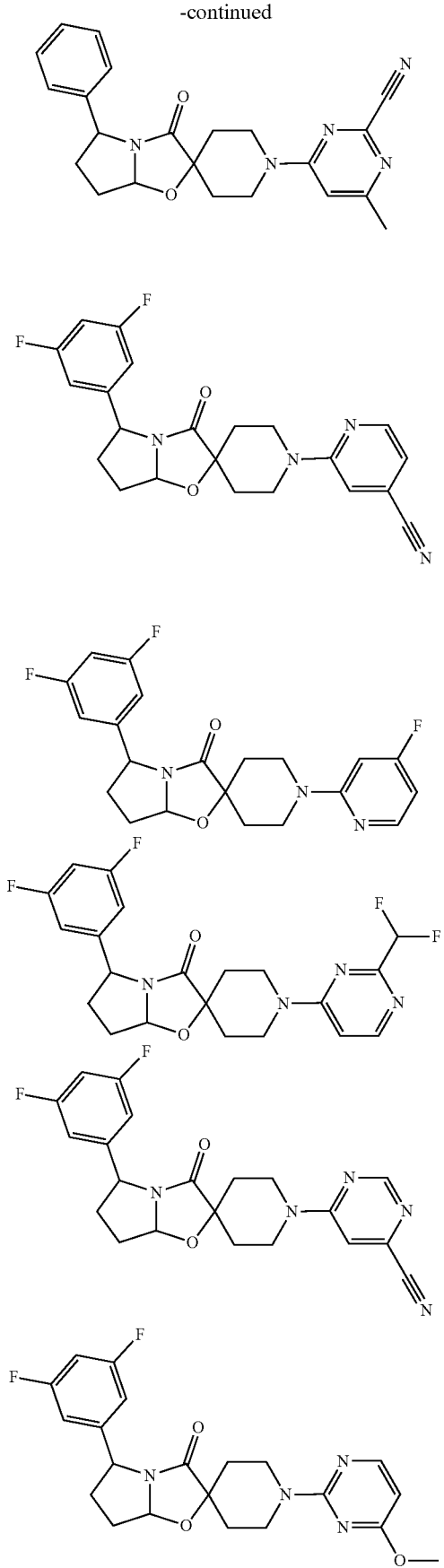
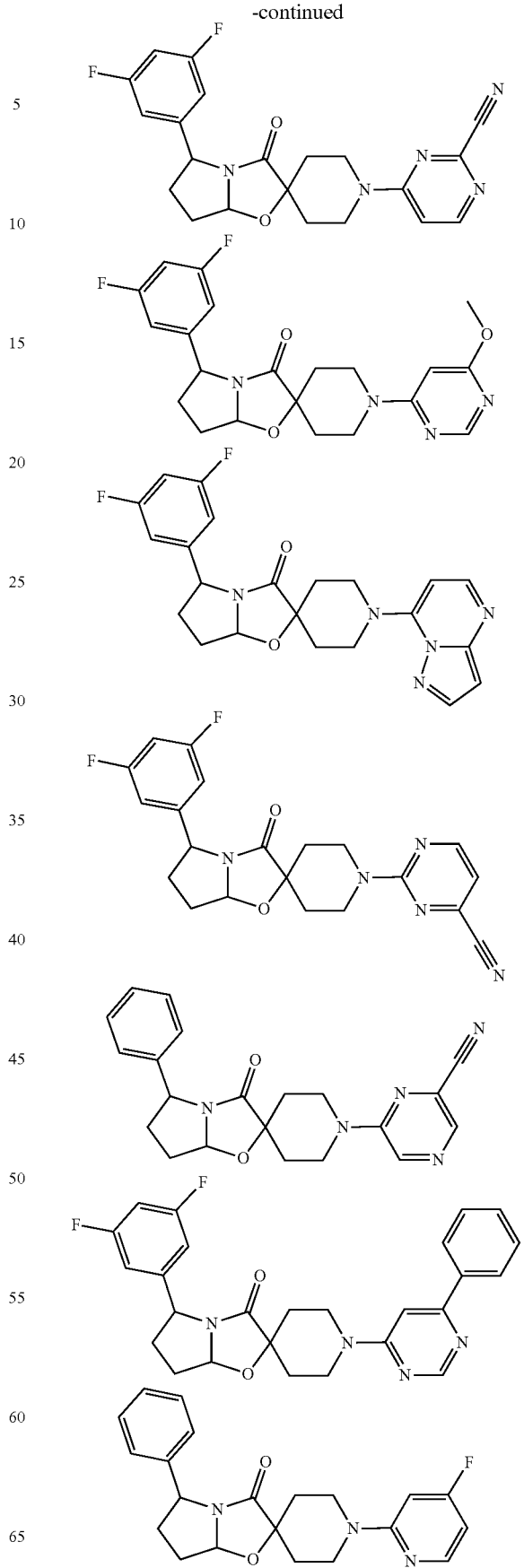

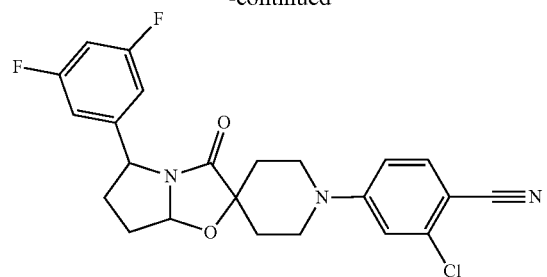
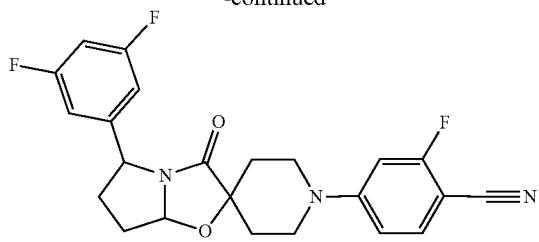
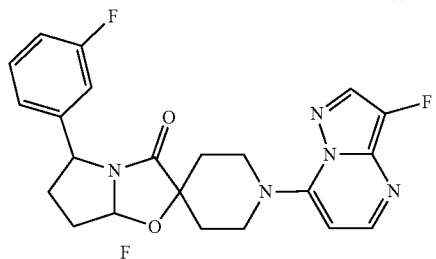
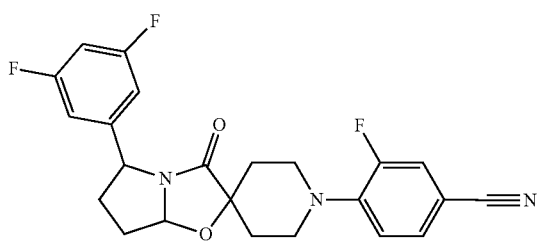
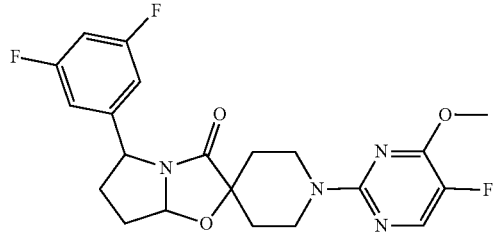
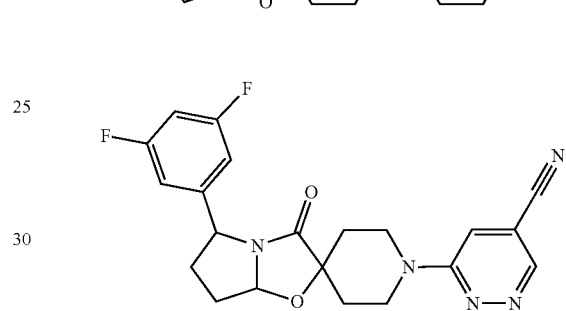
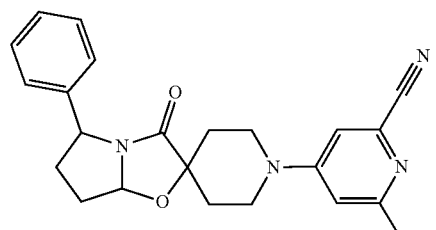
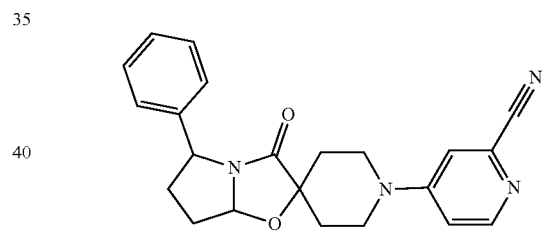
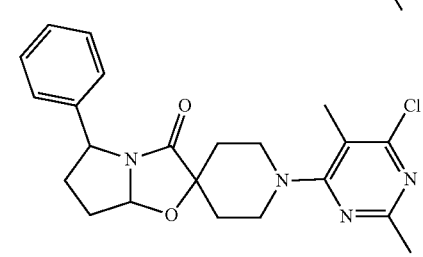
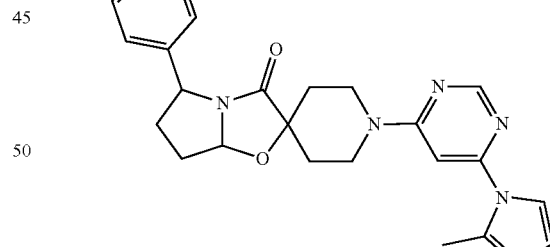
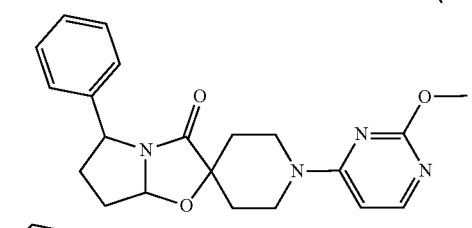
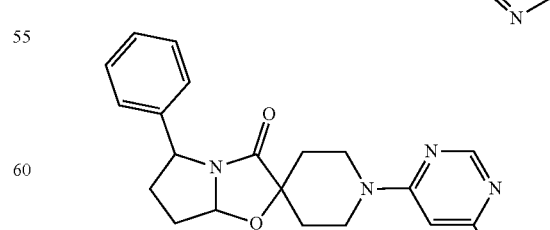
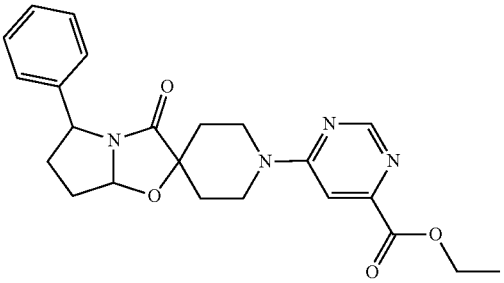

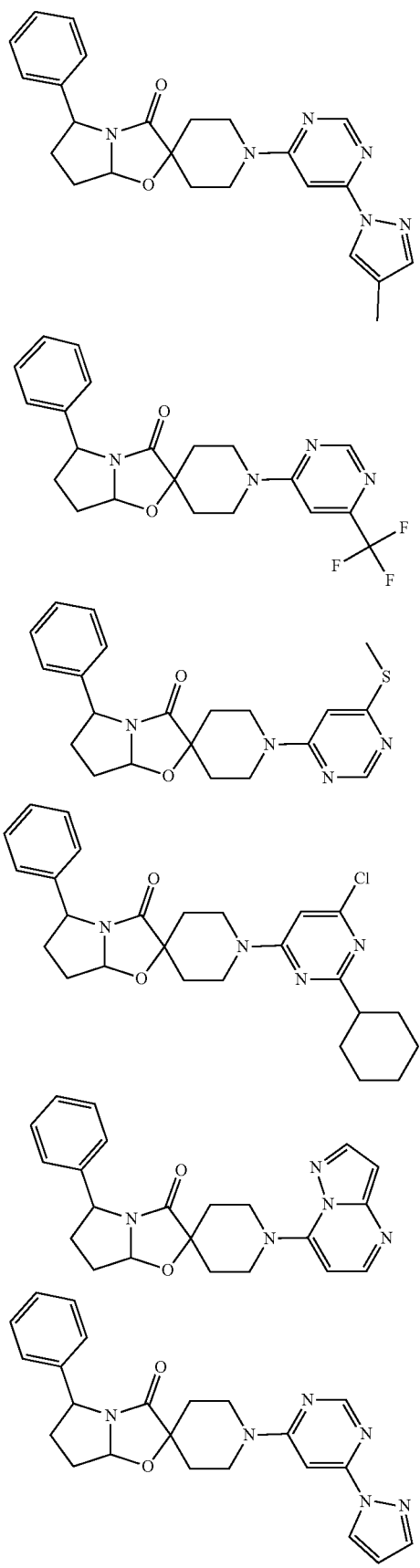
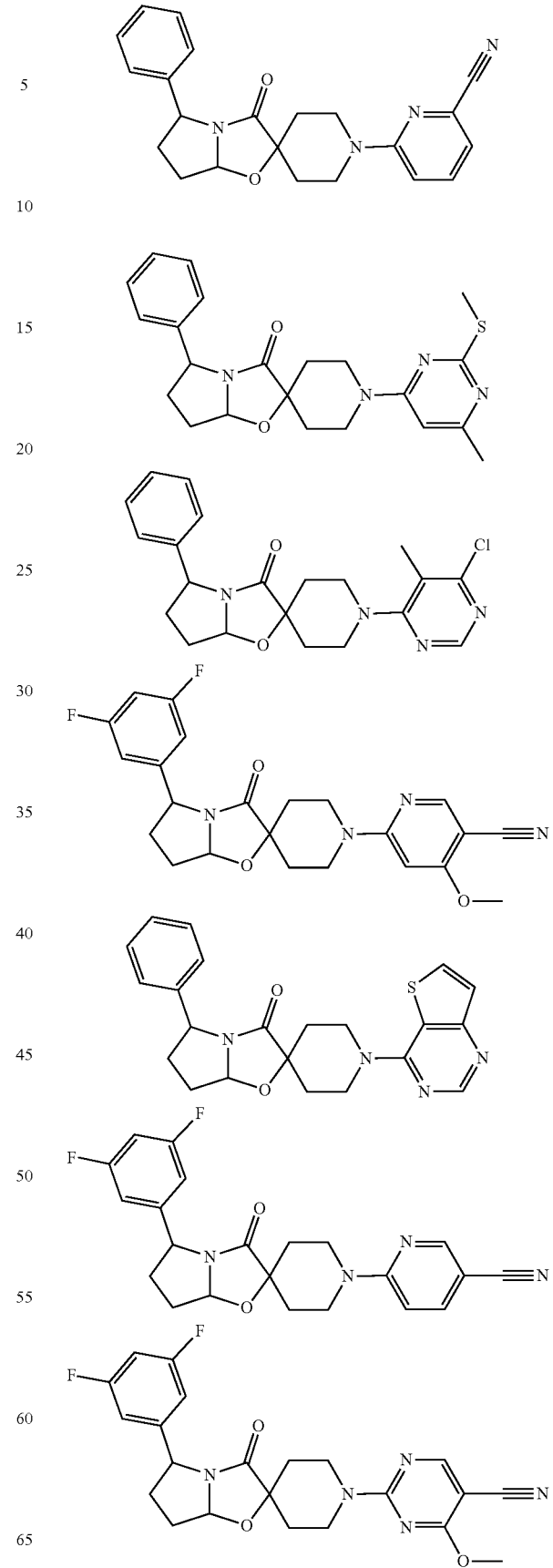

-continued
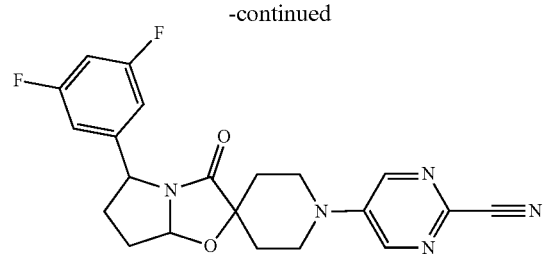
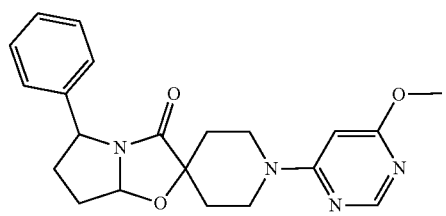
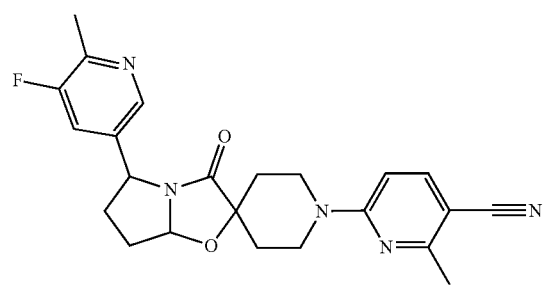
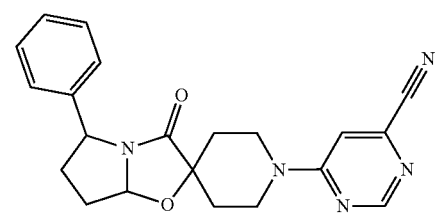
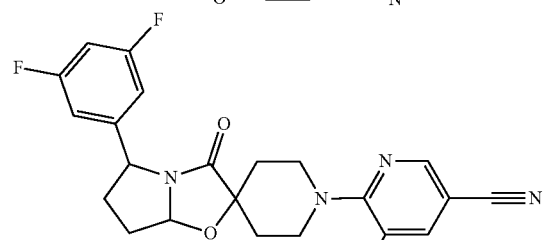
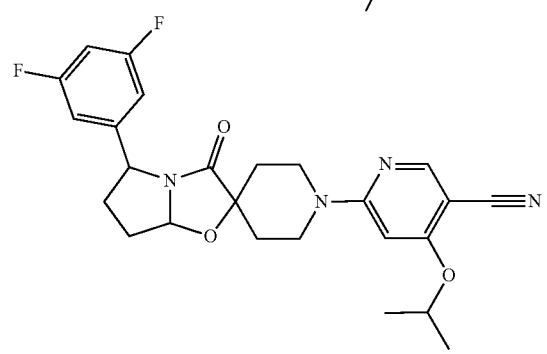
-continued
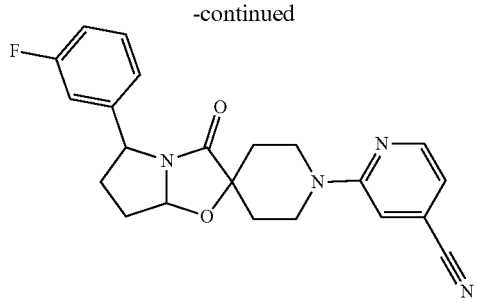
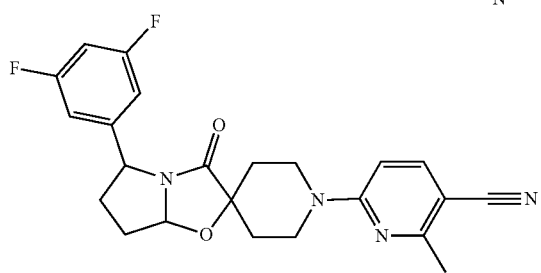
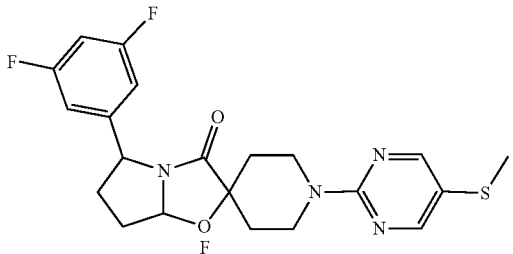
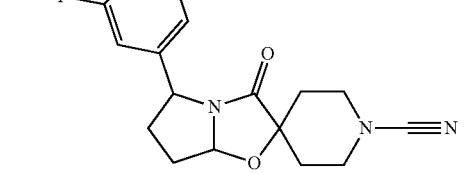
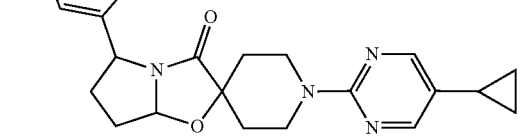
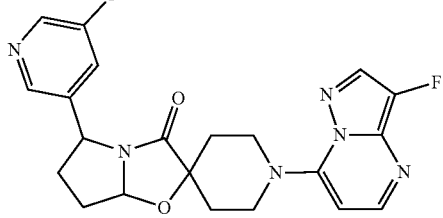
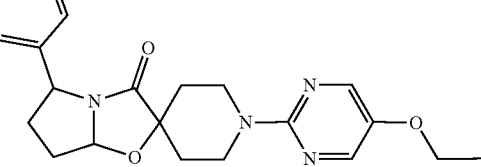

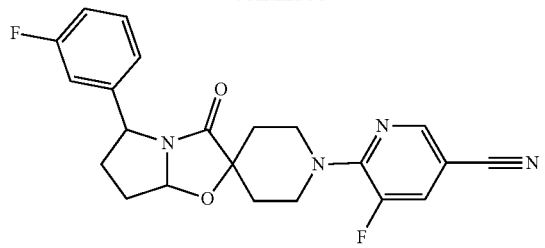
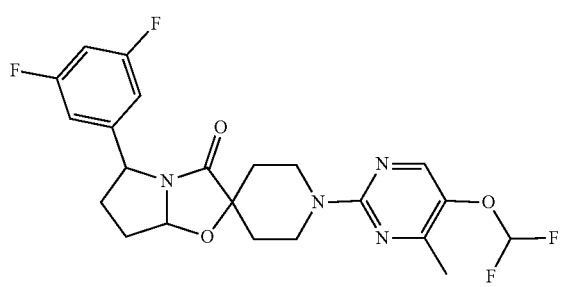
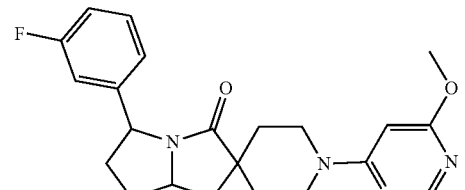
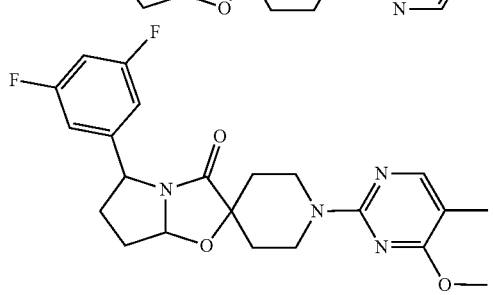
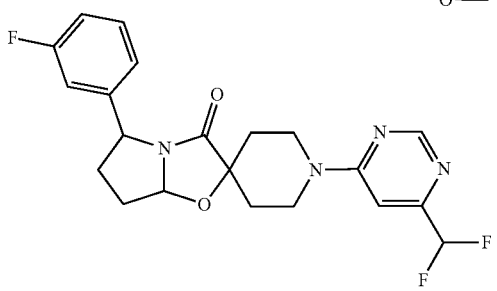
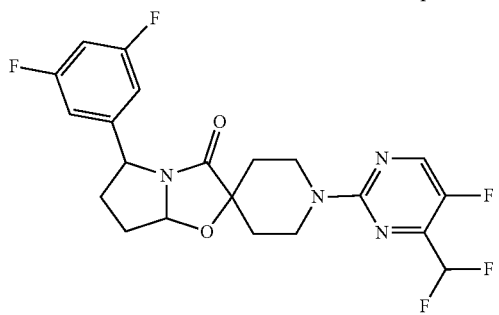
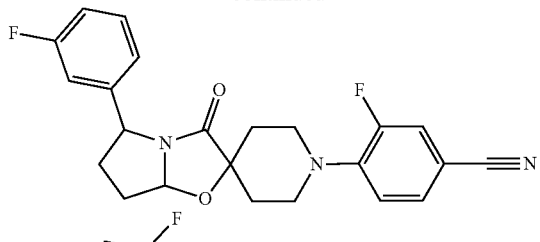
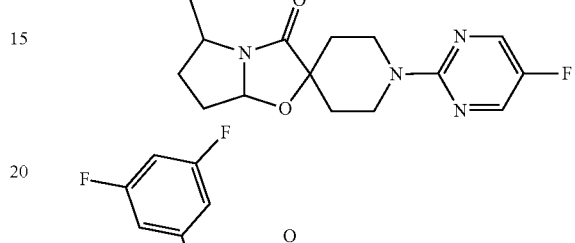
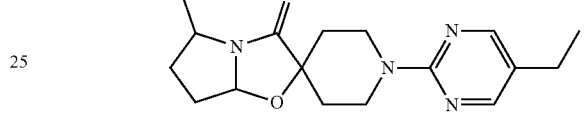
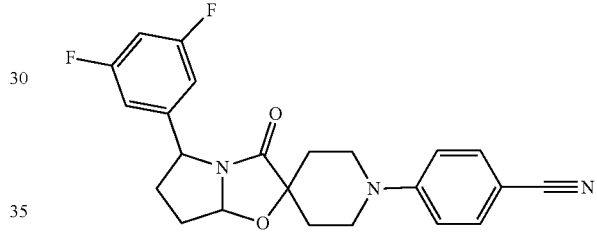
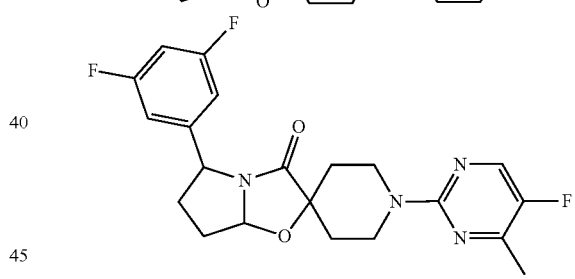
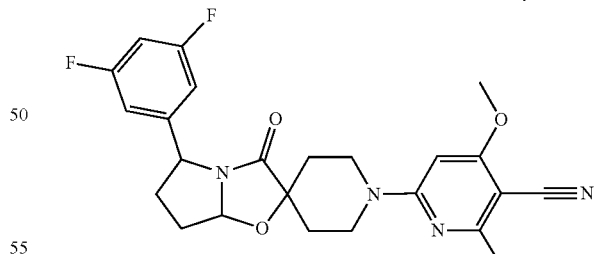
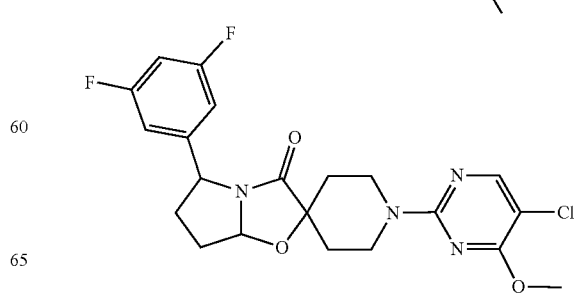

37
-continued
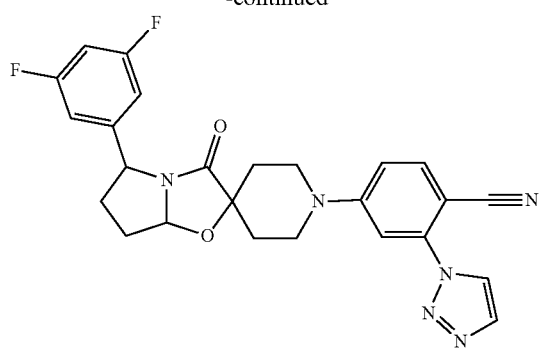
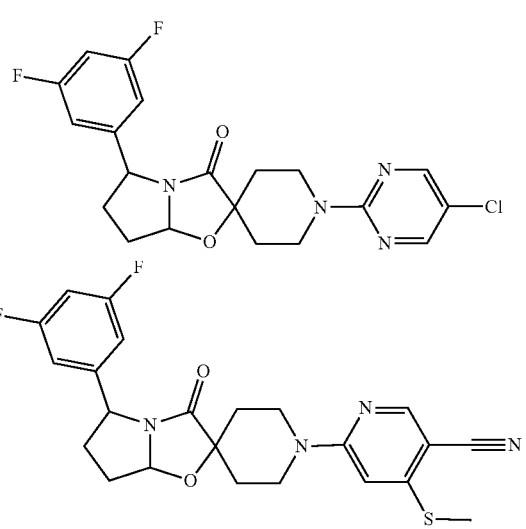
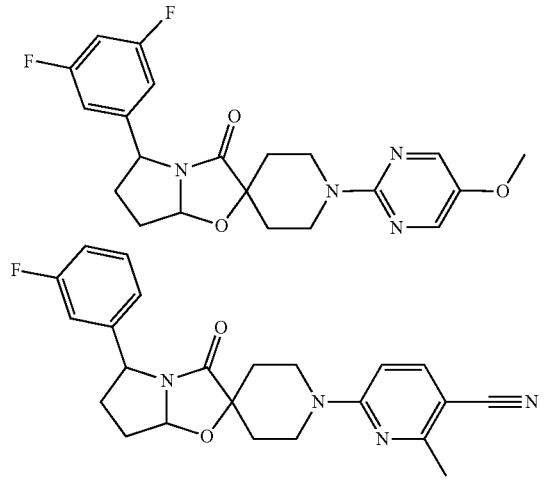
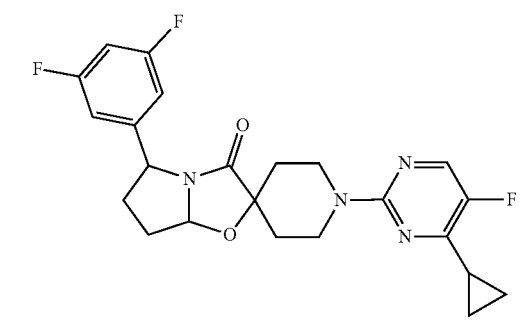
38
-continued
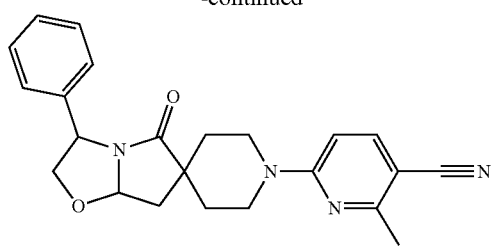
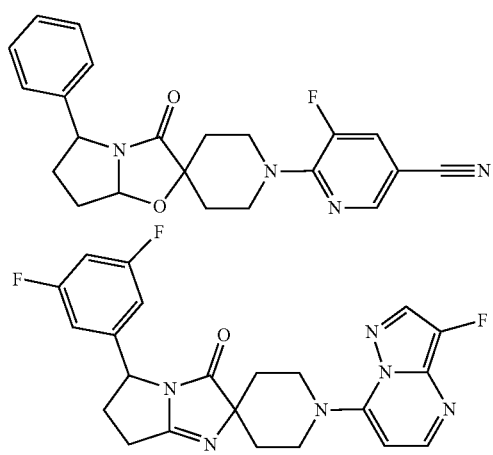
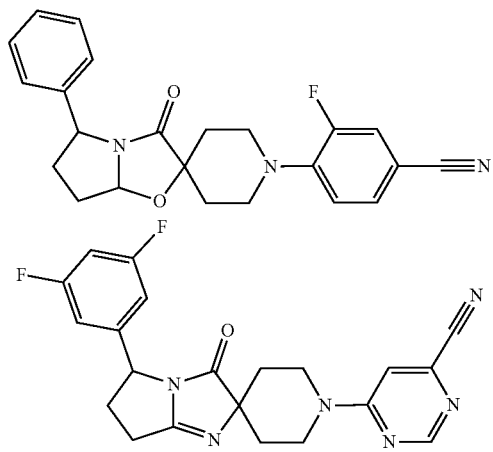
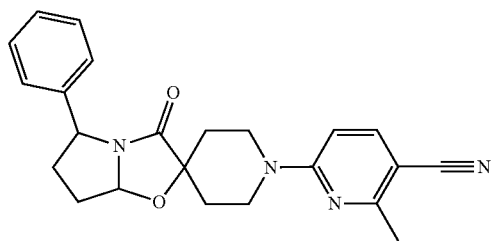
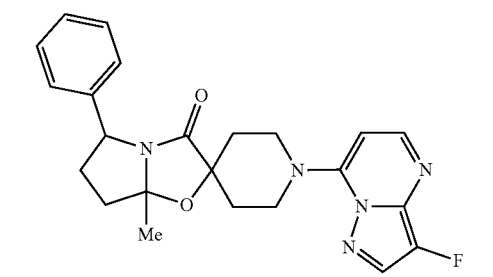

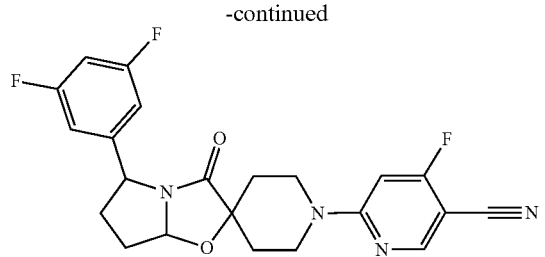
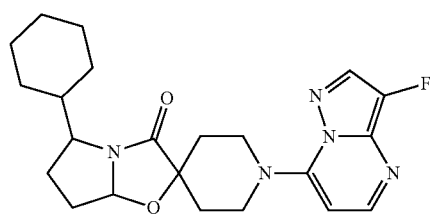
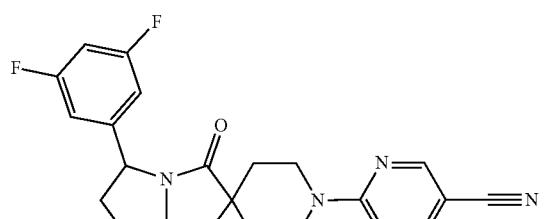
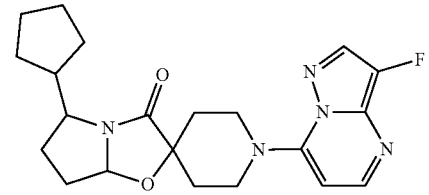
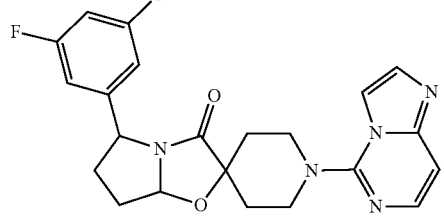
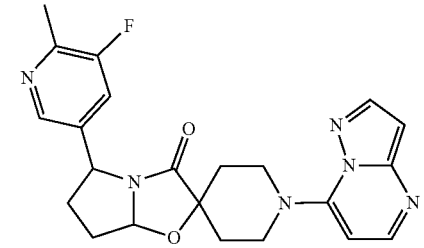
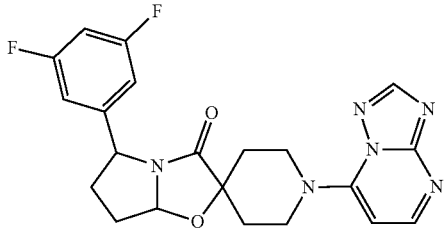
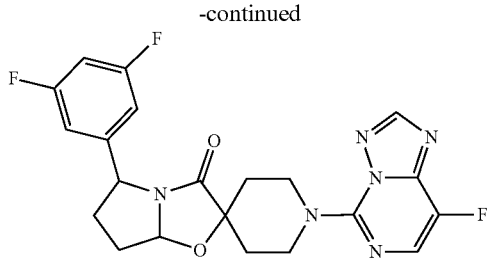
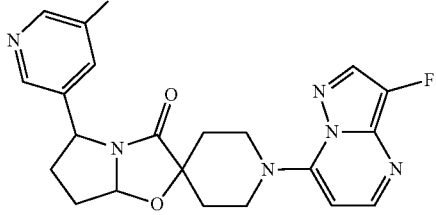
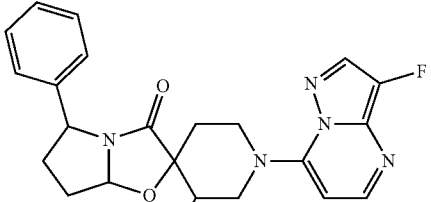
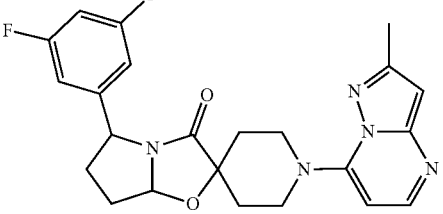
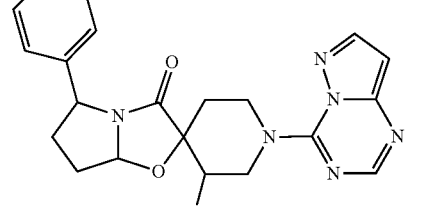
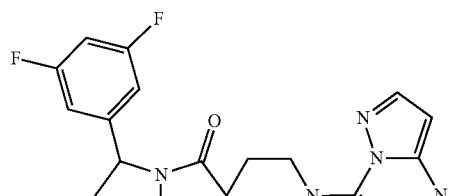
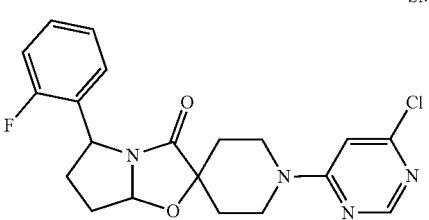

-continued
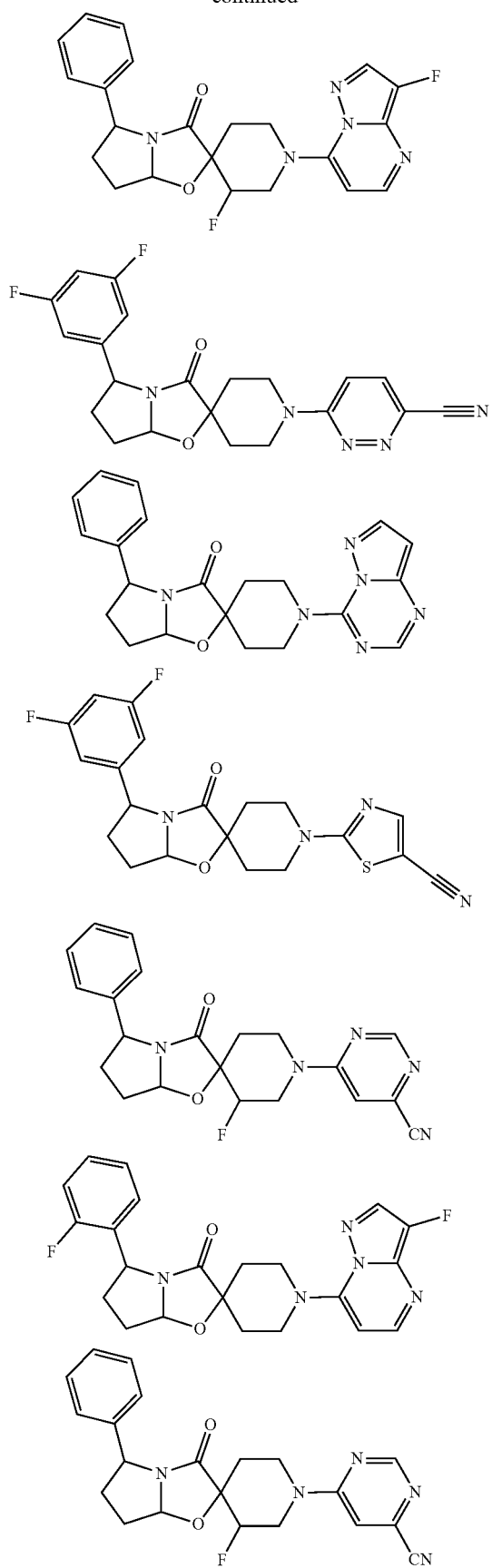
-continued
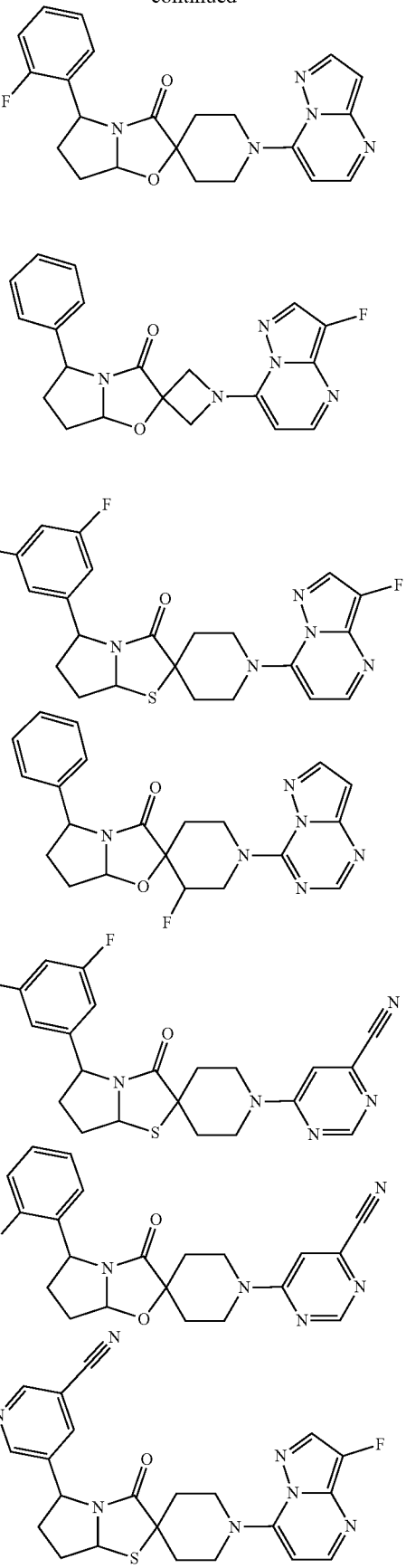

-continued
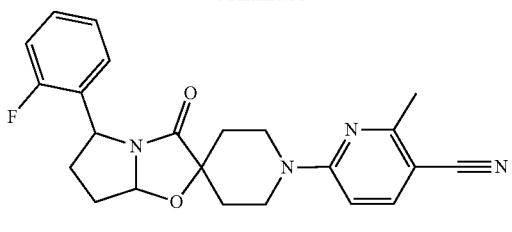
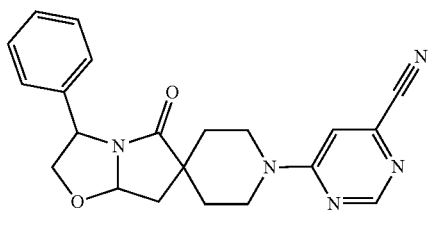
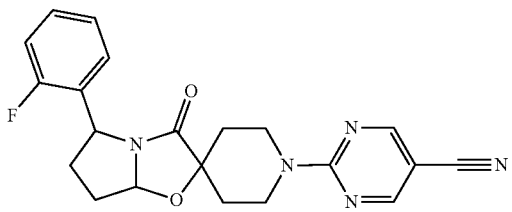
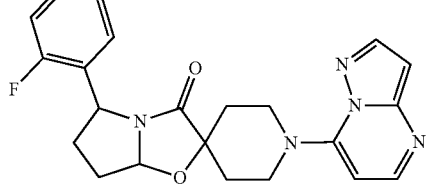
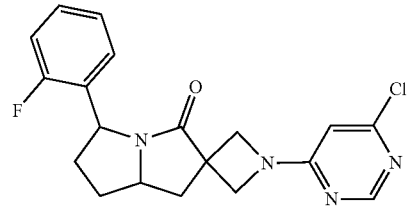
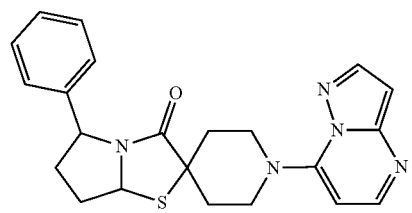
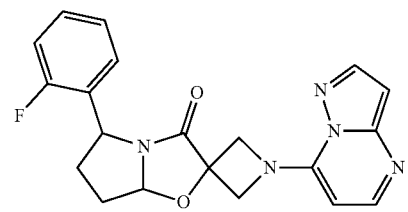
-continued
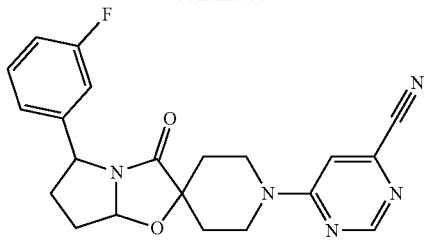
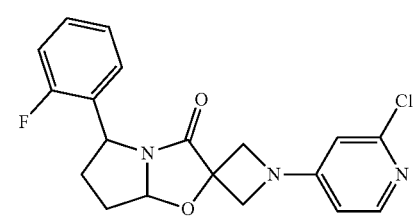
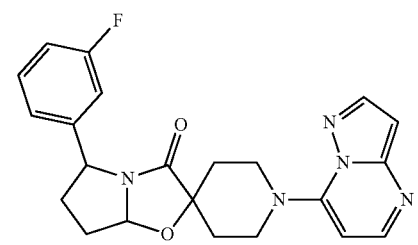
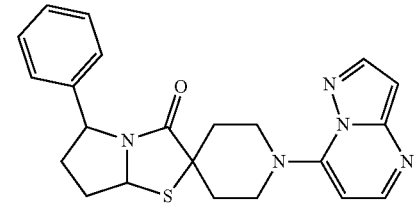
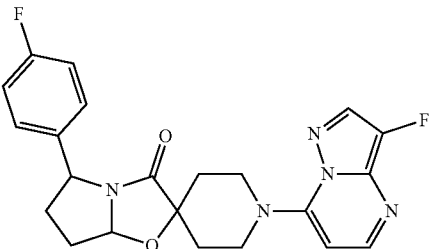
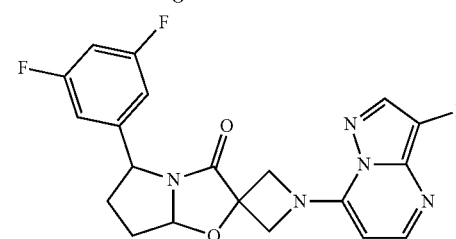
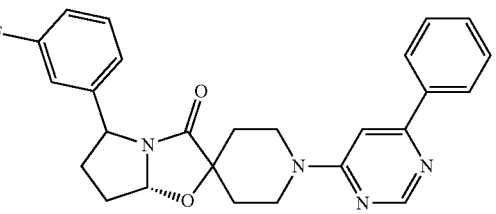

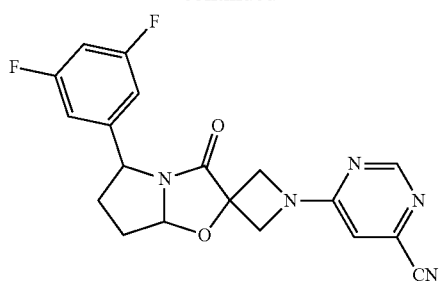
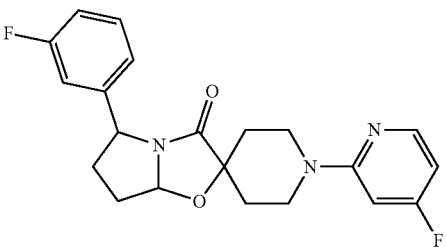
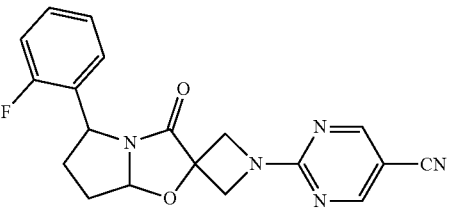
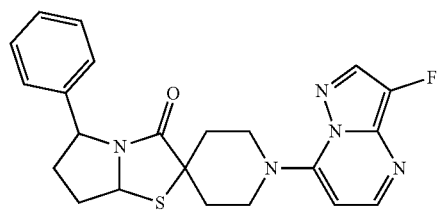
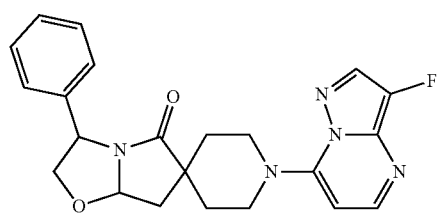
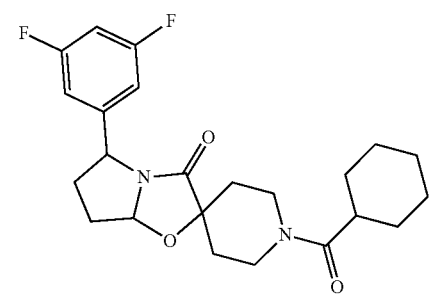
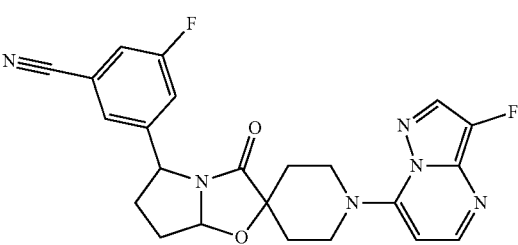
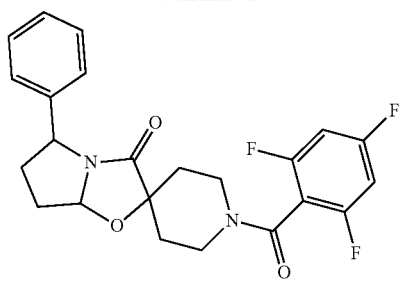
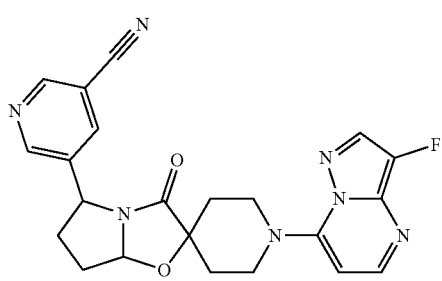
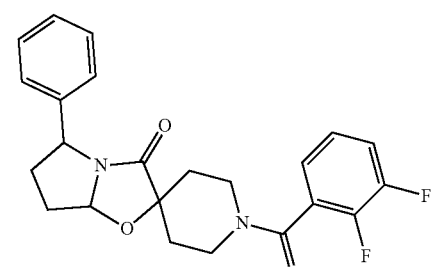
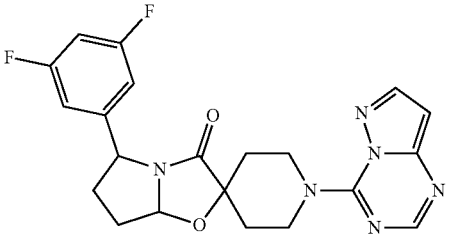
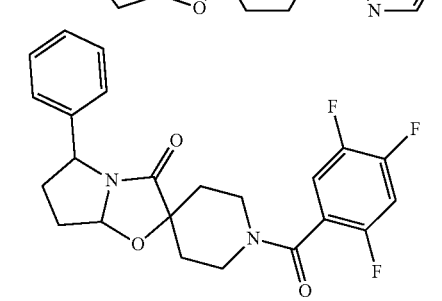
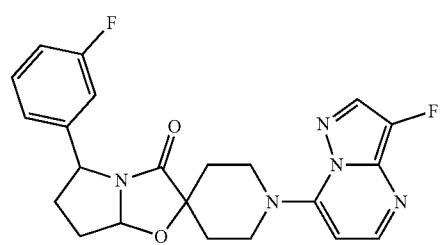

47
-continued
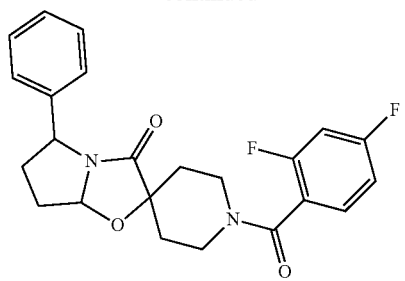
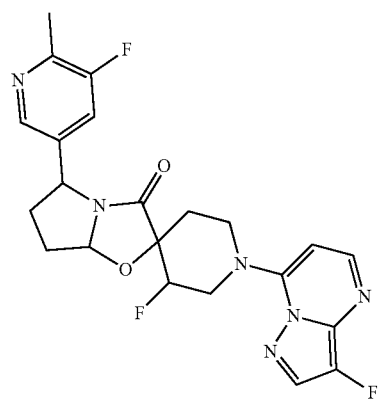
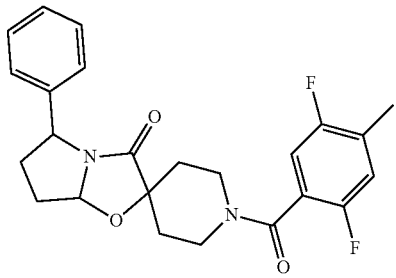
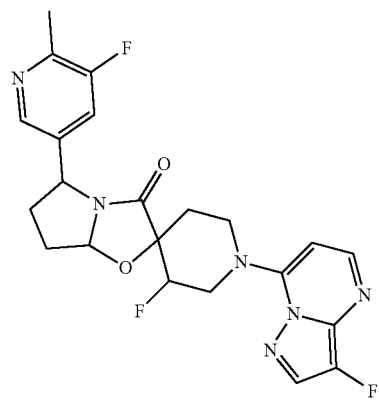
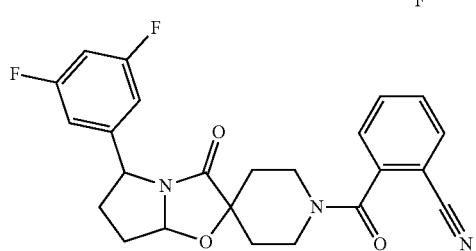
48
-continued
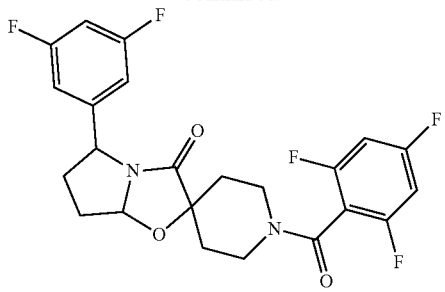
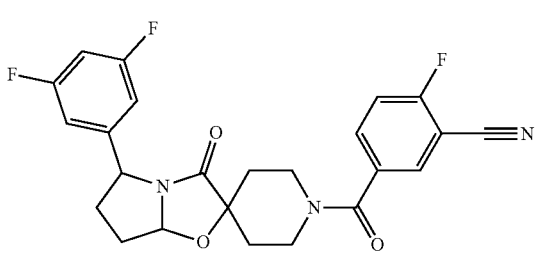
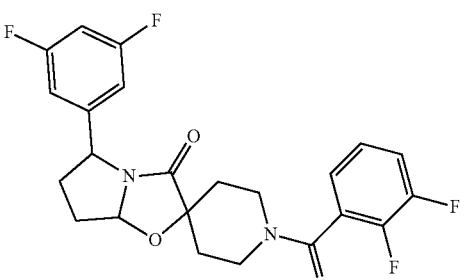
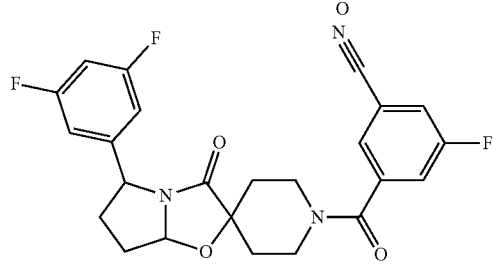
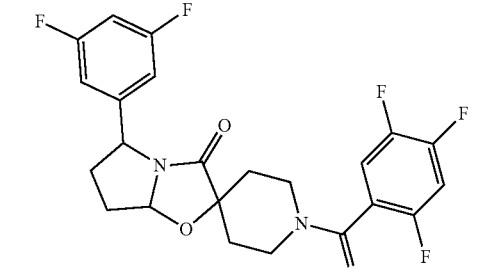
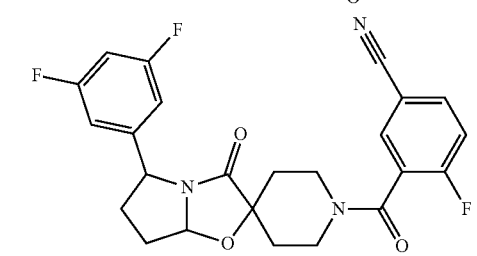

-continued
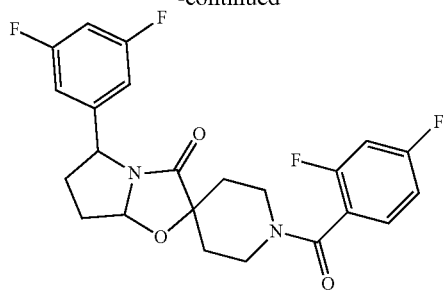
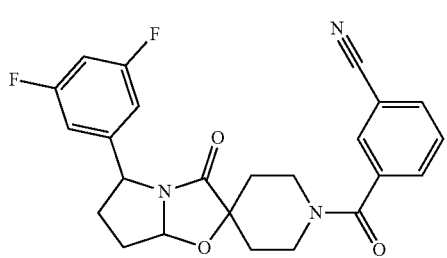
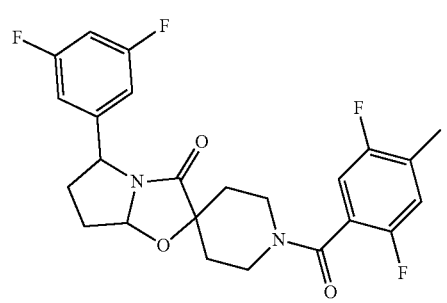
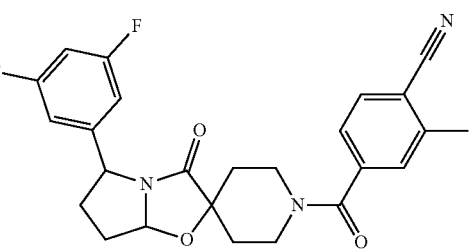
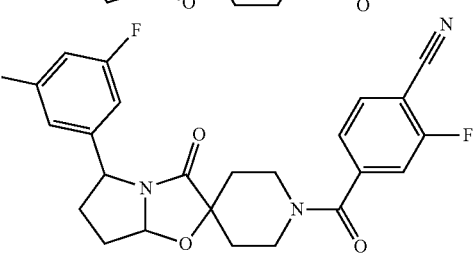
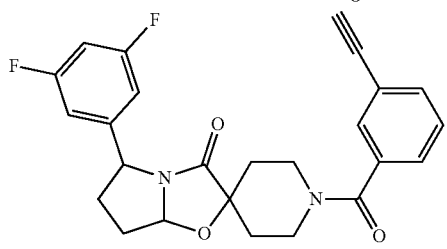
-continued
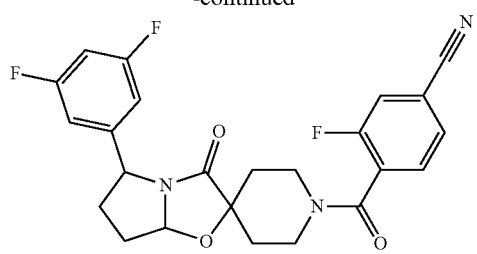
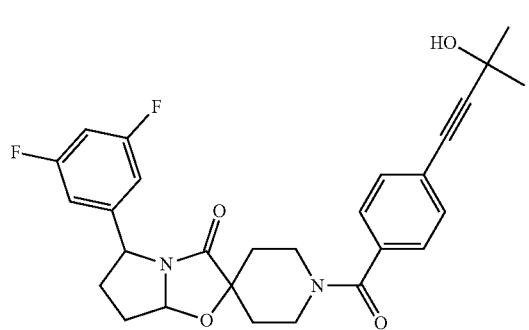
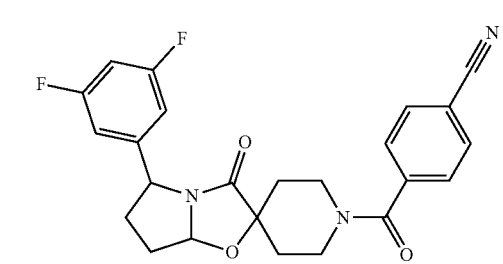
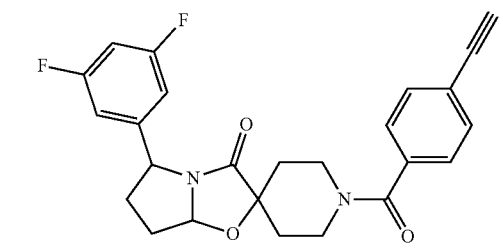
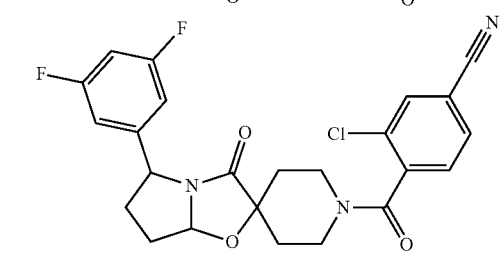
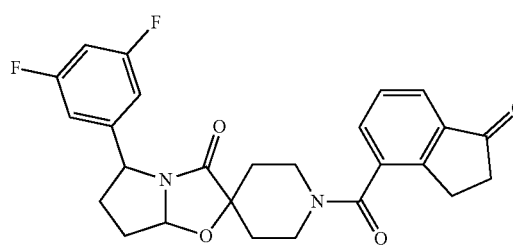

51
-continued
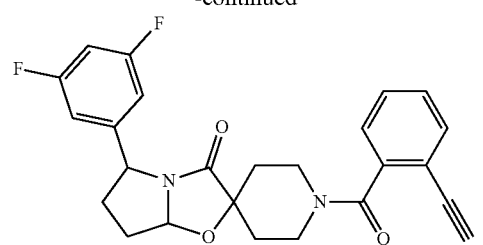
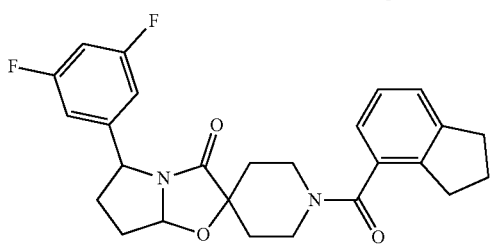
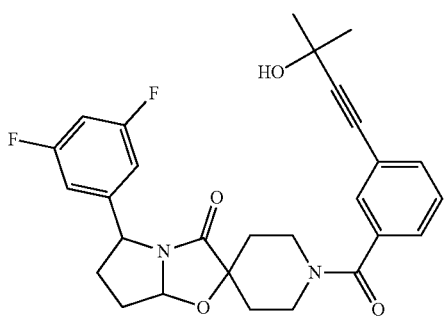
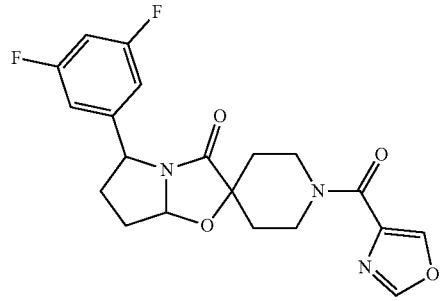
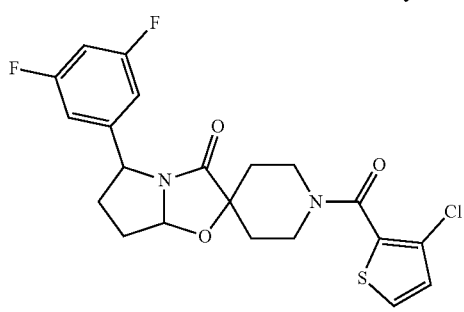
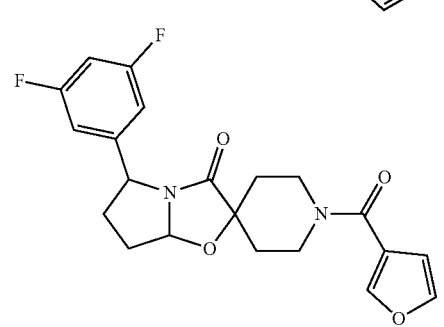
52
-continued
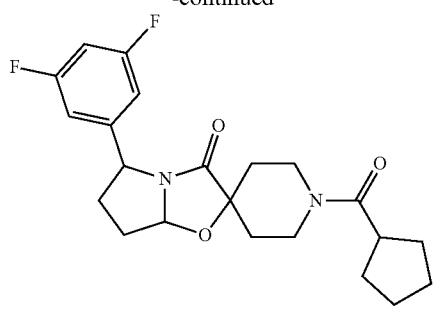
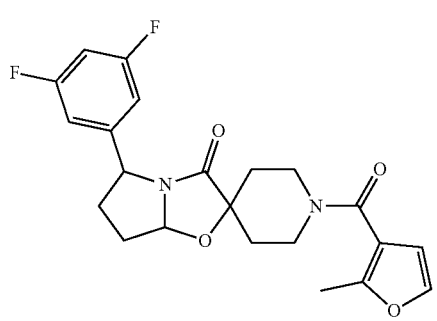
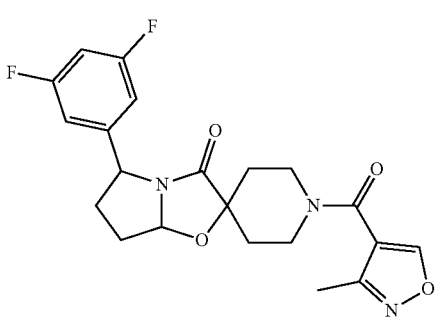
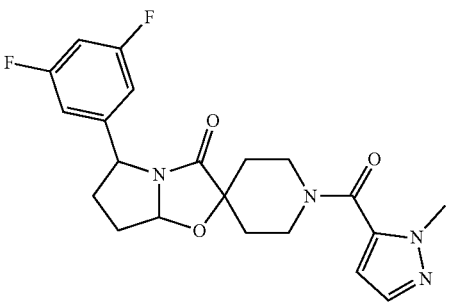
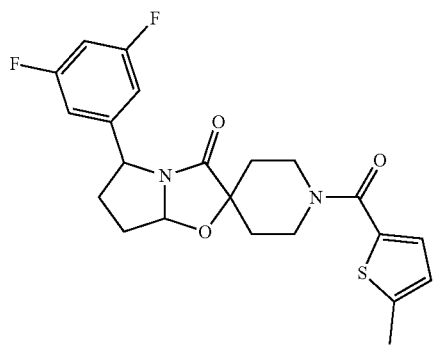

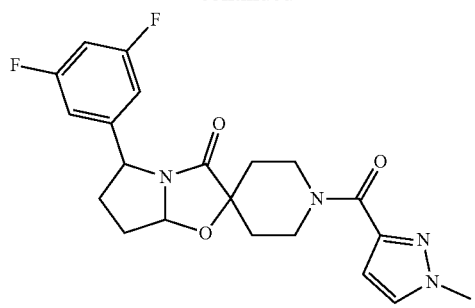
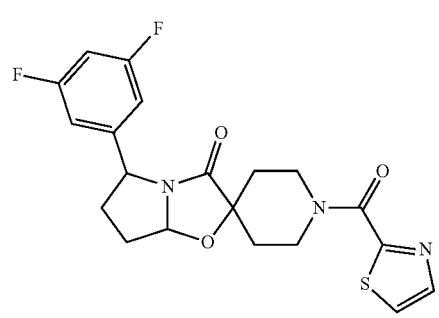
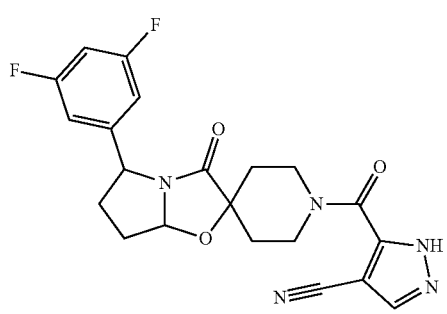
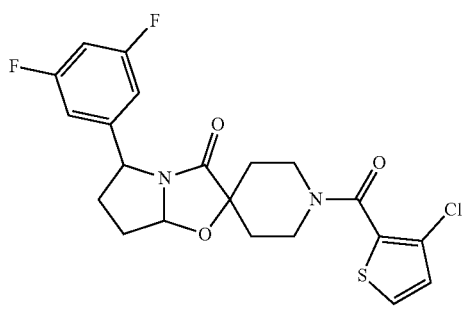
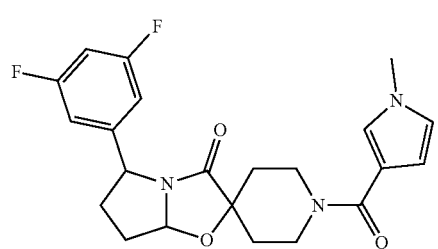
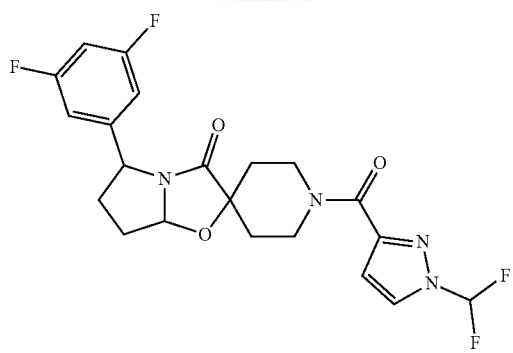
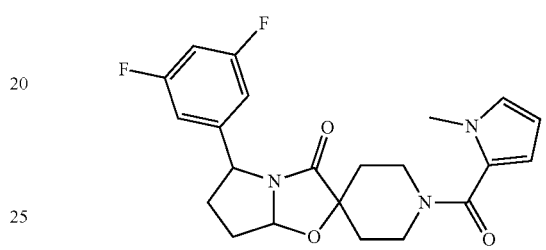
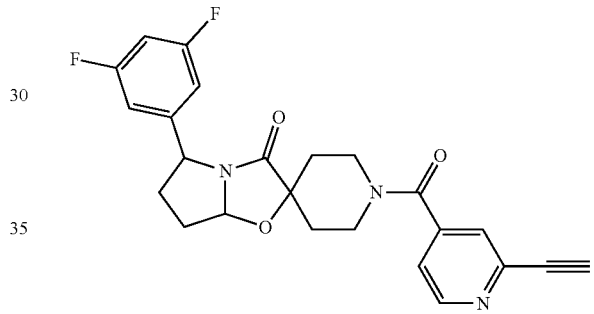
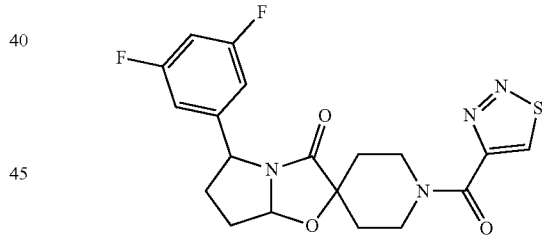
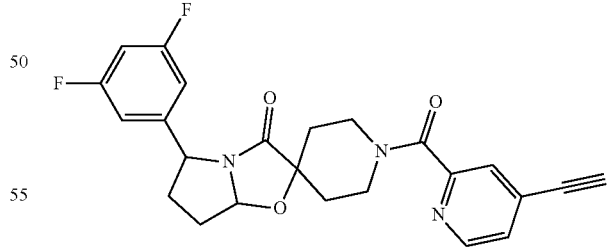
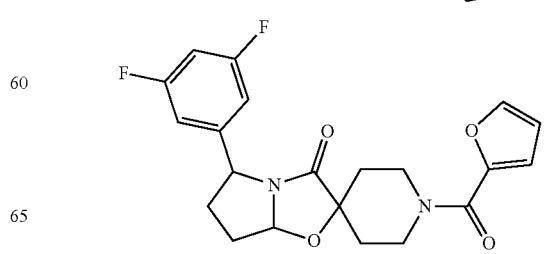

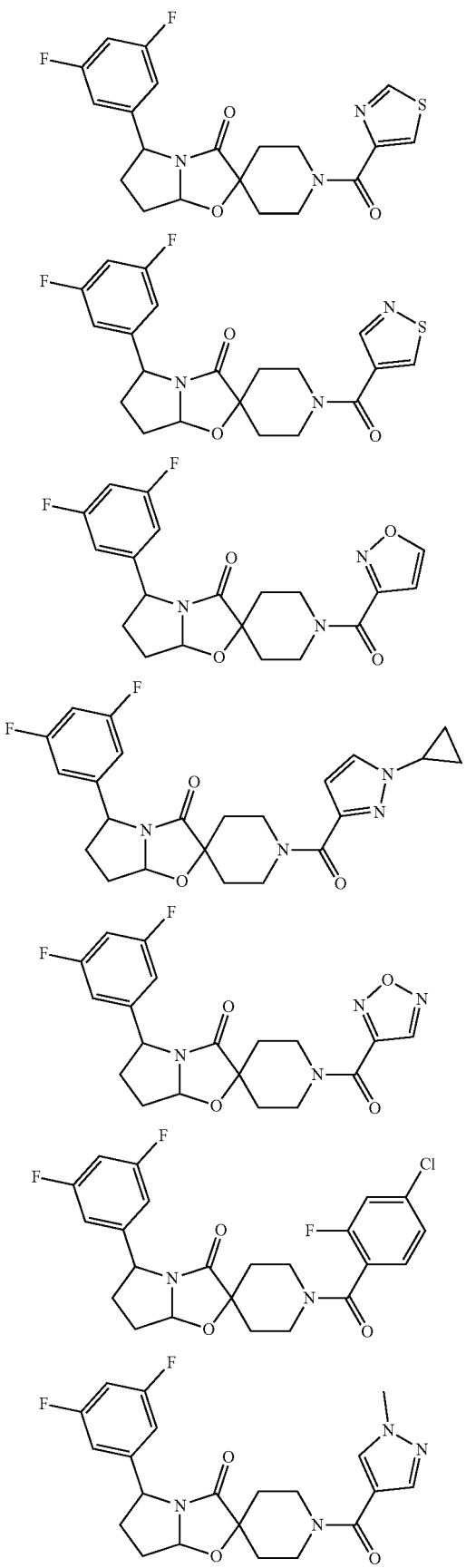
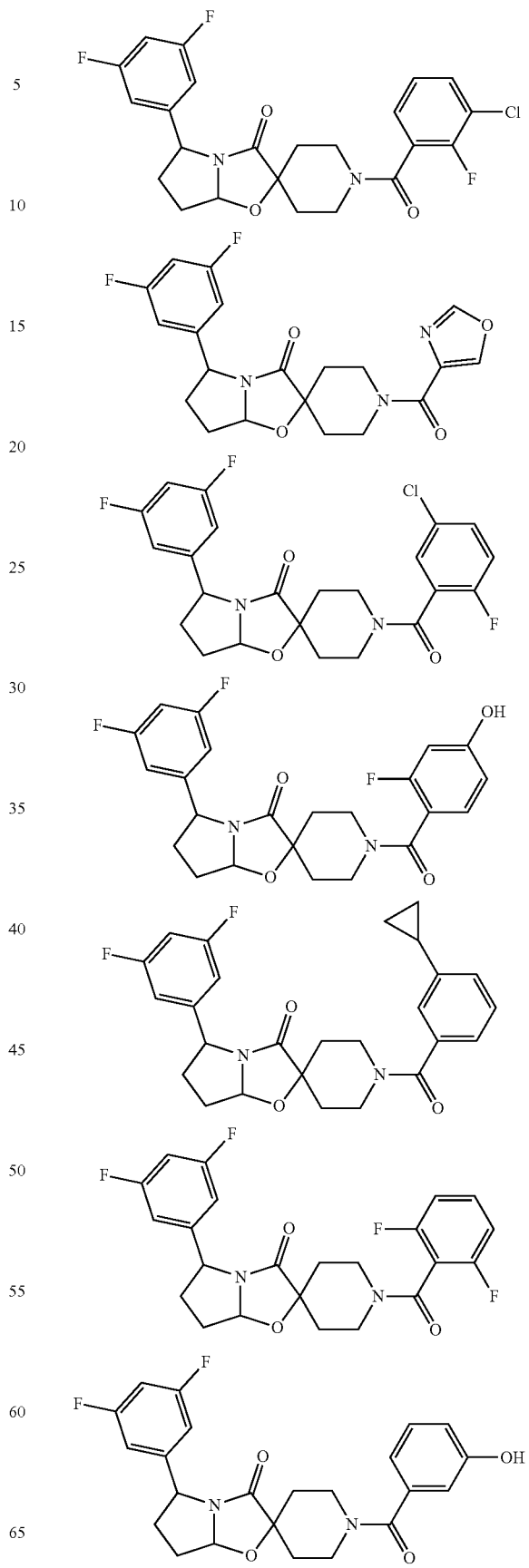

57
-continued
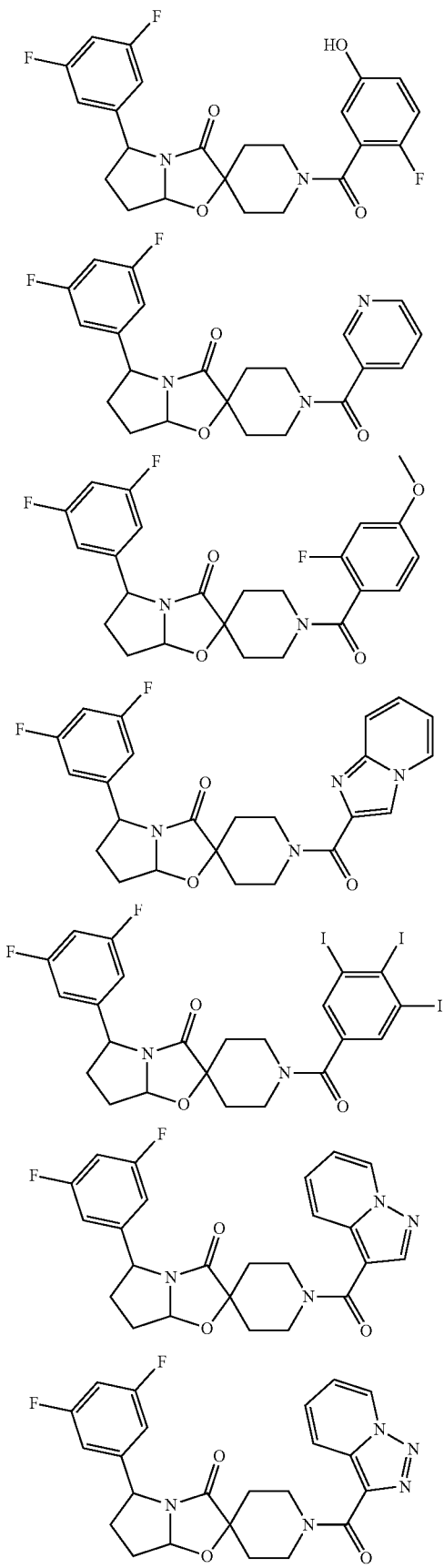
58
-continued
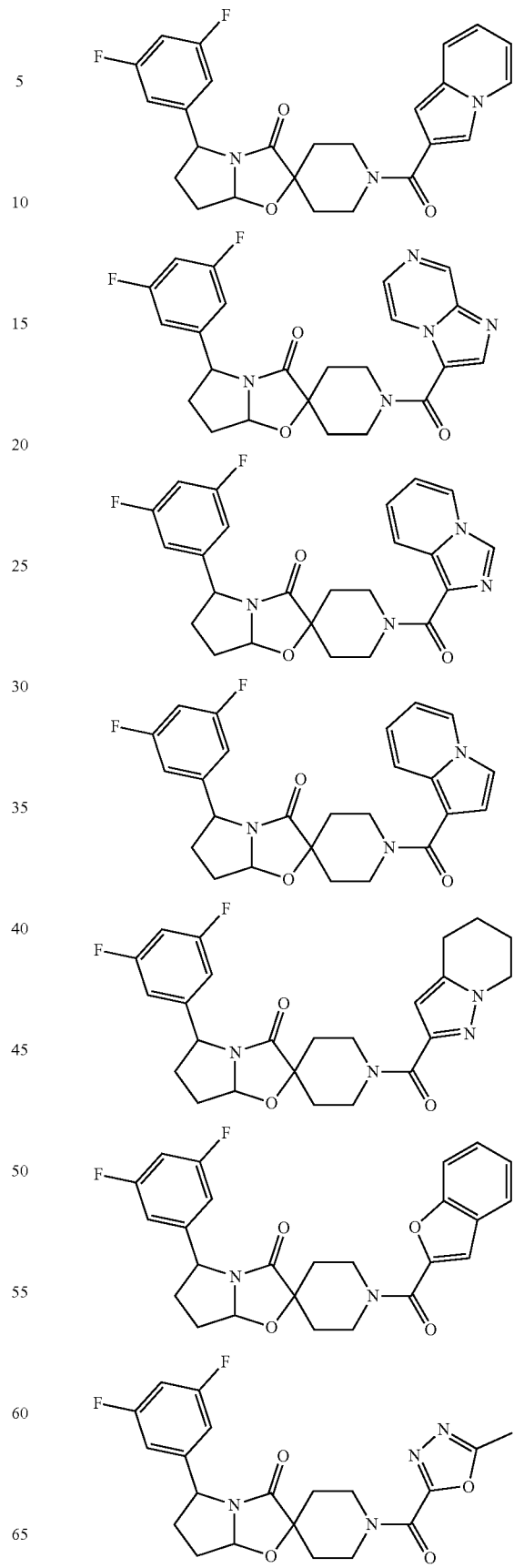

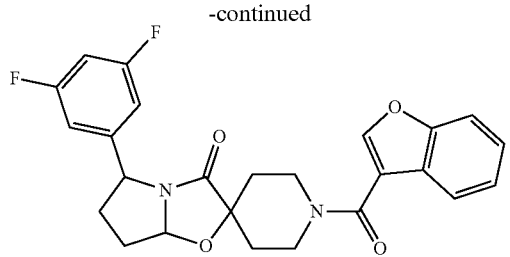
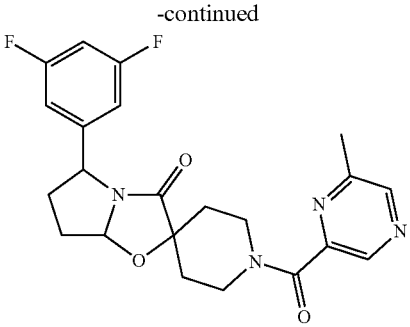
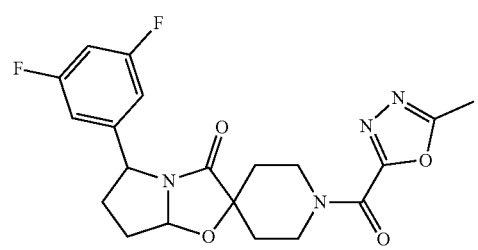
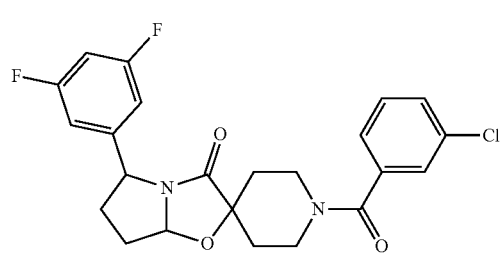
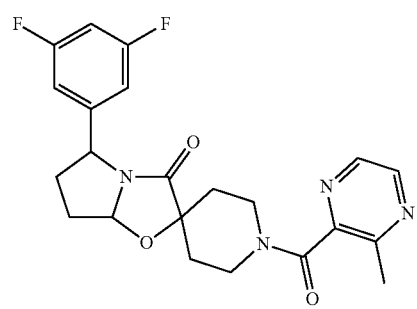
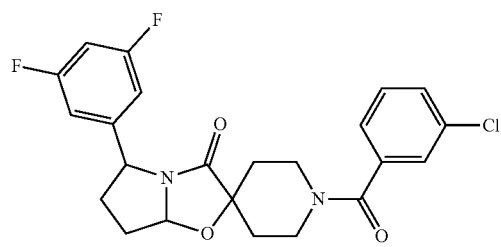
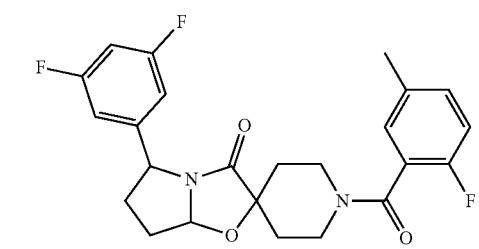
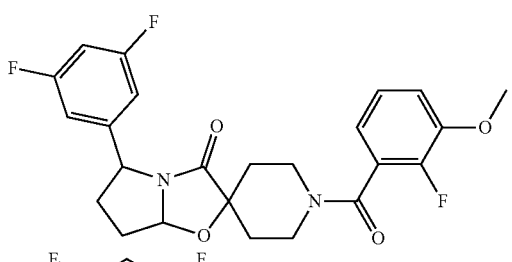
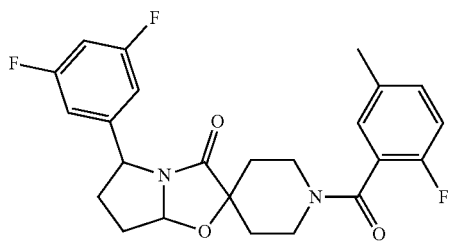
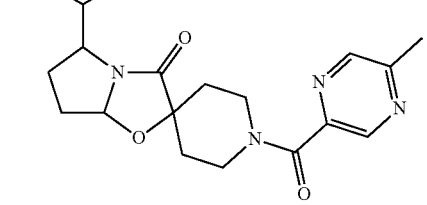
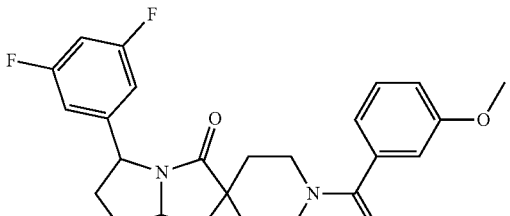
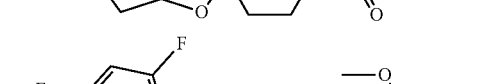
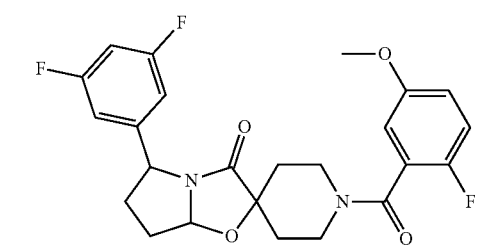
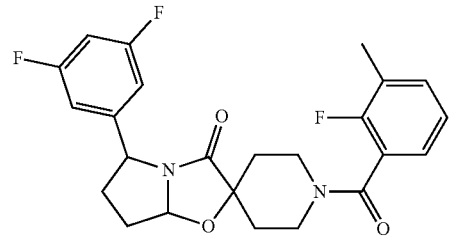
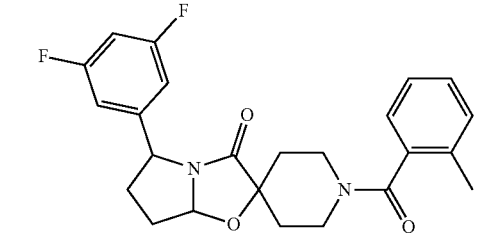

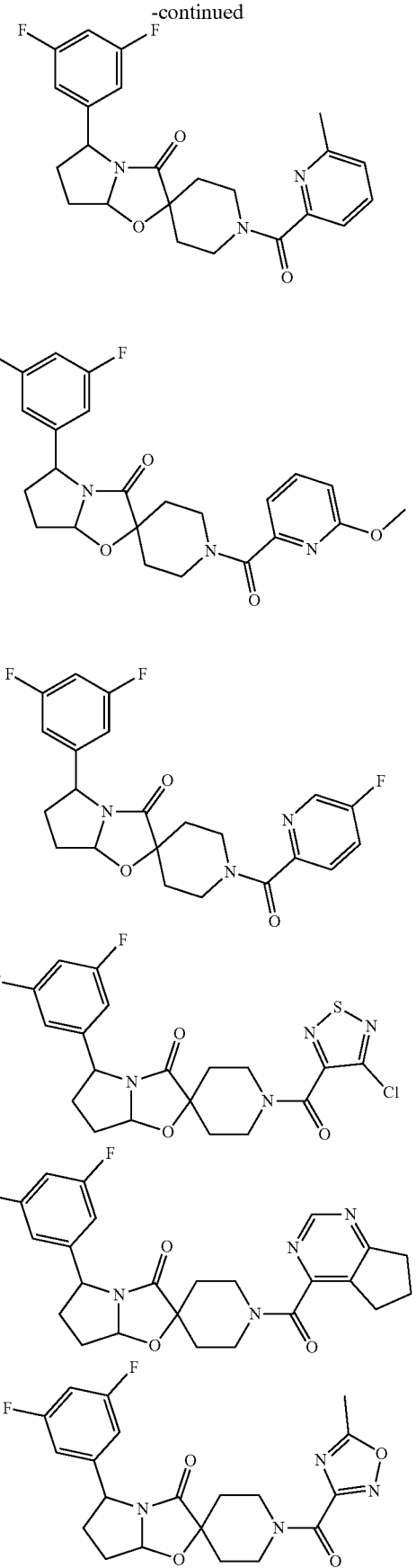
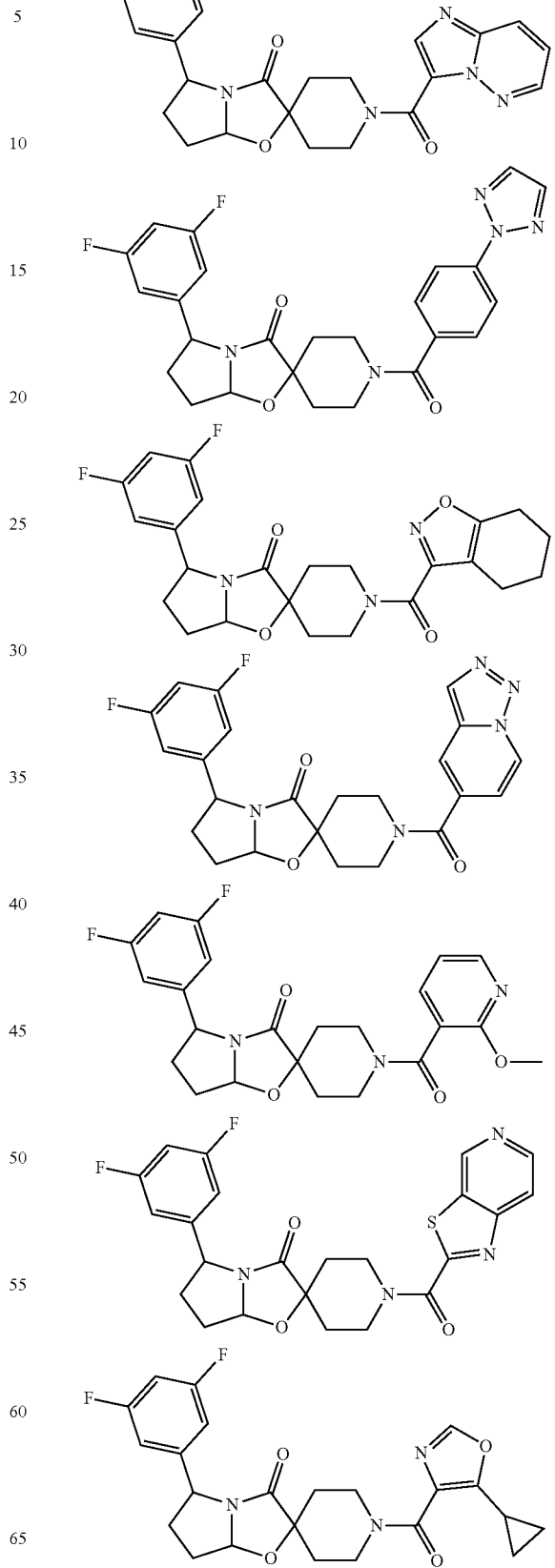

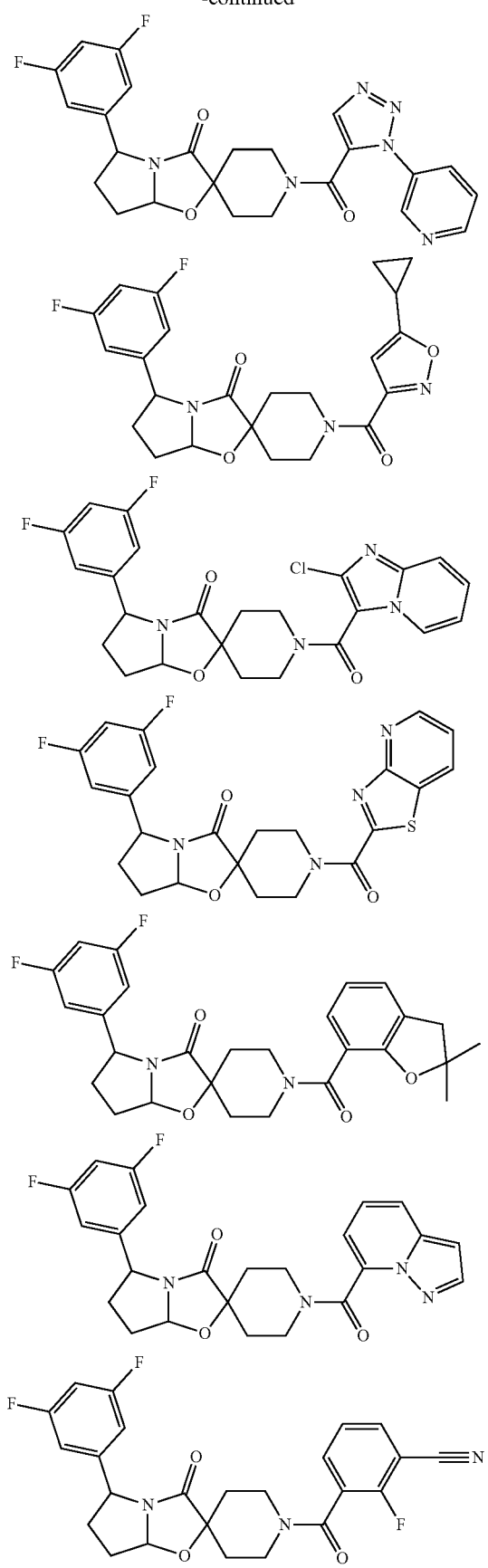
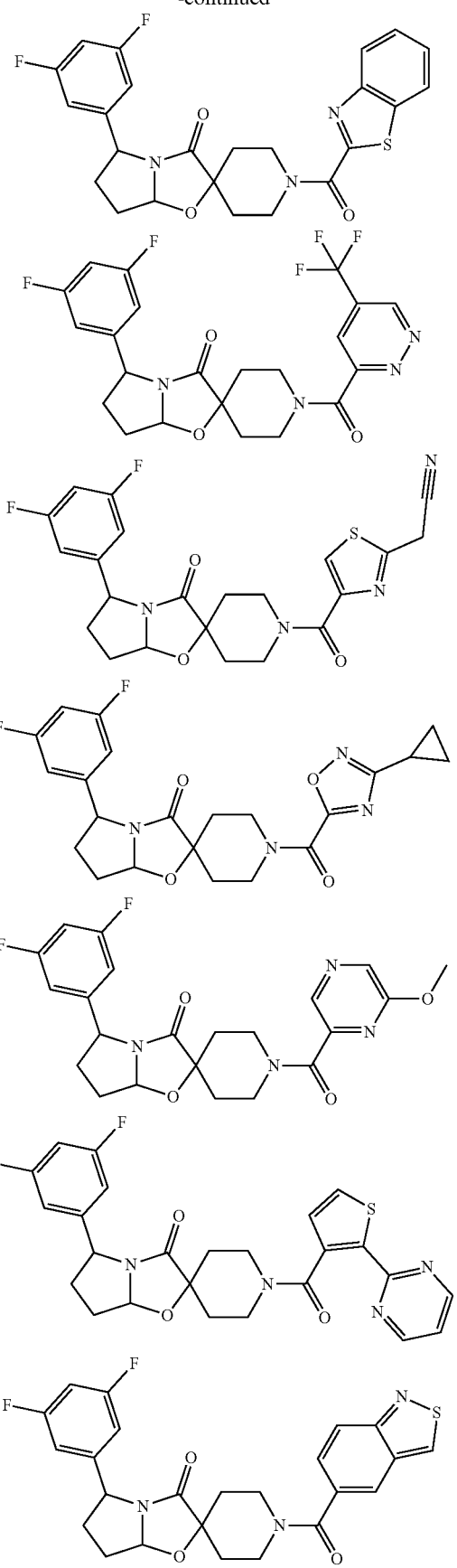

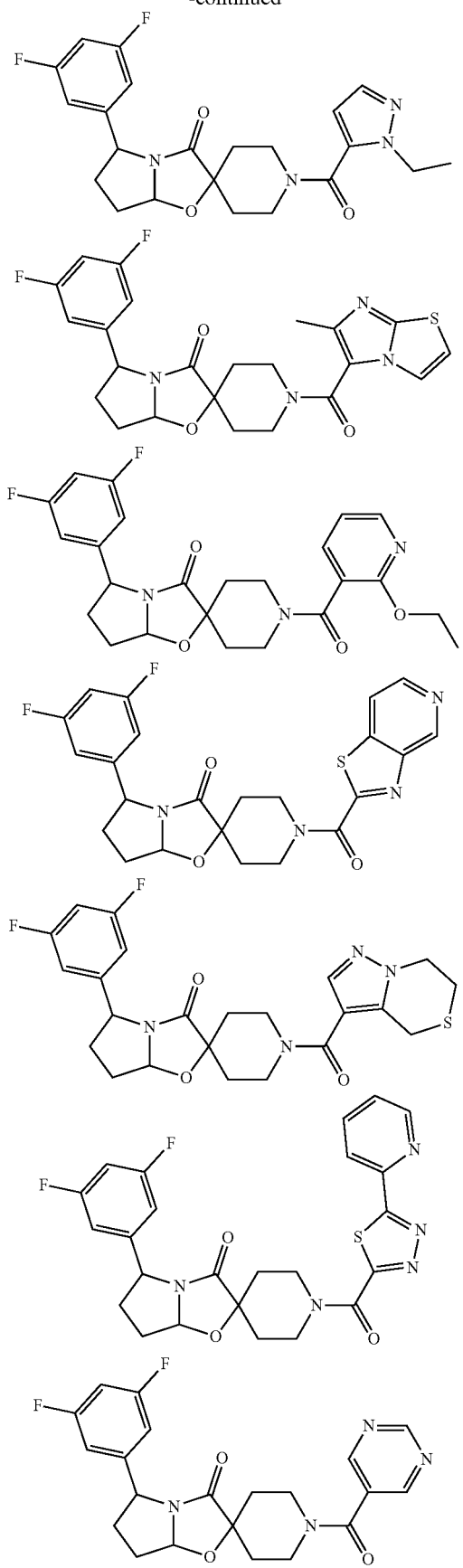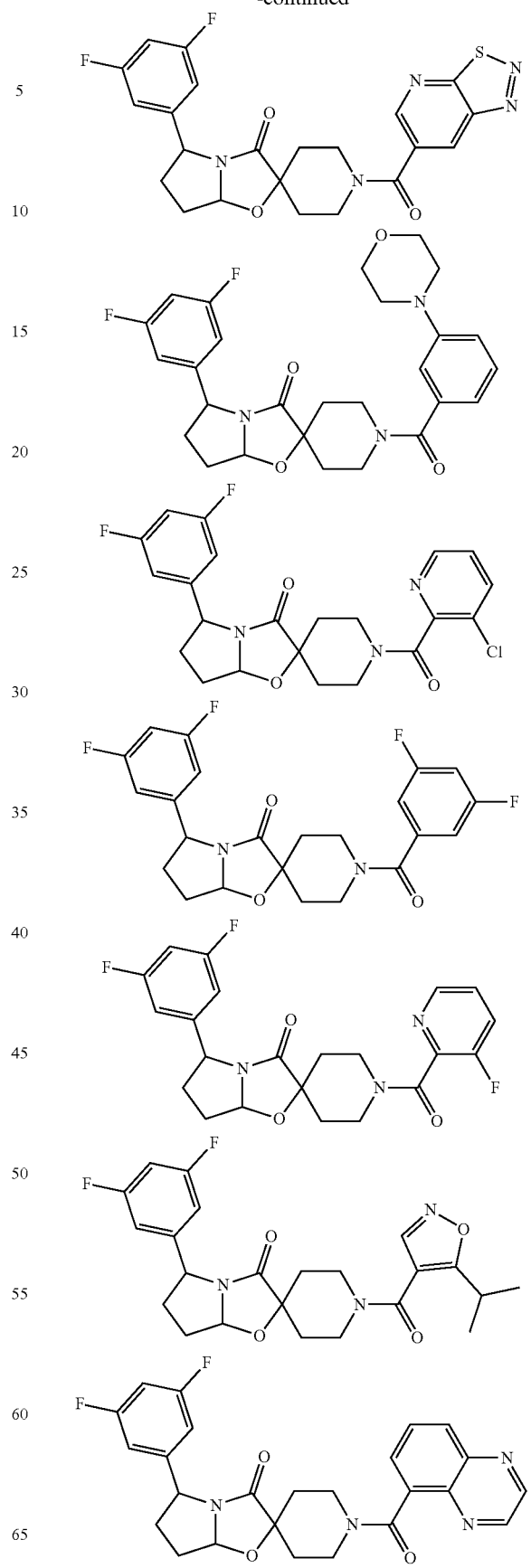

-continued
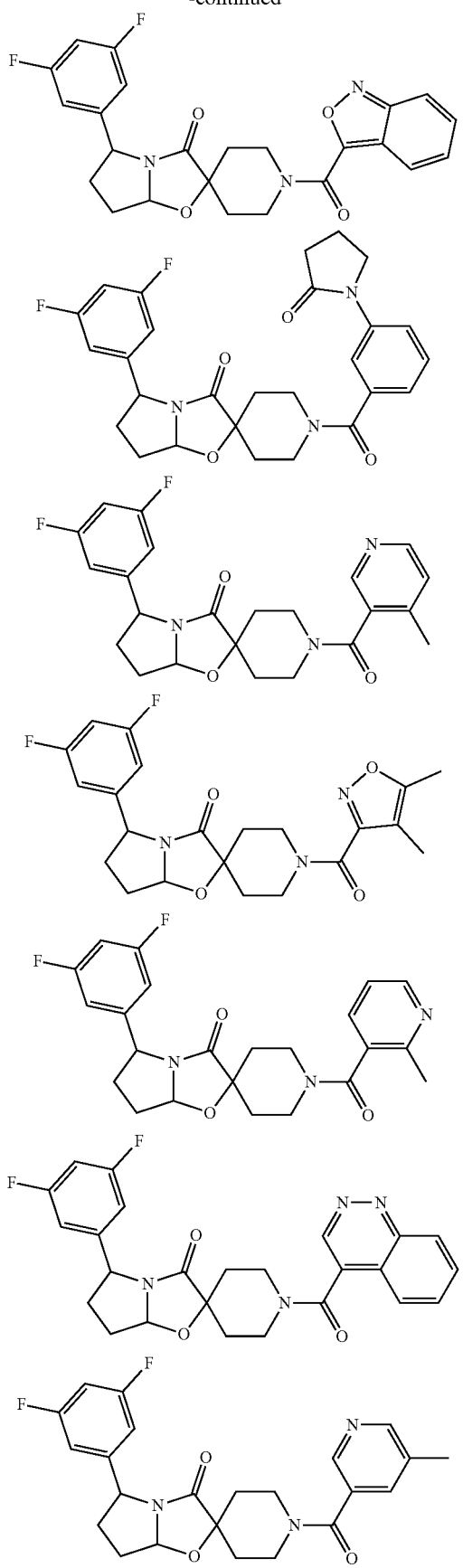
-continued
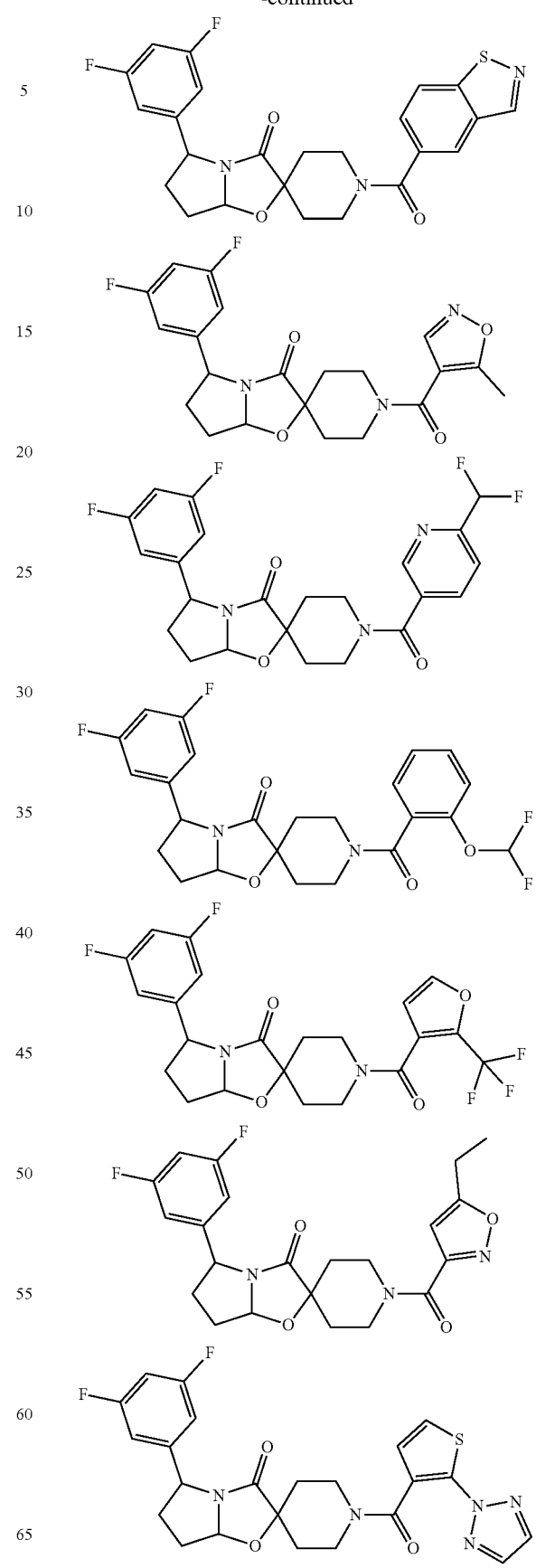

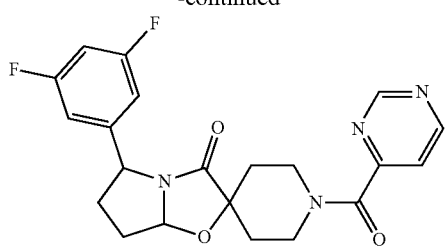
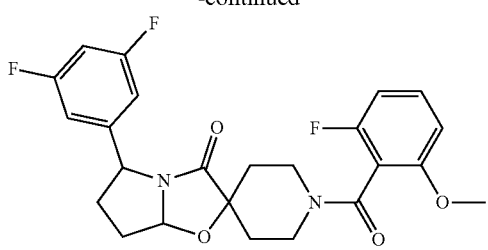
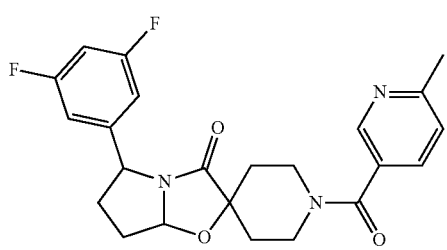
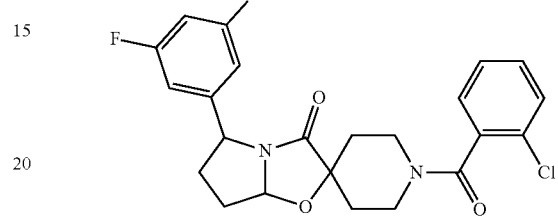
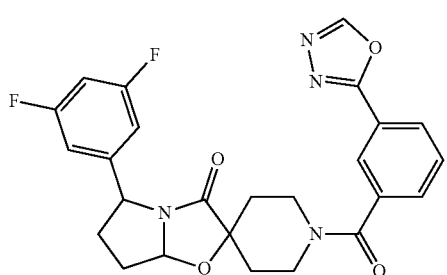
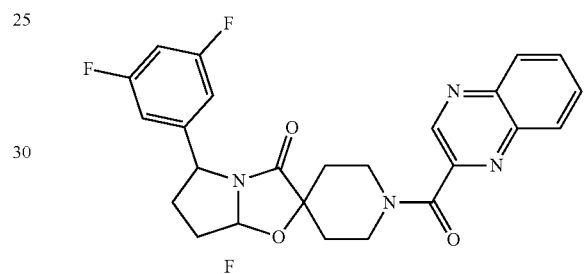
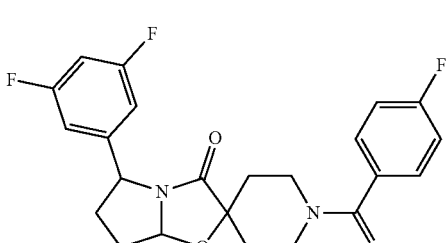
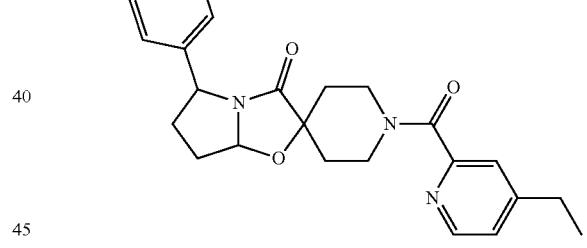
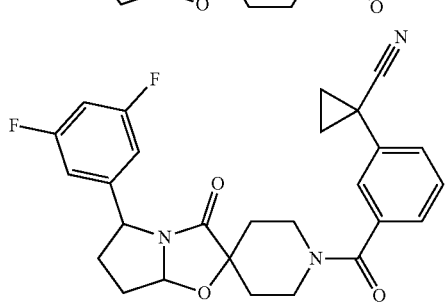
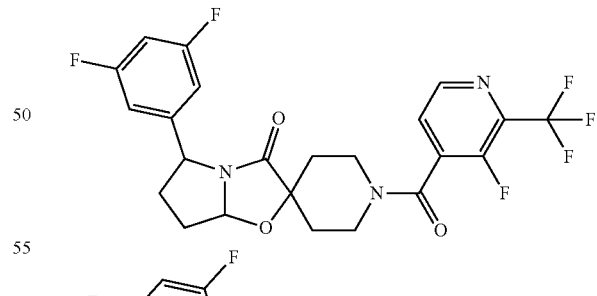
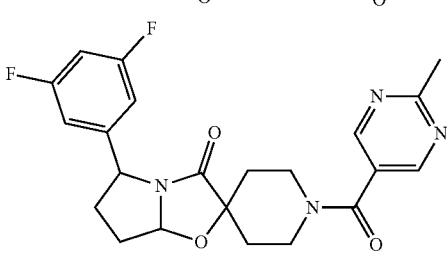
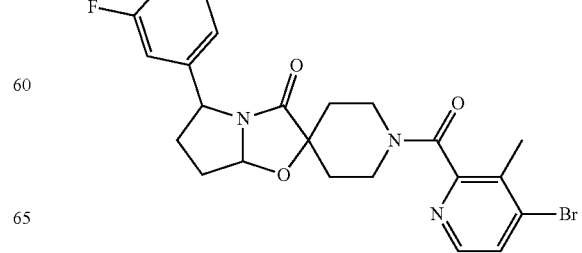

71
-continued
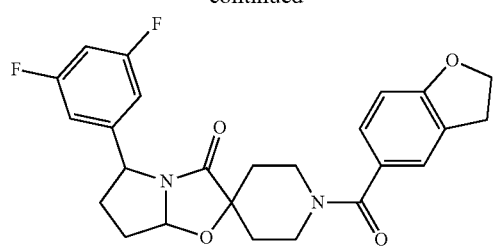
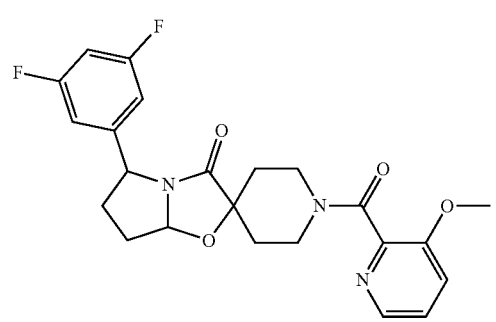
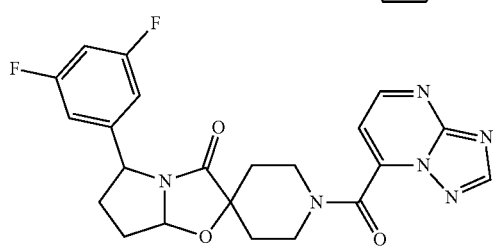
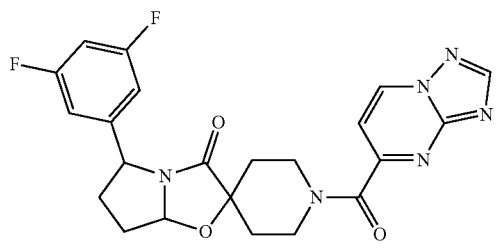
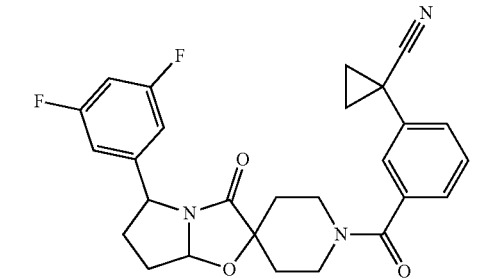
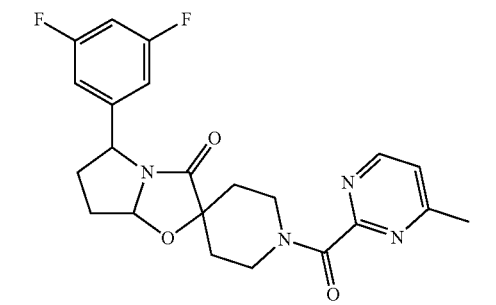
72
-continued
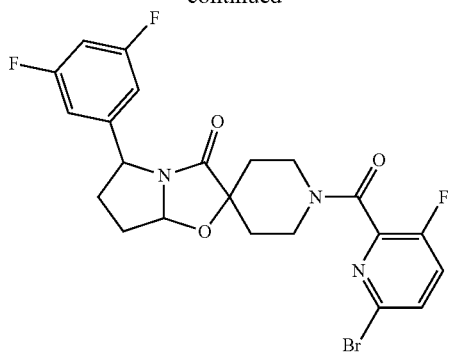
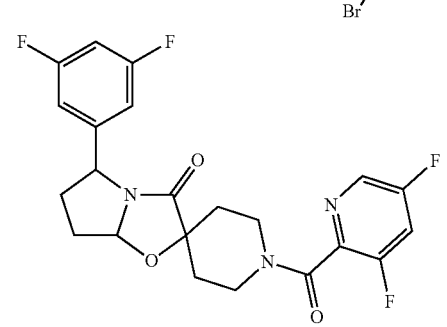
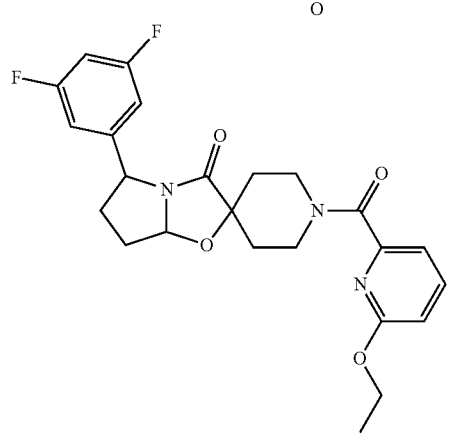
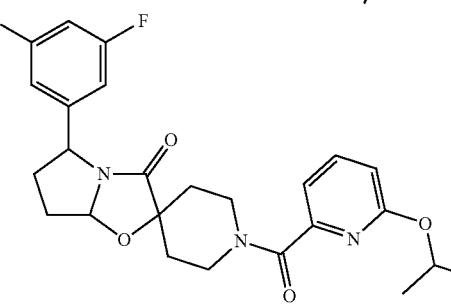
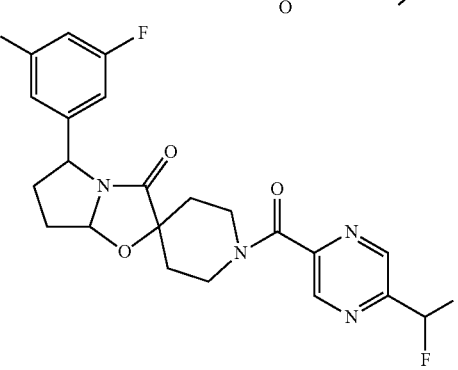

73
-continued
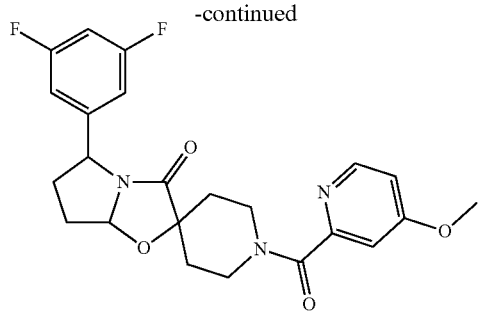
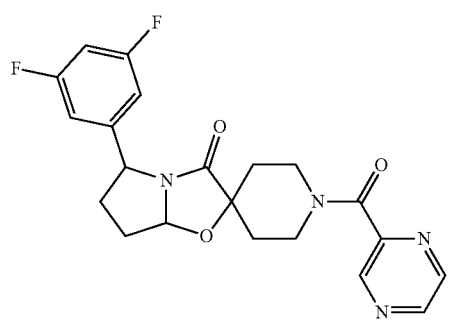
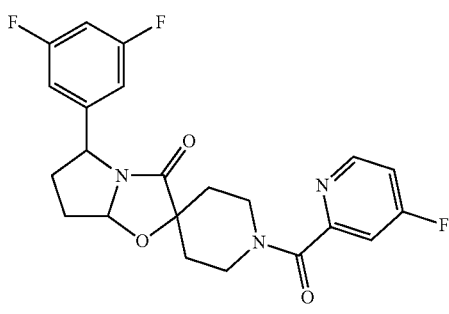
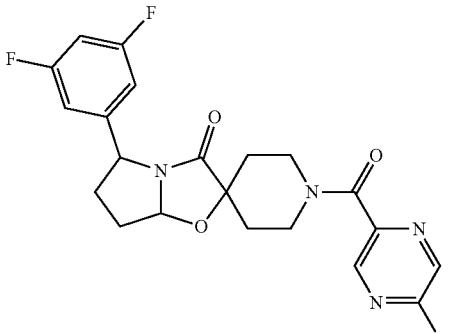
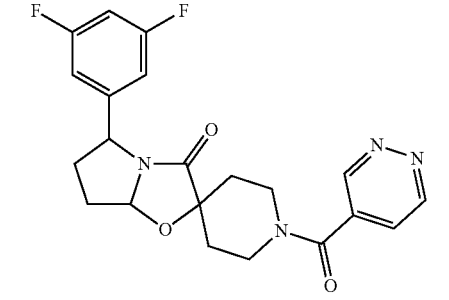
74
-continued
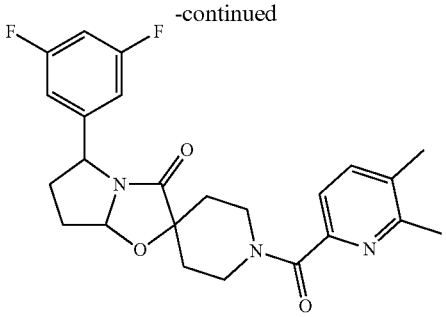
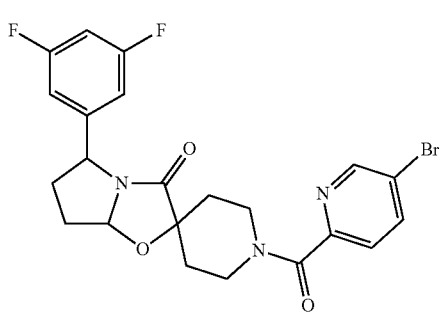
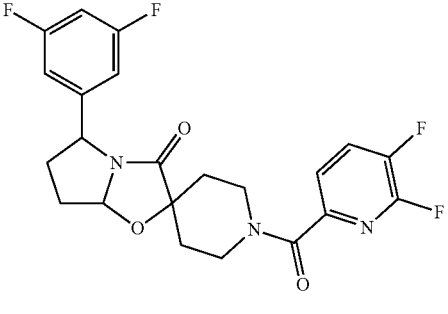
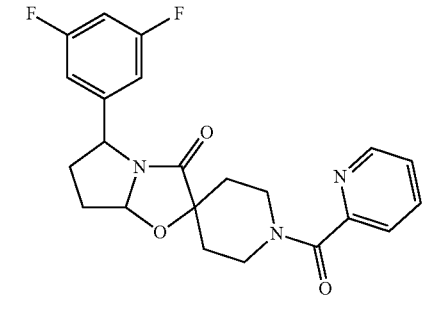
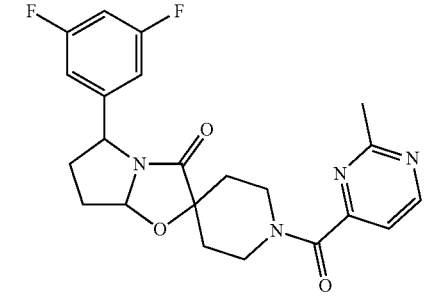

75
-continued
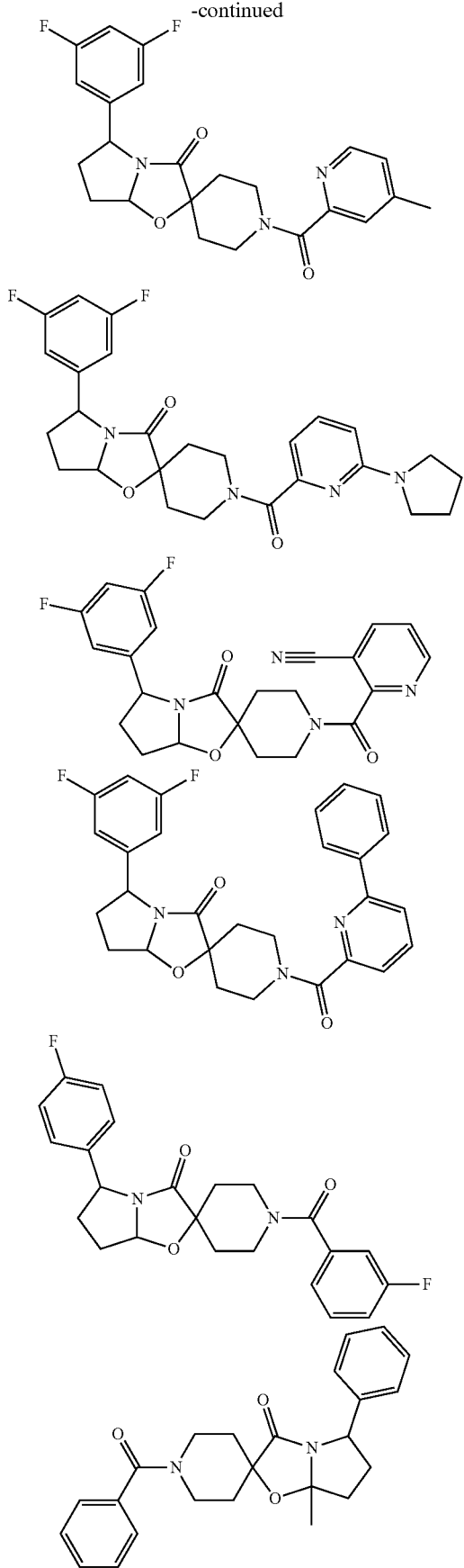
76
-continued
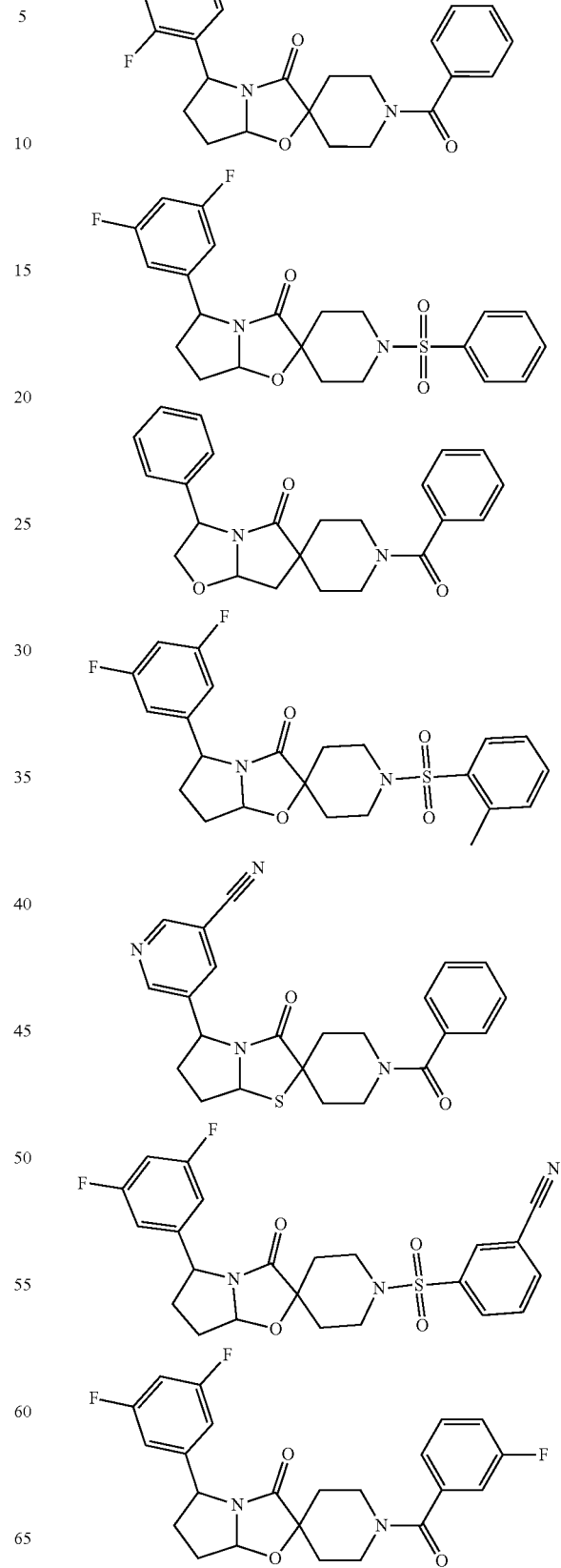

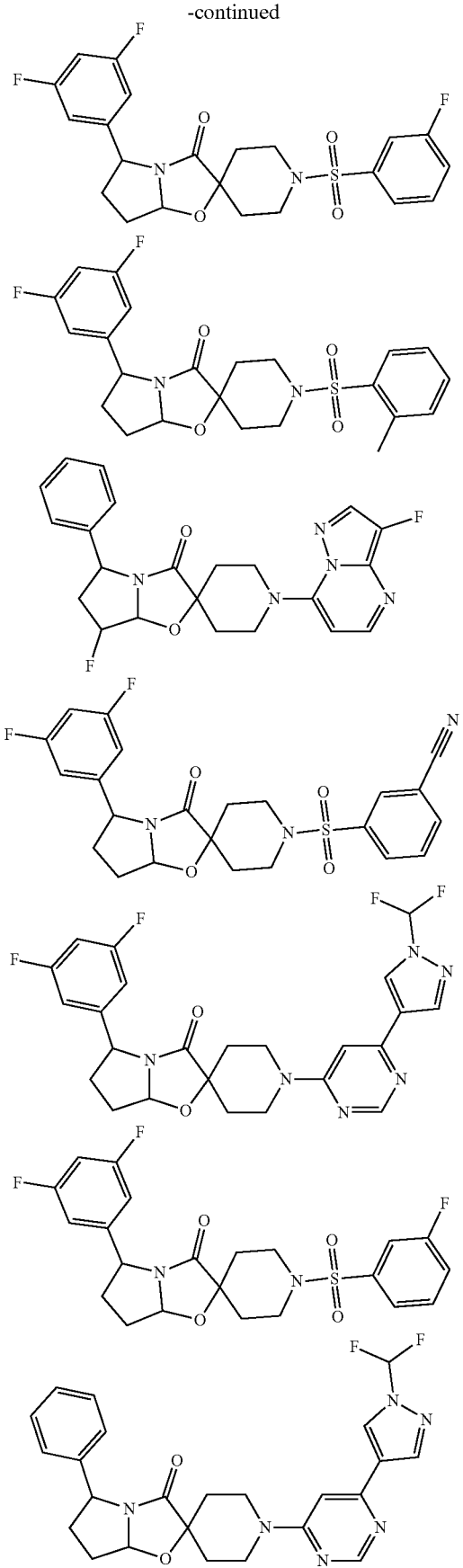
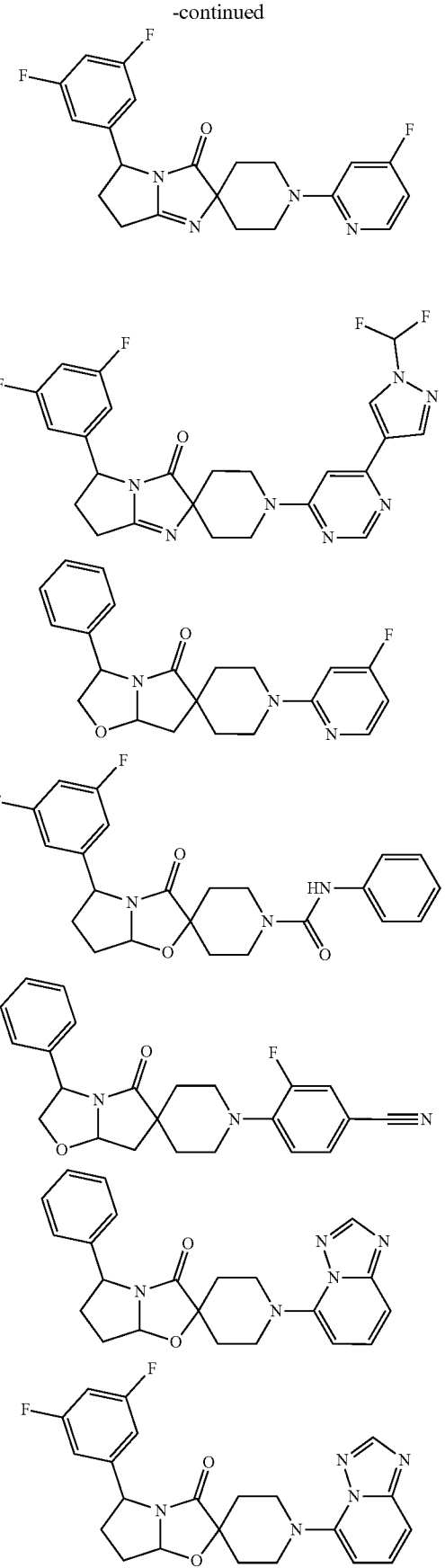

-continued
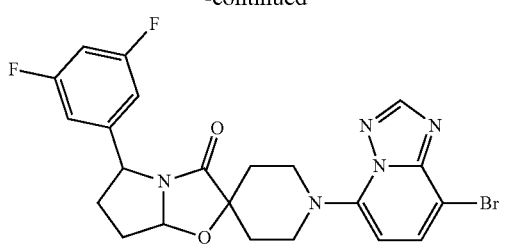
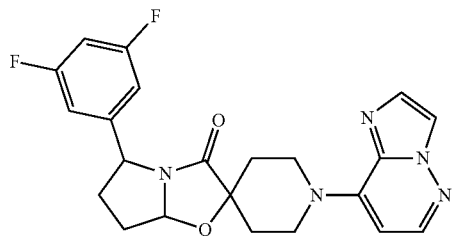
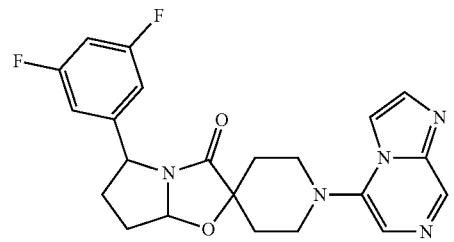
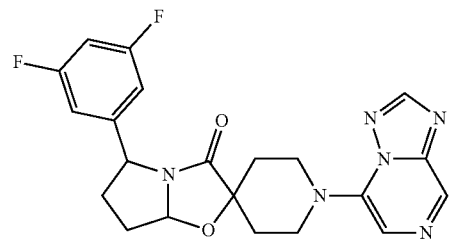
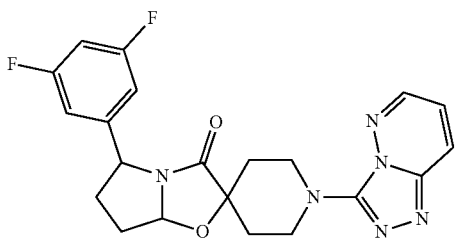
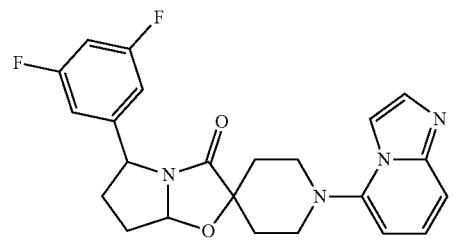
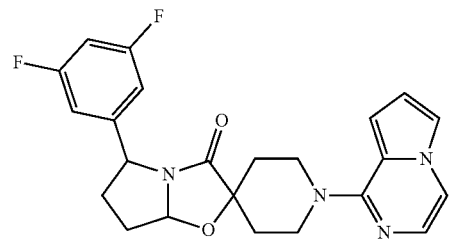
-continued
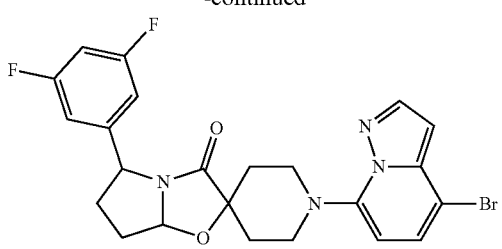
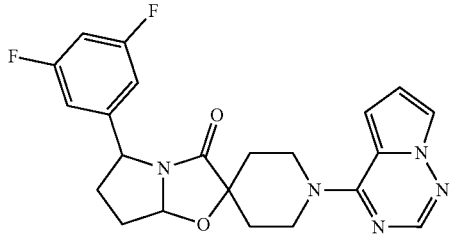
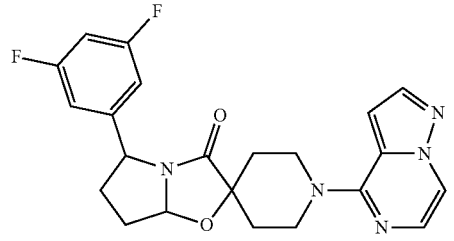
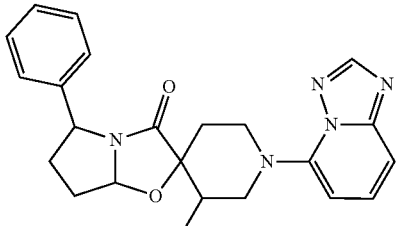
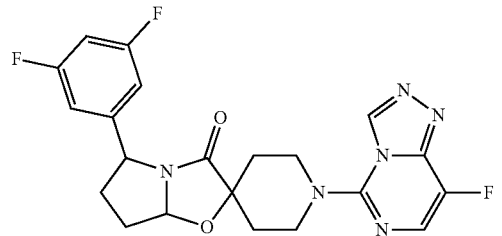
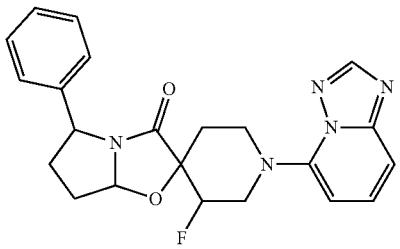
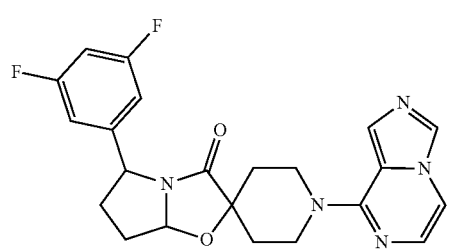

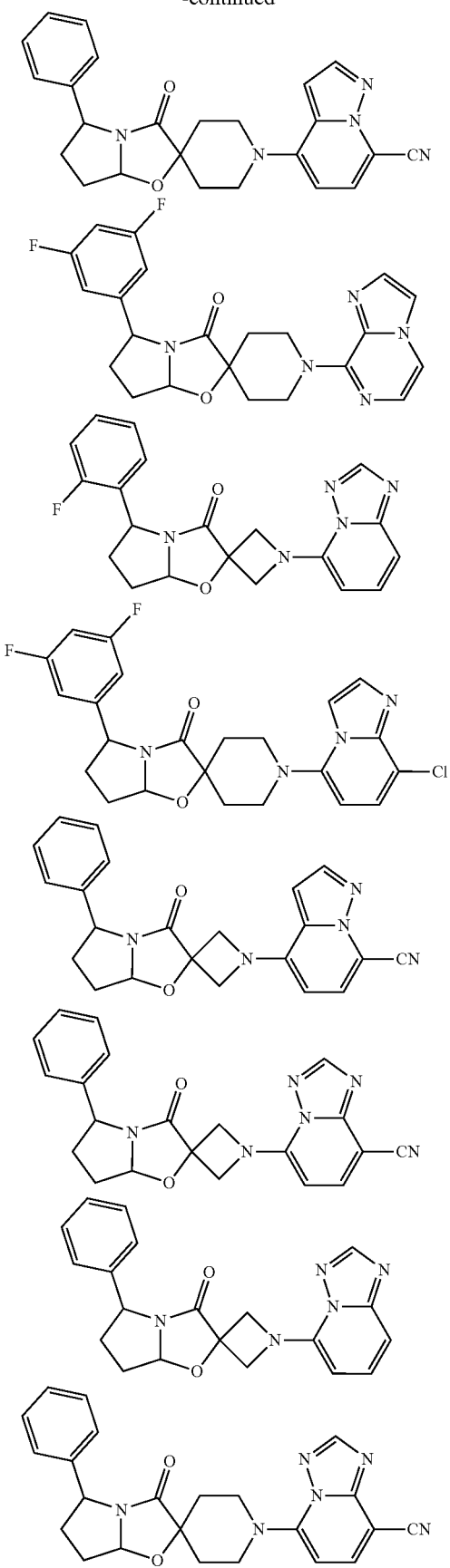
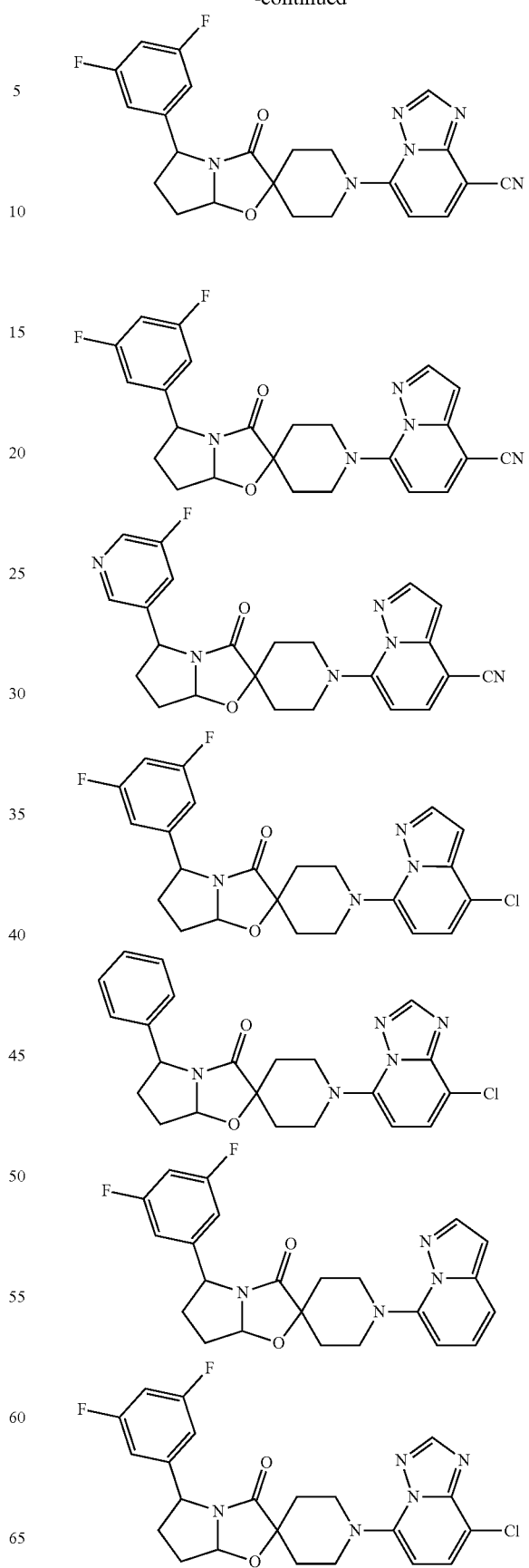

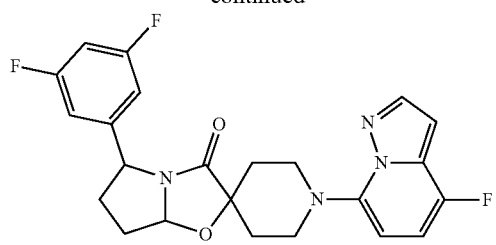
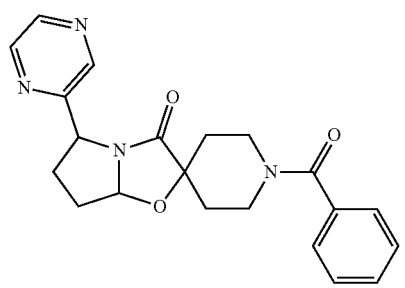
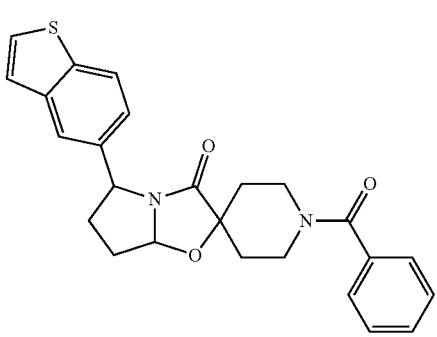
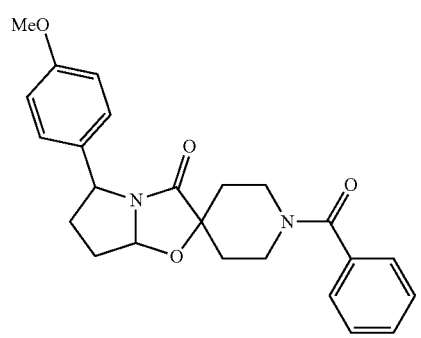
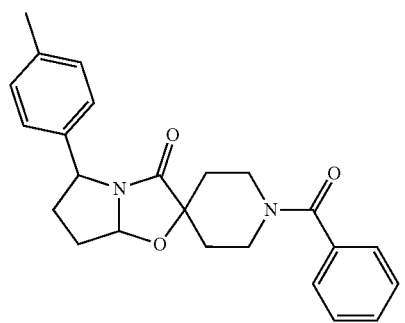
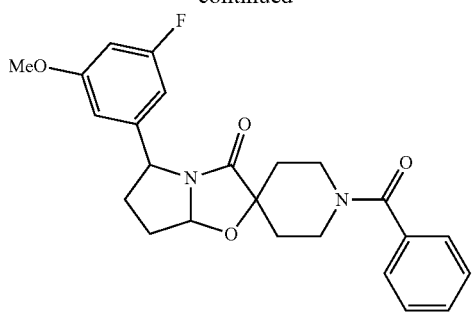
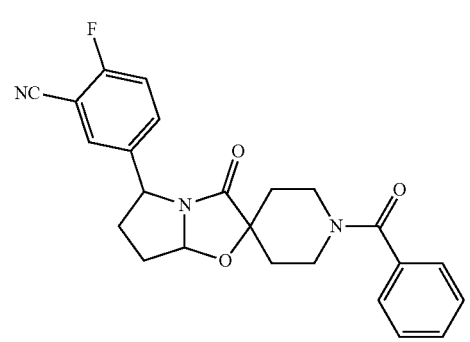
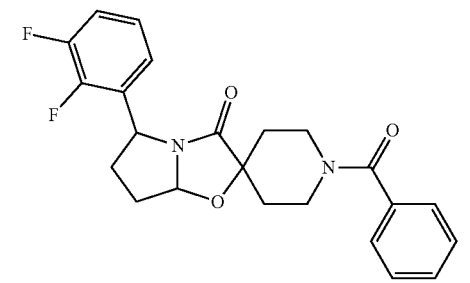
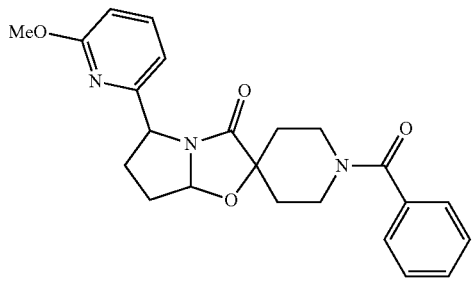
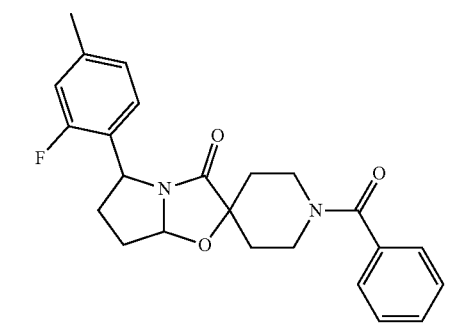

85
-continued
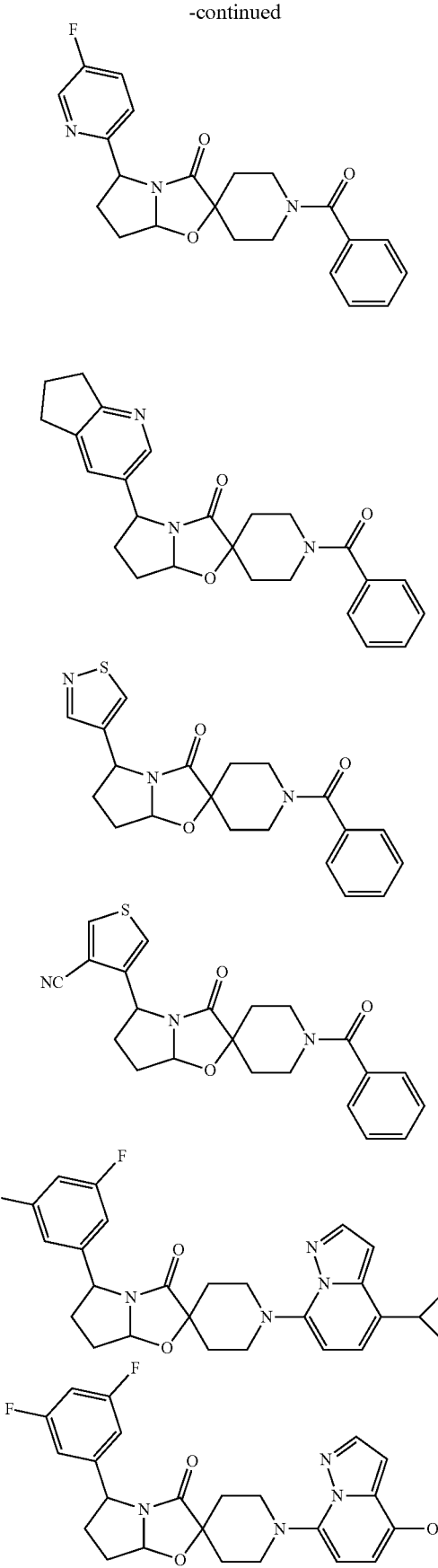
86
-continued
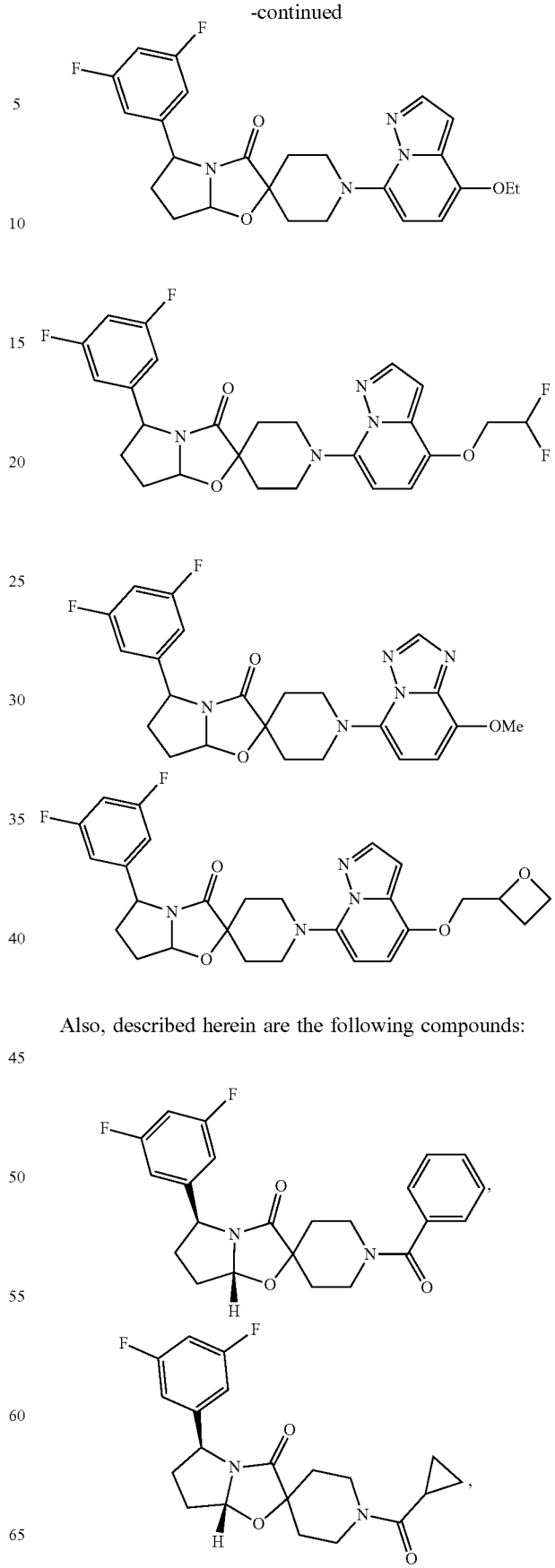
Also, described herein are the following compounds:

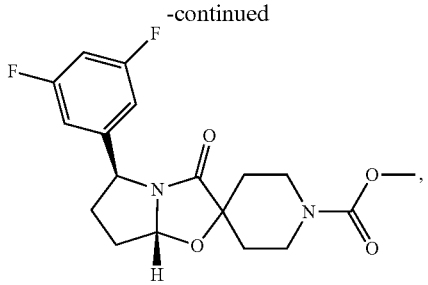
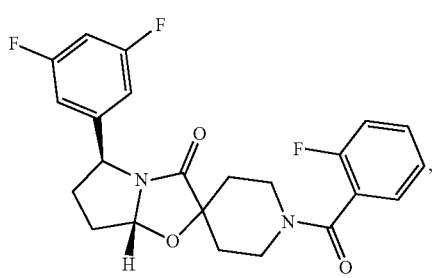
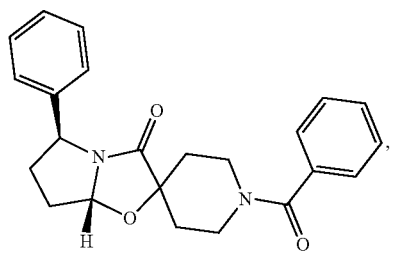
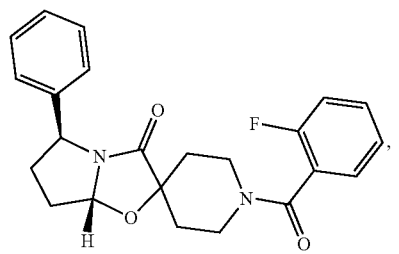
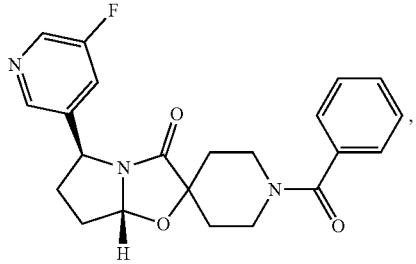
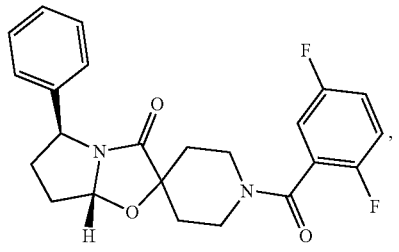
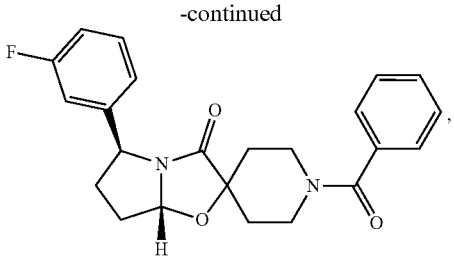
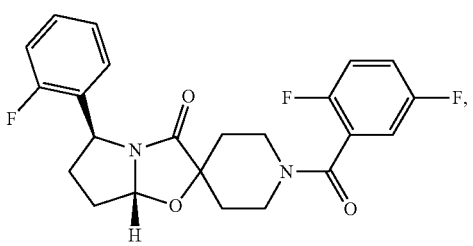
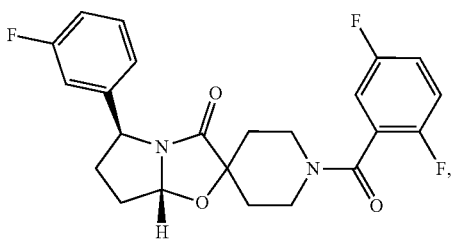
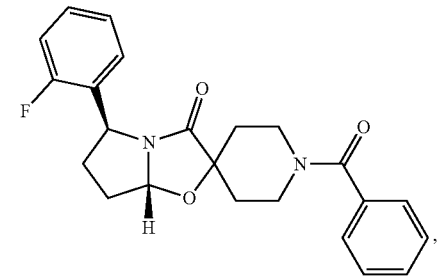
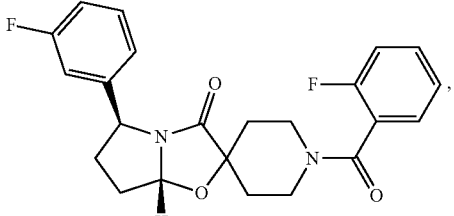
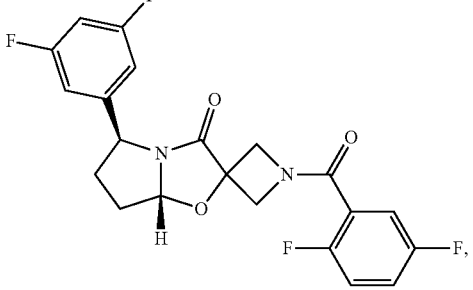

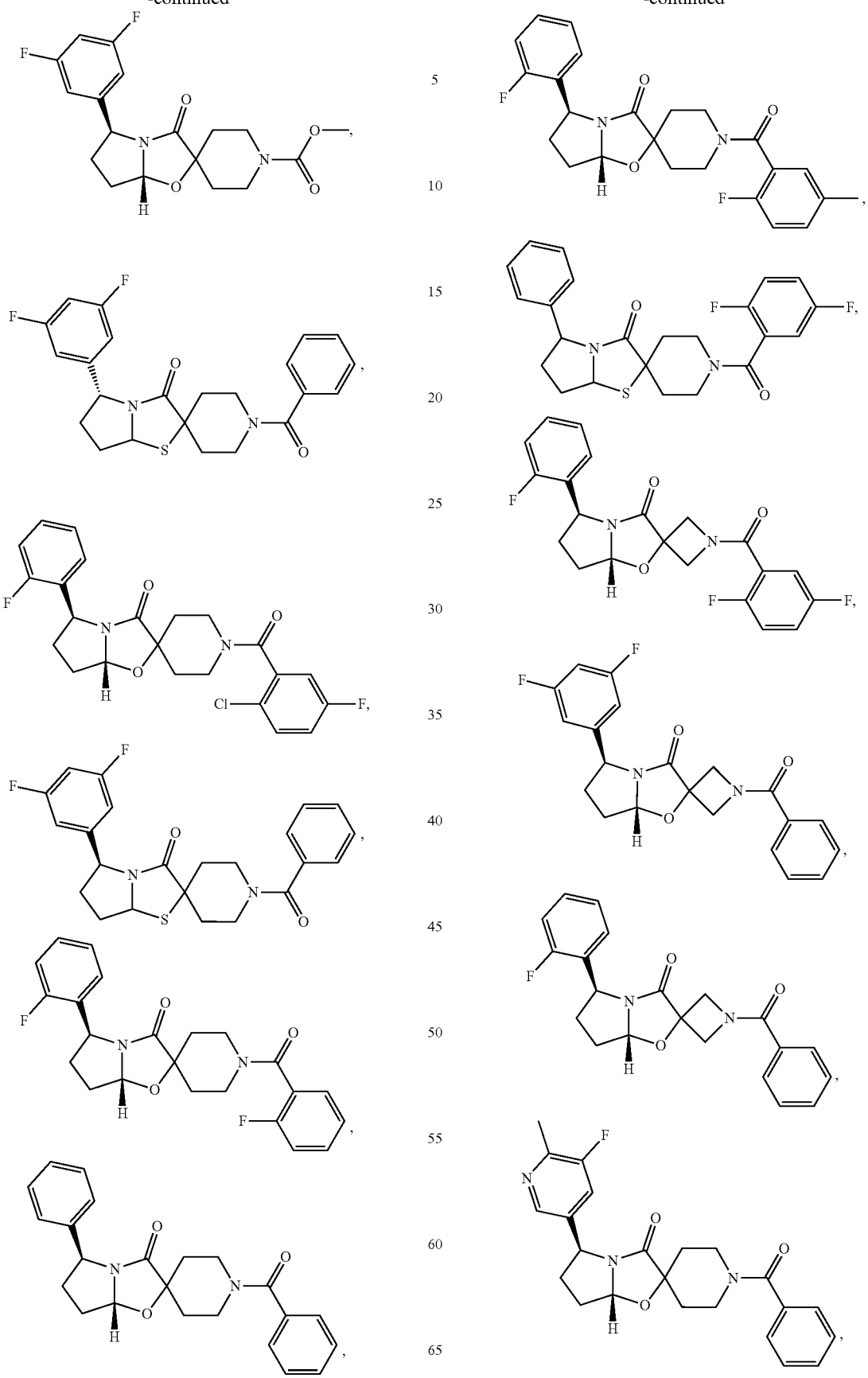

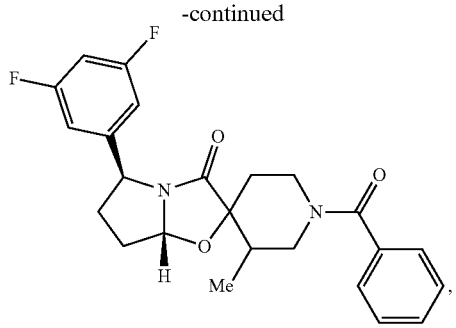
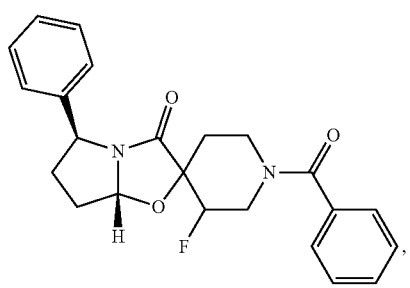
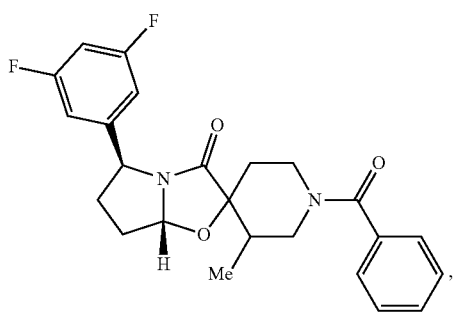
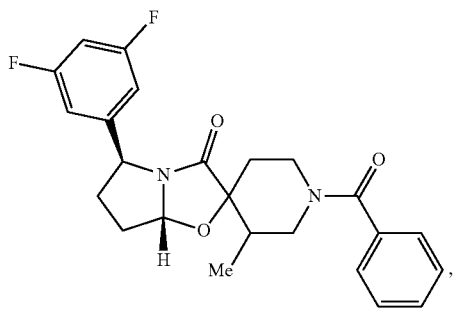
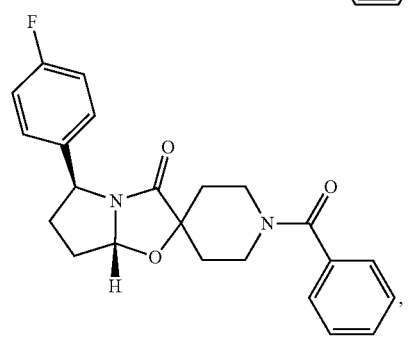
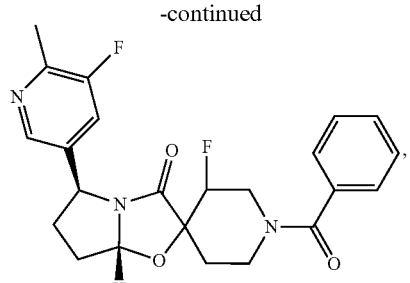
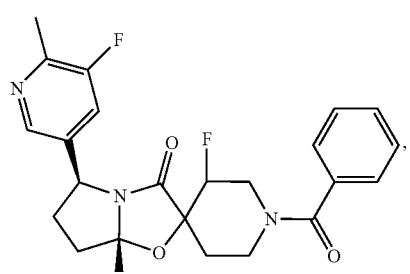
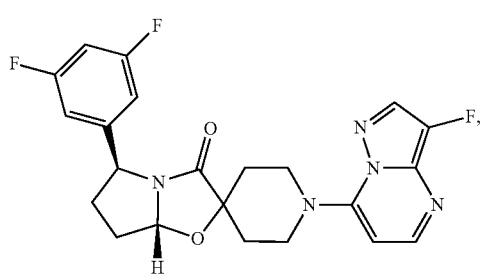
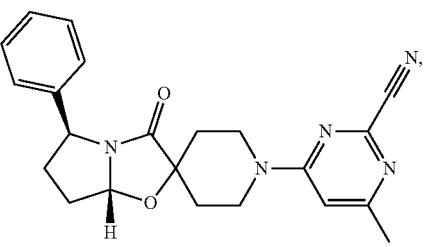
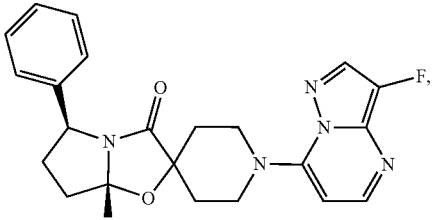
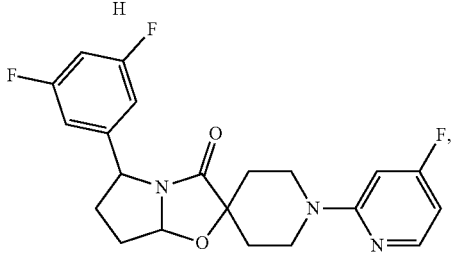

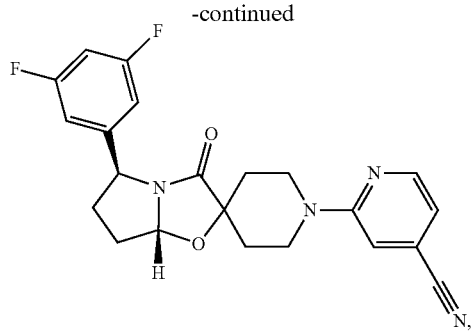
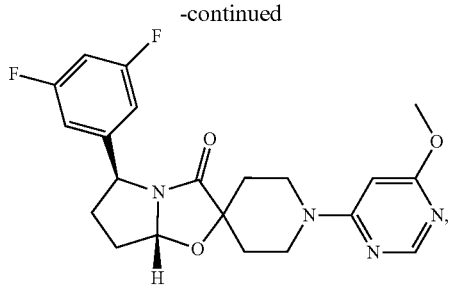

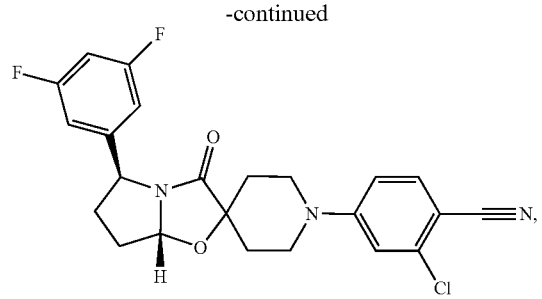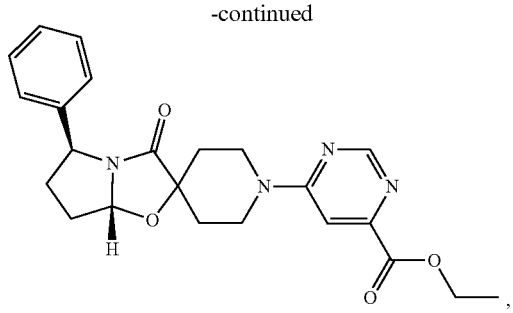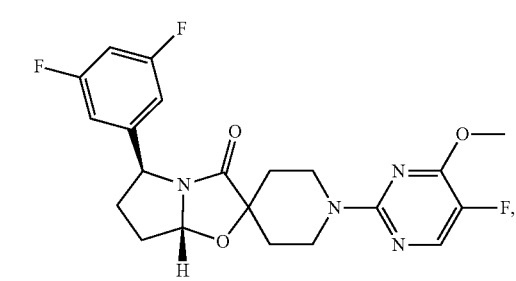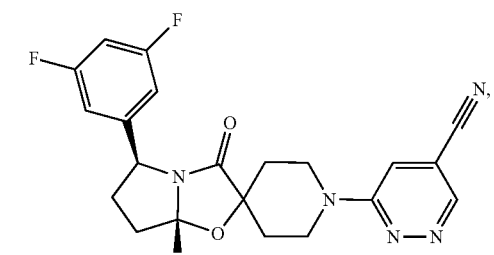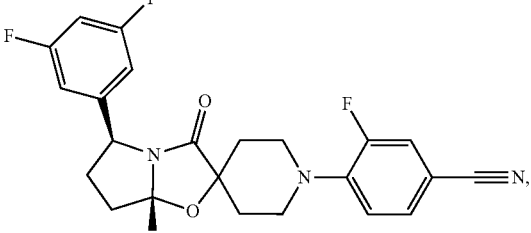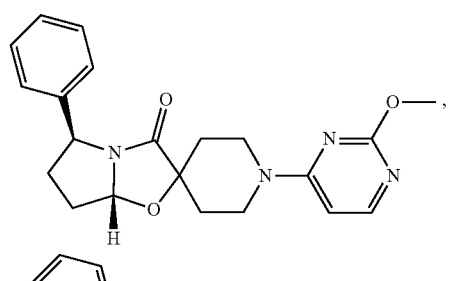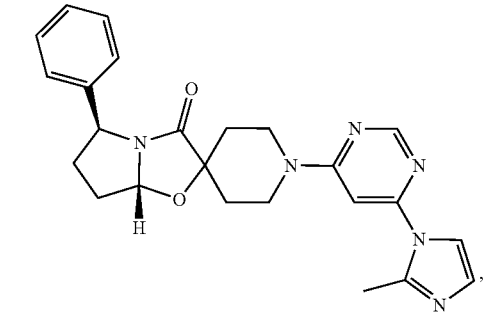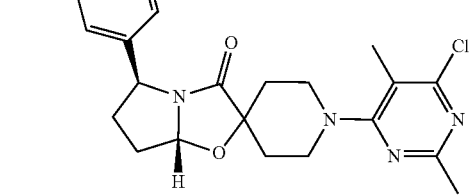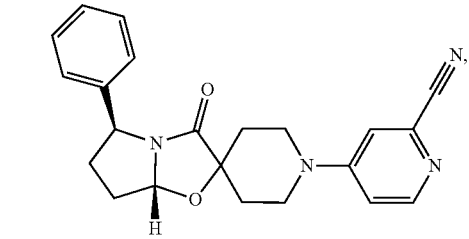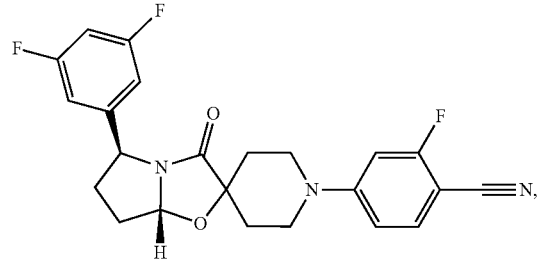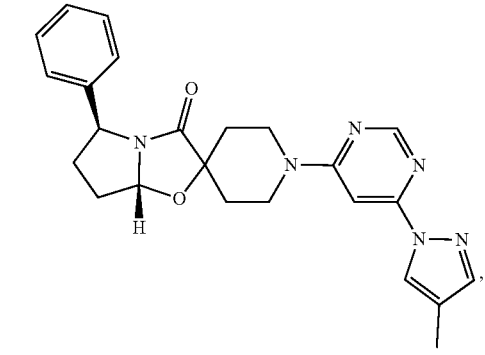

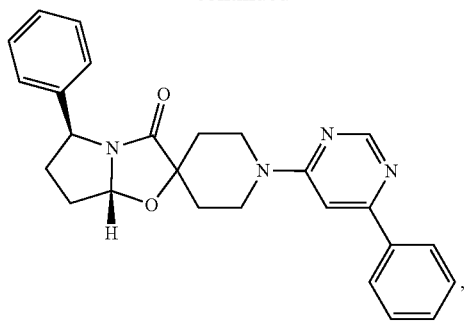
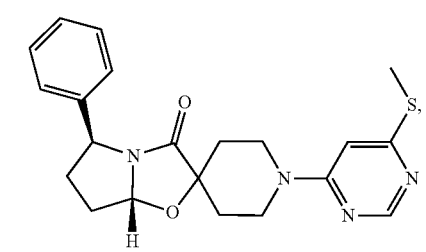
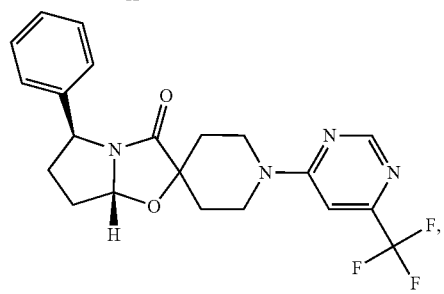
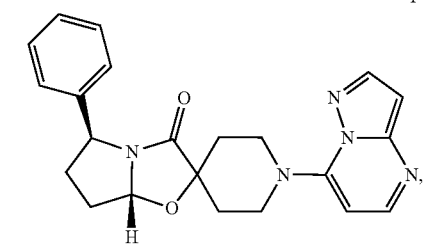
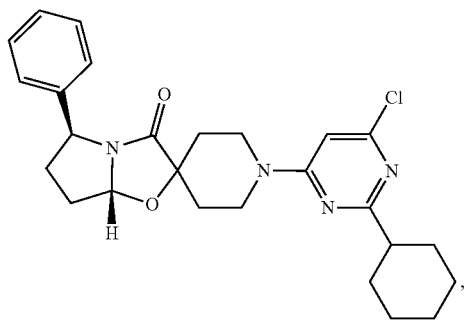
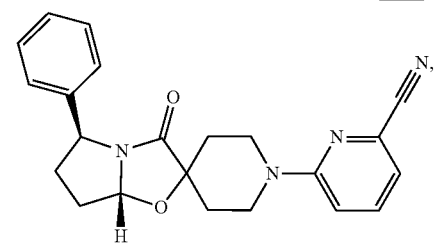
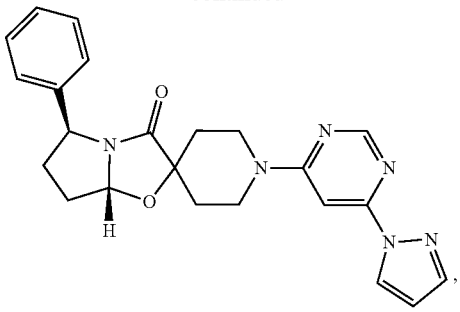
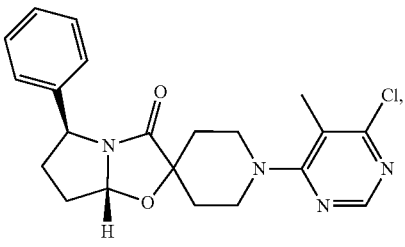
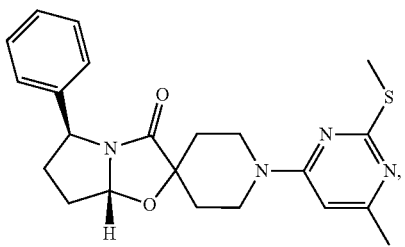
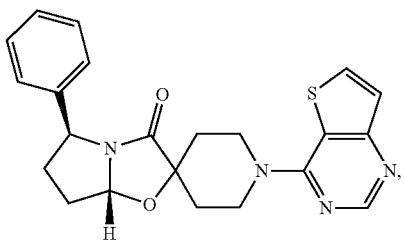
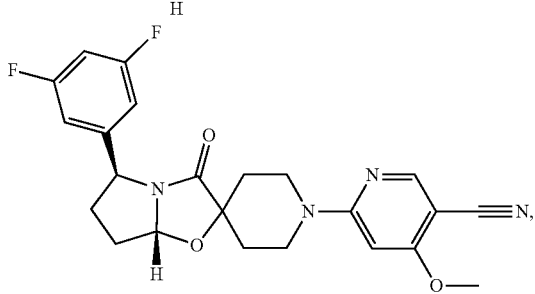
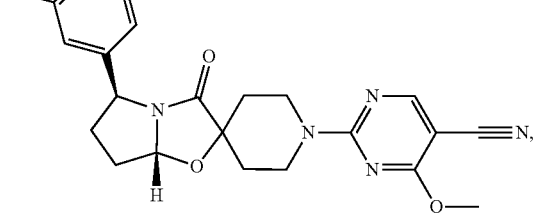

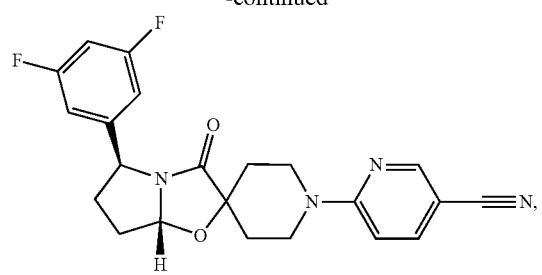
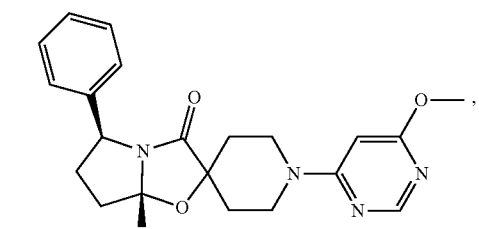
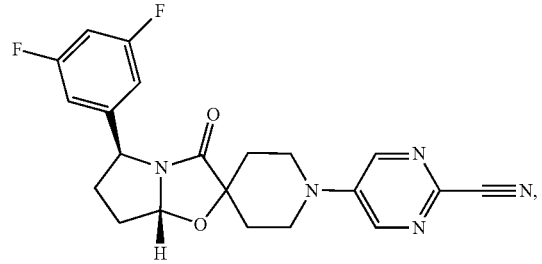
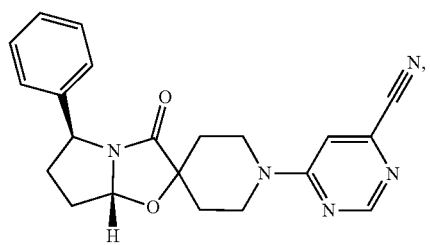
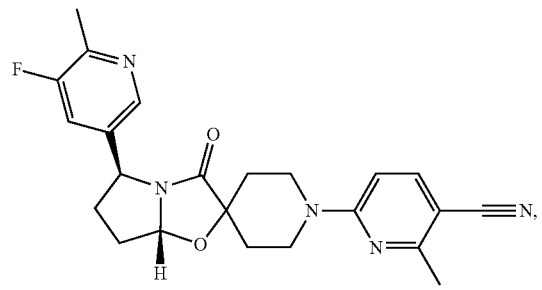
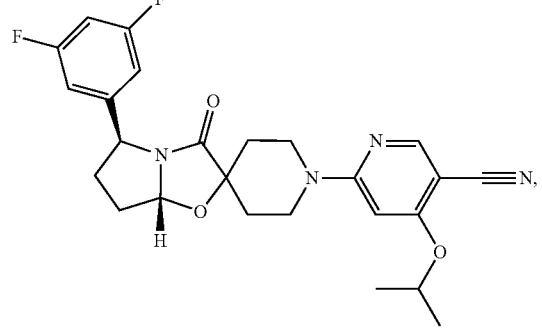
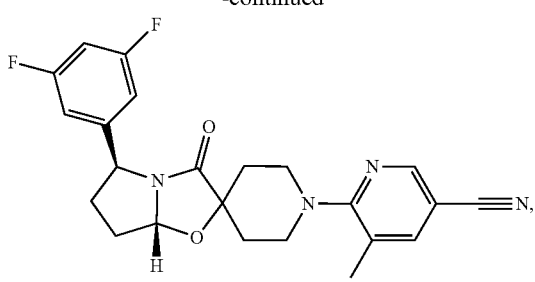
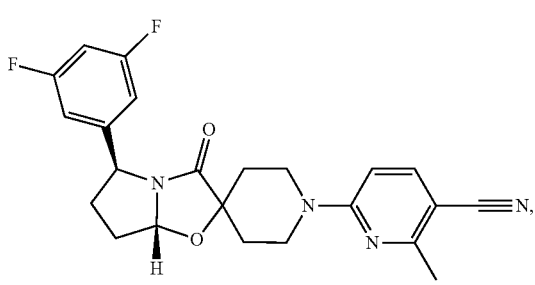
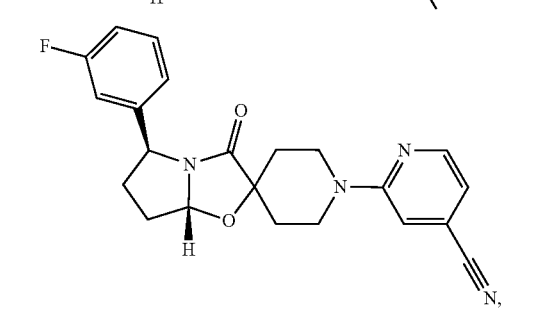
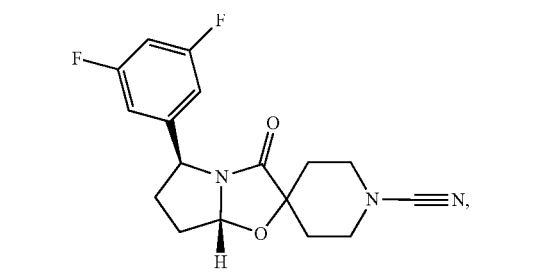
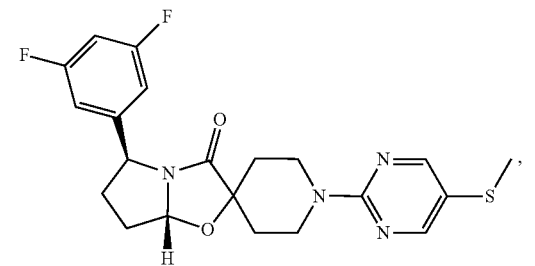
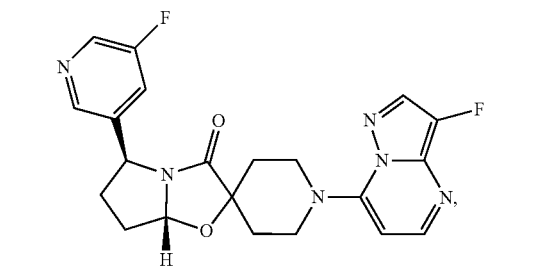

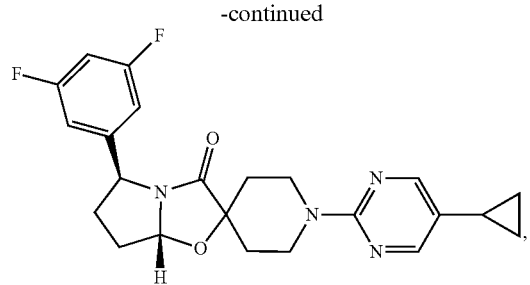
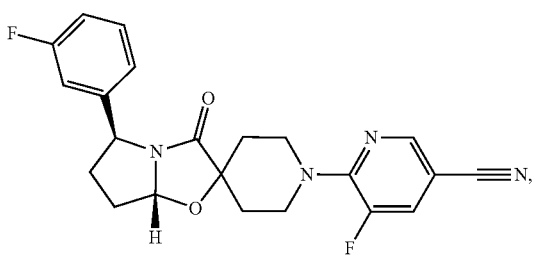
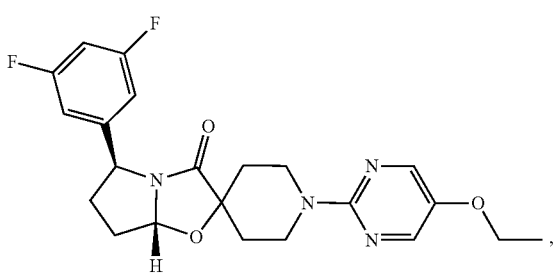
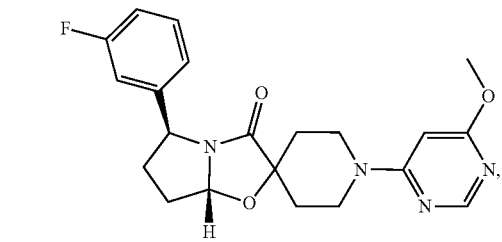
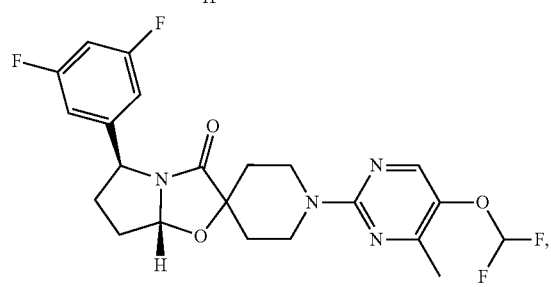
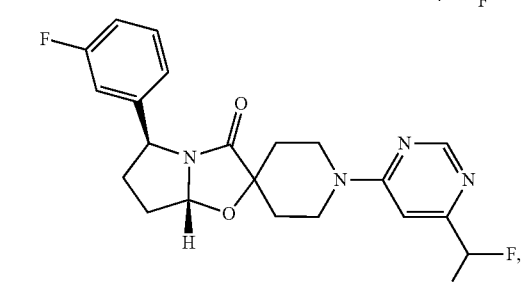
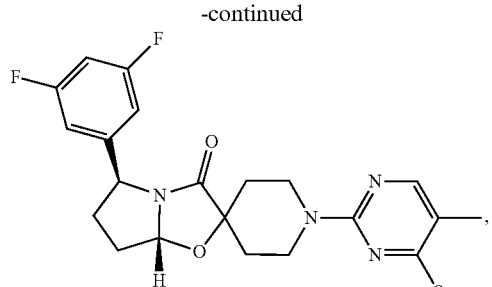
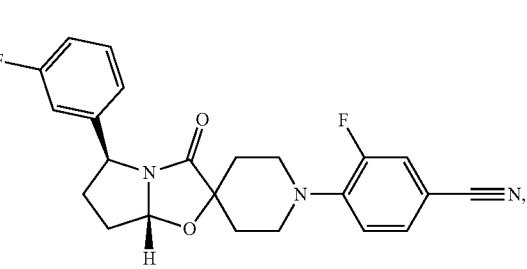
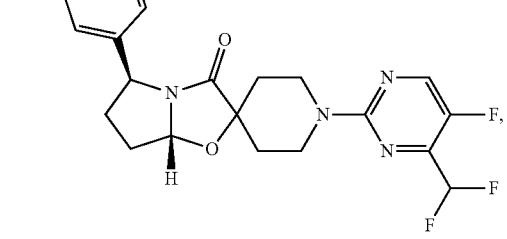
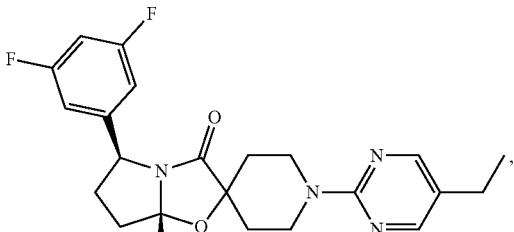
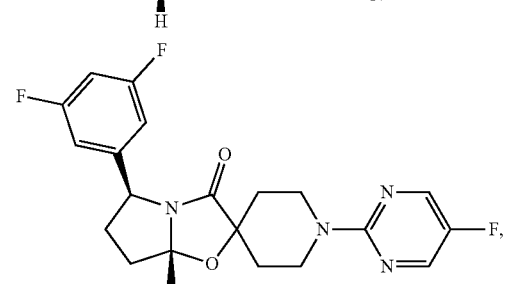
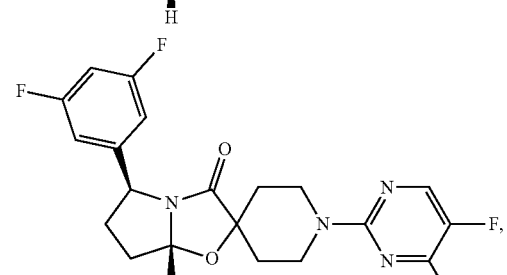

103
-continued
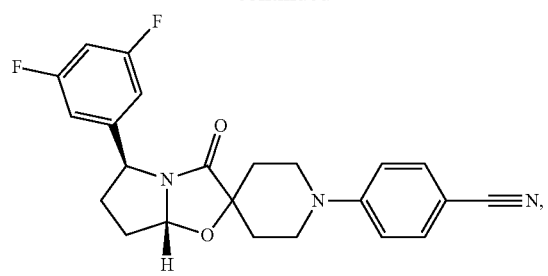
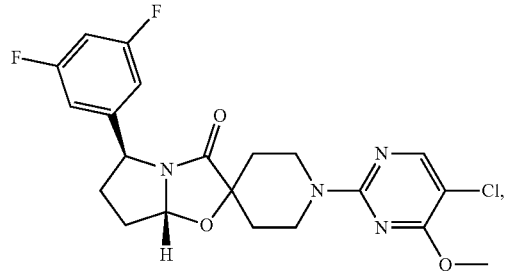
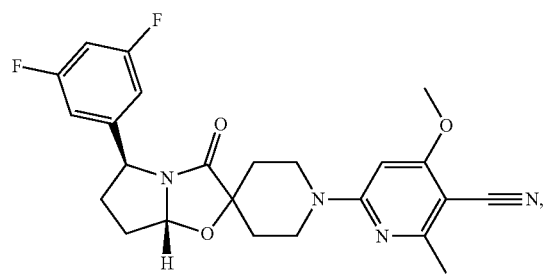
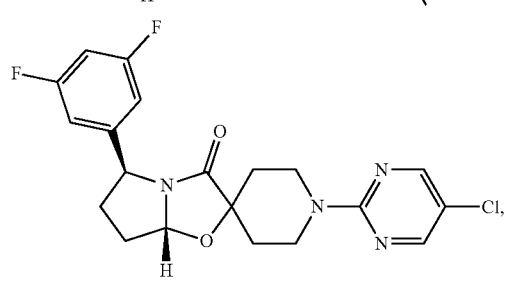
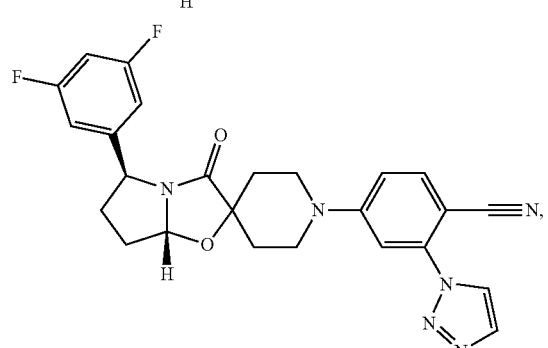
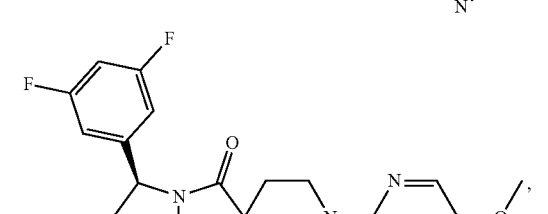
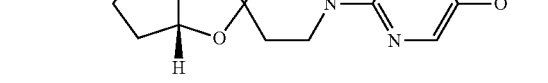
104
-continued
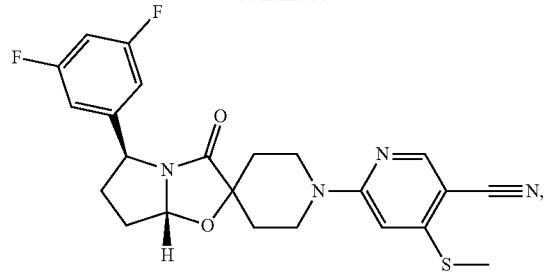
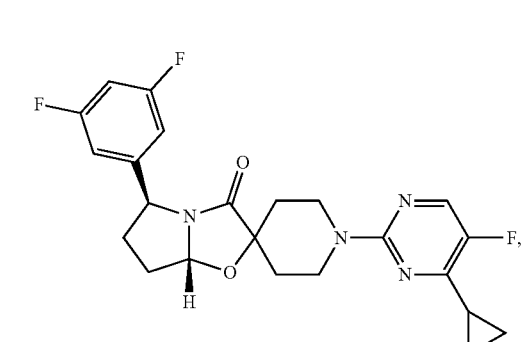
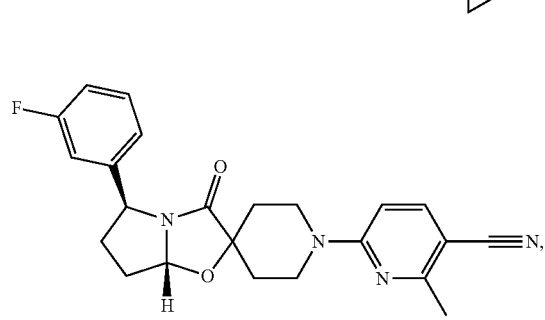
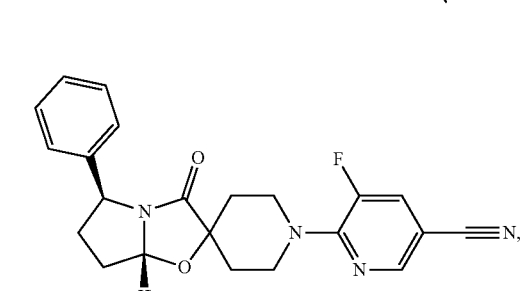
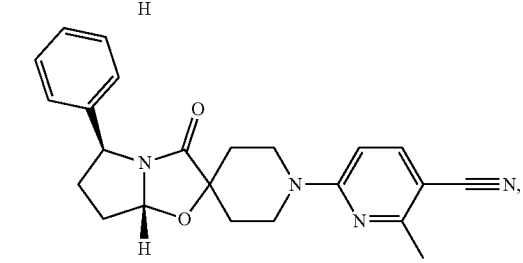
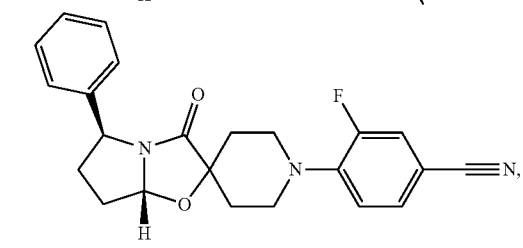

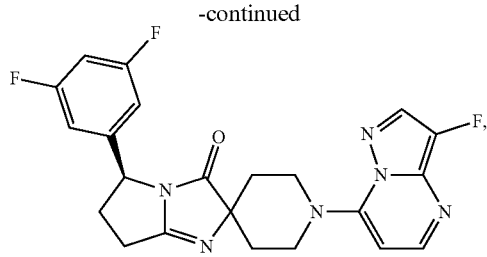
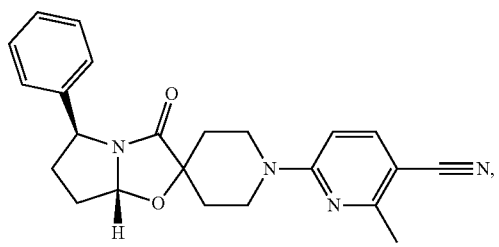
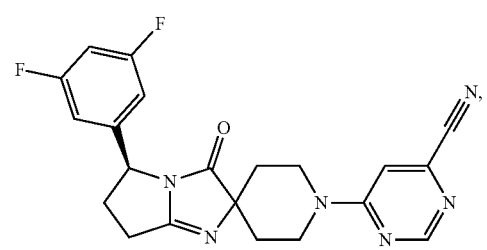
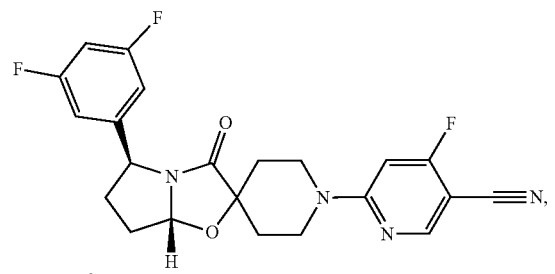
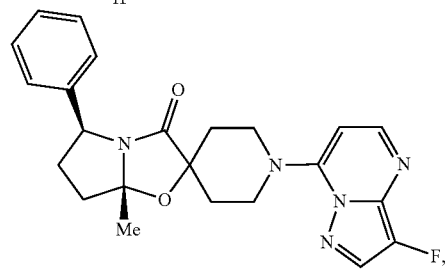
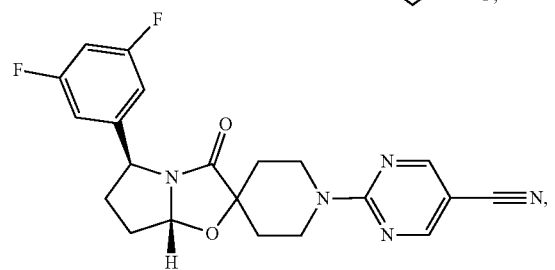
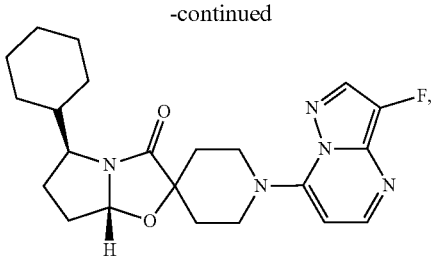
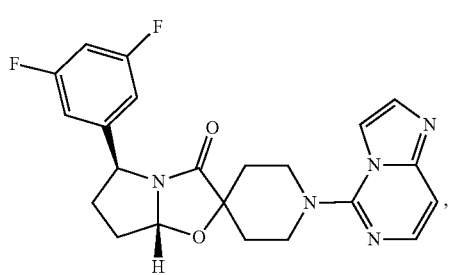
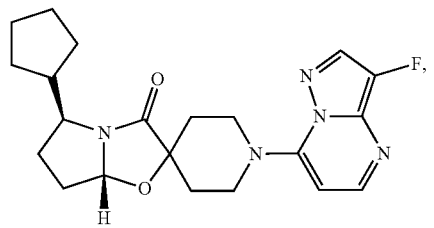
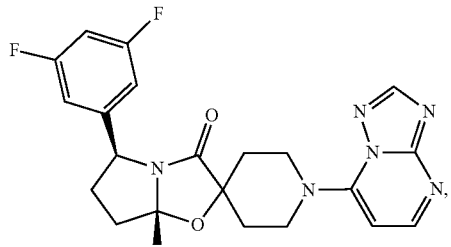
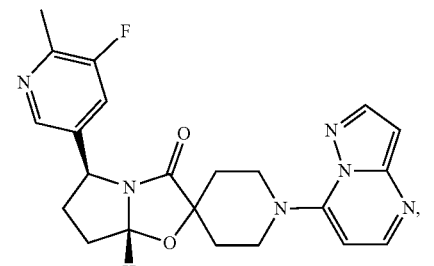
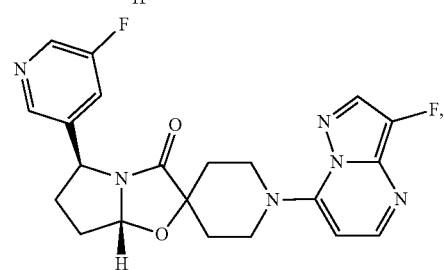

107
-continued
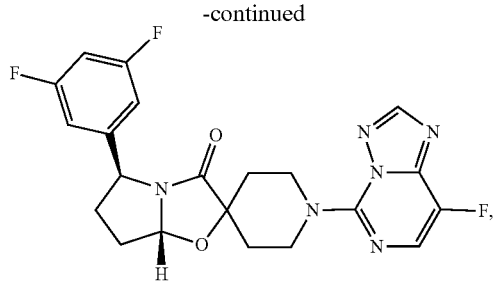
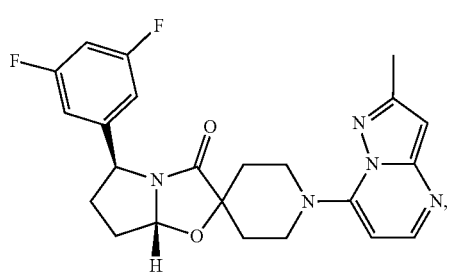
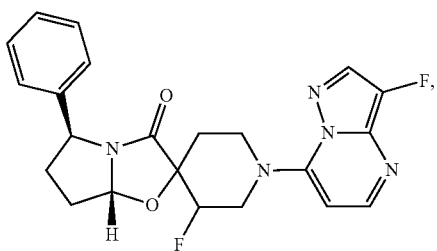
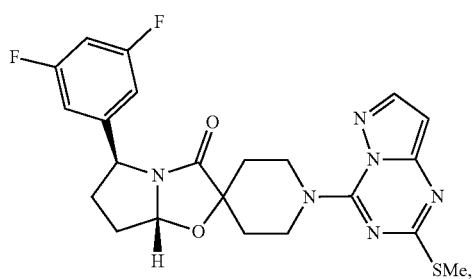
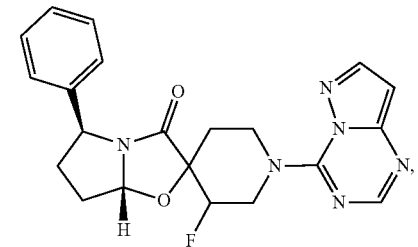
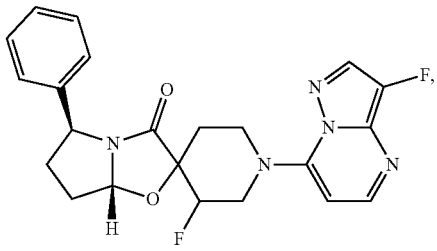
108
-continued
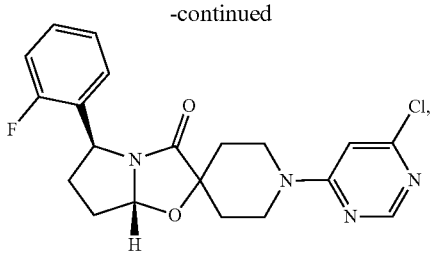
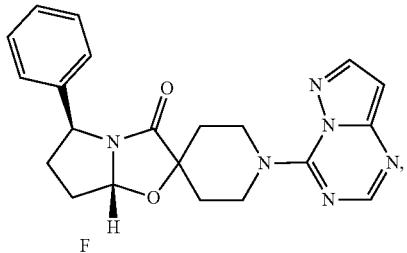
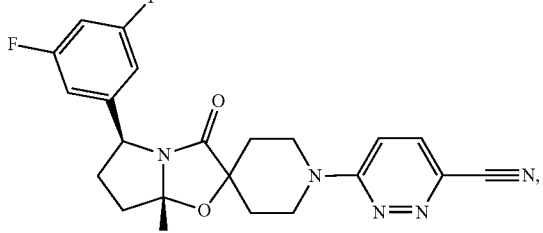
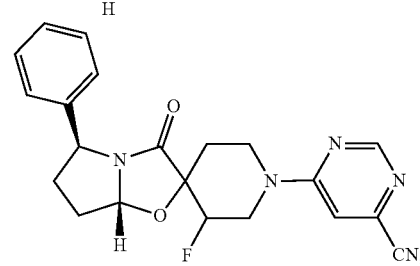
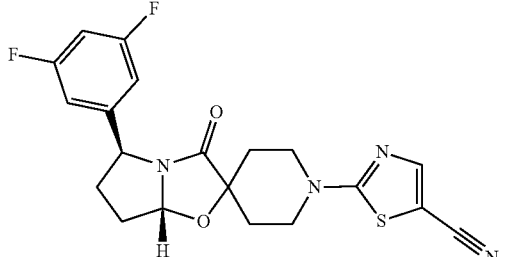
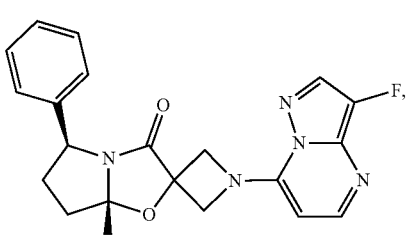
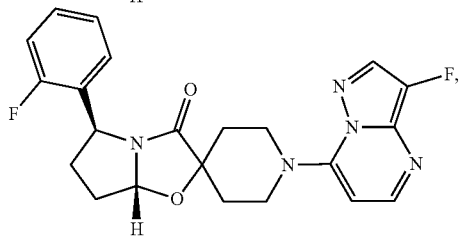

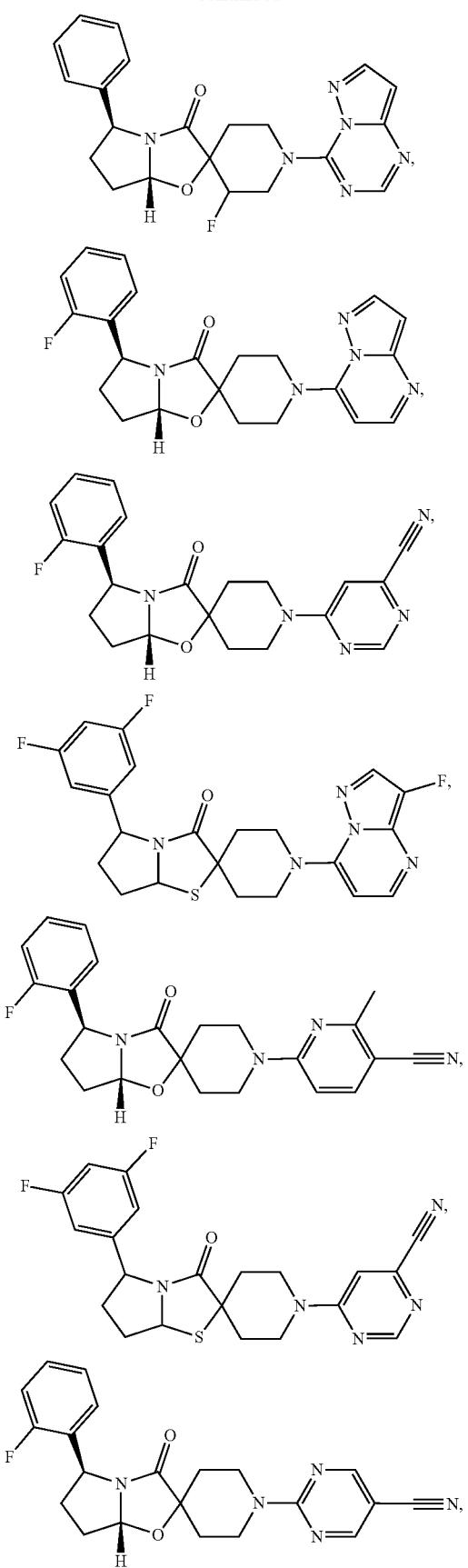
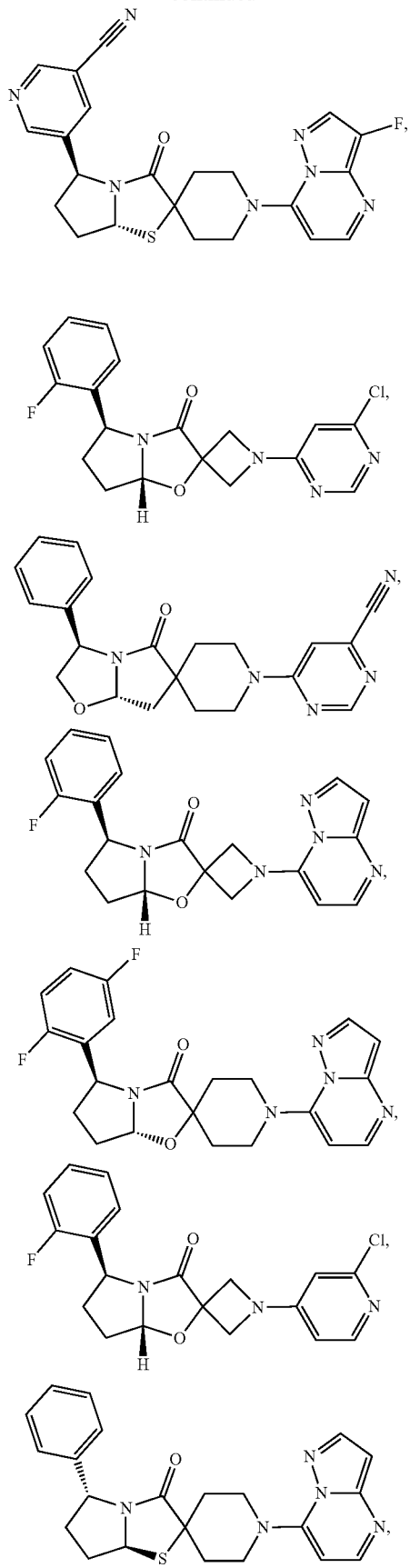

-continued
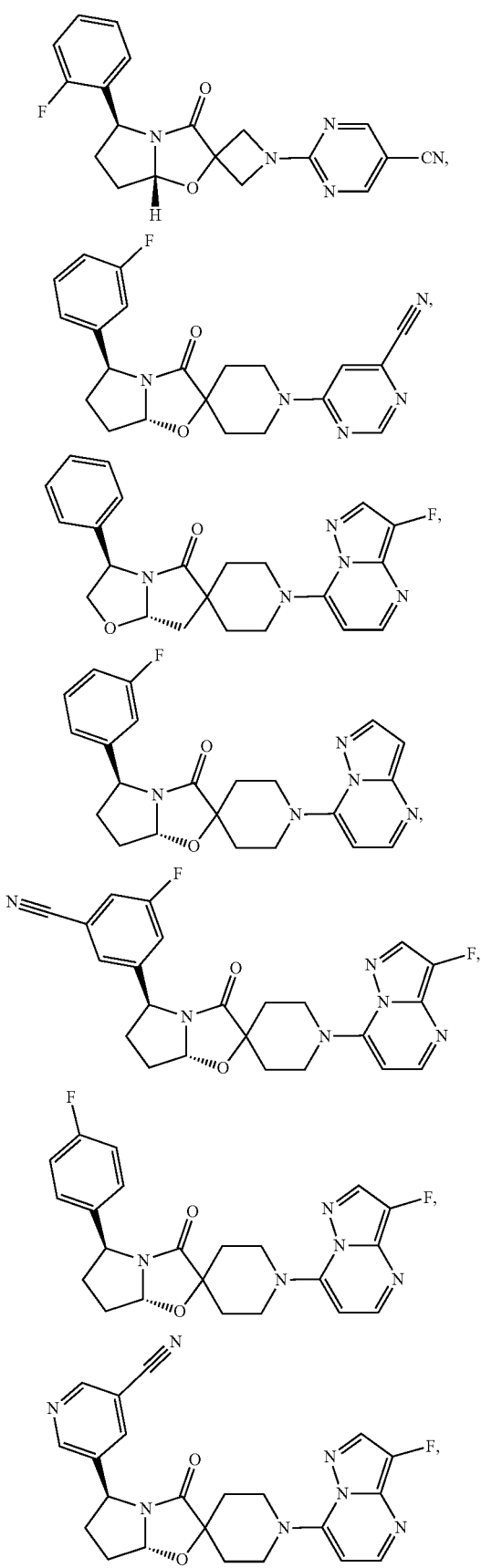
-continued
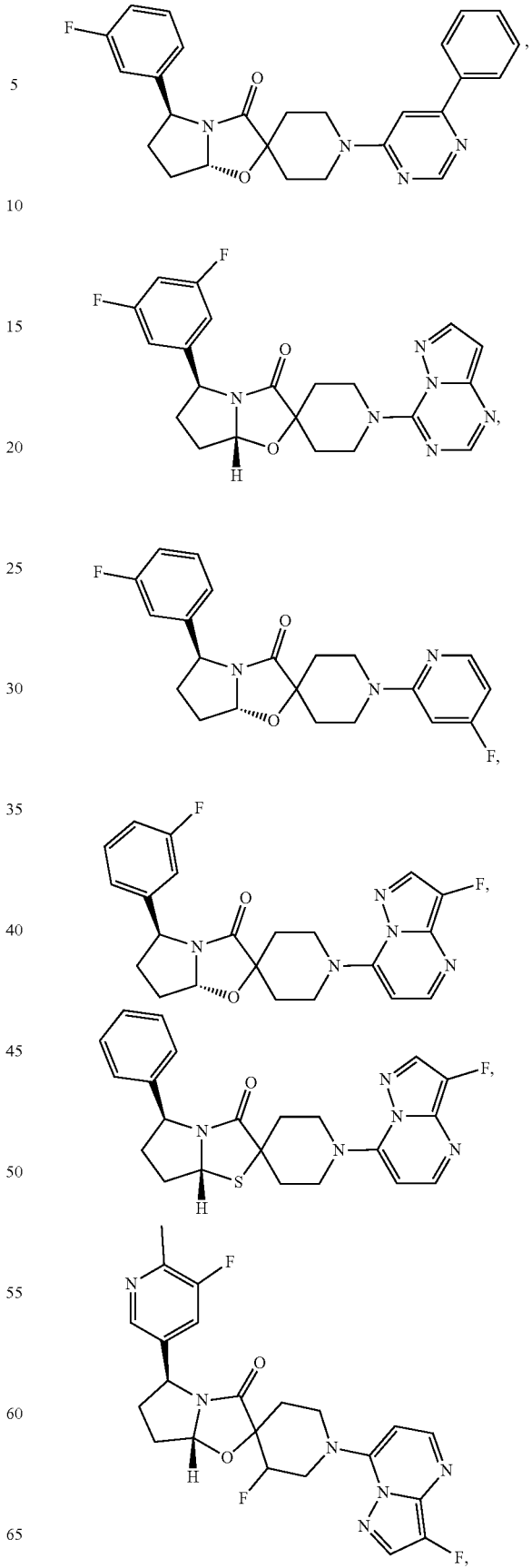

-continued
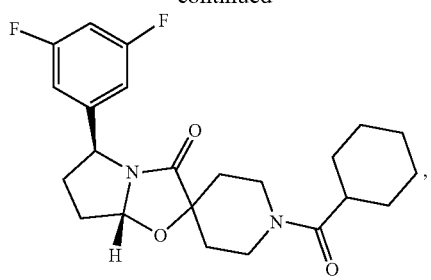
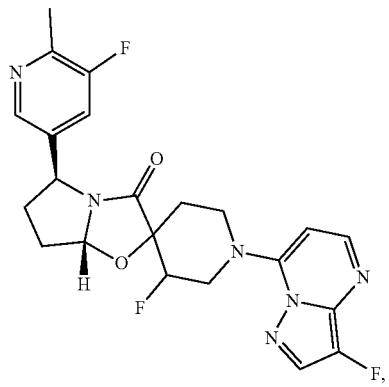
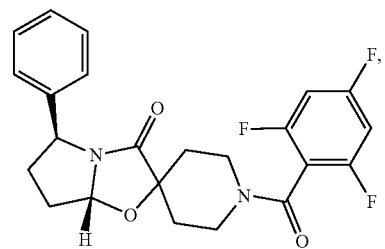
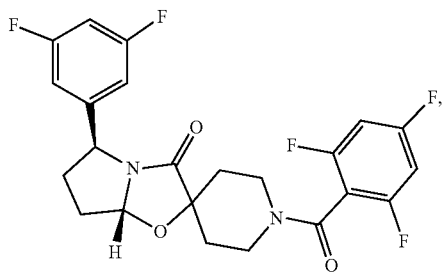
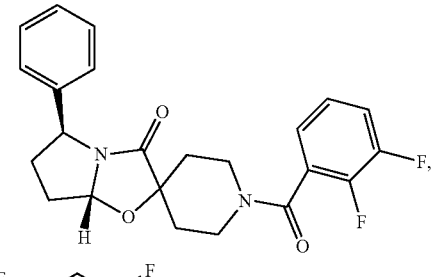
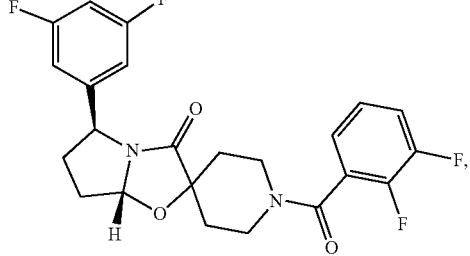
-continued
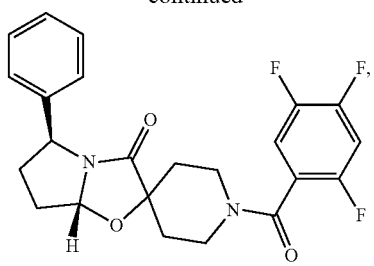
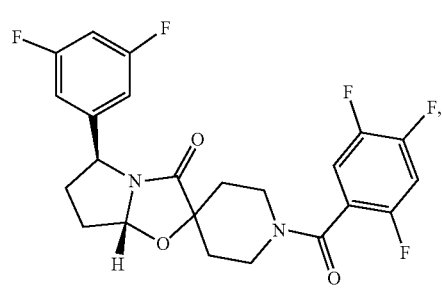
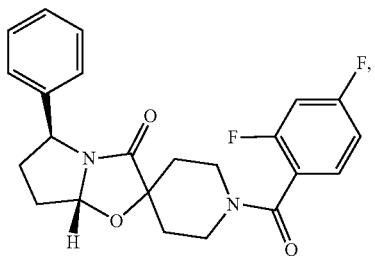
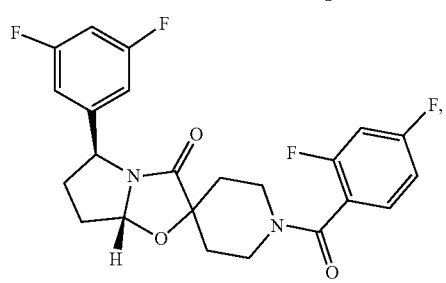
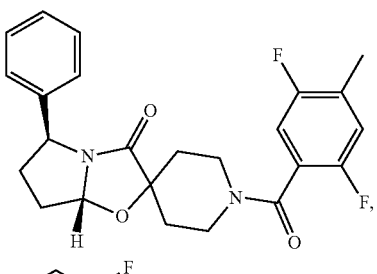
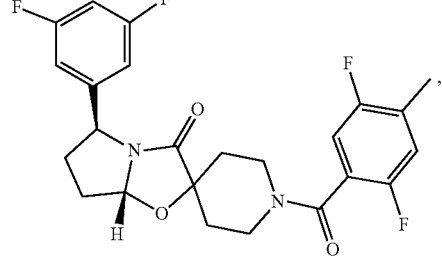

115
-continued
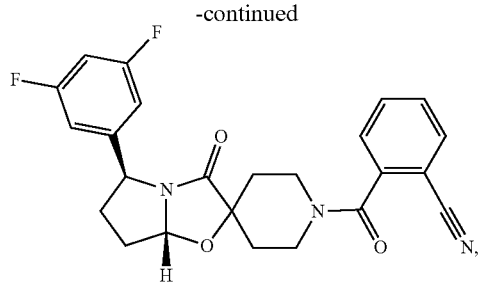
116
-continued
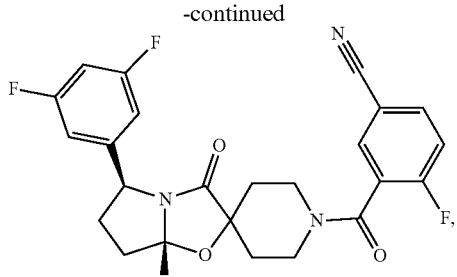
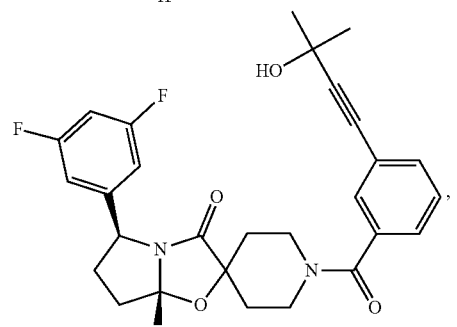
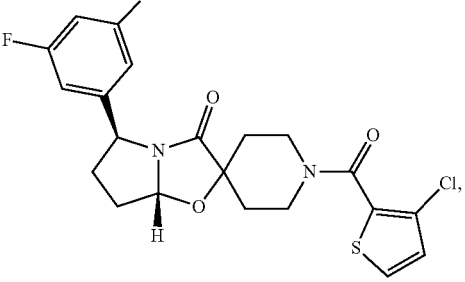

117
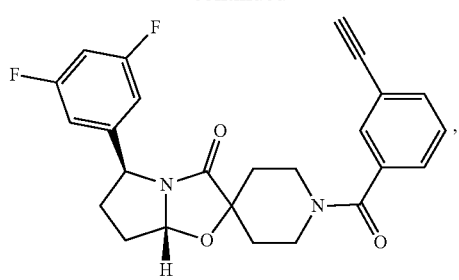
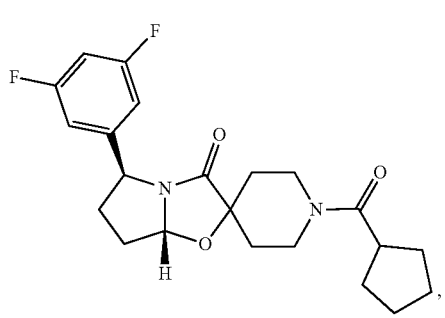
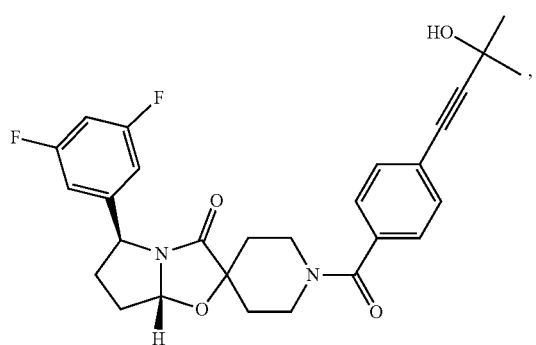
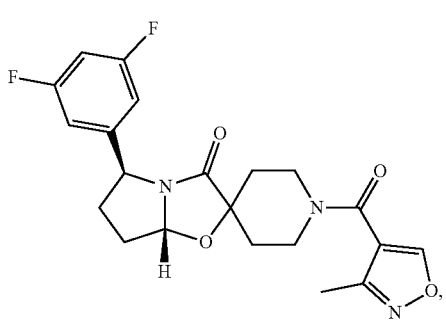
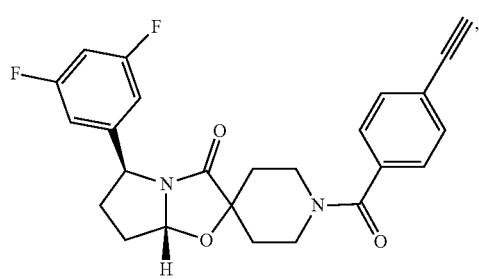
118
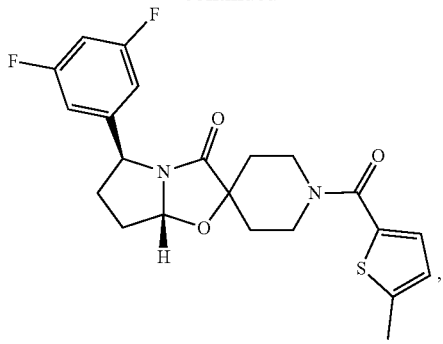
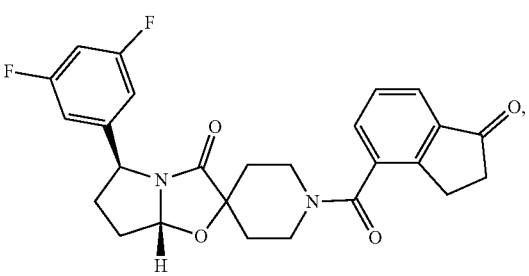
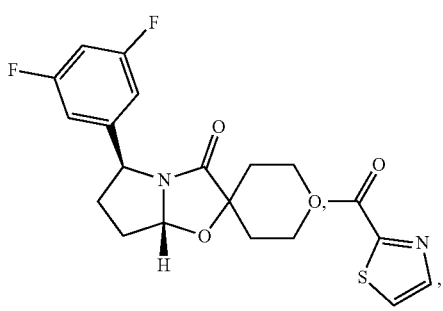
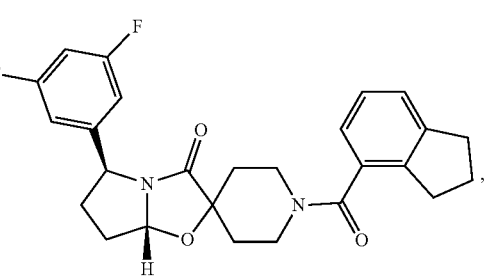
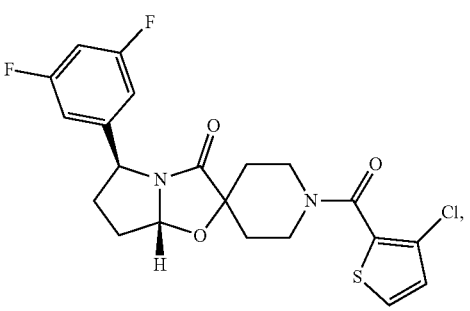

119
-continued
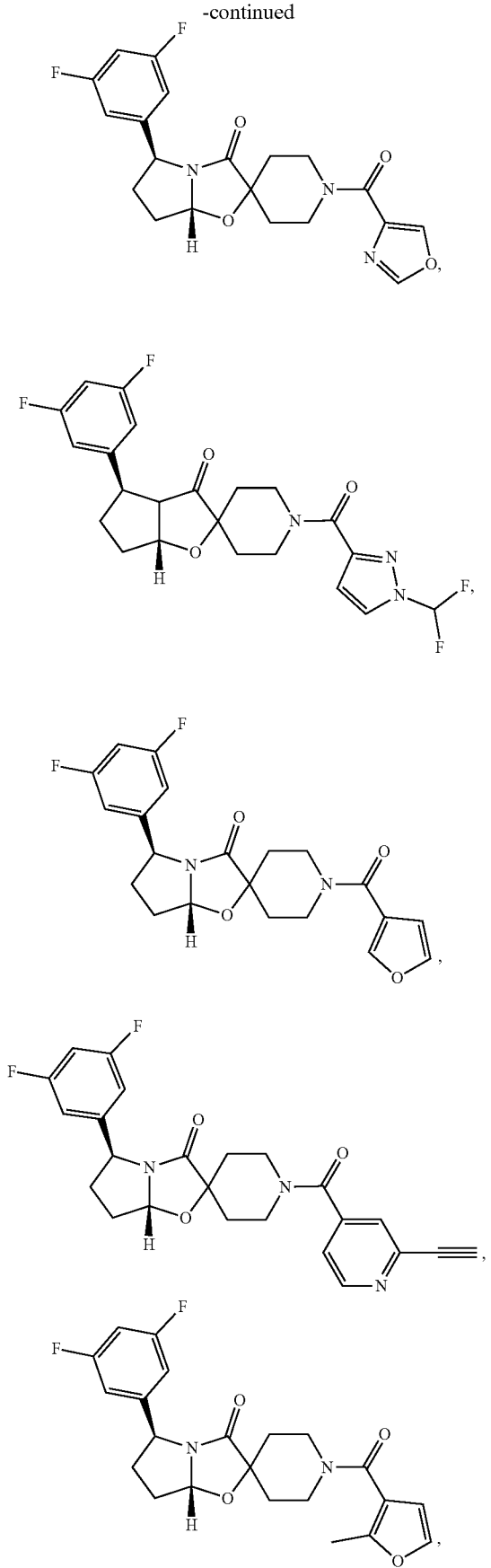
120
-continued
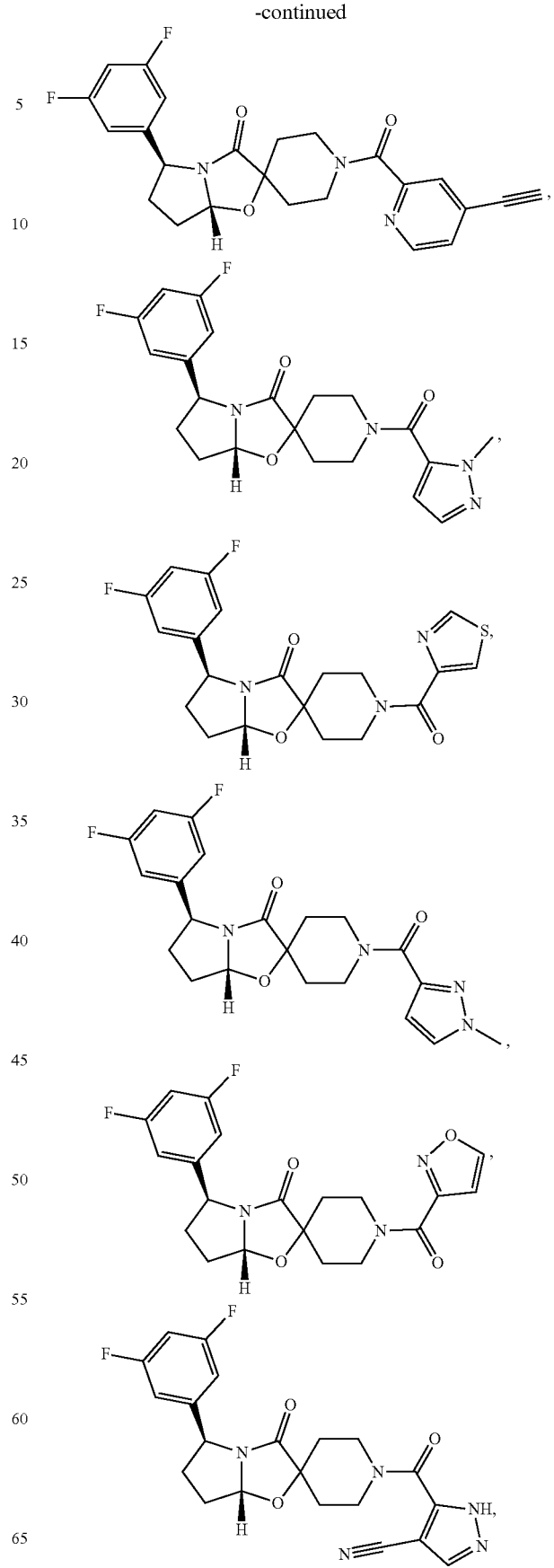

121
-continued
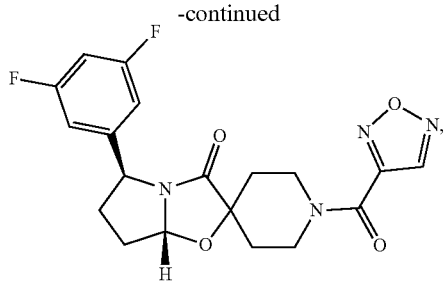
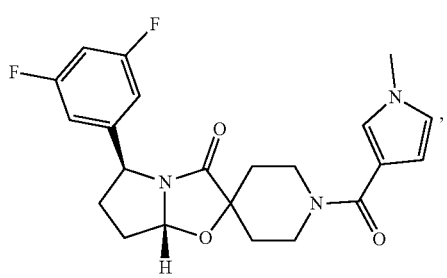
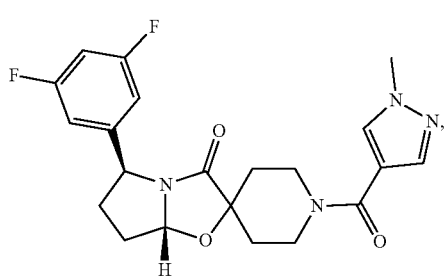
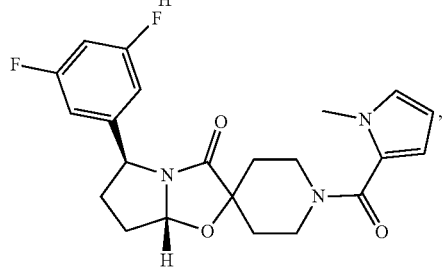
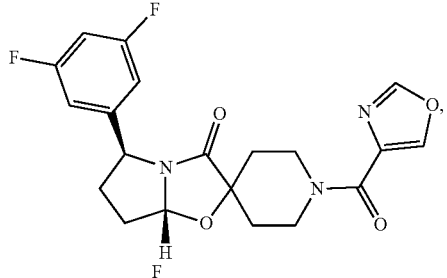
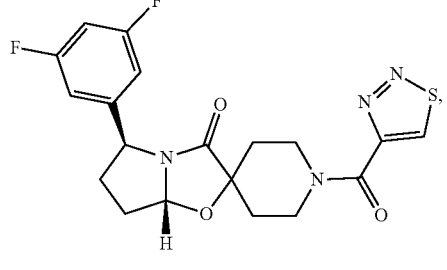
122
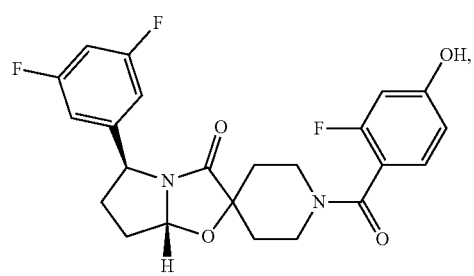
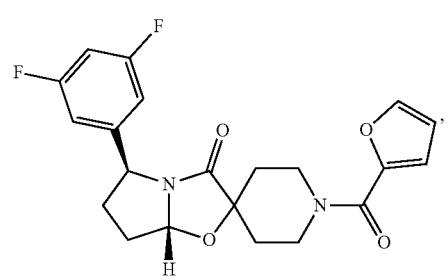
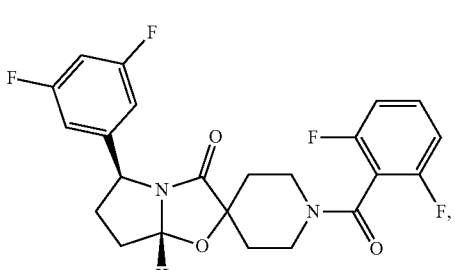
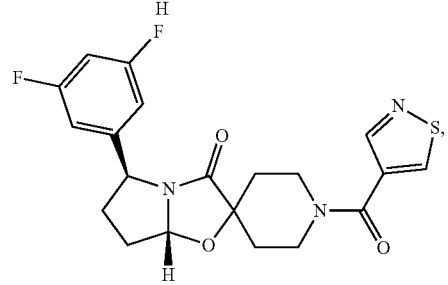
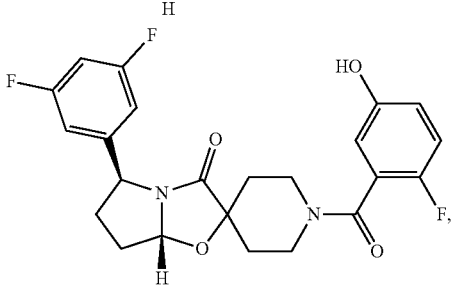
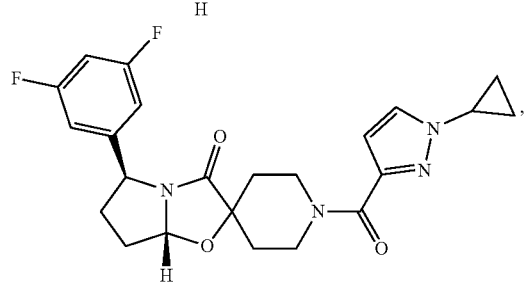

123
-continued
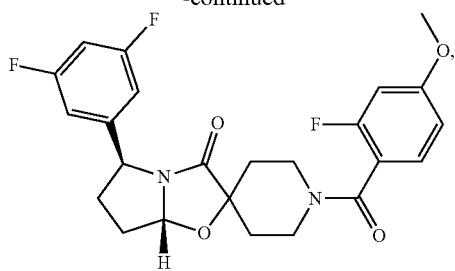
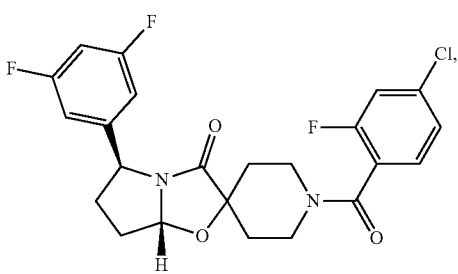
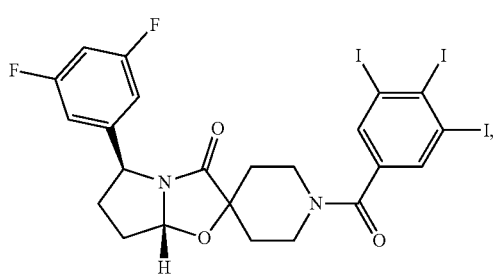
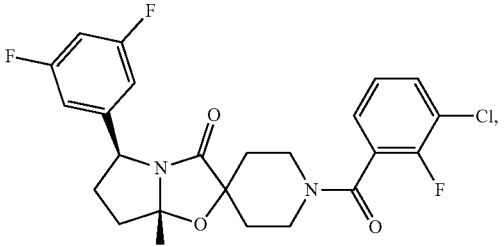
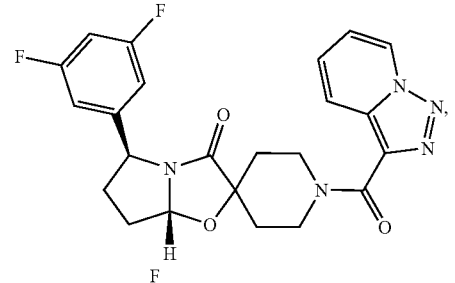
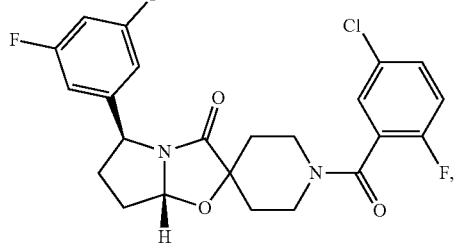
124
-continued
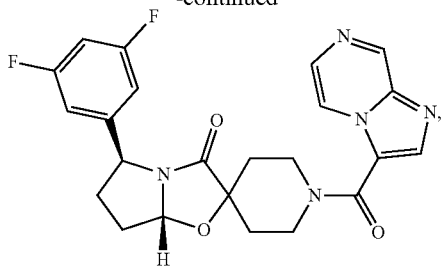
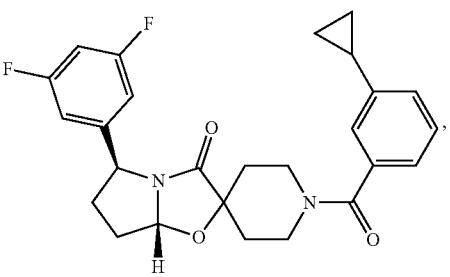
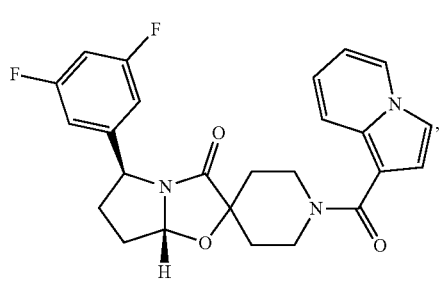
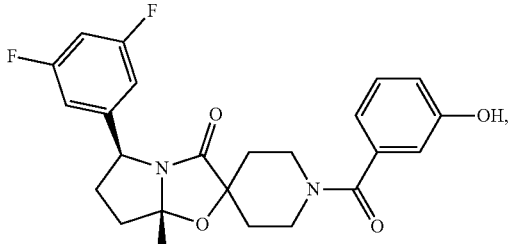
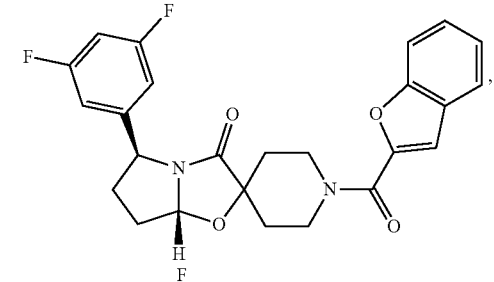
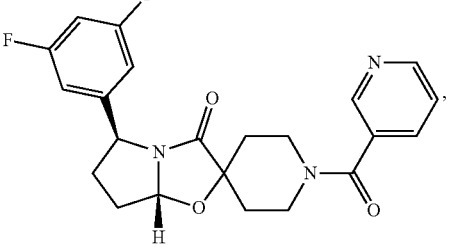

125
-continued
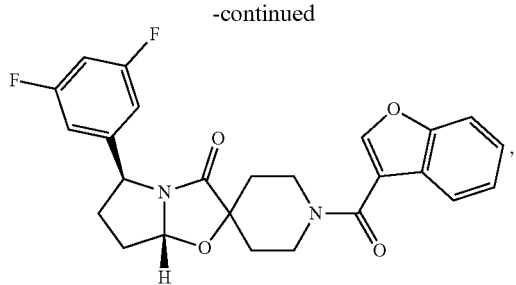
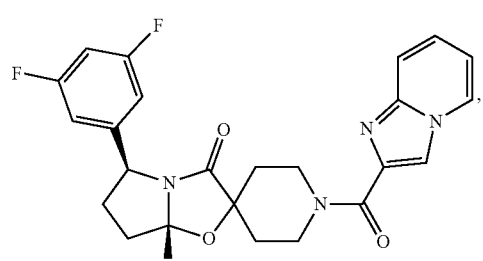
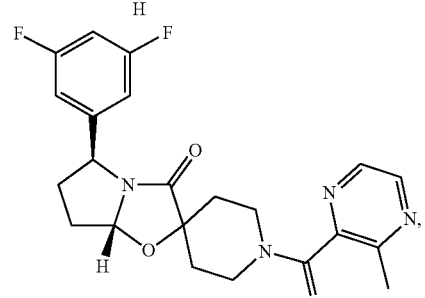
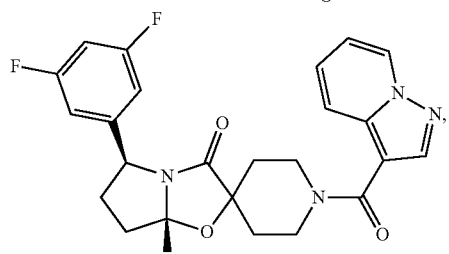
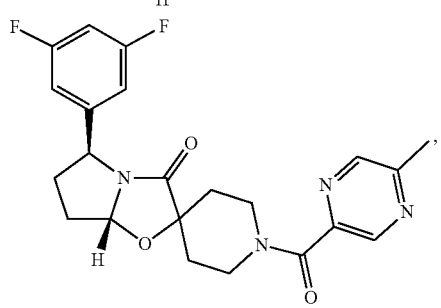
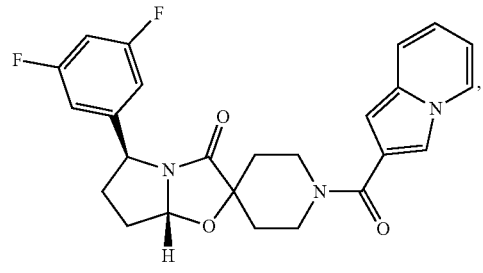
126
-continued
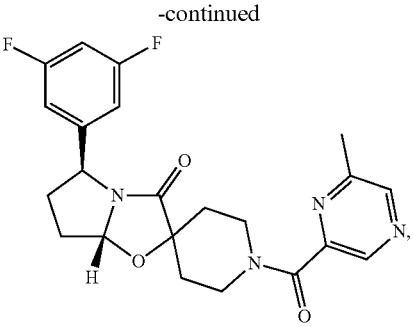
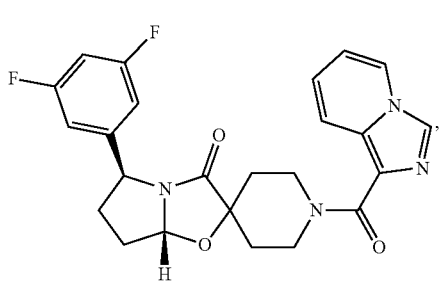
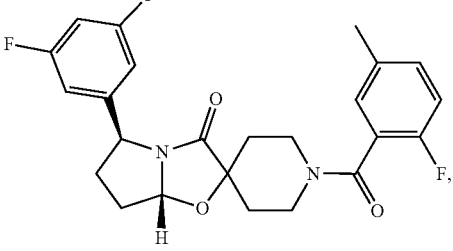
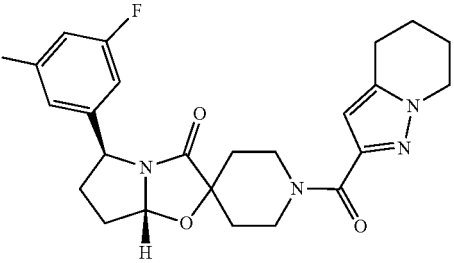
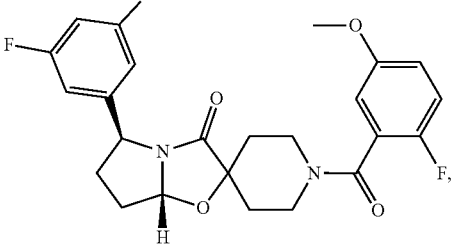
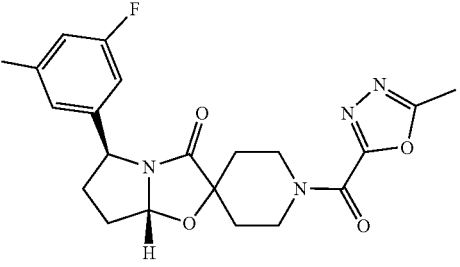

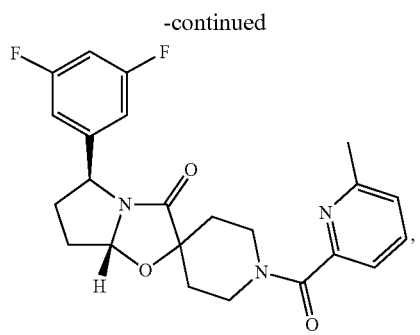
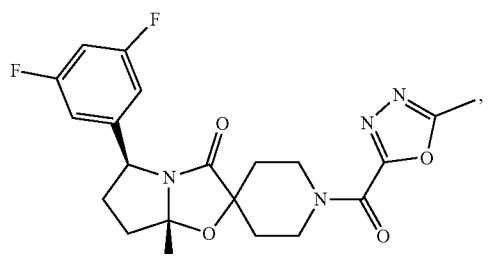
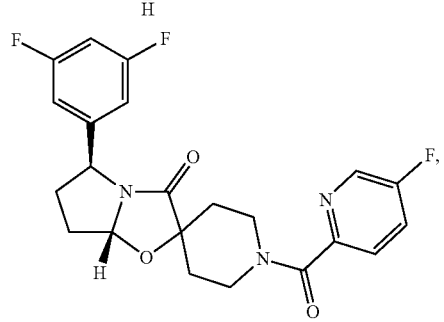
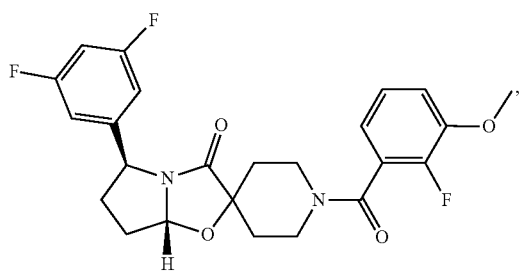
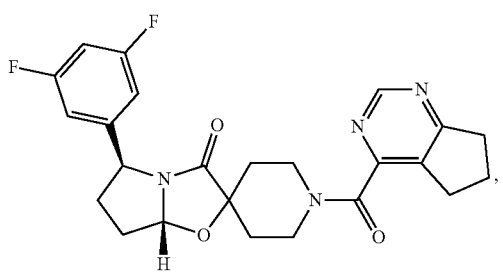
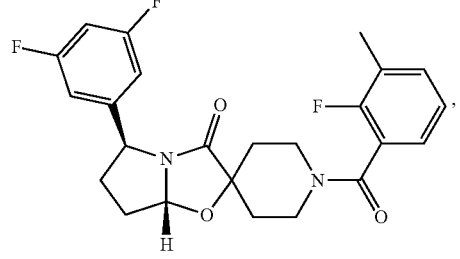
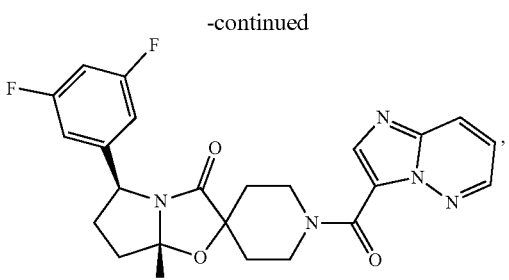
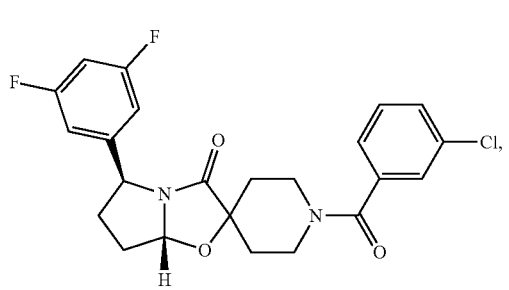
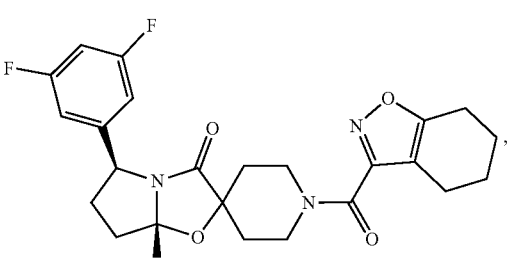
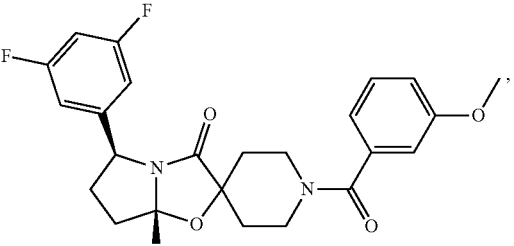
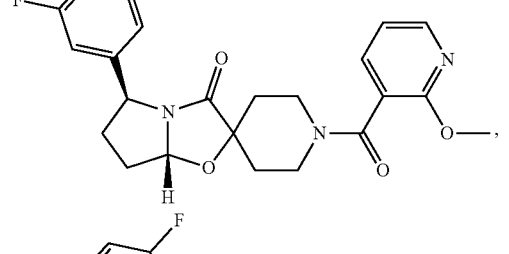
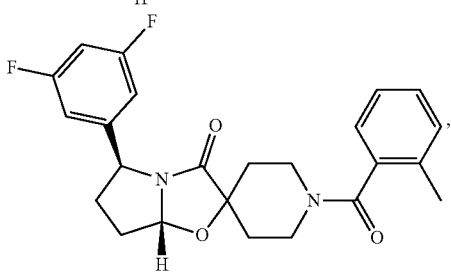

129
-continued
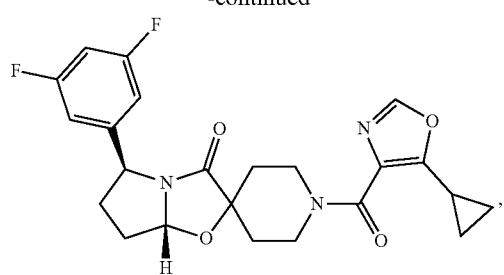
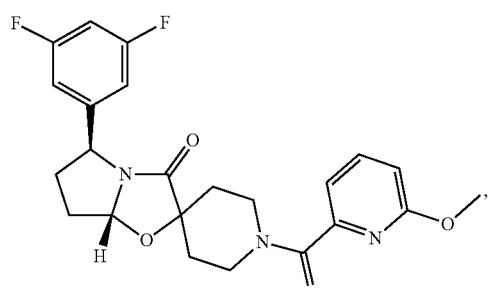
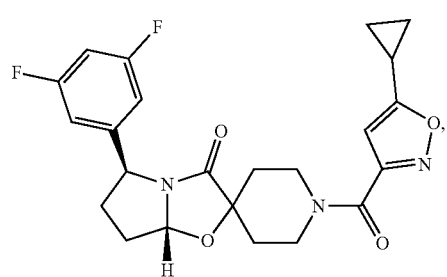
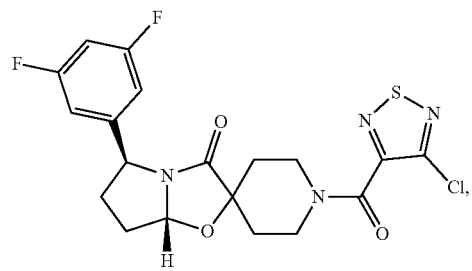
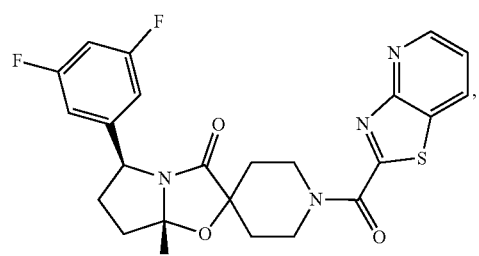
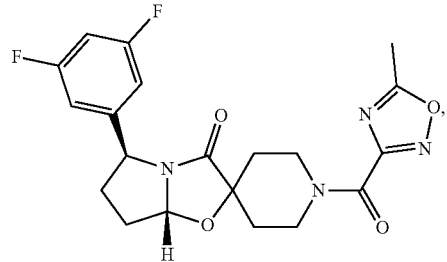
130
-continued
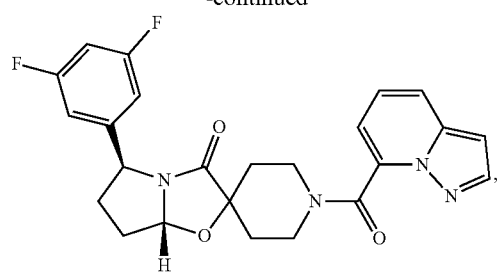
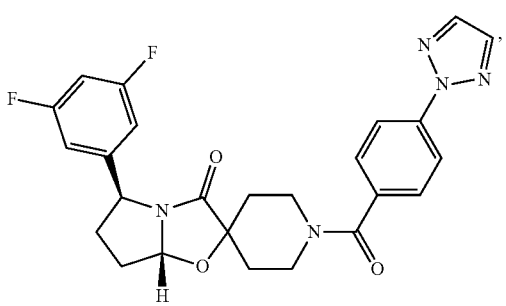
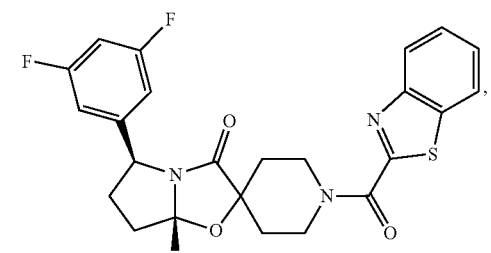
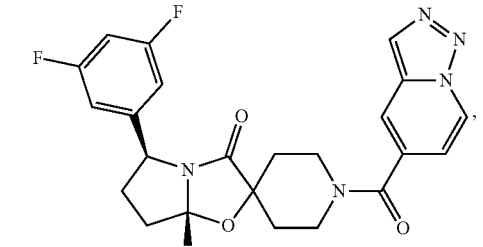
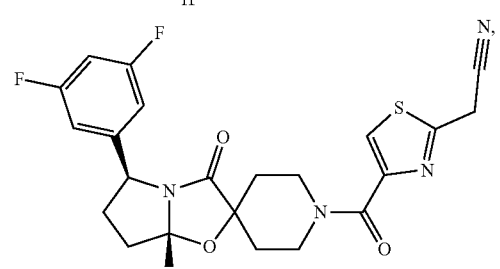
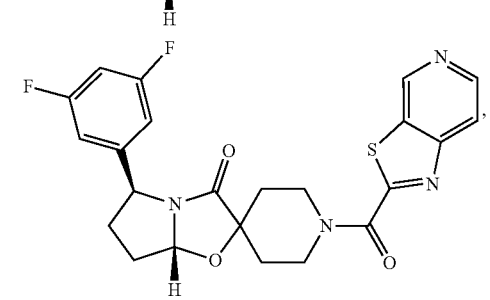

131
-continued
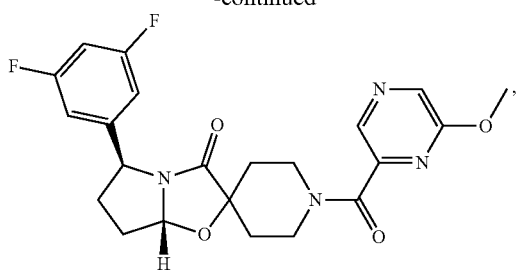
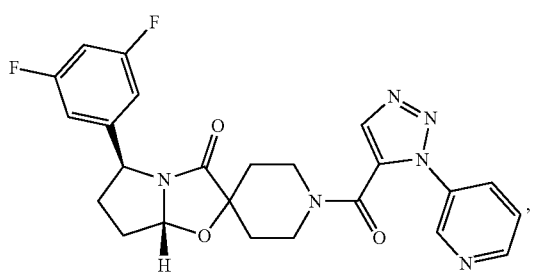
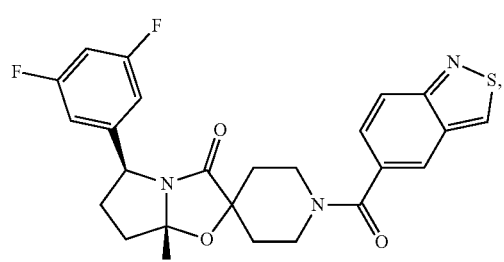
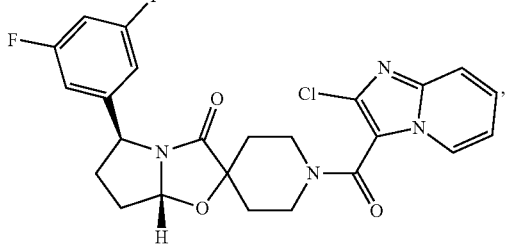
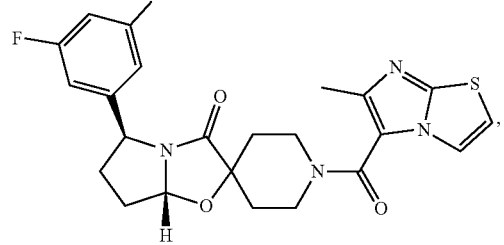
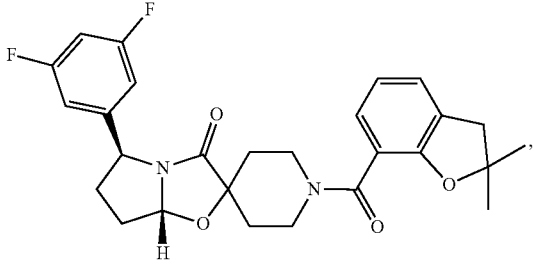
132
-continued
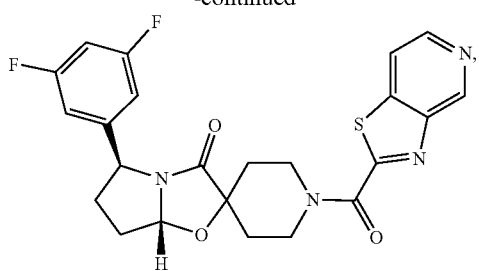
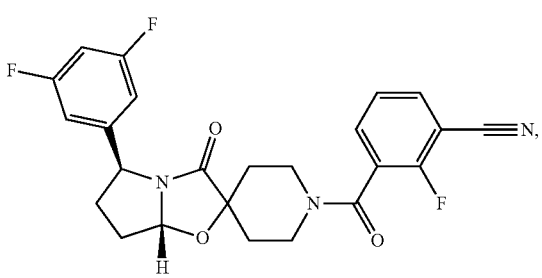
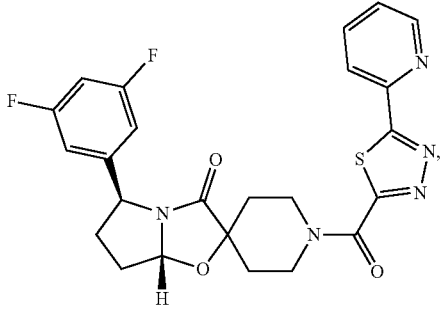
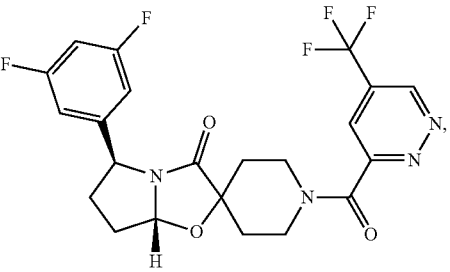
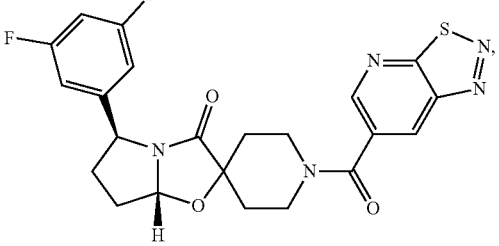
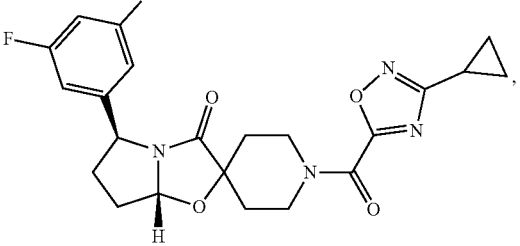

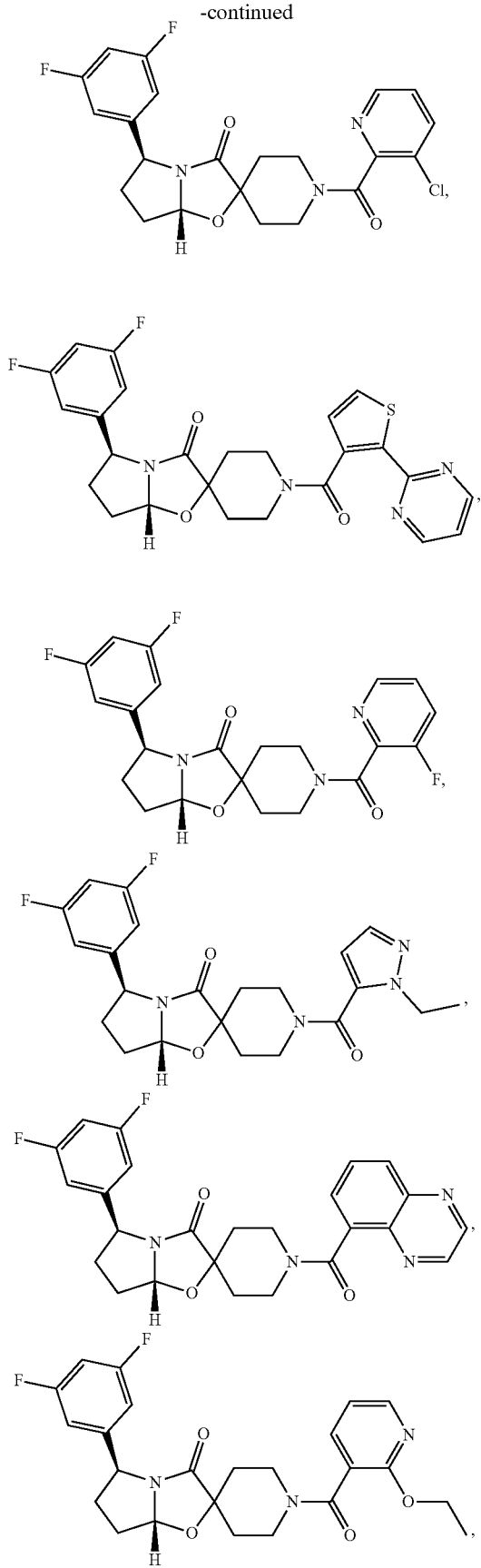
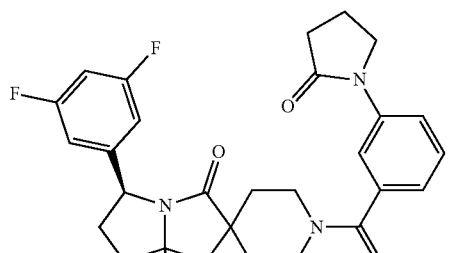
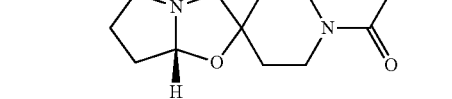

135
-continued
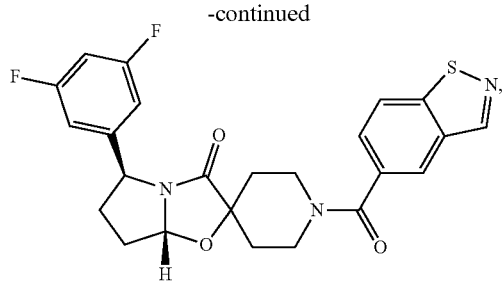
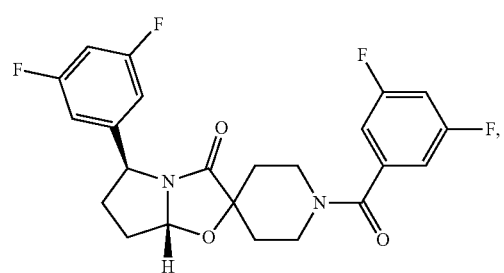
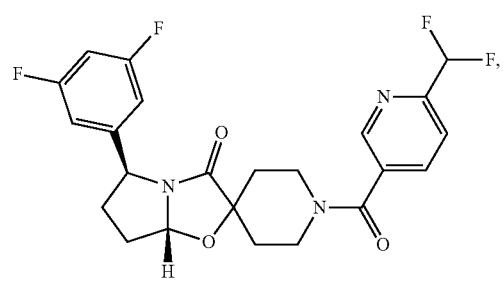
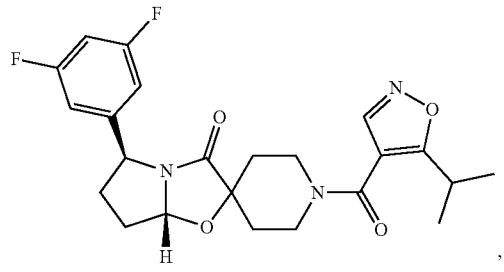
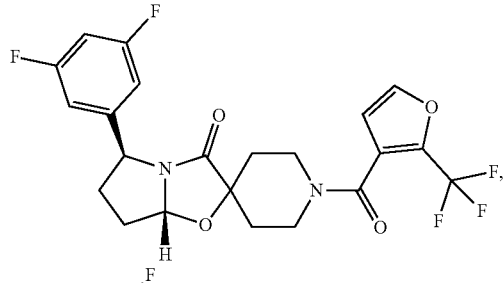
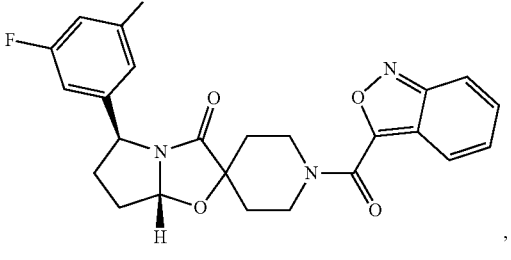
136
-continued
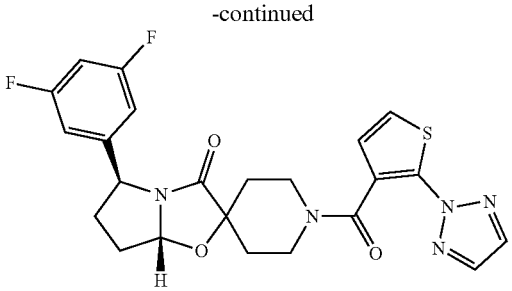
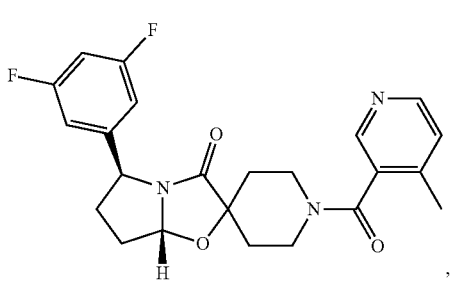
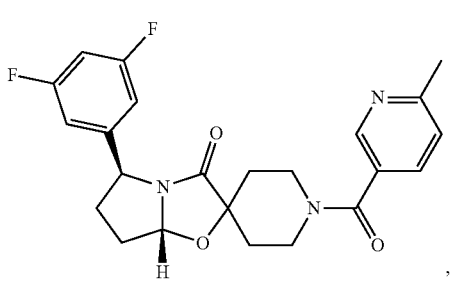
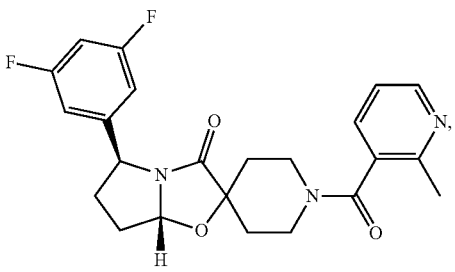
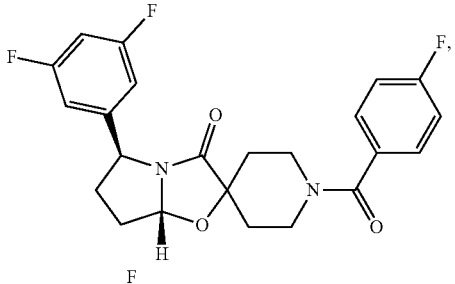
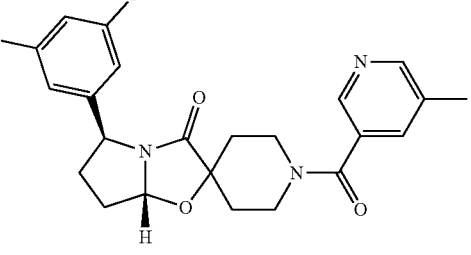

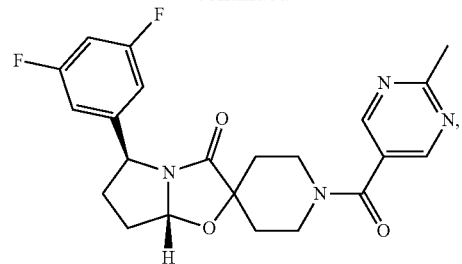
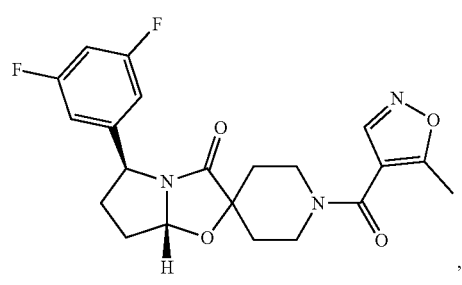
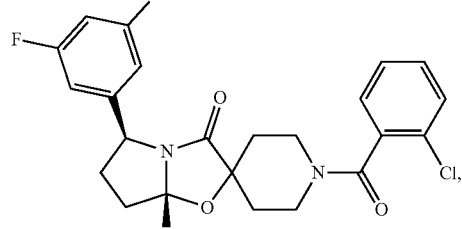
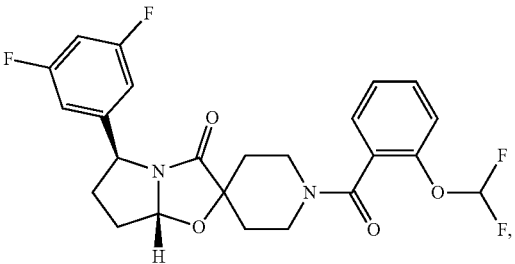
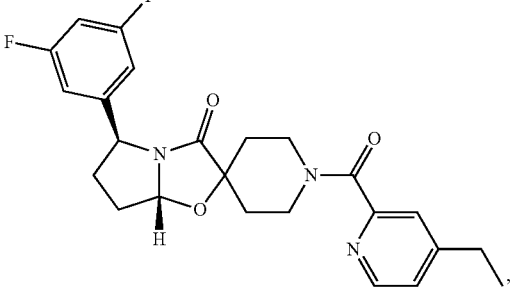
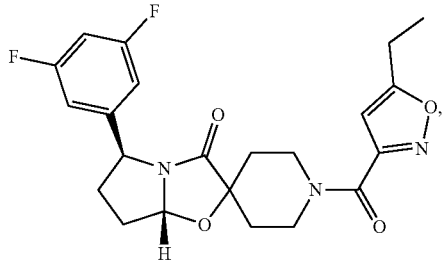
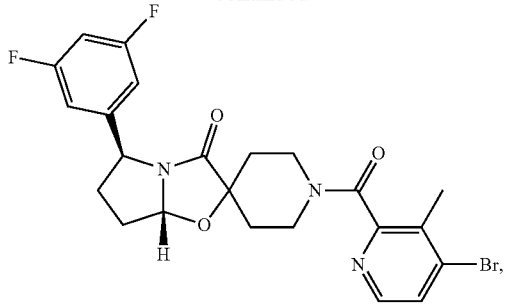
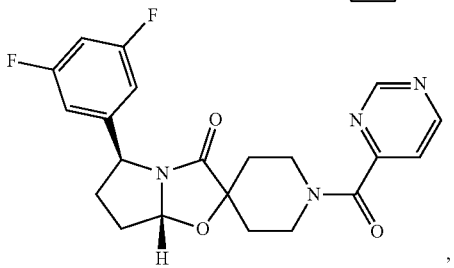
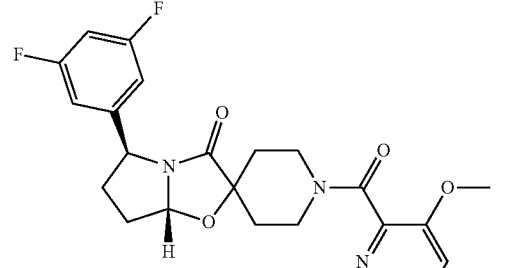
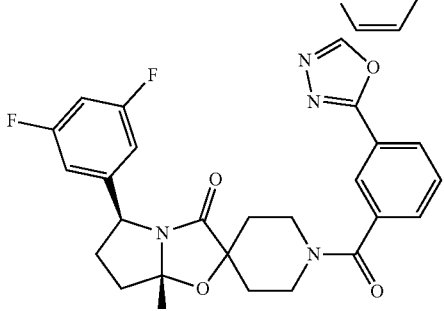
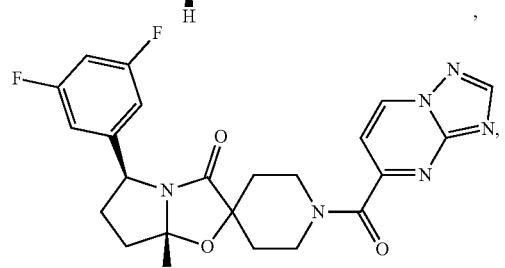
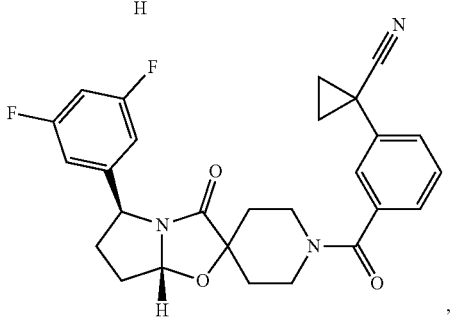

-continued
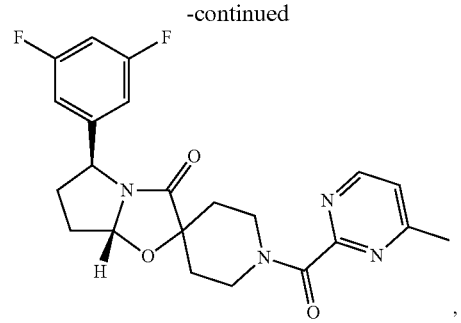
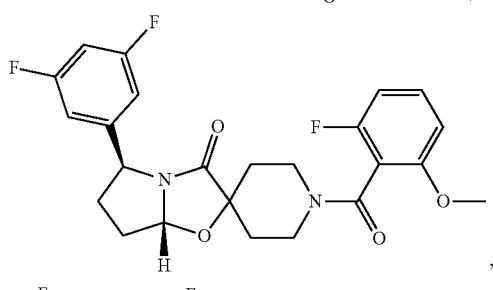
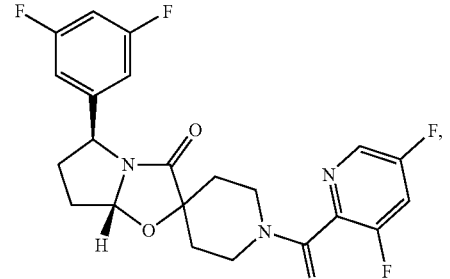
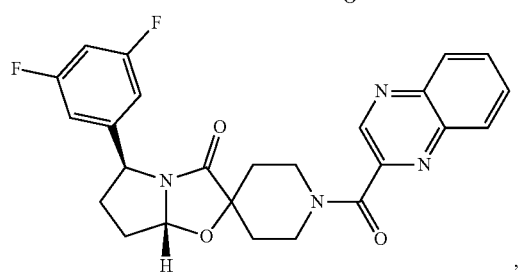
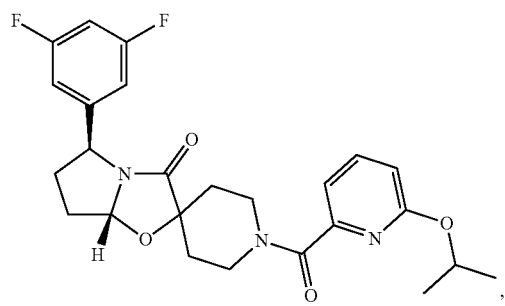
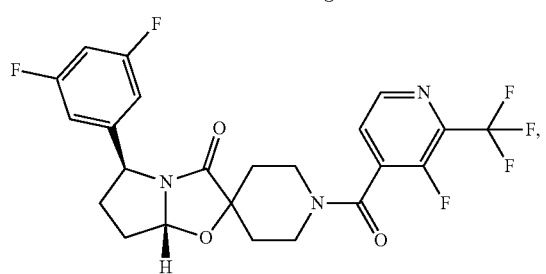
-continued
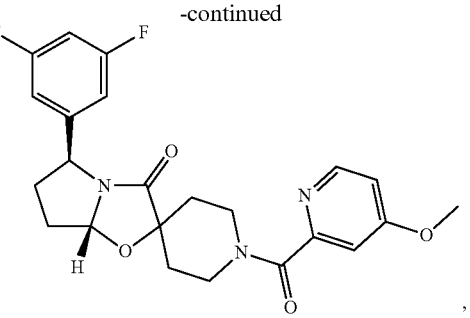
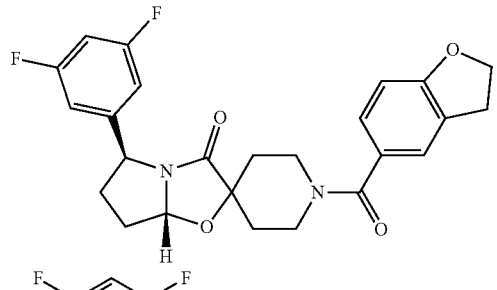
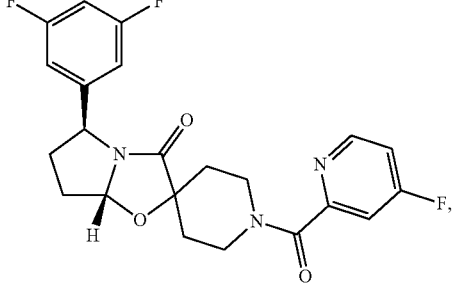
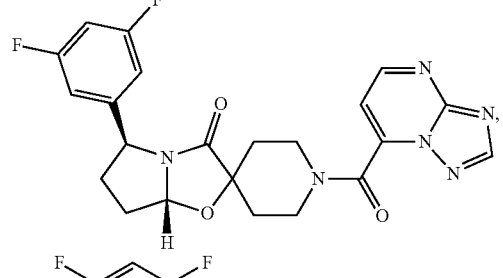
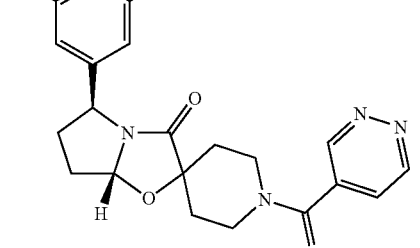
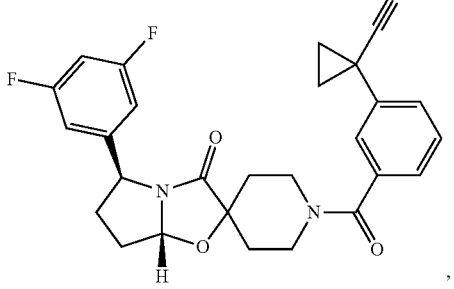

141
-continued
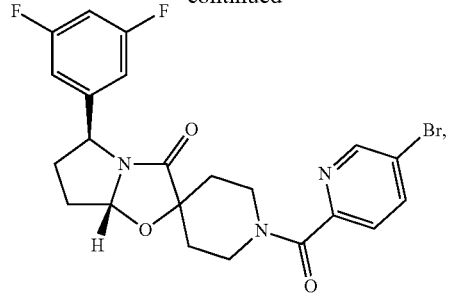
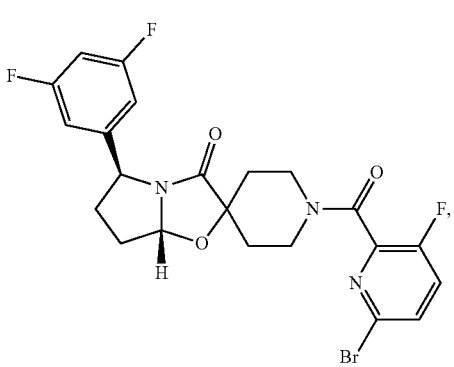
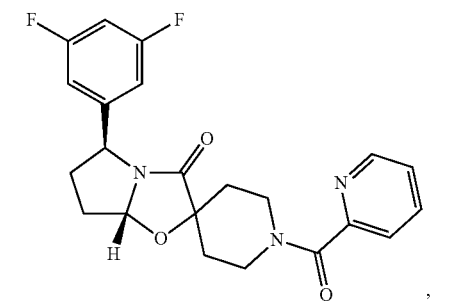
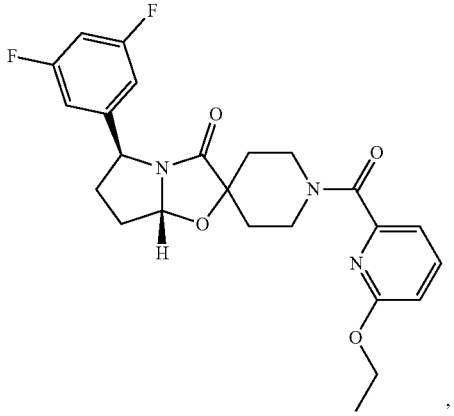
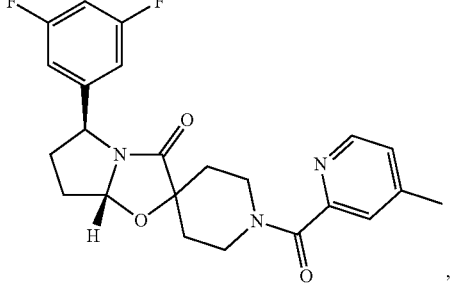
142
-continued
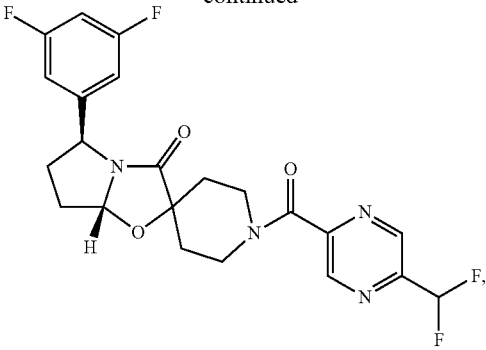
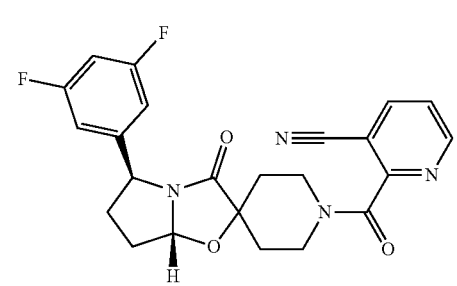
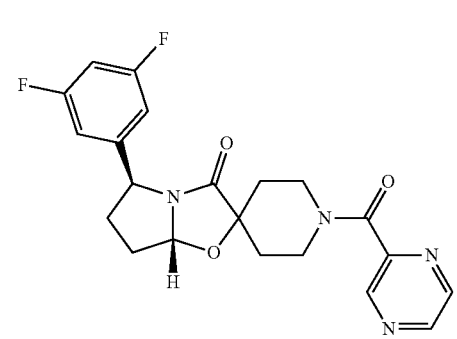
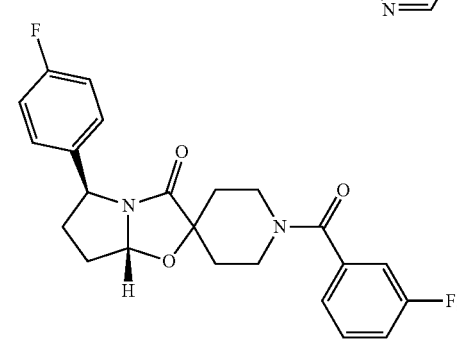
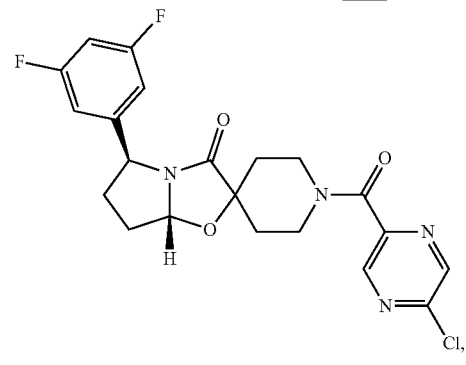

-continued
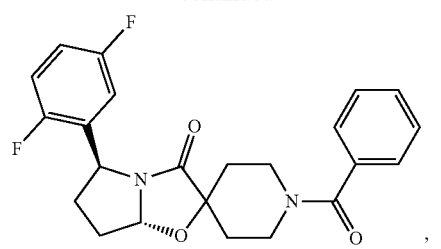
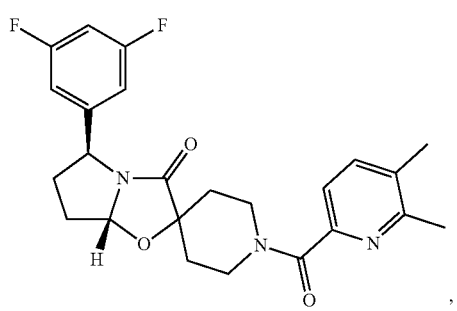
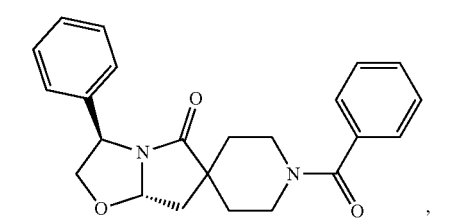
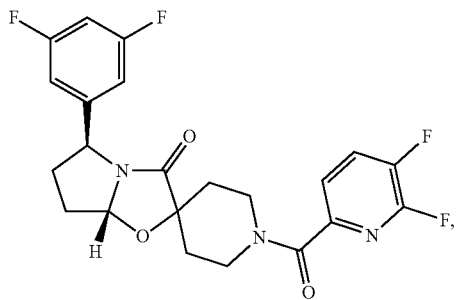
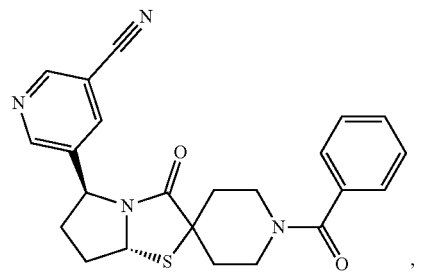
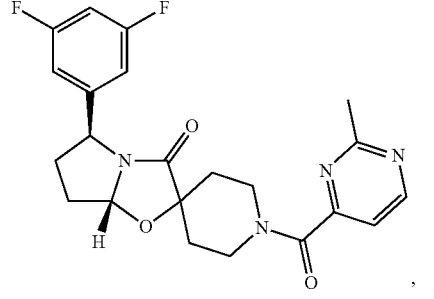
-continued
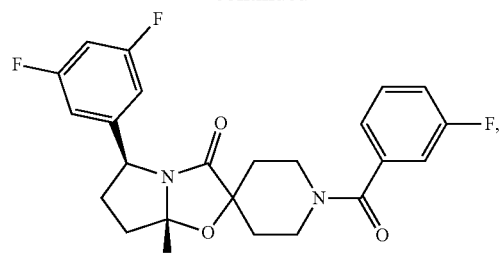
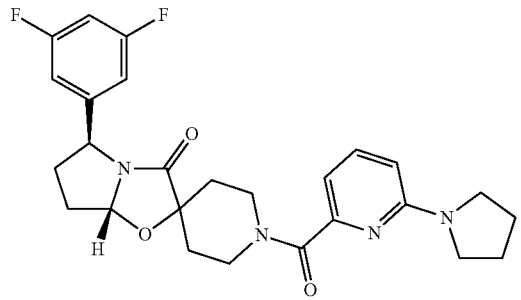
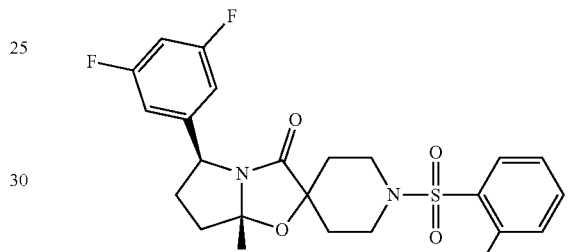
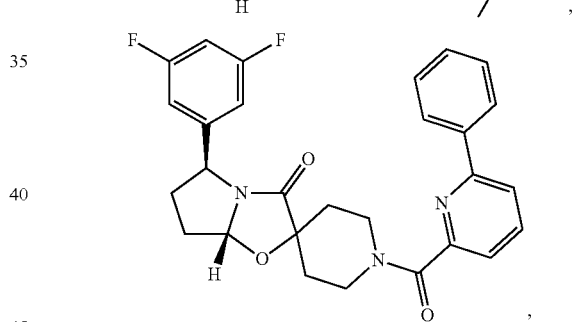
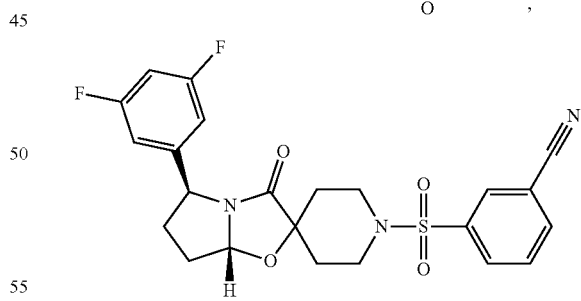
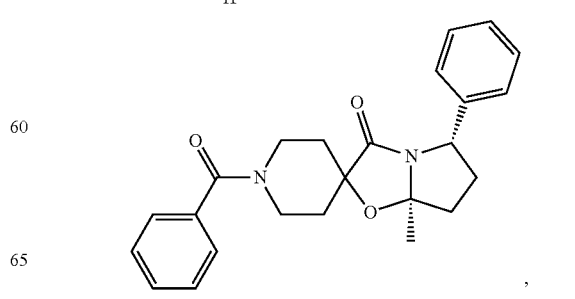

145
-continued

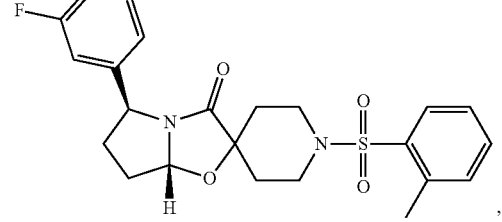
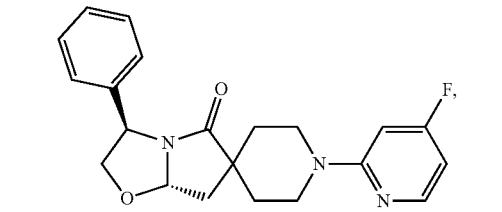
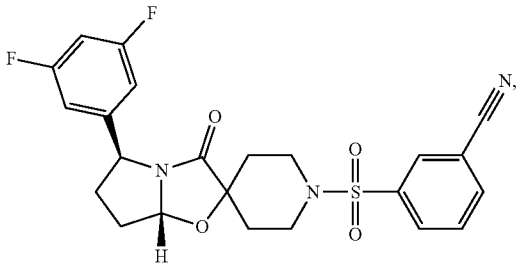
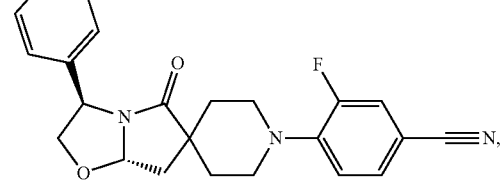
146
-continued
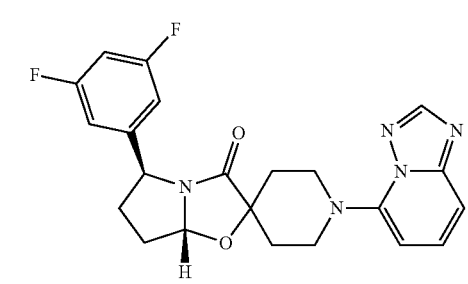
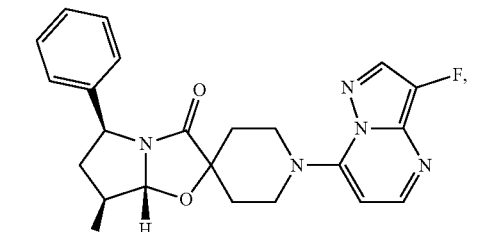
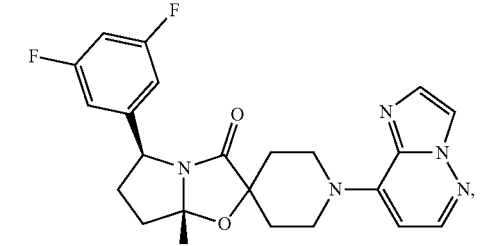
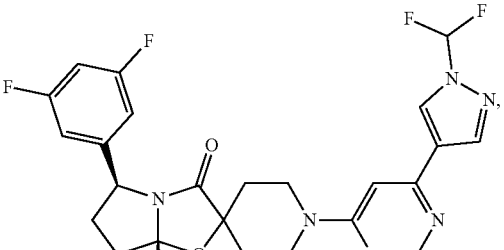
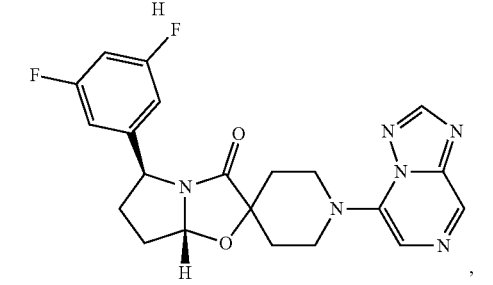

147
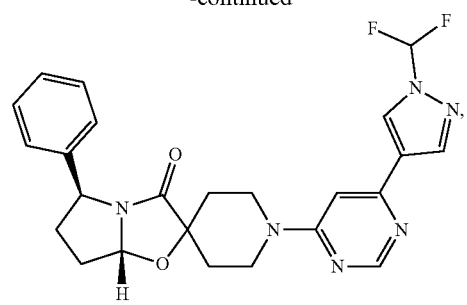
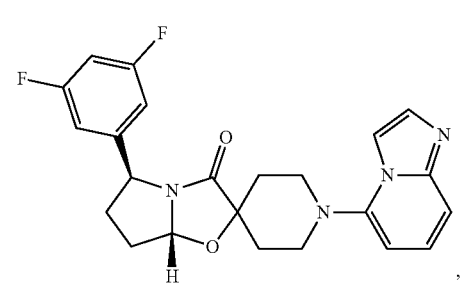
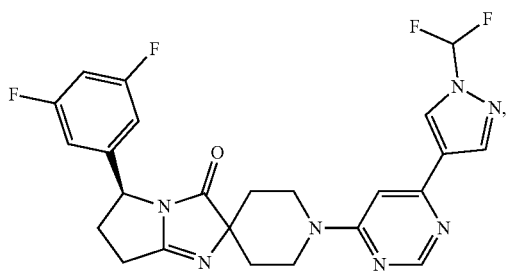
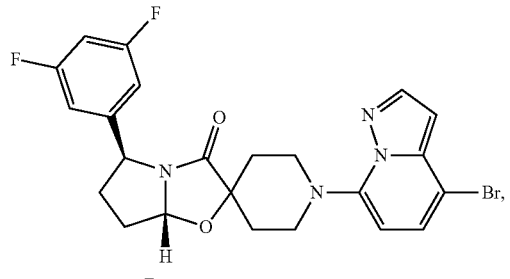
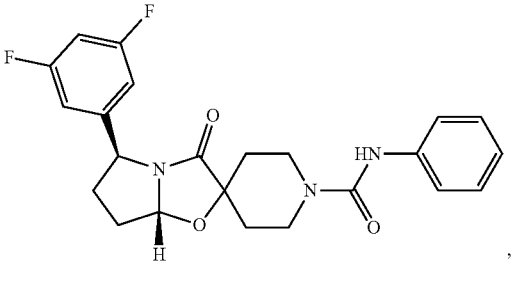
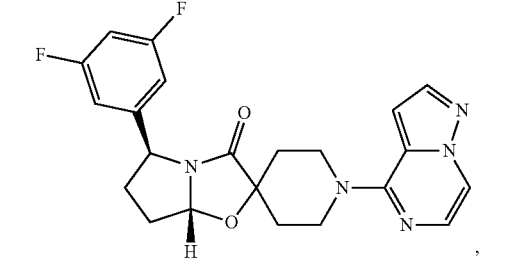
148
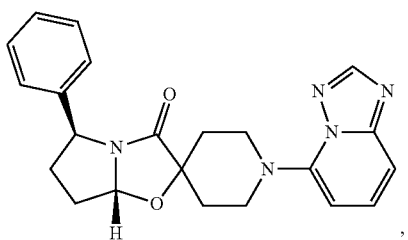
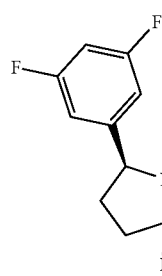
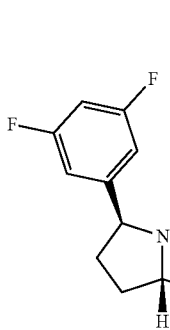
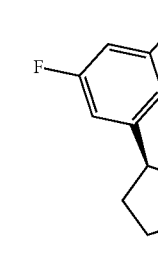
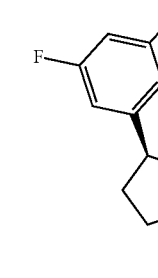
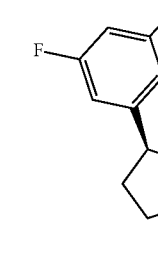

-continued
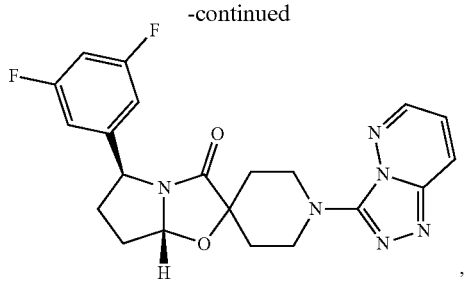
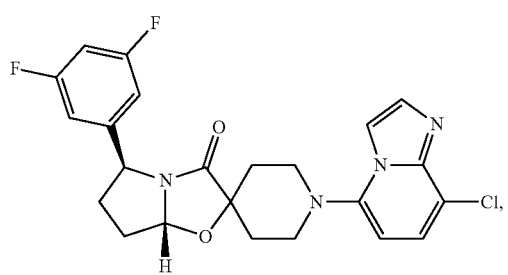
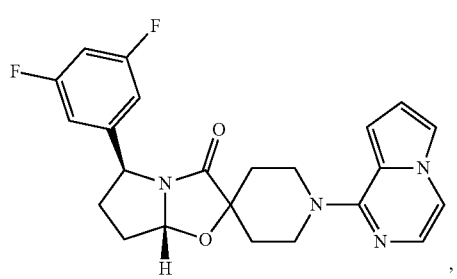
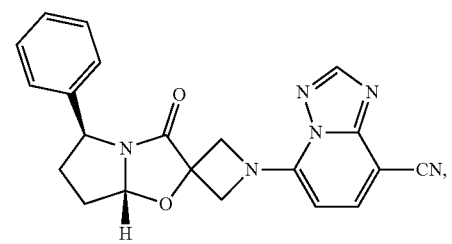
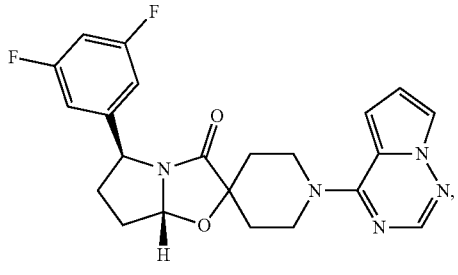
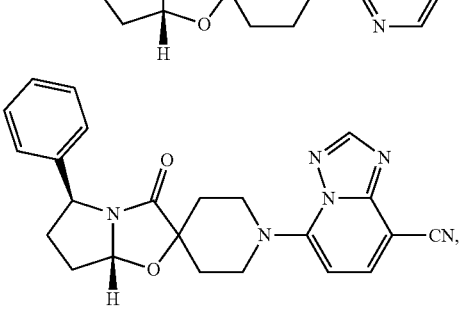
-continued
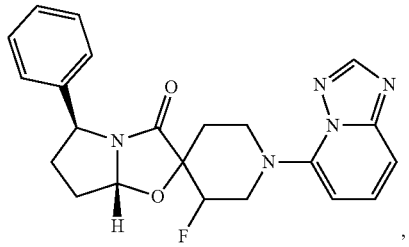
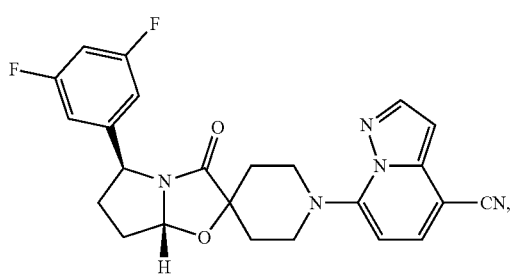
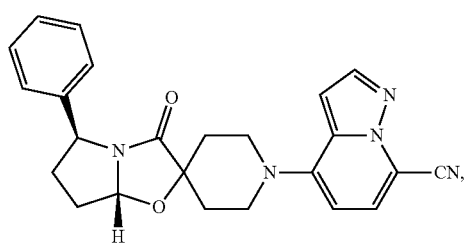
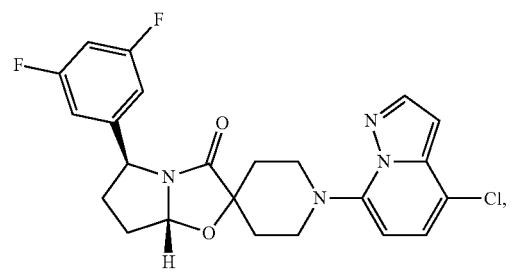
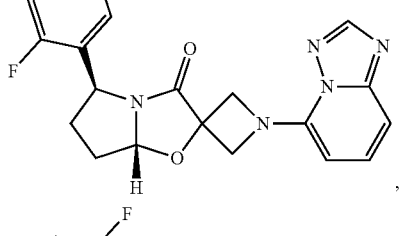
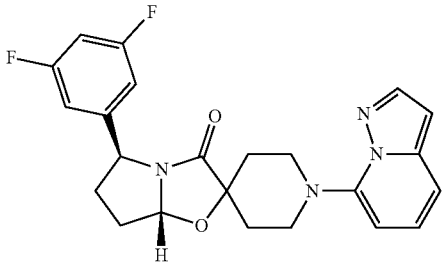

151
-continued
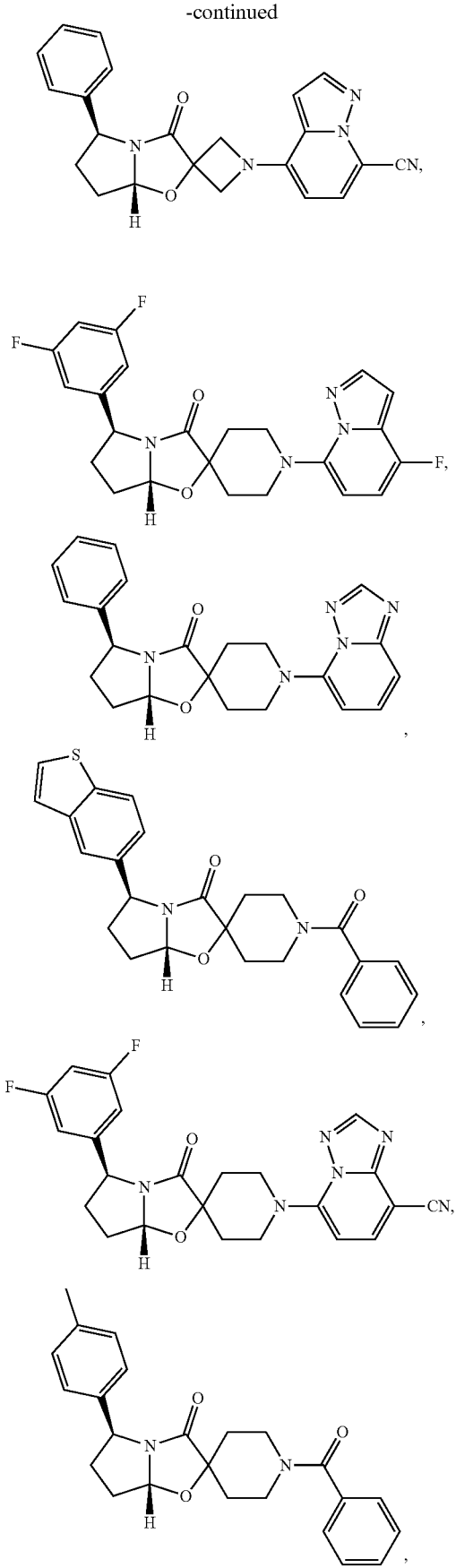
152
-continued
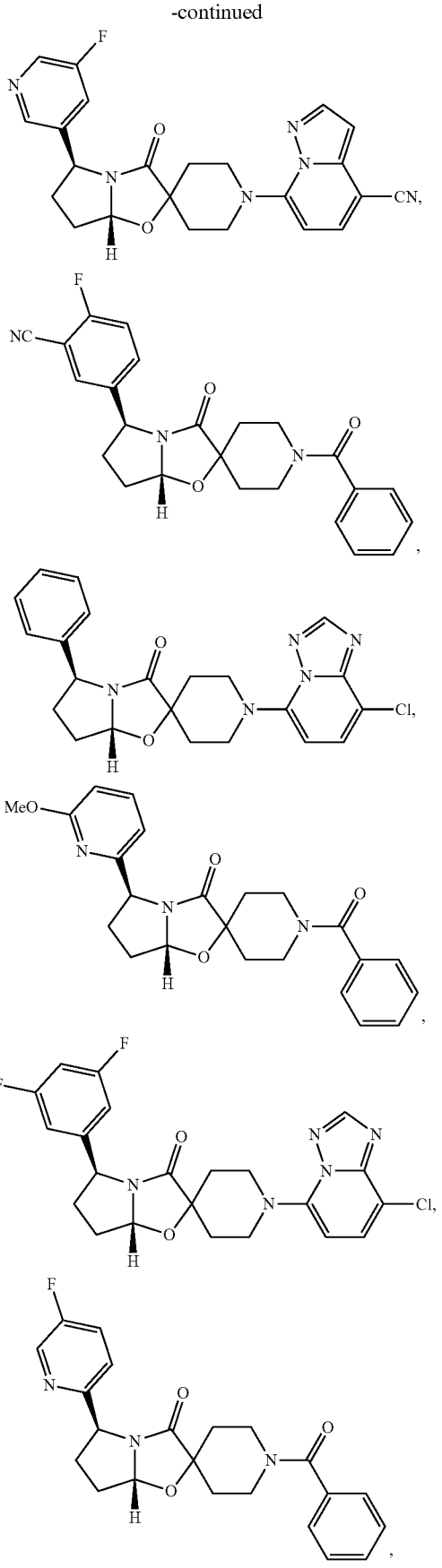

153
-continued
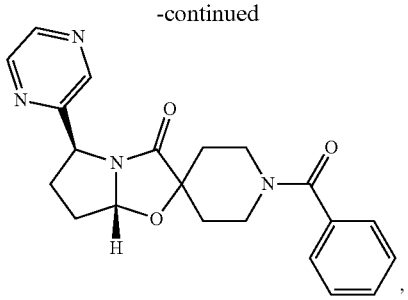,
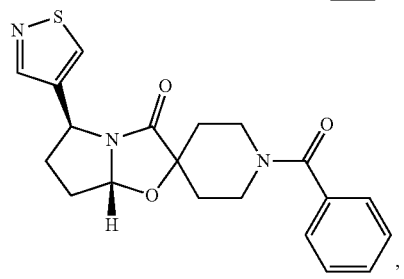,
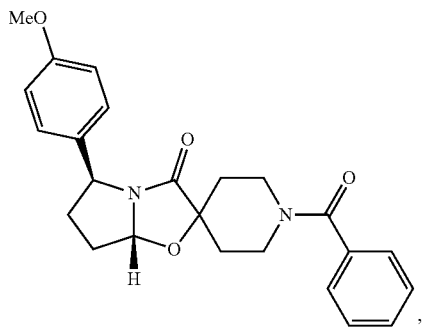,
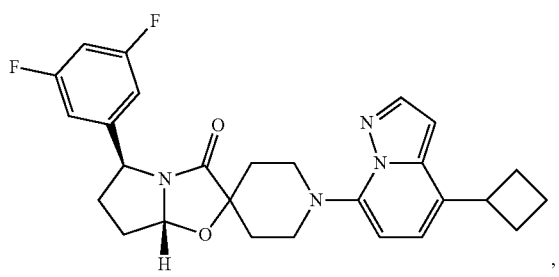,
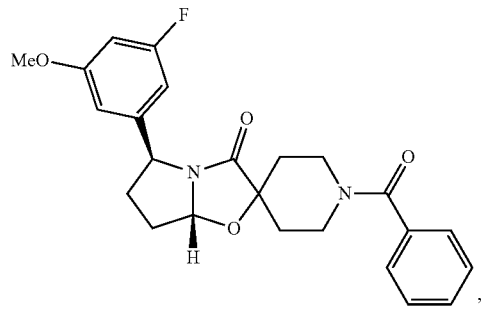,
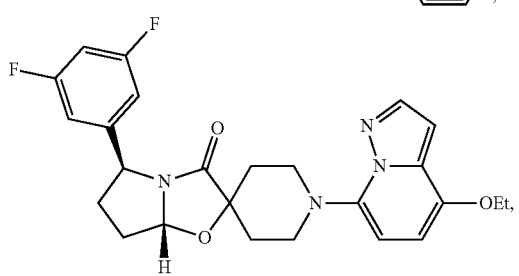,
154
-continued
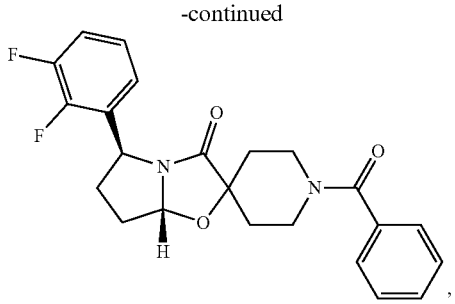,
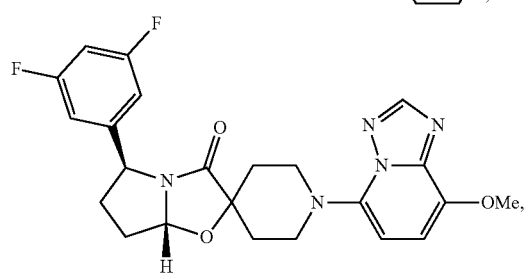,
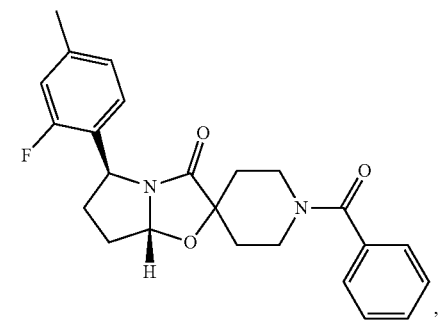,
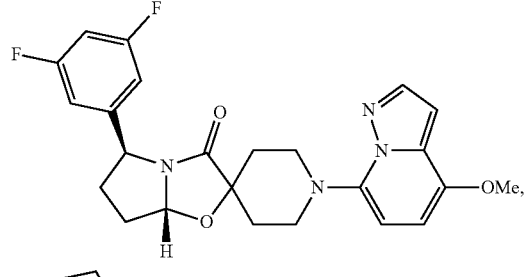,
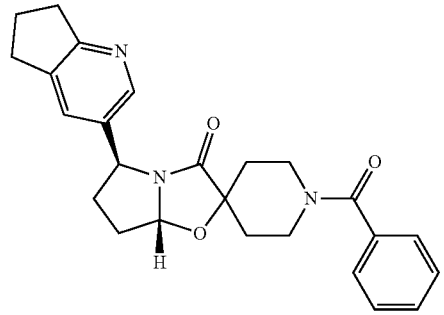,
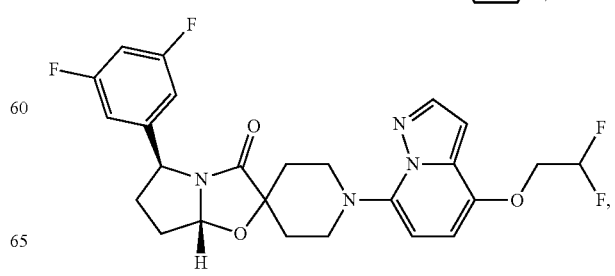, -continued

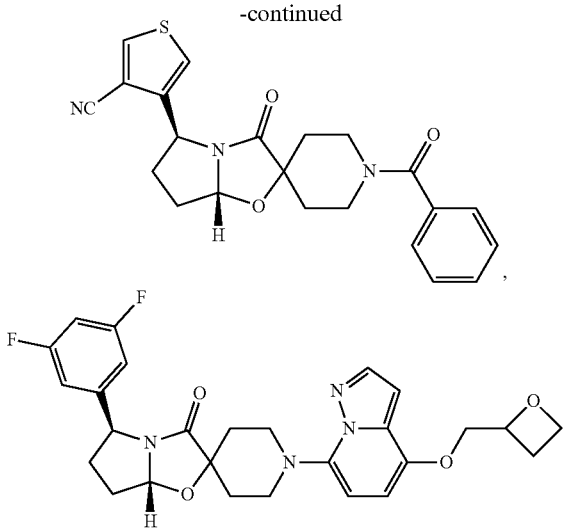

or a pharmaceutically acceptable salt thereof.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "$C_1$-$C_6$alkyl" applies to" $C_1$-$C_6$alkyl"as well as the" $C_1$-$C_6$alkyl"portions of" $C_1$-$C_6$alkylaryl," "halo$C_1$-$C_6$alkyl, "$C_1$-$C_6$alkylheteroaryl," etc.

The term "alkoxy" means an alkyl-O— group in which the alkyl group encompasses straight alkyl having a carbon number of 1 to 10 and branched alkyl having a carbon number of 3 to 10. Non-limiting examples of suitable alkoxy groups include methoxy, ethoxy, n-propoxy, isopropoxy and n-butoxy. The bond to the parent moiety is through the ether oxygen.

"Effective amount" or "therapeutically effective amount" is meant to describe an amount of compound or a composition used in the methods of the present invention effective in inhibiting the above-noted diseases or enzyme activity and thus producing the desired therapeutic, ameliorative, inhibitory or preventative effect. For oral dosing (e.g. capsules or tablets), an "effective amount" of a compound of the invention may be spread across more than one capsule or tablet (so that composition claims still cover a single tablet even if 2 tablets are needed for effective dosing).

The term "halogen" includes fluorine, chlorine, bromine, or iodine.

The term "$C_1$-$C_6$alkyl" encompasses straight alkyl having a carbon number of 1 to 6 and branched alkyl having a carbon number of 3 to 6. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like.

The term "$C_3$-$C_6$cycloalkyl" encompasses bridged, saturated, or unsaturated cycloalkyl groups having 3 to 6 carbons. Examples of cycloalkyl include cyclopropyl, cyclobutyl, cyclopentyl and cyclohexyl.

The term "$C_3$-$C_{10}$cycloalkyl" encompasses bridged, saturated, or unsaturated cycloalkyl groups having 3 to 10 carbons. "Cycloalkyl" also includes non-aromatic rings as well as monocyclic, non-aromatic rings or aromatic rings fused to a saturated cycloalkyl group. Examples of cycloalkyl include cyclopropyl, cyclobutyl, cyclopentyl, cyclohexyl, cycloheptyl, tetrahydronaphthyl, decahydronaphthyl, indanyl and the like. Examples described by structure include,

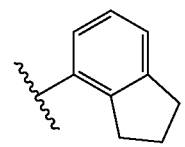

The term "heteroaryl" means a monocyclic or multicyclic, including bicyclic, aromatic heterocycloalkyl that contains at least one ring heteroatom selected from O, S and N. Examples of heteroaryl groups include pyridyl (pyridinyl), oxazolyl, azabenzothiazole, benzothiazole, imidazolyl, triazolyl, furyl, triazinyl, thienyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl, and the like.

The term "heterocycloalkyl" means mono- or bicyclic or bridged, partially unsaturated or saturated rings containing at least one heteroatom selected from N, S and O, each of said rings having from 3 to 10 atoms in which the point of attachment may be carbon or nitrogen. Examples include azetidine, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl, dihydrocyclopentapyridinyl, and the like. The term also includes partially unsaturated monocyclic rings that are not aromatic, such as 2- or 4-pyridones attached through the nitrogen or n-substituted-(1H, 3H)-pyrimidine-2,4-diones (N-substituted uracils). The term also includes bridged rings such as 5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5-diazabicyclo[2.2.2]octyl, 2-azabicyclo[2.2.2]octyl, and 3-azabicyclo[3.2.2]nonyl, and azabicyclo[2.2.1]heptanyl. Examples described by structure include,

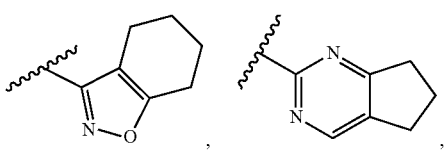

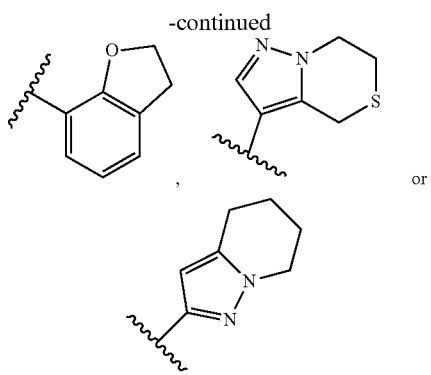

, or

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, n-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, n-ethylmorpholine, n-ethylpiperidinyl, glucamine, glucosamine, histidine, hydrabamine, isopropylamine, lysine, methylglucamine, morpholine, piperazine, piperidinyl, polyamine resins, procaine, purines, theobromine, triethylamine, trimethylamine, tripropylamine, tromethamine, and the like.

The term "patient" refers to a mammalian patient, preferably a human patient, receiving or about to receive medical treatment.

The compounds of the present invention may contain one or more asymmetric centers and can thus occur as racemates, racemic mixtures, single enantiomers, diastereomeric mixtures, and individual diastereomers. The present invention is meant to comprehend all such isomeric forms of these compounds.

Some of the compounds described herein contain olefinic double bonds, and unless specified otherwise, are meant to include both E and Z geometric isomers.

Some of the compounds described herein contain substituted cycloalkanes having cis- and trans-isomers, and unless specified otherwise, are meant to include both cis- and trans-geometric isomers.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that the present invention is meant to include the pharmaceutically acceptable salts, and also salts that are not pharmaceutically acceptable, of the compounds described herein, when they are used as precursors to the free compounds or their pharmaceutically acceptable salts or in other synthetic manipulations.

Solvates, and in particular, the hydrates of the compounds of the structural formulas described herein are included in the present invention as well.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. A $^3H$, $^{11}C$, $^{18}F$ labeled compound may be used for PET or SPECT or other imaging studies. Isotopically-enriched compounds can be prepared without undue experimentation by conventional techniques well known to those skilled in the art or by processes analogous to those described in the Schemes and Examples herein using appropriate isotopically-enriched reagents or Intermediates.

It should be noted that chemically unstable compounds are excluded from the embodiments contained herein.

Methods of Treatment

The compounds described herein may be particularly useful for the prevention, treatment or amelioration of RIPK1-mediated diseases or disorders. Such RIPK1-mediated diseases or disorders are likely to be regulated at least in part by programmed necrosis, apoptosis or the production of inflammatory cytokines.

The compounds of the Formulae described herein, or pharmaceutically acceptable salts thereof, may be particularly useful for the treatment of the following RIPK1-mediated diseases or disorders: inflammatory bowel disease (including Crohn's disease and ulcerative colitis), psoriasis, retinal detachment, retinal degeneration, retinitis pigmentosa, macular degeneration, age-related macular degeneration, pancreatitis, atopic dermatitis, arthritis (including rheumatoid arthritis, spondyloarthritis, gout, systemic onset juvenile idiopathic arthritis (SoJIA), psoriatic arthritis), lupus, systemic lupus erythematosus (SLE), Sjogren's syndrome, systemic scleroderma, anti-phospholipid syndrome (APS), vasculitis, osteoarthritis, liver damage/diseases, autoimmune hepatitis, autoimmune hepatobiliary diseases, primary sclerosing cholangitis (PSC), acetaminophen toxicity, hepatotoxicity), non-alcoholic steatohepatitis (NASH), alcoholic steatohepatitis (ASH), autoimmune hepatitis, non-alcoholic fatty liver disease (NAFLD), kidney damage/injury (nephritis, renal transplant, surgery, administration of nephrotoxic drugs e.g., cisplatin, acute kidney injury (AKI)), Celiac disease, autoimmune idiopathic thrombocytopenic purpura (autoimmune ITP), transplant rejection (rejection of transplant organs, tissues and cells), ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), progressive supranuclear palsy (PSP), neonatal brain injury, neonatal hypoxic brain injury, traumatic brain injury, allergic diseases (including asthma and atopic dermatitis), peripheral nerve injury, burns, multiple sclerosis, type I diabetes, type II diabetes, obesity, Wegener's granulomatosis, pulmonary sarcoidosis, Behcet's disease, interleukin-I converting enzyme (ICE, also known as caspase-1) associated fever syndrome, chronic obstructive pulmonary disease (COPD), cigarette smoke-induced damage, cystic fibrosis, tumor necrosis factor receptor-associated periodic syndrome (TRAPS), a neoplastic tumor, melanoma, metastasis, breast cancer, non-small cell lung carcinoma (NSCLC), radiation induced necrosis, ischemic kidney damage, ophthalmologic ischemia, intracerebral hemorrhage, subarachnoid hemorrhage, periodontitis, NEMO-mutations (mutations of NF-kappa-B essential modulator gene (also known as IKK gamma or IKKG)), particularly, NEMO-deficiency syndrome, HOIL-1 deficiency ((also known as RBCK1) heme-oxidized IRP 2 ubiquitin ligase-1 deficiency), linear ubiquitin chain assembly complex (LUBAC) deficiency syndrome, hematological and solid organ malignancies, bacterial infections and viral infections (such as influenza, *Staphylococcus*, and *Mycobacterium* (tuberculosis)), and Lysosomal storage diseases (particularly, Gaucher disease, and including GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs, and Wolman disease), spinal cord injury, Stevens-Johnson syndrome, fibrosis, complement-mediated cytotoxicity, toxic epidermal necrolysis, and/or for the treatment of cells ex vivo to preserve vitality and function.

The compounds of the Formulae described herein, and pharmaceutically acceptable salts thereof, may be useful for the treatment of glaucoma.

The compounds of the Formulae described herein, and pharmaceutically acceptable salts thereof, may be particularly useful for treatment of pancreatic ductal adenocarcinoma, hepatocellular carcinoma, mesothelioma, or melanoma.

The compounds of the Formulae described herein, and pharmaceutically acceptable salts thereof, may be particularly useful for the treatment of the following RIPK1-mediated disease or disorder: rheumatoid arthritis, inflammatory bowel disease (including Crohn's disease and ulcerative colitis), and psoriasis.

The treatment of the above-noted diseases/disorders may concern, more specifically, the amelioration of organ injury or damage sustained as a result of the noted diseases/disorders. For example, the compounds of this invention may be particularly useful for amelioration of brain tissue injury or damage following ischemic brain injury or traumatic brain injury, or for amelioration of heart tissue injury or damage following myocardial infarction, or for amelioration of brain tissue injury or damage associated with Huntington's disease, Alzheimer's disease or Parkinson's disease, or for amelioration of liver tissue injury or damage associated with non-alcoholic steatohepatitis, alcoholic steatohepatitis, autoimmune hepatitis autoimmune hepatobiliary diseases, or primary sclerosing cholangitis, or overdose of acetaminophen. The compounds of this invention may be particularly useful for the amelioration of organ injury or damage sustained as a result of radiation therapy, or amelioration of spinal tissue injury or damage following spinal cord injury or amelioration of liver tissue injury or damage associated acute liver failure. The compounds of this invention may be particularly useful for amelioration of auditory disorders, such as noise-induced hearing loss or auditory disorders following the administration of ototoxic drugs or substances e.g., cisplatin.

The compounds of this invention (i.e., Compounds of Formula I, II, III, IV or V) may be particularly useful for amelioration of solid organ tissue (particularly kidney, liver, and heart and/or lung) injury or damage following transplant or the administration of nephrotoxic drugs or substances e.g., cisplatin. It will be understood that amelioration of such tissue damage may be achieved where possible, by pre-treatment with a compound of the Formulae described herein, or a pharmaceutically acceptable salt thereof; for example, by pre-treatment of a patient prior to administration of cisplatin or pre-treatment of an organ or the organ recipient prior to transplant surgery. Amelioration of such tissue damage may be achieved by treatment with a compound of the Formulae described herein, or a pharmaceutically acceptable salt thereof, during transplant surgery.

Amelioration of such tissue damage may also be achieved by short-term treatment of a patient with a compound of the Formulae described herein, or a pharmaceutically acceptable salt thereof, after transplant surgery.

In one embodiment, the compounds of the Formulae described herein, and pharmaceutically acceptable salts thereof, may be useful for the treatment of retinal detachment, macular degeneration, and retinitis pigmentosa.

In another embodiment, the compounds of the Formulae described herein, and pharmaceutically acceptable salts thereof, may be useful for the treatment of multiple sclerosis.

In one embodiment, the compounds of the Formulae described herein, and pharmaceutically acceptable salts thereof, may be useful for the treatment of traumatic brain injury.

In another embodiment, the compounds of the Formulae described herein, and pharmaceutically acceptable salts thereof, may be useful for the treatment of Huntington's Disease or Niemann-Pick disease.

In another embodiment, the compounds of the Formulae described herein, and pharmaceutically acceptable salts thereof, may be useful for the treatment of ALS, PSP, and Alzheimer's disease.

In another embodiment, the compounds of the Formulae described herein, and pharmaceutically acceptable salts thereof, may be useful for the treatment of age-related macular degeneration.

The treatment of retinal detachment, macular degeneration, retinitis pigmentosa, multiple sclerosis, traumatic brain injury, Huntington's Disease, Alzheimer's Disease, amyotrophic lateral sclerosis, and Niemann-Pick disease may concern, more specifically, the amelioration of organ injury or damage sustained as a result of these diseases/disorders. For example, the compounds described herein may be particularly useful for amelioration of brain tissue injury or damage following traumatic brain injury, or for amelioration of brain tissue injury or damage associated of Huntington's Disease, Alzheimer's Disease, amyotrophic lateral sclerosis, and Niemann-Pick disease.

In another embodiment, the compounds of the Formulae described herein, and pharmaceutically acceptable salts thereof, may be useful for the treatment of retinal detachment, macular degeneration, and retinitis pigmentosa, and the amelioration of brain tissue injury or damage as a result of multiple sclerosis, traumatic brain injury, Huntington's Disease, Alzheimer's Disease, amyotrophic lateral sclerosis, and Niemann-Pick disease.

In another embodiment, the compounds of the Formulae described herein, and pharmaceutically acceptable salts thereof, may be useful for the treatment of Crohn's disease, ulcerative colitis, psoriasis, rheumatoid arthritis, spondyloarthritis, systemic onset juvenile idiopathic arthritis (SoJIA), and osteoarthritis.

In yet another embodiment, the compounds of the Formulae described herein, and pharmaceutically acceptable salts thereof, may be useful for the treatment of psoriasis, rheumatoid arthritis, and ulcerative and colitis.

In another embodiment, the compounds of the Formulae described herein, and pharmaceutically acceptable salts thereof, may be useful for the treatment of lupus, inflammatory bowel disease (IBD), Crohn's disease, and ulcerative colitis.

In another embodiment, the compounds of the Formulae described herein, and pharmaceutically acceptable salts thereof, may be useful for the treatment of cerebrovascular accident (CVA, stroke), Huntington's disease, Alzheimer's disease, ALS, traumatic brain injury, multiple sclerosis, Gaucher disease, Niemann-Pick disease, and spinal cord injury.

In another embodiment, the compounds of the Formulae described herein, and pharmaceutically acceptable salts thereof, may be useful for the treatment of ALS.

In another embodiment, the compounds of the Formulae described herein, and pharmaceutically acceptable salts thereof, may be useful for the treatment of multiple sclerosis.

In another embodiment, the compounds of the Formulae described herein, and pharmaceutically acceptable salts thereof, may be useful for the treatment of pancreatic ductal adenocarcinoma (PDAC), metastasis, melanoma, breast cancer, non-small cell lung carcinoma (NSCLC), and radiation induced necrosis.

In another embodiment, the compounds of the Formulae described herein, and pharmaceutically acceptable salts thereof, may be useful for the treatment of PDAC, metastasis, melanoma, breast cancer, and nNSCLC.

In another embodiment, the compounds of the Formulae described herein, and pharmaceutically acceptable salts thereof, may be useful for the treatment of PDAC.

In another embodiment, the compounds of the Formulae described herein, and pharmaceutically acceptable salts thereof, may be useful for the treatment of intracerebral hemorrhage and subarachnoid hemorrhage.

In another embodiment, the compounds of the Formulae described herein, and pharmaceutically acceptable salts thereof, may be useful for the treatment of type II diabetes and obesity.

In another embodiment, the compounds of the Formulae described herein, and pharmaceutically acceptable salts thereof, may be useful for the treatment of atherosclerosis.

In another embodiment, the compounds of the Formulae described herein, or a pharmaceutically acceptable salt thereof, may be useful for the treatment of vasculitis.

In another embodiment, the compounds of the Formulae described herein, and pharmaceutically acceptable salts thereof, may be useful for the treatment of dependent inflammation and cell death that occurs in inherited and sporadic diseases including Alzheimer's disease, amyotrophic lateral sclerosis, multiple sclerosis, Parkinson's disease, chronic traumatic encephalopathy, rheumatoid arthritis, ulcerative colitis, inflammatory bowel disease, psoriasis as well as acute tissue injury caused by stroke, traumatic brain injury, encephalitis.

In another embodiment, the compounds of the Formulae described herein, and pharmaceutically acceptable salts thereof, may be useful for the treatment of ischemic kidney damage, ophthalmologic ischemia, intracerebral hemorrhage, and subarachnoid hemorrhage.

In another embodiment, the compounds of the Formulae described herein, and pharmaceutically acceptable salts thereof, may be useful for the treatment of non-alcoholic steatohepatitis (NASH), alcoholic steatohepatitis (ASH), autoimmune hepatitis, and non-alcoholic fatty liver disease (NAFLD).

The compounds of the invention, particularly the compounds of the Formulae described herein, and pharmaceutically acceptable salts thereof, may be particularly useful for the treatment of the RIPK1-mediated, cancer-related diseases or disorders. Gong et al., The role of necroptosis in cancer biology and therapy, Molecular Cancer (2019) 18:100. In one aspect the human has a solid tumor. In one aspect the tumor is selected from head and neck cancer, gastric cancer, melanoma, renal cell carcinoma (RCC), esophageal cancer, NSCLC, prostate cancer, colorectal cancer, ovarian cancer, pancreatic cancer, and pancreatic ductal adenocarcinoma. In one aspect the human has one or more of the following: colorectal cancer (CRC), esophageal cancer, cervical, bladder, breast cancer, head and neck cancer, ovarian cancer, melanoma, RCC, EC squamous cell carcinoma, non-small cell lung carcinoma, mesothelioma, prostate cancer, and pancreatic ductal adenocarcinoma. In another aspect, the human has a liquid tumor such as diffuse large B cell lymphoma (DLBCL), multiple myeloma, chronic lyphomblastic leukemia (CLL), follicular lymphoma, acute myeloid leukemia and chronic myelogenous leukemia.

The present disclosure also relates to a method for treating or lessening the severity of a cancer selected from: brain (gliomas), glioblastomas, astrocytomas, Bannayan-Zonana syndrome, Cowden disease, Lhermitte-Duclos disease, breast cancer, triple negative breast cancer, inflammatory breast cancer, Wilm's tumor, Ewing's sarcoma, Rhabdomyosarcoma, ependymoma, medulloblastoma, colon cancer, head and neck cancer (including squamous cell carcinoma of head and neck), kidney cancer, lung cancer (including lung squamous cell carcinoma, lung adenocarcinoma, lung small cell carcinoma, and non-small cell lung carcinoma), liver cancer (including hepatocellular carcinoma), melanoma, ovarian cancer, pancreatic cancer (including squamous pancreatic cancer), prostate cancer, sarcoma, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma megakaryoblastic leukemia, multiple myeloma, acute megakaryocytic leukemia, promyelocytic leukemia, erythroleukemia, malignant lymphoma, Hodgkin's lymphoma, Non-Hodgkin's lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, cancer of the uterus, renal cancer (including kidney clear cell cancer, kidney papillary cancer, renal cell carcinoma), mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like. Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate grade (or aggressive) or high-grade (very aggressive). Indolent B cell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphomas (T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues"

include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

Thus, in one aspect, the invention relates to a method for treating any of the RIPK1-mediated diseases or disorders described herein comprising administering to a patient in need thereof an effective amount of a compound of Formula I, II, III, IV, or V, or a pharmaceutically acceptable salt thereof. In another embodiment, the method comprises administering to a patient in need thereof a pharmaceutical composition comprising an effective amount of a pharmaceutical composition comprising an effective amount compound of any of Formulae I, II, III, IV, or V, or a pharmaceutically acceptable salt thereof, and a pharmaceutically acceptable carrier.

The invention further relates to the use of a compound of Formula I, II, III, IV, or V, or a pharmaceutically acceptable salt thereof, to treat any of the diseases or disorders described herein in a patient in need thereof. In another embodiment, the invention relates to the use of a pharmaceutical composition comprising a compound of Formula I, II, III, IV, or V, or a pharmaceutically acceptable salt thereof, and a pharmaceutically acceptable carrier, to treat any of the diseases or disorders described herein in a patient in need thereof Pharmaceutical Compositions Compounds described herein may be administered orally or parenterally. As formulated into a dosage form suitable for administration, the compounds described herein can be used as a pharmaceutical composition for the prevention, treatment, or remedy of the above diseases.

Thus, the invention relates to a pharmaceutical composition comprising an effective amount of a compound of Formula I, II, III, IV, or V, as defined herein, or a pharmaceutically acceptable salt thereof, and a pharmaceutically acceptable carrier. The pharmaceutical composition may further comprise an effective amount of another active agent for the treatment of the same or a different disease or disorder. In one embodiment, the additional therapeutic agent is effective against RIPK1-mediated diseases or disorders.

In clinical use of the compounds described herein, usually, the compound is formulated into various preparations together with pharmaceutically acceptable additives according to the dosage form and may then be administered. By "pharmaceutically acceptable" it is meant the additive, carrier, diluent or excipient must be compatible with the other ingredients of the formulation and not deleterious to the recipient thereof. As such, various additives ordinarily used in the field of pharmaceutical preparations are usable. Specific examples thereof include gelatin, lactose, sucrose, titanium oxide, starch, crystalline cellulose, hydroxypropyl methylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, hydroxypropyl cyclodextrin, and the like.

Preparations to be formed with those additives include, for example, solid preparations such as tablets, capsules, granules, powders and suppositories; and liquid preparations such as syrups, elixirs and injections. These may be formulated according to conventional methods known in the field of pharmaceutical preparations. The liquid preparations may also be in such a form that may be dissolved or suspended in water or in any other suitable medium in their use. Especially for injections, if desired, the preparations may be dissolved or suspended in physiological saline or glucose liquid, and a buffer or a preservative may be optionally added thereto.

The pharmaceutical compositions may contain a compound of the invention (i.e., a compound of any of Formulas I, II, III, IV, or V) in an amount of from 1 to 99.9% by weight, preferably from 1 to 60% by weight of the composition. The compositions may further contain any other therapeutically-effective compounds.

In case where the compounds of the invention are used for prevention or treatment for the above-mentioned diseases, the dose and the dosing frequency may be varied, depending on the sex, the age, the body weight and the disease condition of the patient and on the type and the range of the intended remedial effect. In general, when orally administered, the dose may be from 0.001 to 50 mg/kg of body weight/day, and it may be administered at a time or in several times. In specific embodiments, the dose is from about 0.01 to about 25 mg/kg/day, in particular embodiments, from about 0.05 to about 10 mg/kg/day. For oral administration, the compositions are preferably provided in the form of tablets or capsules containing from 0.01 mg to 1,000 mg. In specific embodiments, the dose is 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 or 1,000 milligrams of a compound described herein. This dosage regimen may be adjusted to provide the optimal therapeutic response.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds described herein or the other drugs may have utility, where the combination of the drugs together are safer or more effective than either drug alone. Such other drug(s) may be administered in an amount commonly used therefore, contemporaneously or sequentially with a compound described herein or a pharmaceutically acceptable salt thereof. When a compound described herein is used contemporaneously with one or more other drugs, the pharmaceutical composition may in specific embodiments contain such other drugs and the compound described herein or its pharmaceutically acceptable salt in unit dosage form. However, the combination therapy may also include therapies in which the compound described herein or its pharmaceutically acceptable salt and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound described herein or a pharmaceutically acceptable salt thereof.

Abbreviations

The abbreviations used herein have the following tabulated meanings. Abbreviations not tabulated below have their meanings as commonly used unless specifically stated otherwise.

| | |
|---|---|
| 9-BBN | 9-Borabicyclo[3.3.1]nonane |
| ACN | acetonitrile |
| AcOH | acetic acid |
| Boc | tert-butoxycarbamate |
| $Boc_2O$ | di-tert-butyl dicarbonate |
| $CH_3NO_2$ | nitromethane |
| $CH_3SO_3H$ | methane sulfonic acid |
| $CuCl_3$ | copper III chloride |
| DCM | dichloromethane |
| DIAD | diisopropyl azodicarboxylate |
| DIEA | diisopropylethylamine |
| DIPEA | diisopropylethylamine |
| DMA | dimethylacetamide |
| DMF | dimethylformamide |
| DMSO | dimethylsulfoxide |
| DMP | Dess-Martin periodinane |
| dtbbpy | 4,4'-di-tert-butyl-2,2'-dipyridyl |
| EI | electron ionization |
| Et | ethyl |
| EtOAc | ethyl acetate |
| EtOH | ethanol |
| $FeSO_4$ | ferrous sulfate |
| $H_2O$ | water |
| HATU | (1-[bis(dimethylamino)methylene]-1H-1,2,3-triazolo[4,5-b]pyridinium 3-oxide hexafluorophosphate |
| HCl | hydrochloric acid |
| $^1$H NMR | proton nuclear magnetic resonance |
| HOBt | hydroxybenzotriazole |
| HPLC | high performance liquid chromatography |
| Hunig's Base | diisopropylethylamine |
| $Ir[dF(CF_3)ppy]_2(dtbpy)$ | [4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) |
| $K_2CO_3$ | potassium carbonate |
| $K_4Fe(CN)_6 \cdot 3H_2O$ | potassium ferrocyanide trihydrate |
| LC/MS | liquid chromatography coupled to mass spectrometer |
| LiOH | lithium hydroxide |
| $MgSO_4$ | magnesium Sulfate |
| MeCN | acetonitrile |
| MeOH | methanol |
| MHz | megahertz |
| MS | mass spectrum |
| Ms-Cl | methanesulfonyl chloride (mesyl chloride) |
| MTBE | methyl tert-butyl ether |
| $NaHCO_3$ | Sodium bicarbonate |
| $Na_2SO_4$ | Sodium sulfate |
| NaOH | Sodium hydroxide |
| $NaBH_4$ | Sodium borohydride |
| NBS | N-bromosuccinamide |
| NCS | N-chlorosuccinamide |
| $NH_4Cl$ | ammonium chloride |
| $NH_4HCO_3$ | ammonium bicabonate |
| $NH_4OH$ | ammonium hydroxide |
| $Ni(dtbbpy)Cl_2$ | [4,4'-Bis(1,1-dimethylethyl)-2,2'-bipyridine] nickel (II) dichloride |
| $NiCl_2$ | Nickel chloride |
| NMR | nuclear magnetic resonance |
| o/n | Overnight |
| RT | room temperature |
| Selectfluor | 1-chloromethyl-4-fluoro-1,4-diazoniabicyclo[2.2.2]octane bis(tetrafluoroborate) |
| SFC | Supercritical fluid chromatography |
| SnAr | Nucleophilic Aromatic Substitution |
| TEA | Triethylamine |
| TFA | trifluoroacetic acid |
| THF | tetrahydrofuran |
| TLC | thin layer chromatography |
| TsOH | toluene sulfonic acid |
| XPhos-Pd-G3 | (2-dicyclohexylphosphino-2',4',6'-triisopropyl-1,1'-biphenyl)[2-(2'-amino-1,1'-biphenyl)]palladium(II) methanesulfonate |
| $ZnI_2$ | Zinc iodide |

General Synthetic Schemes

General Synthetic Scheme I

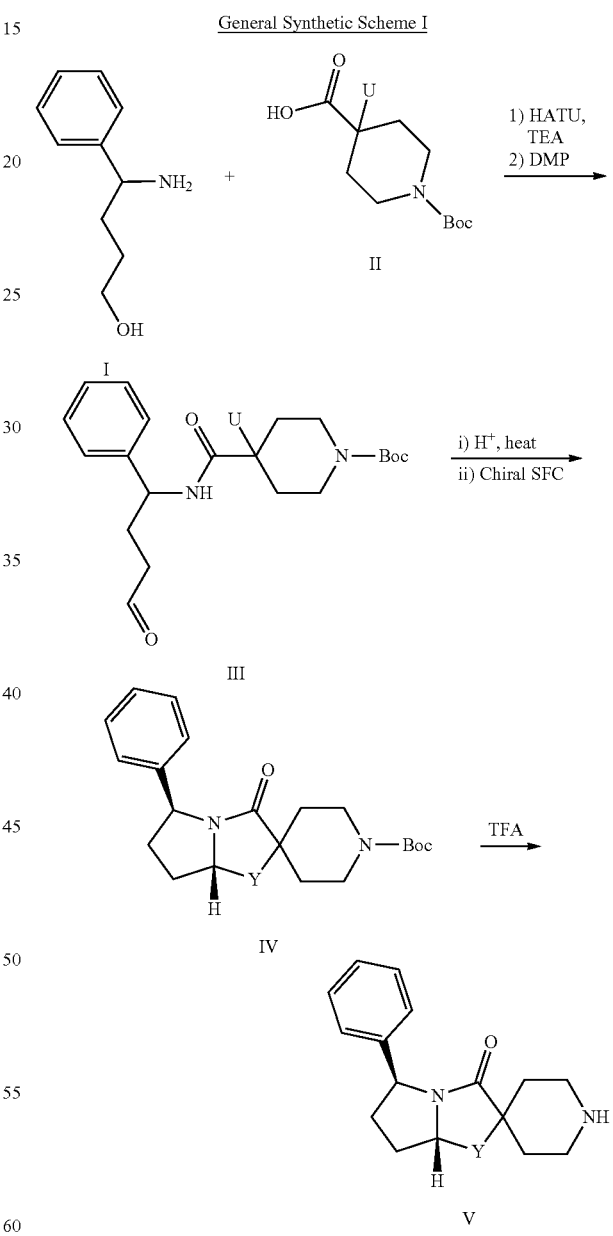

Beginning from racemic amino alcohols I, the amines can be coupled with the corresponding hydroxy acids II. The pendant primary alcohol can be oxidized to the aldehyde III, which is primed for ring closing cyclization under mild acidic conditions. Enantiomeric mixture can be separated using chiral SFC chromatography (or carried on to the unprotected piperidine if previously resolved) to afford the desired (5'S,7a'R) enantiomer. Finally, strong acid conditions can remove the protecting group(s) and afford the unprotected amine V.

General Synthetic Scheme II

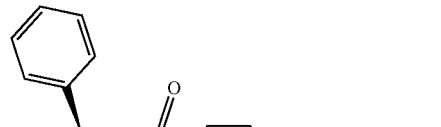

$\xrightarrow{\text{X—Ar}}$
base, heat

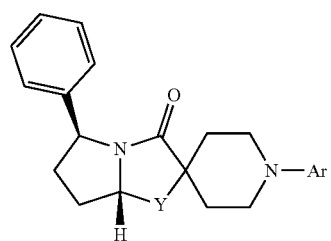

Spiro amino functionalizations to install aryl and heteroaryl components can be largely conducted using traditional SnAr conditions. In polar aprotic solvents, such as DMA or DMF, base is added and the mixtures are heated until completion. In cases where SnAr chemistry is not viable, palladium (Pd) cross-coupling conditions were instituted. Both approaches can be implemented into library format.

General Synthetic Scheme III

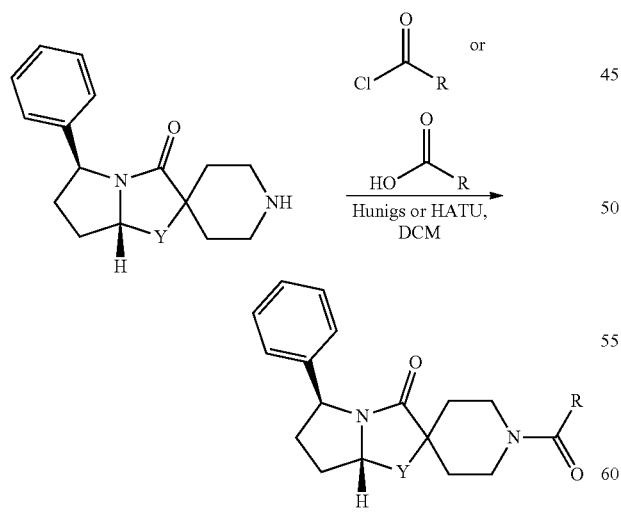

Spiro aminos can be reacted with various carbonyl acid reagents to access disubstituted amides, depending largely on availably of the acid coupling component using standard (peptide) coupling procedures.

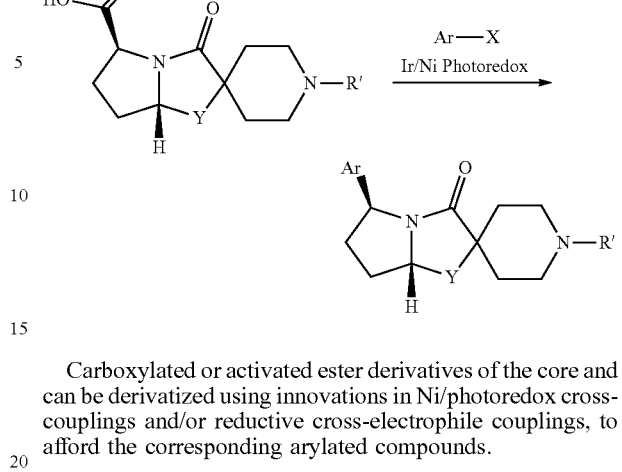

Carboxylated or activated ester derivatives of the core and can be derivatized using innovations in Ni/photoredox cross-couplings and/or reductive cross-electrophile couplings, to afford the corresponding arylated compounds.

INTERMEDIATES

Intermediate I-1. Preparation of (5'S,7a'R)-5'-(3,5-difluorophenyl)tetrahydro-3'H-spiro[piperidine-4,2'-pyrrolo[2,1-b]oxazol]-3'-one hydrochloride

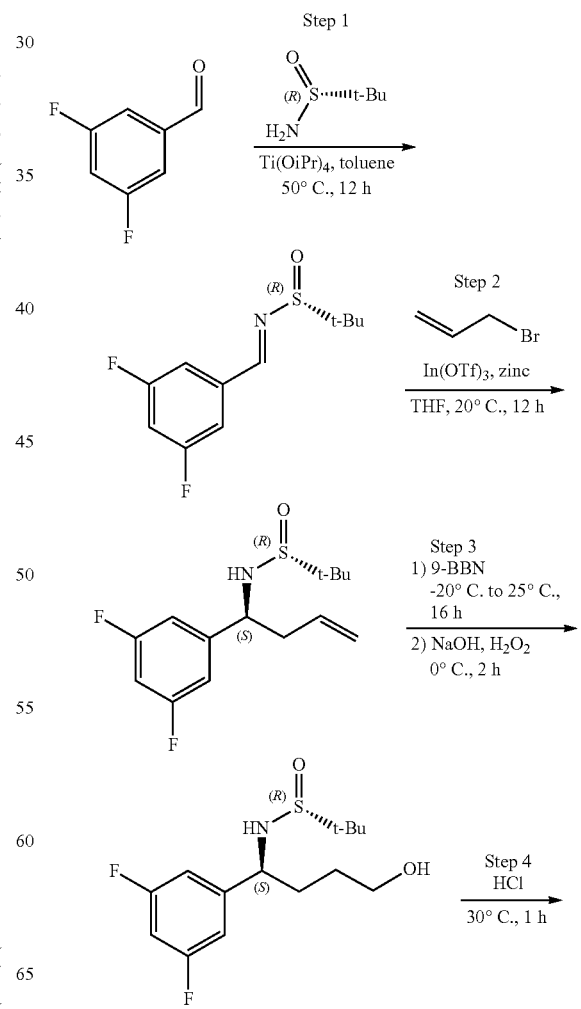

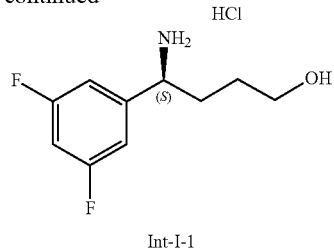

Int-I-1

Step 1. (R,E)-N-(3,5-difluorobenzylidene)-2-methylpropane-2-sulfinamide

Titanium(IV) isopropoxide (525 g, 1.85 mol) and (R)-2-methylpropane-2-sulfinamide (194 g, 1.60 mol) were added to a solution of 3,5-difluorobenzaldehyde (175 g, 1.23 mol) in toluene (3000 mL) at 20° C. The reaction mixture was stirred at 50° C. for 12 h. Saturated aqueous NaHCO₃ (1000 mL) was added to the reaction and the resultant suspension was filtered through celite. The filtered cake was washed with EtOAc (500 mL) and the filtrate was separated into organic and aqueous layers. The aqueous layer was extracted with EtOAc (500 mL×3) and then the combined organic layers were washed with brine (1000 mL), dried (Na₂SO₄), filtered, and concentrated under reduced pressure. The residue was purified by silica gel chromatography (petroleum ether/ethyl acetate=10:1) to give (R,E)-N-(3,5-difluorobenzylidene)-2-methylpropane-2-sulfinamide.

Step 2. (R)—N—((S)-1-(3,5-difluorophenyl)but-3-en-1-yl)-2-methylpropane-2-sulfinamide Zinc (213 g, 3.27 mol), indium(III) trifluoromethanesulfonate (1020 g, 1.82 mol), and 3-bromoprop-1-ene (146 g, 1.21 mol) were added to a stirred mixture of (R,E)-N-(3,5-difluorobenzylidene)-2-methylpropane-2-sulfinamide (298 g, 1.21 mol) in THF (2970 mL) at 20° C. The reaction mixture was stirred at 20° C. for 12 h. The reaction was diluted with EtOAc (2000 mL), washed with brine (1000 mL), dried (Na₂SO₄), filtered, and concentrated under reduced pressure. The crude residue was purified by silica gel chromatography (petroleum ether/ethyl acetate=5:1) to give (R)—N—((S)-1-(3,5-difluorophenyl)but-3-en-1-yl)-2-methylpropane-2-sulfinamide.

Step 3. (R)—N—((S)-1-(3,5-difluorophenyl)-4-hydroxybutyl)-2-methylpropane-2-sulfinamide (R)—N—((S)-1-(3,5-difluorophenyl)but-3-en-1-yl)-2-methylpropane-2-sulfinamide (334 g, 1.16 mol) was reacted with 9-BBN (0.5 M solution in THF; 6.96 L, 3.48 mol,) at 0° C. and gradually warmed to room temperature over 3 h until all starting material was consumed. The reaction mixture was cooled to 0° C. and hydrogen peroxide (30% aqueous solution; 1.2 L, 11.6 mol) was added dropwise, followed by addition of NaOH (8.82 M aqueous solution; 1.3 L, 11.6 mol). The resulting mixture was warmed to room temperature and stirred for 3 h. The reaction was quenched by addition of water (2 L) and extracted with ethyl acetate (3×1 L). The combined organic layers were dried (Na₂SO₄), filtered, and concentrated under reduced pressure. The resulting residue was purified by silica gel chromatography (EtOAc/hexanes=60:40) to afford (R)—N—((S)-1-(3,5-difluorophenyl)-4-hydroxybutyl)-2-methylpropane-2-sulfinamide.

Step 4. (S)-4-amino-4-(3,5-difluorophenyl)butan-1-ol, HCl

A solution of (R)—N—((S)-1-(3,5-difluorophenyl)-4-hydroxybutyl)-2-methylpropane-2-sulfinamide (178 g, 579 mmol) in HCl (1.77 L, 4 M solution in methanol) was stirred at 30° C. for 1 h. The reaction mixture was concentrated under reduced pressure. Water (300 mL) was added to the crude residue, followed by the addition of saturated aqueous NaHCO₃ until a pH of 8 was achieved. The solution was extracted with EtOAc (100 mL×3). The organic layer was washed with brine (100 mL), dried over anhydrous Na₂SO₄, filtered, and concentrated under reduced pressure to give (S)-4-amino-4-(3,5-difluorophenyl)butan-1-ol, HCl. MS (ESI) m/z $C_{10}H_{14}ClF_2NO$ [M+H]⁺ calc'd 202, found 202. ¹H NMR (400 MHz, CDCl₃) δ 6.86 (d, J=6.6 Hz, 2H), 6.70 (t, J=8.8 Hz, 1H), 3.87-4.05 (m, 1H), 3.67 (d, J=13.5 Hz, 2H), 2.27 (s, 3H), 1.78-1.97 (m, 1H), 1.57-1.78 (m, 3H).

Compounds presented in Table 1 were prepared in accordance with the synthetic routes in Intermediate I-1, using procedures analogous to those described above.

TABLE 1

| Intermediate | Structure | Name |
|---|---|---|
| I-2 | ![NH₂ structure with phenyl and OH] | (S)-4-amino-4-phenylbutan-1-ol |
| I-3 | ![NH₂ structure with 3-fluorophenyl and OH] | (S)-4-amino-4-(3-fluorophenyl)butan-1-ol |
| I-4 | ![NH₂ structure with 2-fluorophenyl and OH] | (S)-4-amino-4-(2-fluorophenyl)butan-1-ol |

Intermediate I-5. Preparation of (S)-1-(4-fluorophenyl)but-3-en-1-amine

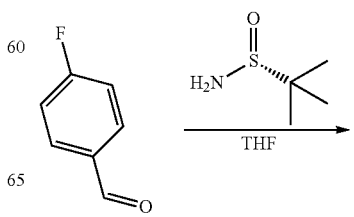

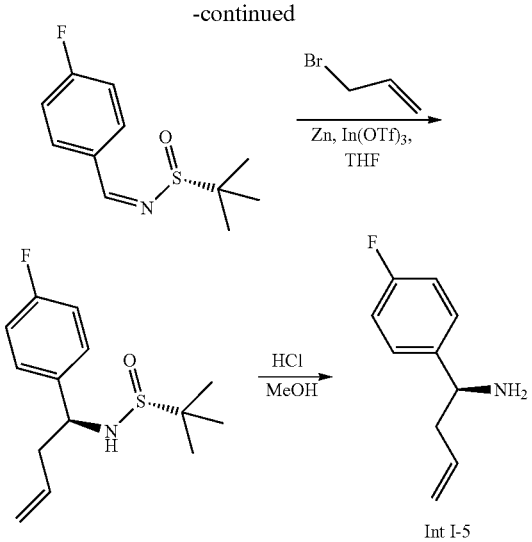

Int I-5

Step 1. (R,Z)—N-(4-fluorobenzylidene)-2-methyl-propane-2-sulfinamide

Titanium (IV) isopropoxide (17.2 g, 60.4 mmol) was added to a solution consisting of 4-fluorobenzaldehyde (5.0 g, 40 mmol) and (R)-2-methylpropane-2-sulfinamide (6.35 g, 52.4 mmol) in dry THF (100 mL) at room temperature. The reaction mixture was stirred and heated for 1 h at 50° C. Saturated aqueous sodium chloride (70 mL) was added to the reaction. The mixture was diluted with $H_2O$ (50 mL) and filtered through a pad of celite. The resultant filtrate was extracted with EtOAc (80 mL×3) and washed with saturated aqueous sodium chloride (50 mL×2). The organic layers were collected, dried ($Na_2SO_4$), and concentrated under reduced pressure. The residue was purified by flash silica gel chromatography (ISCO $SiO_2$ 40 g; ethyl acetate in pet. ether 0-5%) to give (R,Z)—N-(4-fluorobenzylidene)-2-methyl-propane-2-sulfinamide. MS (ESI) m/z $C_{11}H_{15}FNOS$ [M+H]$^+$ calc'd 228, found 228. $^1$H NMR (400 MHz, DMSO-$d_6$) δ 8.56 (s, 1H), 8.07-7.98 (m, 2H), 7.38 (t, J=8.8 Hz, 2H), 1.18 (s, 9H).

Step 2. (R)—N—((S)-1-(4-fluorophenyl)but-3-en-1-yl)-2-methylpropane-2-sulfinamide 3-bromoprop-1-ene (2.13 g, 17.6 mmol) was added to a stirring solution of (R,Z)—N-(4-fluorobenzylidene)-2-methylpropane-2-sulfinamide (2.0 g, 8.8 mmol), indium(III) trifluoromethanesulfonate (7.42 g, 13.2 mmol) and zinc (1.15 g, 17.6 mmol) in THF (50 mL) at room temperature. The mixture was stirred for 16 h and quenched with brine (100 mL). The mixture was extracted with EtOAc (60 mL×3) and the combined organics were dried ($Na_2SO_4$), filtered, and concentrated under reduced pressure. The residue was purified by flash silica gel chromatography (ISCO $SiO_2$ 40 g; ethyl acetate in petroleum ether, 0-45%) to give (R)—N—((S)-1-(4-fluorophenyl)but-3-en-1-yl)-2-methyl-propane-2-sulfinamide. MS (ESI) m/z $C_{14}H_{21}FNOS$ [M+H]$^+$ calc'd 270, found 270.

Step 3. (S)-1-(4-fluorophenyl)but-3-en-1-amine

HCl/MeOH (4 M) (20 mL) was added in one portion to (R)—N—((S)-1-(4-fluorophenyl)but-3-en-1-yl)-2-methyl-propane-2-sulfinamide (1.49 g, 5.53 mmol) and the mixture was stirred at room temperature for 3 h. The solvent was removed under reduced pressure, water (10 mL) was added to the residue and the pH was adjust to neutral with 1 M NaOH solution. The mixture was diluted with EtOAc (25 mL) and the organic layer was separated. The aqueous was re-extracted with EtOAc (20 mL×3) and the combined organic layers were washed with brine (10 mL), dried ($Na_2SO_4$), filtered, and concentrated under reduced pressure to give (S)-1-(4-fluorophenyl)but-3-en-1-amine. MS (ESI) m/z $C_{10}H_{13}FN$ [M+H]$^+$ calc'd 166, found 166.

Each of the elaborated amines presented in Table 2 below were prepared in accordance with the synthetic routes in Intermediate I-5, using procedures analogous to those described above.

TABLE 2

| Intermediate | Structure | Name |
|---|---|---|
| I-6 | 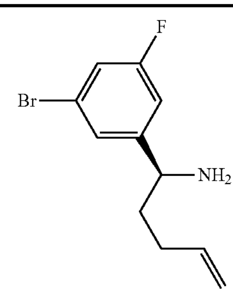 | (S)-1-(3-bromo-5-fluorophenyl)pent-4-en-1-amine |
| I-7 | 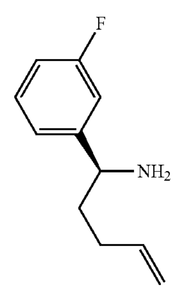 | (S)-1-(3-fluorophenyl)pent-4-en-1-amine |
| I-8 | 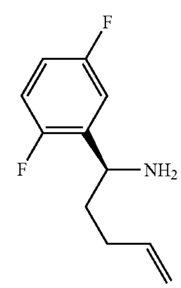 | (S)-1-(2,5-difluorophenyl)pent-4-en-1-amine |
| I-9 | 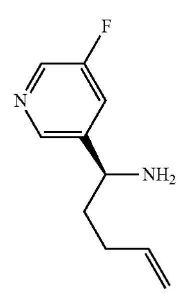 | (S)-1-(5-fluoropyridin-3-yl)pent-4-en-1-amine |

TABLE 2-continued

| Intermediate | Structure | Name |
|---|---|---|
| I-10 | 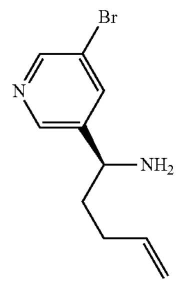 | (S)-1-(5-bromopyridin-3-yl)pent-4-en-1-amine |
| I-11 | 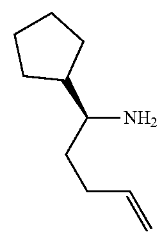 | (S)-1-cyclopentylpent-4-en-1-amine |
| I-12 | 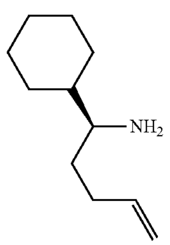 | (S)-1-cyclohexylpent-4-en-1-amine |

Intermediate I-13. Preparation of 7-chloro-3-fluoropyrazolo[1,5-a]pyrimidine

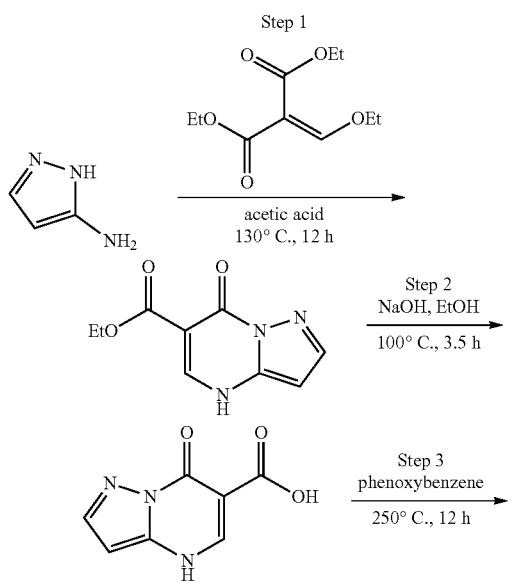

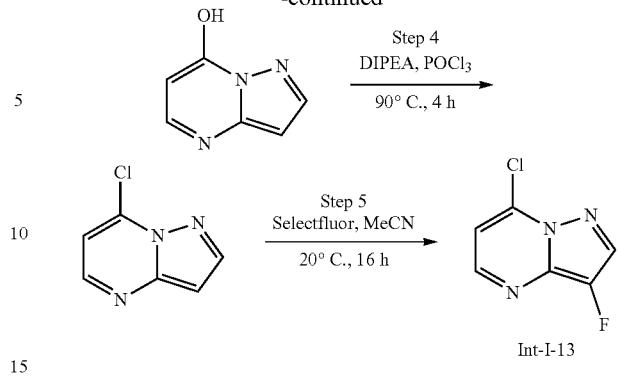

Step 1. Ethyl 7-oxo-4,7-dihydropyrazolo[1,5-a]pyrimidine-6-carboxylate 1H-pyrazol-5-amine (400 g, 4.82 mol), acetic acid (20 L, 349 mol), and 1,3-diethyl 2-(ethoxymethylidene) propanedioate (2080 g, 9.62 mol) were placed in a 20 L round-bottom flask purged and maintained with an inert atmosphere of nitrogen. The resulting solution was stirred for 12 h at 130° C. in an oil bath. The solids were collected by filtration, washed with EtOH to give ethyl 7-oxo-4H,7H-pyrazolo [1,5-a] pyrimidine-6-carboxylate.

Step 2. 7-Oxo-4,7-dihydropyrazolo[1,5-a]pyrimidine-6-carboxylic acid

A solution of ethyl 7-oxo-4H,7H-pyrazolo[1,5-a]pyrimidine-6-carboxylate (550 g, 2657 mmol, 1.00 equivalent) in ethanol (2750 mL) and a solution of sodium hydroxide (275 g, 6875 mmol, 2.50 equivalent) in water (2500 mL) was placed in a 5000 mL round-bottom flask purged and maintained with an inert atmosphere of nitrogen. The resulting solution was stirred for 12 h at 90° C. in an oil bath. The solids were collected by filtration. The resulting solid was dissolved in 2500 mL of water and to this was added 1500 g citric acid. The solids were collected by filtration, washed with H$_2$O. This resulted in 460 g of 7-oxo-4H, 7H-pyrazolo [1,5-a]pyrimidine-6-carboxylic acid.

Step 3. Pyrazolo[1,5-a]pyrimidin-7-ol 7-oxo-4H,7H-pyrazolo[1,5-a]pyrimidine-6-carboxylic acid (460 g, 2.57 mol) and phenoxybenzene (3795 mL, 23.9 mol), were placed into a 10 L round-bottom flask purged and maintained with an inert atmosphere of nitrogen. The resulting solution was stirred for 12 h at 250° C. The solids were collected by filtration, washed with n-hexane, and concentrated to give pyrazolo [1,5-a] pyrimidin-7-ol.

Step 4. 7-Chloropyrazolo[1,5-a]pyrimidine

Phosphoroyl trichloride (1406 g, 9170 mmol), pyrazolo [1,5-a]pyrimidin-7-ol (340 g, 1058 mmol) and DIEA (468 g, 3527 mmol) were placed into a 5000 mL round-bottom flask, purged and maintained with an inert atmosphere of nitrogen. The resulting solution was stirred for 4 h at 90° C. The resulting solution was poured into ice water and the solution was extracted with dichloromethane (1000 mL×3). The organic layers were combined and concentrated under vacuum to give 7-chloropyrazolo [1,5-a] pyrimidine.

Step 5. 7-Chloro-3-fluoropyrazolo[1,5-a]pyrimidine (I-13)

A mixture of 7-chloropyrazolo[1,5-a]pyrimidine (250 g, 1.63 mol) in MeCN (5000 mL) was added to a 10 L, three-necked round-bottom flask purged and maintained with an inert atmosphere of nitrogen. Selectfluor (694 g, 1.96 mol) was stirred at 25° C. for 16 h. The mixture was poured into water (3000 mL) and extracted with EtOAc (1000 mL×3). The combined organic phase was dried (Na$_2$SO$_4$), filtered, and concentrated under pressure. The resulting crude product was purified by reverse phase chromatography (eluting with 20% to 45% MeCN/water). The product to concentrated under reduced pressure to afford 7-chloro-3-fluoropyrazolo [1,5-a]pyrimidine. MS (ESI) m/z C$_6$H$_4$ClFN$_3$ [M+H]$^+$ calc'd 172, found 172. $^1$H NMR (400 MHz, CDCl$_3$), δ 8.42-8.39 (m, 1H), 8.24-8.18 (m, 1H), 7.06-7.01 (m, 1H).

Intermediate I-14A and Intermediate I-14B. Preparation of 1-(tert-butyl) 4-methyl (3[R and S],4[S and R])-4-hydroxy-3-methylpiperidine-1,4-dicarboxylate and 1-(tert-butyl) 4-methyl (3[R and S],4[R and S])-4-hydroxy-3-methylpiperidine-1,4-dicarboxylate

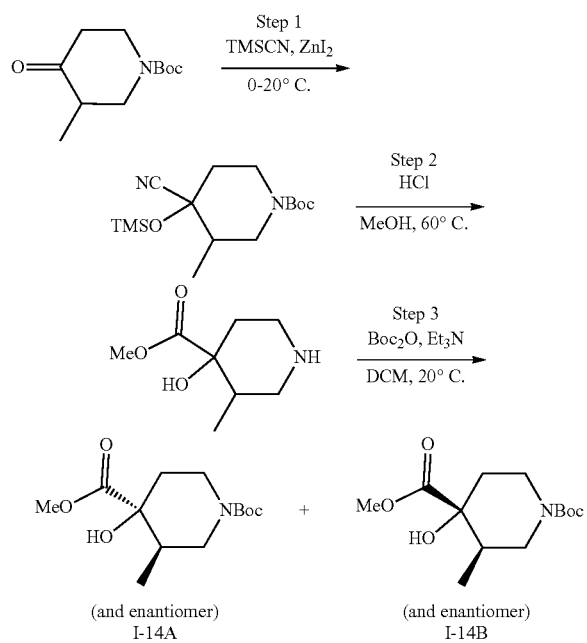

Step 1. tert-Butyl 4-cyano-3-methyl-4-((trimethylsilyl)oxy)piperidine-1-carboxylate A solution of tert-butyl 3-methyl-4-oxopiperidine-1-carboxylate (15.0 g, 70.3 mmol) in trimethylsilyl cyanide (60 mL) was cooled to 0° C. and treated with ZnI$_2$ (0.673 g, 2.11 mmol). The resulting mixture was stirred at 20° C. for 16 h. The reaction solution was directly concentrated under reduced pressure to provide tert-butyl 4-cyano-3-methyl-4-((trimethylsilyl)oxy)piperidine-1-carboxylate, which was used in the subsequent reaction without further purification.

Step 2. Synthesis of methyl 4-hydroxy-3-methylpiperidine-4-carboxylate

A solution of tert-butyl 4-cyano-3-methyl-4-((trimethylsilyl)oxy)piperidine-1-carboxylate (18.3 g, 58.7 mmol) in HCl (4 M in MeOH, 300 mL) was stirred at 60° C. for 2 h. After cooling, the reaction mixture was directly concentrated under reduced pressure to provide methyl 4-hydroxy-3-methylpiperidine-4-carboxylate, which was used in the subsequent reaction without further purification. MS (ESI) m/z C$_8$H$_{16}$NO$_3$ [M+H]$^+$ calc'd 174, found 174.

Step 3. Preparation of 1-(tert-butyl) 4-methyl (3[R and S],4[S and R])-4-hydroxy-3-methylpiperidine-1,4-dicarboxylate (I-14A) and 1-(tert-butyl) 4-methyl (3[R and S],4[R and S])-4-hydroxy-3-methylpiperidine-1,4-dicarboxylate (I-14B)

A mixture of methyl 4-hydroxy-3-methylpiperidine-4-carboxylate (12.0 g, 69.3 mmol) in DCM (350 mL) was treated with triethylamine (48.3 mL, 346 mmol) and Boc$_2$O (32.2 mL, 139 mmol). The resulting mixture was stirred at 20° C. for 3 h. The reaction was partitioned with EtOAc (400 mL) and water (400 mL), then extracted with EtOAc (400 mL, ×2). The combined organic layers were washed with brine (400 mL), dried (Na$_2$SO$_4$), filtered, and concentrated under reduced pressure. The residue was purified by flash silica gel chromatography (EtOAc/petroleum ether, 0-20%) to afford 1-(tert-butyl) 4-methyl (3[R and S],4[S and R])-4-hydroxy-3-methylpiperidine-1,4-dicarboxylate as the first eluting peak, and 1-(tert-butyl) 4-methyl (3[R and S],4[R and S])-4-hydroxy-3-methylpiperidine-1,4-dicarboxylate as the second eluting peak. MS (ESI) m/z C$_8$H$_{16}$NO$_3$ [M+H–100]$^+$ calc'd 174, found 174.

The elaborated hydroxy-ester presented in Table 3 below was prepared as the second eluting peak in accordance with the synthetic route in Intermediate I-14A and I-14B, using a procedure analogous to that described above.

TABLE 3

| Intermediate | Structure | Name |
| --- | --- | --- |
| I-14C | ![structure](and enantiomer) | 1-(tert-butyl) 4-methyl(3R,4S)-3-fluoro-4-hydroxypiperidine-1,4-dicarboxylate |

Intermediate I-15A. Preparation of (3[R and S],4[R and S])-1-(tert-butoxycarbonyl)-4-hydroxy-3-methylpiperidine-4-carboxylic acid

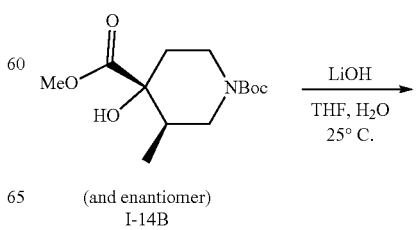

(and enantiomer)
I-14B

-continued

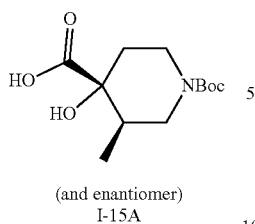

(and enantiomer)
I-15A

A mixture of 1-(tert-butyl) 4-methyl (3[R and S],4[R and S])-4-hydroxy-3-methylpiperidine-1,4-dicarboxylate (6.0 g, 22.0 mmol) in THF (108 mL) and water (36 mL) was treated with LiOH (1.58 g, 65.9 mmol). The resulting mixture was stirred at 25° C. for 12 h. The reaction was partitioned with EtOAc (150 mL) and water (200 mL), and the aqueous layer was acidified with 2 M HCl until pH 4 was achieved. The aqueous layer was then extracted with EtOAc (150 mL, ×2). The combined organic layers were dried ($Na_2SO_4$), filtered, and concentrated under reduced pressure to afford (3[R and S],4[R and S])-1-(tert-butoxycarbonyl)-4-hydroxy-3-methylpiperidine-4-carboxylic acid. $^1$H NMR (400 MHz, MeOD-$d_4$) δ 3.72-3.63 (m, 1H), 3.61-3.54 (m, 1H), 3.45 (br s, 2H), 2.07-1.97 (m, 1H), 1.89-1.79 (m, 1H), 1.63-1.53 (m, 1H), 1.46 (s, 9H), 0.93 (d, J=6.8 Hz, 3H).

The elaborated hydroxy-acids presented in Table 4 below were prepared in accordance with the synthetic route in Intermediate I-15A, using a procedure analogous to that described above.

TABLE 4

| Intermediate | Structure | Name |
|---|---|---|
| I-15B | (and enantiomer) | (3R,4S)-1-(tert-butoxycarbonyl)-4-hydroxy-3-methylpiperidine-4-carboxylic acid |
| I-15C | (and enantiomer) | (3R,4S)-1-(tert-butoxycarbonyl)-3-fluoro-4-hydroxypiperidine-4-carboxylic acid |

Intermediate I-16. Preparation of (5'S,7a'R)-5'-(3,5-difluorophenyl)tetrahydro-3'H-spiro[azetidine-3,2'-pyrrolo[2,1-b]oxazol]-3'-one

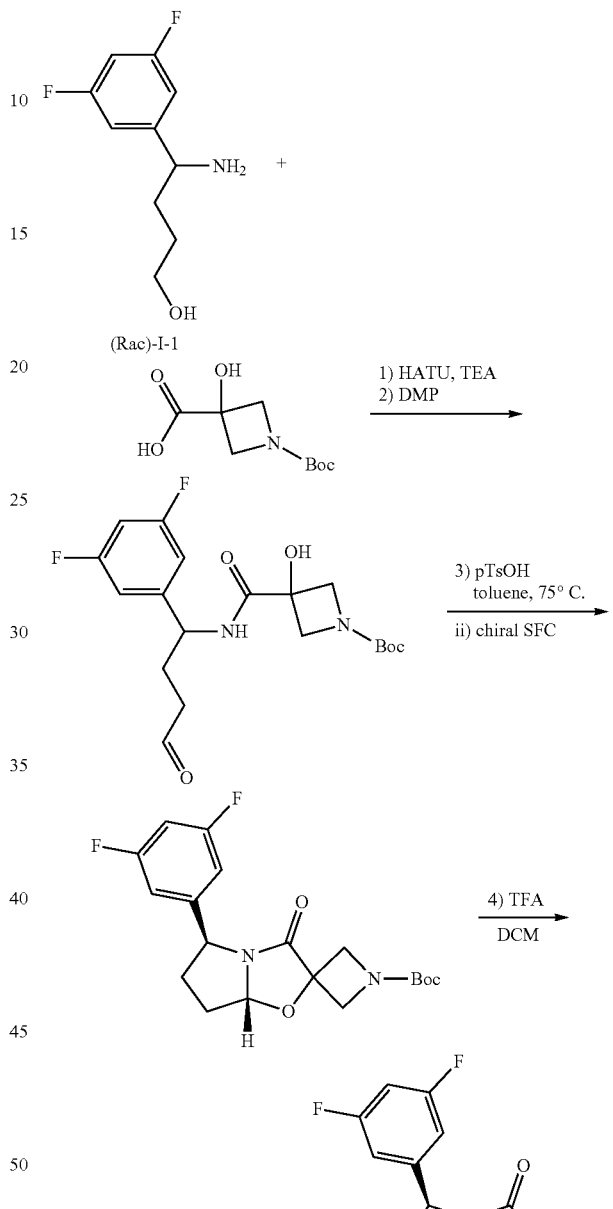

Step 1. tert-Butyl 3-((1-(3,5-difluorophenyl)-4-hydroxybutyl)carbamoyl)-3-hydroxyazetidine-1-carboxylate 1-(tert-butoxycarbonyl)-3-hydroxyazetidine-3-carboxylic acid (366 mg, 1.68 mmol), 4-amino-4-(3,5-difluorophenyl)butan-1-ol, HCl (I-1, racemic) (400 mg, 1.68 mmol), and HATU (672 mg, 1.77 mmol) in dry acetonitrile (16.8 ml)

were added to a 250 mL flask. The mixture was cooled to 0° C. after which triethylamine (0.469 ml, 3.37 mmol) was added in one portion. The mixture was stirred and warmed to room temperature overnight. The mixture was concentrated and the residue was purified via ISCO SiO$_2$ 24 g column (3:1 ethyl acetate/EtOH in hexanes, 20-60%). The desired fractions were combined and the volatiles evaporated to afford tert-butyl 3-((1-(3,5-difluorophenyl)-4-hydroxybutyl)carbamoyl)-3-hydroxyazetidine-1-carboxylate. MS (ESI) m/z C$_{19}$H$_{26}$F$_2$N$_2$NaO$_5$ [M+Na]$^+$ calc'd 423, found 423.

Step 2. tert-Butyl 3-((1-(3,5-difluorophenyl)-4-oxobutyl)carbamoyl)-3-hydroxyazetidine-1-carboxylate Tert-Butyl 3-((1-(3,5-difluorophenyl)-4-hydroxybutyl)carbamoyl)-3-hydroxyazetidine-1-carboxylate (815 mg, 2.03 mmol) was added to a 100 mL flask and dissolved in DCM (20 ml) under argon. The mixture was chilled to 0° C. and DMP (1.38 g, 3.26 mmol) was added in one portion. The mixture was allowed to stir at 0° C. for 60 min. The mixture was diluted with DCM (20 mL) and quenched with saturated aqueous Na$_2$S$_2$O$_3$ (5 mL) and stirred vigorously for 10 min. The organics were washed with saturated aqueous NaHCO$_3$ (15 mL), then brine (15 mL) and collected. The organics were dried (MgSO$_4$), filtered, and concentrated to afford tert-butyl 3-((1-(3,5-difluorophenyl)-4-oxobutyl)carbamoyl)-3-hydroxyazetidine-1-carboxylate which was carried on without further purification. MS (ESI) m/z C$_{19}$H$_{24}$F$_2$N$_2$NaO$_5$ [M+Na]$^+$ calc'd 421, found 421.

Step 3. tert-Butyl 5'-(3,5-difluorophenyl)-3'-oxotetrahydro-3'H-spiro[azetidine-3,2'-pyrrolo[2,1-b]oxazole]-1-carboxylate TsOH (136 mg, 0.71 mmol) was added in one portion to crude tert-butyl 3-((1-(3,5-difluorophenyl)-4-oxobutyl)carbamoyl)-3-hydroxyazetidine-1-carboxylate (811 mg, 2.03 mmol) dissolved in dry toluene (20.3 ml) at room temperature. The mixture was heated to 75° C. and allowed to stir overnight. The solvent was removed under vacuum and the residue was purified via flash silica gel chromatography (ISCO SiO$_2$ 12 g; ethyl acetate in hexanes, 10-60%). The desired fractions were combined and the volatiles evaporated to afford tert-butyl 5'-(3,5-difluorophenyl)-3'-oxotetrahydro-3'H-spiro[azetidine-3,2'-pyrrolo[2,1-b]oxazole]-1-carboxylate as a mixture of enantiomers. The material was subjected to chiral SFC chromatography (Lux-4, 21×250 mm, 5 um; Modifier: 20% MeOH with 0.1% NH$_4$OH, 70 ml/min). Peak 2 was collected and concentrated to afford the desired enantiomer. MS (ESI) m/z C$_{19}$H$_{22}$F$_2$N$_2$NaO$_4$ [M+Na]$^+$ calc'd 403, found 403.

Step 4. (5'S,7a'R)-5'-(3,5-difluorophenyl)tetrahydro-3'H-spiro[azetidine-3,2'-pyrrolo[2,1-b]oxazol]-3'-one (I-16)

tert-Butyl (5'S,7a'R)-5'-(3,5-difluorophenyl)-3'-oxotetrahydro-3'H-spiro[azetidine-3,2'-pyrrolo[2,1-b]oxazole]-1-carboxylate (150 mg, 0.394 mmol) in DCM and TFA (30 µL, 0.39 mmol) was added to a vial at room temperature. The mixture was stirred at room temperature overnight. The volatiles were removed under reduced pressure to afford (5'S,7a'R)-5'-(3,5-difluorophenyl)tetrahydro-3'H-spiro[azetidine-3,2'-pyrrolo[2,1-b]oxazol]-3'-one, which was taken forward in crude form. MS (ESI) m/z C$_{14}$H$_{15}$F$_2$N$_2$O$_2$[M+H]$^+$ calc'd 281, found 281.

Each of the elaborated azetidines presented in Table 5 below were prepared in accordance with the synthetic routes in Intermediate I-16, using procedures analogous to those described above.

TABLE 5

| Intermediate | Structure | Name |
| --- | --- | --- |
| I-16A | 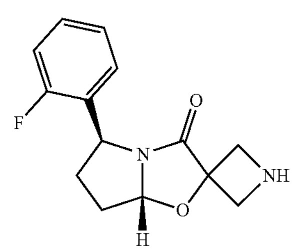 [SMILES: O=C1N2[C@@H](CC[C@H]2c2ccccc2F)OC12CNC2] | (5'S,7a'R)-5'-(2-fluorophenyl)tetrahydro-3'H-spiro[azetidine-3,2'-pyrrolo[2,1-b]oxazol]-3'-one, HCl |
| I-16B | 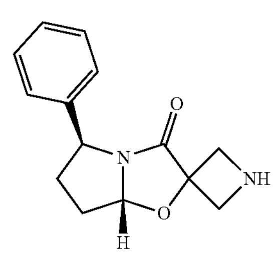 [SMILES: O=C1N2[C@@H](CC[C@H]2c2ccccc2)OC12CNC2] | (5'S,7a'R)-5'-phenyltetrahydro-3'H-spiro[azetidine-3,2'-pyrrolo[2,1-b]oxazol]-3'-one |

Intermediate I-17. Preparation of (3'R,7a'S)-3'-phenyltetrahydro-5'H-spiro[piperidine-4,6'-pyrrolo[2,1-b]oxazol]-5'-one, HCl

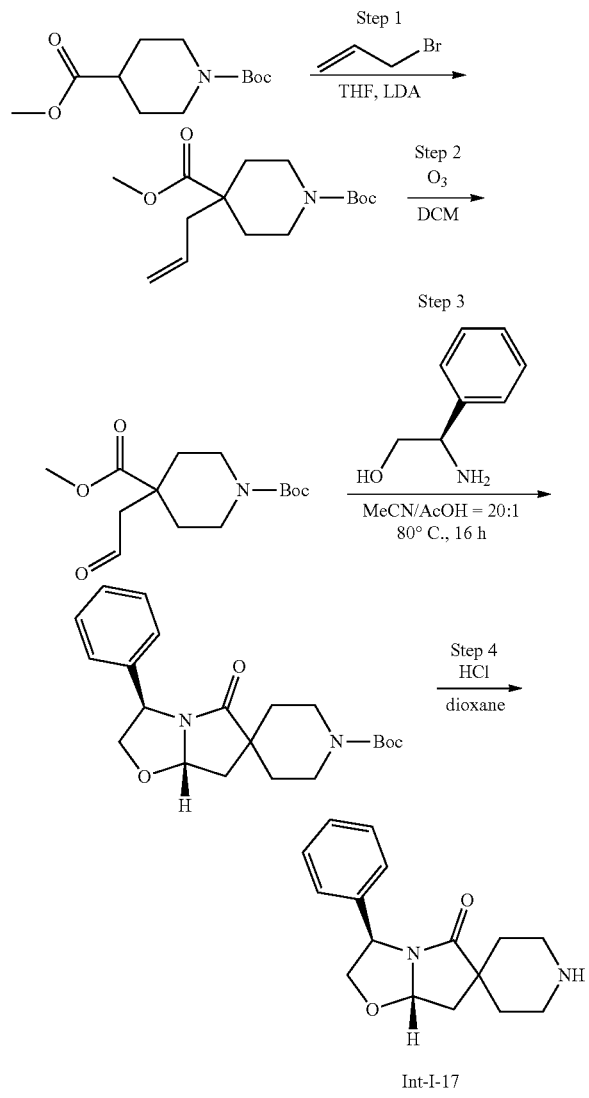

Int-I-17

Step 1. 1-(tert-Butyl) 4-methyl 4-allylpiperidine-1,4-dicarboxylate

Lithium diisopropylamide (6.17 mL, 12.3 mmol) was added to a solution of 1-(tert-butyl) 4-methyl piperidine-1,4-dicarboxylate (2.0 g, 8.2 mmol) in THF (30 mL) at −78° C. The mixture was stirred at −78° C. for 30 min. A solution of 3-bromoprop-1-ene (1.49 g, 12.3 mmol) in THF (5 mL) was added dropwise and the mixture was stirred at 0° C. for 5 h. The mixture was quenched with water (20 mL) and extracted with EtOAc (20 mL×2). The combined organic layer was washed with brine (40 mL), dried ($Na_2SO_4$), filtered, and concentrated in vacuum. The residue was purified by flash silica gel chromatography (ISCO $SiO_2$ 20 g; EtOAc in Pet. ether 0-20%) to give 1-(tert-butyl) 4-methyl 4-allylpiperidine-1,4-dicarboxylate.

Step 2. 1-(tert-Butyl) 4-methyl 4-(2-oxoethyl)piperidine-1,4-dicarboxylate

A solution of 1-(tert-butyl) 4-methyl 4-allylpiperidine-1,4-dicarboxylate (2.0 g, 7.1 mmol) in DCM (40 mL) was bubbled with $O_3$ for 20 min at −78° C. Triphenylphosphine (2.22 g, 8.47 mmol) was added in one portion and the mixture was stirred at 20° C. for 3 h. The mixture was concentrated in vacuum and purified by flash silica gel chromatography (ISCO $SiO_2$ 20 g; EtOAc in Pet. ether 0-20%) to give 1-(tert-butyl) 4-methyl 4-(2-oxoethyl)piperidine-1,4-dicarboxylate. $^1$H NMR (400 MHz, $CDCl_3$) δ 9.72 (s, 1H), 3.72, (s, 3H), 3.68-3.66 (m, 2H), 3.24-3.18 (m, 2H), 2.70 (s, 2H), 2.13-2.10 (m, 2H), 1.54-1.49 (m, 2H), 1.45 (s, 9H).

Step 3. tert-Butyl (3'R,7a'S)-5'-oxo-3'-phenyltetrahydro-5'H-spiro[piperidine-4,6'-pyrrolo[2,1-b]oxazole]-1-carboxylate A mixture of 1-(tert-butyl) 4-methyl 4-(2-oxoethyl)piperidine-1,4-dicarboxylate (1.30 g, 4.56 mmol) and (R)-2-amino-2-phenylethan-1-ol (0.625 g, 4.56 mmol) in MeCN/AcOH=20:1 (22 mL) (v/v) was stirred at 80° C. for 16 h. The mixture was concentrated in vacuum and purified by flash silica gel chromatography (ISCO $SiO_2$ 20 g; EtOAc in Pet. Ether 0-20%) to give tert-butyl (3'R,7a'S)-5'-oxo-3'-phenyltetrahydro-5'H-spiro[piperidine-4,6'-pyrrolo[2,1-b]oxazole]-1-carboxylate. MS (ESI) m/z $C_{21}H_{29}N_2O_4$ [M+H−56]$^+$ calc'd 317, found 371.

Step 4. (3'R,7a'S)-3'-phenyltetrahydro-5'H-spiro[piperidine-4,6'-pyrrolo[2,1-b]oxazol]-5'-one, HCl (I-17)

A mixture of tert-butyl (3'R,7a'S)-5'-oxo-3'-phenyltetrahydro-5'H-spiro[piperidine-4,6'-pyrrolo[2,1-b]oxazole]-1-carboxylate (1.30 g, 3.49 mmol) in 4M HCl in dioxane (15 mL) was stirred at 20° C. for 2 h. The mixture was concentrated in vacuum and the residue was purified by prep-HPLC (Instrument EH, C18 150*25 mm*5 um, Condition water ($NH_4HCO_3$)-ACN, Begin B 20, End B 50, (Gradient Time(min) 10 100% B, Hold Time(min) 2) to give (3'R,7a'S)-3'-phenyltetrahydro-5'H-spiro[piperidine-4,6'-pyrrolo[2,1-b]oxazol]-5'-one, HCl. MS (ESI) m/z $C_{16}H_{21}N_2O_2$ [M+H]$^+$ calc'd 273, found 273.

Intermediate I-18. Preparation of 5'-(3,5-difluorophenyl)-6',7'-dihydro-3'H,5'H-spiro[piperidine-4,2'-pyrrolo[1,2-a]imidazol]-3'-one

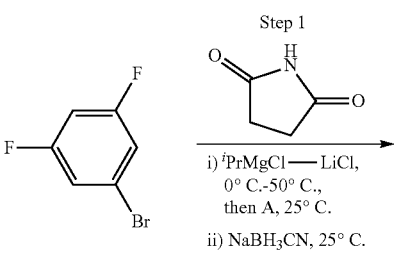

-continued

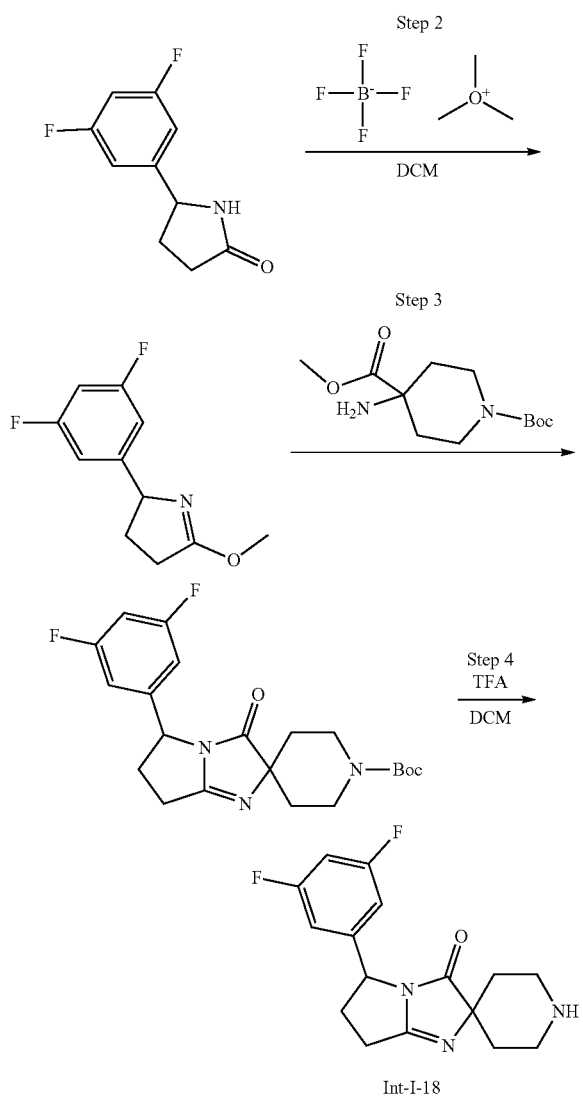

Step 1. 5-(3,5-Difluorophenyl)pyrrolidin-2-one

Isopropylmagnesium chloride lithium chloride complex (97 mL, 126 mmol) was added to a solution of 1-bromo-3,5-difluorobenzene (14.6 g, 76 mmol) in THF (110 mL) at 0° C. The mixture was heated at 50° C. for 1 h and cooled to −78° C. where a solution of pyrrolidine-2,5-dione (5.0 g, 51 mmol) in DCM (5 mL) was added. The mixture was stirred at 25° C. for 16 h. Cyanoborohydride sodium (3.81 g, 60.6 mmol) was added to the resulting mixture at 25° C. The mixture was stirred at 25° C. for 1 h. The reaction was acidified to pH=3-4 with HCl (6 M) (at 0° C.), stirred for 30 min at room temperature, and neutralized with aqueous NaOH (3 M). The reaction was partitioned with DCM (600 mL) and water (2 L). The combined organic layers were dried (Na$_2$SO$_4$), filtered, and concentrated under reduced pressure. The residue was purified by silica gel chromatography (ethyl acetate/hexanes, 0-100%) to afford 5-(3,5-difluorophenyl)pyrrolidin-2-one. MS (ESI) m/z C$_{10}$H$_{10}$F$_2$NO [M+H]$^+$ calc'd 198, found 198.

Step 2. 2-(3,5-Difluorophenyl)-5-methoxy-3,4-dihydro-2H-pyrrole

Dimethyloxonium tetrafluoroborate (1.8 g, 13.2 mmol) was added to a solution of 5-(3,5-difluorophenyl)pyrrolidin-2-one (2.0 g, 10.1 mmol) in DCM (20 mL) at room temperature. The mixture was stirred at 25° C. for 16 h. The mixture was quenched with saturated aqueous NaHCO$_3$ (30 mL), and extracted with DCM (20 mL×3). The combined organic layers were dried (Na$_2$SO$_4$), filtered, and concentrated under reduced pressure to afford 2-(3,5-difluorophenyl)-5-methoxy-3,4-dihydro-2H-pyrrole. MS (ESI) m/z C$_{11}$H$_{12}$F$_2$NO [M+H]$^+$ calc'd 212, found 212.

Step 3. tert-Butyl 5'-(3,5-difluorophenyl)-3'-oxo-6',7'-dihydro-3'H,5'H-spiro[piperidine-4,2'-pyrrolo[1,2-a]imidazole]-1-carboxylate 2-(3,5-difluorophenyl)-5-methoxy-3,4-dihydro-2H-pyrrole (2.9 g, 9.6 mmol) was added to a solution of 1-(tert-butyl) 4-methyl 4-aminopiperidine-1,4-dicarboxylate (2.73 g, 10.6 mmol) in n-BuOH (40 mL) at 20° C. The mixture was stirred at 120° C. for 30 h. The reaction was cooled to room temperature and partitioned with ethyl acetate (100 mL) and water (200 mL). The aqueous layer was extracted with EtOAc (80 mL×2), the combined organic layers were washed with brine (250 mL), dried (Na$_2$SO$_4$), filtered and concentrated under reduced pressure. The residue was purified by prep-HPLC(TFA), then re-purified by flash silica gel chromatography (0-5% MeOH/DCM) to give tert-butyl 5'-(3,5-difluorophenyl)-3'-oxo-6',7'-dihydro-3'H,5'H-spiro[piperidine-4,2'-pyrrolo[1,2-a]imidazole]-1-carboxylate. MS (ESI) m/z C$_{21}$H$_{25}$F$_2$N$_3$O$_3$ [M+H]$^+$ calc'd 406, found 406.

Step 4. 5'-(3,5-difluorophenyl)-6',7'-dihydro-3'H,5'H-spiro[piperidine-4,2'-pyrrolo[1,2-a]imidazol]-3'-one (I-18)

TFA (2 mL) was added to a solution of tert-butyl 5'-(3,5-difluorophenyl)-3'-oxo-6',7'-dihydro-3'H,5'H-spiro[piperidine-4,2'-pyrrolo[1,2-a]imidazole]-1-carboxylate (280 mg, 0.552 mmol) in DCM (6 mL) at 20° C. The mixture was stirred at 20° C. for 2 h. The mixture was concentrated to afford 5'-(3,5-difluorophenyl)-6',7'-dihydro-3'H,5'H-spiro[piperidine-4,2'-pyrrolo[1,2-a]imidazol]-3'-one (racemic). MS (ESI) m/z C$_{16}$H$_{17}$F$_2$N$_3$O [M+H]$^+$ calc'd 306, found 306.

Intermediate I-19. Preparation of 1-(2-bromopyridin-4-yl)-5'-(3,5-difluorophenyl)-6',7'-dihydro-3'H,5'H-spiro[piperidine-4,2'-pyrrolo[1,2-a]imidazol]-3'-one

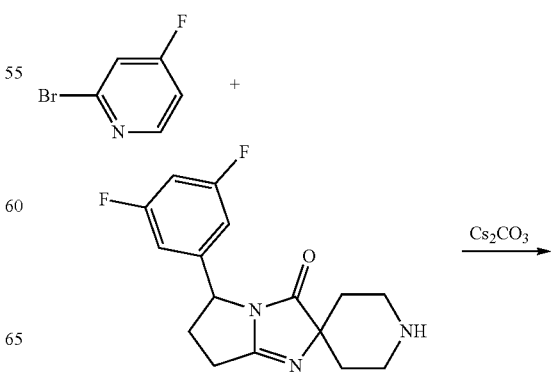

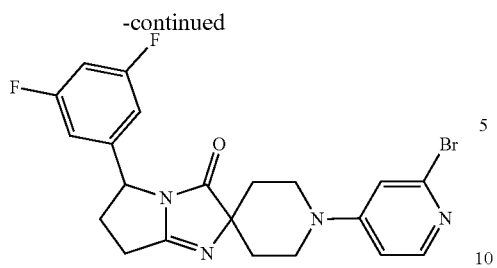

2-bromo-4-fluoropyridine (9.2 mg, 0.052 mmol) and Cs$_2$CO$_3$ (25.6 mg, 0.079 mmol) were added to a solution of 5'-(3,5-difluorophenyl)-6',7'-dihydro-3'H,5'H-spiro[piperidine-4,2'-pyrrolo[1,2-a]imidazol]-3'-one (10 mg, 0.026 mmol) in t-amyol alcohol (0.5 mL). The mixture was stirred at 100° C. for 16 h under N$_2$. LCMS showed desired product was formed. The mixture was filtered and the filtrate was concentrated to give a residue which was purified by preparative HPLC (Instrument ed; Method Column Boston Prime C18 150 mm×30 mm×5 m; Condition water (0.05% NH$_3$/H$_2$O+10 mM NH$_4$HCO$_3$)-ACN (Gradient Time 10 min); 100% B Hold Time (min) 2 FlowRate (mL/min) 25; Injections 1) to afford 1-(2-bromopyridin-4-yl)-5'-(3,5-difluorophenyl)-6',7'-dihydro-3'H,5'H-spiro[piperidine-4,2'-pyrrolo[1,2-a]imidazol]-3'-one. MS (ESI) m/z C$_{21}$H$_{19}$BrF$_2$N$_4$O [M+H]$^+$ calc'd 461, found 461 and 463. $^1$H NMR (400 MHz, METHANOL-d$_4$) δ 7.89 (d, J=6.0 Hz, 1H), 7.06 (d, J=2.4 Hz, 1H), 6.97-6.83 (m, 4H), 5.07 (dd, J=5.2, 8.0 Hz, 1H), 3.96 (br d, J=14.0 Hz, 2H), 3.47 (br t, J=10.8 Hz, 2H), 3.03-2.66 (m, 3H), 2.28-2.45 (m, 1H), 1.92-2.04 (m, 2H), 1.68-1.83 (m, 2H).

Intermediate I-20. Preparation of (5'S,7a'R)-5'-(4-fluorophenyl)tetrahydro-3'H-spiro[piperidine-4,2'-pyrrolo[2,1-b]oxazol]-3'-one, TFA

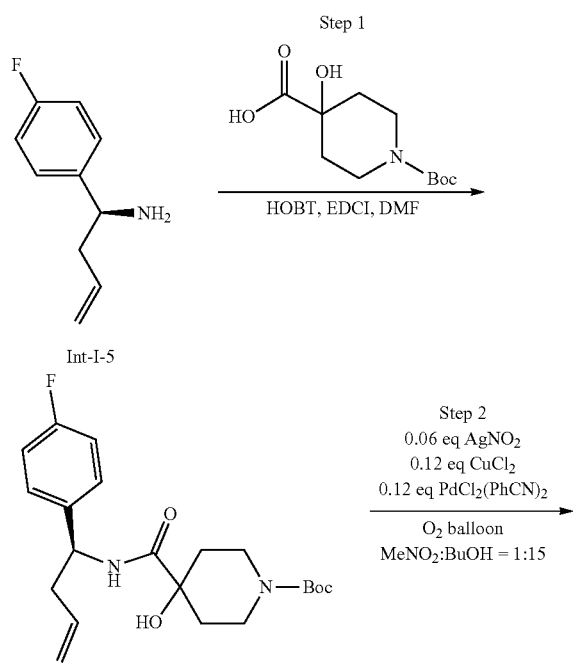

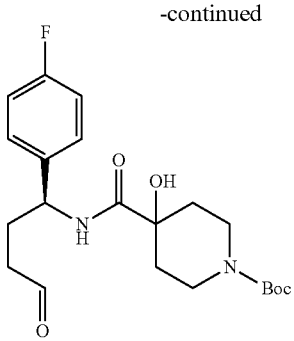

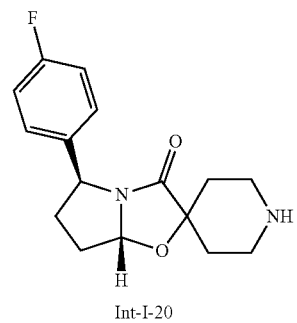

Int-I-20

Step 1. (S)-4-((1-(4-fluorophenyl)but-3-en-1-yl)carbamoyl)-4-hydroxypiperidine-1-carboxylate TEA (2.29 mL, 16.4 mmol), 1-Ethyl-3-(3-dimethylaminopropyl)carbodiimide (1.57 g, 8.21 mmol) and HOBT (1.26 mg, 8.21 mmol) was added to a stirred solution of 1-(tert-butoxycarbonyl)-4-hydroxypiperidine-4-carboxylic acid (2.01 g, 8.21 mmol) in DMF (10 mL) at room temperature. (S)-1-(4-Fluorophenyl)but-3-en-1-amine (904 mg, 5.47 mmol, I-5) was added in one portion and stirred for 17 h. The reaction mixture was quenched with water (50 mL) and extracted with EtOAc (50 mL×3). The combined organic phases were washed with brine (30 mL), dried (Na$_2$SO$_4$), filtered, and concentrated under reduced pressure. The residue was purified by flash silica gel chromatography (ISCO SiO$_2$ 80 g; 0-50% ethyl acetate in pet. ether) to give tert-butyl (S)-4-((1-(4-fluorophenyl)but-3-en-1-yl)carbamoyl)-4-hydroxypiperidine-1-carboxylate. MS (ESI) m/z C$_{21}$H$_{30}$FN$_2$O$_4$[M+1-Boc] calc'd 293, found 293.

Step 2. tert-Butyl 4-((2S)-2-(4-fluorophenyl)-5-hydroxypyrrolidine-1-carbonyl)-4-hydroxypiperidine-1-carboxylate Copper (II) chloride (4.1 mg, 0.031 mmol) and bis(benzonitrile)palladium chloride (11.7 mg, 0.031 mmol) were added to a stirred mixture of silver nitrate (2.35 mg, 0.015 mmol) in t-butanol (3 mL) and nitromethane (0.2 mL). The mixture was stirred at room temperature for 5 min. Rac-tert-butyl (R)-4-((1-(4-fluorophenyl)but-3-en-1-yl)carbamoyl)-4-hydroxypiperidine-1-carboxylate (100 mg, 0.255 mmol) was added in one portion and the mixture was stirred at room temperature for 40 h. The mixture was filtered and the filtrate was concentrated under reduced pressure to give crude tert-butyl (S)-4-((1-(4-fluorophenyl)-4-oxobutyl)carbamoyl)-4-hydroxypiperidine-1-carboxylate, which was not further purified. MS (ESI) m/z C$_{21}$H$_{30}$FN$_2$O$_5$ [M+H]$^+$ calc'd 409, found 409.

Step 3. (5'S,7a'R)-5'-(4-fluorophenyl)tetrahydro-3'H-spiro[piperidine-4,2'-pyrrolo[2,1-b]oxazol]-3'-one, TFA (I-20)

A solution of tert-butyl (R)-4-((1-(4-fluorophenyl)-4-oxobutyl)carbamoyl)-4-hydroxypiperidine-1-carboxylate (200 mg, 0.490 mmol) in MeCN (3 mL) was heated to 80° C. Then methanesulfonic acid (141 mg, 1.47 mmol) was added at 80° C. The resulting mixture was stirred at 80° C. for 16 h. The residue was purified by Prep-HPLC (Instrument Method Column Phenomenex Synergi (C18 150×21.2 mm×4 um) water (0.1% TFA)-MeCN to give (5'S,7a'R)-5'-(4-fluorophenyl)tetrahydro-3'H-spiro[piperidine-4,2'-pyrrolo[2,1-b]oxazol]-3'-one, TFA as a tan solid. MS (ESI) m/z $C_{16}H_{20}FN_2O_2[M+1]^+$ calc'd 291, found 291.

Each of the elaborated piperidines presented in Table 6 below were prepared in accordance with the synthetic routes in Intermediate I-20, using procedures analogous to those described above.

TABLE 6

| Intermediate | Structure | Name | Exact Mass [M + H]+ |
|---|---|---|---|
| I-20A | 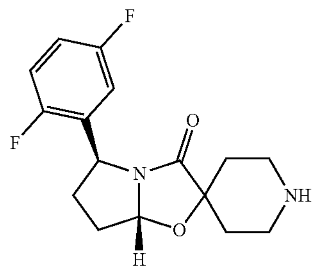 [SMILES: O=C1N2[C@@H](CC[C@H]2c2cc(F)ccc2F)OC12CCNCC2] | (5'S,7a'R)-5'-(2,5-difluorophenyl)tetrahydro-3'H-spiro[piperidine-4,2'-pyrrolo[2,1-b]oxazol]-3'-one | Calc'd 309, found 309 |
| I-20B | 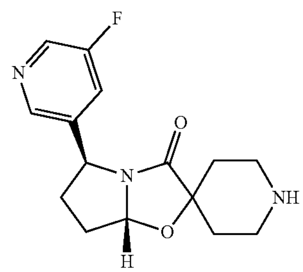 [SMILES: O=C1N2[C@@H](CC[C@H]2c2cncc(F)c2)OC12CCNCC2] | (5'S,7a'R)-5'-(5-fluoropyridin-3-yl)tetrahydro-3'H-spiro[piperidine-4,2'-pyrrolo[2,1-b]oxazol]-3'-one | Calc'd 292, found 292 |
| I-20C | 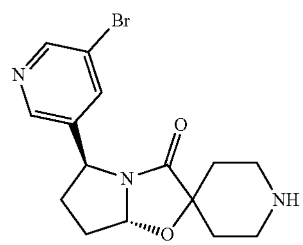 [SMILES: O=C1N2[C@@H](CC[C@H]2c2cncc(Br)c2)OC12CCNCC2] | (5'S,7a'R)-5'-(5-bromopyridin-3-yl)tetrahydro-3'H-spiro[piperidine-4,2'-pyrrolo[2,1-b]oxazol]-3'-one | Calc'd 354, found 354 |
| I-20D | 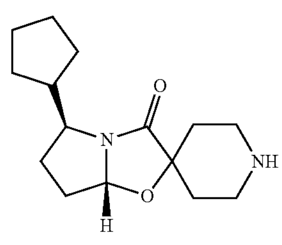 [SMILES: O=C1N2[C@@H](CC[C@H]2C2CCCC2)OC12CCNCC2] | (5'S,7a'R)-5'-cyclopentyltetrahydro-3'H-spiro[piperidine-4,2'-pyrrolo[2,1-b]oxazol]-3'-one | Calc'd 265, found 265 |
| I-20E | 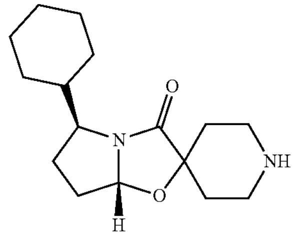 [SMILES: O=C1N2[C@@H](CC[C@H]2C2CCCCC2)OC12CCNCC2] | 5'S,7a'R)-5'-cyclohexyltetrahydro-3'H-spiro[piperidine-4,2'-pyrrolo[2,1-b]oxazol]-3'-one | Calc'd 279, found 279 |

| Intermediate | Structure | Name | Exact Mass [M + H]+ |
|---|---|---|---|
| I-20F | 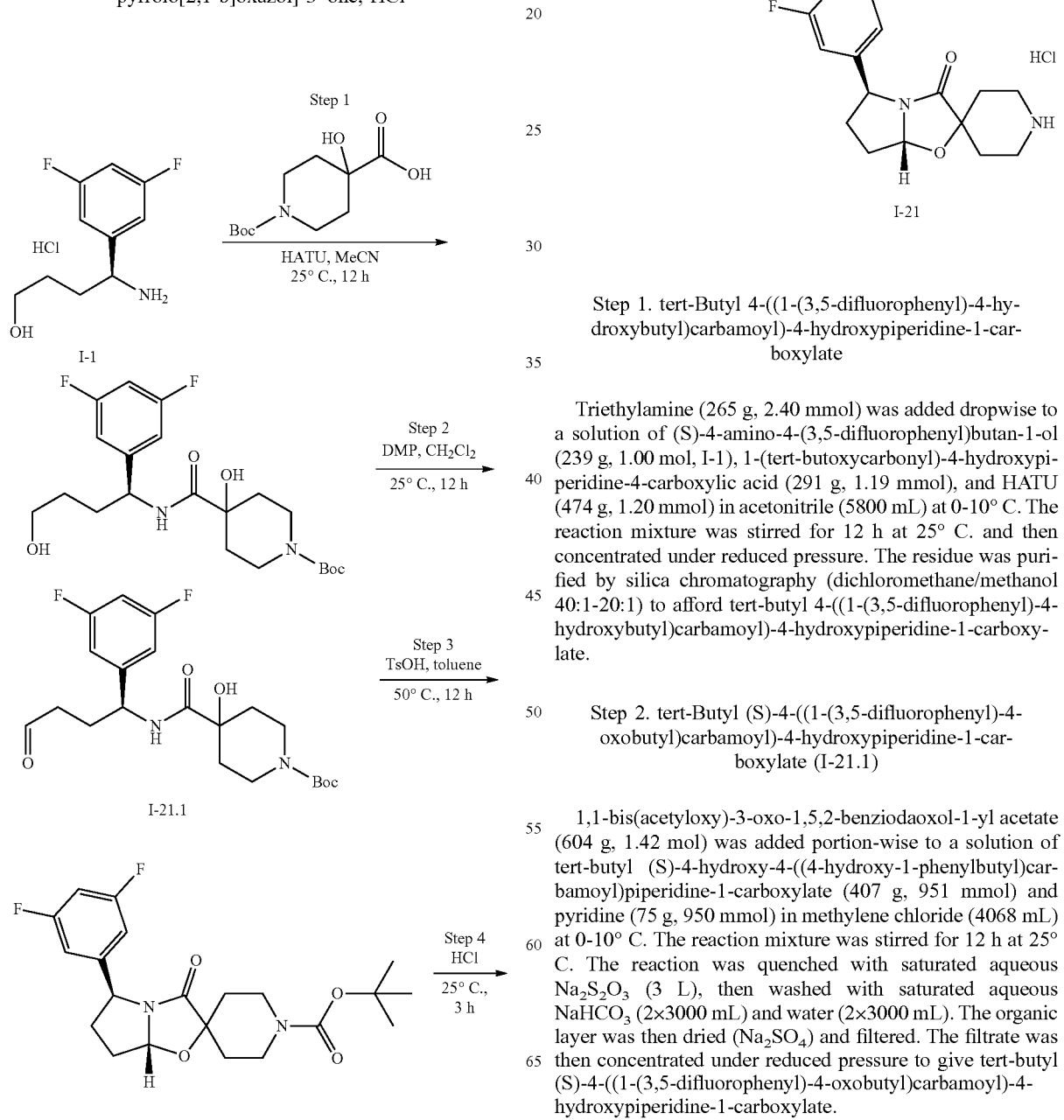 | (5'S)-5'-(3-bromo-5-fluorophenyl)tetrahydro-3'H-spiro[piperidine-4,2'-pyrrolo[2,1-b]oxazol]-3'-one | Calc'd 369, found 369 |

Intermediate I-21. Preparation of (5'S,7a'R)-5'-(3,5-difluorophenyl)tetrahydro-3'H-spiro[piperidine-4,2'-pyrrolo[2,1-b]oxazol]-3'-one, HCl

Step 1. tert-Butyl 4-((1-(3,5-difluorophenyl)-4-hydroxybutyl)carbamoyl)-4-hydroxypiperidine-1-carboxylate Triethylamine (265 g, 2.40 mmol) was added dropwise to a solution of (S)-4-amino-4-(3,5-difluorophenyl)butan-1-ol (239 g, 1.00 mol, I-1), 1-(tert-butoxycarbonyl)-4-hydroxypiperidine-4-carboxylic acid (291 g, 1.19 mmol), and HATU (474 g, 1.20 mmol) in acetonitrile (5800 mL) at 0-10° C. The reaction mixture was stirred for 12 h at 25° C. and then concentrated under reduced pressure. The residue was purified by silica chromatography (dichloromethane/methanol 40:1-20:1) to afford tert-butyl 4-((1-(3,5-difluorophenyl)-4-hydroxybutyl)carbamoyl)-4-hydroxypiperidine-1-carboxylate.

Step 2. tert-Butyl (S)-4-((1-(3,5-difluorophenyl)-4-oxobutyl)carbamoyl)-4-hydroxypiperidine-1-carboxylate (I-21.1)

1,1-bis(acetyloxy)-3-oxo-1,5,2-benziodaoxol-1-yl acetate (604 g, 1.42 mol) was added portion-wise to a solution of tert-butyl (S)-4-hydroxy-4-((4-hydroxy-1-phenylbutyl)carbamoyl)piperidine-1-carboxylate (407 g, 951 mmol) and pyridine (75 g, 950 mmol) in methylene chloride (4068 mL) at 0-10° C. The reaction mixture was stirred for 12 h at 25° C. The reaction was quenched with saturated aqueous $Na_2S_2O_3$ (3 L), then washed with saturated aqueous $NaHCO_3$ (2×3000 mL) and water (2×3000 mL). The organic layer was then dried ($Na_2SO_4$) and filtered. The filtrate was then concentrated under reduced pressure to give tert-butyl (S)-4-((1-(3,5-difluorophenyl)-4-oxobutyl)carbamoyl)-4-hydroxypiperidine-1-carboxylate.

Step 3. tert-Butyl (5'S,7a'R)-5'-(3,5-difluorophenyl)-3'-oxotetrahydro-3'H-spiro[piperidine-4,2'-pyrrolo[2,1-b]oxazole]-1-carboxylate A solution of tert-butyl (S)-4-((1-(3,5-difluorophenyl)-4-oxobutyl)carbamoyl)-4-hydroxypiperidine-1-carboxylate (239 g, 561 mmol) and TsOH (48 g, 279 mmol) in toluene (2389 mL) was stirred for 12 h at 50° C. The reaction mixture was diluted with ethyl acetate (2000 mL) and the organic layer was then washed with saturated aqueous NaHCO$_3$ (2×1500 mL) and water (3×1500 mL). The organic layer was dried (Na$_2$SO$_4$), filtered, and the filtrate was then concentrated under reduced pressure. The residue was purified by silica chromatography (petroleum ether/ethyl acetate 2:1) to give tert-butyl (5'S,7a'R)-5'-(3,5-difluorophenyl)-3'-oxotetrahydro-3'H-spiro[piperidine-4,2'-pyrrolo[2,1-b]oxazole]-1-carboxylate. MS (ESI) m/z C$_{21}$H$_{26}$F$_2$N$_2$NaO$_4$ [M+Na]$^+$ calc'd 431, found 431.

Step 4. (5'S,7a'R)-5'-(3,5-difluorophenyl)tetrahydro-3'H-spiro[piperidine-4,2'-pyrrolo[2,1-b]oxazol]-3'-one hydrochloride (1-21)

A solution of tert-butyl (5'S,7a'R)-5'-(3,5-difluorophenyl)-3'-oxotetrahydro-3'H-spiro[piperidine-4,2'-pyrrolo[2,1-b]oxazole]-1-carboxylate (73.9 g, 1.00 equiv) in HCl (739 mL, 4.0 M solution in 1,4-dioxane) was stirred for 3 h at 25° C. The reaction was filtered and the collected solids were washed with diethyl ether (3×100 mL) and then dried (Na$_2$SO$_4$) to give (5'S,7a'R)-5'-(3,5-difluorophenyl)tetrahydro-3'H-spiro[piperidine-4,2'-pyrrolo[2,1-b]oxazol]-3'-one, HCl. MS (ESI) m/z C$_{16}$H$_{19}$F$_2$N$_2$O$_2$[M+H]$^+$ calc'd 309, found 309. $^1$H-NMR (400 MHz, D$_2$O) δ 6.91-6.76 (m, 3H), 5.83 (dd, J=7.9, 5.0 Hz, 1H), 4.95 (t, J=8.1 Hz, 1H), 3.50-3.37 (m, 2H), 3.28 (td, J=12.6, 3.5 Hz, 1H), 3.17 (td, J=12.8, 3.6 Hz, 1H), 2.71 (dtd, J=13.2, 7.6, 1.9 Hz, 1H), 2.35-2.21 (m, 2H), 2.24-2.11 (m, 1H), 2.08-1.89 (m, 3H), 1.75 (tt, J=12.0, 7.8 Hz, 1H).

Each compound presented in Table 7 below were prepared in accordance with the synthetic routes in Intermediate I-21, using a combination of intermediates from Table 1, I-15A-C, and I-29 using procedures analogous to those described above.

TABLE 7

| Intermediate | Structure | Name | Exact Mass [M + H]$^+$ |
|---|---|---|---|
| I-21A | 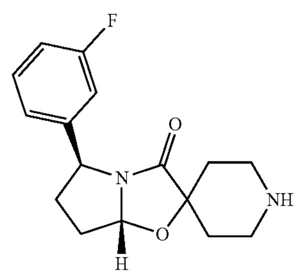 [SMILES: O=C1N2[C@@H](CC[C@H]2c2cccc(F)c2)OC12CCNCC2] | (5'S,7a'R)-5'-(3-fluorophenyl)tetrahydro-3'H-spiro[piperidine-4,2'-pyrrolo[2,1-b]oxazol]-3'-one | Calc'd 291, found 291 |
| I-21B | 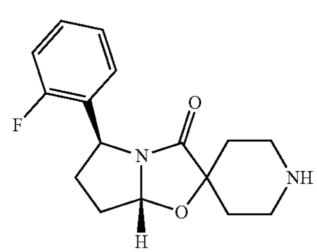 [SMILES: O=C1N2[C@@H](CC[C@H]2c2ccccc2F)OC12CCNCC2] | (5'S,7a'R)-5'(2-fluorophenyl)tetrahydro-3'H-spiro[piperidine-4,2'-pyrrolo[2,1-b]oxazol]-3'-one | Calc'd 291, found 291 |
| I-21C | 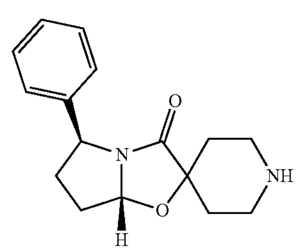 [SMILES: O=C1N2[C@@H](CC[C@H]2c2ccccc2)OC12CCNCC2] | (5'S,7a'R)-5'-phenyltetrahydro-3'H-spiro[piperidine-4,2'-pyrrolo[2,1-b]oxazol]-3'-one | Calc'd 273, found 273 |

TABLE 7-continued

| Intermediate | Structure | Name | Exact Mass [M + H]+ |
|---|---|---|---|
| I-21D | 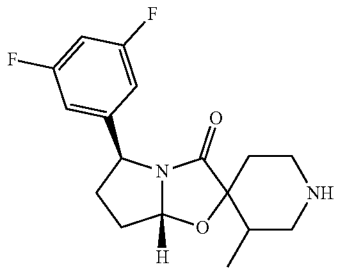 [SMILES: CC1CNCCC12O[C@@H]1CC[C@@H](c3cc(F)cc(F)c3)N1C2=O] | (5'S,7a'R)-5'-(3,5-difluorophenyl)-3-methyltetrahydro-3'H-spiro[piperidine-4,2'-pyrrolo[2,1-b]oxazol]-3'-one | Calc'd 323, found 323 |
| I-21E | 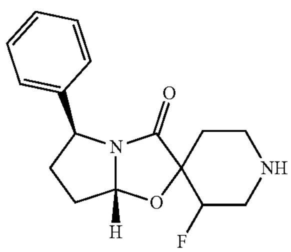 [SMILES: O=C1N2[C@@H](CC[C@H]2c2ccccc2)OC12CCNCC2F] | (5'S,7a'R)-3-fluoro-5'-phenyltetrahydro-3'H-spiro[piperidine-4,2'-pyrrolo[2,1-b]oxazol]-3'-one | Calc'd 291, found 291 |
| I-21F | 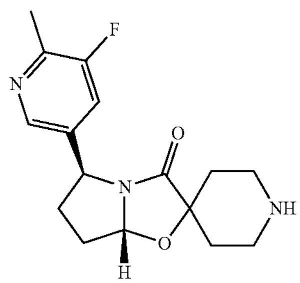 [SMILES: Cc1ncc([C@@H]2CC[C@H]3OC4(CCNCC4)C(=O)N32)cc1F] | (5'S,7a'R)-5'-(5-fluoro-6-methylpyridin-3-yl)tetrahydro-3'H-spiro[piperidine-4,2'-pyrrolo[2,1-b]oxazol]-3'-one | Calc'd 306, found 306 |

Intermediate I-22. (5'S,7a'R)-5'-Phenyltetrahydro-3'H-spiro[piperidine-4,2'-pyrrolo[2,1-b]thiazol]-3'-one

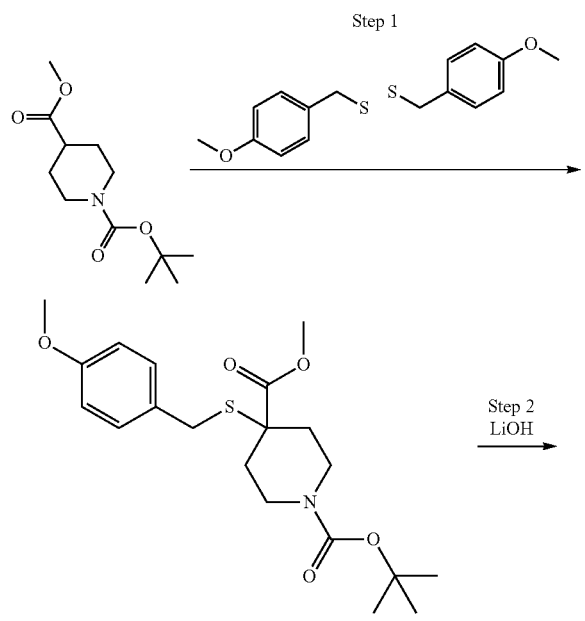

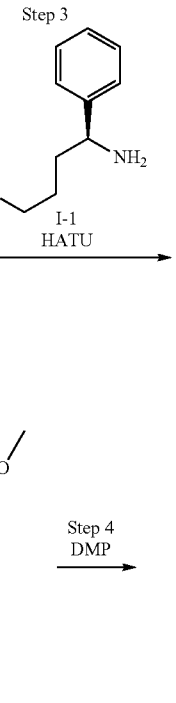

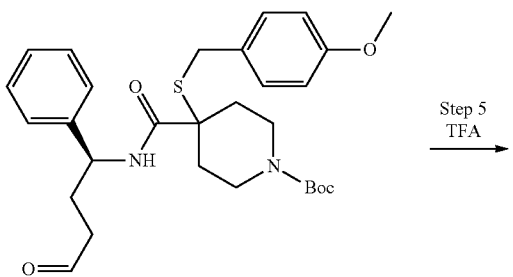

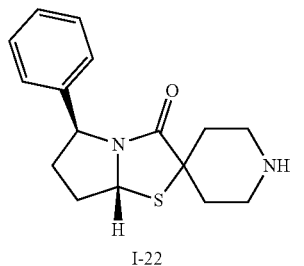

I-22

Step 1. 1-(tert-Butyl) 4-methyl 4-((4-methoxybenzyl)thio)piperidine-1,4-dicarboxylate Under an atmosphere of argon, diisopropylamine (5.86 ml, 41.1 mmol) was added to THF (50.0 ml), and cooled to −70° C. Then lithium diisopropylamide in THF (17.8 ml, 26.7 mmol, 1.6M) was added, and the mixture warmed to −5° C., then cooled again to −75° C. A solution of 1-(tert-butyl) 4-methyl piperidine-1,4-dicarboxylate (5.0 g, 20.6 mmol) in THF (12.5 ml) was added, and the mixture stirred at −25° C. for 1 h. 1,2-Bis(4-methoxybenzyl)disulfane (6.30 g, 20.55 mmol) was added over 5 min in THF (12.5 ml) and the mixture was stirred at room temperature overnight. The reaction mixture was diluted with ethyl acetate (200 mL), washed with water (100 mL) and saturated sodium hydrogen carbonate (100 mL), dried over (Na$_2$SO$_4$) and evaporated. The crude was purified by silica gel chromatography (ethyl acetate/hexane) to give 1-(tert-butyl) 4-methyl 4-((4-methoxybenzyl)thio)piperidine-1,4-dicarboxylate. MS (ESI) m/z calc'd for C$_{20}$H$_{29}$NO$_5$S [M+H]+ 396 found 396.

Step 2. 1-(tert-Butoxycarbonyl)-4-((4-methoxybenzyl)thio)piperidine-4-carboxylic acid A mixture of the 1-(tert-butyl) 4-methyl 4-((4-methoxybenzyl)thio)piperidine-1,4-dicarboxylate-(7.0 g, 17.7 mmol), LiOH (4.24 g, 17.7 mmol), MeOH (17.7 ml), THF (124 ml) and water (35.4 ml) was stirred at 60° C. for 12 h. The organic solvents were removed in vacuo and the resulting mixture was acidified to pH 5 with 2 M HCl, then extracted with EtOAc (2 mL×3). The organic layers were dried (MgSO$_4$), filtered, and concentrated. The crude product was purified by flash silica gel chromatography (ISCO®; 120 g SepaFlash® Silica Flash Column, 0~100% EtOAc/DCM) then 0~10% MeOH/DCM to give pure 1-(tert-butoxycarbonyl)-4-((4-methoxybenzyl)thio)piperidine-4-carboxylic acid. MS (ESI) m/z calc'd for C$_{19}$H$_{28}$NO$_5$S [M+H]+ 382 found 382.

Step 3. tert-Butyl (R)-4-((4-hydroxy-1-phenylbutyl)carbamoyl)-4-((4-methoxybenzyl)thio) piperidine-1-carboxylate A solution of 1-(tert-butoxycarbonyl)-4-((4-methoxybenzyl)thio)piperidine-4-carboxylic acid (300 mg, 0.786 mmol) and HATU (359 mg, 0.944 mmol) in ACN (10.0 ml) was stirred at room temperature for 10 min. (S)-4-amino-4-phenylbutan-1-ol (130 mg, 0.786 mmol) and DIEA (0.412 ml, 2.36 mmol) were added to the mixture was added. The reaction was stirred at room temperature for 24 h. The mixture was concentrated and purified by silica gel column chromatography (5% MeOH/DCM) to provide tert-butyl (R)-4-((4-hydroxy-1-phenylbutyl)carbamoyl)-4-((4-methoxybenzyl)thio)piperidine-1-carboxylate. MS (ESI) m/z C$_{29}$H$_{41}$N$_2$O$_5$S [M+H]+ calc'd 529, found 529.

Step 4. tert-Butyl (R)-4-((4-methoxybenzyl)thio)-4-((4-oxo-1-phenylbutyl)carbamoyl) piperidine-1-carboxylate Dess-Martin Periodinane (424 mg, 0.999 mmol) was added to a solution of tert-butyl (R)-4-((4-hydroxy-1-phenylbutyl)carbamoyl)-4-((4-methoxybenzyl)thio)piperidine-1-carboxylate (264 mg, 0.499 mmol) in acetonitrile (5.0 ml) and the reaction mixture was stirred at 100° C. for 2 h. The mixture was diluted with EtOAc (20 mL) and filtered through a pad of celite. The filtrate was concentrated and the crude material was taken up in EtOAc, washed with saturated aqueous NaHCO$_3$ (2×), brine, dried (Na$_2$SO$_4$), filtered, and concentrated to give tert-butyl (R)-4-((4-methoxybenzyl)thio)-4-((4-oxo-1-phenylbutyl)carbamoyl)piperidine-1-carboxylate. The crude material was taken to next step without purification. MS (ESI) m/z C$_{29}$H$_{39}$N$_2$O$_5$S [M+H]+ calc'd 527, found 527.

Step 5. (5'S,7a'R)-5'-Phenyltetrahydro-3'H-spiro[piperidine-4,2'-pyrrolo[2,1-b]thiazol]-3'-one (I-22)

tert-butyl (R)-4-((4-methoxybenzyl)thio)-4-((4-oxo-1-phenylbutyl)carbamoyl)piperidine-1-carboxylate (260 mg, 0.494 mmol), acetonitrile (5.0 ml) and TFA (0.5 ml, 6.49 mmol) were added to a round bottom flask. The resulting mixture was stirred at 70° C. for 2 h. The reaction mixture was concentrated, taken up in EtOAc, washed with saturated aqueous NaHCO$_3$ (2×), brine, dried (Na$_2$SO$_4$), filtered, and concentrated. The crude product was purified by flash silica gel chromatography (ISCO®; 24 g SepaFlash® Silica Flash Column, 0-10% MeOH/DCM) to give (5'S,7a'R)-5'-phenyltetrahydro-3'H-spiro[piperidine-4,2'-pyrrolo[2,1-b]thiazol]-3'-one. MS (ESI) m/z C$_{16}$H$_{21}$N$_2$OS [M+H]+ calc'd 289, found 289.

Compounds presented in Table 8 below were prepared in accordance with the synthetic routes in Intermediate I-22, using procedures analogous to those described above.

TABLE 8

| Intermediate | Structure | Name | Exact Mass [M + H]+ |
|---|---|---|---|
| I-22A | 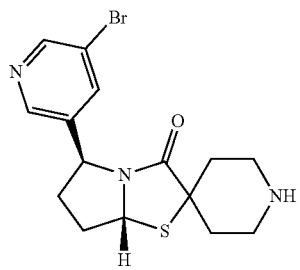 [SMILES: O=C1N2[C@@H](CC[C@H]2c2cncc(Br)c2)SC12CCNCC2] | (5'S,7a'R)-5'-(5-bromopyridin-3-yl)tetrahydro-3'H-spiro[piperidine-4,2'-pyrrolo[2,1-b]thiazol]-3'-one | Calc'd 368, found 368 |
| I-22B | 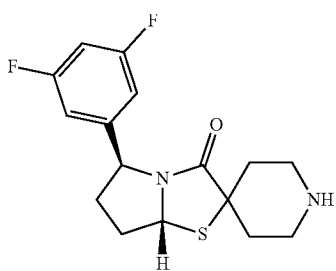 [SMILES: O=C1N2[C@@H](CC[C@H]2c2cc(F)cc(F)c2)SC12CCNCC2] | (5'S,7a'R)-5'-(3,5-difluorophenyl)tetrahydro-3'H-spiro[piperidine-4,2'-pyrrolo[2,1-b]thiazol]-3'-one | Calc'd 325, found 325 |

Intermediate I-23. Preparation of 5-((5'S)-3'-oxotetrahydro-3'H-spiro[piperidine-4,2'-pyrrolo[2,1-b]oxazol]-5'-yl)nicotinonitrile

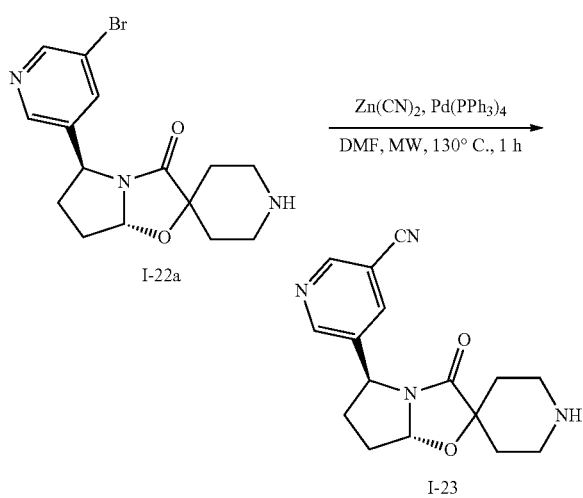

Tetrakis(triphenylphosphine)palladium(0) (10 mg, 8.7 µmol) was added to a mixture of (5'S,7a'R)-5'-(5-bromopyridin-3-yl)tetrahydro-3'H-spiro[piperidine-4,2'-pyrrolo[2,1-b]oxazol]-3'-one (30 mg, 0.085 mmol, I-22A), dicyanozinc (30 mg, 0.26 mmol) in DMF (1 mL) under $N_2$. Then the mixture was stirred at 130° C. on MW for 1 h. The mixture was filtered and concentrated. The residue was purified by preparative HPLC (Boston Green ODS 150×30 mm×5 um, Condition water (0.1% TFA)-MeCN Begin B 3, End B 33 Gradient Time(min) 10, 100% B Hold Time(min) 2 Flow-Rate (ml/min) 25, Injections 2 to give 5-((5'S)-3'-oxotetrahydro-3'H-spiro[piperidine-4,2'-pyrrolo[2,1-b]oxazol]-5'-yl)nicotinonitrile. MS (ESI) m/z $C_{16}H_{19}N_4O_2$ [M+H]+ calc'd 299, found 299.

Compounds presented in Table 9 below were prepared in accordance with the synthetic routes in Intermediate I-23, using procedures analogous to those described above.

TABLE 9

| Intermediate | Structure | Name | Exact Mass [M + H]+ |
|---|---|---|---|
| I-23A | 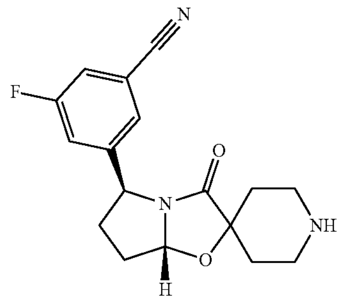 [SMILES: N#Cc1cc(F)cc([C@@H]2CC[C@H]3OC4(CCNCC4)C(=O)N32)c1] | 3-fluoro-5-((5'S)-3'-oxotetrahydro-3'H-spiro[piperidine-4,2'-pyrrolo[2,1-b]oxazol]-5'-yl)benzonitrile | Calc'd 316, found 316 |
| I-23B | 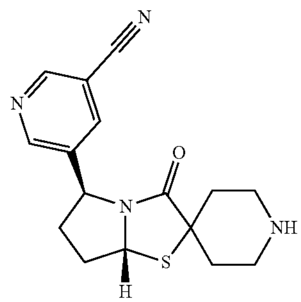 [SMILES: N#Cc1cncc([C@@H]2CC[C@H]3SC4(CCNCC4)C(=O)N32)c1] | 5-((5'S,7a'R)-3'-oxotetrahydro-3'H-spiro[piperidine-4,2'-pyrrolo[2,1-b]thiazol]-5'-yl)nicotinonitrile | Calc'd 315, found 315 |

Intermediate I-24. Preparation of 1-(tert-butyl) 5'-methyl (5'S)-3'-oxotetrahydro-3'H-spiro[piperidine-4,2'-pyrrolo[2,1-b]oxazole]-1,5'-dicarboxylate

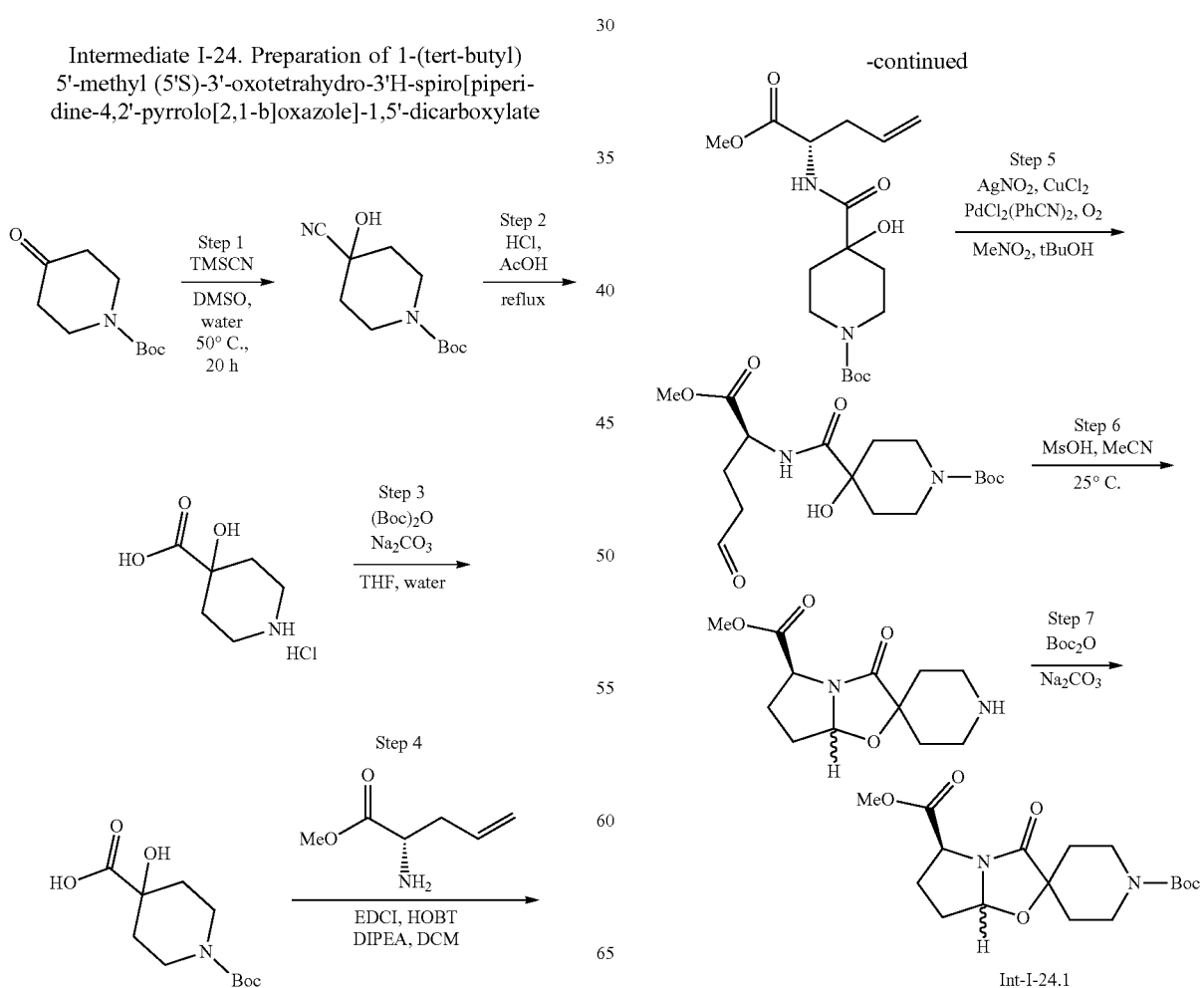

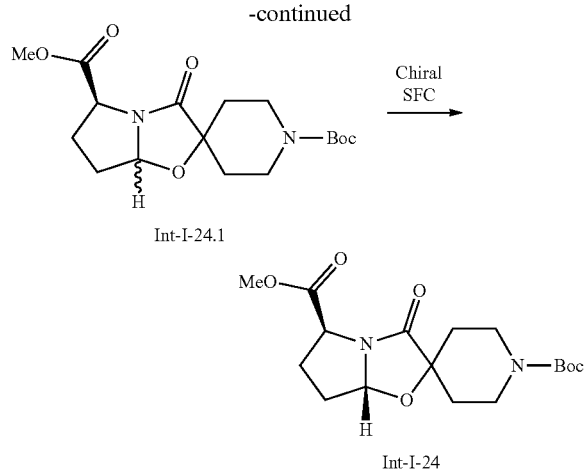

Step 1. tert-Butyl 4-cyano-4-hydroxypiperidine-1-carboxylate

Trimethylsilyl cyanide (209 g) was added dropwise to a stirred solution of tert-butyl 4-oxopiperidine-1-carboxylate (300 g) in DMSO:$H_2O$=5:1 (20 L) at 25° C. under an atmosphere of nitrogen. The solution was stirred for 20 h at 50° C. under an atmosphere of nitrogen. The reaction mixture was diluted with water (10 L) and then extracted with (1:5) ethyl acetate:MTBE (6 L×2). The combined organic layers were washed with saturated aqueous solutions of $NaHCO_3$ (6 L×2), saturated aqueous $FeSO_4$ (6 L×2), and brine (6 L×2), respectively. The organic layer was dried over anhydrous $Na_2SO_4$ and then filtered. The filtrate was then concentrated under reduced pressure to give tert-butyl 4-cyano-4-hydroxypiperidine-1-carboxylate, which was used in the next step directly without further purification.

Step 2. 4-Hydroxypiperidine-4-carboxylic acid, HCl tert-butyl 4-cyano-4-hydroxypiperidine-1-carboxylate (30 g) was added to a stirred mixture of HCl (97.5 mL) and acetic acid (97.5 mL) at room temperature under $N_2$ atmosphere. The mixture was stirred overnight at 115° C. under an atmosphere of nitrogen. The reaction mixture was cooled to room temperature and concentrated under reduced pressure. The residue was dissolved in acetonitrile (3 L) and the precipitated solids were collected by filtration and washed with acetonitrile (3 L) to give 4-hydroxypiperidine-4-carboxylic acid, HCl. The crude product was used in the next step directly without further purification.

Step 3. 1-(tert-Butoxycarbonyl)-4-hydroxypiperidine-4-carboxylic acid

Sodium carbonate (1.46 g) and di-tert-butyl dicarbonate (1.95 g) were added to a solution of 4-hydroxypiperidine-4-carboxylic acid (1 g) in THF (10 mL) and $H_2O$ (10 mL) at 0-5° C. The resulting mixture was stirred for 3 h at 25° C. The reaction mixture was extracted with EtOAc (2×10 mL). The mixture was acidified to pH 4-5 with 1N HCl. The aqueous layers were washed with EtOAc (3×10 mL). Combined organic layers were dried ($Na_2SO_4$). After filtration, the filtrate was concentrated under reduced pressure to give 1-(tert-butoxycarbonyl)-4-hydroxypiperidine-4-carboxylic acid, which was used in the next step directly without further purification.

Step 4. tert-Butyl (S)-4-hydroxy-4-((1-methoxy-1-oxopent-4-en-2-yl)carbamoyl)piperidine-1-carboxylate DIEA (38.4 mL), 1-Ethyl-3-(3-dimethylaminopropyl)carbodiimide (16.35 g) and HOBT (11.52 g) were added to a stirred solution of 1-(tert-butoxycarbonyl)-4-hydroxypiperidine-4-carboxylic acid (10 g) and methyl (2S)-2-aminopent-4-enoate (19 g) in THF (100 mL) at room temperature, under nitrogen and stirred overnight at room temperature. The reaction mixture was washed with 5% aqueous HCl (10 L), 5% aqueous $NaHCO_3$ (10 L), then saturated aqueous sodium chloride (5L×2), respectively, and the organics were dried ($Na_2SO_4$) and filtered. The filtrate was concentrated under reduced pressure. The residue was purified by silica gel column chromatography, eluted with petroleum ether/ethyl acetate (10:1) to afford tert-butyl 4-hydroxy-4-{[(2S)-1-methoxy-1-oxopent-4-en-2-yl]carbamoyl}piperidine-1-carboxylate.

Step 5. tert-Butyl (S)-4-hydroxy-4-((1-methoxy-1,5-dioxopentan-2-yl)carbamoyl)piperidine-1-carboxylate Bis(benzonitrile), dichloropalladium (1.29 g) and tert-butyl 4-hydroxy-4-{[(2S)-1-methoxy-1-oxopent-4-en-2-yl]carbamoyl}piperidine-1-carboxylate (10 g) dissolved in t-butanol:$CH_3NO_2$=15:1 (12V, 120 mL) were added dropwise to a stirred solution of silver nitrite (0.26 g) and $CuCl_2$ (0.45 g) in t-butanol:$CH_3NO_2$=15:1 (4V, 40 mL) at room temperature, under an atmosphere of oxygen, and the mixture was stirred at room temperature overnight. The reaction mixture was purged with air, filtered, and the filter cake was washed with t-butanol:$CH_3NO_2$=15:1 (2×100 mL). The filtrate was concentrated under reduced pressure to give tert-butyl (S)-4-hydroxy-4-((1-methoxy-1,5-dioxopentan-2-yl)carbamoyl)piperidine-1-carboxylate. The crude product was used in the next step directly without further purification.

Step 6. Methyl (5'S)-3'-oxotetrahydro-3'H-spiro[piperidine-4,2'-pyrrolo[2,1-b]oxazole]-5'-carboxylate $CH_3SO_3H$ (7.74 g) was added dropwise to a stirred solution of tert-butyl 4-hydroxy-4-{[(2S)-1-methoxy-1,5-dioxopentan-2-yl]carbamoyl} piperidine-1-carboxylate (10 g) in MeCN (150 mL) at room temperature, under nitrogen atmosphere. The resulting mixture was stirred for 5 h at room temperature under nitrogen atmosphere. The reaction mixture was concentrated to dryness under reduced pressure to give methyl (5'S)-3'-oxotetrahydro-3'H-spiro[piperidine-4,2'-pyrrolo[2,1-b]oxazole]-5'-carboxylate, which was used in the next step directly without further purification.

Step 7. 1-(tert-Butyl) 5'-methyl (5'S)-3'-oxotetrahydro-3'H-spiro[piperidine-4,2'-pyrrolo[2,1-b]oxazole]-1,5'-dicarboxylate (Int-I-24.1)

$Na_2CO_3$ (400 mg) and di-tert-butyl dicarbonate (900 μL) were added to a stirred solution of methyl (5'S)-3'-oxotetrahydrospiro[piperidine-4,2'-pyrrolo[2,1-b][1,3]oxazole]-5'-carboxylate (500 mg) in THF (19 mL):$H_2O$ (1 mL) at room temperature, under nitrogen atmosphere and stirred overnight. The mixture was extracted with EtOAc (3×10 mL) and the combined organic layers were washed with brine, dried (Na$_2$SO$_4$), and filtered. The filtrate was concentrated under reduced pressure and the crude product was re-crystallized from petroleum ether/ethyl acetate (10:1) to afford 1-tert-butyl 5-methyl (5'S)-3'-oxo-tetrahydrospiro[piperidine-4,2'-pyrrolo[2,1-b][1,3]oxazole]-1,5'-dicarboxylate. MS (ESI) m/z C$_{17}$H$_{27}$N$_2$O$_6$ [M+H]$^+$ calc'd 355, found 355. $^1$H NMR (400 MHz, CDCl$_3$): δ 5.66-5.50 (m, 1H), 4.56 (dd, J=8.5, 5.7 Hz, 1H), 4.06-3.86 (m, 2H), 3.75 (d, J=8.2 Hz, 3H), 3.27-3.03 (m, 2H), 2.40 (dtd, J=13.7, 8.7, 5.1 Hz, 1H), 2.29-2.19 (m, 1H), 2.19-2.04 (m, 1H), 2.03-1.50 (m, 5H), 1.45 (s, 9H).

Chiral SFC. 1-(tert-butyl) 5'-methyl (5'S,7a'R)-3'-oxotetrahydro-3'H-spiro[piperidine-4,2'-pyrrolo[2,1-b]oxazole]-1,5'-dicarboxylate (I-24)

The diastereomeric mixture of 1-(tert-butyl) 5'-methyl (5'S)-3'-oxotetrahydro-3'H-spiro[piperidine-4,2'-pyrrolo[2,1-b]oxazole]-1,5'-dicarboxylate (4 g, 11.29 mmol) was submitted to chiral SFC purification (Column & Dimensions: Lux-4, 21×250 mm, 5 um; UV Wavelength: 215 nm; Flow Rate: 80 ml/min; Modifier: 10% MeOH with 0.1% NH$_4$OH; Instrument: Sepiatec 2). Peak 1 was collected and concentrated to afford 1-(tert-butyl) 5'-methyl (5'S,7a'R)-3'-oxotetrahydro-3'H-spiro[piperidine-4,2'-pyrrolo[2,1-b]oxazole]-1,5'-dicarboxylate (2.7 g). MS (ESI) m/z C$_{17}$H$_{27}$N$_2$O$_6$ [M+H]$^+$ calc'd 355, found 355.

Intermediate I-25. Preparation of (5'S,7a'R)-1-benzoyl-3'-oxotetrahydro-3'H-spiro [piperidine-4,2'-pyrrolo[2,1-b]oxazole]-5'-carboxylic acid

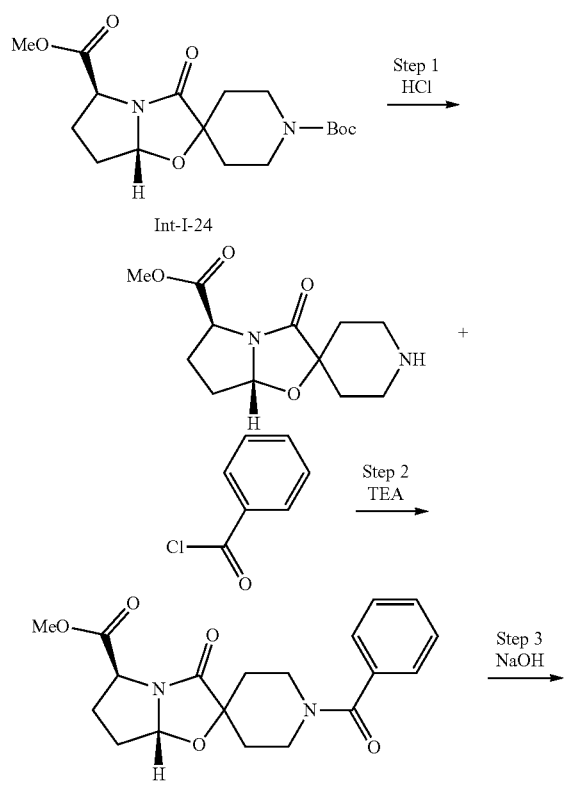

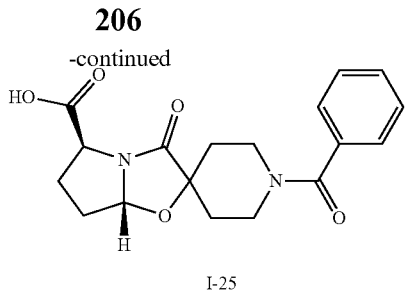

I-25

Step 1. Methyl (5'S,7a'R)-3'-oxotetrahydro-3'H-spiro[piperidine-4,2'-pyrrolo[2,1-b]oxazole]-5'-carboxylate HCl (3.53 ml, 14.1 mmol) (4 M in dioxane) was added to a solution of 1-(tert-butyl) 5'-methyl (5'S,7a'R)-3'-oxotetrahydro-3'H-spiro[piperidine-4,2'-pyrrolo[2,1-b]oxazole]-1,5'-dicarboxylate (1 g, 2.82 mmol, I-24) in DCM (28.2 ml) at room temperature, and the resulting mixture was stirred over the weekend. The reaction was quenched with saturated aqueous NaHCO$_3$ (30 mL), then stirred at room temperature for 15 min. The layers were separated, and the pH of the aqueous layer was confirmed to be basic. The aqueous layer was then extracted 2× with DCM (30 mL). The aqueous layer was then extracted (3×) with 25% isopropanol in chloroform (30 mL). The organic layer was dried (MgSO$_4$), filtered and concentrated to provide methyl (5'S,7a'R)-3'-oxotetrahydro-3'H-spiro[piperidine-4,2'-pyrrolo[2,1-b]oxazole]-5'-carboxylate which was directly without purification.

Step 2. Methyl (5'S,7a'R)-1-benzoyl-3'-oxotetrahydro-3'H-spiro[piperidine-4,2'-pyrrolo[2,1-b]oxazole]-5'-carboxylate Methyl (5'S,7a'R)-3'-oxotetrahydro-3'H-spiro[piperidine-4,2'-pyrrolo[2,1-b]oxazole]-5'-carboxylate (417 mg, 1.64 mmol) was dissolved in DCM (14.3 mL). TEA (686 µL, 4.92 mmol) was added in one portion and the solution was cooled in an ice bath. Benzoyl chloride (0.209 mL, 1.80 mmol) (diluted with DCM (1.5 ml)) was added slowly and the reaction was warmed to 25° C. and stirred for 1 h. Water (20 mL) and DCM (10 mL) were added, and the phases were separated and the aqueous phase was extracted twice with DCM (20 mL). The combined organics were dried (MgSO$_4$), filtered and concentrated. The crude residue was purified by ISCO on a RediSep Gold 24 g column, eluting with 0-100% (25% EtOH in EtOAc) in Hexanes, to provide methyl (5'S,7a'R)-1-benzoyl-3'-oxotetrahydro-3'H-spiro[piperidine-4,2'-pyrrolo[2,1-b]oxazole]-5'-carboxylate. MS (ESI) m/z C$_{19}$H$_{23}$N$_2$O$_5$ [M+H]$^+$ calc'd 359, found 359.

Step 3. (5'S)-1-Benzoyl-3'-oxotetrahydro-3'H-spiro[piperidine-4,2'-pyrrolo[2,1-b]oxazole]-5'-carboxylic acid (I-25)

NaOH (891 µL, 1.783 mmol) was added to methyl (5'S)-1-benzoyl-3'-oxotetrahydro-3'H-spiro[piperidine-4,2'-pyrrolo[2,1-b]oxazole]-5'-carboxylate (300 mg, 0.837 mmol) in ethanol (837 µL), and the resulting mixture was stirred at room temperature for 2 h. DCM (8 mL) and 1 M HCl (8 mL) were added, and the resulting mixture was stirred for 5 min at room temperature. The layers were then separated, and the aqueous layer was checked for pH to ensure acidic. The aqueous layer was then extracted 3× with DCM (10 mL). The combined organic layers were dried (MgSO4), and concentrated to provide (5'S)-1-benzoyl-3'-oxotetrahydro-3'H-spiro[piperidine-4,2'-pyrrolo[2,1-b]oxazole]-5'-carboxylic acid. MS (ESI) m/z $C_{18}H_{21}N_2O_5$ [M+H]$^+$ calc'd 345, found 345.

Intermediate I-26. Preparation of (5'S,7a'R)-1-(4-bromopyrazolo[1,5-a]pyridin-7-yl)-5'-(5-fluoropyridin-3-yl)tetrahydro-3'H-spiro[piperidine-4,2'-pyrrolo[2,1-b]oxazol]-3'-one

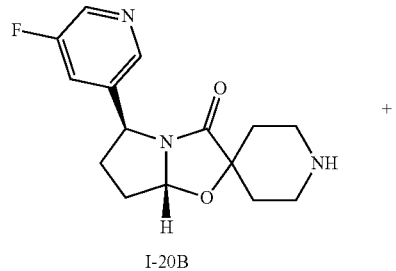

I-20B

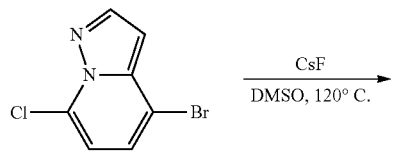

CsF
DMSO, 120° C.

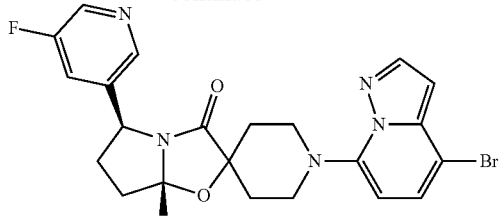

I-26

A scintillation vial containing (5'S,7a'R)-5'-(5-fluoropyridin-3-yl)tetrahydro-3'H-spiro[piperidine-4,2'-pyrrolo[2,1-b]oxazol]-3'-one (40 mg, 0.137 mmol), 4-bromo-7-chloropyrazolo[1,5-a]pyridine (48 mg, 0.206 mmol, I-20B) and CsF (63 mg, 0.412 mmol) was taken up in DMSO (1.4 mL), and the resulting mixture was stirred for 16 h at 120° C. After cooling, the reaction was partitioned with EtOAc (10 mL), water (3 mL), and saturated aqueous NaHCO$_3$ (3 mL). The layers were separated, and the aqueous layer was extracted with EtOAc (15 mL, ×2). The combined organic layers were washed with water (5 mL) and brine (5 mL), dried (MgSO$_4$), filtered and concentrated under reduced pressure. The residue was purified by flash silica gel chromatography (MeOH/DCM, 0-50%) to afford (5'S,7a'R)-1-(4-bromopyrazolo[1,5-a]pyridin-7-yl)-5'-(5-fluoropyridin-3-yl)tetrahydro-3'H-spiro[piperidine-4,2'-pyrrolo[2,1-b]oxazol]-3'-one. MS (ESI) m/z $C_{22}H_{22}BrFN_5O_2$[M+H]$^+$ calc'd 486, found 486, 488.

Compounds presented in Table 10 below were prepared in accordance with the synthetic route in Intermediate I-26, using a procedure analogous to that described above.

TABLE 10

| Intermediate | Structure | Name |
|---|---|---|
| I-26A | 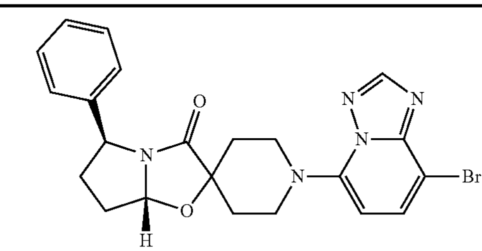 | (5'S,7a'R)-1-(8-bromo-[1,2,4]triazolo[1,5-a]pyridin-5-yl)-5'-phenyltetrahydro-3'H-spiro[piperidine-4,2'-pyrrolo[2,1-b]oxazol]-3'-one |
| I-26B | 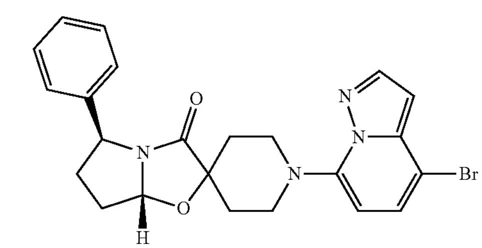 [SMILES: O=C1N2[C@@H](CC[C@H]2c2ccccc2)OC12CCN(c1ccc(Br)c3ccnn13)CC2] | (5'S,7a'R)-1-(4-bromopyrazolo[1,5-a]pyridin-7-yl)-5'-phenyltetrahydro-3'H-spiro[piperidine-4,2'-pyrrolo[2,1-b]oxazol]-3'-one |
| I-26C | 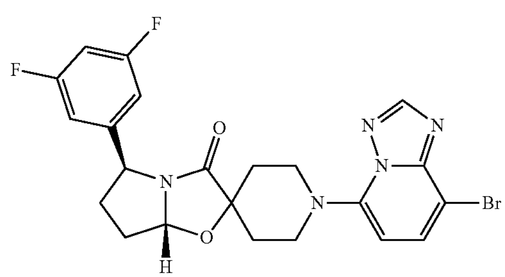 [SMILES: O=C1N2[C@@H](CC[C@H]2c2cc(F)cc(F)c2)OC12CCN(c1ccc(Br)c3ncnn13)CC2] | (5'S,7a'R)-1-(8-bromo-[1,2,4]triazolo[1,5-a]pyridin-5-yl)-5'-(3,5-difluorophenyl)tetrahydro-3'H-spiro[piperidine-4,2'-pyrrolo[2,1-b]oxazol]-3'-one |

TABLE 10-continued

| Intermediate | Structure | Name |
|---|---|---|
| I-26D | 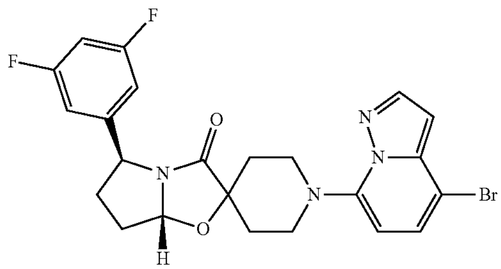 [SMILES: O=C1N2[C@@H](CC[C@H]2c2cc(F)cc(F)c2)OC12CCN(c1ccc(Br)c3ccnn13)CC2] | (5'S,7a'R)-1-(4-bromopyrazolo[1,5-a]pyridin-7-yl)-5'-(3,5-difluorophenyl)tetrahydro-3'H-spiro[piperidine-4,2'-pyrrolo[2,1-b]oxazol]-3'-one |
| I-26E | 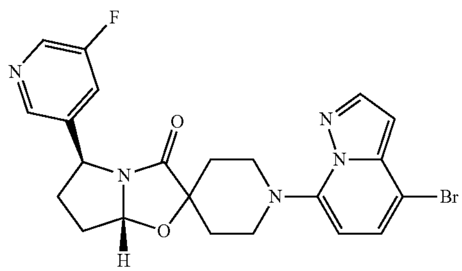 [SMILES: O=C1N2[C@@H](CC[C@H]2c2cncc(F)c2)OC12CCN(c1ccc(Br)c3ccnn13)CC2] | (5'S,7a'R)-1-(4-bromopyrazolo[1,5-a]pyridin-7-yl)-5'-(5-fluoropyridin-3-yl)tetrahydro-3'H-spiro[piperidine-4,2'-pyrrolo[2,1-b]oxazol]-3'-one |
| I-26F | 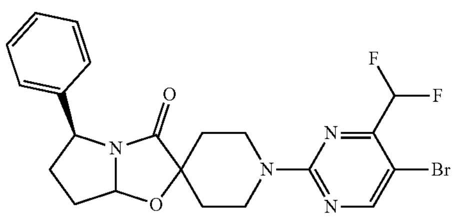 [SMILES: O=C1N2C(CC[C@H]2c2ccccc2)OC12CCN(c1ncc(Br)c(C(F)F)n1)CC2] | (5'S)-1-(5-bromo-4-(difluoromethyl)pyrimidin-2-yl)-5'-phenyltetrahydro-3'H-spiro[piperidine-4,2'-pyrrolo[2,1-b]oxazol]-3'-one |
| I-26G | 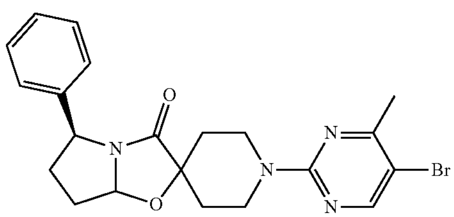 [SMILES: Cc1nc(N2CCC3(CC2)OC2CC[C@@H](c4ccccc4)N2C3=O)ncc1Br] | (5'S)-1-(5-bromo-4-methylpyrimidin-2-yl)-5'-phenyltetrahydro-3'H-spiro[piperidine-4,2'-pyrrolo[2,1-b]oxazol]-3'-one |
| I-26H | 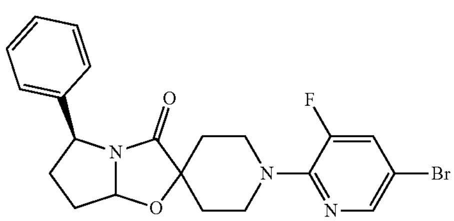 [SMILES: O=C1N2C(CC[C@H]2c2ccccc2)OC12CCN(c1ncc(Br)cc1F)CC2] | (5'S)-1-(5-bromo-3-fluoropyridin-2-yl)-5'-phenyltetrahydro-3'H-spiro[piperidine-4,2'-pyrrolo[2,1-b]oxazol]-3'-one |
| I-26I | 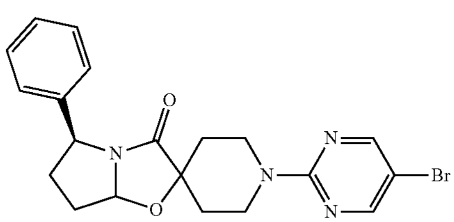 [SMILES: O=C1N2C(CC[C@H]2c2ccccc2)OC12CCN(c1ncc(Br)cn1)CC2] | (5'S)-1-(5-bromopyrimidin-2-yl)-5'-phenyltetrahydro-3'H-spiro[piperidine-4,2'-pyrrolo[2,1-b]oxazol]-3'-one |

TABLE 10-continued

| Intermediate | Structure | Name |
|---|---|---|
| I-26J | 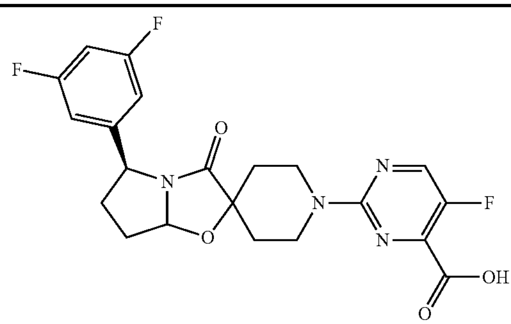 | 2-((5'S)-5'-(3,5-difluorophenyl)-3'-oxotetrahydro-3'H-spiro[piperidine-4,2'-pyrrolo[2,1-b]oxazol]-1-yl)-5-fluoropyrimidine-4-carboxylic acid |

Intermediate I-27. Preparation of (5'S)-7'-fluoro-5'-phenyltetrahydro-3'H-spiro [piperidine-4,2'-pyrrolo[2,1-b]oxazol]-3'-one, TFA

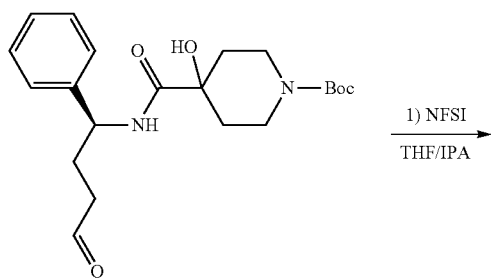

1) NFSI
THF/IPA

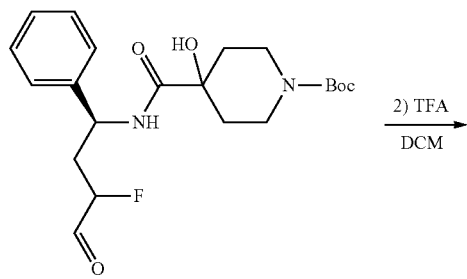

2) TFA
DCM

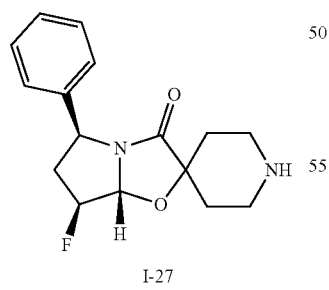

I-27

Step 1. tert-Butyl 4-(((1s)-3-fluoro-4-oxo-1-phenyl-butyl)carbamoyl)-4-hydroxypiperidine-1-carboxylate (5S)-(−)-2,2,3-Trimethyl-5-benzyl-4-imidazolidinone dichloroacetic acid (8.0 mg, 0.023 mmol) (prepared analogous to I-21.1) and N-fluorobenzenesulfonimide (121 mg, 0.384 mmol) in THF (466 µL) and 2-Propanol (46.6 µL) were added to a 20 mL vial. The mixture was stirred until homogenous at room temperature then chilled to −10° C. After 5 min, tert-butyl (S)-4-hydroxy-4-((4-oxo-1-phenyl-butyl)carbamoyl)piperidine-1-carboxylate (30 mg, 0.077 mmol) was added (as a mixture in 100 µL THF) and stirred. The reaction mixture was quenched at −0° C. with 60 µL Me$_2$S and diluted with diethyl ether, then saturated aqueous NaHCO$_3$. The organics were extracted with Et$_2$O/EtOAc (5 mL×3), dried (MgSO$_4$), filtered, and concentrated. tert-Butyl 4-(((1s)-3-fluoro-4-oxo-1-phenylbutyl)carbamoyl)-4-hydroxypiperidine-1-carboxylate was carried on crude to the next step. MS (ESI) m/z C$_{21}$H$_{29}$FN$_2$O$_5$[M+H-Boc]$^+$ calc'd 309, found 309.

Step 2. (5'S)-7'-fluoro-5'-phenyltetrahydro-3'H-spiro [piperidine-4,2'-pyrrolo[2,1-b]oxazol]-3'-one, TFA (I-27)

tert-Butyl 4-(((1S)-3-fluoro-4-oxo-1-phenylbutyl)carbamoyl)-4-hydroxypiperidine-1-carboxylate (31 mg, 0.077 mmol) was added to DCM (500 µL) followed by TFA (70 µL). The mixture was capped and heated overnight at 50° C. The mixture was concentrated to afford (5'S)-7'-fluoro-5'-phenyltetrahydro-3'H-spiro[piperidine-4,2'-pyrrolo[2,1-b]oxazol]-3'-one, TFA and was used in the next step without further purification. MS (ESI) m/z C$_{16}$H$_{20}$FN$_2$O$_2$[M+H]$^+$ calc'd 291, found 291.

Intermediate I-28. Preparation of (5'S,7a'R)-7a'-methyl-5'-phenyltetrahydro-3'H-spiro[piperidine-4,2'-pyrrolo[2,1-b]oxazol]-3'-one

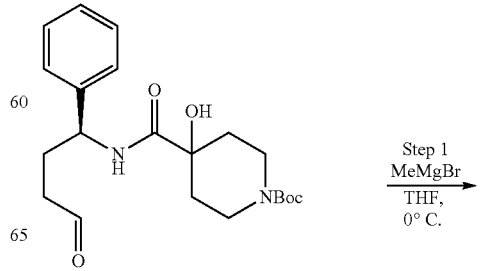

Step 1
MeMgBr
THF,
0° C.

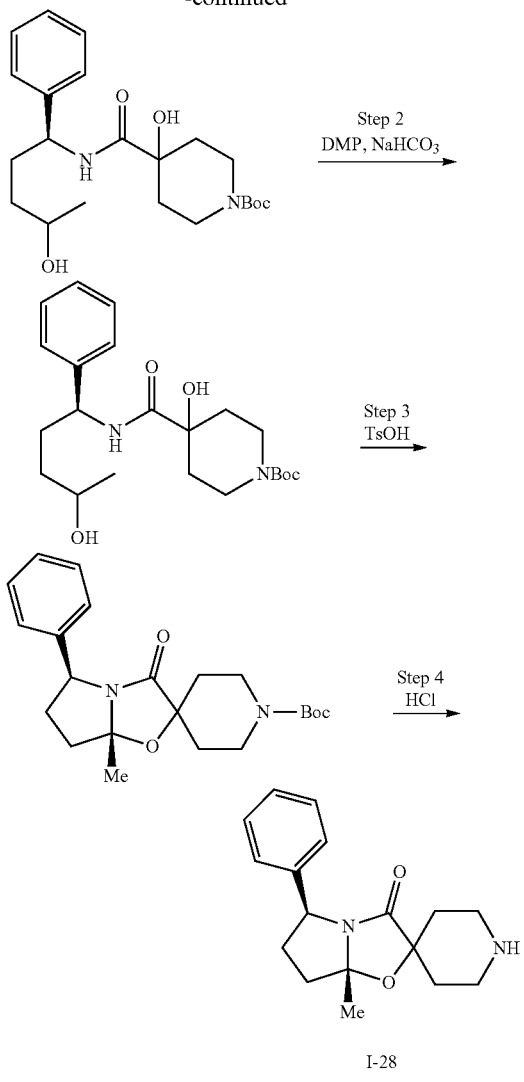

Step 1. tert-Butyl 4-hydroxy-4-(((1S)-4-hydroxy-1-phenylpentyl)carbamoyl)piperidine-1-carboxylate Methylmagnesium bromide (3.4 M in 2-Methyl THF, 1.32 mL, 4.48 mmol) was added to a solution of tert-butyl (S)-4-hydroxy-4-((4-oxo-1-phenylbutyl)carbamoyl)piperidine-1-carboxylate (350 mg, 0.896 mmol) (prepared analogous to I-21.1) in THF (8.9 mL), at 0° C. The reaction mixture was stirred for 20 min, and quenched cold with saturated aqueous NH$_4$Cl. The resulting mixture was diluted with DCM (20 mL) and allowed to warm to room temperature. The aqueous layer was extracted with DCM (20 mL×2), dried (Na$_2$SO$_4$), filtered, and concentrated under reduced pressure. The residue was purified by flash silica gel chromatography with ELS detector (ethyl acetate/hexanes, 0-100%) to afford tert-butyl 4-hydroxy-4-(((1S)-4-hydroxy-1-phenylpentyl)carbamoyl)piperidine-1-carboxylate. MS (ESI) m/z C$_{22}$H$_{34}$N$_2$O$_5$ [M+H]$^+$ calc'd, 407 found 407.

Step 2. tert-Butyl (S)-4-hydroxy-4-((4-oxo-1-phenylpentyl)carbamoyl)piperidine-1-carboxylate tert-butyl 4-hydroxy-4-(((1S)-4-hydroxy-1-phenylpentyl)carbamoyl)piperidine-1-carboxylate (220 mg, 0.541 mmol) and sodium bicarbonate (54.6 mg, 0.649 mmol) in dry DCM (5.4 mL) were added to a flask. The mixture was cooled to 0° C. and Dess-Martin periodinane (275 mg, 0.649 mmol) was added in one portion and the ice bath was removed after 5 min, mixture allowed to stir at room temperature for 1 h. The mixture was diluted with DCM (5 mL) and quenched with 10% aqueous Na$_2$S$_2$O$_3$ and vigorously stirred for 10 min. The aqueous layer was extracted with DCM (10 mL), dried (Na$_2$SO$_4$), filtered and the solvent was evaporated under reduced pressure to afford tert-butyl (S)-4-hydroxy-4-((4-oxo-1-phenylpentyl)carbamoyl)piperidine-1-carboxylate. MS (ESI) m/z C$_{22}$H$_{32}$NaN$_2$O$_5$[M+Na]$^+$ calc'd, 427 found 427.

Step 3. tert-Butyl (5'S,7a'R)-7a'-methyl-3'-oxo-5'-phenyltetrahydro-3'H-spiro[piperidine-4,2'-pyrrolo[2,1-b]oxazole]-1-carboxylate Tosic acid (50.3 mg, 0.265 mmol) was added to a crude mixture of tert-butyl (S)-4-hydroxy-4-((4-oxo-1-phenylpentyl)carbamoyl)piperidine-1-carboxylate (214 mg, 0.529 mmol) in toluene/THF 5:1 (5.2 mL). The mixture was stirred at 60° C. for 2 h and allowed to stir at room temperature overnight. The reaction was partitioned with EtOAc (20 mL) and saturated aqueous NaHCO$_3$. The layers were separated, the organic layer was dried (Na$_2$SO$_4$), filtered, and concentrated to provide tert-butyl (5'S,7a'R)-7a'-methyl-3'-oxo-5'-phenyltetrahydro-3'H-spiro[piperidine-4,2'-pyrrolo[2,1-b]oxazole]-1-carboxylate. MS (ESI) m/z C$_{18}$H$_{23}$N$_2$O$_4$ [M+H-(tert-butyl)]$^+$ calc'd, 331 found 331.

Step 4. (5'S,7a'R)-7a'-methyl-5'-phenyltetrahydro-3'H-spiro[piperidine-4,2'-pyrrolo[2,1-b]oxazol]-3'-one (I-28)

HCl (4M in dioxanes, 408 µL, 1.63 mmol) was added dropwise to a solution of tert-butyl (5'S,7a'R)-7a'-methyl-3'-oxo-5'-phenyltetrahydro-3'H-spiro[piperidine-4,2'-pyrrolo[2,1-b]oxazole]-1-carboxylate (126 mg, 0.326 mmol) in DCM (1.3 mL). The mixture was allowed to stir for 15 min then concentrated under reduced pressure to provide (5'S,7a'R)-7a'-methyl-5'-phenyltetrahydro-3'H-spiro[piperidine-4,2'-pyrrolo[2,1-b]oxazol]-3'-one, HCl. MS (ESI) m/z C$_{17}$H$_{23}$N$_2$O$_2$ [M+H-(tert-butyl)]$^+$ calc'd, 287 found 287.

Intermediate I-29. Preparation of (S)-4-amino-4-(5-fluoro-6-methylpyridin-3-yl)butan-1-ol

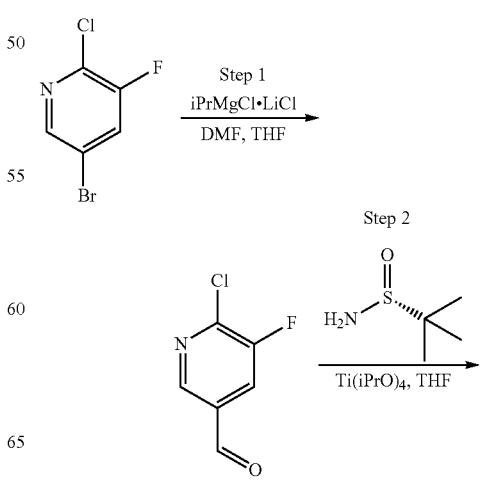

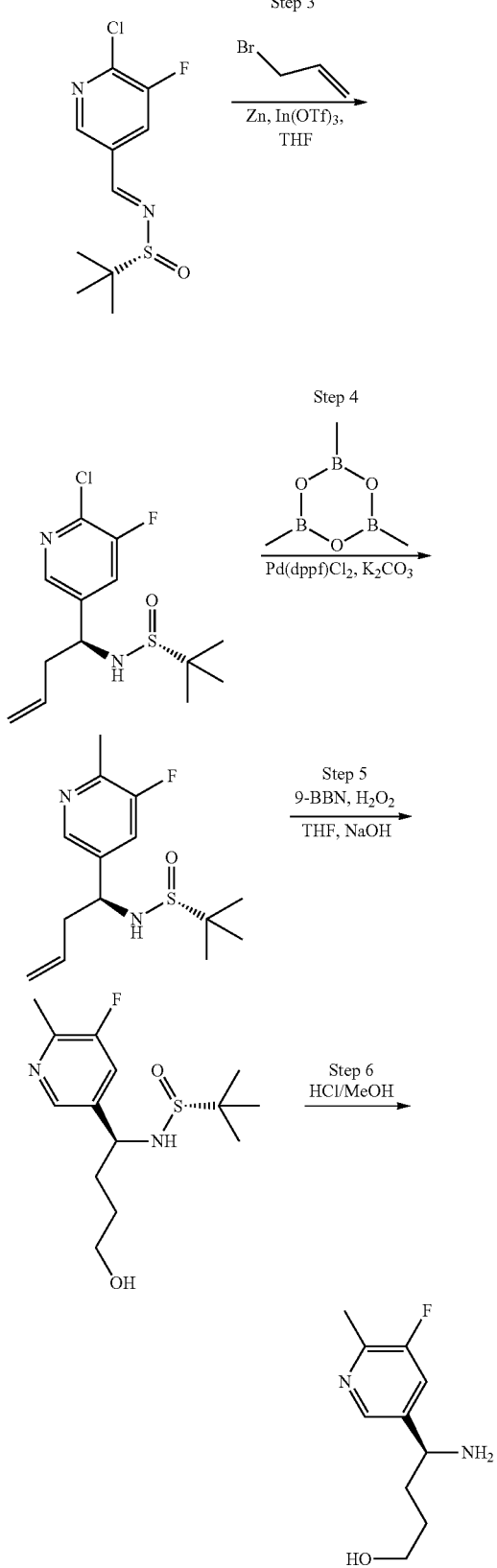

Step 1. 6-Chloro-5-fluoronicotinaldehyde iPrMgCl—LiCl (1.3 M in THF) (70 mL, 91 mmol) was added dropwise to a solution of 5-bromo-2-chloro-3-fluoropyridine (16 g, 76 mmol) in THF (250 mL) at −20° C. The mixture was stirred at −20° C. for 10 min, then DMF (77 mL, 997 mmol) was added dropwise to the mixture at −20° C. The mixture was stirred at −20° C. for 30 min. The mixture was quenched with aqueous NH$_4$Cl (200 mL), extracted with EtOAc (80 mL×2) and the combined organic layers were washed with brine, dried (Na$_2$SO$_4$), filtered, and the filtrate was concentrated in vacuo. The residue was purified by flash silica gel chromatography (ISCO®; 120 g Agela® Silica Flash Column, Eluent of 12% EtOAc/Pet. ether gradient @ 40 mL/min) to afford 6-chloro-5-fluoronicotinaldehyde. $^1$H NMR (400 MHz, MeOD-d$_4$) δ 8.32-8.28 (m, 1H), 7.80-7.71 (m, 1H).

Step 2. (R,E)-N-((6-chloro-5-fluoropyridin-3-yl)methylene)-2-methylpropane-2-sulfinamide (R)-2-methylpropane-2-sulfinamide (8.7 g, 71.7 mmol) and tetraisopropoxytitanium (25 mL, 83 mmol) were added to a stirred mixture of 6-chloro-5-fluoronicotinaldehyde (8.8 g, 55.2 mmol) in THF (200 mL) at 20° C. and the mixture was stirred at 20° C. for 12 h. The mixture was added to saturated sodium chloride (200 mL), filtered, and extracted with EtOAc (50 mL×3). The combined organic layers were dried (Na$_2$SO$_4$), filtered, and concentrated. The residue was purified by flash silica gel chromatography (ISCO®; 120 g SepaFlash® Silica Flash Column, eluent of 10% ethyl acetate/pet. ether gradient @ 35 mL/min) to give (R,E)-N-((6-chloro-5-fluoropyridin-3-yl)methylene)-2-methylpropane-2-sulfinamide. $^1$H NMR (400 MHz, MeOD-d$_4$) δ 8.71 (d, J=2.0 Hz, 1H), 8.67 (d, J=1.2 Hz, 1H), 8.20-8.24 (m, 1H), 1.28 (s, 9H).

Step 3. (R)—N—((S)-1-(6-chloro-5-fluoropyridin-3-yl)but-3-en-1-yl)-2-methylpropane-2-sulfinamide 3-bromoprop-1-ene (4.60 mL, 53.3 mmol) was added to a stirred solution of (R,E)-N-((6-chloro-5-fluoropyridin-3-yl)methylene)-2-methylpropane-2-sulfinamide (7.0 g, 26.6 mmol), indium(III) trifluoromethanesulfonate (22.5 g, 40.0 mmol) and zinc (3.48 g, 53.3 mmol) in THF (500 mL) and the resulting mixture was stirred at 20° C. for 12 h. The mixture was quenched with brine (400 mL) and extracted with ethyl acetate (100 mL×3). The combined organic fractions were dried (Na$_2$SO$_4$), filtered, and concentrated. The residue was purified by flash silica gel chromatography (ISCO®; 80 g SepaFlash® Silica Flash Column, eluent of 40% ethyl acetate/pet. ether gradient @ 35 mL/min) to give (R)—N—((S)-1-(6-chloro-5-fluoropyridin-3-yl)but-3-en-1-yl)-2-methylpropane-2-sulfinamide. $^1$H NMR (400 MHz, MeOD-d$_4$) δ 8.20 (d, J=1.6 Hz, 1H), 7.73-7.77 (m, 1H), 5.68-5.82 (m, 1H), 5.03-5.14 (m, 2H), 4.53 (t, J=7.2 Hz, 1H), 2.75 (td, J=6.8, 14.0 Hz, 1H), 2.55-2.67 (m, 1H), 1.21 (s, 9H).

Step 4. (R)—N—((S)-1-(5-fluoro-6-methylpyridin-3-yl)but-3-en-1-yl)-2-methylpropane-2-sulfinamide Tetrakis(triphenylphosphine)palladium(0) (0.960 g, 1.312 mmol) was added to a solution of (R)—N—((S)-1-(6-chloro-5-fluoropyridin-3-yl)but-3-en-1-yl)-2-methylpropane-2-sulfinamide (8.0 g, 26.2 mmol), 2,4,6-trimethyl-1,3,5,2,4,6-trioxatriborinane (9.88 g, 39.4 mmol), K$_2$CO$_3$ (10.9 g, 79 mmol) in dioxane (80 mL) and water (8 mL) under $N_2$. The resulting mixture was stirred at 100° C. for 12 h. Water (100 mL) was added, and the mixture was extracted with EtOAc (20 mL×2). The combined organic layers were washed with brine (50 mL), dried ($Na_2SO_4$), filtered, and concentrated. The residue was purified by flash silica gel chromatography (ISCO®; 120 g SepaFlash® Silica Flash Column, eluent of 100% ethyl acetate/pet. ether gradient @ 35 mL/min) to give (R)—N—((S)-1-(5-fluoro-6-methylpyridin-3-yl)but-3-en-1-yl)-2-methylpropane-2-sulfinamide. $^1$H NMR (400 MHz, MeOD-$d_4$) δ 8.22 (s, 1H), 7.53-7.57 (m, 1H), 5.67-5.81 (m, 1H), 5.02-5.12 (m, 2H), 4.48 (t, J=7.2 Hz, 1H), 2.67-2.80 (m, 1H), 2.54-2.66 (m, 1H), 2.49 (d, J=2.8 Hz, 3H), 1.20 (s, 9H)

Step 5. (R)—N—((S)-1-(5-fluoro-6-methylpyridin-3-yl)-4-hydroxybutyl)-2-methylpropane-2-sulfinamide 9-BBN (151 mL, 76 mmol) (0.5 M in THF) was added dropwise to a solution of (R)—N—((S)-1-(5-fluoro-6-methylpyridin-3-yl)but-3-en-1-yl)-2-methylpropane-2-sulfinamide (4.3 g, 15.1 mmol) in THF (200 mL) at −20° C. After the addition, the reaction was stirred at −20° C. and warmed to room temperature over 16 h. The mixture was cooled to 0° C. and then treated with NaOH (1 M) (60.5 mL, 60.5 mmol), hydrogen peroxide (60.5 mL, 691 mmol) and stirred for 2 h. The reaction mixture was quenched with water (150 mL) and extracted with EtOAc (50 mL×2). The combined organic layers were washed with brine (100 mL), dried ($Na_2SO_4$), filtered, and concentrated. The residue was purified by flash silica gel chromatography (ISCO®; 80 g SepaFlash® Silica Flash Column, eluent of 10% MeOH/EA gradient @ 40 mL/min) to give (R)—N—((S)-1-(5-fluoro-6-methylpyridin-3-yl)-4-hydroxybutyl)-2-methylpropane-2-sulfinamide. MS (ESI) m/z $C_{14}H_{24}FN_2O_2S$ [M+H]$^+$ calc'd 303, found 303. $^1$H NMR (400 MHz, MeOD-d4) δ 8.24 (s, 1H), 7.54-7.58 (m, 1H), 4.42 (t, J=7.2 Hz, 1H), 3.56 (t, J=6.4 Hz, 2H), 2.49 (d, J=2.8 Hz, 3H), 1.96-2.08 (m, 1H), 1.84-1.95 (m, 1H), 1.55-1.67 (m, 1H), 1.38-1.51 (m, 1H), 1.19 (s, 9H).

Step 6. (S)-4-Amino-4-(5-fluoro-6-methylpyridin-3-yl)butan-1-ol (I-29)

A mixture of (R)—N—((S)-1-(5-fluoro-6-methylpyridin-3-yl)-4-hydroxybutyl)-2-methylpropane-2-sulfinamide (2.4 g, 7.94 mmol) in MeOH (20 mL) was added HCl/MeOH (4 M) (3 mL) and the resulting mixture was stirred at 20° C. for 3 h. The reaction was directly concentrated to give (S)-4-amino-4-(5-fluoro-6-methylpyridin-3-yl)butan-1-ol. MS (ESI) m/z $C_{10}H_{16}FN_2O$ [M+H]$^+$ calc'd 199, found 199. $^1$H NMR (400 MHz, MeOD-$d_4$) δ 8.39-8.43 (m, 1H), 8.16-8.20 (m, 1H), 7.56-7.60 (m, 1H), 6.84-7.02 (m, 3H), 4.91-5.01 (m, 2H), 4.65-4.71 (m, 1H).

Intermediate I-30. Preparation of (5'S)-2-methyl-5'-phenyltetrahydro-3'H-spiro[piperidine-4,2'-pyrrolo[2,1-b]oxazol]-3'-one

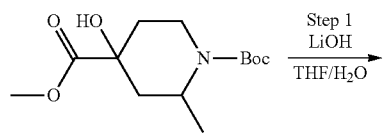

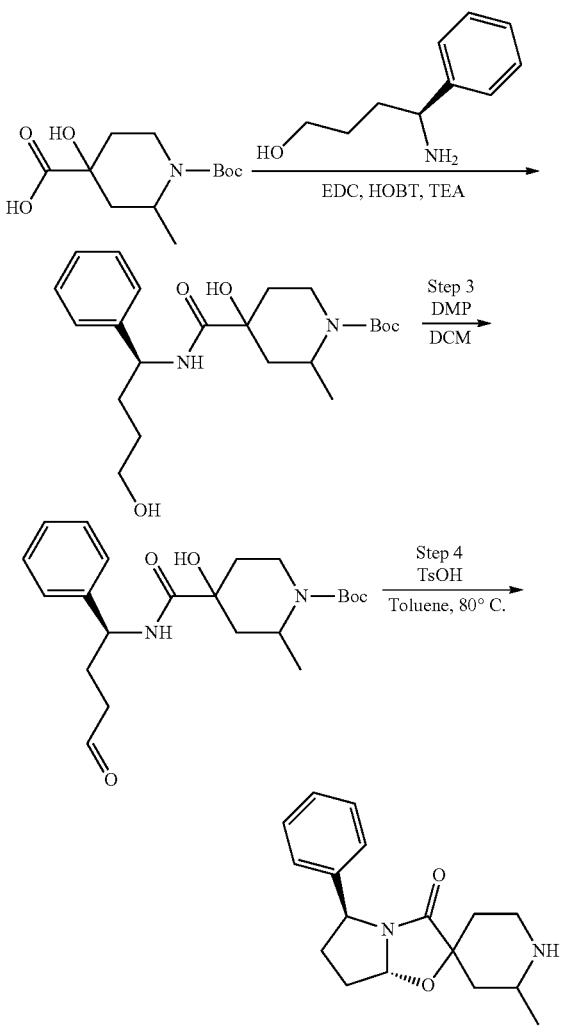

Step 1. 1-(tert-Butoxycarbonyl)-4-hydroxy-2-methylpiperidine-4-carboxylic acid

To a solution of 1-(tert-butyl) 4-methyl 4-hydroxy-2-methylpiperidine-1,4-dicarboxylate (6 g, 22.0 mmol) in THF:Water=3:1 (150 ml) was added lithium hydroxide (2.63 g, 110 mmol) and the resulting mixture was stirred at 20° C. for 12 h. To the mixture was added water (200 mL) and the aqueous was extracted with EtOAc (1×150 mL). The aqueous phase was acidified with 2 M HCl to PH-4, extracted with EtOAc (2×150 mL). The combined organic layers were dried ($Na_2SO_4$), filtered, and concentrated in vacuo to give 1-(tert-butoxycarbonyl)-4-hydroxy-2-methylpiperidine-4-carboxylic acid (5 g, 79% yield).

Step 2. tert-Butyl 4-hydroxy-4-(((S)-4-hydroxy-1-phenylbutyl)carbamoyl)-2-methylpiperidine-1-carboxylate To a flask were added 1-(tert-butoxycarbonyl)-4-hydroxy-2-methylpiperidine-4-carboxylic acid (643 mg, 2.48 mmol), (S)-4-amino-4-phenylbutan-1-ol hydrochloride (500 mg, 2.48 mmol), TEA (1.04 ml, 7.44 mmol), EDC (713 mg, 3.72 mmol) and HOBT (569 mg, 3.72 mmol) in DMF (10 mL) was stirred at 25° C. for 16 h to give yellow mixture. To the reaction mixture was added water (10 mL) and extracted with EtOAc (20 mL×3). The combined organic phases were washed with brine (20 mL), dried (Na$_2$SO$_4$), filtered, and concentrated under reduced pressure. The residue was purified by flash silica gel chromatography (ISCO®; 12 g SepaFlash® Silica Flash Column, eluent of 75% ethyl acetate/pet. ether gradient @ 40 mL/min) to give tert-butyl 4-hydroxy-4-(((S)-4-hydroxy-1-phenylbutyl)carbamoyl)-2-methylpiperidine-1-carboxylate (690 mg) as colorless oil.

Step 3. tert-Butyl 4-hydroxy-2-methyl-4-(((S)-4-oxo-1-phenylbutyl) carbamoyl) piperidine-1-carboxylate To a solution of tert-butyl 4-hydroxy-4-(((S)-4-hydroxy-1-phenylbutyl)carbamoyl)-2-methylpiperidine-1-carboxylate (690 mg, 1.70 mmol) in DCM (12 mL) was added DMP (1.08 g, 2.55 mmol) at 0° C. The resulting mixture was stirred at 20° C. for 16 h. To the reaction was added sat. aq. NaHCO$_3$ (8 mL) and extracted with DCM (12 mL×2). The combined organic layers were dried (Na$_2$SO$_4$), filtered and concentrated to give tert-butyl 4-hydroxy-2-methyl-4-(((S)-4-oxo-1-phenylbutyl) carbamoyl) piperidine-1-carboxylate (670 mg) as yellow oil, which was used in the next step without further purification.

Step 4. (5'S)-2-Methyl-5'-phenyltetrahydro-3'H-spiro[piperidine-4,2'-pyrrolo[2,1-b]oxazol]-3'-one (I-30)

To a solution of tert-butyl 4-hydroxy-2-methyl-4-(((S)-4-oxo-1-phenylbutyl)carbamoyl) piperidine-1-carboxylate (670 mg, 1.66 mmol) in Toluene (12 mL) was added p-Toluenesulfonic acid monohydrate (315 mg, 1.66 mmol) and the resulting mixture was stirred at 80° C. for 12 h. Then the precipitate was filtered off and the filtrate was concentrated. The residue was purified by preparative HPLC (Instrument EJ; Method Column Boston Green ODS 150×30 mm×5 um Condition water (TFA)-ACN Begin B 30 End B 50 Gradient Time (min) 10 100% B Hold Time(min) 2 FlowRate (mL/min) 25) to give (5'S)-2-methyl-5'-phenyltetrahydro-3'H-spiro[piperidine-4,2'-pyrrolo[2,1-b]oxazol]-3'-one. MS (ESI) m/z C$_{17}$H$_{23}$N$_2$O$_2$ [M+H]$^+$ calc'd 287, found 287. $^1$H NMR (400 MHz, CDCl$_3$): δ 7.31-7.40 (m, 3H), 7.29 (s, 1H), 7.23 (br d, J=8.0 Hz, 2H), 5.59-5.73 (m, 1H), 5.06 (t, J=7.6 Hz, 1H), 3.43 (br d, J=7.2 Hz, 2H), 3.19-3.37 (m, 3H), 2.59-2.68 (m, 1H), 2.25-2.33 (m, 1H), 2.10 (br d, J=6.0 Hz, 2H), 1.67-1.86 (m, 2H), 1.33-1.41 (m, 3H).

Intermediate I-31. Preparation of (5'S)-2-methyl-5'-phenyltetrahydro-3'H-spiro[piperidine-4,2'-pyrrolo[2,1-b]oxazol]-3'-one

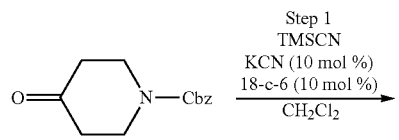

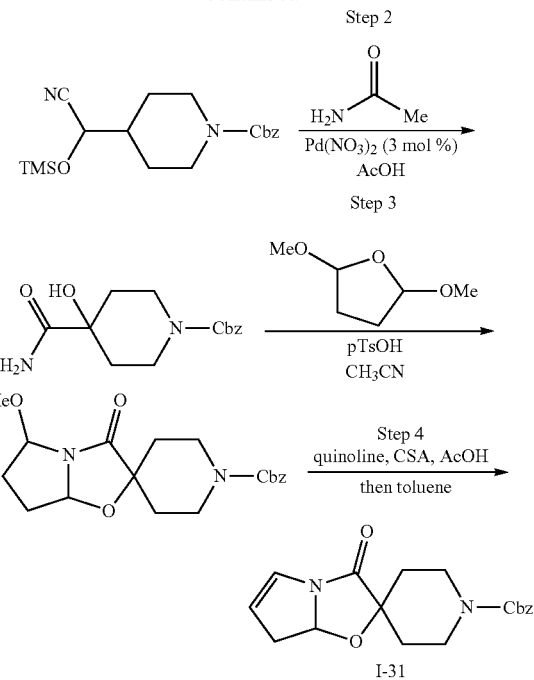

Step 1. Benzyl 4-cyano-4-((trimethylsilyl)oxy)piperidine-1-carboxylate

Benzyl 4-oxopiperidine-1-carboxylate (10.0 g, 42.9 mmol) was charged to a flask and dissolved in CH$_2$Cl$_2$ (21 mL). 18-crown-6 (1.13 g, 4.29 mmol) and KCN (0.279 g, 4.29 mmol) were added at room temperature. The resulting solution was cooled down to 0° C. and TMS-CN (6.90 ml, 51.4 mmol) was added dropwise under N$_2$ atmosphere (exothermic process). Ice-bath was removed and reaction was aged at the ambient temperature for 5 h. Reaction was quenched with NaHCO$_3$ (aq. sat. 50 mL). Layers were separated and aqueous layer was backwashed with CH$_2$Cl$_2$ (15 mL×2). The combined organic layer was dried (Na$_2$SO$_4$), filtered and concentrated. Benzyl 4-cyano-4-((trimethylsilyl)oxy)piperidine-1-carboxylate was isolated as an oil and used without additional purification.

Step 2. Benzyl 4-carbamoyl-4-hydroxypiperidine-1-carboxylate

Benzyl 4-cyano-4-((trimethylsilyl)oxy)piperidine-1-carboxylate (14.8 g, 42.9 mmol) was dissolved in acetic acid (42.9 mL) and sequentially treated with the palladium(II) nitrate dihydrate (343 mg, 1.29 mmol) and acetamide (10.1 g, 171 mmol) under inert atmosphere. The resulting mixture was heated to 50° C. and aged for 13 h. The cake was washed with EtOAc (50 mL), and solution was concentrated. The residue was partitioned in with EtOAc (50 mL)/aq. NaHCO$_3$ (5 w/w %, 50 mL), and the organics were washed with NaHCO$_3$ (5 w/w % aq., 50 mL) thrice. The aqueous layer was backwashed with EtOAc (50 mL×2). Combined organic phase was washed with brine (150 mL), dried (Na$_2$SO$_4$), and concentrated to afford benzyl 4-carbamoyl-4-hydroxypiperidine-1-carboxylate as a solid and was used without additional purification.

221

Step 3. Benzyl 5'-methoxy-3'-oxotetrahydro-3'H-spiro[piperidine-4,2'-pyrrolo[2,1-b]oxazole]-1-carboxylate Benzyl 4-carbamoyl-4-hydroxypiperidine-1-carboxylate (11.9 g, 42.8 mmol) was dissolved in acetonitrile (86 mL) and treated with 2,5-dimethoxytetrahydrofuran (6.93 mL, 53.4 mmol). p-Toluenesulfonic acid hydrate (813 mg, 4.28 mmol) was added to the solution, which was further heated to 35 C for 14 h. The mixture was quenched with NaHCO$_3$ (5 w/w % aq., 10 mL) and concentrated. The resulting oil was partitioned in EtOAc (100 mL)/aq. NaHCO$_3$ (5 w/w %, 100 mL) and the layers were separated. The aqueous layer was backwashed with EtOAc (30 mL×2). The combined organic layer was washed with brine (100 mL), dried (Na$_2$SO$_4$), and concentrated in vacuo. The residue was purified by flash silica gel chromatography (ISCO®; 120 g SepaFlash® Silica Flash Column, eluent of 75% ethyl acetate/ethanol and hexanes gradient) to give benzyl 5'-methoxy-3'-oxotetrahydro-3'H-spiro[piperidine-4,2'-pyrrolo[2,1-b]oxazole]-1-carboxylate as colorless oil.

Step 4. Benzyl 3'-oxo-7',7a'-dihydro-3'H-spiro[piperidine-4,2'-pyrrolo[2,1-b]oxazole]-1-carboxylate (I-31)

Benzyl 5'-methoxy-3'-oxotetrahydro-3'H-spiro[piperidine-4,2'-pyrrolo[2,1-b]oxazole]-1-carboxylate (10.4 g, 28.9 mmol) was dissolved in acetic acid (577 mL) and transferred into 2-neck round-bottom flask queried with addition funnel and distillation head. Quinoline (2.56 mL, 21.7 mmol) and camphorsulfonic acid (3.35 g, 14.4 mmol) were added to the solution under inert atmosphere. The resulting mixture was brought to the reflux. Acetic acid was slowly added to the solution to substitute distilled amount. The process continued for 2 h, and the conversion was monitored by NMR of aliquots. Once complete substitution of methoxide was attained, acetic acid was distilled out from the reaction and the residue was redissolved in dry toluene (577 mL). The distillation with continuous refilling using toluene continued for additional 4 h. Once >90% conversion by H NMR was achieved the residual solvent was removed and the resulting mixture was redissolved in EtOAc (200 mL). The organic layer was washed with HCl (aq. 1M, 150 mL x 2), brine (200 mL), dried (Na$_2$SO$_4$), and concentrated. The crude product was purified by flash silica gel chromatography (ISCO®; 120 g SepaFlash® Silica Flash Column, eluent of 75% ethyl acetate/ethanol and hexanes gradient) to obtain benzyl 3'-oxo-7',7a'-dihydro-3'H-spiro[piperidine-4,2'-pyrrolo[2,1-b]oxazole]-1-carboxylate as colorless oil. The enantiomers were resolved by chiral SFC (column AD-H 21×250 mm, 5 m, UV wavelength=215 nm, flow rate=70 mL/min).

Intermediate I-32. Preparation of ((5'S,7a'R)-5'-(3,5-difluorophenyl)tetrahydro-3'H-8-azaspiro[bicyclo[3.2.1]octane-3,2'-pyrrolo[2,1-b]oxazol]-3'-one

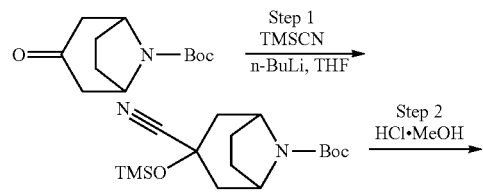

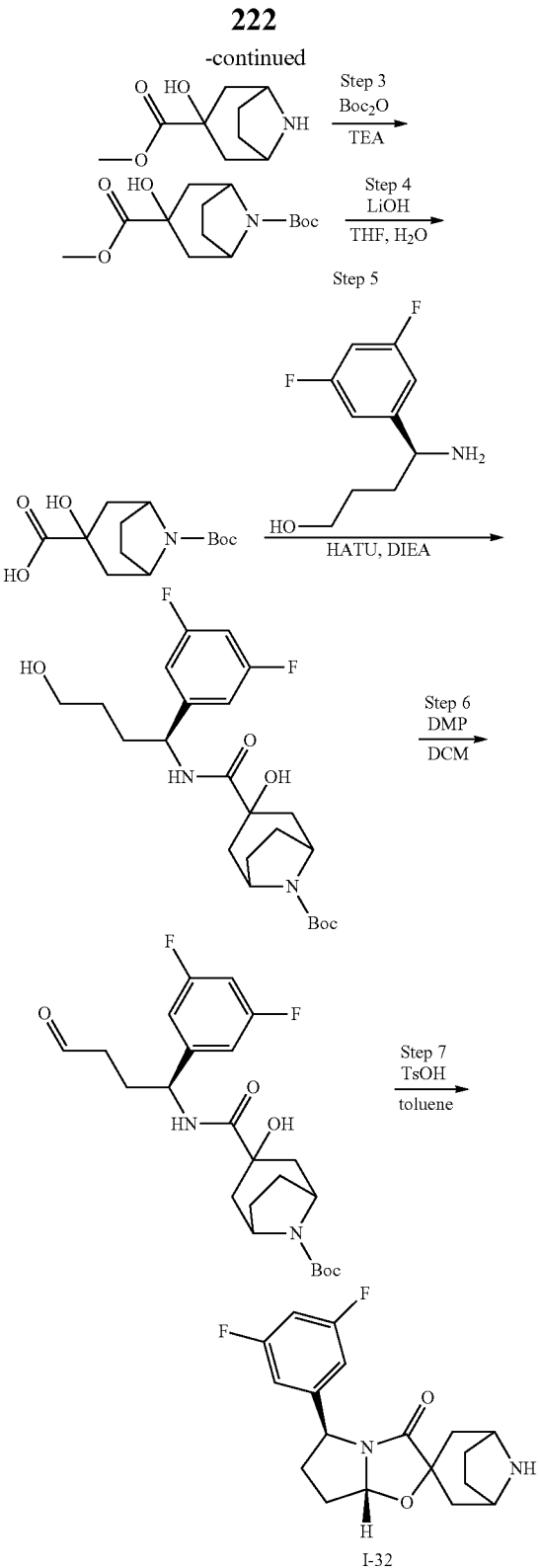

Step 1. tert-Butyl 3-cyano-3-((trimethylsilyl)oxy)-8-azabicyclo[3.2.1]octane-8-carboxylate To a solution of tert-butyl 3-oxo-8-azabicyclo[3.2.1]octane-8-carboxylate (10 g, 44 mmol), trimethylsilanecarbonitrile (7.10 mL, 53.3 mmol) in THF (200 mL) was added butyllithium (1.06 mL, 2.66 mmol) under $N_2$. The mixture was stirred at 20° C. for 12 h. The reaction mixture was quenched with water (200 mL) and extracted with EtOAc (200 mL×3) and the organic layers were washed with brine (200 mL×2), dried ($Na_2SO_4$), filtered, and concentrated. The residue was purified by flash silica gel chromatography (ISCO®; 120 g SepaFlash® Silica Flash Column, eluent of 5% ethyl acetate/pet. ether gradient @ 35 mL/min) to afford product tert-butyl 3-cyano-3-((trimethylsilyl)oxy)-8-azabicyclo[3.2.1]octane-8-carboxylate (13 g).

Step 2. Methyl 3-hydroxy-8-azabicyclo[3.2.1]octane-3-carboxylate

A solution of tert-butyl-cyano-3-((trimethylsilyl)oxy)-8-azabicyclo[3.2.1]octane-8-carboxylate (6.5 g, 20.0 mmol) in HCl-MeOH (4 M, 100 mL) was stirred at 60° C. for 12 h. The reaction mixture was concentrated to give crude methyl 3-hydroxy-8-azabicyclo[3.2.1]octane-3-carboxylate (3.7 g), which will be used in next step directly.

Step 3. 8-(tert-Butyl) 3-methyl (1R,3r,5S)-3-hydroxy-8-azabicyclo[3.2.1]octane-3,8-dicarboxylate To a solution of methyl 3-hydroxy-8-azabicyclo[3.2.1]octane-3-carboxylate (3.7 g, 20.0 mmol) in DCM (70 mL) was added di-tert-butyl dicarbonate (5.51 mL, 24.0 mmol) and triethylamine (13.9 mL, 100 mmol) at 20° C., and the resulting mixture was stirred at 20° C. for 2 h. The solution was concentrated and the residue was purified by flash silica gel chromatography (ISCO®; 120 g SepaFlash® Silica Flash Column, eluent of 10% EtOAc/Pet.ether gradient @ 45 mL/min) to give 8-(tert-butyl) 3-methyl (1R,3r,5S)-3-hydroxy-8-azabicyclo[3.2.1]octane-3,8-dicarboxylate.

Step 4. 8-(tert-Butoxycarbonyl)-3-hydroxy-8-azabicyclo[3.2.1]octane-3-carboxylic acid A mixture of 8-(tert-butyl) 3-methyl 3-hydroxy-8-azabicyclo[3.2.1]octane-3,8-dicarboxylate (4.7 g, 16.5 mmol) and LiOH (1.18 g, 49.4 mmol) in THF (40 mL) and $H_2O$ (14 mL) was stirred at 25° C. for 2 h. The solvent was evaporated, then the reaction mixture was quenched with aq. 1 M HCl (10 mL) and extracted with EtOAc (50 mL×3). The combined organic phases were washed with brine (50 mL×2), dried ($Na_2SO_4$), filtered, and concentrated under reduced pressure to give 8-(tert-butoxycarbonyl)-3-hydroxy-8-azabicyclo[3.2.1]octane-3-carboxylic acid.

Step 5. tert-Butyl 3-(((S)-1-(3,5-difluorophenyl)-4-hydroxybutyl)carbamoyl)-3-hydroxy-8-azabicyclo[3.2.1]octane-8-carboxylate To a solution of 8-(tert-butoxycarbonyl)-3-hydroxy-8-azabicyclo[3.2.1]octane-3-carboxylic acid (350 mg, 1.29 mmol), N-ethyl-N-isopropylpropan-2-amine (0.676 mL, 3.87 mmol), HATU (981 mg, 2.58 mmol) in DMF (10 mL) was added (S)-4-amino-4-(3,5-difluorophenyl)butan-1-ol (286 mg, 1.41 mmol) and the resulting mixture was stirred at 20° C. for 12 h. The reaction mixture was diluted with DCM (50 mL) and washed with water (25 mL×3). The organics were dried ($Na_2SO_4$), filtered, and concentrated. The mixture was purified by HPLC [(Instrument ed; Method Column Boston Prime C18 150 mm×30 mm×5 um; Condition water ($NH_3H_2O+NH_4HCO_3$)—CAN; FlowRate 25 mL/min)] to give tert-butyl 3-(((S)-1-(3,5-difluorophenyl)-4-hydroxybutyl)carbamoyl)-3-hydroxy-8-azabicyclo[3.2.1]octane-8-carboxylate. MS (ESI) m/z $C_{23}H_{33}F_2N_2O_5[M+H]^+$ calc'd 455, found 455. $^1H$ NMR (500 MHz, $CDCl_3$): δ 6.73-6.79 (m, 2H), 6.68 (tt, J=8.8, 2.0 Hz, 1H), 4.80-4.91 (m, 1H), 4.28 (br s, 2H), 3.68 (br s, 2H), 2.13-2.25 (m, 2H), 1.86-1.99 (m, 4H), 1.53-1.68 (m, 4H), 1.53-1.69 (m, 1H), 1.49 (s, 9H).

Step 6. tert-Butyl 3-(((S)-1-(3,5-difluorophenyl)-4-oxobutyl)carbamoyl)-3-hydroxy-8-azabicyclo[3.2.1]octane-8-carboxylate To a solution of tert-butyl 3-(((S)-1-(3,5-difluorophenyl)-4-hydroxybutyl)carbamoyl)-3-hydroxy-8-azabicyclo[3.2.1]octane-8-carboxylate (400 mg, 0.880 mmol), Pyridine (71 uL, 0.88 mmol) in DCM (10 mL) was added DMP (747 mg, 1.76 mmol) at 0° C. and the resulting mixture was stirred at 20° C. for 1 h. The reaction was quenched with sat. aq. $Na_2SO_3$ (15 mL) and stirred for 10 min. Sat. aq. $NaHCO_3$ (15 mL) was added and the mixture was extracted with DCM (10 mL×2). The combined organic layers were dried ($Na_2SO_4$), filtered and concentrated to give tert-butyl 3-(((S)-1-(3,5-difluorophenyl)-4-oxobutyl)carbamoyl)-3-hydroxy-8-azabicyclo[3.2.1]octane-8-carboxylate, which was used in the next step without further purification.

Step 7. (5'S,7a'R)-5'-(3,5-Difluorophenyl)tetrahydro-3'H-8-azaspiro[bicyclo[3.2.1]octane-3,2'-pyrrolo[2,1-b]oxazol]-3'-one To a mixture of tert-butyl 3-(((S)-1-(3,5-difluorophenyl)-4-oxobutyl)carbamoyl)-3-hydroxy-8-azabicyclo[3.2.1]octane-8-carboxylate (400 mg, 0.884 mmol) in Acetonitrile (6 mL) was added TsOH (0.166 mL, 2.65 mmol) and the resulting mixture was stirred at 80° C. for 2 h. The crude mixture was concentrated and purified by HPLC [(Instrument EK; Method Column Boston Uni C18 40 mm×150×5 um; Condition water (TFA)-CAN Begin B 25 End B 55 Gradient Time (min) 10; FlowRate 60 mL/min)] to give (5'S,7a'R)-5'-(3,5-difluorophenyl)tetrahydro-3'H-8-azaspiro[bicyclo[3.2.1]octane-3,2'-pyrrolo[2,1-b]oxazol]-3'-one. MS (ESI) m/z $C_{18}H_{21}F_2N_2O_2[M+H]^+$ calc'd 335, found 335.

Intermediate I-33. Preparation of 3'-(3,5-difluorophenyl)dihydro-1'H,3'H,5'H-spiro[piperidine-4,6'-pyrrolo[1,2-c]oxazol]-5'-one

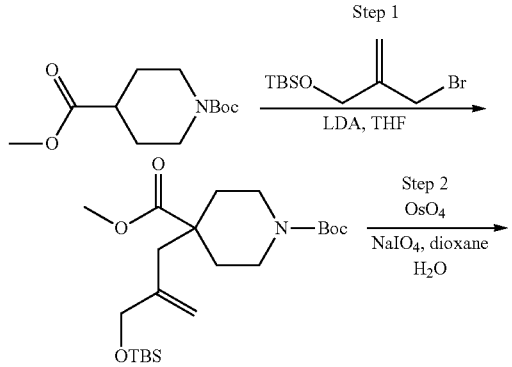

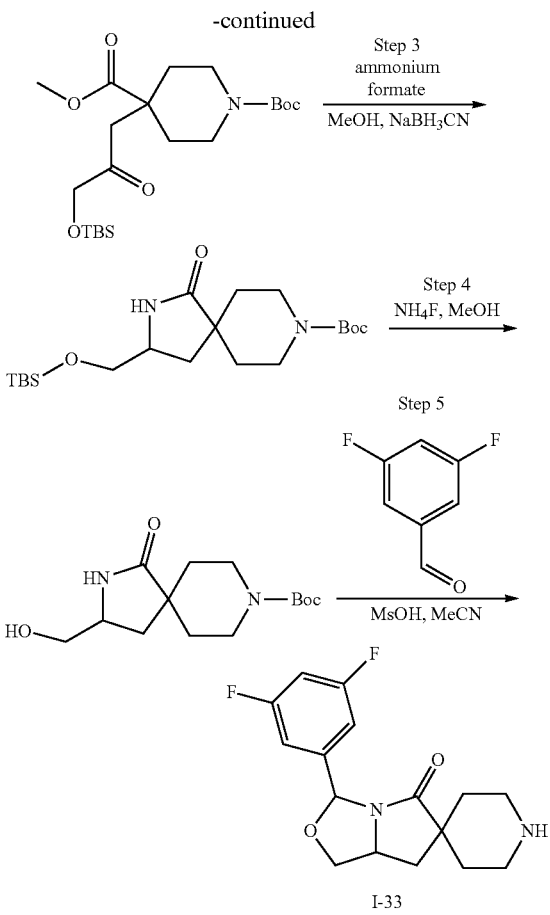

Step 1. 1-(tert-Butyl) 4-methyl 4-(2-(((tert-butyldimethylsilyl) oxy) methyl) allyl) piperidine-1, 4-dicarboxylate To a solution of 1-(tert-butyl) 4-methyl piperidine-1, 4-dicarboxylate (4.0 g, 16.4 mmol) in THF (70 mL) was added LDA (12.3 ml, 24.7 mmol) at −78° C. The mixture was stirred at this temperature for 30 min. Then a solution of ((2-(bromomethyl) allyl) oxy) (tert-butyl) dimethylsilane (5.23 g, 19.73 mmol) in THF (10 mL) was added at −78° C. After the addition, the mixture was warmed to 20° C. and stirred at 20° C. for 16 h. The mixture was quenched with water (20 mL), extracted with EtOAc (30 mL×2), and the organic layer was dried (Na₂SO₄), filtered and concentrated in vacuum. The residue was purified by flash silica gel chromatography (ISCO®; 20 g SepaFlash® Silica Flash Column, Eluent of 0-20% EtOAc/Pet.ether gradient @ 25 mL/min) to give 1-(tert-butyl) 4-methyl 4-(2-(((tert-butyldimethylsilyl) oxy) methyl) allyl) piperidine-1, 4-dicarboxylate (3.5 g) as an oil.

Step 2. 1-(tert-Butyl) 4-methyl 4-(3-((tert-butyldimethylsilyl) oxy)-2-oxopropyl) piperidine-1, 4-dicarboxylate To a solution of 1-(tert-butyl) 4-methyl 4-(2-(((tert-butyldimethylsilyl)oxy)methyl)allyl)piperidine-1,4-dicarboxylate (3.0 g, 7.01 mmol) in Dioxane (60 mL) and Water (20 mL) was added 2,6-dimethylpyridine (1.50 g, 14.0 mmol) and OsO₄ (0.25 g, 0.983 mmol) at 0° C. The mixture was stirred at this temperature for 10 min. Sodium periodate (6.00 g, 28.1 mmol) was added and the mixture was stirred at 20° C. for 3 h. The mixture was quenched with sat. aq. Na₂SO₃ (300 mL), adjusted to pH=10, and extracted with EtOAc (200 mL). The organic layers were washed with brine (100 mL), dried (Na₂SO₄), filtered and concentrated in vacuum. The residue was purified by flash silica gel chromatography (ISCO®; 40 g SepaFlash® Silica Flash Column, Eluent of 0-10% EtOAc/Pet.ether gradient @ 30 mL/min) to give 1-(tert-butyl) 4-methyl 4-(3-((tert-butyldimethylsilyl) oxy)-2-oxopropyl) piperidine-1, 4-dicarboxylate (1.6 g) as a brown oil.

Step 3. tert-Butyl 3-(((tert-butyldimethylsilyl)oxy) methyl)-1-oxo-2,8-diazaspiro[4.5]decane-8-carboxylate To a solution of 1-(tert-butyl) 4-methyl 4-(3-((tert-butyldimethylsilyl)oxy)-2-oxopropyl)piperidine-1,4-dicarboxylate (1.5 g, 3.49 mmol) in MeOH (40 ml) was added ammonium formate (2.20 g, 34.9 mmol) and NaCNBH₄ (0.549 g, 8.73 mmol). The mixture was sealed and stirred at 40° C. for 16 h. The mixture was concentrated in vacuum and the residue was purified by flash silica gel chromatography (ISCO®; 12 g SepaFlash® Silica Flash Column, Eluent of 10-60% EtOAc/Pet.ether gradient @ 25 mL/min) to give tert-butyl 3-(((tert-butyldimethylsilyl)oxy)methyl)-1-oxo-2,8-diazaspiro[4.5]decane-8-carboxylate (750 mg) as a white solid. MS (ESI) m/z $C_{20}H_{39}N_2O_4Si$ [M+H]⁺ calc'd 399, found 399.

Step 4. tert-Butyl 3-(hydroxymethyl)-1-oxo-2,8-diazaspiro[4.5]decane-8-carboxylate To a solution of tert-butyl 3-(((tert-butyldimethylsilyl) oxy) methyl)-1-oxo-2, 8-diazaspiro [4.5] decane-8-carboxylate (650 mg, 1.63 mmol) in MeOH (10 mL) was added NH₄F (604 mg, 16.3 mmol). The mixture was stirred at 40° C. for 16 h. The solvent was evaporated under reduced pressure, and the crude was diluted with H₂O (10 mL) and extracted with DCM (20 mL×3). The combined organics were washed with brine (15 mL), dried (Na₂SO₄), filtered and the solvent was evaporated under reduced pressure to give tert-butyl 3-(hydroxymethyl)-1-oxo-2,8-diazaspiro [4.5]decane-8-carboxylate (470 mg, 91% yield) as a white solid which used in next step directly. MS (ESI) m/z $C_{14}H_{24}N_2NaO_4$ [M+Na]⁺ calc'd 307, found 307. ¹H NMR (400 MHz, CDCl₃): δ 6.58 (s, 1H), 4.01 (br s, 2H), 3.68-3.85 (m, 2H), 3.41-3.53 (m, 1H), 2.82-3.08 (m, 3H), 2.19 (br dd, J=12.8, 7.6 Hz, 1H), 1.87-1.98 (m, 1H), 1.72-1.84 (m, 2H), 1.62 (br dd, J=12.4, 7.6 Hz, 1H), 1.46 (s, 10H).

Step 5. 3'-(3,5-Difluorophenyl)dihydro-1'H,3'H,5'H-spiro[piperidine-4,6'-pyrrolo[1,2-c]oxazol]-5'-one To a mixture of tert-butyl 3-(hydroxymethyl)-1-oxo-2,8-diazaspiro[4.5]decane-8-carboxylate (200 mg, 0.703 mmol), 3,5-difluorobenzaldehyde (100 mg, 0.703 mmol) in Acetonitrile (3 mL) was added MsOH (0.132 mL, 2.11 mmol) and the resulting mixture was stirred at 80° C. for 1 h. The mixture was purified by HPLC (Instrument EE; Method Column YMC-Actus Triart C18 150*30 mm*5 um; Condition water (TFA)-CAN Begin B 25 End B 45 Gradient Time (min) 10.5; 100% B Hold Time (min) 1.5 FlowRate (mL/min) 40; Injection 3) to give 3'-(3,5-difluorophenyl)dihydro- 1'H,3'H,5'H-spiro[piperidine-4,6'-pyrrolo[1,2-c]oxazol]-5'-one as yellow oil. MS (ESI) m/z $C_{16}H_{19}F_2N_2O_2[M+H]^+$ calc'd 309, found 309.

Intermediate I-34. Preparation of (5'S,7a'R)-7'-hydroxy-5'-phenyltetrahydro-3'H-spiro[piperidine-4,2'-pyrrolo[2,1-b]oxazol]-3'-one

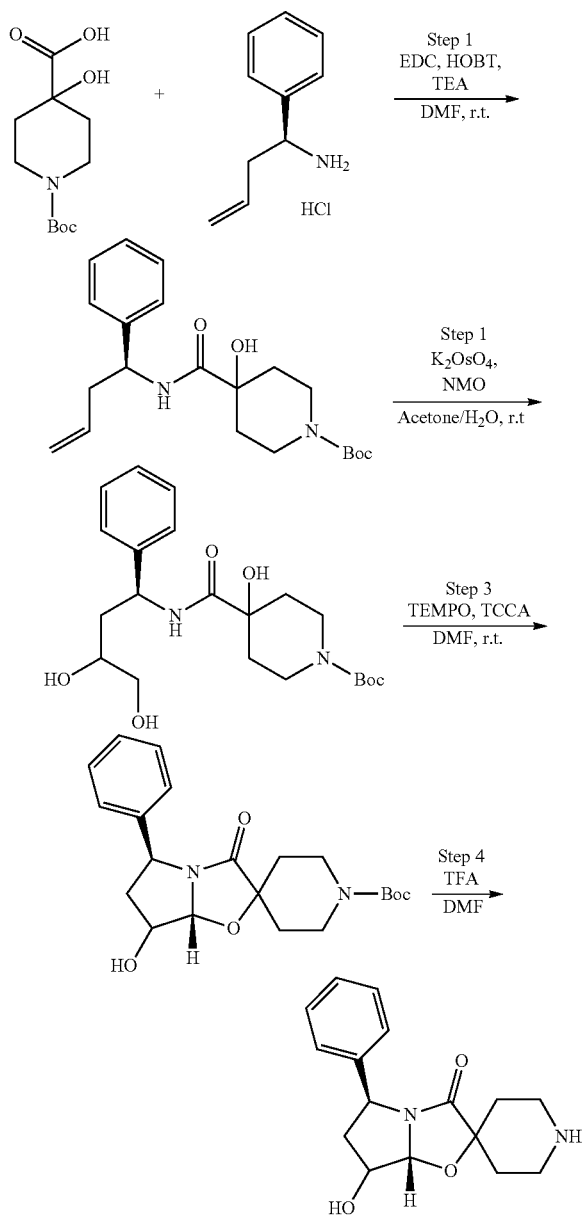

I-34

Step 1. tert-Butyl (S)-4-hydroxy-4-((1-phenylbut-3-en-1-yl)carbamoyl)piperidine-1-carboxylate A mixture of (S)-1-phenylbut-3-en-1-amine hydrochloride (2.50 g, 8.15 mmol), 1-(tert-butoxycarbonyl)-4-hydroxypiperidine-4-carboxylic acid (2.0 g, 8.15 mmol), HOBT (1.87 g, 12.2 mmol), EDC (2.34 g, 12.2 mmol) and TEA (3.41 mL, 24.5 mmol) in DMF (30 mL) was stirred at 25° C. for 16 h to give yellow mixture. The reaction mixture was diluted with water (150 mL) and extracted with EtOAc (100 mL×3). The combined organic phases were washed with brine (50 mL), dried (Na$_2$SO$_4$), filtered and concentrated under reduced pressure. The residue was purified by flash silica gel chromatography (ISCO®; 4 g SepaFlash® Silica Flash Column, eluent of 0-35% ethyl acetate/pet. ether gradient @ 60 mL/min) to afford tert-butyl (S)-4-hydroxy-4-((1-phenylbut-3-en-1-yl)carbamoyl)piperidine-1-carboxylate. MS (ESI) m/z $C_{21}H_{31}N_2O_4$ [M+H]$^+$ calc'd 375, found 375.

Step 2. tert-Butyl 4-(((1S)-3,4-dihydroxy-1-phenylbutyl)carbamoyl)-4-hydroxypiperidine-1-carboxylate To a solution of tert-butyl (S)-4-hydroxy-4-((1-phenylbut-3-en-1-yl)carbamoyl)piperidine-1-carboxylate (2.7 g, 7.21 mmol) in Acetone (21 mL) and Water (7 mL) was added NMO (2.11 g, 18.0 mmol), potassium osmate(vi) dihydrate (0.266 g, 0.721 mmol) and the resulting mixture was stirred at 25° C. for 12 h. The reaction mixture was quenched with aq. Na$_2$S$_2$O$_3$ (40 mL) and extracted with ethyl acetate (25 mL×3). The combined organic layers were washed with brine (30 mL), dried (Na$_2$SO$_4$), filtered and concentrated. The residue was purified by flash silica gel chromatography (ISCO®; 20 g SepaFlash® Silica Flash Column, eluent of 100% ethyl acetate/pet. ether gradient @ 35 mL/min) to give tert-butyl 4-(((1S)-3,4-dihydroxy-1-phenylbutyl)carbamoyl)-4-hydroxypiperidine-1-carboxylate (1.9 g) as a solid. $^1$H NMR (500 MHz, CD$_3$OD) δ 7.28-7.38 (m, 4H), 7.19-7.26 (m, 1H), 4.98-5.21 (m, 1H), 3.85-4.01 (m, 2H), 3.39-3.66 (m, 3H), 2.96-3.23 (m, 2H), 2.02-2.06 (m, 1H), 1.76-2.01 (m, 3H), 1.47-1.61 (m, 2H), 1.43-1.47 (m, 9H).

Step 3. tert-Butyl (5'S,7a'R)-7'-hydroxy-3'-oxo-5'-phenyltetrahydro-3'H-spiro[piperidine-4,2'-pyrrolo[2,1-b]oxazole]-1-carboxylate To a solution of tert-butyl 4-(((1S)-3,4-dihydroxy-1-phenylbutyl)carbamoyl)-4-hydroxypiperidine-1-carboxylate (700 mg, 1.71 mmol), trichloroisocyanuric acid (418 mg, 1.80 mmol) in DCM (15 mL), was added TEMPO (2.68 mg, 0.017 mmol) at 0° C. and the resulting mixture was stirred at 25° C. for 12 h. The reaction mixture was concentrated and the residue was purified by flash silica gel chromatography (ISCO®; 4 g SepaFlash® Silica Flash Column, eluent of 40% ethyl acetate/pet. ether gradient @ 35 mL/min) to give tert-butyl (5'S,7a'R)-7'-hydroxy-3'-oxo-5'-phenyltetrahydro-3'H-spiro[piperidine-4,2'-pyrrolo[2,1-b]oxazole]-1-carboxylate as colorless oil. MS (ESI) m/z $C_{21}H_{29}N_2O_5$ [M+H]$^+$ calc'd 389, found 389.

Step 4. (5'S,7a'R)-7'-hydroxy-5'-phenyltetrahydro-3'H-spiro[piperidine-4,2'-pyrrolo[2,1-b]oxazol]-3'-one A mixture of tert-butyl (5'S,7a'R)-7'-hydroxy-3'-oxo-5'-phenyltetrahydro-3'H-spiro[piperidine-4,2'-pyrrolo[2,1-b]oxazole]-1-carboxylate (50 mg, 0.129 mmol) in DCM (2 mL) was added TFA (0.2 mL) and the resulting mixture was stirred at 25° C. for 2 h. The reaction was concentrated to give (5'S,7a'R)-7'-hydroxy-5'-phenyltetrahydro-3'H-spiro[piperidine-4,2'-pyrrolo[2,1-b]oxazol]-3'-one, TFA as colorless oil, which was used to next step without further purification. MS (ESI) m/z $C_{16}H_{21}N_2O_3$ [M+H]$^+$ calc'd 289, found 289.

EXAMPLES

Example 1.1

(5'S,7a'R)-1-Benzoyl-5'-(3,5-difluorophenyl)tetrahydro-3'H-spiro[piperidine-4,2'-pyrrolo[2,1-b]oxazol]-3'-one

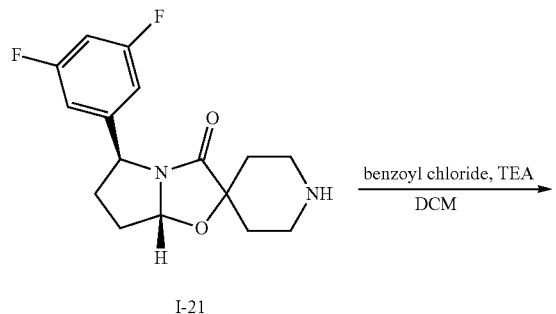

I-21

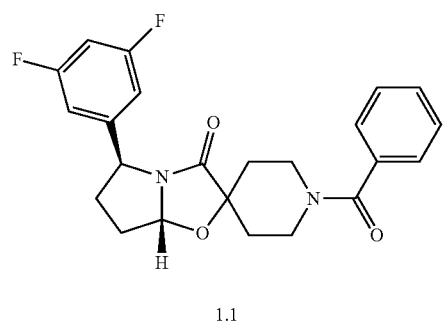

1.1

(5'S,7a'R)-5'-(3,5-difluorophenyl)tetrahydro-3'H-spiro[piperidine-4,2'-pyrrolo[2,1-b]oxazol]-3'-one, HCl (I-21) (1.59 g, 4.61 mmol) was added to a 250 mL round bottom flask, followed by dry DCM (15.4 ml). The mixture was chilled to 0° C. and triethylamine (1.29 ml, 9.22 mmol) was added in a single portion. Benzoyl chloride (563 µL, 4.84 mmol) was added dropwise over 1 min. After 10 min, the mixture was slowly warmed to room temperature over 30 min. The solvents were evaporated and the resulting oil was taken up in EtOAc (50 mL). The organics were washed with saturated aqueous $NH_4Cl$ (15 ml), then saturated aqueous $NaHCO_3$ (15 mL), then brine. The organics were dried ($MgSO_4$), filtered, and concentrated. The oil was taken up in isopropanol (10 mL) in a 250 mL flask and heated, until fully soluble. The mixture was stirred at room temperature and allowed to cool for 5 min, then hexanes (50 mL) was added in one portion. The mixture stirred at room temperature overnight and the resulting precipitate was filtered to afford (5'S,7a'R)-1-benzoyl-5'-(3,5-difluorophenyl)tetrahydro-3'H-spiro[piperidine-4,2'-pyrrolo[2,1-b]oxazol]-3'-one. MS (ESI) m/z $C_{23}H_{23}F_2N_2O_3$ [M+H]+ calc'd 413, found 413. $^1$H NMR (499 MHz, DMSO-d6) δ 7.50-7.36 (m, 5H), 7.14 (t, J=9.4 Hz, 1H), 7.07 (d, J=6.7 Hz, 2H), 5.80 (s, 1H), 4.94 (t, J=7.8 Hz, 1H), 4.31 (s, 1H), 3.58 (s, 1H), 3.18 (d, J=5.1 Hz, 2H), 2.64 (s, 1H), 2.19 (dd, J=7.2, 4.9 Hz, 1H), 1.86 (ddd, J=19.6, 12.9, 7.2 Hz, 2H), 1.70 (d, J=43.0 Hz, 3H).

Compounds in Table 11 below were prepared from the following intermediates: Intermediate I-21 (Table 7), I-16 (Table 5), I-19, I-20, I-22 (Table 8), I-35, I-38, I-45, and I-46 using the methods described in Example 1.1.

TABLE 11

| Ex. No. | Structure | Name | Exact Mass [M + H]+ |
|---|---|---|---|
| 1.2 | ![structure] | methyl (5'S,7a'R)-5'-(3,5-difluorophenyl)-3'-oxotetrahydro-1H,3'H-spiro[piperidine-4,2'-pyrrolo[2,1-b][1,3]oxazole]-1-carboxylate | Calc'd 367, found 367 |
| 1.3 | ![structure] | (5'S,7a'R)-1-(benzenecarbonyl)-5'-phenyltetrahydro-3'H-spiro[piperidine-4,2'-pyrrolo[2,1-b][1,3]oxazol]-3'-one | Calc'd 377, found 377 |

TABLE 11-continued

| Ex. No. | Structure | Name | Exact Mass [M + H]+ |
|---|---|---|---|
| 1.4 | 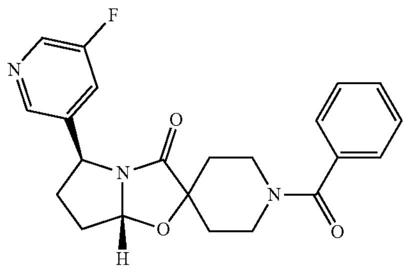 [SMILES: O=C(c1ccccc1)N1CCC2(CC1)O[C@@H]1CC[C@@H](c3cncc(F)c3)N1C2=O] | (5'S,7a'R)-1-(benzenecarbonyl)-5'-(5-fluoropyridin-3-yl)tetrahydro-3'H-spiro[piperidine-4,2'-pyrrolo[2,1-b][1,3]oxazol]-3'-one | Calc'd 396, found 396 |
| 1.5 | 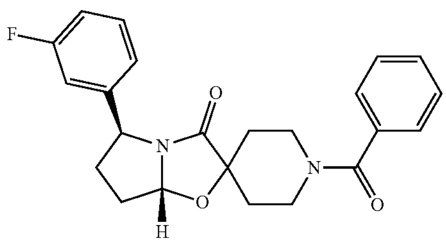 [SMILES: O=C(c1ccccc1)N1CCC2(CC1)O[C@@H]1CC[C@@H](c3cccc(F)c3)N1C2=O] | (5'S,7a'R)-1-(benzenecarbonyl)-5'-(3-fluorophenyl)tetrahydro-3'H-spiro[piperidine-4,2'-pyrrolo[2,1-b][1,3]oxazol]-3'-one | Calc'd 395, found 395 |
| 1.6 | 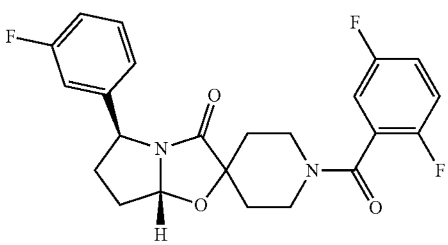 [SMILES: O=C(c1cc(F)ccc1F)N1CCC2(CC1)O[C@@H]1CC[C@@H](c3cccc(F)c3)N1C2=O] | (5'S,7a'R)-1-(2,5-difluorobenzene-1-carbonyl)-5'-(3-fluorophenyl)tetrahydro-3'H-spiro[piperidine-4,2'-pyrrolo[2,1-b][1,3]oxazol]-3'-one | Calc'd 431, found 431 |
| 1.7 | 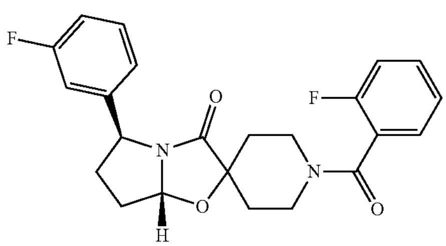 [SMILES: O=C(c1ccccc1F)N1CCC2(CC1)O[C@@H]1CC[C@@H](c3cccc(F)c3)N1C2=O] | (5'S,7a'R)-1-(2-fluorobenzene-1-carbonyl)-5'-(3-fluorophenyl)tetrahydro-3'H-spiro[piperidine-4,2'-pyrrolo[2,1-b][1,3]oxazol]-3'-one | Calc'd 413, found 413 |
| 1.8 | 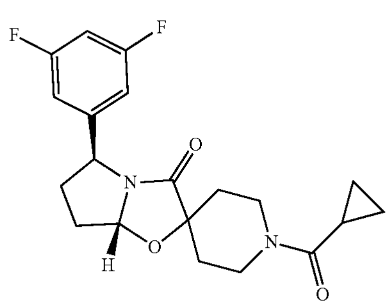 [SMILES: O=C(C1CC1)N1CCC2(CC1)O[C@@H]1CC[C@@H](c3cc(F)cc(F)c3)N1C2=O] | (5'S,7a'R)-1-(cyclopropanecarbonyl)-5'-(3,5-difluorophenyl)tetrahydro-3'H-spiro[piperidine-4,2'-pyrrolo[2,1-b][1,3]oxazol]-3'-one | Calc'd 377, found 377 |

TABLE 11-continued

| Ex. No. | Structure | Name | Exact Mass [M + H]+ |
|---|---|---|---|
| 1.9 | 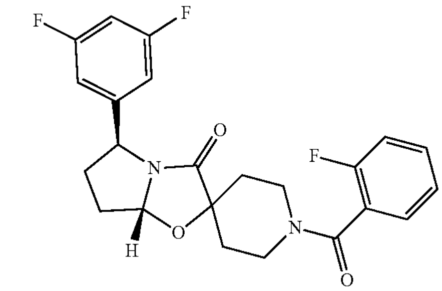 [SMILES: O=C(c1ccccc1F)N1CCC2(CC1)O[C@@H]1CC[C@@H](c3cc(F)cc(F)c3)N1C2=O] | (5'S,7a'R)-5'-(3,5-difluorophenyl)-1-(2-fluorobenzene-1-carbonyl)tetrahydro-3'H-spiro[piperidine-4,2'-pyrrolo[2,1-b][1,3]oxazol]-3'-one | Calc'd 431, found 431 |
| 1.10 | 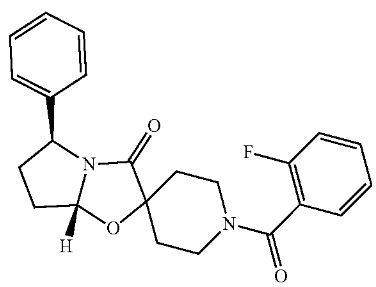 [SMILES: O=C(c1ccccc1F)N1CCC2(CC1)O[C@@H]1CC[C@@H](c3ccccc3)N1C2=O] | (5'S,7a'R)-1-(2-fluorobenzene-1-carbonyl)-5'-phenyltetrahydro-3'H-spiro[piperidine-4,2'-pyrrolo[2,1-b][1,3]oxazol]-3'-one | Calc'd 395, found 395 |
| 1.11 | 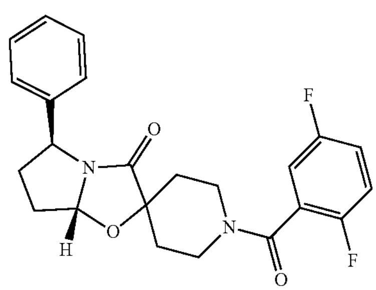 [SMILES: O=C(c1cc(F)ccc1F)N1CCC2(CC1)O[C@@H]1CC[C@@H](c3ccccc3)N1C2=O] | (5'S,7a'R)-1-(2,5-difluorobenzene-1-carbonyl)-5'-phenyltetrahydro-3'H-spiro[piperidine-4,2'-pyrrolo[2,1-b][1,3]oxazol]-3'-one | Calc'd 413, found 413 |
| 1.12 | 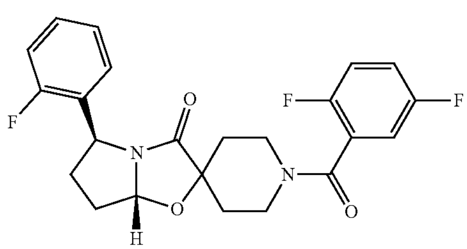 [SMILES: O=C(c1cc(F)ccc1F)N1CCC2(CC1)O[C@@H]1CC[C@@H](c3ccccc3F)N1C2=O] | (5'S,7a'R)-1-(2,5-difluorobenzoyl)-5'-(2-fluorophenyl)tetrahydro-3'H-spiro[piperidine-4,2'-pyrrolo[2,1-b]oxazol]-3'-one | Calc'd 431, found 431 |
| 1.13 | 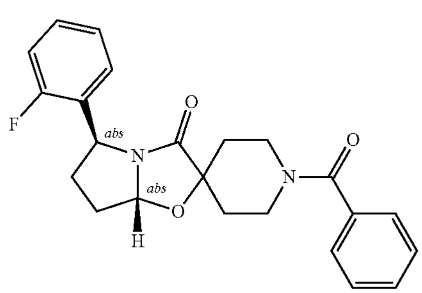 [SMILES: O=C(c1ccccc1)N1CCC2(CC1)O[C@@H]1CC[C@@H](c3ccccc3F)N1C2=O] | (5'S,7a'R)-1-benzoyl-5'-(2-fluorophenyl)tetrahydro-3'H-spiro[piperidine-4,2'-pyrrolo[2,1-b]oxazol]-3'-one | Calc'd 395, found 395 |

TABLE 11-continued

| Ex. No. | Structure | Name | Exact Mass [M + H]+ |
|---|---|---|---|
| 1.14 | 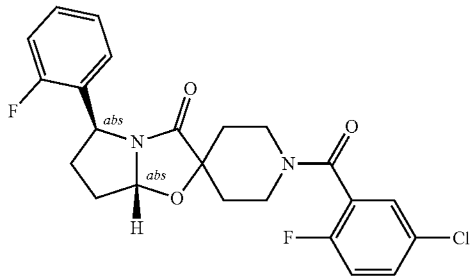 [SMILES: O=C(c1cc(Cl)ccc1F)N1CCC2(CC1)O[C@@H]1CC[C@@H](c3ccccc3F)N1C2=O] | (5'S,7a'R)-1-(5-chloro-2-fluorobenzoyl)-5'-(2-fluorophenyl)tetrahydro-3'H-spiro[piperidine-4,2'-pyrrolo[2,1-b]oxazol]-3'-one | Calc'd 447, found 447 |
| 1.15 | 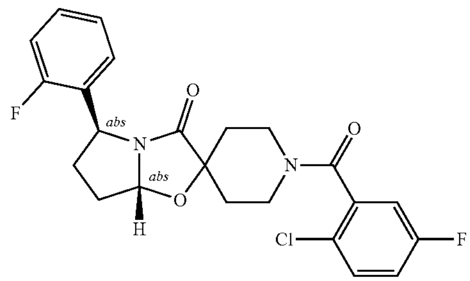 [SMILES: O=C(c1cc(F)ccc1Cl)N1CCC2(CC1)O[C@@H]1CC[C@@H](c3ccccc3F)N1C2=O] | (5'S,7a'R)-1-(2-chloro-5-fluorobenzoyl)-5'-(2-fluorophenyl)tetrahydro-3'H-spiro[piperidine-4,2'-pyrrolo[2,1-b]oxazol]-3'-one | Calc'd 447, found 447 |
| 1.16 | 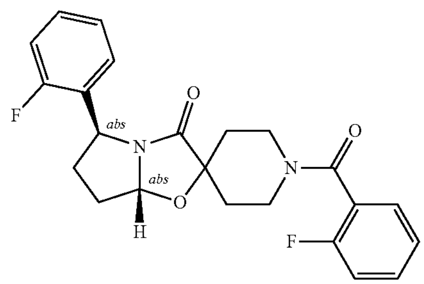 [SMILES: O=C(c1ccccc1F)N1CCC2(CC1)O[C@@H]1CC[C@@H](c3ccccc3F)N1C2=O] | (5'S,7a'R)-1-(2-fluorobenzoyl)-5'-(2-fluorophenyl)tetrahydro-3'H-spiro[piperidine-4,2'-pyrrolo[2,1-b]oxazol]-3'-one | Calc'd 413, found 413 |
| 1.17 | 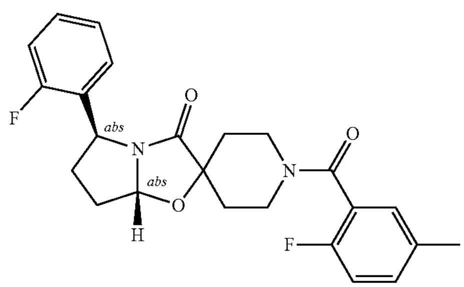 [SMILES: Cc1ccc(F)c(C(=O)N2CCC3(CC2)O[C@@H]2CC[C@@H](c4ccccc4F)N2C3=O)c1] | (5'S,7a'R)-1-(2-fluoro-5-methylbenzoyl)-5'-(2-fluorophenyl)tetrahydro-3'H-spiro[piperidine-4,2'-pyrrolo[2,1-b]oxazol]-3'-one | Calc'd 427, found 427 |
| 1.18 | 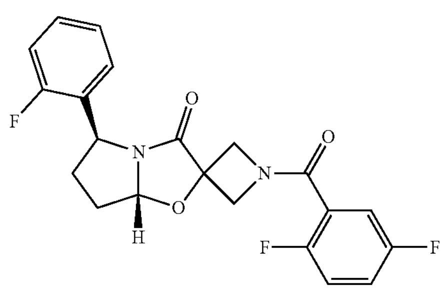 [SMILES: O=C(c1cc(F)ccc1F)N1CC2(C1)O[C@@H]1CC[C@@H](c3ccccc3F)N1C2=O] | (5'S,7a'R)-1-(2,5-difluorobenzoyl)-5'-(2-fluorophenyl)tetrahydro-3'H-spiro[azetidine-3,2'-pyrrolo[2,1-b]oxazol]-3'-one | Calc'd 403, found 403 |

TABLE 11-continued

| Ex. No. | Structure | Name | Exact Mass [M + H]+ |
|---|---|---|---|
| 1.19 | 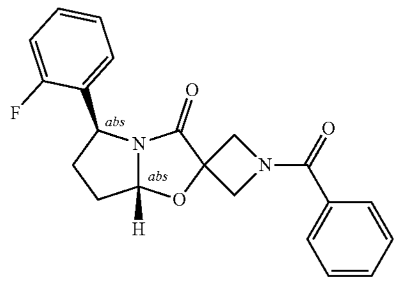 [SMILES: O=C(c1ccccc1)N1CC2(C1)O[C@@H]1CC[C@@H](c3ccccc3F)N1C2=O] | (5'S,7a'R)-1-benzoyl-5'-(2-fluorophenyl)tetrahydro-3'H-spiro[azetidine-3,2'-pyrrolo[2,1-b]oxazol]-3'-one | Calc'd 367, found 367 |
| 1.20 | 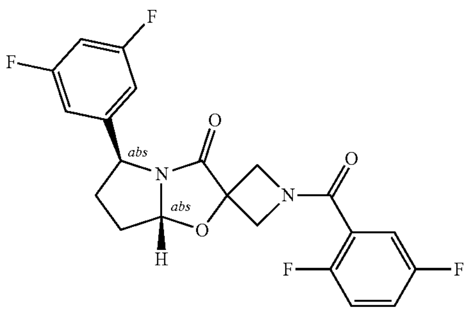 [SMILES: O=C(c1cc(F)ccc1F)N1CC2(C1)O[C@@H]1CC[C@@H](c3cc(F)cc(F)c3)N1C2=O] | (5'S,7a'R)-1-(2,5-difluorobenzoyl)-5'-(3,5-difluorophenyl)tetrahydro-3'H-spiro[azetidine-3,2'-pyrrolo[2,1-b]oxazol]-3'-one | Calc'd 421, found 421 |
| 1.21 | 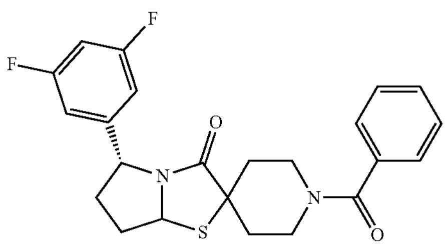 [SMILES: O=C(c1ccccc1)N1CCC2(CC1)SC1CC[C@H](c3cc(F)cc(F)c3)N1C2=O] | (5'R)-1-benzoyl-5'-(3,5-difluorophenyl)tetrahydro-3'H-spiro[piperidine-4,2'-pyrrolo[2,1-b]thiazol]-3'-one | Calc'd 429, found 429 |
| 1.22 | 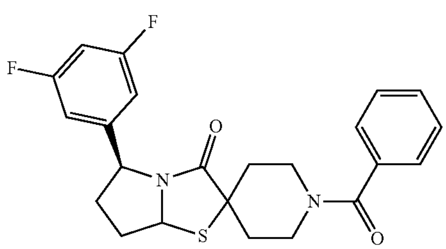 [SMILES: O=C(c1ccccc1)N1CCC2(CC1)SC1CC[C@@H](c3cc(F)cc(F)c3)N1C2=O] | (5'S)-1-benzoyl-5'-(3,5-difluorophenyl)tetrahydro-3'H-spiro[piperidine-4,2'-pyrrolo[2,1-b]thiazol]-3'-one | Calc'd 429, found 429 |
| 1.23 | 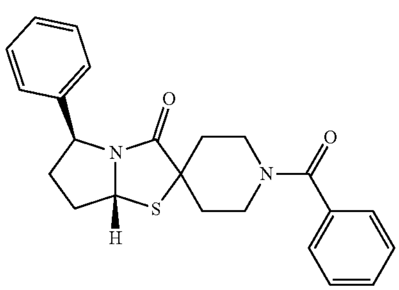 [SMILES: O=C(c1ccccc1)N1CCC2(CC1)S[C@@H]1CC[C@@H](c3ccccc3)N1C2=O] | (5'S,7a'R)-1-(benzenecarbonyl)-5'-phenyltetrahydro-3'H-spiro[piperidine-4,2'-pyrrolo[2,1-b][1,3]thiazol]-3'-one | Calc'd 393, found 393 |

TABLE 11-continued

| Ex. No. | Structure | Name | Exact Mass [M + H]+ |
|---|---|---|---|
| 1.24 | 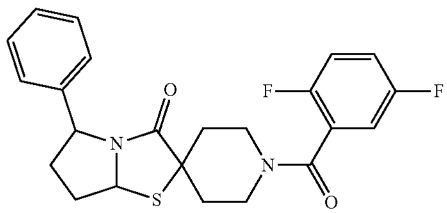 [SMILES: O=C(c1cc(F)ccc1F)N1CCC2(CC1)SC1CCC(c3ccccc3)N1C2=O] | 1-(2,5-difluorobenzene-1-carbonyl)-5'-phenyltetrahydro-3'H-spiro[piperidine-4,2'-pyrrolo[2,1-b][1,3]thiazol]-3'-one | Calc'd 429, found 429 |
| 1.25 | 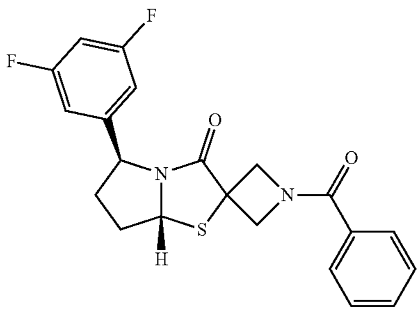 [SMILES: O=C(c1ccccc1)N1CC2(C1)S[C@@H]1CC[C@@H](c3cc(F)cc(F)c3)N1C2=O] | (5'S,7a'R)-1-benzoyl-5'-(3,5-difluorophenyl)tetrahydro-3'H-spiro[azetidine-3,2'-pyrrolo[2,1-b]thiazol]-3'-one | Calc'd 401, found 401 |

Compounds in Table 12 below were prepared from common intermediates from Table 7, I-47 and from Table 3 described above using the methods described in Example 1.1. Example 2.1 was prepared using a slightly modified procedure wherein the reaction was run in THF, using DIEA as base, and the reaction was run at 20° C. for 12 h. Examples 2.4-2.7 were purified by SFC, and SFC conditions are listed following the table.

TABLE 12

| Ex. No. | Structure | Name | Exact Mass [M + H]+ |
|---|---|---|---|
| 2.1 | 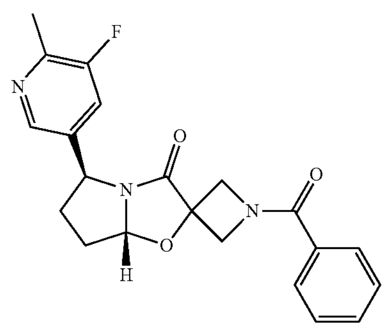 [SMILES: Cc1ncc([C@@H]2CC[C@H]3OC4(CN(C(=O)c5ccccc5)C4)C(=O)N32)cc1F] | (5'S,7a'R)-1-benzoyl-5'-(5-fluoro-6-methylpyridin-3-yl)tetrahydro-3'H-spiro[piperidine-4,2'-pyrrolo[2,1-b]oxazol]-3'-one, TFA salt. | Calc'd 410, found 410 |
| 2.2 | 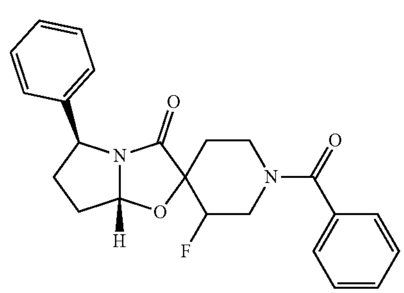 [SMILES: O=C(c1ccccc1)N1CCC2(O[C@@H]3CC[C@@H](c4ccccc4)N3C2=O)C(F)C1] | (3[R or S],4[S or R], 5'S,7a'R)-1-benzoyl-3-fluoro-5'-phenyltetrahydro-3'H-spiro[piperidine-4,2'-pyrrolo[2,1-b]oxazol]-3'-one | Calc'd 395, found 395 |

TABLE 12-continued

| Ex. No. | Structure | Name | Exact Mass [M + H]+ |
|---|---|---|---|
| 2.3 | 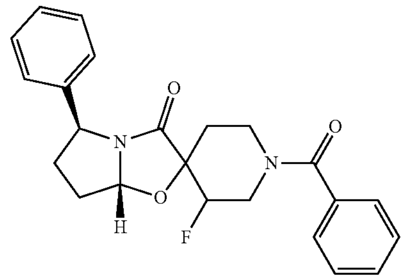 [SMILES: O=C(c1ccccc1)N1CCC2(O[C@@H]3CC[C@@H](c4ccccc4)N3C2=O)C(F)C1] | (3[S or R],4[R or S], 5'S,7a'R)-1-benzoyl-3-fluoro-5'-phenyltetrahydro-3'H-spiro[piperidine-4,2'-pyrrolo[2,1-b]oxazol]-3'-one | Calc'd 395, found 395 |
| 2.4 | 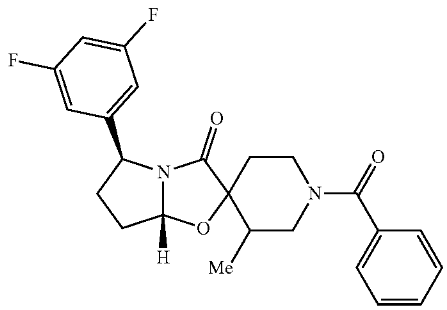 [SMILES: CC1CN(C(=O)c2ccccc2)CCC12O[C@@H]1CC[C@@H](c3cc(F)cc(F)c3)N1C2=O] | (3[R or S],4[R or S], 5'S,7a'R)-1-benzoyl-5'-(3,5-difluorophenyl)-3-methyltetrahydro-3'H-spiro[piperidine-4,2'-pyrrolo[2,1-b]oxazol]-3'-one | Calc'd 427, found 427 |
| 2.5 | 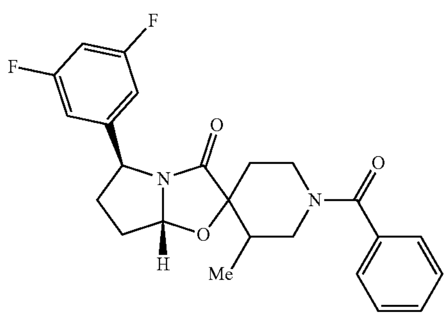 [SMILES: CC1CN(C(=O)c2ccccc2)CCC12O[C@@H]1CC[C@@H](c3cc(F)cc(F)c3)N1C2=O] | (3[S or R],4[R or S], 5'S,7a'R)-1-benzoyl-5'-(3,5-difluorophenyl)-3-methyltetrahydro-3'H-spiro[piperidine-4,2'-pyrrolo[2,1-b]oxazol]-3'-one | Calc'd 427, found 427 |
| 2.6 | 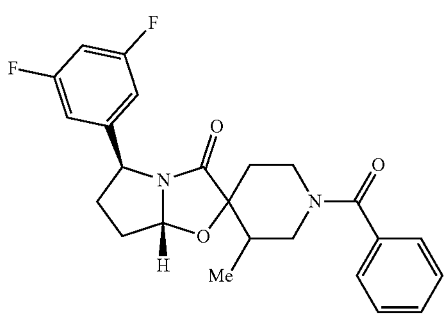 [SMILES: CC1CN(C(=O)c2ccccc2)CCC12O[C@@H]1CC[C@@H](c3cc(F)cc(F)c3)N1C2=O] | (3[S or R],4[S or R], 5'S,7a'R)-1-benzoyl-5'-(3,5-difluorophenyl)-3-methyltetrahydro-3'H-spiro[piperidine-4,2'-pyrrolo[2,1-b]oxazol]-3'-one | Calc'd 427, found 427 |
| 2.7 | 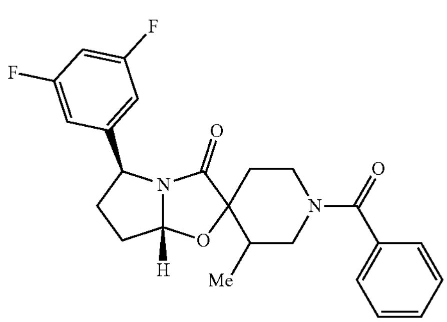 [SMILES: CC1CN(C(=O)c2ccccc2)CCC12O[C@@H]1CC[C@@H](c3cc(F)cc(F)c3)N1C2=O] | (3[R or S],4[S or R], 5'S,7a'R)-1-benzoyl-5'-(3,5-difluorophenyl)-3-methyltetrahydro-3'H-spiro[piperidine-4,2'-pyrrolo[2,1-b]oxazol]-3'-one | Calc'd 427, found 427 |

TABLE 12-continued

| Ex. No. | Structure | Name | Exact Mass [M + H]+ |
|---|---|---|---|
| 2.8 | 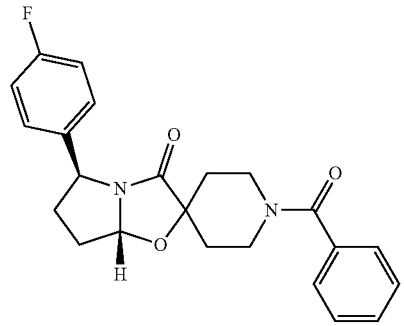 [SMILES: O=C(c1ccccc1)N1CCC2(CC1)O[C@@H]1CC[C@@H](c3ccc(F)cc3)N1C2=O] | (5'S,7a'R)-1-benzoyl-5'-(4-fluorophenyl)tetrahydro-3'H-spiro[piperidine-4,2'-pyrrolo[2,1-b]oxazol]-3'-one | Calc'd 395, found 395 |
| 2.9 | 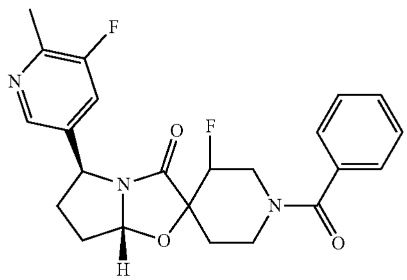 [SMILES: Cc1ncc([C@@H]2CC[C@H]3OC4(CCN(C(=O)c5ccccc5)CC4F)C(=O)N32)cc1F] | (5'S,7a'R)-1-(benzenecarbonyl)-3-fluoro-5'-(5-fluoro-6-methylpyridin-3-yl)tetrahydro-3'H-spiro[piperidine-4,2'-pyrrolo[2,1-b][1,3]oxazol]-3'-one | Calc'd 428, found 428 |
| 2.10 | 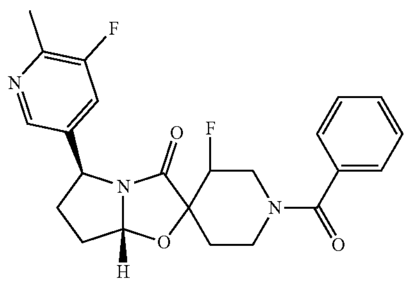 [SMILES: Cc1ncc([C@@H]2CC[C@H]3OC4(CCN(C(=O)c5ccccc5)CC4F)C(=O)N32)cc1F] | (5'S,7a'R)-1-(benzenecarbonyl)-3-fluoro-5'-(5-fluoro-6-methylpyridin-3-yl)tetrahydro-3'H-spiro[piperidine-4,2'-pyrrolo[2,1-b][1,3]oxazol]-3'-one | Calc'd 428, found 428 |

Examples 2.4/2.5/2.6/2.7

(5'S,7a'R)-1-benzoyl-5'-(3,5-difluorophenyl)-3-methyl-tetrahydro-3'H-spiro[piperidine-4,2'-pyrrolo[2,1-b]oxazol]-3'-one was purified by CHIRAL-Prep SFC [Column: Lux-4, 21×250 mm: 30% [0.1% NH₄OH in MeOH]/CO₂; Flow rate: 70 mL/min; First Eluting Peak (2.4); Second Eluting Peak (2.5); Third Eluting Peak (2.6); Fourth Eluting Peak (2.7)].

Example 3.1

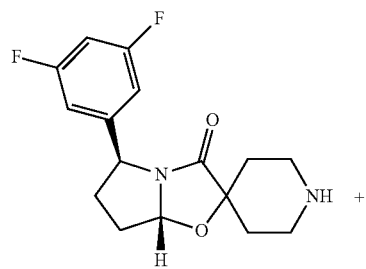

I-21

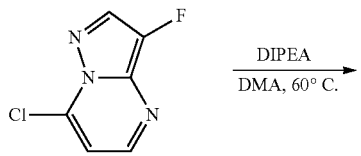

-continued

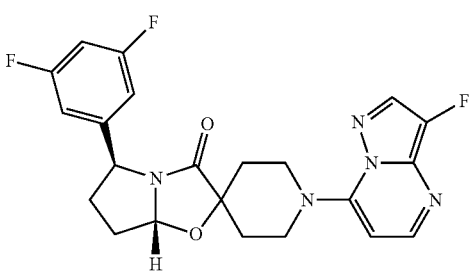

3.1

(5'S,7a'R)-5'-(3,5-Difluorophenyl)-1-(3-fluoropyrazolo[1,5-a]pyrimidin-7-yl)tetrahydro-3'H-spiro[piperidine-4,2'-pyrrolo[2,1-b]oxazol]-3'-one (5'S,7a'R)-5'-(3,5-difluorophenyl)tetrahydro-3'H-spiro[piperidine-4,2'-pyrrolo[2,1-b]oxazol]-3'-one, HCl (75 mg, 0.24 mmol) (I-21) and 7-chloro-3-fluoropyrazolo[1,5-a]pyrimidine (42 mg, 0.24 mmol) in DMA (1622 μL) were added to a flask. Hunig's Base (85 μL, 0.49 mmol) was added in one portion and the mixture was heated to 55° C. for 90 min. The solvents were removed and the residue was purified via flash silica gel chromatography (ISCO SiO₂ 4 g; ethyl acetate in hexanes, 20-70%). The desired fractions were combined and the volatiles evaporated to afford (5'S,7a'R)-5'-(3,5-difluorophenyl)-1-(3-fluoropyrazolo[1,5-a]pyrimidin-7-yl)tetrahydro-3'H-spiro[piperidine-4,2'-pyrrolo[2,1-b]oxazol]-3'-one. MS (ESI) m/z $C_{22}H_{21}F_3N_5O_2$[M+H]⁺ calc'd 404, found 404. ¹H NMR (499 MHz, DMSO-d6) δ 8.28 (dd, J=11.2, 4.2 Hz, 2H), 7.19-7.01 (m, 3H), 6.47 (d, J=5.0 Hz, 1H), 5.93-5.77 (m, 1H), 4.96 (t, J=7.8 Hz, 1H), 4.37 (d, J=12.7 Hz, 1H), 4.28 (d, J=12.7 Hz, 1H), 3.49 (t, J=10.9 Hz, 1H), 2.65 (dq, J=13.3, 7.7, 6.8 Hz, 1H), 2.20 (d, J=12.3 Hz, 2H), 2.12 (td, J=13.7, 4.4 Hz, 1H), 2.02-1.84 (m, 2H), 1.81 (t, J=13.8 Hz, 1H), 1.70 (tt, J=11.5, 7.6 Hz, 1H).

Example 4.1

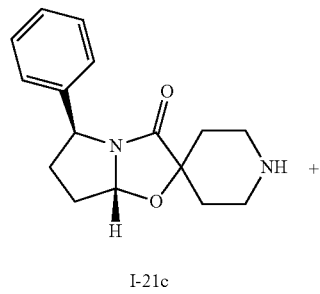

I-21c

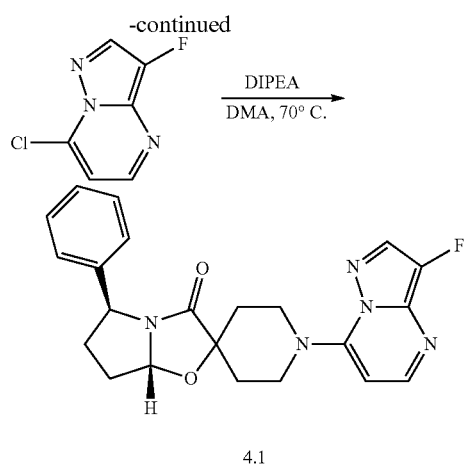

4.1

(5'S,7a'R)-5'-Phenyltetrahydro-3'H-spiro[piperidine-4,2'-pyrrolo[2,1-b]oxazol]-3'-one (I-21C) (13 mg, 0.048 mmol) was added to a vial with 7-chloro-3-fluoropyrazolo[1,5-a]pyrimidine (8.19 mg, 0.048 mmol) in DMA (477 μL). N-ethyl-N-isopropylpropan-2-amine (26 μL, 0.143 mmol) was added to the mixture and the mixture was capped and heated to 75° C. for 60 min. The residue was purified via flash silica gel chromatography (ISCO SiO₂ 4 g; ethyl acetate in hexanes, 30-70%). The desired fractions were combined and the volatiles evaporated to afford (5'S,7a'R)-1-(3-fluoropyrazolo[1,5-a]pyrimidin-7-yl)-5'-phenyltetrahydro-3'H-spiro[piperidine-4,2'-pyrrolo[2,1-b]oxazol]-3'-one. MS (ESI) m/z $C_{22}H_{23}FN_5O_2$[M+H]⁺ calc'd 408, found 408. ¹H NMR (499 MHz, DMSO-d6) δ 8.29 (dd, J=12.9, 4.2 Hz, 2H), 7.43-7.18 (m, 5H), 6.47 (d, J=5.1 Hz, 1H), 5.83 (dd, J=7.1, 5.1 Hz, 1H), 4.94 (t, J=7.8 Hz, 1H), 4.38 (d, J=13.0 Hz, 1H), 4.29 (d, J=12.6 Hz, 1H), 3.49 (t, J=10.7 Hz, 1H), 3.39 (d, J=12.2 Hz, 2H), 2.64 (ddd, J=13.0, 7.8, 5.3 Hz, 1H), 2.22 (dd, J=7.1, 4.5 Hz, 1H), 2.16-2.04 (m, 2H), 2.00-1.83 (m, 2H), 1.83-1.63 (m, 2H).

Compounds in Table 13 below were prepared from common Intermediate I-21 or from intermediates described in Tables 7, 8, or 9 using the methods described in Example 4.1.

TABLE 13

| Ex. No. | Structure | Name | Exact Mass [M + H]⁺ |
|---|---|---|---|
| 4.2 | 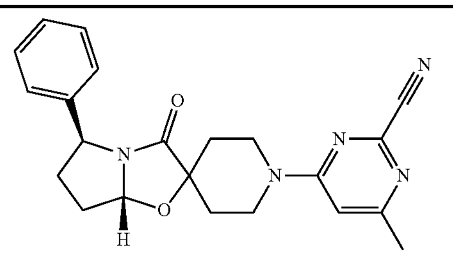 | 4-methyl-6-[(5'S,7a'R)-3'-oxo-5'-phenyltetrahydro-1H,3'H-spiro[piperidine-4,2'-pyrrolo[2,1-b][1,3]oxazol]-1-yl]pyrimidine-2-carbonitrile | Calc'd 390, found 390 |
| 4.3 | 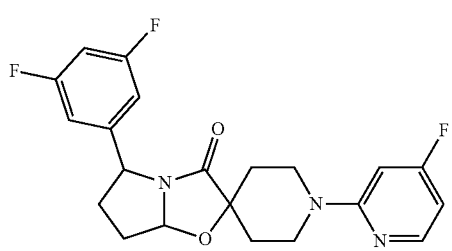 [SMILES: O=C1N2C(CCC2c2cc(F)cc(F)c2)OC12CCN(c1cc(F)ccn1)CC2] | 5'-(3,5-difluorophenyl)-1-(4-fluoropyridin-2-yl)tetrahydro-3'H-spiro[piperidine-4,2'-pyrrolo[2,1-b][1,3]oxazol]-3'-one | Calc'd 404, found 404 |

TABLE 13-continued

| Ex. No. | Structure | Name | Exact Mass [M + H]+ |
|---|---|---|---|
| 4.4 | 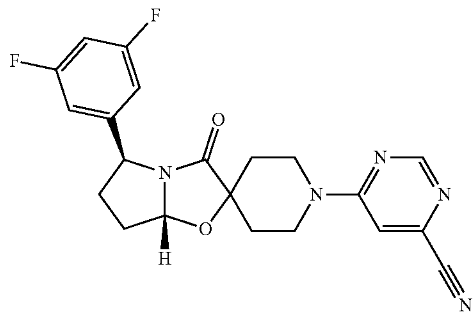 [SMILES: N#Cc1cc(N2CCC3(CC2)O[C@@H]2CC[C@@H](c4cc(F)cc(F)c4)N2C3=O)ncn1] | 6-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]pyrimidine-4-carbonitrile | Calc'd 412, found 412 |
| 4.5 | 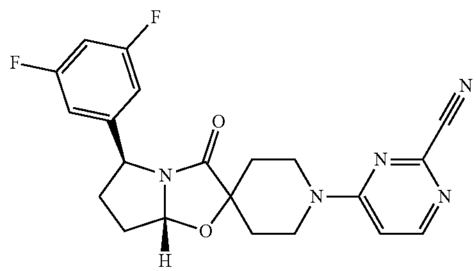 [SMILES: N#Cc1nccc(N2CCC3(CC2)O[C@@H]2CC[C@@H](c4cc(F)cc(F)c4)N2C3=O)n1] | 4-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]pyrimidine-2-carbonitrile | Calc'd 412, found 412 |
| 4.6 | 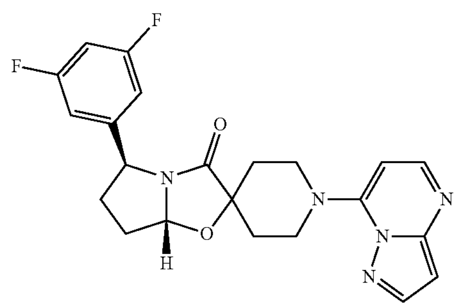 [SMILES: O=C1N2[C@@H](CC[C@H]2c2cc(F)cc(F)c2)OC12CCN(c1ccnc3ccnn13)CC2] | (5'S,7a'R)-5'-(3,5-difluorophenyl)-1-(pyrazolo[1,5-a]pyrimidin-7-yl)tetrahydro-3'H-spiro[piperidine-4,2'-pyrrolo[2,1-b][1,3]oxazol]-3'-one | Calc'd 426, found 426 |
| 4.7 | 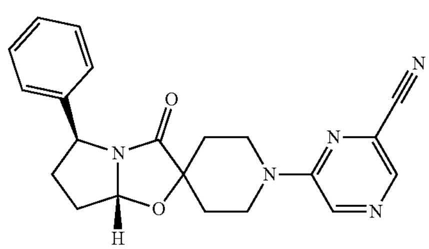 [SMILES: N#Cc1cncc(N2CCC3(CC2)O[C@@H]2CC[C@@H](c4ccccc4)N2C3=O)n1] | 6-[(5'S,7a'R)-3'-oxo-5'-phenyltetrahydro-1H,3'H-spiro[piperidine-4,2'-pyrrolo[2,1-b][1,3]oxazol]-1-yl]pyrazine-2-carbonitrile | Calc'd 376, found 376 |
| 4.8 | 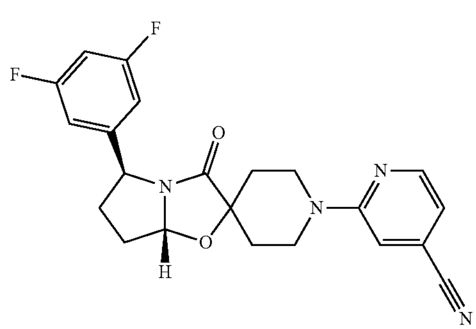 [SMILES: N#Cc1ccnc(N2CCC3(CC2)O[C@@H]2CC[C@@H](c4cc(F)cc(F)c4)N2C3=O)c1] | 2-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]pyridine-4-carbonitrile | Calc'd 411, found 411 |

TABLE 13-continued

| Ex. No. | Structure | Name | Exact Mass [M + H]+ |
|---|---|---|---|
| 4.9 | 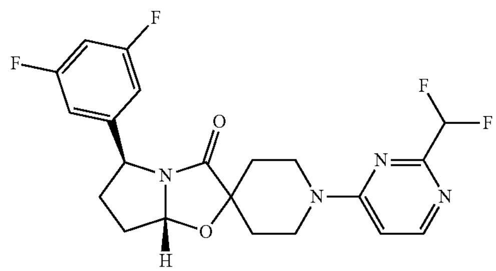 [SMILES: O=C1N2[C@@H](CC[C@H]2c2cc(F)cc(F)c2)OC12CCN(c1ccnc(C(F)F)n1)CC2] | (5'S,7a'R)-1-[2-(difluoromethyl)pyrimidin-4-yl]-5'-(3,5-difluorophenyl)tetrahydro-3'H-spiro[piperidine-4,2'-pyrrolo[2,1-b][1,3]oxazol]-3'-one | Calc'd 437, found 437 |
| 4.10 | 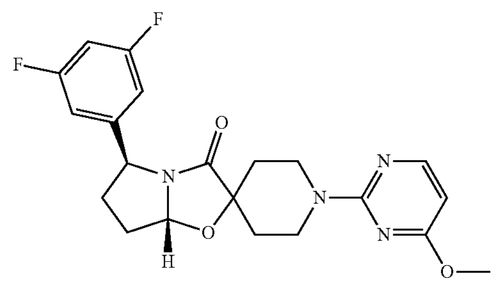 [SMILES: COc1ccnc(N2CCC3(CC2)O[C@@H]2CC[C@@H](c4cc(F)cc(F)c4)N2C3=O)n1] | (5'S,7a'R)-5'-(3,5-difluorophenyl)-1-(4-methoxypyrimidin-2-yl)tetrahydro-3'H-spiro[piperidine-4,2'-pyrrolo[2,1-b][1,3]oxazol]-3'-one | Calc'd 417, found 417 |
| 4.11 | 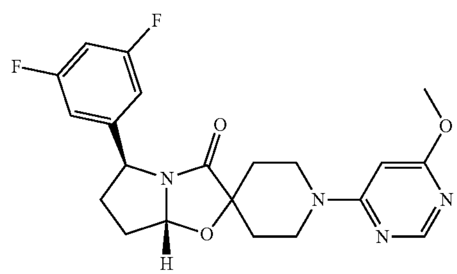 [SMILES: COc1cc(N2CCC3(CC2)O[C@@H]2CC[C@@H](c4cc(F)cc(F)c4)N2C3=O)ncn1] | (5'S,7a'R)-5'-(3,5-difluorophenyl)-1-(6-methoxypyrimidin-4-yl)tetrahydro-3'H-spiro[piperidine-4,2'-pyrrolo[2,1-b][1,3]oxazol]-3'-one | Calc'd 417, found 417 |
| 4.12 | 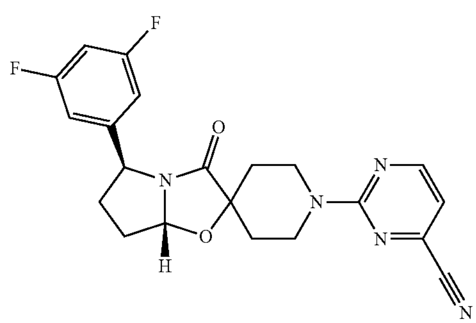 [SMILES: N#Cc1ccnc(N2CCC3(CC2)O[C@@H]2CC[C@@H](c4cc(F)cc(F)c4)N2C3=O)n1] | 2-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]pyrimidine-4-carbonitrile | Calc'd 412, found 412 |
| 4.13 | 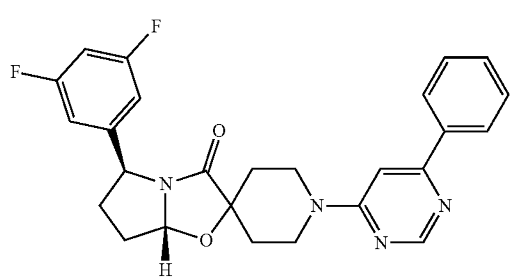 [SMILES: O=C1N2[C@@H](CC[C@H]2c2cc(F)cc(F)c2)OC12CCN(c1cc(-c3ccccc3)ncn1)CC2] | (5'S,7a'R)-5'-(3,5-difluorophenyl)-1-(6-phenylpyrimidin-4-yl)tetrahydro-3'H-spiro[piperidine-4,2'-pyrrolo[2,1-b][1,3]oxazol]-3'-one | Calc'd 463, found 463 |

TABLE 13-continued

| Ex. No. | Structure | Name | Exact Mass [M + H]+ |
|---|---|---|---|
| 4.14 | 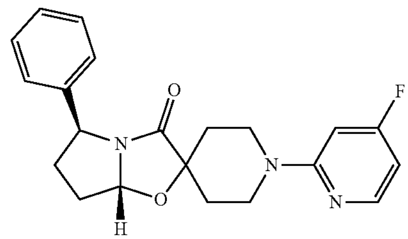 [SMILES: O=C1N2[C@@H](CC[C@H]2c2ccccc2)OC12CCN(c1cc(F)ccn1)CC2] | (5'S,7a'R)-1-(4-fluoropyridin-2-yl)-5'-phenyltetrahydro-3'H-spiro[piperidine-4,2'-pyrrolo[2,1-b][1,3]oxazol]-3'-one | Calc'd 368, found 368 |
| 4.15 | 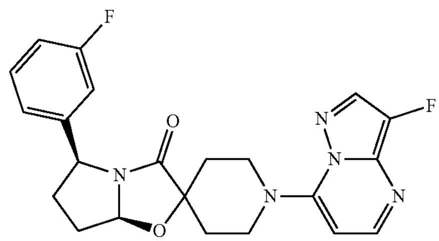 [SMILES: O=C1N2[C@H](CC[C@H]2c2cccc(F)c2)OC12CCN(c1ccnc3c(F)cnn13)CC2] | (5'S,7a'S)-5'-(3-fluorophenyl)-1-(3-fluoropyrazolo[1,5-a]pyrimidin-7-yl)tetrahydro-3'H-spiro[piperidine-4,2'-pyrrolo[2,1-b][1,3]oxazol]-3'-one | Calc'd 426, found 426 |
| 4.16 | 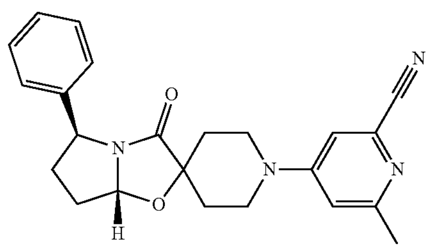 [SMILES: Cc1cc(N2CCC3(CC2)O[C@@H]2CC[C@@H](c4ccccc4)N2C3=O)cc(C#N)n1] | 6-methyl-4-[(5'S,7a'R)-3'-oxo-5'-phenyltetrahydro-1H,3'H-spiro[piperidine-4,2'-pyrrolo[2,1-b][1,3]oxazol]-1-yl]pyridine-2-carbonitrile | Calc'd 389, found 389 |
| 4.17 | 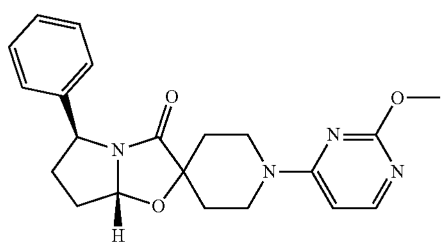 [SMILES: COc1nccc(N2CCC3(CC2)O[C@@H]2CC[C@@H](c4ccccc4)N2C3=O)n1] | (5'S,7a'R)-1-(2-methoxypyrimidin-4-yl)-5'-phenyltetrahydro-3'H-spiro[piperidine-4,2'-pyrrolo[2,1-b][1,3]oxazol]-3'-one | Calc'd 381, found 381 |
| 4.18 | 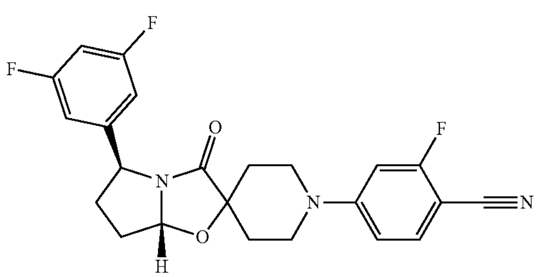 [SMILES: N#Cc1ccc(N2CCC3(CC2)O[C@@H]2CC[C@@H](c4cc(F)cc(F)c4)N2C3=O)cc1F] | 4-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-2-fluorobenzonitrile | Calc'd 428, found 428 |
| 4.19 | 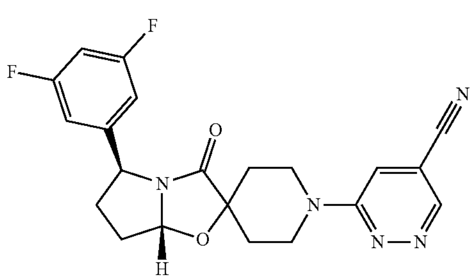 [SMILES: N#Cc1cnnc(N2CCC3(CC2)O[C@@H]2CC[C@@H](c4cc(F)cc(F)c4)N2C3=O)c1] | 6-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]pyridazine-4-carbonitrile | Calc'd 412, found 412 |

TABLE 13-continued

| Ex. No. | Name | Exact Mass [M + H]+ |
|---|---|---|
| 4.20 | 2-chloro-4-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]benzonitrile | Calc'd 444, found 444 |
| 4.21 | (5'S,7a'R)-5'-(3,5-difluorophenyl)-1-(5-fluoro-4-methoxypyrimidin-2-yl)tetrahydro-3'H-spiro[piperidine-4,2'-pyrrolo[2,1-b][1,3]oxazol]-3'-one | Calc'd 435, found 435 |
| 4.22 | (5'S,7a'R)-1-(6-chloro-2,5-dimethylpyrimidin-4-yl)-5'-phenyltetrahydro-3'H-spiro[piperidine-4,2'-pyrrolo[2,1-b][1,3]oxazol]-3'-one | Calc'd 413, found 413 |
| 4.23 | ethyl 6-[(5'S,7a'R)-3'-oxo-5'-phenyltetrahydro-1H,3'H-spiro[piperidine-4,2'-pyrrolo[2,1-b][1,3]oxazol]-1-yl]pyrimidine-4-carboxylate | Calc'd 423, found 423 |
| 4.24 | 4-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-3-fluorobenzonitrile | Calc'd 428, found 428 |

TABLE 13-continued

| Ex. No. | Structure | Name | Exact Mass [M + H]+ |
|---|---|---|---|
| 4.25 | 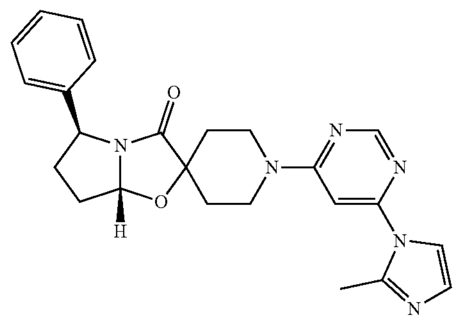 [SMILES: Cc1nccn1-c1cc(N2CCC3(CC2)O[C@@H]2CC[C@@H](c4ccccc4)N2C3=O)ncn1] | (5'S,7a'R)-1-[6-(2-methyl-1H-imidazol-1-yl)pyrimidin-4-yl]-5'-phenyltetrahydro-3'H-spiro[piperidine-4,2'-pyrrolo[2,1-b][1,3]oxazol]-3'-one | Calc'd 431, found 431 |
| 4.26 | 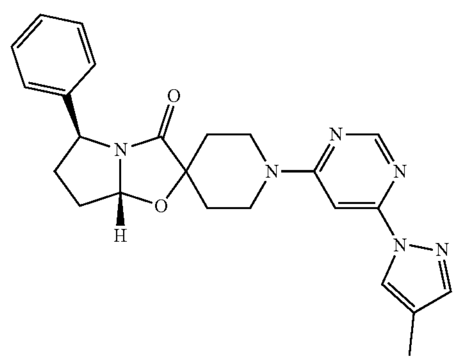 [SMILES: Cc1cnn(-c2cc(N3CCC4(CC3)O[C@@H]3CC[C@@H](c5ccccc5)N3C4=O)ncn2)c1] | (5'S,7a'R)-1-[6-(4-methyl-1H-pyrazol-1-yl)pyrimidin-4-yl]-5'-phenyltetrahydro-3'H-spiro[piperidine-4,2'-pyrrolo[2,1-b][1,3]oxazol]-3'-one | Calc'd 431, found 431 |
| 4.27 | 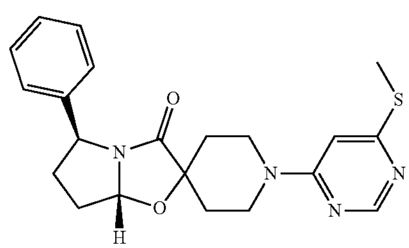 [SMILES: CSc1cc(N2CCC3(CC2)O[C@@H]2CC[C@@H](c4ccccc4)N2C3=O)ncn1] | (5'S,7a'R)-1-[6-(methylsulfanyl)pyrimidin-4-yl]-5'-phenyltetrahydro-3'H-spiro[piperidine-4,2'-pyrrolo[2,1-b][1,3]oxazol]-3'-one | Calc'd 397, found 397 |
| 4.28 | 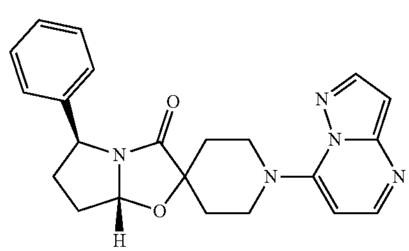 [SMILES: O=C1N2[C@@H](CC[C@H]2c2ccccc2)OC12CCN(c1ccnc3ccnn13)CC2] | (5'S,7a'R)-5'-phenyl-1-(pyrazolo[1,5-a]pyrimidin-7-yl)tetrahydro-3'H-spiro[piperidine-4,2'-pyrrolo[2,1-b][1,3]oxazol]-3'-one | Calc'd 390, found 390 |
| 4.29 | 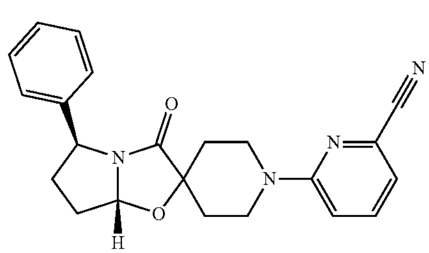 [SMILES: N#Cc1cccc(N2CCC3(CC2)O[C@@H]2CC[C@@H](c4ccccc4)N2C3=O)n1] | 6-[(5'S,7a'R)-3'-oxo-5'-phenyltetrahydro-1H,3'H-spiro[piperidine-4,2'-pyrrolo[2,1-b][1,3]oxazol]-1-yl]pyridine-2-carbonitrile | Calc'd 375, found 375 |

TABLE 13-continued

| Ex. No. | Structure | Name | Exact Mass [M + H]+ |
|---|---|---|---|
| 4.30 | 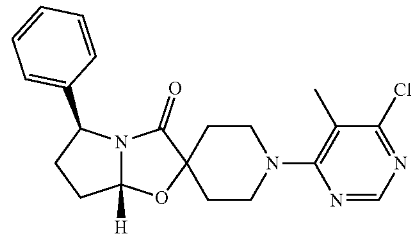 [SMILES: Cc1c(Cl)ncnc1N1CCC2(CC1)O[C@@H]1CC[C@@H](c3ccccc3)N1C2=O] | (5'S,7a'R)-1-(6-chloro-5-methylpyrimidin-4-yl)-5'-phenyltetrahydro-3'H-spiro[piperidine-4,2'-pyrrolo[2,1-b][1,3]oxazol]-3'-one | Calc'd 399, found 399 |
| 4.31 | 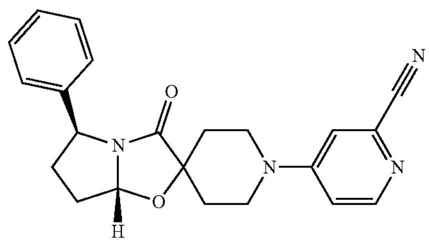 [SMILES: N#Cc1cc(N2CCC3(CC2)O[C@@H]2CC[C@@H](c4ccccc4)N2C3=O)ccn1] | 4-[(5'S,7a'R)-3'-oxo-5'-phenyltetrahydro-1H,3'H-spiro[piperidine-4,2'-pyrrolo[2,1-b][1,3]oxazol]-1-yl]pyridine-2-carbonitrile | Calc'd 375, found 375 |
| 4.32 | 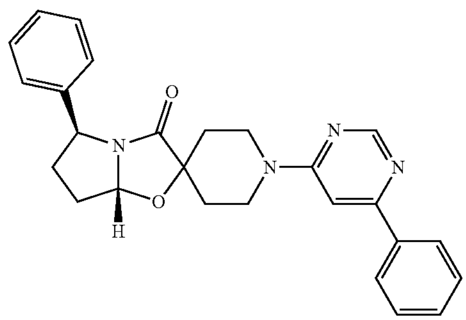 [SMILES: O=C1N2[C@@H](CC[C@H]2c2ccccc2)OC12CCN(c1cc(-c3ccccc3)ncn1)CC2] | (5'S,7a'R)-5'-phenyl-1-(6-phenylpyrimidin-4-yl)tetrahydro-3'H-spiro[piperidine-4,2'-pyrrolo[2,1-b][1,3]oxazol]-3'-one | Calc'd 427, found 427 |
| 4.33 | 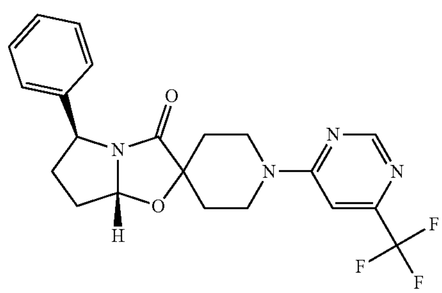 [SMILES: O=C1N2[C@@H](CC[C@H]2c2ccccc2)OC12CCN(c1cc(C(F)(F)F)ncn1)CC2] | (5'S,7a'R)-5'-phenyl-1-[6-(trifluoromethyl)pyrimidin-4-yl]tetrahydro-3'H-spiro[piperidine-4,2'-pyrrolo[2,1-b][1,3]oxazol]-3'-one | Calc'd 419, found 419 |
| 4.34 | 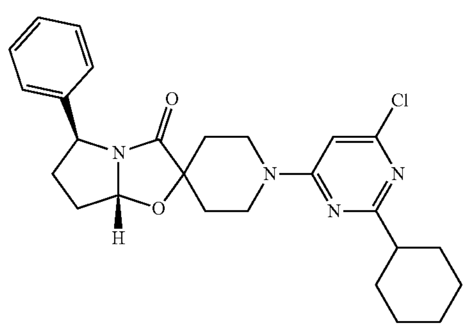 [SMILES: O=C1N2[C@@H](CC[C@H]2c2ccccc2)OC12CCN(c1cc(Cl)nc(C3CCCCC3)n1)CC2] | (5'S,7a'R)-1-(6-chloro-2-cyclohexylpyrimidin-4-yl)-5'-phenyltetrahydro-3'H-spiro[piperidine-4,2'-pyrrolo[2,1-b][1,3]oxazol]-3'-one | Calc'd 467, found 467 |

TABLE 13-continued

| Ex. No. | Structure | Name | Exact Mass [M + H]+ |
|---|---|---|---|
| 4.35 | 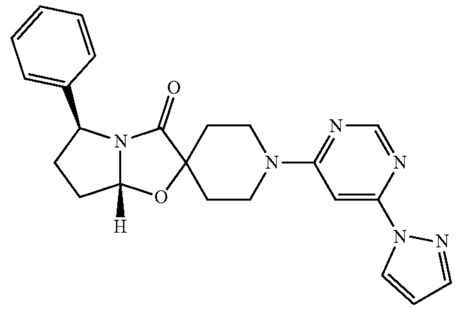 [SMILES: O=C1N2[C@@H](CC[C@H]2c2ccccc2)OC12CCN(c1cc(-n3cccn3)ncn1)CC2] | (5'S,7a'R)-5'-phenyl-1-[6-(1H-pyrazol-1-yl)pyrimidin-4-yl]tetrahydro-3'H-spiro[piperidine-4,2'-pyrrolo[2,1-b][1,3]oxazol]-3'-one | Calc'd 417, found 417 |
| 4.36 | 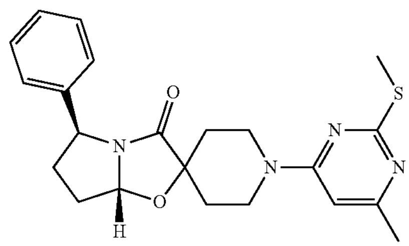 [SMILES: CSc1nc(C)cc(N2CCC3(CC2)O[C@@H]2CC[C@@H](c4ccccc4)N2C3=O)n1] | (5'S,7a'R)-1-[6-methyl-2-(methylsulfanyl)pyrimidin-4-yl]-5'-phenyltetrahydro-3'H-spiro[piperidine-4,2'-pyrrolo[2,1-b][1,3]oxazol]-3'-one | Calc'd 411, found 411 |
| 4.37 | 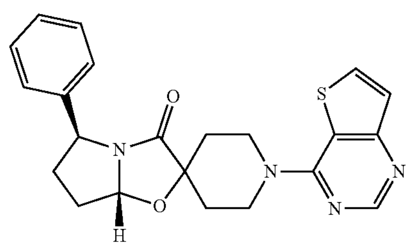 [SMILES: O=C1N2[C@@H](CC[C@H]2c2ccccc2)OC12CCN(c1ncnc3ccsc13)CC2] | (5'S,7a'R)-5'-phenyl-1-(thieno[3,2-d]pyrimidin-4-yl)tetrahydro-3'H-spiro[piperidine-4,2'-pyrrolo[2,1-b][1,3]oxazol]-3'-one | Calc'd 407, found 407 |
| 4.38 | 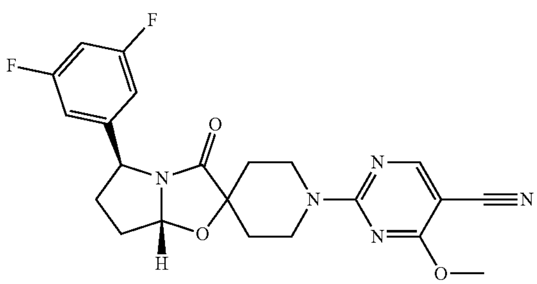 [SMILES: COc1nc(N2CCC3(CC2)O[C@@H]2CC[C@@H](c4cc(F)cc(F)c4)N2C3=O)ncc1C#N] | 2-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-4-methoxypyrimidine-5-carbonitrile | Calc'd 442, found 442 |
| 4.39 | 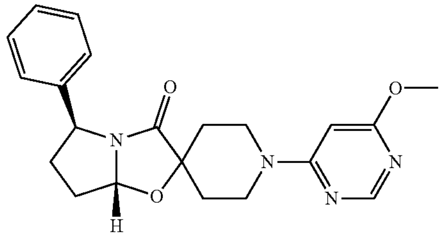 | (5'S,7a'R)-1-(6-methoxypyrimidin-4-yl)-5'-phenyltetrahydro-3'H-spiro[piperidine-4,2'-pyrrolo[2,1-b][1,3]oxazol]-3'-one | Calc'd 381, found 381 |

TABLE 13-continued

| Ex. No. | Structure | Name | Exact Mass [M + H]+ |
|---|---|---|---|
| 4.40 | 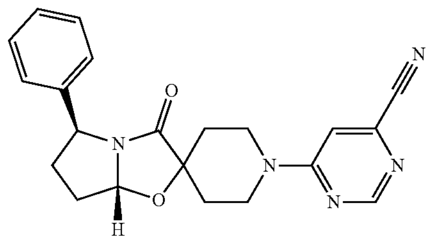 [SMILES: N#Cc1cc(N2CCC3(CC2)O[C@@H]2CC[C@@H](c4ccccc4)N2C3=O)ncn1] | 6-[(5'S,7a'R)-3'-oxo-5'-phenyltetrahydro-1H,3'H-spiro[piperidine-4,2'-pyrrolo[2,1-b][1,3]oxazol]-1-yl]pyrimidine-4-carbonitrile | Calc'd 376, found 376 |
| 4.41 | 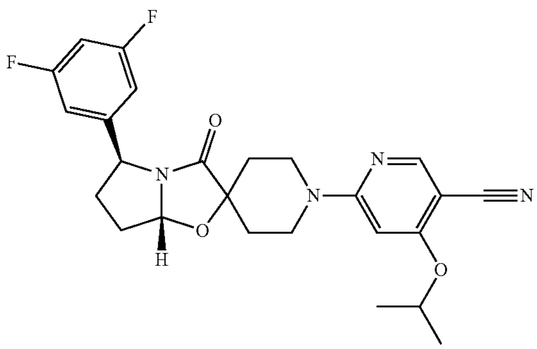 [SMILES: CC(C)Oc1cc(N2CCC3(CC2)O[C@@H]2CC[C@@H](c4cc(F)cc(F)c4)N2C3=O)ncc1C#N] | 6-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-4-[(propan-2-yl)oxy]pyridine-3-carbonitrile | Calc'd 469, found 469 |
| 4.42 | 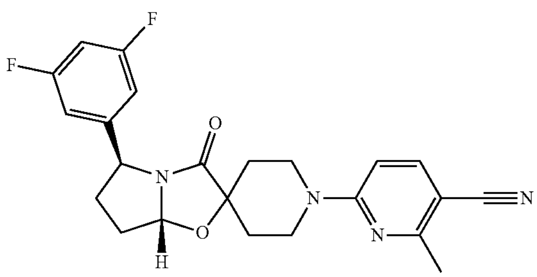 [SMILES: Cc1nc(N2CCC3(CC2)O[C@@H]2CC[C@@H](c4cc(F)cc(F)c4)N2C3=O)ccc1C#N] | 6-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-2-methylpyridine-3-carbonitrile | Calc'd 425, found 425 |
| 4.43 | 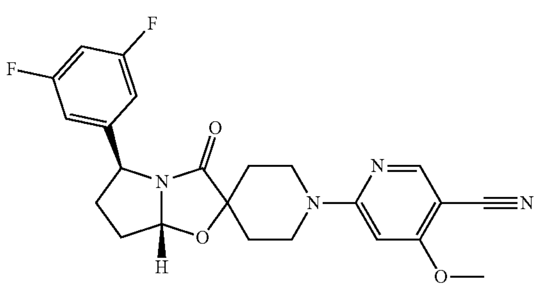 | 6-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-4-methoxypyridine-3-carbonitrile | Calc'd 441, found 441 |
| 4.44 | 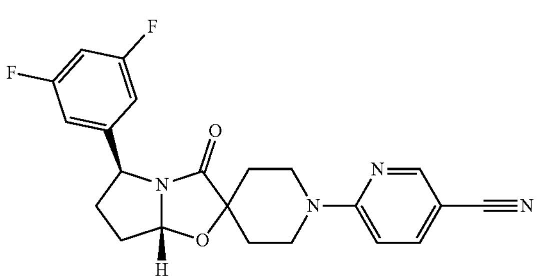 [SMILES: N#Cc1ccc(N2CCC3(CC2)O[C@@H]2CC[C@@H](c4cc(F)cc(F)c4)N2C3=O)nc1] | 6-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]pyridine-3-carbonitrile | Calc'd 411, found 411 |

TABLE 13-continued

| Ex. No. | Structure | Name | Exact Mass [M + H]+ |
|---|---|---|---|
| 4.45 | 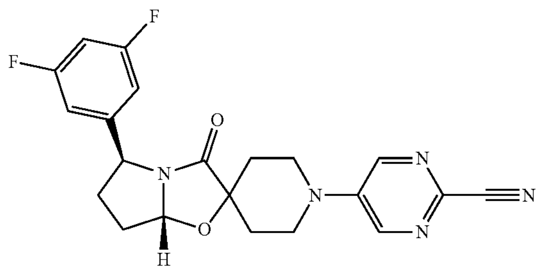 [SMILES: N#Cc1ncc(N2CCC3(CC2)O[C@@H]2CC[C@@H](c4cc(F)cc(F)c4)N2C3=O)cn1] | 5-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]pyrimidine-2-carbonitrile | Calc'd 412, found 412 |
| 4.46 | 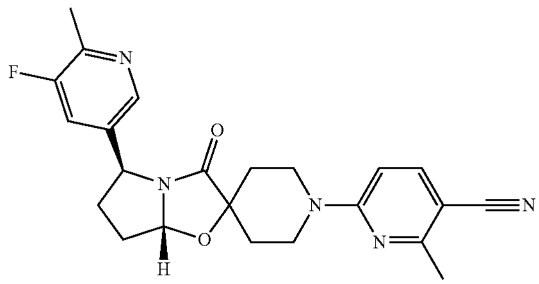 [SMILES: Cc1ncc([C@@H]2CC[C@H]3OC4(CCN(c5ccc(C#N)c(C)n5)CC4)C(=O)N32)cc1F] | 6-[(5'S,7a'R)-5'-(5-fluoro-6-methylpyridin-3-yl)-3'-oxotetrahydro-1H,3'H-spiro[piperidine-4,2'-pyrrolo[2,1-b][1,3]oxazol]-1-yl]-2-methylpyridine-3-carbonitrile | Calc'd 422, found 422 |
| 4.47 | 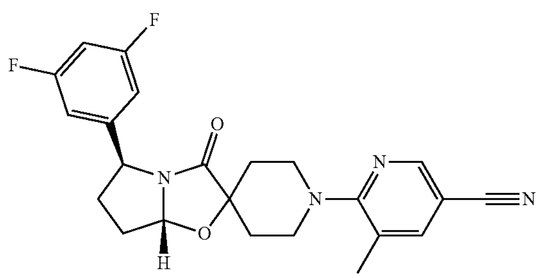 [SMILES: Cc1cc(C#N)cnc1N1CCC2(CC1)O[C@@H]1CC[C@@H](c3cc(F)cc(F)c3)N1C2=O] | 6-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-5-methylpyridine-3-carbonitrile | Calc'd 425, found 425 |
| 4.48 | 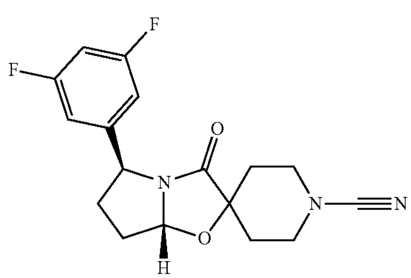 [SMILES: N#CN1CCC2(CC1)O[C@@H]1CC[C@@H](c3cc(F)cc(F)c3)N1C2=O] | (5'S,7a'R)-5'-(3,5-difluorophenyl)-3'-oxotetrahydro-1H,3'H-spiro[piperidine-4,2'-pyrrolo[2,1-b][1,3]oxazole]-1-carbonitrile | Calc'd 334, found 334 |
| 4.49 | 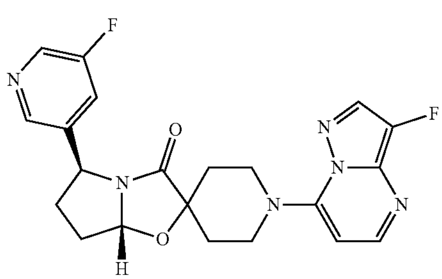 [SMILES: O=C1N2[C@@H](CC[C@H]2c2cncc(F)c2)OC12CCN(c1ccnc3c(F)cnn13)CC2] | (5'S,7a'R)-1-(3-fluoropyrazolo[1,5-a]pyrimidin-7-yl)-5'-(5-fluoropyridin-3-yl)tetrahydro-3'H-spiro[piperidine-4,2'-pyrrolo[2,1-b][1,3]oxazol]-3'-one | Calc'd 427, found 427 |

TABLE 13-continued

| Ex. No. | Structure | Name | Exact Mass [M + H]+ |
|---|---|---|---|
| 4.50 | 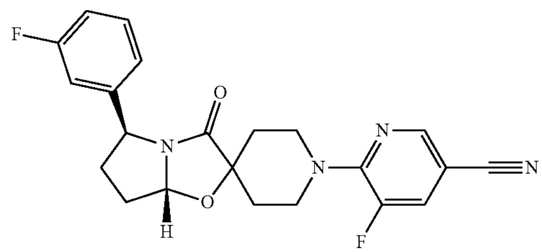 [SMILES: N#Cc1cnc(N2CCC3(CC2)O[C@@H]2CC[C@@H](c4cccc(F)c4)N2C3=O)c(F)c1] | 5-fluoro-6-[(5'S,7a'R)-5'-(3-fluorophenyl)-3'-oxotetrahydro-1H,3'H-spiro[piperidine-4,2'-pyrrolo[2,1-b][1,3]oxazol]-1-yl]pyridine-3-carbonitrile | Calc'd 411, found 411 |
| 4.51 | 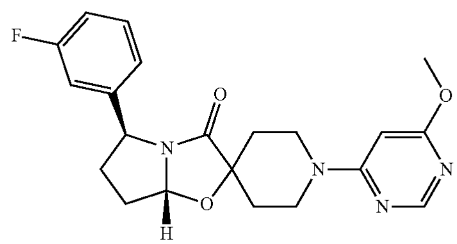 [SMILES: COc1cc(N2CCC3(CC2)O[C@@H]2CC[C@@H](c4cccc(F)c4)N2C3=O)ncn1] | (5'S,7a'R)-5'-(3-fluorophenyl)-1-(6-methoxypyrimidin-4-yl)tetrahydro-3'H-spiro[piperidine-4,2'-pyrrolo[2,1-b][1,3]oxazol]-3'-one | Calc'd 399, found 399 |
| 4.52 | 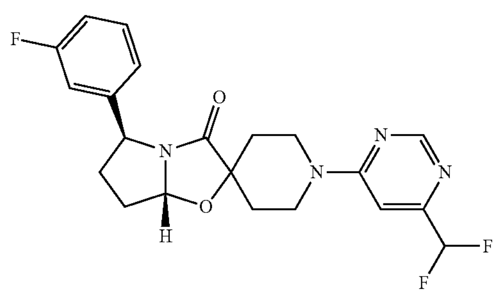 [SMILES: O=C1N2[C@@H](CC[C@H]2c2cccc(F)c2)OC12CCN(c1cc(C(F)F)ncn1)CC2] | (5'S,7a'R)-1-[6-(difluoromethyl)pyrimidin-4-yl]-5'-(3-fluorophenyl)tetrahydro-3'H-spiro[piperidine-4,2'-pyrrolo[2,1-b][1,3]oxazol]-3'-one | Calc'd 419, found 419 |
| 4.53 | 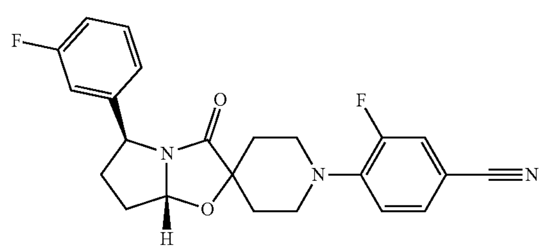 [SMILES: N#Cc1ccc(N2CCC3(CC2)O[C@@H]2CC[C@@H](c4cccc(F)c4)N2C3=O)c(F)c1] | 3-fluoro-4-[(5'S,7a'R)-5'-(3-fluorophenyl)-3'-oxotetrahydro-1H,3'H-spiro[piperidine-4,2'-pyrrolo[2,1-b][1,3]oxazol]-1-yl]benzonitrile | Calc'd 410, found 410 |
| 4.54 | 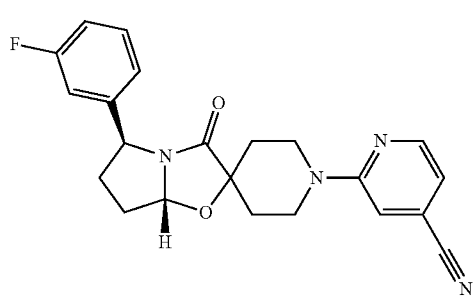 [SMILES: N#Cc1ccnc(N2CCC3(CC2)O[C@@H]2CC[C@@H](c4cccc(F)c4)N2C3=O)c1] | 2-[(5'S,7a'R)-5'-(3-fluorophenyl)-3'-oxotetrahydro-1H,3'H-spiro[piperidine-4,2'-pyrrolo[2,1-b][1,3]oxazol]-1-yl]pyridine-4-carbonitrile | Calc'd 393, found 393 |

TABLE 13-continued

| Ex. No. | Structure | Name | Exact Mass [M + H]+ |
|---|---|---|---|
| 4.55 | 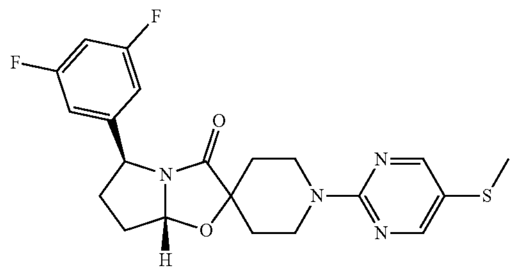 [SMILES: CSc1cnc(N2CCC3(CC2)O[C@@H]2CC[C@@H](c4cc(F)cc(F)c4)N2C3=O)nc1] | (5'S,7a'R)-5'-(3,5-difluorophenyl)-1-[5-(methylsulfanyl)pyrimidin-2-yl]tetrahydro-3'H-spiro[piperidine-4,2'-pyrrolo[2,1-b][1,3]oxazol]-3'-one | Calc'd 433, found 433 |
| 4.56 | 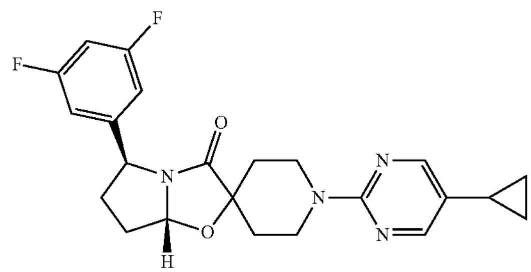 [SMILES: O=C1N2[C@@H](CC[C@H]2c2cc(F)cc(F)c2)OC12CCN(c1ncc(C3CC3)cn1)CC2] | (5'S,7a'R)-1-(5-cyclopropylpyrimidin-2-yl)-5'-(3,5-difluorophenyl)tetrahydro-3'H-spiro[piperidine-4,2'-pyrrolo[2,1-b][1,3]oxazol]-3'-one | Calc'd 427, found 427 |
| 4.57 | 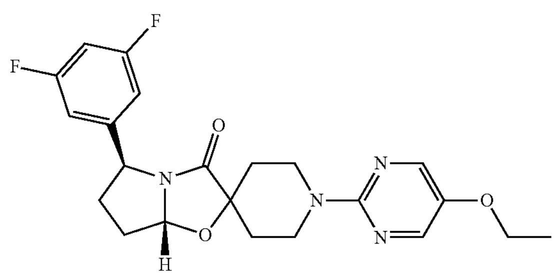 [SMILES: CCOc1cnc(N2CCC3(CC2)O[C@@H]2CC[C@@H](c4cc(F)cc(F)c4)N2C3=O)nc1] | (5'S,7a'R)-5'-(3,5-difluorophenyl)-1-(5-ethoxypyrimidin-2-yl)tetrahydro-3'H-spiro[piperidine-4,2'-pyrrolo[2,1-b][1,3]oxazol]-3'-one | Calc'd 431, found 431 |
| 4.58 | 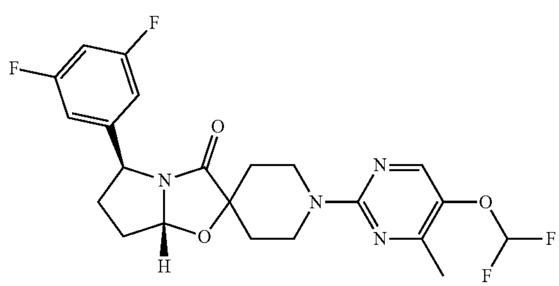 [SMILES: Cc1nc(N2CCC3(CC2)O[C@@H]2CC[C@@H](c4cc(F)cc(F)c4)N2C3=O)ncc1OC(F)F] | (5'S,7a'R)-1-[5-(difluoromethoxy)-4-methylpyrimidin-2-yl]-5'-(3,5-difluorophenyl)tetrahydro-3'H-spiro[piperidine-4,2'-pyrrolo[2,1-b][1,3]oxazol]-3'-one | Calc'd 467, found 467 |
| 4.59 | 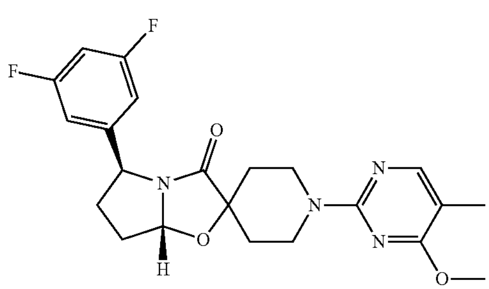 [SMILES: COc1nc(N2CCC3(CC2)O[C@@H]2CC[C@@H](c4cc(F)cc(F)c4)N2C3=O)ncc1C] | (5'S,7a'R)-5'-(3,5-difluorophenyl)-1-(4-methoxy-5-methylpyrimidin-2-yl)tetrahydro-3'H-spiro[piperidine-4,2'-pyrrolo[2,1-b][1,3]oxazol]-3'-one | Calc'd 431, found 431 |

TABLE 13-continued

| Ex. No. | Structure | Name | Exact Mass [M + H]+ |
|---|---|---|---|
| 4.60 | 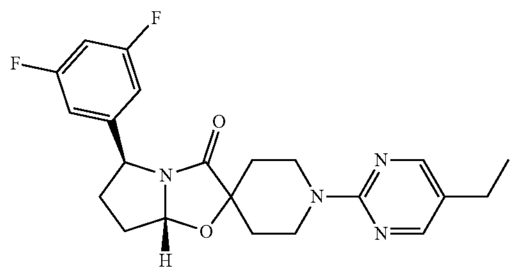 [SMILES: CCc1cnc(N2CCC3(CC2)O[C@@H]2CC[C@@H](c4cc(F)cc(F)c4)N2C3=O)nc1] | (5'S,7a'R)-5'-(3,5-difluorophenyl)-1-(5-ethylpyrimidin-2-yl)tetrahydro-3'H-spiro[piperidine-4,2'-pyrrolo[2,1-b][1,3]oxazol]-3'-one | Calc'd 415, found 415 |
| 4.61 | 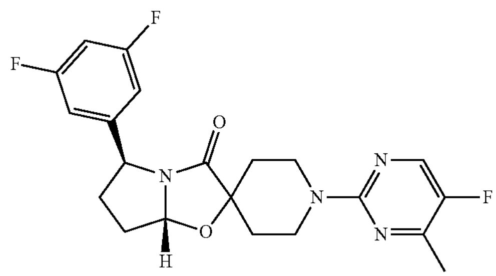 [SMILES: Cc1nc(N2CCC3(CC2)O[C@@H]2CC[C@@H](c4cc(F)cc(F)c4)N2C3=O)ncc1F] | (5'S,7a'R)-5'-(3,5-difluorophenyl)-1-(5-fluoro-4-methylpyrimidin-2-yl)tetrahydro-3'H-spiro[piperidine-4,2'-pyrrolo[2,1-b][1,3]oxazol]-3'-one | Calc'd 419, found 419 |
| 4.62 | 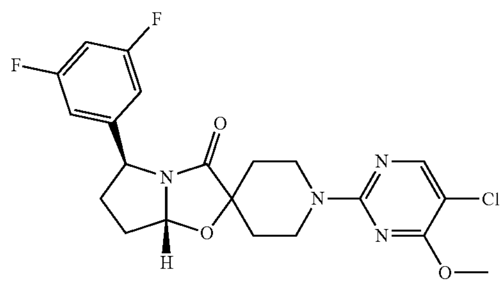 [SMILES: COc1nc(N2CCC3(CC2)O[C@@H]2CC[C@@H](c4cc(F)cc(F)c4)N2C3=O)ncc1Cl] | (5'S,7a'R)-1-(5-chloro-4-methoxypyrimidin-2-yl)-5'-(3,5-difluorophenyl)tetrahydro-3'H-spiro[piperidine-4,2'-pyrrolo[2,1-b][1,3]oxazol]-3'-one | Calc'd 451, found 451 |
| 4.63 | 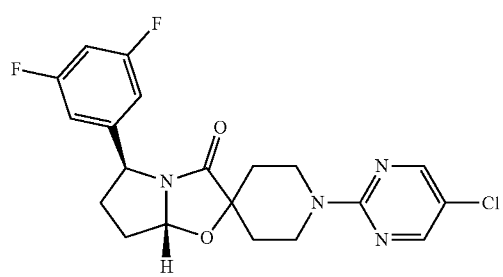 [SMILES: O=C1N2[C@@H](CC[C@H]2c2cc(F)cc(F)c2)OC12CCN(c1ncc(Cl)cn1)CC2] | (5'S,7a'R)-1-(5-chloropyrimidin-2-yl)-5'-(3,5-difluorophenyl)tetrahydro-3'H-spiro[piperidine-4,2'-pyrrolo[2,1-b][1,3]oxazol]-3'-one | Calc'd 421, found 421 |
| 4.64 | 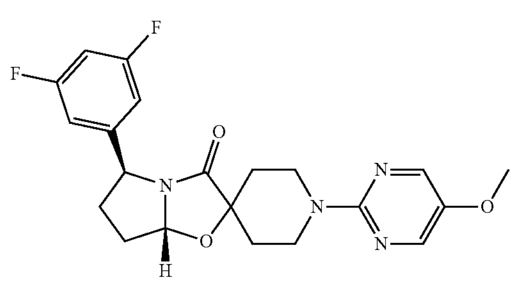 [SMILES: COc1cnc(N2CCC3(CC2)O[C@@H]2CC[C@@H](c4cc(F)cc(F)c4)N2C3=O)nc1] | (5'S,7a'R)-5'-(3,5-difluorophenyl)-1-(5-methoxypyrimidin-2-yl)tetrahydro-3'H-spiro[piperidine-4,2'-pyrrolo[2,1-b][1,3]oxazol]-3'-one | Calc'd 417, found 417 |

TABLE 13-continued

| Ex. No. | Structure | Name | Exact Mass [M + H]+ |
|---|---|---|---|
| 4.65 | 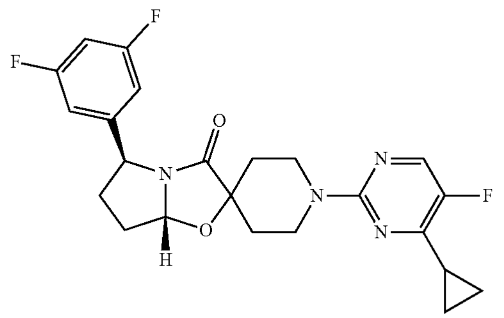 [SMILES: O=C1N2[C@@H](CC[C@H]2c2cc(F)cc(F)c2)OC12CCN(c1ncc(F)c(C3CC3)n1)CC2] | (5'S,7a'R)-1-(4-cyclopropyl-5-fluoropyrimidin-2-yl)-5'-(3,5-difluorophenyl)tetrahydro-3'H-spiro[piperidine-4,2'-pyrrolo[2,1-b][1,3]oxazol]-3'-one | Calc'd 445, found 445 |
| 4.66 | 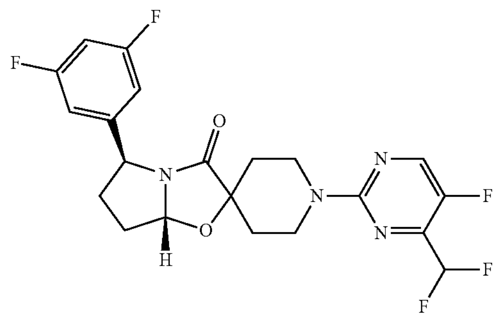 [SMILES: O=C1N2[C@@H](CC[C@H]2c2cc(F)cc(F)c2)OC12CCN(c1ncc(F)c(C(F)F)n1)CC2] | (5'S,7a'R)-1-[4-(difluoromethyl)-5-fluoropyrimidin-2-yl]-5'-(3,5-difluorophenyl)tetrahydro-3'H-spiro[piperidine-4,2'-pyrrolo[2,1-b][1,3]oxazol]-3'-one | Calc'd 455, found 455 |
| 4.67 | 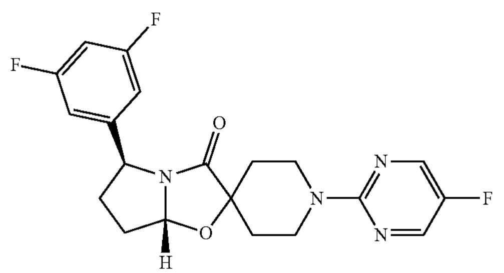 [SMILES: O=C1N2[C@@H](CC[C@H]2c2cc(F)cc(F)c2)OC12CCN(c1ncc(F)cn1)CC2] | (5'S,7a'R)-5'-(3,5-difluorophenyl)-1-(5-fluoropyrimidin-2-yl)tetrahydro-3'H-spiro[piperidine-4,2'-pyrrolo[2,1-b][1,3]oxazol]-3'-one | Calc'd 405, found 405 |
| 4.68 | 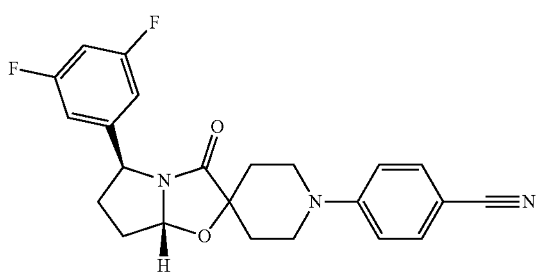 [SMILES: N#Cc1ccc(N2CCC3(CC2)O[C@@H]2CC[C@@H](c4cc(F)cc(F)c4)N2C3=O)cc1] | 4-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]benzonitrile | Calc'd 410, found 410 |
| 4.69 | 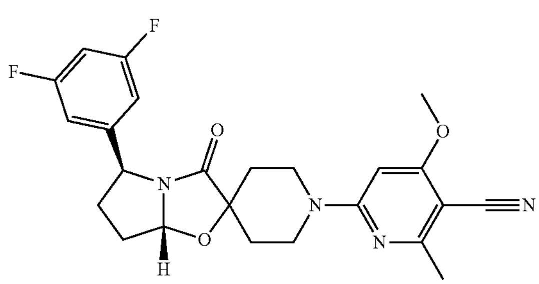 [SMILES: COc1cc(N2CCC3(CC2)O[C@@H]2CC[C@@H](c4cc(F)cc(F)c4)N2C3=O)nc(C)c1C#N] | 6-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-4-methoxy-2-methylpyridine-3-carbonitrile | Calc'd 455, found 455 |

TABLE 13-continued

| Ex. No. | Structure | Name | Exact Mass [M + H]+ |
| --- | --- | --- | --- |
| 4.70 | 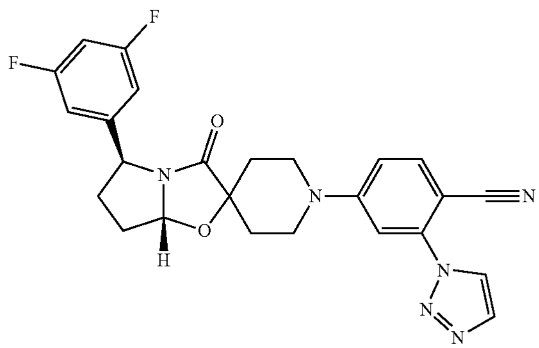 [SMILES: N#Cc1ccc(N2CCC3(CC2)O[C@@H]2CC[C@@H](c4cc(F)cc(F)c4)N2C3=O)cc1-n1ccnn1] | 4-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-2-(1H-1,2,3-triazol-1-yl)benzonitrile | Calc'd 477, found 477 |
| 4.71 | 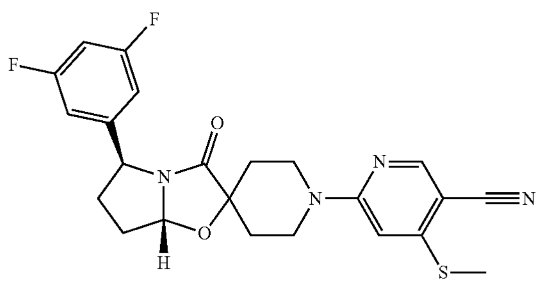 | 6-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-4-(methylsulfanyl)pyridine-3-carbonitrile | Calc'd 457, found 457 |
| 4.72 | 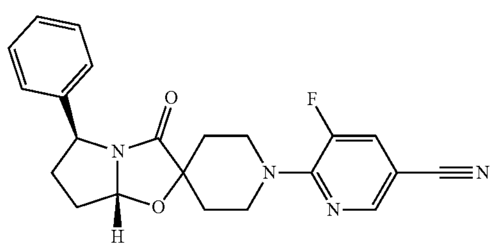 [SMILES: N#Cc1cnc(N2CCC3(CC2)O[C@@H]2CC[C@@H](c4ccccc4)N2C3=O)c(F)c1] | 5-fluoro-6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carbonitrile | Calc'd 393, found 393 |
| 4.73 | 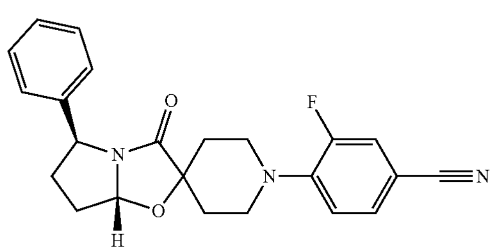 | 3-fluoro-4-[(5'S,7a'R)-3'-oxo-5'-phenyltetrahydro-1H,3'H-spiro[piperidine-4,2'-pyrrolo[2,1-b][1,3]oxazol]-1-yl]benzonitrile | Calc'd 392, found 392 |
| 4.74 | 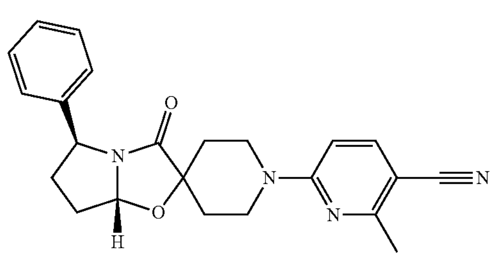 [SMILES: Cc1nc(N2CCC3(CC2)O[C@@H]2CC[C@@H](c4ccccc4)N2C3=O)ccc1C#N] | 2-methyl-6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carbonitrile | Calc'd 389, found 389 |

TABLE 13-continued

| Ex. No. | Structure | Name | Exact Mass [M + H]+ |
|---|---|---|---|
| 4.75 | 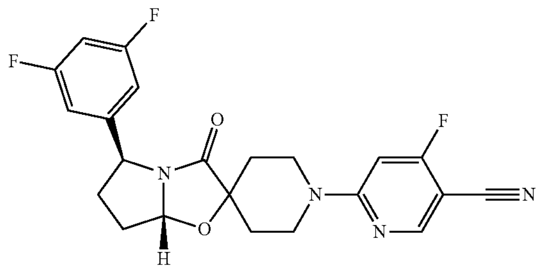 [SMILES: N#Cc1cnc(N2CCC3(CC2)O[C@@H]2CC[C@@H](c4cc(F)cc(F)c4)N2C3=O)cc1F] | 6-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-4-fluoropyridine-3-carbonitrile | Calc'd 429, found 429 |
| 4.76 | 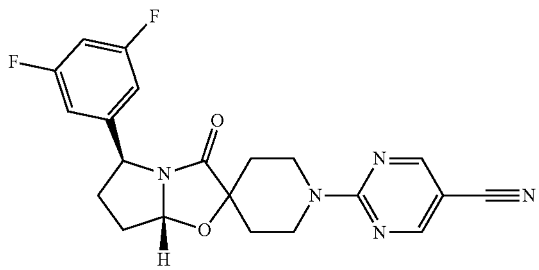 [SMILES: N#Cc1cnc(N2CCC3(CC2)O[C@@H]2CC[C@@H](c4cc(F)cc(F)c4)N2C3=O)nc1] | 2-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]pyrimidine-5-carbonitrile | Calc'd 412, found 412 |
| 4.77 | 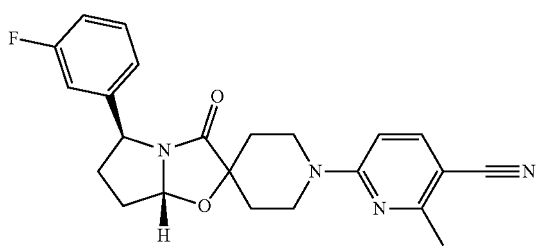 [SMILES: Cc1nc(N2CCC3(CC2)O[C@@H]2CC[C@@H](c4cccc(F)c4)N2C3=O)ccc1C#N] | 6-[(5'S,7a'R)-5'-(3-fluorophenyl)-3'-oxotetrahydro-1H,3'H-spiro[piperidine-4,2'-pyrrolo[2,1-b][1,3]oxazol]-1-yl]-2-methylpyridine-3-carbonitrile | Calc'd 407, found 407 |
| 4.78 | 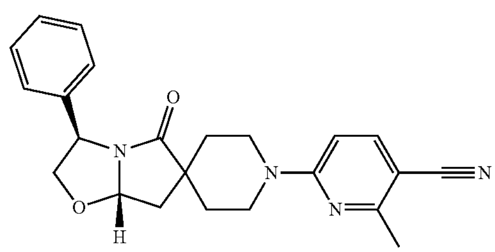 [SMILES: Cc1nc(N2CCC3(CC2)C[C@@H]2OC[C@@H](c4ccccc4)N2C3=O)ccc1C#N] | 2-methyl-6-[(3'R,7a'S)-5'-oxo-3'-phenyltetrahydro-1H,5'H-spiro[piperidine-4,6'-pyrrolo[2,1-b][1,3]oxazol]-1-yl]pyridine-3-carbonitrile | Calc'd 389, found 389 |
| 4.79 | 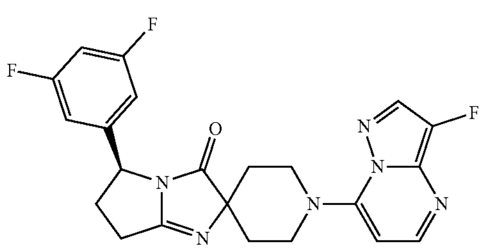 [SMILES: O=C1N2C(=NC13CCN(c1ccnc4c(F)cnn14)CC3)CC[C@H]2c1cc(F)cc(F)c1] | (S)-5'-(3,5-difluorophenyl)-1-(3-fluoropyrazolo[1,5-a]pyrimidin-7-yl)-6',7'-dihydro-3'H,5'H-spiro[piperidine-4,2'-pyrrolo[1,2-a]imidazol]-3'-one | Calc'd 441, found 441 |
| 4.80 | 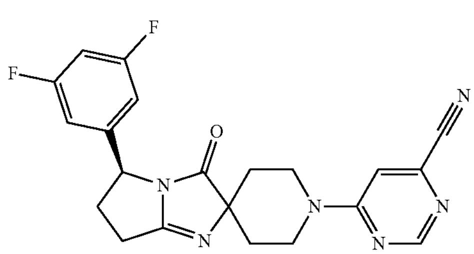 [SMILES: N#Cc1cc(N2CCC3(CC2)N=C2CC[C@@H](c4cc(F)cc(F)c4)N2C3=O)ncn1] | (S)-[5'-(3,5-difluorophenyl)-3'-oxo-6',7'-dihydro-1H,3'H,5'H-spiro[piperidine-4,2'-pyrrolo[1,2-a]imidazol]-1-yl]pyrimidine-4-carbonitrile | Calc'd 409, found 409 |

TABLE 13-continued

| Ex. No. | Name | Exact Mass [M + H]+ |
|---|---|---|
| 4.81 | (5'S,7a'R)-1-(3-fluoropyrazolo[1,5-a]pyrimidin-7-yl)-7a'-methyl-5'-phenyltetrahydro-3'H-spiro[piperidine-4,2'-pyrrolo[2,1-b][1,3]oxazol]-3'-one | Calc'd 422, found 422 |
| 4.82 | (5'S,7a'R)-5'-(3,5-difluorophenyl)-1-(imidazo[1,2-c]pyrimidin-5-yl)tetrahydro-3'H-spiro[piperidine-4,2'-pyrrolo[2,1-b]oxazol]-3'-one, TFA salt | Calc'd 426, found 426 |
| 4.83 | (5'S,7a'R)-1-([1,2,4]triazolo[1,5-a]pyrimidin-7-yl)-5'-(3,5-difluorophenyl)tetrahydro-3'H-spiro[piperidine-4,2'-pyrrolo[2,1-b]oxazol]-3'-one, TFA salt | Calc'd 427, found 427 |
| 4.84 | (5'S,7a'R)-1-(3-fluoropyrazolo[1,5-a]pyrimidin-7-yl)-5'-(5-fluoropyridin-3-yl)tetrahydro-3'H-spiro[piperidine-4,2'-pyrrolo[2,1-b]oxazol]-3'-one, TFA salt | Calc'd 427, found 427 |
| 4.85 | (5'S,7a'R)-5'-(3,5-difluorophenyl)-1-(2-methylpyrazolo[1,5-a]pyrimidin-7-yl)tetrahydro-3'H-spiro[piperidine-4,2'-pyrrolo[2,1-b]oxazol]-3'-one, TFA salt | Calc'd 440, found 440 |

TABLE 13-continued

| Ex. No. | Structure | Name | Exact Mass [M + H]+ |
|---|---|---|---|
| 4.86 | 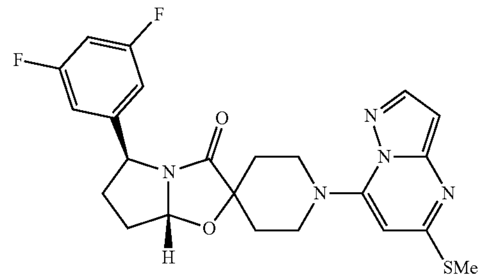 [SMILES: CSc1cc(N2CCC3(CC2)O[C@@H]2CC[C@@H](c4cc(F)cc(F)c4)N2C3=O)n2nccc2n1] | (5'S,7a'R)-5'-(3,5-difluorophenyl)-1-(2-(methylthio)pyrazolo[1,5-a][1,3,5]triazin-4-yl)tetrahydro-3'H-spiro[piperidine-4,2'-pyrrolo[2,1-b]oxazol]-3'-one, TFA salt | Calc'd 473, found 473 |
| 4.87 | 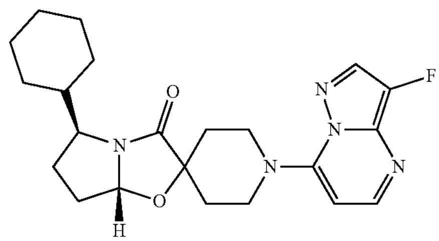 [SMILES: O=C1N2[C@@H](CC[C@H]2C2CCCCC2)OC12CCN(c1ccnc3c(F)cnn13)CC2] | (5'S,7a'R)-5'-cyclohexyl-1-(3-fluoropyrazolo[1,5-a]pyrimidin-7-yl)tetrahydro-3'H-spiro[piperidine-4,2'-pyrrolo[2,1-b]oxazol]-3'-one, TFA salt | Calc'd 414, found 414 |
| 4.88 | 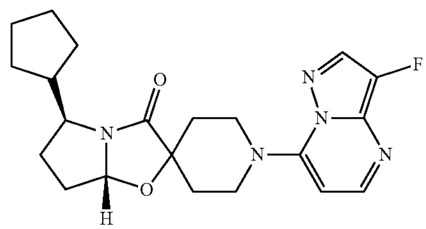 [SMILES: O=C1N2[C@@H](CC[C@H]2C2CCCC2)OC12CCN(c1ccnc3c(F)cnn13)CC2] | (5'S,7a'R)-5'-cyclopentyl-1-(3-fluoropyrazolo[1,5-a]pyrimidin-7-yl)tetrahydro-3'H-spiro[piperidine-4,2'-pyrrolo[2,1-b]oxazol]-3'-one, TFA salt | Calc'd 400, found 400 |
| 4.89 | 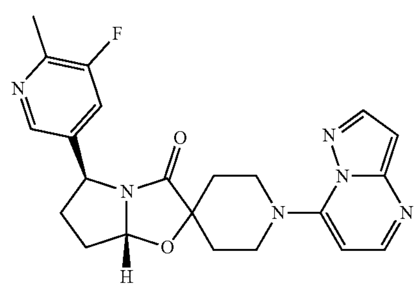 [SMILES: Cc1ncc([C@@H]2CC[C@H]3OC4(CCN(c5ccnc6ccnn56)CC4)C(=O)N32)cc1F] | (5'S,7a'R)-5'-(5-fluoro-6-methylpyridin-3-yl)-1-(pyrazolo[1,5-a]pyrimidin-7-yl)tetrahydro-3'H-spiro[piperidine-4,2'-pyrrolo[2,1-b]oxazol]-3'-one | Calc'd 423, found 423 |
| 4.90 | 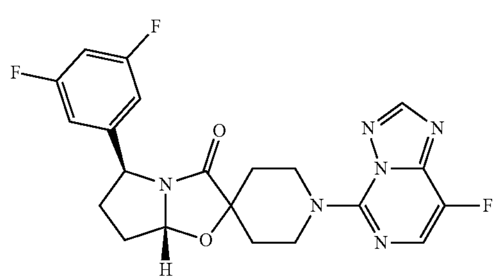 [SMILES: O=C1N2[C@@H](CC[C@H]2c2cc(F)cc(F)c2)OC12CCN(c1ncc(F)c3ncnn13)CC2] | (5'S,7a'R)-5'-(3,5-difluorophenyl)-1-(8-fluoro-[1,2,4]triazolo[1,5-c]pyrimidin-5-yl)tetrahydro-3'H-spiro[piperidine-4,2'-pyrrolo[2,1-b]oxazol]-3'-one, TFA salt | Calc'd 445, found 445 |
| 4.91 | 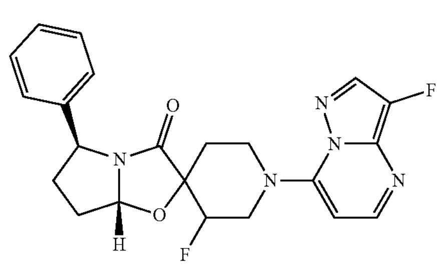 [SMILES: O=C1N2[C@@H](CC[C@H]2c2ccccc2)OC12CCN(c1ccnc3c(F)cnn13)CC2F] | (3[R or S],4[S or R],5'S,7a'R)-3-fluoro-1-(3-fluoropyrazolo[1,5-a]pyrimidin-7-yl)-5'-phenyltetrahydro-3'H-spiro[piperidine-4,2'-pyrrolo[2,1-b]oxazol]-3'-one, TFA salt | Calc'd 426, found 426 |

TABLE 13-continued

| Ex. No. | Structure | Name | Exact Mass [M + H]+ |
|---|---|---|---|
| 4.92 | 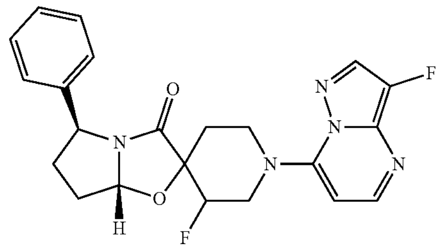 [SMILES: O=C1N2[C@@H](CC[C@H]2c2ccccc2)OC12CCN(c1ccnc3c(F)cnn13)CC2F] | (3[S or R],4[R or S], 5'S,7a'R)-3-fluoro-1-(3-fluoropyrazolo[1,5-a]pyrimidin-7-yl)-5'-phenyltetrahydro-3'H-spiro[piperidine-4,2'-pyrrolo[2,1-b]oxazol]-3'-one, TFA salt | Calc'd 426, found 426 |
| 4.93 | 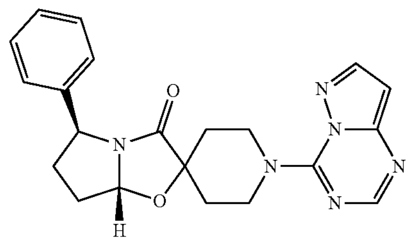 | (5'S,7a'R)-5'-phenyl-1-(pyrazolo[1,5-a][1,3,5]triazin-4-yl)tetrahydro-3'H-spiro[piperidine-4,2'-pyrrolo[2,1-b]oxazol]-3'-one, TFA salt | Calc'd 391, found 391 |
| 4.94 | 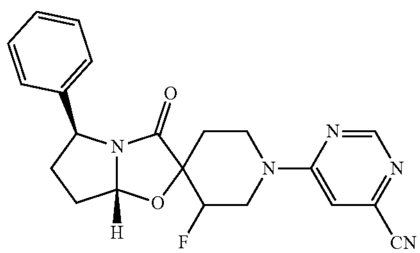 [SMILES: N#Cc1cc(N2CCC3(O[C@@H]4CC[C@@H](c5ccccc5)N4C3=O)C(F)C2)ncn1] | 6-((3[R or S],4[S or R], 5'S,7a'R)-3-fluoro-3'-oxo-5'-phenyltetrahydro-3'H-spiro[piperidine-4,2'-pyrrolo[2,1-b]oxazol]-1-yl)pyrimidine-4-carbonitrile | Calc'd 394, found 394 |
| 4.95 | 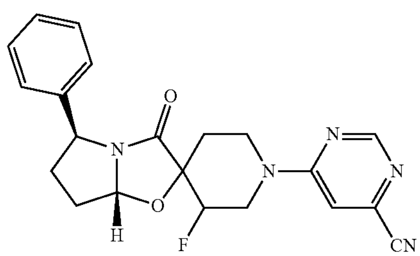 [SMILES: N#Cc1cc(N2CCC3(O[C@@H]4CC[C@@H](c5ccccc5)N4C3=O)C(F)C2)ncn1] | 6-((3[S or R],4[R or S], 5'S,7a'R)-3-fluoro-3'-oxo-5'-phenyltetrahydro-3'H-spiro[piperidine-4,2'-pyrrolo[2,1-b]oxazol]-1-yl)pyrimidine-4-carbonitrile | Calc'd 394, found 394 |
| 4.96 | 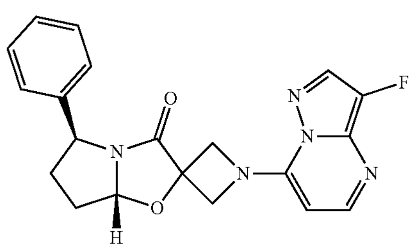 [SMILES: O=C1N2[C@@H](CC[C@H]2c2ccccc2)OC12CN(c1ccnc3c(F)cnn13)C2] | (5'S,7a'R)-1-(3-fluoropyrazolo[1,5-a]pyrimidin-7-yl)-5'-phenyltetrahydro-3'H-spiro[azetidine-3,2'-pyrrolo[2,1-b]oxazol]-3'-one, TFA salt | Calc'd 380, found 380 |
| 4.97 | 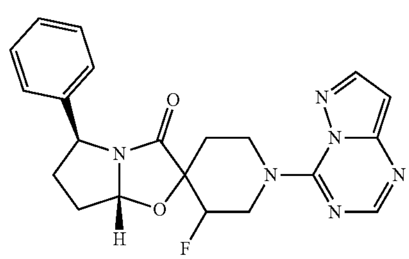 [SMILES: O=C1N2[C@@H](CC[C@H]2c2ccccc2)OC12CCN(c1ncnc3ccnn13)CC2F] | (3[R or S],4[S or R], 5'S,7a'R)-3-fluoro-5'-phenyl-1-(pyrazolo[1,5-a][1,3,5]triazin-4-yl)tetrahydro-3'H-spiro[piperidine-4,2'-pyrrolo[2,1-b]oxazol]-3'-one | Calc'd 409, found 409 |

TABLE 13-continued

| Ex. No. | Structure | Name | Exact Mass [M + H]+ |
|---|---|---|---|
| 4.98 | 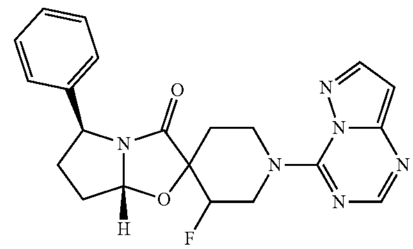 [SMILES: O=C1N2[C@@H](CC[C@H]2c2ccccc2)OC12CCN(c1ncnc3ccnn13)CC2F] | (3[S or R],4[R or S], 5'S,7a'R)-3-fluoro-5'-phenyl-1-(pyrazolo[1,5-a][1,3,5]triazin-4-yl)tetrahydro-3'H-spiro[piperidine-4,2'-pyrrolo[2,1-b]oxazol]-3'-one | Calc'd 409, found 409 |
| 4.99 | 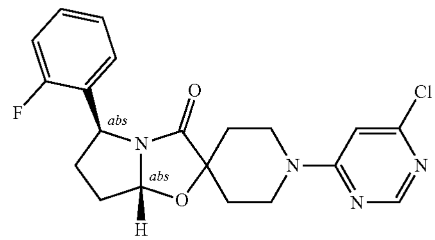 [SMILES: O=C1N2[C@@H](CC[C@H]2c2ccccc2F)OC12CCN(c1cc(Cl)ncn1)CC2] | (5'S,7a'R)-1-(6-chloropyrimidin-4-yl)-5'-(2-fluorophenyl)tetrahydro-3'H-spiro[piperidine-4,2'-pyrrolo[2,1-b]oxazol]-3'-one | Calc'd 403, found 403 |
| 4.100 | 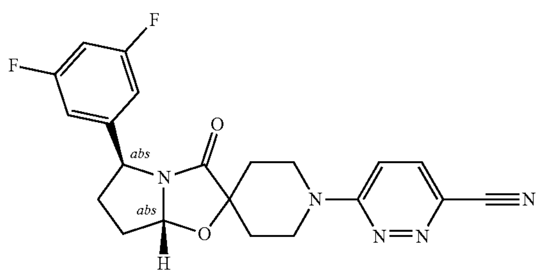 [SMILES: N#Cc1ccc(N2CCC3(CC2)O[C@@H]2CC[C@@H](c4cc(F)cc(F)c4)N2C3=O)nn1] | 6-((5'S,7a'R)-5'-(3,5-difluorophenyl)-3'-oxotetrahydro-3'H-spiro[piperidine-4,2'-pyrrolo[2,1-b]oxazol]-1-yl)pyridazine-3-carbonitrile | Calc'd 412, found 412 |
| 4.101 | 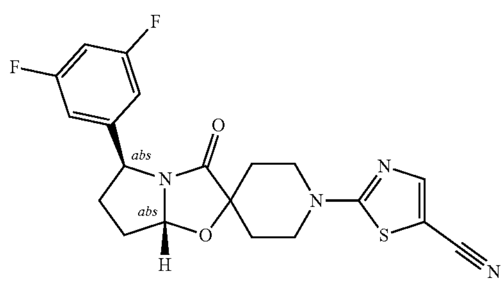 [SMILES: N#Cc1cnc(N2CCC3(CC2)O[C@@H]2CC[C@@H](c4cc(F)cc(F)c4)N2C3=O)s1] | 2-((5'S,7a'R)-5'-(3,5-difluorophenyl)-3'-oxotetrahydro-3'H-spiro[piperidine-4,2'-pyrrolo[2,1-b]oxazol]-1-yl)thiazole-5-carbonitrile | Calc'd 417, found 417 |
| 4.102 | 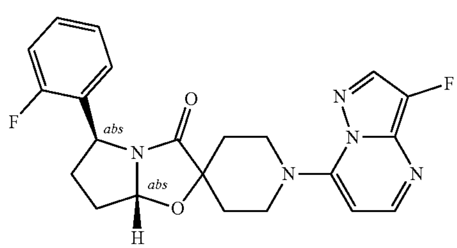 [SMILES: O=C1N2[C@@H](CC[C@H]2c2ccccc2F)OC12CCN(c1ccnc3c(F)cnn13)CC2] | (5'S,7a'R)-5'-(2-fluorophenyl)-1-(3-fluoropyrazolo[1,5-a]pyrimidin-7-yl)tetrahydro-3'H-spiro[piperidine-4,2'-pyrrolo[2,1-b]oxazol]-3'-one | Calc'd 426, found 426 |
| 4.103 | 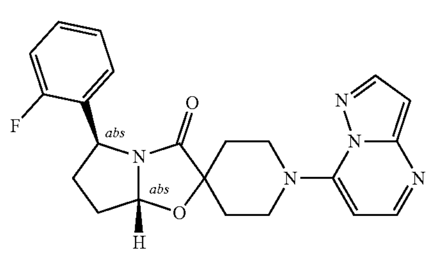 [SMILES: O=C1N2[C@@H](CC[C@H]2c2ccccc2F)OC12CCN(c1ccnc3ccnn13)CC2] | (5'S,7a'R)-5'-(2-fluorophenyl)-1-(pyrazolo[1,5-a]pyrimidin-7-yl)tetrahydro-3'H-spiro[piperidine-4,2'-pyrrolo[2,1-b]oxazol]-3'-one | Calc'd 408, found 408 |

TABLE 13-continued

| Ex. No. | Structure | Name | Exact Mass [M + H]+ |
|---|---|---|---|
| 4.104 | 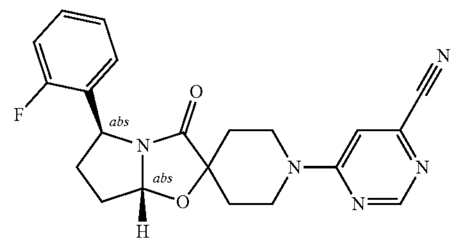 [SMILES: N#Cc1cc(N2CCC3(CC2)O[C@@H]2CC[C@@H](c4ccccc4F)N2C3=O)ncn1] | 6-(((5'S,7a'R)-5'-(2-fluorophenyl)-3'-oxotetrahydro-3'H-spiro[piperidine-4,2'-pyrrolo[2,1-b]oxazol]-1-yl)pyrimidine-4-carbonitrile | Calc'd 394, found 394 |
| 4.105 | 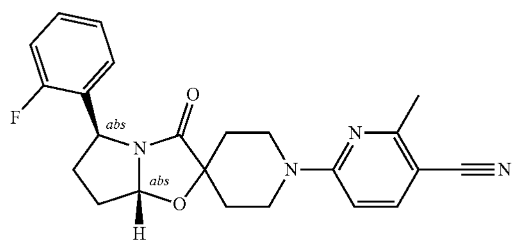 [SMILES: Cc1nc(N2CCC3(CC2)O[C@@H]2CC[C@@H](c4ccccc4F)N2C3=O)ccc1C#N] | 6-(((5'S,7a'R)-5'-(2-fluorophenyl)-3'-oxotetrahydro-3'H-spiro[piperidine-4,2'-pyrrolo[2,1-b]oxazol]-1-yl)-2-methylnicotinonitrile | Calc'd 407, found 407 |
| 4.106 | 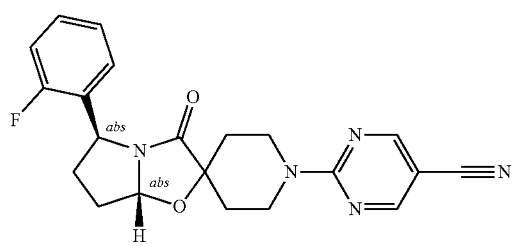 [SMILES: N#Cc1cnc(N2CCC3(CC2)O[C@@H]2CC[C@@H](c4ccccc4F)N2C3=O)nc1] | 2-(((5'S,7a'R)-5'-(2-fluorophenyl)-3'-oxotetrahydro-3'H-spiro[piperidine-4,2'-pyrrolo[2,1-b]oxazol]-1-yl)pyrimidine-5-carbonitrile | Calc'd 394, found 394 |
| 4.107 | 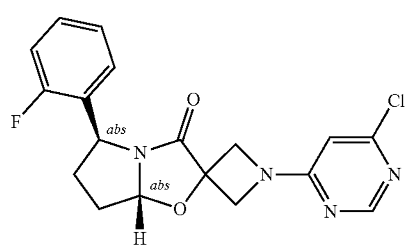 [SMILES: O=C1N2[C@@H](CC[C@H]2c2ccccc2F)OC12CN(c1cc(Cl)ncn1)C2] | (5'S,7a'R)-1-(6-chloropyrimidin-4-yl)-5'-(2-fluorophenyl)tetrahydro-3'H-spiro[azetidine-3,2'-pyrrolo[2,1-b]oxazol]-3'-one | Calc'd 375, found 375 |
| 4.108 | 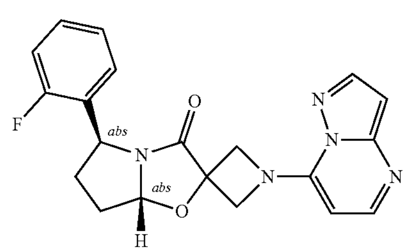 [SMILES: O=C1N2[C@@H](CC[C@H]2c2ccccc2F)OC12CN(c1ccnc3ccnn13)C2] | (5'S,7a'R)-5'-(2-fluorophenyl)-1-(pyrazolo[1,5-a]pyrimidin-7-yl)tetrahydro-3'H-spiro[azetidine-3,2'-pyrrolo[2,1-b]oxazol]-3'-one | Calc'd 380, found 380 |
| 4.109 | 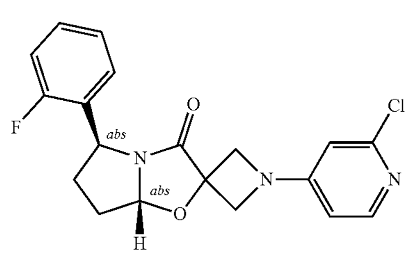 [SMILES: O=C1N2[C@@H](CC[C@H]2c2ccccc2F)OC12CN(c1ccnc(Cl)c1)C2] | (5'S,7a'R)-1-(2-chloropyridin-4-yl)-5'-(2-fluorophenyl)tetrahydro-3'H-spiro[azetidine-3,2'-pyrrolo[2,1-b]oxazol]-3'-one | Calc'd 374, found 374 |

TABLE 13-continued

| Ex. No. | Structure | Name | Exact Mass [M + H]+ |
|---|---|---|---|
| 4.110 | 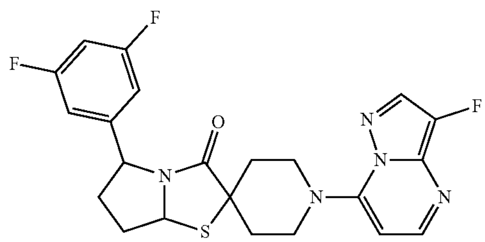 [SMILES: O=C1N2C(CCC2c2cc(F)cc(F)c2)SC12CCN(c1ccnc3c(F)cnn13)CC2] | 5'-(3,5-difluorophenyl)-1-(3-fluoropyrazolo[1,5-a]pyrimidin-7-yl)tetrahydro-3'H-spiro[piperidine-4,2'-pyrrolo[2,1-b]thiazol]-3'-one | Calc'd 460, found 460 |
| 4.111 | 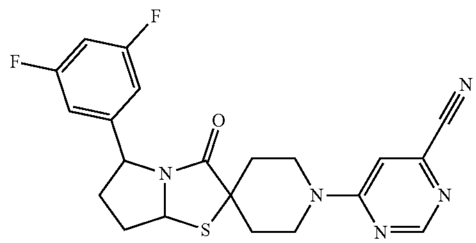 [SMILES: N#Cc1cc(N2CCC3(CC2)SC2CCC(c4cc(F)cc(F)c4)N2C3=O)ncn1] | 6-(5'-(3,5-difluorophenyl)-3'-oxotetrahydro-3'H-spiro[piperidine-4,2'-pyrrolo[2,1-b]thiazol]-1-yl)pyrimidine-4-carbonitrile | Calc'd 428, found 428 |
| 4.112 | 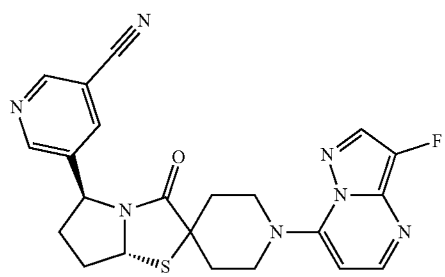 [SMILES: N#Cc1cncc([C@@H]2CC[C@H]3SC4(CCN(c5ccnc6c(F)cnn56)CC4)C(=O)N32)c1] | 5-[(5'S,7a'R)-1-(3-fluoropyrazolo[1,5-a]pyrimidin-7-yl)-3'-oxotetrahydro-3'H-spiro[piperidine-4,2'-pyrrolo[2,1-b][1,3]thiazol]-5'-yl]pyridine-3-carbonitrile | Calc'd 450, found 450 |
| 4.113 | 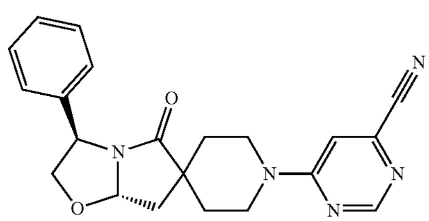 [SMILES: N#Cc1cc(N2CCC3(CC2)C[C@@H]2OC[C@@H](c4ccccc4)N2C3=O)ncn1] | 6-[(3'R,7a'S)-5'-oxo-3'-phenyltetrahydro-1H,5'H-spiro[piperidine-4,6'-pyrrolo[2,1-b][1,3]oxazol]-1-yl]pyrimidine-4-carbonitrile | Calc'd 376, found 376 |
| 4.114 | 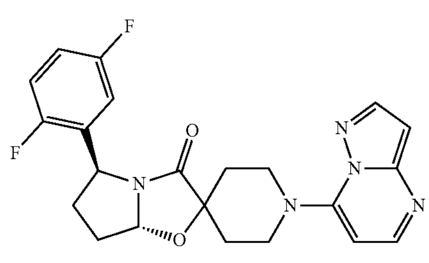 [SMILES: O=C1N2[C@@H](CC[C@H]2c2cc(F)ccc2F)OC12CCN(c1ccnc3ccnn13)CC2] | (5'S,7a'R)-5'-(2,5-difluorophenyl)-1-(pyrazolo[1,5-a]pyrimidin-7-yl)tetrahydro-3'H-spiro[piperidine-4,2'-pyrrolo[2,1-b][1,3]oxazol]-3'-one | Calc'd 426, found 426 |
| 4.115 | 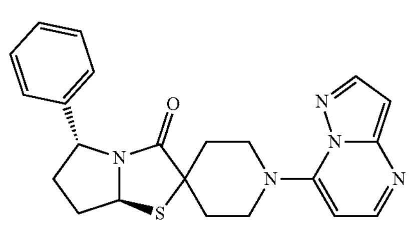 [SMILES: O=C1N2[C@H](CC[C@@H]2c2ccccc2)SC12CCN(c1ccnc3ccnn13)CC2] | (5'R,7a'S)-5'-phenyl-1-(pyrazolo[1,5-a]pyrimidin-7-yl)tetrahydro-3'H-spiro[piperidine-4,2'-pyrrolo[2,1-b]thiazol]-3'-one | Calc'd 406, found 406 |

TABLE 13-continued

| Ex. No. | Structure | Name | Exact Mass [M + H]+ |
|---|---|---|---|
| 4.116 | 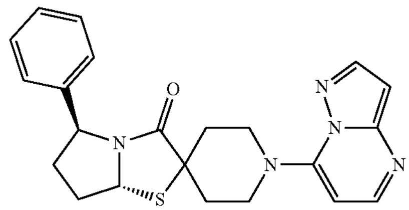 [SMILES: O=C1N2[C@@H](CC[C@H]2c2ccccc2)SC12CCN(c1ccnc3ccnn13)CC2] | (5'S,7a'R)-5'-phenyl-1-(pyrazolo[1,5-a]pyrimidin-7-yl)tetrahydro-3'H-spiro[piperidine-4,2'-pyrrolo[2,1-b]thiazol]-3'-one | Calc'd 406, found 406 |
| 4.117 | 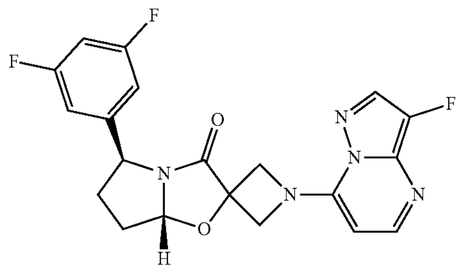 [SMILES: O=C1N2[C@@H](CC[C@H]2c2cc(F)cc(F)c2)OC12CN(c1ccnc3c(F)cnn13)C2] | (5'S,7a'R)-5'-(3,5-difluorophenyl)-1-(3-fluoropyrazolo[1,5-a]pyrimidin-7-yl)tetrahydro-3'H-spiro[azetidine-3,2'-pyrrolo[2,1-b]oxazol]-3'-one | Calc'd 416, found 416 |
| 4.118 | 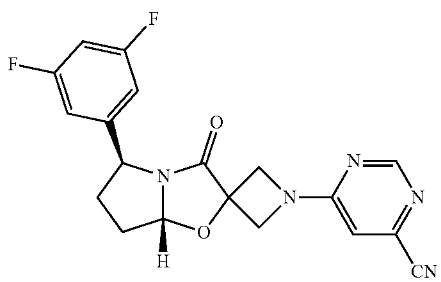 [SMILES: N#Cc1cc(N2CC3(C2)O[C@@H]2CC[C@@H](c4cc(F)cc(F)c4)N2C3=O)ncn1] | 6-((5'S,7a'R)-5'-(3,5-difluorophenyl)-3'-oxotetrahydro-3'H-spiro[azetidine-3,2'-pyrrolo[2,1-b]oxazol]-1-yl)pyrimidine-4-carbonitrile | Calc'd 384, found 384 |
| 4.119 | 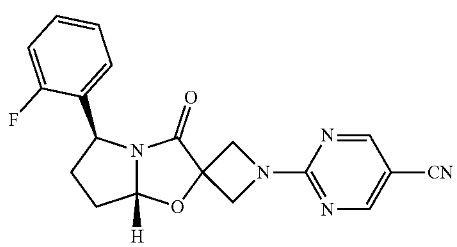 [SMILES: N#Cc1cnc(N2CC3(C2)O[C@@H]2CC[C@@H](c4ccccc4F)N2C3=O)nc1] | 2-((5'S,7a'R)-5'-(2-fluorophenyl)-3'-oxotetrahydro-3'H-spiro[azetidine-3,2'-pyrrolo[2,1-b]oxazol]-1-yl)pyrimidine-5-carbonitrile | Calc'd 366, found 366 |
| 4.120 | 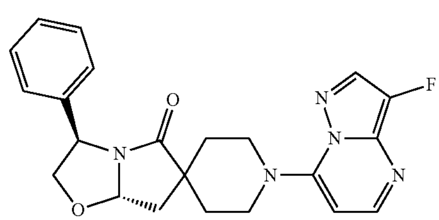 [SMILES: O=C1N2[C@H](CC13CCN(c1ccnc4c(F)cnn14)CC3)OC[C@H]2c1ccccc1] | (3'R,7a'S)-1-(3-fluoropyrazolo[1,5-a]pyrimidin-7-yl)-3'-phenyltetrahydro-5'H-spiro[piperidine-4,6'-pyrrolo[2,1-b][1,3]oxazol]-5'-one | Calc'd 408, found 408 |
| 4.121 | 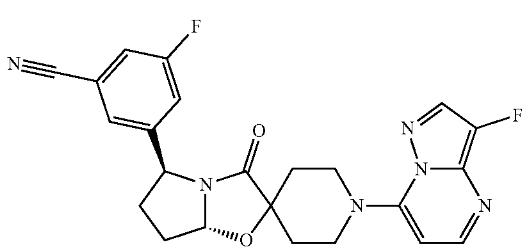 [SMILES: N#Cc1cc(F)cc([C@@H]2CC[C@H]3OC4(CCN(c5ccnc6c(F)cnn56)CC4)C(=O)N32)c1] | 3-fluoro-5-[(5'S,7a'R)-1-(3-fluoropyrazolo[1,5-a]pyrimidin-7-yl)-3'-oxotetrahydro-3'H-spiro[piperidine-4,2'-pyrrolo[2,1-b][1,3]oxazol]-5'-yl]benzonitrile | Calc'd 451, found 451 |

TABLE 13-continued

| Ex. No. | Structure | Name | Exact Mass [M + H]⁺ |
|---|---|---|---|
| 4.122 | 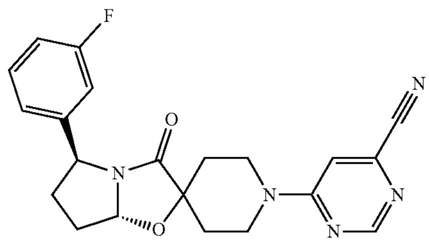 [SMILES: N#Cc1cc(N2CCC3(CC2)O[C@@H]2CC[C@@H](c4cccc(F)c4)N2C3=O)ncn1] | 6-[(5'S,7a'R)-5'-(3-fluorophenyl)-3'-oxotetrahydro-1H,3'H-spiro[piperidine-4,2'-pyrrolo[2,1-b][1,3]oxazol]-1-yl]pyrimidine-4-carbonitrile | Calc'd 394, found 394 |
| 4.123 | 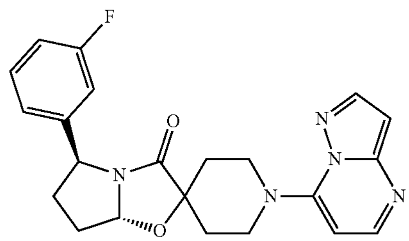 [SMILES: O=C1N2[C@@H](CC[C@H]2c2cccc(F)c2)OC12CCN(c1ccnc3ccnn13)CC2] | (5'S,7a'R)-5'-(3-fluorophenyl)-1-(pyrazolo[1,5-a]pyrimidin-7-yl)tetrahydro-3'H-spiro[piperidine-4,2'-pyrrolo[2,1-b][1,3]oxazol]-3'-one | Calc'd 408, found 408 |
| 4.124 | 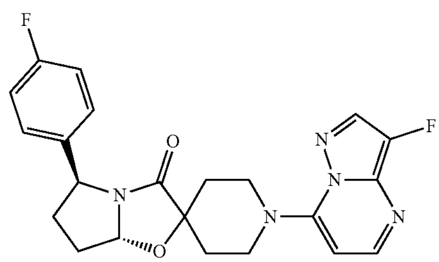 [SMILES: O=C1N2[C@@H](CC[C@H]2c2ccc(F)cc2)OC12CCN(c1ccnc3c(F)cnn13)CC2] | (5'S,7a'R)-5'-(4-fluorophenyl)-1-(3-fluoropyrazolo[1,5-a]pyrimidin-7-yl)tetrahydro-3'H-spiro[piperidine-4,2'-pyrrolo[2,1-b][1,3]oxazol]-3'-one | Calc'd 426, found 426 |
| 4.125 | 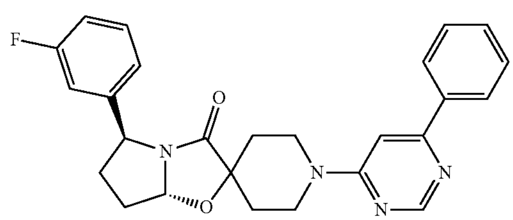 [SMILES: O=C1N2[C@@H](CC[C@H]2c2cccc(F)c2)OC12CCN(c1cc(-c3ccccc3)ncn1)CC2] | (5'S,7a'R)-5'-(3-fluorophenyl)-1-(6-phenylpyrimidin-4-yl)tetrahydro-3'H-spiro[piperidine-4,2'-pyrrolo[2,1-b][1,3]oxazol]-3'-one | Calc'd 445, found 445 |
| 4.126 | 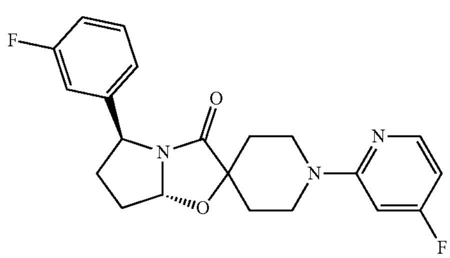 [SMILES: O=C1N2[C@@H](CC[C@H]2c2cccc(F)c2)OC12CCN(c1cc(F)ccn1)CC2] | (5'S,7a'R)-5'-(3-fluorophenyl)-1-(4-fluoropyridin-2-yl)tetrahydro-3'H-spiro[piperidine-4,2'-pyrrolo[2,1-b][1,3]oxazol]-3'-one | Calc'd 386, found 386 |
| 4.127 | 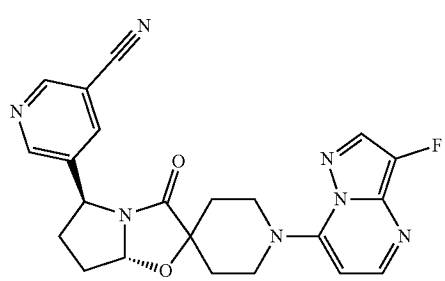 | 5-[(5'S,7a'R)-1-(3-fluoropyrazolo[1,5-a]pyrimidin-7-yl)-3'-oxotetrahydro-3'H-spiro[piperidine-4,2'-pyrrolo[2,1-b][1,3]oxazol]-5'-yl]pyridine-3-carbonitrile | Calc'd 434, found 434 |

TABLE 13-continued

| Ex. No. | Structure | Name | Exact Mass [M + H]+ |
|---|---|---|---|
| 4.128 | 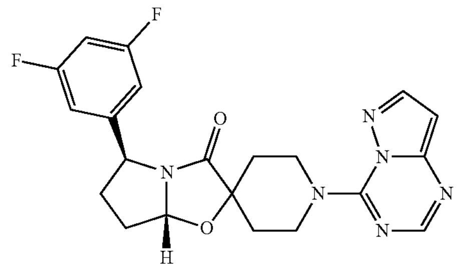 [SMILES: O=C1N2[C@@H](CC[C@H]2c2cc(F)cc(F)c2)OC12CCN(c1ncnc3ccnn13)CC2] | (5'S,7a'R)-5'-(3,5-difluorophenyl)-1-(pyrazolo[1,5-a][1,3,5]triazin-4-yl)tetrahydro-3'H-spiro[piperidine-4,2'-pyrrolo[2,1-b][1,3]oxazol]-3'-one | Calc'd 427, found 427 |
| 4.129 | 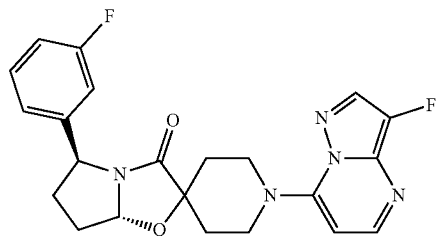 [SMILES: O=C1N2[C@@H](CC[C@H]2c2cccc(F)c2)OC12CCN(c1ccnc3c(F)cnn13)CC2] | (5'S,7a'R)-5'-(3-fluorophenyl)-1-(3-fluoropyrazolo[1,5-a]pyrimidin-7-yl)tetrahydro-3'H-spiro[piperidine-4,2'-pyrrolo[2,1-b][1,3]oxazol]-3'-one | Calc'd 426, found 426 |
| 4.130 | 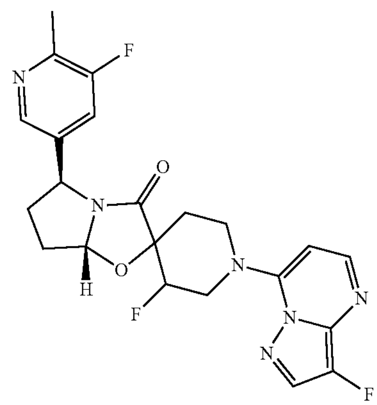 [SMILES: Cc1ncc([C@@H]2CC[C@H]3OC4(CCN(c5ccnc6c(F)cnn56)CC4F)C(=O)N32)cc1F] | (5'S,7a'R)-3-fluoro-5'-(5-fluoro-6-methylpyridin-3-yl)-1-(3-fluoropyrazolo[1,5-a]pyrimidin-7-yl)tetrahydro-3'H-spiro[piperidine-4,2'-pyrrolo[2,1-b][1,3]oxazol]-3'-one | Calc'd 459, found 459 |
| 4.131 | 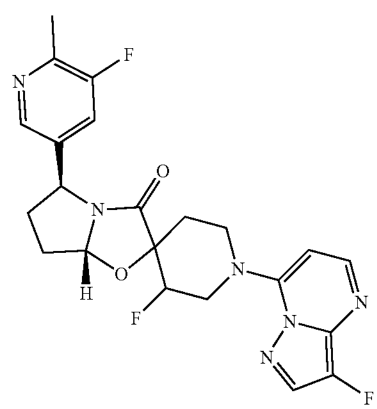 [SMILES: Cc1ncc([C@@H]2CC[C@H]3OC4(CCN(c5ccnc6c(F)cnn56)CC4F)C(=O)N32)cc1F] | (5'S,7a'R)-3-fluoro-5'-(5-fluoro-6-methylpyridin-3-yl)-1-(3-fluoropyrazolo[1,5-a]pyrimidin-7-yl)tetrahydro-3'H-spiro[piperidine-4,2'-pyrrolo[2,1-b][1,3]oxazol]-3'-one | Calc'd 459, found 459 |
| 4.132 | 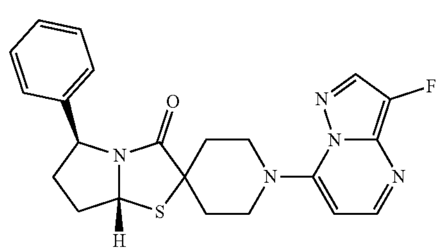 [SMILES: O=C1N2[C@@H](CC[C@H]2c2ccccc2)SC12CCN(c1ccnc3c(F)cnn13)CC2] | (5'S,7a'R)-1-(3-fluoropyrazolo[1,5-a]pyrimidin-7-yl)-5'-phenyltetrahydro-3'H-spiro[piperidine-4,2'-pyrrolo[2,1-b]thiazol]-3'-one | Calc'd 424, found 424 |

TABLE 13-continued

| Ex. No. | Structure | Name | Exact Mass [M + H]+ |
|---|---|---|---|
| 4.133 | 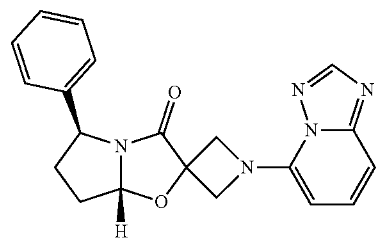 [SMILES: O=C1N2[C@@H](CC[C@H]2c2ccccc2)OC12CN(c1cccc3ncnn13)C2] | (5'S,7a'R)-5'-phenyl-1-([1,2,4]triazolo[1,5-a]pyridin-5-yl)tetrahydro-3'H-spiro[azetidine-3,2'-pyrrolo[2,1-b][1,3]oxazol]-3'-one | Calc'd 362, found 362 |
| 4.134 | 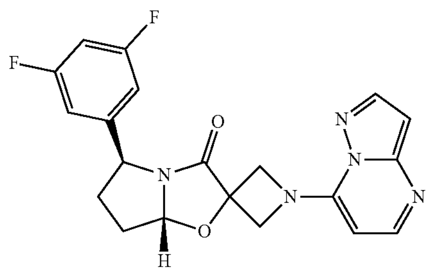 [SMILES: O=C1N2[C@@H](CC[C@H]2c2cc(F)cc(F)c2)OC12CN(c1ccnc3ccnn13)C2] | (5'S,7a'R)-5'-(3,5-difluorophenyl)-1-(pyrazolo[1,5-a]pyrimidin-7-yl)tetrahydro-3'H-spiro[azetidine-3,2'-pyrrolo[2,1-b][1,3]oxazol]-3'-one | Calc'd 398, found 398 |
| 4.135 | 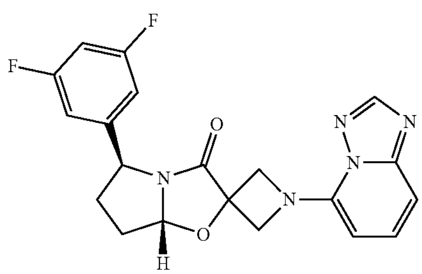 [SMILES: O=C1N2[C@@H](CC[C@H]2c2cc(F)cc(F)c2)OC12CN(c1cccc3ncnn13)C2] | (5'S,7a'R)-5'-(3,5-difluorophenyl)-1-([1,2,4]triazolo[1,5-a]pyridin-5-yl)tetrahydro-3'H-spiro[azetidine-3,2'-pyrrolo[2,1-b][1,3]oxazol]-3'-one | Calc'd 398, found 398 |
| 4.136 | 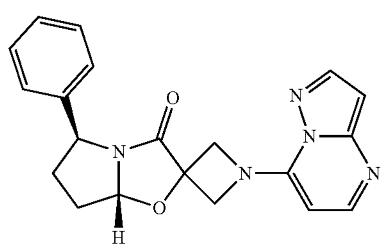 [SMILES: O=C1N2[C@@H](CC[C@H]2c2ccccc2)OC12CN(c1ccnc3ccnn13)C2] | (5'S,7a'R)-5'-phenyl-1-(pyrazolo[1,5-a]pyrimidin-7-yl)tetrahydro-3'H-spiro[azetidine-3,2'-pyrrolo[2,1-b][1,3]oxazol]-3'-one | Calc'd 362, found 362 |
| 4.137 | 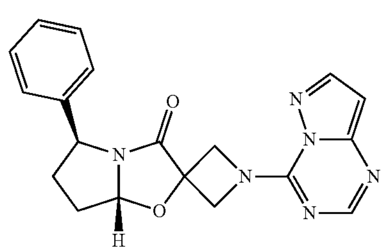 [SMILES: O=C1N2[C@@H](CC[C@H]2c2ccccc2)OC12CN(c1ncnc3ccnn13)C2] | (5'S,7a'R)-5'-phenyl-1-(pyrazolo[1,5-a][1,3,5]triazin-4-yl)tetrahydro-3'H-spiro[azetidine-3,2'-pyrrolo[2,1-b][1,3]oxazol]-3'-one | Calc'd 363, found 363 |

TABLE 13-continued

| Ex. No. | Structure | Name | Exact Mass [M + H]+ |
|---|---|---|---|
| 4.138 | 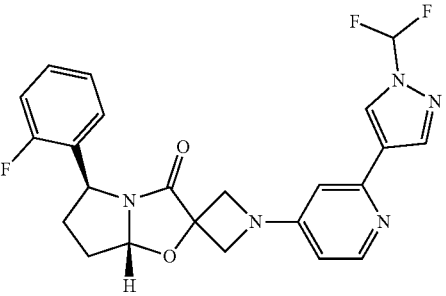 [SMILES: O=C1N2[C@@H](CC[C@H]2c2ccccc2F)OC12CN(c1ccnc(-c3cnn(C(F)F)c3)c1)C2] | (5'S,7a'R)-1-{2-[1-(difluoromethyl)-1H-pyrazol-4-yl]pyridin-4-yl}-5'-(2-fluorophenyl)tetrahydro-3'H-spiro[azetidine-3,2'-pyrrolo[2,1-b][1,3]oxazol]-3'-one | Calc'd 456, found 456 |
| 4.139 | 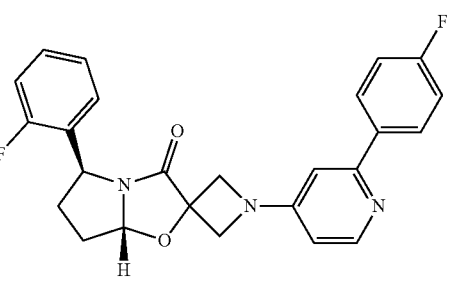 | (5'S,7a'R)-5'-(2-fluorophenyl)-1-[2-(4-fluorophenyl)pyridin-4-yl]tetrahydro-3'H-spiro[azetidine-3,2'-pyrrolo[2,1-b][1,3]oxazol]-3'-one | Calc'd 434, found 434 |
| 4.140 | 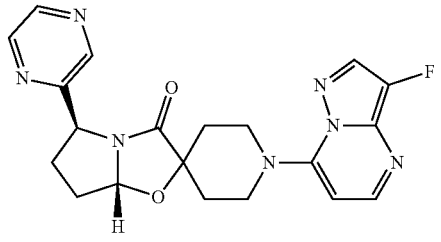 [SMILES: O=C1N2[C@@H](CC[C@H]2c2cnccn2)OC12CCN(c1ccnc3c(F)cnn13)CC2] | (5'S,7a'R)-1-(3-fluoropyrazolo[1,5-a]pyrimidin-7-yl)-5'-(pyrazin-2-yl)tetrahydro-3'H-spiro[piperidine-4,2'-pyrrolo[2,1-b][1,3]oxazol]-3'-one | Calc'd 410, found 410 |
| 4.141 | 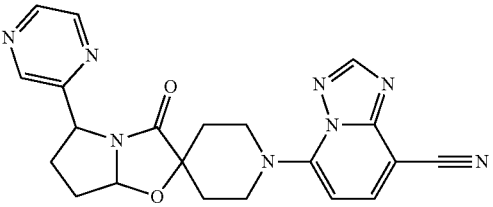 [SMILES: N#Cc1ccc(N2CCC3(CC2)OC2CCC(c4cnccn4)N2C3=O)n2ncnc12] | 5-[3'-oxo-5'-(pyrazin-2-yl)tetrahydro-1H,3'H-spiro[piperidine-4,2'-pyrrolo[2,1-b][1,3]oxazol]-1-yl][1,2,4]triazolo[1,5-a]pyridine-8-carbonitrile | Calc'd 417, found 417 |
| 4.142 | 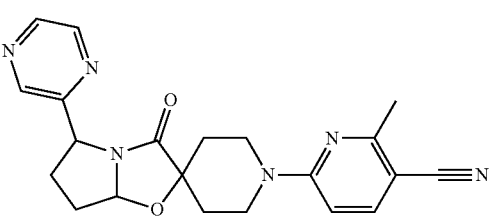 [SMILES: Cc1nc(N2CCC3(CC2)OC2CCC(c4cnccn4)N2C3=O)ccc1C#N] | 2-methyl-6-[3'-oxo-5'-(pyrazin-2-yl)tetrahydro-1H,3'H-spiro[piperidine-4,2'-pyrrolo[2,1-b][1,3]oxazol]-1-yl]pyridine-3-carbonitrile | Calc'd 391, found 391 |
| 4.143 | 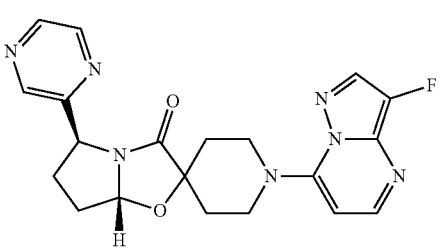 [SMILES: O=C1N2[C@@H](CC[C@H]2c2cnccn2)OC12CCN(c1ccnc3c(F)cnn13)CC2] | (5'S,7a'R)-1-(3-fluoropyrazolo[1,5-a]pyrimidin-7-yl)-5'-(pyrazin-2-yl)tetrahydro-3'H-spiro[piperidine-4,2'-pyrrolo[2,1-b][1,3]oxazol]-3'-one | Calc'd 410, found 410 |

TABLE 13-continued

| Ex. No. | Structure | Name | Exact Mass [M + H]+ |
|---|---|---|---|
| 4.144 | 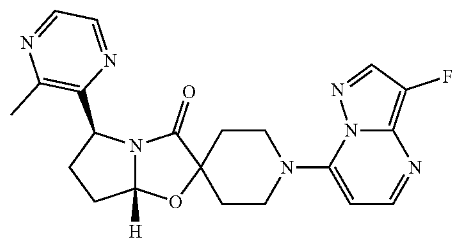 [SMILES: Cc1nccnc1[C@@H]1CC[C@H]2OC3(CCN(c4ccnc5c(F)cnn45)CC3)C(=O)N21] | (5'S,7a'R)-1-(3-fluoropyrazolo[1,5-a]pyrimidin-7-yl)-5'-(3-methylpyrazin-2-yl)tetrahydro-3'H-spiro[piperidine-4,2'-pyrrolo[2,1-b][1,3]oxazol]-3'-one | Calc'd 424, found 424 |
| 4.145 | 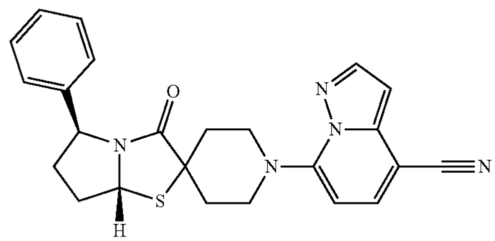 [SMILES: N#Cc1ccc(N2CCC3(CC2)S[C@@H]2CC[C@@H](c4ccccc4)N2C3=O)n2nccc12] | 7-[(5'S,7a'R)-3'-oxo-5'-phenyltetrahydro-1H,3'H-spiro[piperidine-4,2'-pyrrolo[2,1-b][1,3]thiazol]-1-yl]pyrazolo[1,5-a]pyridine-4-carbonitrile | Calc'd 430, found 430 |
| 4.146 | 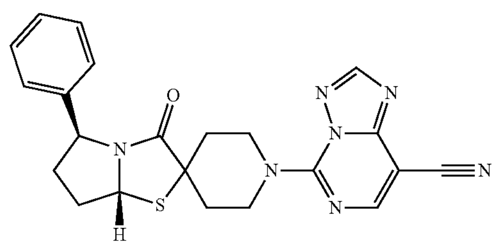 [SMILES: N#Cc1cnc(N2CCC3(CC2)S[C@@H]2CC[C@@H](c4ccccc4)N2C3=O)n2ncnc12] | 5-[(5'S,7a'R)-3'-oxo-5'-phenyltetrahydro-1H,3'H-spiro[piperidine-4,2'-pyrrolo[2,1-b][1,3]thiazol]-1-yl][1,2,4]triazolo[1,5-c]pyrimidine-8-carbonitrile | Calc'd 432, found 432 |
| 4.147 | 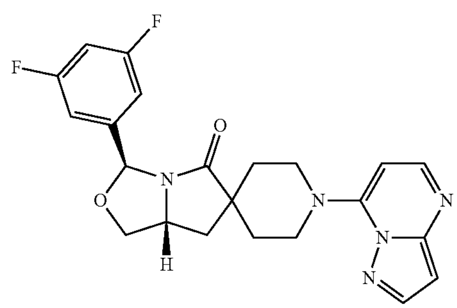 [SMILES: O=C1N2[C@@H](CO[C@H]2c2cc(F)cc(F)c2)CC12CCN(c1ccnc3ccnn13)CC2] | 3'-(3,5-difluorophenyl)-1-(pyrazolo[1,5-a]pyrimidin-7-yl)dihydro-1'H,3'H,5'H-spiro[piperidine-4,6'-pyrrolo[1,2-c][1,3]oxazol]-5'-one | Calc'd 426, found 426 |
| 4.148 | 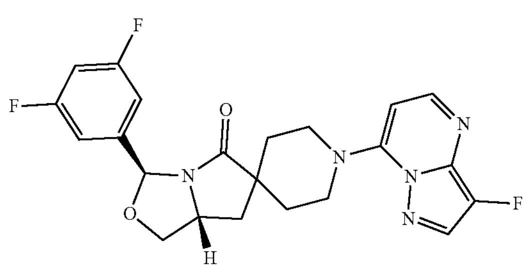 [SMILES: O=C1N2[C@@H](CO[C@H]2c2cc(F)cc(F)c2)CC12CCN(c1ccnc3c(F)cnn13)CC2] | 3'-(3,5-difluorophenyl)-1-(3-fluoropyrazolo[1,5-a]pyrimidin-7-yl)dihydro-1'H,3'H,5'H-spiro[piperidine-4,6'-pyrrolo[1,2-c][1,3]oxazol]-5'-one | Calc'd 444, found 444 |
| 4.149 | 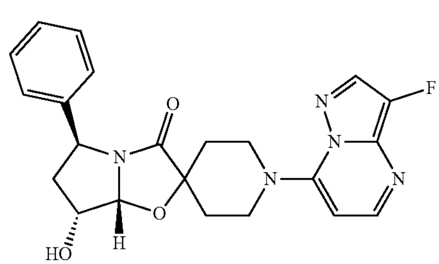 [SMILES: O=C1N2[C@H](OC13CCN(c1ccnc4c(F)cnn14)CC3)[C@H](O)C[C@H]2c1ccccc1] | (5'S,7'R,7a'R)-1-(3-fluoropyrazolo[1,5-a]pyrimidin-7-yl)-7'-hydroxy-5'-phenyltetrahydro-3'H-spiro[piperidine-4,2'-pyrrolo[2,1-b][1,3]oxazol]-3'-one | Calc'd 424, found 424 |

TABLE 13-continued

| Ex. No. | Structure | Name | Exact Mass [M + H]+ |
|---|---|---|---|
| 4.150 | 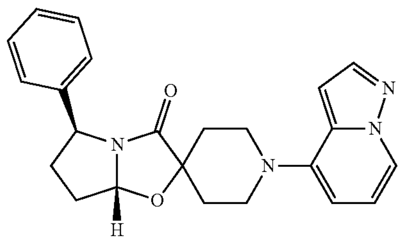 [SMILES: O=C1N2[C@@H](CC[C@H]2c2ccccc2)OC12CCN(c1cccn3nccc13)CC2] | (5'S,7a'R)-5'-phenyl-1-(pyrazolo[1,5-a]pyridin-4-yl)tetrahydro-3'H-spiro[piperidine-4,2'-pyrrolo[2,1-b][1,3]oxazol]-3'-one | Calc'd 389, found 389 |
| 4.151 | 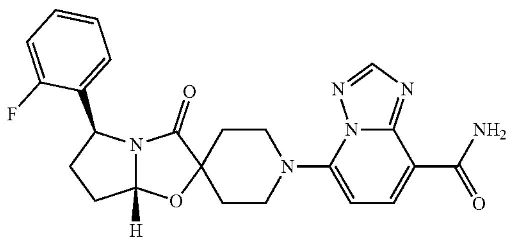 [SMILES: NC(=O)c1ccc(N2CCC3(CC2)O[C@@H]2CC[C@@H](c4ccccc4F)N2C3=O)n2ncnc12] | 5-[(5'S,7a'R)-5'-(2-fluorophenyl)-3'-oxotetrahydro-1H,3'H-spiro[piperidine-4,2'-pyrrolo[2,1-b][1,3]oxazol]-1-yl][1,2,4]triazolo[1,5-a]pyridine-8-carboxamide | Calc'd 451, found 451 |
| 4.152 | 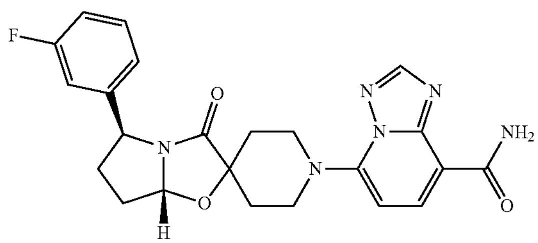 [SMILES: NC(=O)c1ccc(N2CCC3(CC2)O[C@@H]2CC[C@@H](c4cccc(F)c4)N2C3=O)n2ncnc12] | 5-[(5'S,7a'R)-5'-(3-fluorophenyl)-3'-oxotetrahydro-1H,3'H-spiro[piperidine-4,2'-pyrrolo[2,1-b][1,3]oxazol]-1-yl][1,2,4]triazolo[1,5-a]pyridine-8-carboxamide | Calc'd 451, found 451 |
| 4.153 | 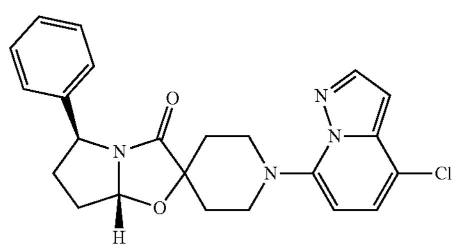 [SMILES: O=C1N2[C@@H](CC[C@H]2c2ccccc2)OC12CCN(c1ccc(Cl)c3ccnn13)CC2] | (5'S,7a'R)-1-(4-chloropyrazolo[1,5-a]pyridin-7-yl)-5'-phenyltetrahydro-3'H-spiro[piperidine-4,2'-pyrrolo[2,1-b][1,3]oxazol]-3'-one | Calc'd 423, found 423 |
| 4.154 | 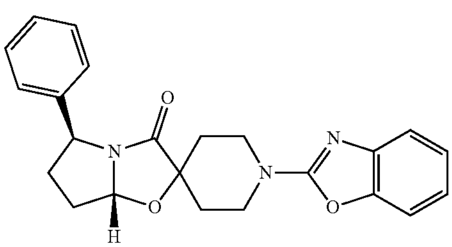 [SMILES: O=C1N2[C@@H](CC[C@H]2c2ccccc2)OC12CCN(c1nc3ccccc3o1)CC2] | (5'S,7a'R)-1-(1,3-benzoxazol-2-yl)-5'-phenyltetrahydro-3'H-spiro[piperidine-4,2'-pyrrolo[2,1-b][1,3]oxazol]-3'-one | Calc'd 390, found 390 |
| 4.155 | 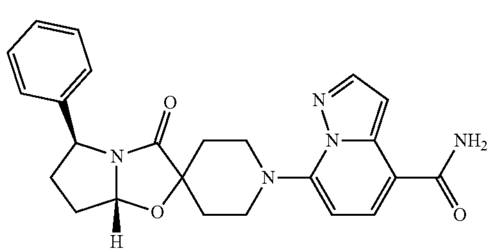 [SMILES: NC(=O)c1ccc(N2CCC3(CC2)O[C@@H]2CC[C@@H](c4ccccc4)N2C3=O)n2nccc12] | 7-[(5'S,7a'R)-3'-oxo-5'-phenyltetrahydro-1H,3'H-spiro[piperidine-4,2'-pyrrolo[2,1-b][1,3]oxazol]-1-yl]pyrazolo[1,5-a]pyridine-4-carboxamide | Calc'd 432, found 432 |

TABLE 13-continued

| Ex. No. | Structure | Name | Exact Mass [M + H]+ |
|---|---|---|---|
| 4.156 | 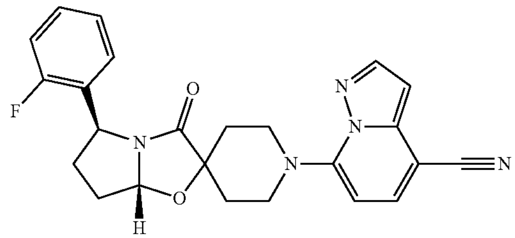 [SMILES: N#Cc1ccc(N2CCC3(CC2)O[C@@H]2CC[C@@H](c4ccccc4F)N2C3=O)n2nccc12] | 7-[(5'S,7a'R)-5'-(2-fluorophenyl)-3'-oxotetrahydro-1H,3'H-spiro[piperidine-4,2'-pyrrolo[2,1-b][1,3]oxazol]-1-yl]pyrazolo[1,5-a]pyridine-4-carbonitrile | Calc'd 432, found 432 |
| 4.157 | 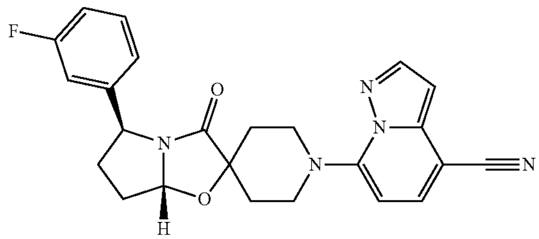 [SMILES: N#Cc1ccc(N2CCC3(CC2)O[C@@H]2CC[C@@H](c4cccc(F)c4)N2C3=O)n2nccc12] | 7-[(5'S,7a'R)-5'-(3-fluorophenyl)-3'-oxotetrahydro-1H,3'H-spiro[piperidine-4,2'-pyrrolo[2,1-b][1,3]oxazol]-1-yl]pyrazolo[1,5-a]pyridine-4-carbonitrile | Calc'd 432, found 432 |
| 4.158 | 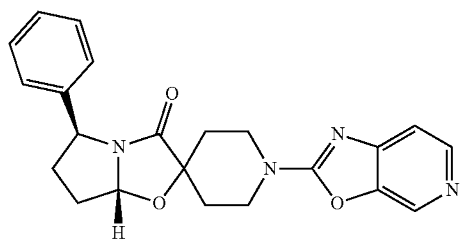 [SMILES: O=C1N2[C@@H](CC[C@H]2c2ccccc2)OC12CCN(c1nc3ccncc3o1)CC2] | (5'S,7a'R)-1-([1,3]oxazolo[5,4-c]pyridin-2-yl)-5'-phenyltetrahydro-3'H-spiro[piperidine-4,2'-pyrrolo[2,1-b][1,3]oxazol]-3'-one | Calc'd 391, found 391 |
| 4.159 | 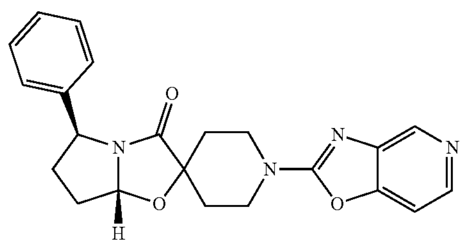 [SMILES: O=C1N2[C@@H](CC[C@H]2c2ccccc2)OC12CCN(c1nc3cnccc3o1)CC2] | (5'S,7a'R)-1-([1,3]oxazolo[4,5-c]pyridin-2-yl)-5'-phenyltetrahydro-3'H-spiro[piperidine-4,2'-pyrrolo[2,1-b][1,3]oxazol]-3'-one | Calc'd 391, found 391 |
| 4.160 | 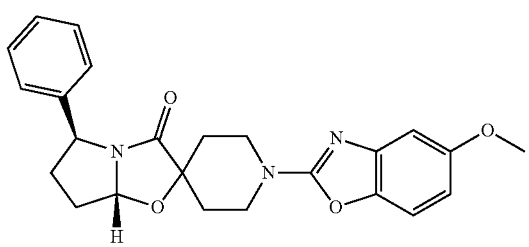 [SMILES: COc1ccc2oc(N3CCC4(CC3)O[C@@H]3CC[C@@H](c5ccccc5)N3C4=O)nc2c1] | (5'S,7a'R)-1-(5-methoxy-1,3-benzoxazol-2-yl)-5'-phenyltetrahydro-3'H-spiro[piperidine-4,2'-pyrrolo[2,1-b][1,3]oxazol]-3'-one | Calc'd 420, found 420 |
| 4.161 | 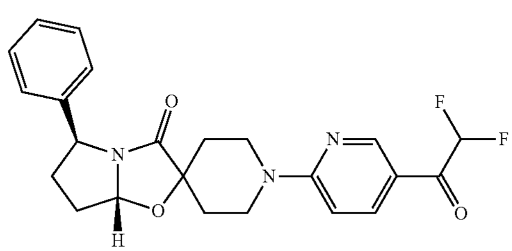 [SMILES: O=C(c1ccc(N2CCC3(CC2)O[C@@H]2CC[C@@H](c4ccccc4)N2C3=O)nc1)C(F)F] | (5'S,7a'R)-1-[5-(difluoroacetyl)pyridin-2-yl]-5'-phenyltetrahydro-3'H-spiro[piperidine-4,2'-pyrrolo[2,1-b][1,3]oxazol]-3'-one | Calc'd 428, found 428 |

TABLE 13-continued

| Ex. No. | Structure | Name | Exact Mass [M + H]+ |
|---|---|---|---|
| 4.162 | 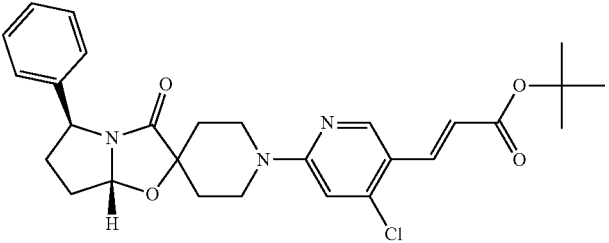 [SMILES: CC(C)(C)OC(=O)/C=C/c1cnc(N2CCC3(CC2)O[C@@H]2CC[C@@H](c4ccccc4)N2C3=O)cc1Cl] | tert-butyl (2E)-3-{4-chloro-6-[(5'S,7a'R)-3'-oxo-5'-phenyltetrahydro-1H,3'H-spiro[piperidine-4,2'-pyrrolo[2,1-b][1,3]oxazol]-1-yl]pyridin-3-yl}prop-2-enoate | Calc'd 510, found 510 |
| 4.163 | 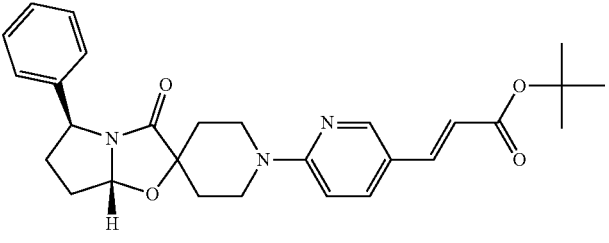 [SMILES: CC(C)(C)OC(=O)/C=C/c1ccc(N2CCC3(CC2)O[C@@H]2CC[C@@H](c4ccccc4)N2C3=O)nc1] | tert-butyl (2E)-3-{6-[(5'S,7a'R)-3'-oxo-5'-phenyltetrahydro-1H,3'H-spiro[piperidine-4,2'-pyrrolo[2,1-b][1,3]oxazol]-1-yl]pyridin-3-yl}prop-2-enoate | Calc'd 476, found 476 |
| 4.164 | 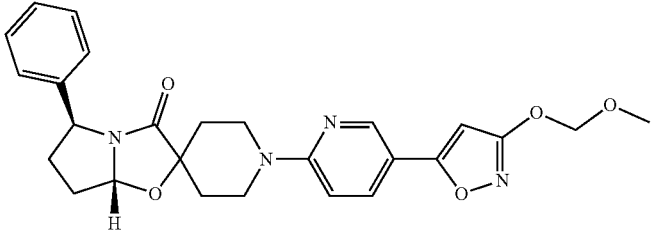 [SMILES: COCOc1cc(-c2ccc(N3CCC4(CC3)O[C@@H]3CC[C@@H](c5ccccc5)N3C4=O)nc2)on1] | (5'S,7a'R)-1-{5-[3-(methoxymethoxy)-1,2-oxazol-5-yl]pyridin-2-yl}-5'-phenyltetrahydro-3'H-spiro[piperidine-4,2'-pyrrolo[2,1-b][1,3]oxazol]-3'-one | Calc'd 477, found 477 |
| 4.165 | 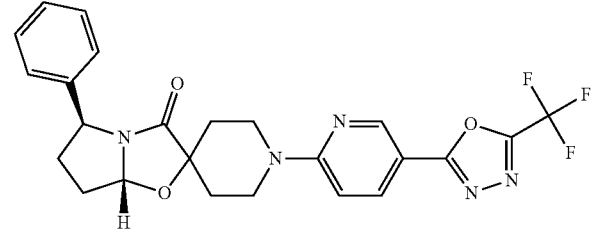 [SMILES: O=C1N2[C@@H](CC[C@H]2c2ccccc2)OC12CCN(c1ccc(-c3nnc(C(F)(F)F)o3)cn1)CC2] | (5'S,7a'R)-5'-phenyl-1-{5-[5-(trifluoromethyl)-1,3,4-oxadiazol-2-yl]pyridin-2-yl}tetrahydro-3'H-spiro[piperidine-4,2'-pyrrolo[2,1-b][1,3]oxazol]-3'-one | Calc'd 486, found 486 |
| 4.166 | 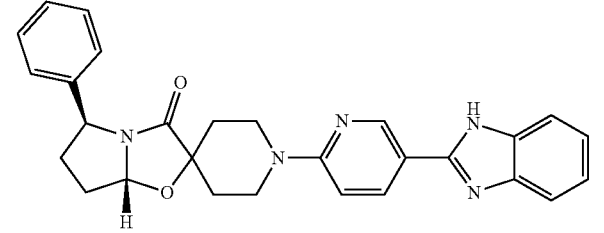 [SMILES: O=C1N2[C@@H](CC[C@H]2c2ccccc2)OC12CCN(c1ccc(-c3nc4ccccc4[nH]3)cn1)CC2] | (5'S,7a'R)-1-[5-(1H-benzimidazol-2-yl)pyridin-2-yl]-5'-phenyltetrahydro-3'H-spiro[piperidine-4,2'-pyrrolo[2,1-b][1,3]oxazol]-3'-one | Calc'd 466, found 466 |
| 4.167 | 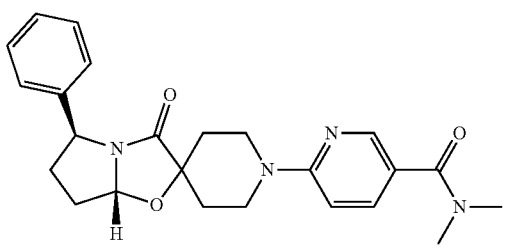 [SMILES: CN(C)C(=O)c1ccc(N2CCC3(CC2)O[C@@H]2CC[C@@H](c4ccccc4)N2C3=O)nc1] | N,N-dimethyl-6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carboxamide | Calc'd 421, found 421 |

TABLE 13-continued

| Ex. No. | Structure | Name | Exact Mass [M + H]+ |
|---|---|---|---|
| 4.168 | 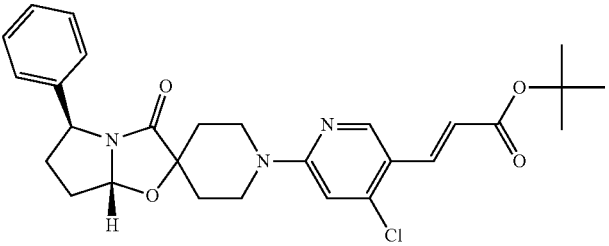 [SMILES: CC(C)(C)OC(=O)/C=C/c1cnc(N2CCC3(CC2)O[C@@H]2CC[C@@H](c4ccccc4)N2C3=O)cc1Cl] | tert-butyl (2E)-3-{4-chloro-6-[(5'S,7a'R)-3'-oxo-5'-phenyltetrahydro-1H,3'H-spiro[piperidine-4,2'-pyrrolo[2,1-b][1,3]oxazol]-1-yl]pyridin-3-yl}prop-2-enoate | Calc'd 510, found 510 |
| 4.169 | 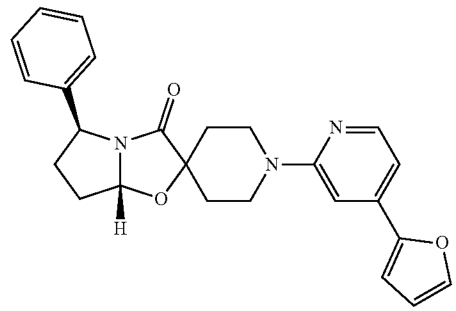 [SMILES: O=C1N2[C@@H](CC[C@H]2c2ccccc2)OC12CCN(c1cc(-c3ccco3)ccn1)CC2] | (5'S,7a'R)-1-[4-(furan-2-yl)pyridin-2-yl]-5'-phenyltetrahydro-3'H-spiro[piperidine-4,2'-pyrrolo[2,1-b][1,3]oxazol]-3'-one | Calc'd 416, found 416 |
| 4.170 | 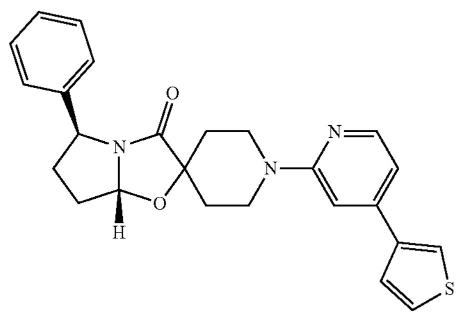 [SMILES: O=C1N2[C@@H](CC[C@H]2c2ccccc2)OC12CCN(c1cc(-c3ccsc3)ccn1)CC2] | (5'S,7a'R)-5'-phenyl-1-[4-(thiophen-3-yl)pyridin-2-yl]tetrahydro-3'H-spiro[piperidine-4,2'-pyrrolo[2,1-b][1,3]oxazol]-3'-one | Calc'd 432, found 432 |
| 4.171 | 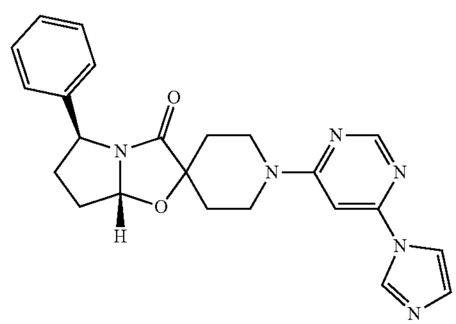 [SMILES: O=C1N2[C@@H](CC[C@H]2c2ccccc2)OC12CCN(c1cc(-n3ccnc3)ncn1)CC2] | (5'S,7a'R)-1-[6-(1H-imidazol-1-yl)pyrimidin-4-yl]-5'-phenyltetrahydro-3'H-spiro[piperidine-4,2'-pyrrolo[2,1-b][1,3]oxazol]-3'-one | Calc'd 417, found 417 |
| 4.172 | 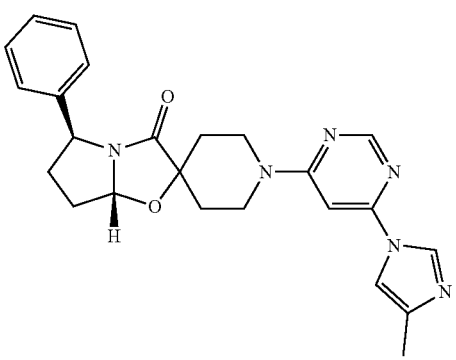 [SMILES: Cc1cn(-c2cc(N3CCC4(CC3)O[C@@H]3CC[C@@H](c5ccccc5)N3C4=O)ncn2)cn1] | (5'S,7a'R)-1-[6-(4-methyl-1H-imidazol-1-yl)pyrimidin-4-yl]-5'-phenyltetrahydro-3'H-spiro[piperidine-4,2'-pyrrolo[2,1-b][1,3]oxazol]-3'-one | Calc'd 431, found 431 |

TABLE 13-continued

| Ex. No. | Structure | Name | Exact Mass [M + H]+ |
|---|---|---|---|
| 4.173 | 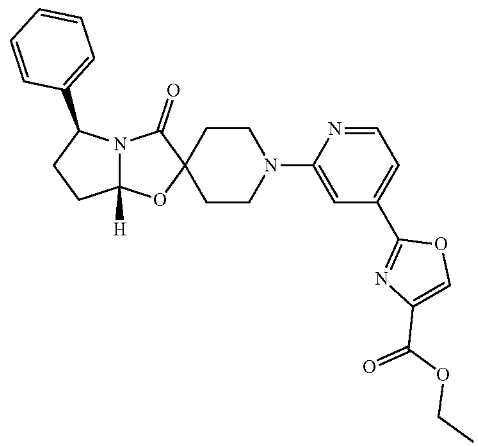 [SMILES: CCOC(=O)c1coc(-c2ccnc(N3CCC4(CC3)O[C@@H]3CC[C@@H](c5ccccc5)N3C4=O)c2)n1] | ethyl 2-{2-[(5'S,7a'R)-3'-oxo-5'-phenyltetrahydro-1H,3'H-spiro[piperidine-4,2'-pyrrolo[2,1-b][1,3]oxazol]-1-yl]pyridin-4-yl}-1,3-oxazole-4-carboxylate | Calc'd 489, found 489 |
| 4.174 | 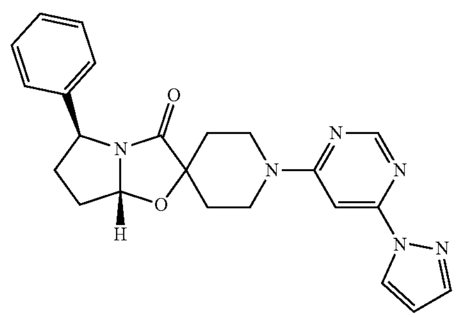 [SMILES: O=C1N2[C@@H](CC[C@H]2c2ccccc2)OC12CCN(c1cc(-n3cccn3)ncn1)CC2] | (5'S,7a'R)-5'-phenyl-1-[6-(1H-pyrazol-1-yl)pyrimidin-4-yl]tetrahydro-3'H-spiro[piperidine-4,2'-pyrrolo[2,1-b][1,3]oxazol]-3'-one | Calc'd 417, found 417 |
| 4.175 | 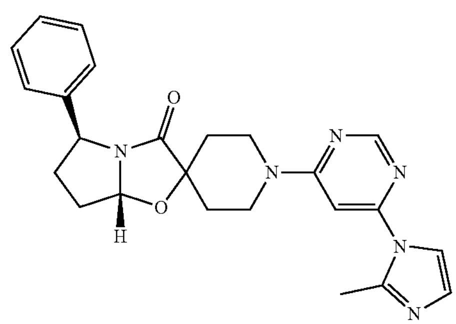 [SMILES: Cc1nccn1-c1cc(N2CCC3(CC2)O[C@@H]2CC[C@@H](c4ccccc4)N2C3=O)ncn1] | (5'S,7a'R)-1-[6-(2-methyl-1H-imidazol-1-yl)pyrimidin-4-yl]-5'-phenyltetrahydro-3'H-spiro[piperidine-4,2'-pyrrolo[2,1-b][1,3]oxazol]-3'-one | Calc'd 431, found 431 |
| 4.176 | 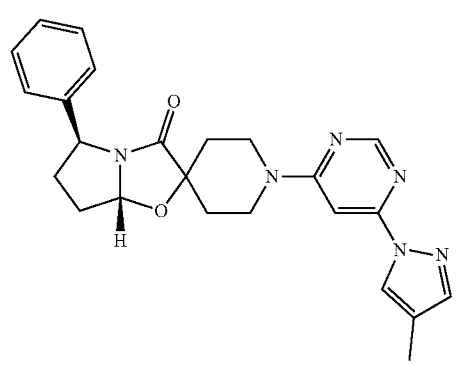 [SMILES: Cc1cnn(-c2cc(N3CCC4(CC3)O[C@@H]3CC[C@@H](c5ccccc5)N3C4=O)ncn2)c1] | (5'S,7a'R)-1-[6-(4-methyl-1H-pyrazol-1-yl)pyrimidin-4-yl]-5'-phenyltetrahydro-3'H-spiro[piperidine-4,2'-pyrrolo[2,1-b][1,3]oxazol]-3'-one | Calc'd 431, found 431 |

TABLE 13-continued

| Ex. No. | Structure | Name | Exact Mass [M + H]+ |
|---|---|---|---|
| 4.177 | 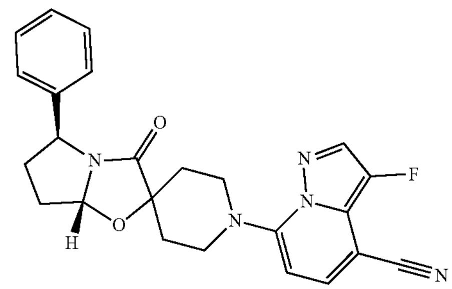 [SMILES: N#Cc1ccc(N2CCC3(CC2)O[C@@H]2CC[C@@H](c4ccccc4)N2C3=O)n2ncc(F)c12] | 3-fluoro-7-[(5'S,7a'R)-3'-oxo-5'-phenyltetrahydro-1H,3'H-spiro[piperidine-4,2'-pyrrolo[2,1-b][1,3]oxazol]-1-yl]pyrazolo[1,5-a]pyridine-4-carbonitrile | Calc'd 432, found 432 |
| 4.178 | 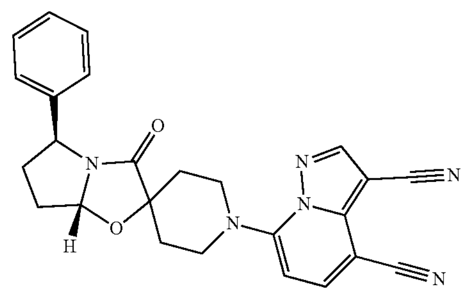 [SMILES: N#Cc1ccc(N2CCC3(CC2)O[C@@H]2CC[C@@H](c4ccccc4)N2C3=O)n2ncc(C#N)c12] | 7-[(5'S,7a'R)-3'-oxo-5'-phenyltetrahydro-1H,3'H-spiro[piperidine-4,2'-pyrrolo[2,1-b][1,3]oxazol]-1-yl]pyrazolo[1,5-a]pyridine-3,4-dicarbonitrile | Calc'd 439, found 439 |
| 4.179 | 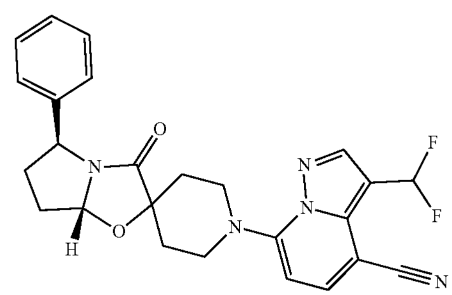 [SMILES: N#Cc1ccc(N2CCC3(CC2)O[C@@H]2CC[C@@H](c4ccccc4)N2C3=O)n2ncc(C(F)F)c12] | 3-(difluoromethyl)-7-[(5'S,7a'R)-3'-oxo-5'-phenyltetrahydro-1H,3'H-spiro[piperidine-4,2'-pyrrolo[2,1-b][1,3]oxazol]-1-yl]pyrazolo[1,5-a]pyridine-4-carbonitrile | Calc'd 464, found 464 |
| 4.180 | 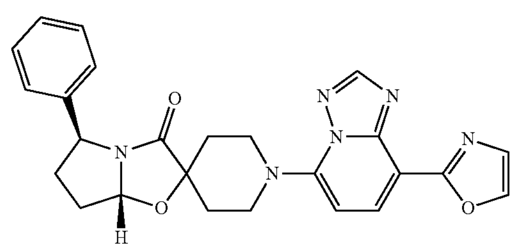 [SMILES: O=C1N2[C@@H](CC[C@H]2c2ccccc2)OC12CCN(c1ccc(-c3ncco3)c3ncnn13)CC2] | (5'S,7a'R)-1-[8-(1,3-oxazol-2-yl)[1,2,4]triazolo[1,5-a]pyridin-5-yl]-5'-phenyltetrahydro-3'H-spiro[piperidine-4,2'-pyrrolo[2,1-b][1,3]oxazol]-3'-one | Calc'd 457, found 457 |
| 4.181 | 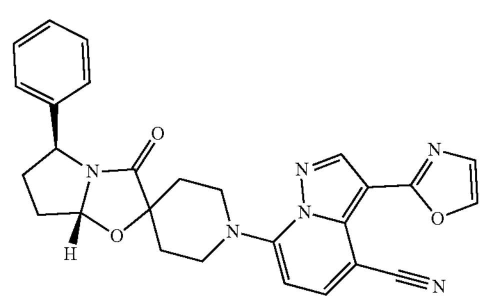 [SMILES: N#Cc1ccc(N2CCC3(CC2)O[C@@H]2CC[C@@H](c4ccccc4)N2C3=O)n2ncc(-c3ncco3)c12] | 3-(1,3-oxazol-2-yl)-7-[(5'S,7a'R)-3'-oxo-5'-phenyltetrahydro-1H,3'H-spiro[piperidine-4,2'-pyrrolo[2,1-b][1,3]oxazol]-1-yl]pyrazolo[1,5-a]pyridine-4-carbonitrile | Calc'd 481, found 481 |

TABLE 13-continued

| Ex. No. | Structure | Name | Exact Mass [M + H]+ |
|---|---|---|---|
| 4.182 | 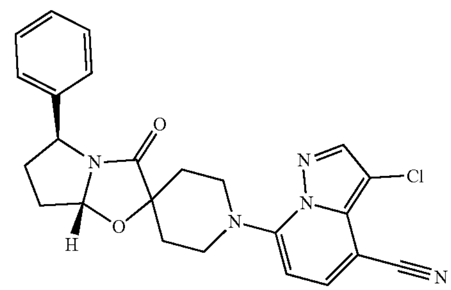 [SMILES: N#Cc1ccc(N2CCC3(CC2)O[C@@H]2CC[C@@H](c4ccccc4)N2C3=O)n2ncc(Cl)c12] | 3-chloro-7-[(5'S,7a'R)-3'-oxo-5'-phenyltetrahydro-1H,3'H-spiro[piperidine-4,2'-pyrrolo[2,1-b][1,3]oxazol]-1-yl]pyrazolo[1,5-a]pyridine-4-carbonitrile | Calc'd 448, found 448 |
| 4.183 | 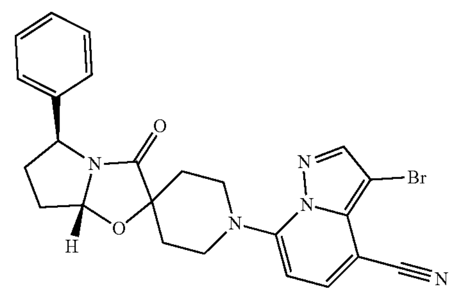 [SMILES: N#Cc1ccc(N2CCC3(CC2)O[C@@H]2CC[C@@H](c4ccccc4)N2C3=O)n2ncc(Br)c12] | 3-bromo-7-[(5'S,7a'R)-3'-oxo-5'-phenyltetrahydro-1H,3'H-spiro[piperidine-4,2'-pyrrolo[2,1-b][1,3]oxazol]-1-yl]pyrazolo[1,5-a]pyridine-4-carbonitrile | Calc'd 492, found 492 |
| 4.184 | 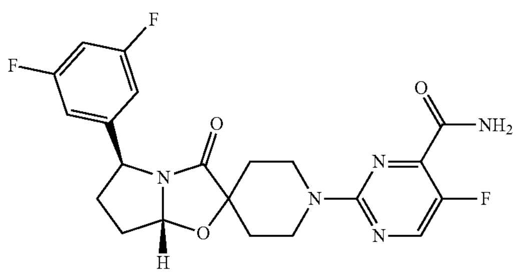 [SMILES: NC(=O)c1nc(N2CCC3(CC2)O[C@@H]2CC[C@@H](c4cc(F)cc(F)c4)N2C3=O)ncc1F] | 2-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-5-fluoropyrimidine-4-carboxamide | Calc'd 448, found 448 |
| 4.185 | 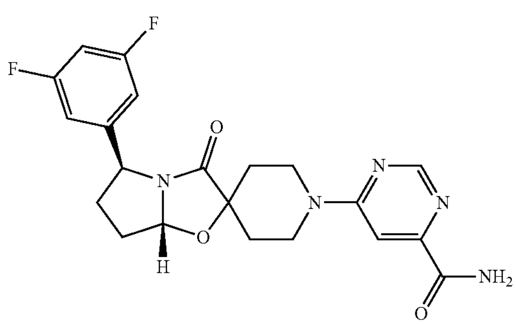 [SMILES: NC(=O)c1cc(N2CCC3(CC2)O[C@@H]2CC[C@@H](c4cc(F)cc(F)c4)N2C3=O)ncn1] | 6-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]pyrimidine-4-carboxamide | Calc'd 430, found 430 |
| 4.186 | 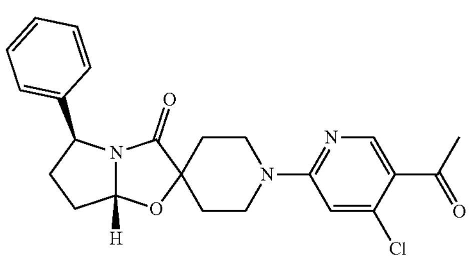 [SMILES: CC(=O)c1cnc(N2CCC3(CC2)O[C@@H]2CC[C@@H](c4ccccc4)N2C3=O)cc1Cl] | (5'S,7a'R)-1-(5-acetyl-4-chloropyridin-2-yl)-5'-phenyltetrahydro-3'H-spiro[piperidine-4,2'-pyrrolo[2,1-b][1,3]oxazol]-3'-one | Calc'd 426, found 426 |

TABLE 13-continued

| Ex. No. | Structure | Name | Exact Mass [M + H]+ |
|---|---|---|---|
| 4.187 | 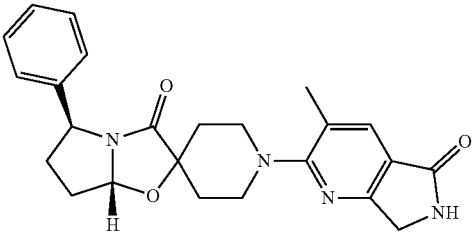 [SMILES: Cc1cc2c(nc1N1CCC3(CC1)O[C@@H]1CC[C@@H](c4ccccc4)N1C3=O)CNC2=O] | (5'S,7a'R)-1-(3-methyl-5-oxo-6,7-dihydro-5H-pyrrolo[3,4-b]pyridin-2-yl)-5'-phenyltetrahydro-3'H-spiro[piperidine-4,2'-pyrrolo[2,1-b][1,3]oxazol]-3'-one | Calc'd 419, found 419 |
| 4.188 | 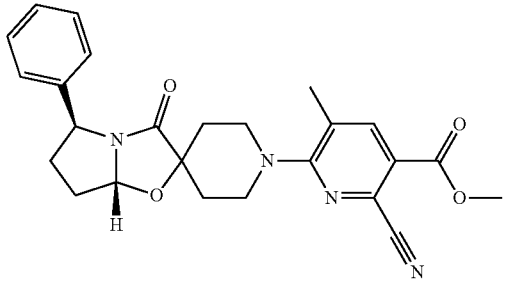 [SMILES: COC(=O)c1cc(C)c(N2CCC3(CC2)O[C@@H]2CC[C@@H](c4ccccc4)N2C3=O)nc1C#N] | methyl 2-cyano-5-methyl-6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carboxylate | Calc'd 447, found 447 |
| 4.189 | 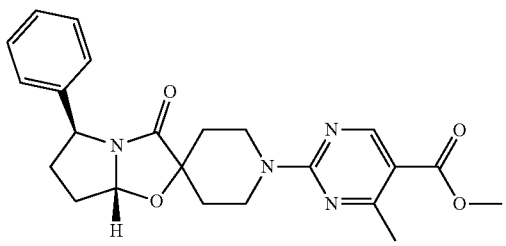 [SMILES: COC(=O)c1cnc(N2CCC3(CC2)O[C@@H]2CC[C@@H](c4ccccc4)N2C3=O)nc1C] | methyl 4-methyl-2-[(5'S,7a'R)-3'-oxo-5'-phenyltetrahydro-1H,3'H-spiro[piperidine-4,2'-pyrrolo[2,1-b][1,3]oxazol]-1-yl]pyrimidine-5-carboxylate | Calc'd 423, found 423 |
| 4.190 | 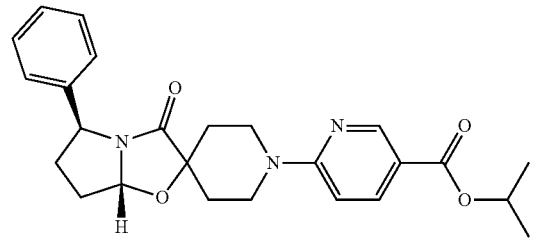 [SMILES: CC(C)OC(=O)c1ccc(N2CCC3(CC2)O[C@@H]2CC[C@@H](c4ccccc4)N2C3=O)nc1] | propan-2-yl 6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carboxylate | Calc'd 436, found 436 |
| 4.191 | 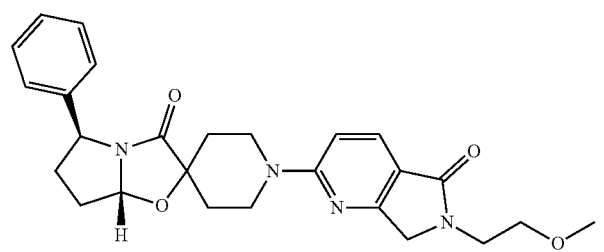 [SMILES: COCCN1Cc2nc(N3CCC4(CC3)O[C@@H]3CC[C@@H](c5ccccc5)N3C4=O)ccc2C1=O] | (5'S,7a'R)-1-[6-(2-methoxyethyl)-5-oxo-6,7-dihydro-5H-pyrrolo[3,4-b]pyridin-2-yl]-5'-phenyltetrahydro-3'H-spiro[piperidine-4,2'-pyrrolo[2,1-b][1,3]oxazol]-3'-one | Calc'd 463, found 4636 |

TABLE 13-continued

| Ex. No. | Structure | Name | Exact Mass [M + H]+ |
|---|---|---|---|
| 4.192 | 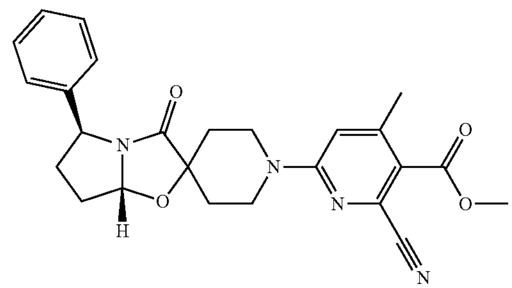 [SMILES: COC(=O)c1c(C)cc(N2CCC3(CC2)O[C@@H]2CC[C@@H](c4ccccc4)N2C3=O)nc1C#N] | methyl 2-cyano-4-methyl-6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carboxylate | Calc'd 447, found 447 |
| 4.193 | 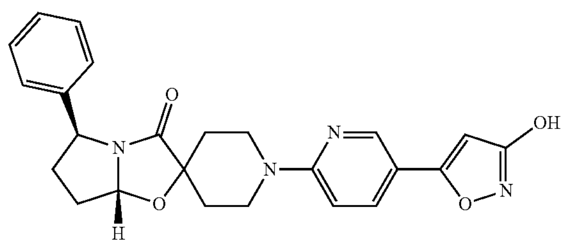 [SMILES: O=C1N2[C@@H](CC[C@H]2c2ccccc2)OC12CCN(c1ccc(-c3cc(O)no3)cn1)CC2] | (5'S,7a'R)-1-[5-(3-hydroxy-1,2-oxazol-5-yl)pyridin-2-yl]-5'-phenyltetrahydro-3'H-spiro[piperidine-4,2'-pyrrolo[2,1-b][1,3]oxazol]-3'-one | Calc'd 433, found 433 |
| 4.194 | 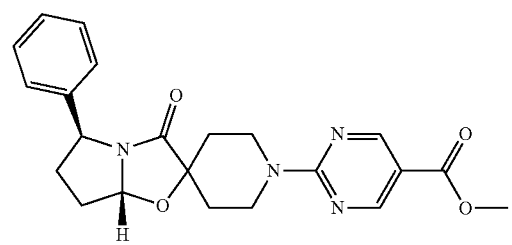 [SMILES: COC(=O)c1cnc(N2CCC3(CC2)O[C@@H]2CC[C@@H](c4ccccc4)N2C3=O)nc1] | methyl 2-[(5'S,7a'R)-3'-oxo-5'-phenyltetrahydro-1H,3'H-spiro[piperidine-4,2'-pyrrolo[2,1-b][1,3]oxazol]-1-yl]pyrimidine-5-carboxylate | Calc'd 409, found 409 |
| 4.195 | 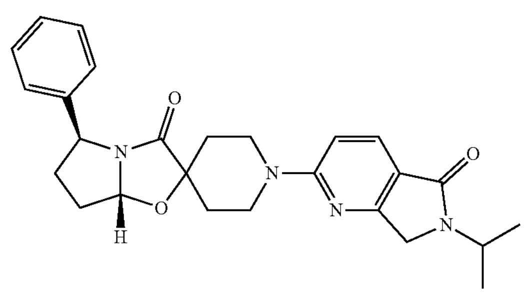 [SMILES: CC(C)N1Cc2nc(N3CCC4(CC3)O[C@@H]3CC[C@@H](c5ccccc5)N3C4=O)ccc2C1=O] | (5'S,7a'R)-1-[5-oxo-6-(propan-2-yl)-6,7-dihydro-5H-pyrrolo[3,4-b]pyridin-2-yl]-5'-phenyltetrahydro-3'H-spiro[piperidine-4,2'-pyrrolo[2,1-b][1,3]oxazol]-3'-one | Calc'd 447, found 447 |
| 4.196 | 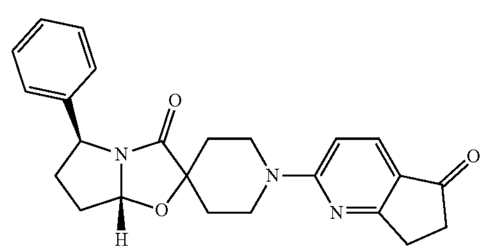 [SMILES: O=C1CCc2nc(N3CCC4(CC3)O[C@@H]3CC[C@@H](c5ccccc5)N3C4=O)ccc21] | (5'S,7a'R)-1-(5-oxo-6,7-dihydro-5H-cyclopenta[b]pyridin-2-yl)-5'-phenyltetrahydro-3'H-spiro[piperidine-4,2'-pyrrolo[2,1-b][1,3]oxazol]-3'-one | Calc'd 404, found 404 |

TABLE 13-continued

| Ex. No. | Structure | Name | Exact Mass [M + H]+ |
|---|---|---|---|
| 4.197 | 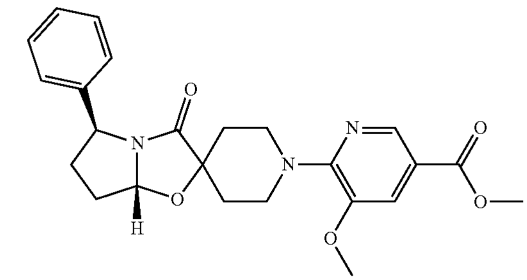 [SMILES: COC(=O)c1cnc(N2CCC3(CC2)O[C@@H]2CC[C@@H](c4ccccc4)N2C3=O)c(OC)c1] | methyl 5-methoxy-6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carboxylate | Calc'd 438, found 438 |
| 4.198 | 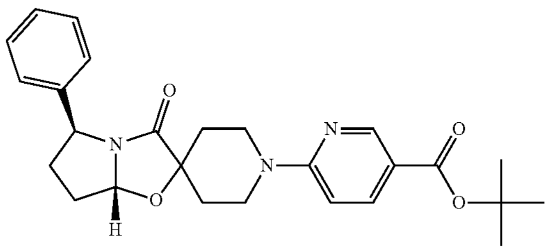 [SMILES: CC(C)(C)OC(=O)c1ccc(N2CCC3(CC2)O[C@@H]2CC[C@@H](c4ccccc4)N2C3=O)nc1] | tert-butyl 6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carboxylate | Calc'd 450, found 450 |
| 4.199 | 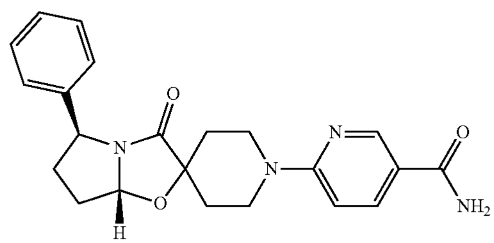 [SMILES: NC(=O)c1ccc(N2CCC3(CC2)O[C@@H]2CC[C@@H](c4ccccc4)N2C3=O)nc1] | 6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carboxamide | Calc'd 393, found 393 |
| 4.200 | 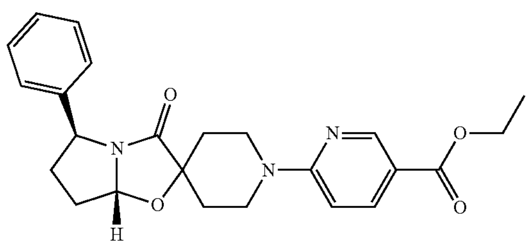 [SMILES: CCOC(=O)c1ccc(N2CCC3(CC2)O[C@@H]2CC[C@@H](c4ccccc4)N2C3=O)nc1] | ethyl 6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carboxylate | Calc'd 422, found 422 |
| 4.201 | 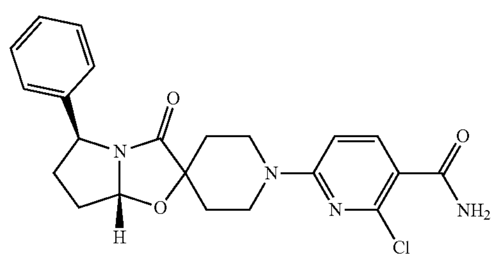 [SMILES: NC(=O)c1ccc(N2CCC3(CC2)O[C@@H]2CC[C@@H](c4ccccc4)N2C3=O)nc1Cl] | 2-chloro-6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carboxamide | Calc'd 427, found 427 |
| 4.202 | 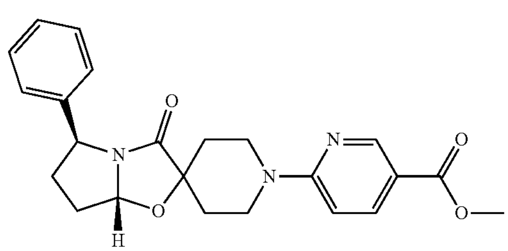 | methyl 6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carboxylate | Calc'd 408, found 408 |

TABLE 13-continued

| Ex. No. | Structure | Name | Exact Mass [M + H]+ |
|---------|-----------|------|---------------------|
| 4.203 | 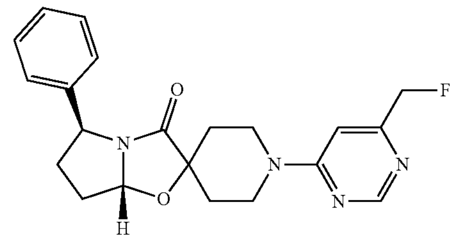 [SMILES: O=C1N2[C@@H](CC[C@H]2c2ccccc2)OC12CCN(c1cc(CF)ncn1)CC2] | (5'S,7a'R)-1-[6-(fluoromethyl)pyrimidin-4-yl]-5'-phenyltetrahydro-3'H-spiro[piperidine-4,2'-pyrrolo[2,1-b][1,3]oxazol]-3'-one | Calc'd 383, found 383 |
| 4.204 | 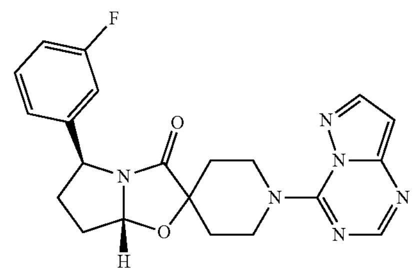 [SMILES: O=C1N2[C@@H](CC[C@H]2c2cccc(F)c2)OC12CCN(c1ncnc3ccnn13)CC2] | (5'S,7a'R)-5'-(3-fluorophenyl)-1-(pyrazolo[1,5-a][1,3,5]triazin-4-yl)tetrahydro-3'H-spiro[piperidine-4,2'-pyrrolo[2,1-b][1,3]oxazol]-3'-one | Calc'd 409, found 409 |
| 4.205 | 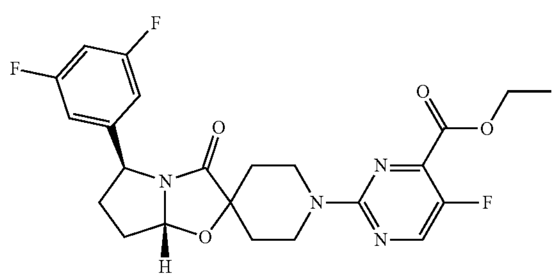 [SMILES: CCOC(=O)c1nc(N2CCC3(CC2)O[C@@H]2CC[C@@H](c4cc(F)cc(F)c4)N2C3=O)ncc1F] | ethyl 2-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-5-fluoropyrimidine-4-carboxylate | Calc'd 477, found 477 |
| 4.206 | 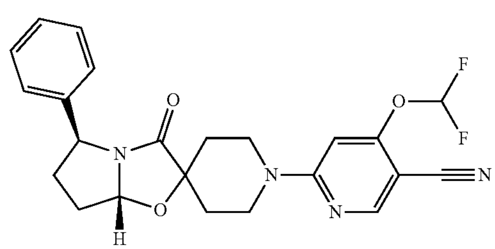 [SMILES: N#Cc1cnc(N2CCC3(CC2)O[C@@H]2CC[C@@H](c4ccccc4)N2C3=O)cc1OC(F)F] | 4-(difluoromethoxy)-6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carbonitrile | Calc'd 441, found 441 |
| 4.207 | 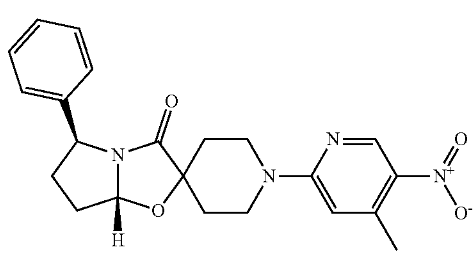 [SMILES: Cc1cc(N2CCC3(CC2)O[C@@H]2CC[C@@H](c4ccccc4)N2C3=O)ncc1[N+](=O)[O-]] | (5'S,7a'R)-1-(4-methyl-5-nitropyridin-2-yl)-5'-phenyltetrahydro-3'H-spiro[piperidine-4,2'-pyrrolo[2,1-b][1,3]oxazol]-3'-one | Calc'd 409, found 409 |

TABLE 13-continued

| Ex. No. | Name | Exact Mass [M + H]+ |
|---|---|---|
| 4.208 | (5'S,7a'R)-1-[4-(4-fluorophenyl)-5-nitropyridin-2-yl]-5'-phenyltetrahydro-3'H-spiro[piperidine-4,2'-pyrrolo[2,1-b][1,3]oxazol]-3'-one | Calc'd 489, found 489 |
| 4.209 | (5'S,7a'R)-1-(4-fluoro-5-hydroxypyridin-2-yl)-5'-phenyltetrahydro-3'H-spiro[piperidine-4,2'-pyrrolo[2,1-b][1,3]oxazol]-3'-one | Calc'd 384, found 384 |
| 4.210 | methyl 4-methoxy-6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carboxylate | Calc'd 438, found 483 |
| 4.211 | methyl 4-chloro-6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carboxylate | Calc'd 442, found 442 |
| 4.212 | 5-[(5'S,7a'R)-3'-oxo-5'-phenyltetrahydro-1H,3'H-spiro[piperidine-4,2'-pyrrolo[2,1-b][1,3]oxazol]-1-yl][1,2,4]triazolo[1,5-a]pyridine-8-carboxamide | Calc'd 433, found 433 |

TABLE 13-continued

| Ex. No. | Structure | Name | Exact Mass [M + H]+ |
|---|---|---|---|
| 4.213 | 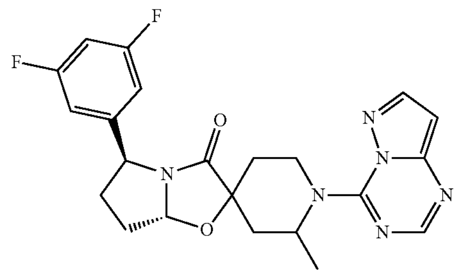 [SMILES: CC1CC2(CCN1c1ncnc3ccnn13)O[C@@H]1CC[C@@H](c3cc(F)cc(F)c3)N1C2=O] | (5'S,7a'R)-5'-(3,5-difluorophenyl)-2-methyl-1-(pyrazolo[1,5-a][1,3,5]triazin-4-yl)tetrahydro-3'H-spiro[piperidine-4,2'-pyrrolo[2,1-b][1,3]oxazol]-3'-one | Calc'd 441, found 441 |
| 4.214 | 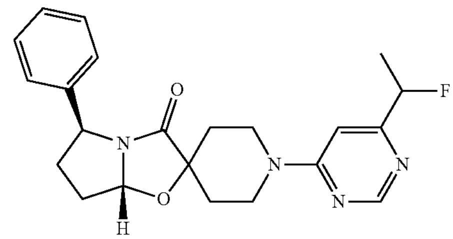 [SMILES: CC(F)c1cc(N2CCC3(CC2)O[C@@H]2CC[C@@H](c4ccccc4)N2C3=O)ncn1] | (5'S,7a'R)-1-[6-(1-fluoroethyl)pyrimidin-4-yl]-5'-phenyltetrahydro-3'H-spiro[piperidine-4,2'-pyrrolo[2,1-b][1,3]oxazol]-3'-one | Calc'd 397, found 397 |
| 4.215 | 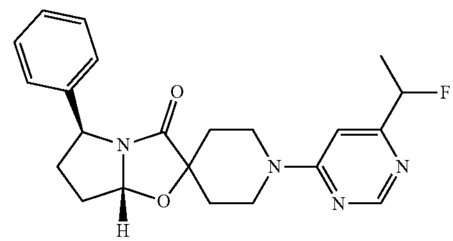 [SMILES: CC(F)c1cc(N2CCC3(CC2)O[C@@H]2CC[C@@H](c4ccccc4)N2C3=O)ncn1] | (5'S,7a'R)-1-[6-(1-fluoroethyl)pyrimidin-4-yl]-5'-phenyltetrahydro-3'H-spiro[piperidine-4,2'-pyrrolo[2,1-b][1,3]oxazol]-3'-one | Calc'd 397, found 397 |
| 4.216 | 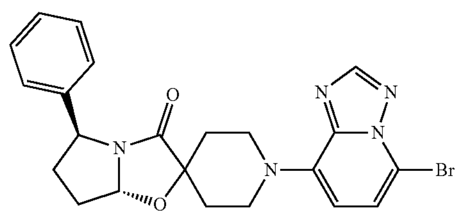 [SMILES: O=C1N2[C@@H](CC[C@H]2c2ccccc2)OC12CCN(c1ccc(Br)n3ncnc13)CC2] | (5'S,7a'R)-1-(5-bromo[1,2,4]triazolo[1,5-a]pyridin-8-yl)-5'-phenyltetrahydro-3'H-spiro[piperidine-4,2'-pyrrolo[2,1-b][1,3]oxazol]-3'-one | Calc'd 468, found 468 |
| 4.217 | 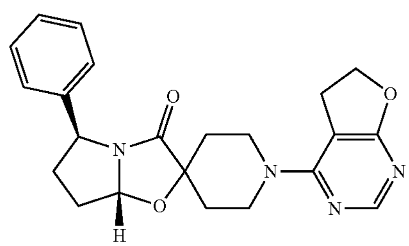 [SMILES: O=C1N2[C@@H](CC[C@H]2c2ccccc2)OC12CCN(c1ncnc3c1CCO3)CC2] | (5'S,7a'R)-1-(5,6-dihydrofuro[2,3-d]pyrimidin-4-yl)-5'-phenyltetrahydro-3'H-spiro[piperidine-4,2'-pyrrolo[2,1-b][1,3]oxazol]-3'-one | Calc'd 393, found 393 |
| 4.218 | 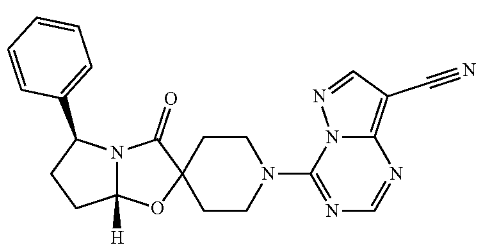 [SMILES: N#Cc1cnn2c(N3CCC4(CC3)O[C@@H]3CC[C@@H](c5ccccc5)N3C4=O)ncnc12] | 4-[(5'S,7a'R)-3'-oxo-5'-phenyltetrahydro-1H,3'H-spiro[piperidine-4,2'-pyrrolo[2,1-b][1,3]oxazol]-1-yl]pyrazolo[1,5-a][1,3,5]triazine-8-carbonitrile | Calc'd 416, found 416 |

TABLE 13-continued

| Ex. No. | Structure | Name | Exact Mass [M + H]+ |
|---|---|---|---|
| 4.219 | 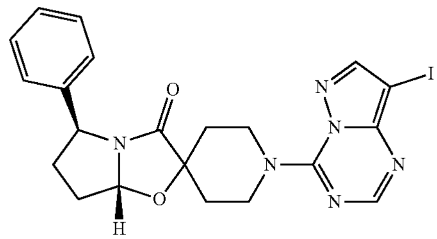 [SMILES: O=C1N2[C@@H](CC[C@H]2c2ccccc2)OC12CCN(c1ncnc3c(I)cnn13)CC2] | (5'S,7a'R)-1-(8-iodopyrazolo[1,5-a][1,3,5]triazin-4-yl)-5'-phenyltetrahydro-3'H-spiro[piperidine-4,2'-pyrrolo[2,1-b][1,3]oxazol]-3'-one | Calc'd 517, found 517 |
| 4.220 | 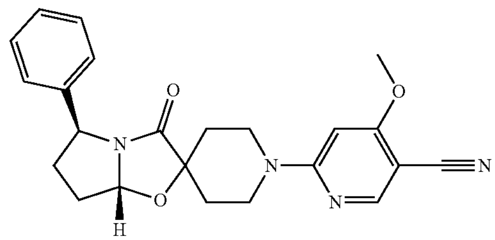 [SMILES: COc1cc(N2CCC3(CC2)O[C@@H]2CC[C@@H](c4ccccc4)N2C3=O)ncc1C#N] | 4-methoxy-6-[(5'S,7a'R)-3'-oxo-5'-phenyltetrahydro-1H,3'H-spiro[piperidine-4,2'-pyrrolo[2,1-b][1,3]oxazol]-1-yl]pyridine-3-carbonitrile | Calc'd 405, found 405 |
| 4.221 | 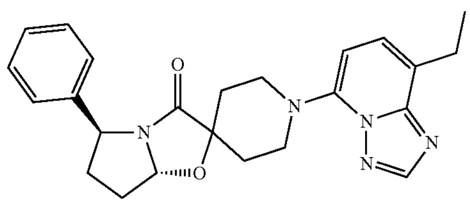 [SMILES: CCc1ccc(N2CCC3(CC2)O[C@@H]2CC[C@@H](c4ccccc4)N2C3=O)n2ncnc12] | (5'S,7a'R)-1-(8-ethyl[1,2,4]triazolo[1,5-a]pyridin-5-yl)-5'-phenyltetrahydro-3'H-spiro[piperidine-4,2'-pyrrolo[2,1-b][1,3]oxazol]-3'-one | Calc'd 418, found 418 |
| 4.222 | 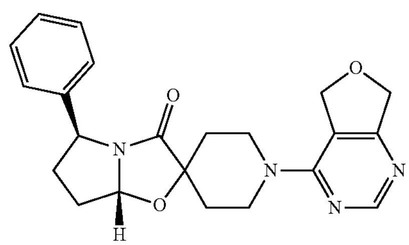 [SMILES: O=C1N2[C@@H](CC[C@H]2c2ccccc2)OC12CCN(c1ncnc3c1COC3)CC2] | (5'S,7a'R)-1-(5,7-dihydrofuro[3,4-d]pyrimidin-4-yl)-5'-phenyltetrahydro-3'H-spiro[piperidine-4,2'-pyrrolo[2,1-b][1,3]oxazol]-3'-one | Calc'd 393, found 393 |
| 4.223 | 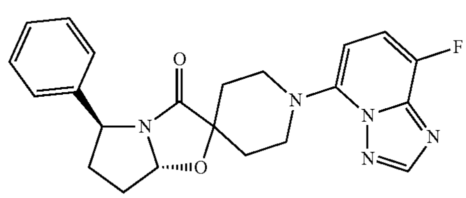 [SMILES: O=C1N2[C@@H](CC[C@H]2c2ccccc2)OC12CCN(c1ccc(F)c3ncnn13)CC2] | (5'S,7a'R)-1-(8-fluoro[1,2,4]triazolo[1,5-a]pyridin-5-yl)-5'-phenyltetrahydro-3'H-spiro[piperidine-4,2'-pyrrolo[2,1-b][1,3]oxazol]-3'-one | Calc'd 408, found 408 |
| 4.224 | 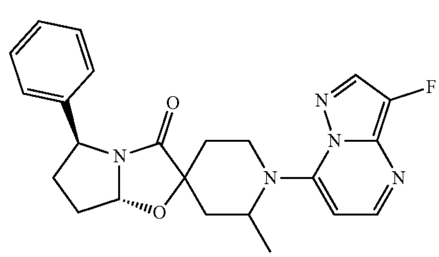 | (4R,5'S,7a'R)-1-(3-fluoropyrazolo[1,5-a]pyrimidin-7-yl)-2-methyl-5'-phenyltetrahydro-3'H-spiro[piperidine-4,2'-pyrrolo[2,1-b][1,3]oxazol]-3'-one | Calc'd 422, found 422 |

TABLE 13-continued

| Ex. No. | Structure | Name | Exact Mass [M + H]+ |
|---|---|---|---|
| 4.225 | 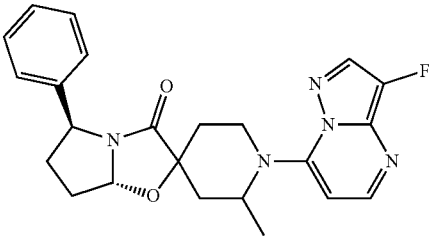 | (4R,5'S,7a'R)-1-(3-fluoropyrazolo[1,5-a]pyrimidin-7-yl)-2-methyl-5'-phenyltetrahydro-3'H-spiro[piperidine-4,2'-pyrrolo[2,1-b][1,3]oxazol]-3'-one | Calc'd 422, found 422 |
| 4.226 | 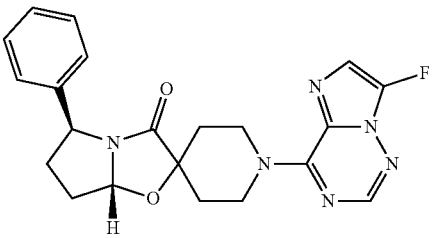 [SMILES: O=C1N2[C@@H](CC[C@H]2c2ccccc2)OC12CCN(c1ncnn3c(F)cnc13)CC2] | (5'S,7a'R)-1-(7-fluoroimidazo[2,1-f][1,2,4]triazin-4-yl)-5'-phenyltetrahydro-3'H-spiro[piperidine-4,2'-pyrrolo[2,1-b][1,3]oxazol]-3'-one | Calc'd 409, found 409 |
| 4.227 | 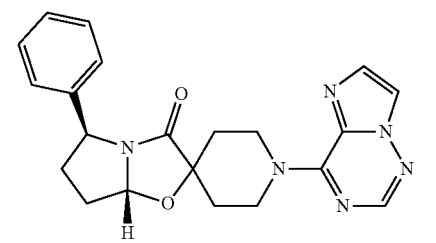 [SMILES: O=C1N2[C@@H](CC[C@H]2c2ccccc2)OC12CCN(c1ncnn3ccnc13)CC2] | (5'S,7a'R)-1-(imidazo[2,1-f][1,2,4]triazin-4-yl)-5'-phenyltetrahydro-3'H-spiro[piperidine-4,2'-pyrrolo[2,1-b][1,3]oxazol]-3'-one | Calc'd 391, found 391 |
| 4.228 | 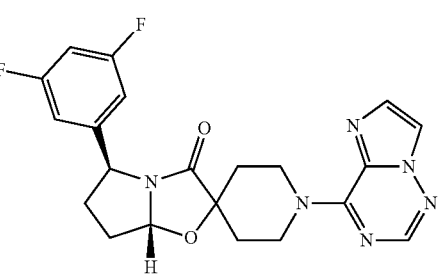 | (5'S,7a'R)-5'-(3,5-difluorophenyl)-1-(imidazo[2,1-f][1,2,4]triazin-4-yl)tetrahydro-3'H-spiro[piperidine-4,2'-pyrrolo[2,1-b][1,3]oxazol]-3'-one | Calc'd 427, found 427 |
| 4.229 | 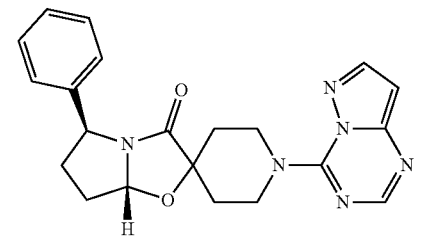 [SMILES: O=C1N2[C@@H](CC[C@H]2c2ccccc2)OC12CCN(c1ncnc3ccnn13)CC2] | (5'S,7a'R)-5'-phenyl-1-(pyrazolo[1,5-a][1,3,5]triazin-4-yl)tetrahydro-3'H-spiro[piperidine-4,2'-pyrrolo[2,1-b][1,3]oxazol]-3'-one | Calc'd 391, found 391 |
| 4.230 | 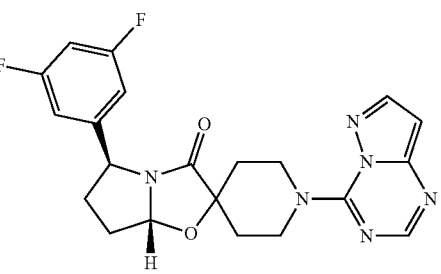 | (5'S,7a'R)-5'-(3,5-difluorophenyl)-1-(pyrazolo[1,5-a][1,3,5]triazin-4-yl)tetrahydro-3'H-spiro[piperidine-4,2'-pyrrolo[2,1-b][1,3]oxazol]-3'-one | Calc'd 427, found 427 |

TABLE 13-continued

| Ex. No. | Structure | Name | Exact Mass [M + H]+ |
|---|---|---|---|
| 4.231 | 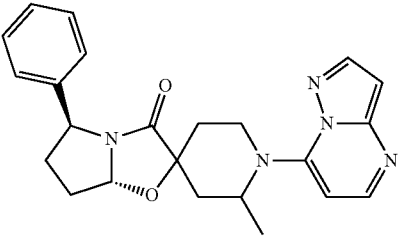 | (4R,5'S,7a'R)-2-methyl-5'-phenyl-1-(pyrazolo[1,5-a]pyrimidin-7-yl)tetrahydro-3'H-spiro[piperidine-4,2'-pyrrolo[2,1-b][1,3]oxazol]-3'-one | Calc'd 404, found 404 |
| 4.232 | 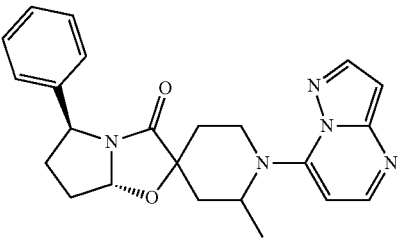 | (4R,5'S,7a'R)-2-methyl-5'-phenyl-1-(pyrazolo[1,5-a]pyrimidin-7-yl)tetrahydro-3'H-spiro[piperidine-4,2'-pyrrolo[2,1-b][1,3]oxazol]-3'-one | Calc'd 404, found 404 |
| 4.233 | 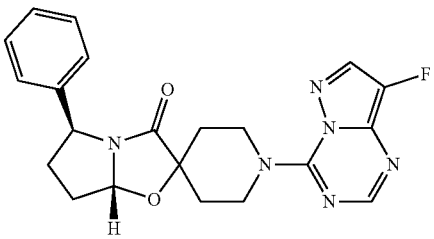 | (5'S,7a'R)-1-(8-fluoropyrazolo[1,5-a][1,3,5]triazin-4-yl)-5'-phenyltetrahydro-3'H-spiro[piperidine-4,2'-pyrrolo[2,1-b][1,3]oxazol]-3'-one | Calc'd 409, found 409 |
| 4.234 | 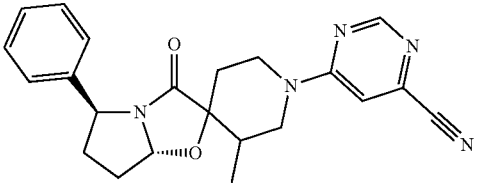 | 6-[(4R,5'S,7a'R)-3-methyl-3'-oxo-5'-phenyltetrahydro-1H,3'H-spiro[piperidine-4,2'-pyrrolo[2,1-b][1,3]oxazol]-1-yl]pyrimidine-4-carbonitrile | Calc'd 390, found 390 |
| 4.235 | 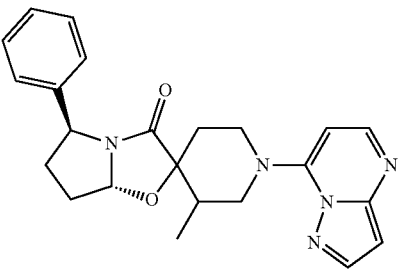 | (4R,5'S,7a'R)-3-methyl-5'-phenyl-1-(pyrazolo[1,5-a]pyrimidin-7-yl)tetrahydro-3'H-spiro[piperidine-4,2'-pyrrolo[2,1-b][1,3]oxazol]-3'-one | Calc'd 404, found 404 |
| 4.236 | 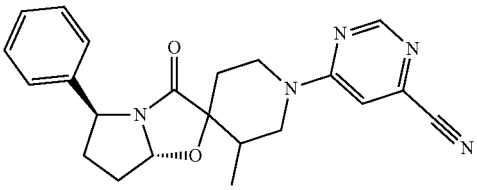 | 6-[(4R,5'S,7a'R)-3-methyl-3'-oxo-5'-phenyltetrahydro-1H,3'H-spiro[piperidine-4,2'-pyrrolo[2,1-b][1,3]oxazol]-1-yl]pyrimidine-4-carbonitrile | Calc'd 390, found 390 |

TABLE 13-continued

| Ex. No. | Structure | Name | Exact Mass [M + H]+ |
|---|---|---|---|
| 4.237 | 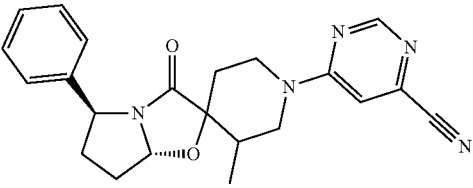 | 6-[(4R,5'S,7a'R)-3-methyl-3'-oxo-5'-phenyltetrahydro-1H,3'H-spiro[piperidine-4,2'-pyrrolo[2,1-b][1,3]oxazol]-1-yl]pyrimidine-4-carbonitrile | Calc'd 390, found 390 |
| 4.238 | 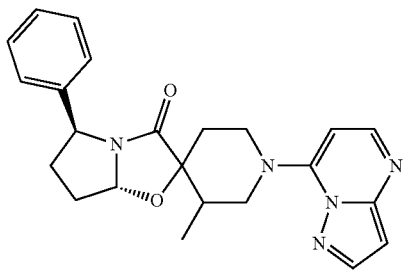 | (4R,5'S,7a'R)-3-methyl-5'-phenyl-1-(pyrazolo[1,5-a]pyrimidin-7-yl)tetrahydro-3'H-spiro[piperidine-4,2'-pyrrolo[2,1-b][1,3]oxazol]-3'-one | Calc'd 404, found 404 |
| 4.239 | 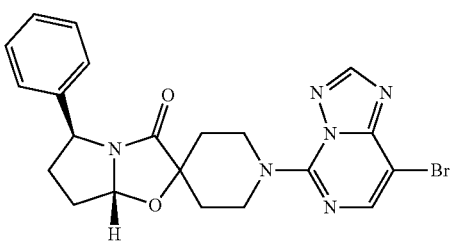 [SMILES: O=C1N2[C@@H](CC[C@H]2c2ccccc2)OC12CCN(c1ncc(Br)c3ncnn13)CC2] | (5'S,7a'R)-1-(8-bromo[1,2,4]triazolo[1,5-c]pyrimidin-5-yl)-5'-phenyltetrahydro-3'H-spiro[piperidine-4,2'-pyrrolo[2,1-b][1,3]oxazol]-3'-one | Calc'd 469, found 469 |
| 4.240 | 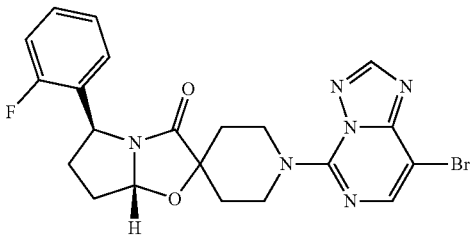 [SMILES: O=C1N2[C@@H](CC[C@H]2c2ccccc2F)OC12CCN(c1ncc(Br)c3ncnn13)CC2] | (5'S,7a'R)-1-(8-bromo[1,2,4]triazolo[1,5-c]pyrimidin-5-yl)-5'-(2-fluorophenyl)tetrahydro-3'H-spiro[piperidine-4,2'-pyrrolo[2,1-b][1,3]oxazol]-3'-one | Calc'd 487, found 487 |
| 4.241 | 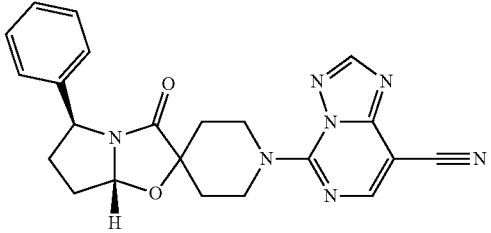 | 5-[(5'S,7a'R)-3'-oxo-5'-phenyltetrahydro-1H,3'H-spiro[piperidine-4,2'-pyrrolo[2,1-b][1,3]oxazol]-1-yl][1,2,4]triazolo[1,5-c]pyrimidine-8-carbonitrile | Calc'd 416, found 416 |
| 4.242 | 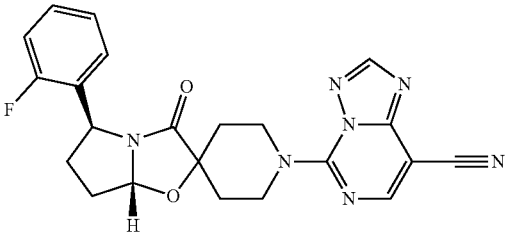 [SMILES: N#Cc1cnc(N2CCC3(CC2)O[C@@H]2CC[C@@H](c4ccccc4F)N2C3=O)n2ncnc12] | 5-[(5'S,7a'R)-5'-(2-fluorophenyl)-3'-oxotetrahydro-1H,3'H-spiro[piperidine-4,2'-pyrrolo[2,1-b][1,3]oxazol]-1-yl][1,2,4]triazolo[1,5-c]pyrimidine-8-carbonitrile | Calc'd 434, found 434 |

TABLE 13-continued

| Ex. No. | Structure | Name | Exact Mass [M + H]⁺ |
|---|---|---|---|
| 4.243 | 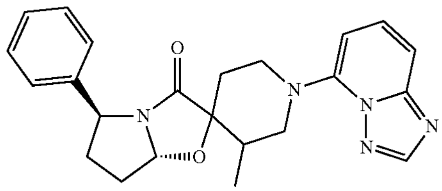 | (4R,5'S,7a'R)-3-methyl-5'-phenyl-1-([1,2,4]triazolo[1,5-a]pyridin-5-yl)tetrahydro-3'H-spiro[piperidine-4,2'-pyrrolo[2,1-b][1,3]oxazol]-3'-one | Calc'd 404, found 404 |
| 4.244 | 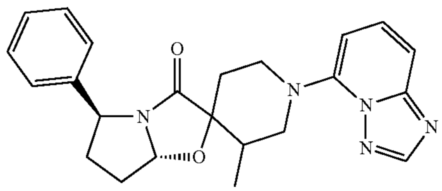 | (4R,5'S,7a'R)-3-methyl-5'-phenyl-1-([1,2,4]triazolo[1,5-a]pyridin-5-yl)tetrahydro-3'H-spiro[piperidine-4,2'-pyrrolo[2,1-b][1,3]oxazol]-3'-one | Calc'd 404, found 404 |
| 4.245 | 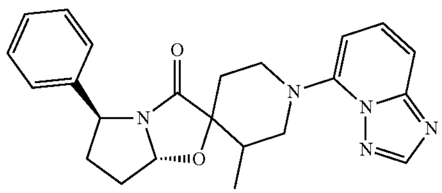 | (4R,5'S,7a'R)-3-methyl-5'-phenyl-1-([1,2,4]triazolo[1,5-a]pyridin-5-yl)tetrahydro-3'H-spiro[piperidine-4,2'-pyrrolo[2,1-b][1,3]oxazol]-3'-one | Calc'd 404, found 404 |
| 4.246 | 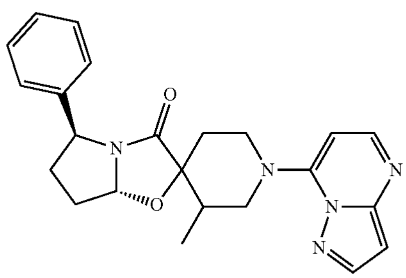 | (4R,5'S,7a'R)-3-methyl-5'-phenyl-1-(pyrazolo[1,5-a]pyrimidin-7-yl)tetrahydro-3'H-spiro[piperidine-4,2'-pyrrolo[2,1-b][1,3]oxazol]-3'-one | Calc'd 404, found 404 |
| 4.247 | 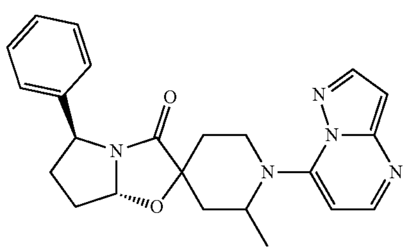 | (4R,5'S,7a'R)-2-methyl-5'-phenyl-1-(pyrazolo[1,5-a]pyrimidin-7-yl)tetrahydro-3'H-spiro[piperidine-4,2'-pyrrolo[2,1-b][1,3]oxazol]-3'-one | Calc'd 404, found 404 |
| 4.248 | 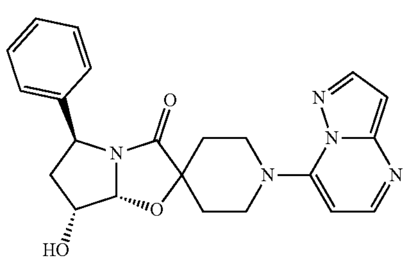 [SMILES: O=C1N2[C@H](OC13CCN(c1ccnc4ccnn14)CC3)[C@H](O)C[C@H]2c1ccccc1] | (5'S,7'R,7a'R)-7'-hydroxy-5'-phenyl-1-(pyrazolo[1,5-a]pyrimidin-7-yl)tetrahydro-3'H-spiro[piperidine-4,2'-pyrrolo[2,1-b][1,3]oxazol]-3'-one | Calc'd 406, found 406 |

TABLE 13-continued

| Ex. No. | Structure | Name | Exact Mass [M + H]+ |
|---|---|---|---|
| 4.249 | 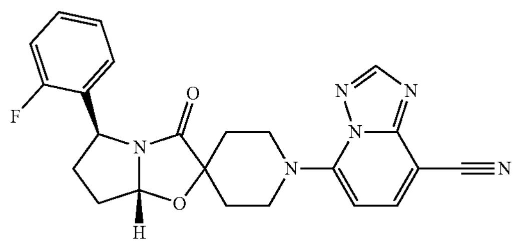 [SMILES: N#Cc1ccc(N2CCC3(CC2)O[C@@H]2CC[C@@H](c4ccccc4F)N2C3=O)n2ncnc12] | 5-[(5'S,7a'R)-5'-(2-fluorophenyl)-3'-oxotetrahydro-1H,3'H-spiro[piperidine-4,2'-pyrrolo[2,1-b][1,3]oxazol]-1-yl][1,2,4]triazolo[1,5-a]pyridine-8-carbonitrile | Calc'd 433, found 433 |
| 4.250 | 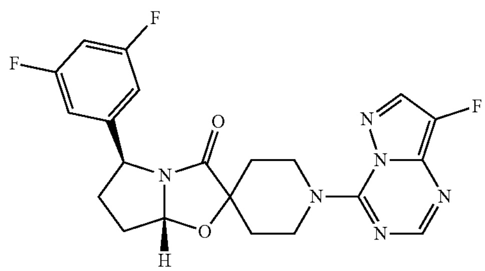 [SMILES: O=C1N2[C@@H](CC[C@H]2c2cc(F)cc(F)c2)OC12CCN(c1ncnc3c(F)cnn13)CC2] | (5'S,7a'R)-5'-(3,5-difluorophenyl)-1-(8-fluoropyrazolo[1,5-a][1,3,5]triazin-4-yl)tetrahydro-3'H-spiro[piperidine-4,2'-pyrrolo[2,1-b][1,3]oxazol]-3'-one | Calc'd 445, found 445 |
| 4.251 | 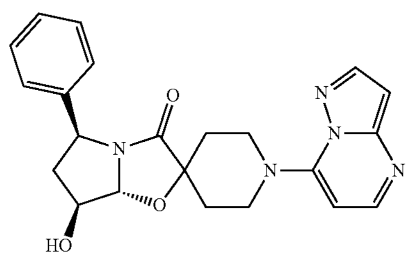 [SMILES: O=C1N2[C@H](OC13CCN(c1ccnc4ccnn14)CC3)[C@@H](O)C[C@H]2c1ccccc1] | (5'S,7'S,7a'R)-7'-hydroxy-5'-phenyl-1-(pyrazolo[1,5-a]pyrimidin-7-yl)tetrahydro-3'H-spiro[piperidine-4,2'-pyrrolo[2,1-b][1,3]oxazol]-3'-one | Calc'd 406, found 406 |
| 4.252 | 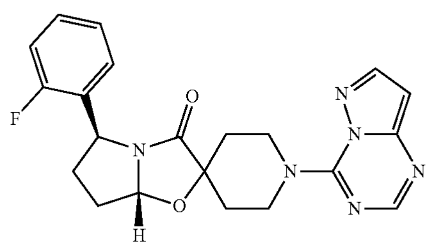 | (5'S,7a'R)-5'-(2-fluorophenyl)-1-(pyrazolo[1,5-a][1,3,5]triazin-4-yl)tetrahydro-3'H-spiro[piperidine-4,2'-pyrrolo[2,1-b][1,3]oxazol]-3'-one | Calc'd 409, found 409 |
| 4.253 | 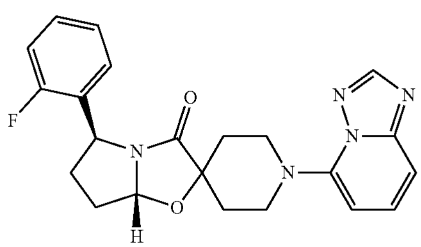 [SMILES: O=C1N2[C@@H](CC[C@H]2c2ccccc2F)OC12CCN(c1cccc3ncnn13)CC2] | (5'S,7a'R)-5'-(2-fluorophenyl)-1-([1,2,4]triazolo[1,5-a]pyridin-5-yl)tetrahydro-3'H-spiro[piperidine-4,2'-pyrrolo[2,1-b][1,3]oxazol]-3'-one | Calc'd 408, found 408 |
| 4.254 | 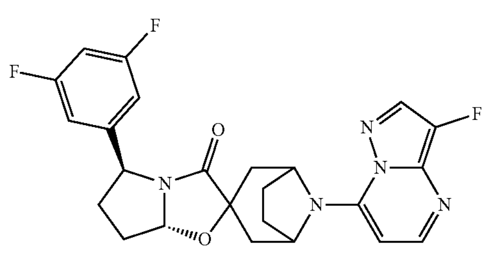 | (5'S,7a'R)-5'-(3,5-difluorophenyl)-8-(3-fluoropyrazolo[1,5-a]pyrimidin-7-yl)tetrahydro-3'H-spiro[8-azabicyclo[3.2.1]octane-3,2'-pyrrolo[2,1-b][1,3]oxazol]-3'-one | Calc'd 470, found 470 |

TABLE 13-continued

| Ex. No. | Structure | Name | Exact Mass [M + H]+ |
|---|---|---|---|
| 4.255 | 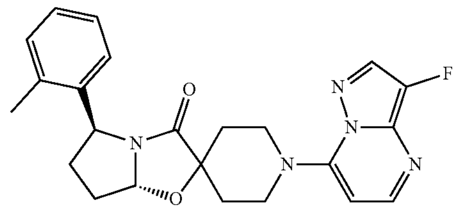 [SMILES: Cc1ccccc1[C@@H]1CC[C@H]2OC3(CCN(c4ccnc5c(F)cnn45)CC3)C(=O)N21] | (5'S,7a'R)-1-(3-fluoropyrazolo[1,5-a]pyrimidin-7-yl)-5'-(2-methylphenyl)tetrahydro-3'H-spiro[piperidine-4,2'-pyrrolo[2,1-b][1,3]oxazol]-3'-one | Calc'd 422, found 422 |
| 4.256 | 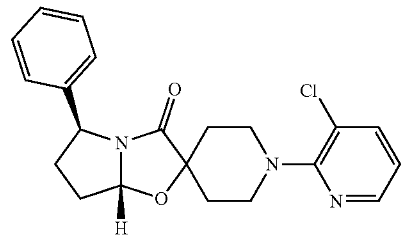 [SMILES: O=C1N2[C@@H](CC[C@H]2c2ccccc2)OC12CCN(c1ncccc1Cl)CC2] | (5'S,7a'R)-1-(3-chloropyridin-2-yl)-5'-phenyltetrahydro-3'H-spiro[piperidine-4,2'-pyrrolo[2,1-b][1,3]oxazol]-3'-one | Calc'd 384, found 384 |
| 4.257 | 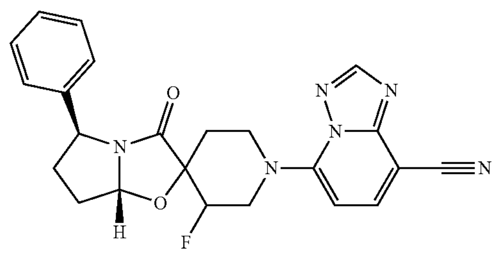 [SMILES: N#Cc1ccc(N2CCC3(O[C@@H]4CC[C@@H](c5ccccc5)N4C3=O)C(F)C2)n2ncnc12] | 5-[(5'S,7a'R)-3-fluoro-3'-oxo-5'-phenyltetrahydro-1H,3'H-spiro[piperidine-4,2'-pyrrolo[2,1-b][1,3]oxazol]-1-yl][1,2,4]triazolo[1,5-a]pyridine-8-carbonitrile | Calc'd 433, found 433 |
| 4.258 | 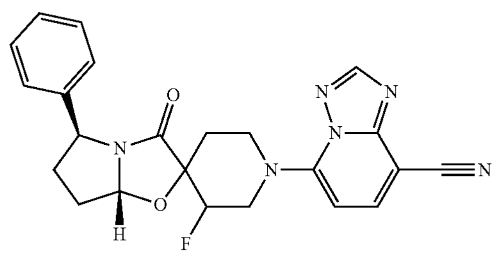 [SMILES: N#Cc1ccc(N2CCC3(O[C@@H]4CC[C@@H](c5ccccc5)N4C3=O)C(F)C2)n2ncnc12] | 5-[(5'S,7a'R)-3-fluoro-3'-oxo-5'-phenyltetrahydro-1H,3'H-spiro[piperidine-4,2'-pyrrolo[2,1-b][1,3]oxazol]-1-yl][1,2,4]triazolo[1,5-a]pyridine-8-carbonitrile | Calc'd 433, found 433 |
| 4.259 | 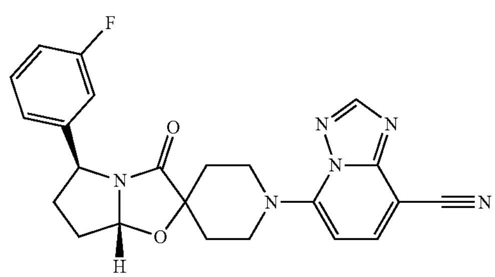 [SMILES: N#Cc1ccc(N2CCC3(CC2)O[C@@H]2CC[C@@H](c4cccc(F)c4)N2C3=O)n2ncnc12] | 5-[(5'S,7a'R)-5'-(3-fluorophenyl)-3'-oxotetrahydro-1H,3'H-spiro[piperidine-4,2'-pyrrolo[2,1-b][1,3]oxazol]-1-yl][1,2,4]triazolo[1,5-a]pyridine-8-carbonitrile | Calc'd 433, found 433 |
| 4.260 | 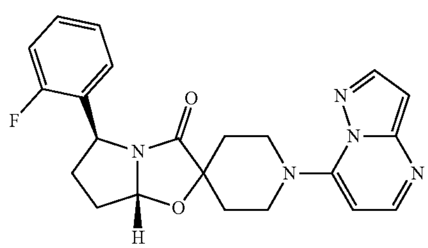 [SMILES: O=C1N2[C@@H](CC[C@H]2c2ccccc2F)OC12CCN(c1ccnc3ccnn13)CC2] | (5'S,7a'R)-5'-(2-fluorophenyl)-1-(pyrazolo[1,5-a]pyrimidin-7-yl)tetrahydro-3'H-spiro[piperidine-4,2'-pyrrolo[2,1-b][1,3]oxazol]-3'-one | Calc'd 408, found 408 |

TABLE 13-continued

| Ex. No. | Structure | Name | Exact Mass [M + H]+ |
|---|---|---|---|
| 4.261 | 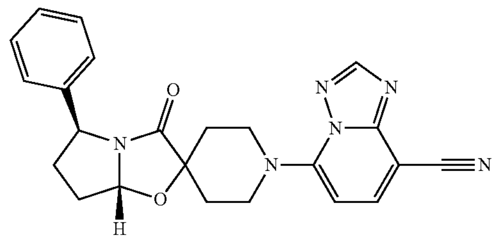 [SMILES: N#Cc1ccc(N2CCC3(CC2)O[C@@H]2CC[C@@H](c4ccccc4)N2C3=O)n2ncnc12] | 5-[(5'S,7a'R)-3'-oxo-5'-phenyltetrahydro-1H,3'H-spiro[piperidine-4,2'-pyrrolo[2,1-b][1,3]oxazol]-1-yl][1,2,4]triazolo[1,5-a]pyridine-8-carbonitrile | Calc'd 415, found 415 |
| 4.262 | 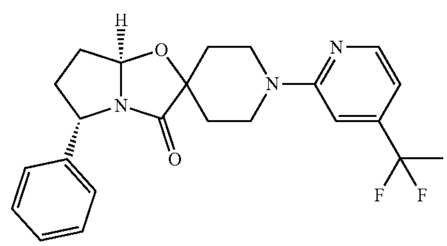 [SMILES: CC(F)(F)c1ccnc(N2CCC3(CC2)O[C@@H]2CC[C@@H](c4ccccc4)N2C3=O)c1] | (5'S,7a'R)-1-[4-(1,1-difluoroethyl)pyridin-2-yl]-5'-phenyltetrahydro-3'H-spiro[piperidine-4,2'-pyrrolo[2,1-b][1,3]oxazol]-3'-one | Calc'd 414, found 414 |
| 4.263 | 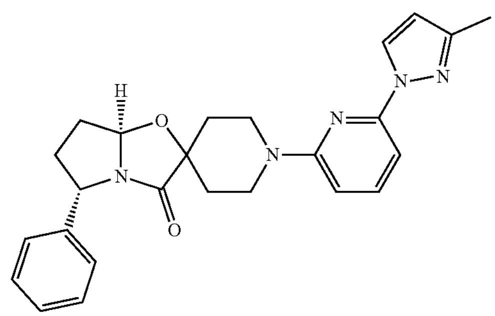 [SMILES: Cc1ccn(-c2cccc(N3CCC4(CC3)O[C@@H]3CC[C@@H](c5ccccc5)N3C4=O)n2)n1] | (5'S,7a'R)-1-[6-(3-methyl-1H-pyrazol-1-yl)pyridin-2-yl]-5'-phenyltetrahydro-3'H-spiro[piperidine-4,2'-pyrrolo[2,1-b][1,3]oxazol]-3'-one | Calc'd 430, found 430 |
| 4.264 | 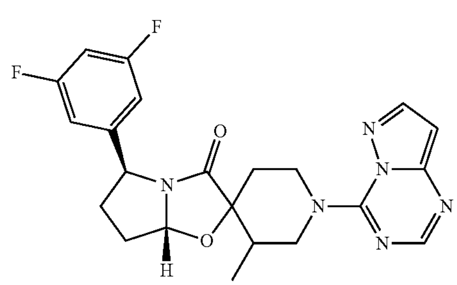 [SMILES: CC1CN(c2ncnc3ccnn23)CCC12O[C@@H]1CC[C@@H](c3cc(F)cc(F)c3)N1C2=O] | (5'S,7a'R)-5'-(3,5-difluorophenyl)-3-methyl-1-(pyrazolo[1,5-a][1,3,5]triazin-4-yl)tetrahydro-3'H-spiro[piperidine-4,2'-pyrrolo[2,1-b][1,3]oxazol]-3'-one | Calc'd 441, found 441 |
| 4.265 | 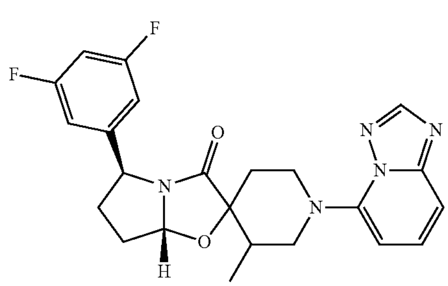 [SMILES: CC1CN(c2cccc3ncnn23)CCC12O[C@@H]1CC[C@@H](c3cc(F)cc(F)c3)N1C2=O] | (5'S,7a'R)-5'-(3,5-difluorophenyl)-3-methyl-1-([1,2,4]triazolo[1,5-a]pyridin-5-yl)tetrahydro-3'H-spiro[piperidine-4,2'-pyrrolo[2,1-b][1,3]oxazol]-3'-one | Calc'd 440, found 440 |

TABLE 13-continued

| Ex. No. | Structure | Name | Exact Mass [M + H]+ |
|---|---|---|---|
| 4.266 | 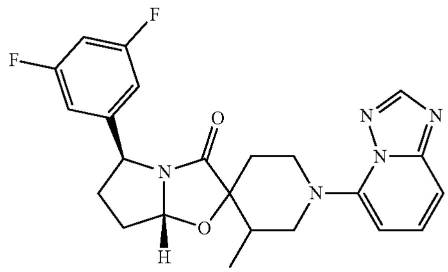 [SMILES: CC1CN(c2cccc3ncnn23)CCC12O[C@@H]1CC[C@@H](c3cc(F)cc(F)c3)N1C2=O] | (5'S,7a'R)-5'-(3,5-difluorophenyl)-3-methyl-1-([1,2,4]triazolo[1,5-a]pyridin-5-yl)tetrahydro-3'H-spiro[piperidine-4,2'-pyrrolo[2,1-b][1,3]oxazol]-3'-one | Calc'd 440, found 440 |
| 4.267 | 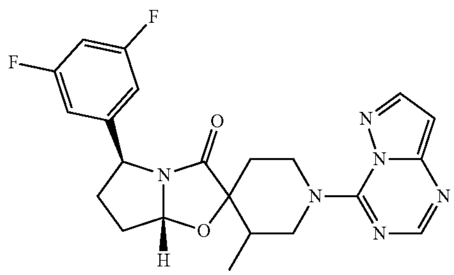 [SMILES: CC1CN(c2ncnc3ccnn23)CCC12O[C@@H]1CC[C@@H](c3cc(F)cc(F)c3)N1C2=O] | (5'S,7a'R)-5'-(3,5-difluorophenyl)-3-methyl-1-(pyrazolo[1,5-a][1,3,5]triazin-4-yl)tetrahydro-3'H-spiro[piperidine-4,2'-pyrrolo[2,1-b][1,3]oxazol]-3'-one | Calc'd 441, found 441 |
| 4.268 | 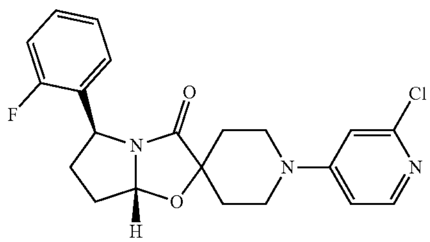 [SMILES: O=C1N2[C@@H](CC[C@H]2c2ccccc2F)OC12CCN(c1ccnc(Cl)c1)CC2] | (5'S,7a'R)-1-(2-chloropyridin-4-yl)-5'-(2-fluorophenyl)tetrahydro-3'H-spiro[piperidine-4,2'-pyrrolo[2,1-b][1,3]oxazol]-3'-one | Calc'd 402, found 402 |
| 4.269 | 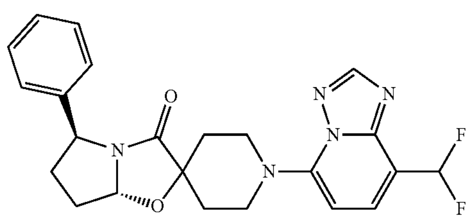 [SMILES: O=C1N2[C@@H](CC[C@H]2c2ccccc2)OC12CCN(c1ccc(C(F)F)c3ncnn13)CC2] | (5'S,7a'R)-1-[8-(difluoromethyl)[1,2,4]triazolo[1,5-a]pyridin-5-yl]-5'-phenyltetrahydro-3'H-spiro[piperidine-4,2'-pyrrolo[2,1-b][1,3]oxazol]-3'-one | Calc'd 440, found 440 |
| 4.270 | 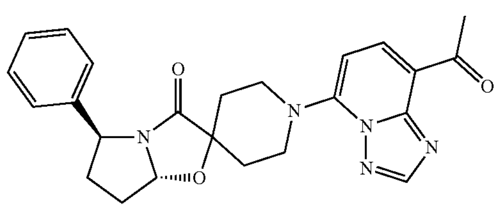 [SMILES: CC(=O)c1ccc(N2CCC3(CC2)O[C@@H]2CC[C@@H](c4ccccc4)N2C3=O)n2ncnc12] | (5'S,7a'R)-1-(8-acetyl[1,2,4]triazolo[1,5-a]pyridin-5-yl)-5'-phenyltetrahydro-3'H-spiro[piperidine-4,2'-pyrrolo[2,1-b][1,3]oxazol]-3'-one | Calc'd 432, found 432 |
| 4.271 | 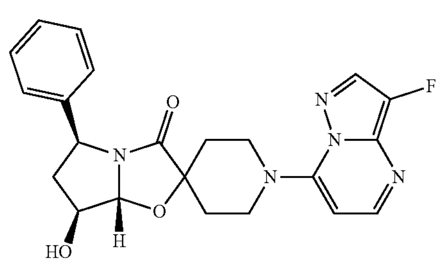 [SMILES: O=C1N2[C@H](OC13CCN(c1ccnc4c(F)cnn14)CC3)[C@@H](O)C[C@H]2c1ccccc1] | (5'S,7'S,7a'R)-1-(3-fluoropyrazolo[1,5-a]pyrimidin-7-yl)-7'-hydroxy-5'-phenyltetrahydro-3'H-spiro[piperidine-4,2'-pyrrolo[2,1-b][1,3]oxazol]-3'-one | Calc'd 424, found 424 |

TABLE 13-continued

| Ex. No. | Structure | Name | Exact Mass [M + H]+ |
|---|---|---|---|
| 4.272 | 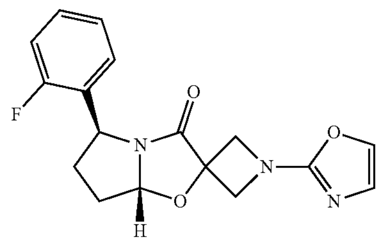 [SMILES: O=C1N2[C@@H](CC[C@H]2c2ccccc2F)OC12CN(c1ncco1)C2] | (5'S,7a'R)-5'-(2-fluorophenyl)-1-(1,3-oxazol-2-yl)tetrahydro-3'H-spiro[azetidine-3,2'-pyrrolo[2,1-b][1,3]oxazol]-3'-one | Calc'd 330, found 330 |
| 4.273 | 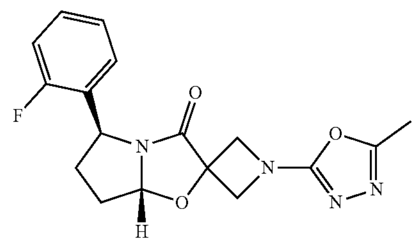 [SMILES: Cc1nnc(N2CC3(C2)O[C@@H]2CC[C@@H](c4ccccc4F)N2C3=O)o1] | (5'S,7a'R)-5'-(2-fluorophenyl)-1-(5-methyl-1,3,4-oxadiazol-2-yl)tetrahydro-3'H-spiro[azetidine-3,2'-pyrrolo[2,1-b][1,3]oxazol]-3'-one | Calc'd 345, found 345 |

Example 5.1

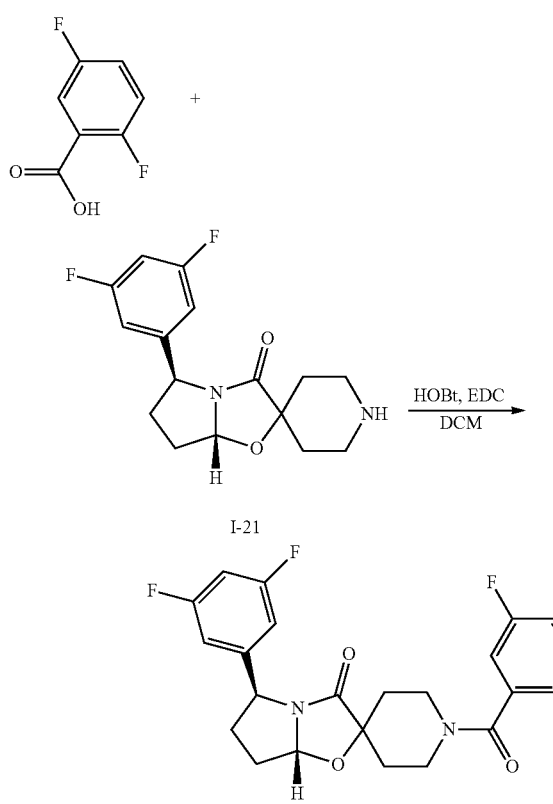

5.1

(5'S,7a'R)-1-(2,5-Difluorobenzoyl)-5'-(3,5-difluorophenyl)tetrahydro-3'H-spiro[piperidine-4,2'-pyrrolo[2,1-b]oxazol]-3'-one (5'S,7a'R)-5'-(3,5-Difluorophenyl)tetrahydro-3'H-spiro[piperidine-4,2'-pyrrolo[2,1-b]oxazol]-3'-one (12 mg, 0.039 mmol) was added to a vial with DCM (389 µL) at room temperature. HOBT (7.2 mg, 0.047 mmol) and 1-ethyl-3-(3-dimethylaminopropyl)carbodiimide (9.0 mg, 0.047 mmol) were added followed by 2,5-difluorobenzoic acid (7.38 mg, 0.047 mmol) in one portion. The mixture stirred was at room temperature for 3 h. The mixture was concentrated and taken up in DMA and residue was purified by preparative HPLC Reverse phase (C-18), eluting with acetonitrile/water+0.05% NH$_3$, to give (5'S,7a'R)-1-(2,5-difluorobenzoyl)-5'-(3,5-difluorophenyl)tetrahydro-3'H-spiro[piperidine-4,2'-pyrrolo[2,1-b]oxazol]-3'-one as a solid. MS (ESI) m/z C$_{23}$H$_{21}$F$_4$N$_2$O$_3$[M+H]+ calc'd 449, found 449. $^1$H NMR (499 MHz, DMSO-d6) δ 7.38 (tt, J=8.6, 4.2 Hz, 3H), 7.18-6.99 (m, 3H), 5.79 (ddd, J=28.3, 7.1, 5.0 Hz, 1H), 5.00-4.84 (m, 1H), 4.45-4.23 (m, 1H), 3.51-3.35 (m, 1H), 3.29-3.11 (m, 2H), 2.63 (tdd, J=10.7, 8.0, 5.3 Hz, 1H), 2.25-2.10 (m, 2H), 1.92-1.80 (m, 2H), 1.80-1.53 (m, 3H).

Compounds in Table 14 below were prepared from common intermediate I-21 or from compounds listed in Table 7 using the methods described in Example 5.1.

TABLE 14

| Ex. No | Structure | Name | Exact Mass [M + H]+ |
|---|---|---|---|
| 5.2 | 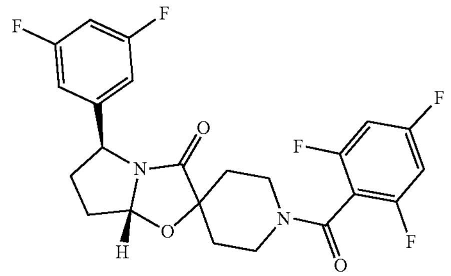 [SMILES: O=C(c1c(F)cc(F)cc1F)N1CCC2(CC1)O[C@@H]1CC[C@@H](c3cc(F)cc(F)c3)N1C2=O] | (5'S,7a'R)-5'-(3,5-difluorophenyl)-1-(2,4,6-trifluorobenzene-1-carbonyl)tetrahydro-3'H-spiro[piperidine-4,2'-pyrrolo[2,1-b][1,3]oxazol]-3'-one | Calc'd 467, found 467 |
| 5.3 | 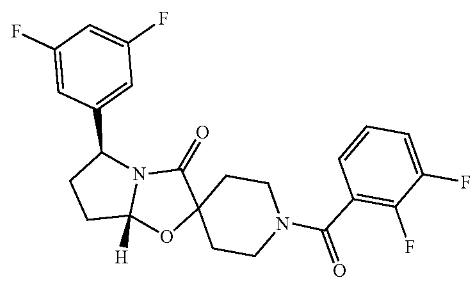 [SMILES: O=C(c1cccc(F)c1F)N1CCC2(CC1)O[C@@H]1CC[C@@H](c3cc(F)cc(F)c3)N1C2=O] | (5'S,7a'R)-1-(2,3-difluorobenzene-1-carbonyl)-5'-(3,5-difluorophenyl)tetrahydro3'H-spiro[piperidine-4,2'-pyrrolo[2,1-b][1,3]oxazol]-3'-one | Calc'd 449, found 449 |
| 5.4 | 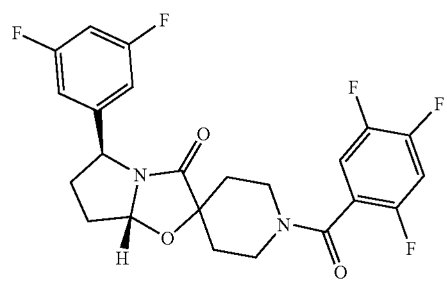 [SMILES: O=C(c1cc(F)c(F)cc1F)N1CCC2(CC1)O[C@@H]1CC[C@@H](c3cc(F)cc(F)c3)N1C2=O] | (5'S,7a'R)-5'-(3,5-difluorophenyl)-1-(2,4,5-trifluorobenzene-1-carbonyl)tetrahydro-3'H-spiro[piperidine-4,2'-pyrrolo[2,1-b][1,3]oxazol]-3'-one | Calc'd 467, found 467 |
| 5.5 | 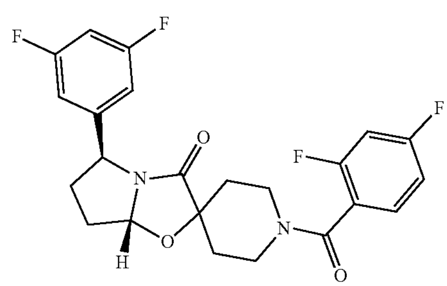 [SMILES: O=C(c1ccc(F)cc1F)N1CCC2(CC1)O[C@@H]1CC[C@@H](c3cc(F)cc(F)c3)N1C2=O] | (5'S,7a'R)-1-(2,4-difluorobenzene-1-carbonyl)5'-(3,5-difluorophenyl)tetrahydro-3'H-spiro[piperidine-4,2'-pyrrolo[2,1-b][1,3]oxazol]-3'-one | Calc'd 449, found 449 |
| 5.6 | 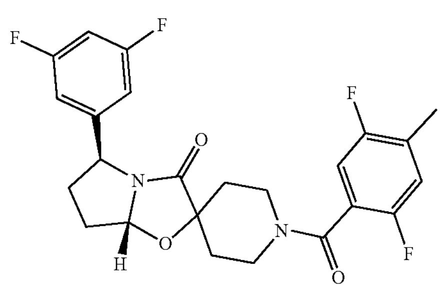 [SMILES: Cc1cc(F)c(C(=O)N2CCC3(CC2)O[C@@H]2CC[C@@H](c4cc(F)cc(F)c4)N2C3=O)cc1F] | (5'S,7a'R)-1-(2,5-difluoro-4-methylbenzene-1-carbonyl)-5'-(3,5-difluorophenyl)tetrahydro-3'H-spiro[piperidine-4,2'-pyrrolo[2,1-b][1,3]oxazol]-3'-one | Calc'd 463, found 463 |

TABLE 14-continued

| Ex. No | Structure | Name | Exact Mass [M + H]+ |
|---|---|---|---|
| 5.7 | 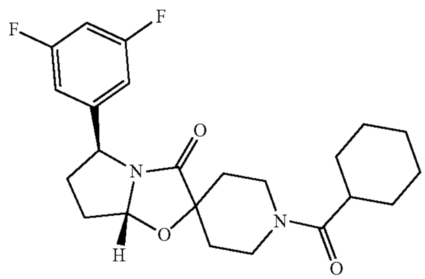 [SMILES: O=C(C1CCCCC1)N1CCC2(CC1)O[C@@H]1CC[C@@H](c3cc(F)cc(F)c3)N1C2=O] | (5'S,7a'R)-1-(cyclohexane-carbonyl)-5'-(3,5-difluoro-phenyl)tetrahydro-3'H-spiro[piperidine-4,2'-pyrrolo[2,1-b][1,3]oxazol]-3'-one | Calc'd 419, found 419 |
| 5.8 | 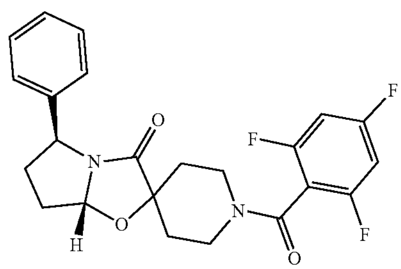 [SMILES: O=C(c1c(F)cc(F)cc1F)N1CCC2(CC1)O[C@@H]1CC[C@@H](c3ccccc3)N1C2=O] | (5'S,7a'R)-5'-phenyl-1-(2,4,6-trifluorobenzene-1-carbonyl)tetrahydro-3'H-spiro[piperidine-4,2'-pyrrolo[2,1-b][1,3]oxazol]-3'-one | Calc'd 431, found 431 |
| 5.9 | 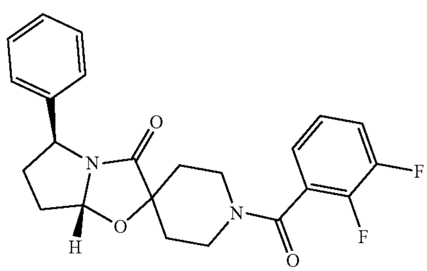 [SMILES: O=C(c1cccc(F)c1F)N1CCC2(CC1)O[C@@H]1CC[C@@H](c3ccccc3)N1C2=O] | (5'S,7a'R)-1-(2,3-difluorobenzene-1-car-bonyl)-5'-phenyltetra-hydro-3'H-spiro[piperi-dine-4,2'-pyrrolo[2,1-b][1,3]oxazol]-3'-one | Calc'd 413, found 413 |
| 5.10 | 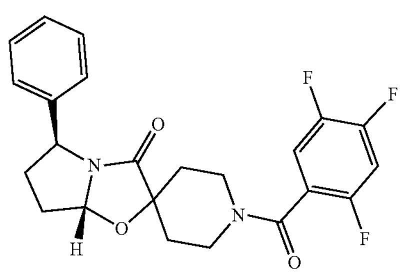 [SMILES: O=C(c1cc(F)c(F)cc1F)N1CCC2(CC1)O[C@@H]1CC[C@@H](c3ccccc3)N1C2=O] | (5'S,7a'R)-5'-phenyl-1-(2,4,5-trifluorobenzene-1-carbonyl)tetrahydro-3'H-spiro[piperidine-4,2'-pyrrolo[2,1-b][1,3]oxazol]-3'-one | Calc'd 431, found 431 |
| 5.11 | 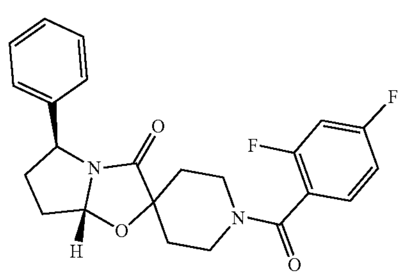 [SMILES: O=C(c1ccc(F)cc1F)N1CCC2(CC1)O[C@@H]1CC[C@@H](c3ccccc3)N1C2=O] | (5'S,7a'R)-1-(2,4-difluoro-benzene-1-carbonyl)-5'-phenyltetrahydro-3'H-spiro[piperidine-4,2'-pyrrolo[2,1-b][1,3]oxazol]-3'-one | Calc'd 413, found 413 |

TABLE 14-continued

| Ex. No | Structure | Name | Exact Mass [M + H]+ |
| --- | --- | --- | --- |
| 5.12 | 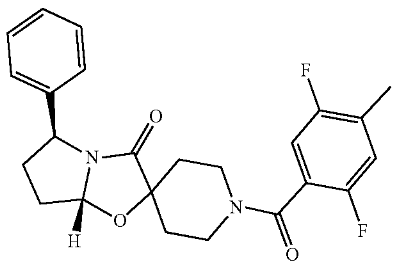 [SMILES: Cc1cc(F)c(C(=O)N2CCC3(CC2)O[C@@H]2CC[C@@H](c4ccccc4)N2C3=O)cc1F] | (5'S,7a'R)-1-(2,5-difluoro-4-methylbenzene-1-carbonyl)-5'-phenyltetrahydro-3'H-spiro[piperidine-4,2'-pyrrolo[2,1-b][1,3]oxazol]-3'-one | Calc'd 427, found 427 |
| 5.13 | 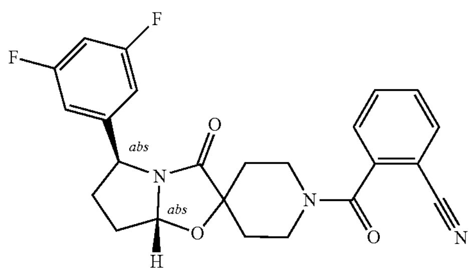 [SMILES: N#Cc1ccccc1C(=O)N1CCC2(CC1)O[C@@H]1CC[C@@H](c3cc(F)cc(F)c3)N1C2=O] | 2-((5'S,7a'R)-5'-(3,5-difluorophenyl)-3'-oxotetrahydro-3'H-spiro[piperidine-4,2'-pyrrolo-[2,1-b]oxazole]-1-carbonyl)benzonitrile | Calc'd 438, found 438 |
| 5.14 | 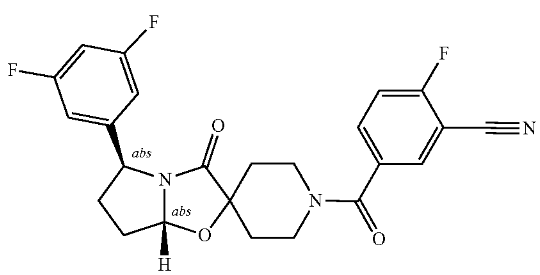 [SMILES: N#Cc1cc(C(=O)N2CCC3(CC2)O[C@@H]2CC[C@@H](c4cc(F)cc(F)c4)N2C3=O)ccc1F] | 5-((5'S,7a'R)-5'-(3,5-difluorophenyl)-3'-oxotetrahydro-3'H-spiro[piperidine-4,2'-pyrrolo-[2,1-b]oxazole]-1-carbonyl)-2-fluorobenzonitrile | Calc'd 456, found 456 |
| 5.15 | 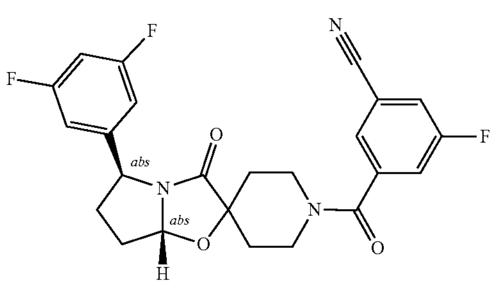 [SMILES: N#Cc1cc(F)cc(C(=O)N2CCC3(CC2)O[C@@H]2CC[C@@H](c4cc(F)cc(F)c4)N2C3=O)c1] | 3-((5'S,7a'R)-5'-(3,5-difluorophenyl)-3'-oxotetrahydro-3'H-spiro[piperidine-4,2'-pyrrolo-[2,1-b]oxazole]-1-carbonyl)-5-fluorobenzonitrile | Calc'd 456, found 456 |
| 5.16 | 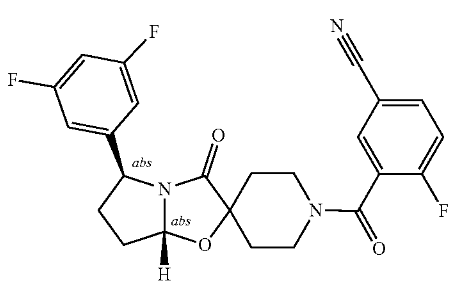 [SMILES: N#Cc1ccc(F)c(C(=O)N2CCC3(CC2)O[C@@H]2CC[C@@H](c4cc(F)cc(F)c4)N2C3=O)c1] | 3-((5'S,7a'R)-5'-(3,5-difluorophenyl)-3'-oxotetrahydro-3'H-spiro[piperidine-4,2'-pyrrolo-[2,1-b]oxazole]-1-carbonyl)-4-fluorobenzonitrile | Calc'd 456, found 456 |

TABLE 14-continued

| Ex. No | Structure | Name | Exact Mass [M + H]+ |
|---|---|---|---|
| 5.17 | 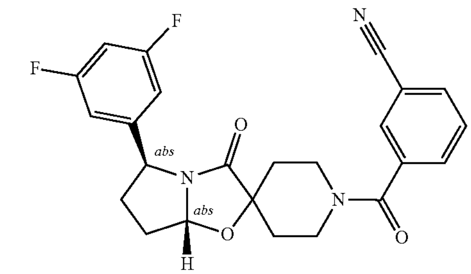 [SMILES: N#Cc1cccc(C(=O)N2CCC3(CC2)O[C@@H]2CC[C@@H](c4cc(F)cc(F)c4)N2C3=O)c1] | 3-((5'S,7a'R)-5'-(3,5-difluorophenyl)-3'-oxo-tetrahydro-3'H-spiro[piperidine-4,2'-pyrrolo[2,1-b]oxazole]-1-carbonyl)benzonitrile | Calc'd 438, found 438 |
| 5.18 | 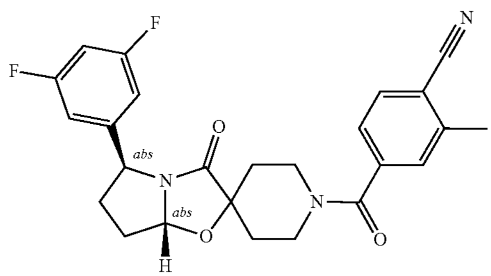 [SMILES: Cc1cc(C(=O)N2CCC3(CC2)O[C@@H]2CC[C@@H](c4cc(F)cc(F)c4)N2C3=O)ccc1C#N] | 4-((5'S,7a'R)-5'-(3,5-difluorophenyl)-3'-oxo-tetrahydro-3'H-spiro[piperidine-4,2'-pyrrolo[2,1-b]oxazole]-1-carbonyl)-2-methylbenzonitrile | Calc'd 452, found 452 |
| 5.19 | 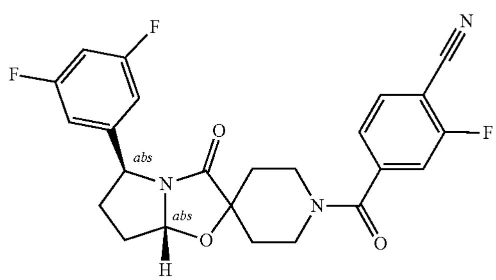 [SMILES: N#Cc1ccc(C(=O)N2CCC3(CC2)O[C@@H]2CC[C@@H](c4cc(F)cc(F)c4)N2C3=O)cc1F] | 4-((5'S,7a'R)-5'-(3,5-difluorophenyl)-3'-oxo-tetrahydro-3'H-spiro[piperidine-4,2'-pyrrolo[2,1-b]oxazole]-1-carbonyl)-2-fluorobenzonitrile | Calc'd 456, found 456 |
| 5.20 | 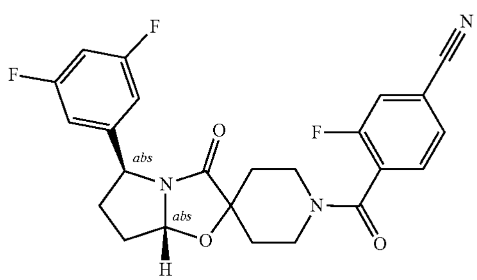 [SMILES: N#Cc1ccc(C(=O)N2CCC3(CC2)O[C@@H]2CC[C@@H](c4cc(F)cc(F)c4)N2C3=O)c(F)c1] | 4-((5'S,7a'R)-5'-(3,5-difluorophenyl)-3'-oxo-tetrahydro-3'H-spiro[piperidine-4,2'-pyrrolo[2,1-b]oxazole]-1-carbonyl)-3-fluorobenzonitrile | Calc'd 456, found 456 |
| 5.21 | 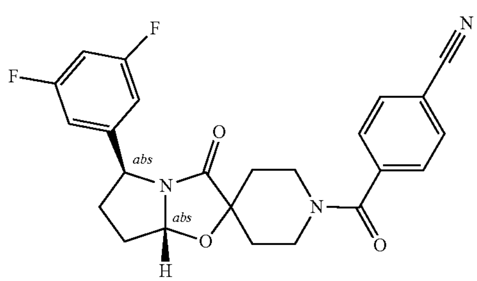 [SMILES: N#Cc1ccc(C(=O)N2CCC3(CC2)O[C@@H]2CC[C@@H](c4cc(F)cc(F)c4)N2C3=O)cc1] | 4-((5'S,7a'R)-5'-(3,5-difluorophenyl)-3'-oxo-tetrahydro-3'H-spiro[piperidine-4,2'-pyrrolo[2,1-b]oxazole]-1-carbonyl)benzonitrile | Calc'd 438, found 438 |

TABLE 14-continued

| Ex. No | Structure | Name | Exact Mass [M + H]+ |
|---|---|---|---|
| 5.22 | 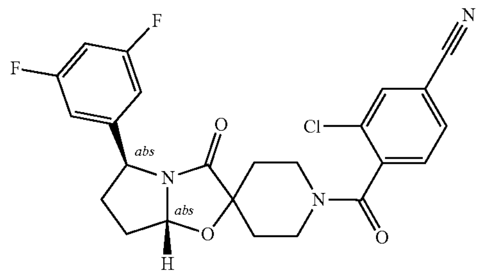 [SMILES: N#Cc1ccc(C(=O)N2CCC3(CC2)O[C@@H]2CC[C@@H](c4cc(F)cc(F)c4)N2C3=O)c(Cl)c1] | 3-chloro-4-((5'S,7a'R)-5'-(3,5-difluorophenyl)-3'-oxotetrahydro-3'H-spiro[piperidine-4,2'-pyrrolo[2,1-b]oxazole]-1-carbonyl)benzonitrile | Calc'd 472, found 472 |
| 5.23 | 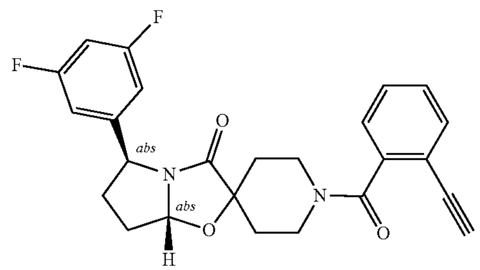 [SMILES: C#Cc1ccccc1C(=O)N1CCC2(CC1)O[C@@H]1CC[C@@H](c3cc(F)cc(F)c3)N1C2=O] | (5'S,7a'R)-5'-(3,5-difluorophenyl)-1-(2-ethynylbenzoyl)tetrahydro-3'H-spiro[piperidine-4,2'-pyrrolo[2,1-b]oxazol]-3'-one | Calc'd 437, found 437 |
| 5.24 | 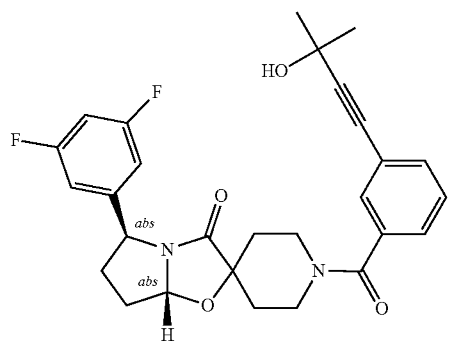 [SMILES: CC(C)(O)C#Cc1cccc(C(=O)N2CCC3(CC2)O[C@@H]2CC[C@@H](c4cc(F)cc(F)c4)N2C3=O)c1] | (5'S,7a'R)-5'-(3,5-difluorophenyl)-1-(3-(3-hydroxy-3-methylbut-1-yn-1-yl)benzoyl)tetrahydro-3'H-spiro[piperidine-4,2'-pyrrolo[2,1-b]oxazol]-3'-one | Calc'd 495, found 495 |
| 5.25 | 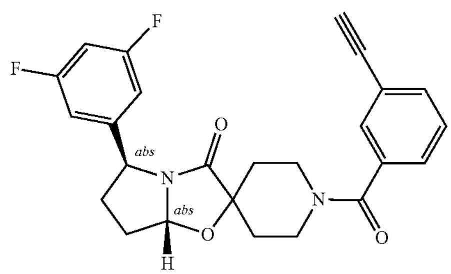 [SMILES: C#Cc1cccc(C(=O)N2CCC3(CC2)O[C@@H]2CC[C@@H](c4cc(F)cc(F)c4)N2C3=O)c1] | (5'S,7a'R)-5'-(3,5-difluorophenyl)-1-(3-ethynylbenzoyl)tetrahydro-3'H-spiro[piperidine-4,2'-pyrrolo[2,1-b]oxazol]-3'-one | Calc'd 437, found 437 |
| 5.26 | 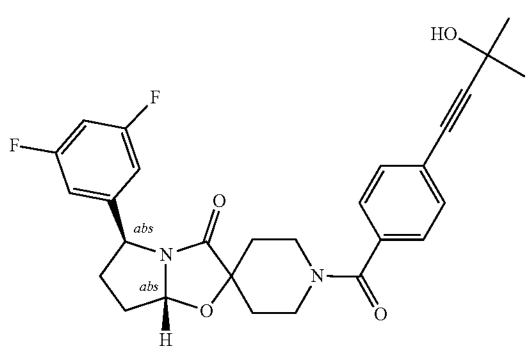 [SMILES: CC(C)(O)C#Cc1ccc(C(=O)N2CCC3(CC2)O[C@@H]2CC[C@@H](c4cc(F)cc(F)c4)N2C3=O)cc1] | (5'S,7a'R)-5'-(3,5-difluorophenyl)-1-(4-(3-hydroxy-3-methylbut-1-yn-1-yl)benzoyl)tetrahydro-3'H-spiro[piperidine-4,2'-pyrrolo[2,1-b]oxazol]-3'-one | Calc'd 495, found 495 |

TABLE 14-continued

| Ex. No | Structure | Name | Exact Mass [M + H]+ |
|---|---|---|---|
| 5.27 | 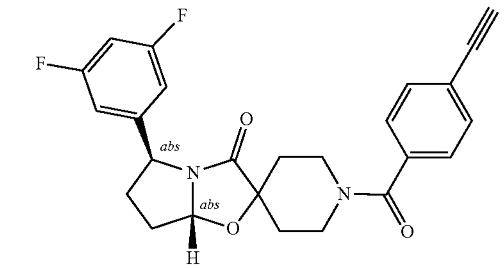 [SMILES: C#Cc1ccc(C(=O)N2CCC3(CC2)O[C@@H]2CC[C@@H](c4cc(F)cc(F)c4)N2C3=O)cc1] | (5'S,7a'R)-5'-(3,5-difluorophenyl)-1-(4-ethynylbenzoyl)tetrahydro-3'H-spiro[piperidine-4,2'-pyrrolo[2,1-b]oxazol]-3'-one | Calc'd 437, found 437 |
| 5.28 | 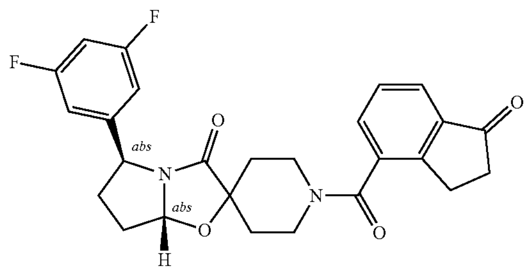 [SMILES: O=C1CCc2c1cccc2C(=O)N1CCC2(CC1)O[C@@H]1CC[C@@H](c3cc(F)cc(F)c3)N1C2=O] | (5'S,7a'R)-5'-(3,5-difluorophenyl)-1-(1-oxo-2,3-dihydro-1H-indene-4-carbonyl)tetrahydro-3'H-spiro[piperidine-4,2'-pyrrolo[2,1-b]oxazol]-3'-one | Calc'd 467, found 467 |
| 5.29 | 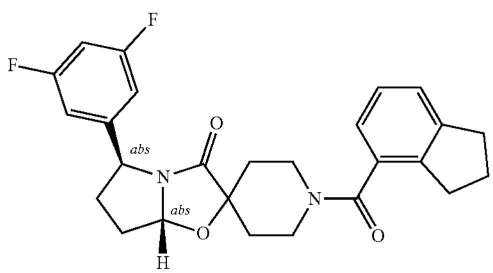 [SMILES: O=C(c1cccc2c1CCC2)N1CCC2(CC1)O[C@@H]1CC[C@@H](c3cc(F)cc(F)c3)N1C2=O] | (5'S,7a'R)-5'-(3,5-difluorophenyl)-1-(2,3-dihydro-1H-indene-4-carbonyl)-tetrahydro-3'H-spiro[piperidine-4,2'-pyrrolo[2,1-b]oxazol]-3'-one | Calc'd 453, found 453 |
| 5.30 | 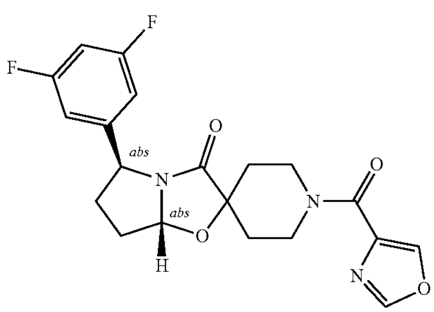 [SMILES: O=C(c1cocn1)N1CCC2(CC1)O[C@@H]1CC[C@@H](c3cc(F)cc(F)c3)N1C2=O] | (5'S,7a'R)-5'-(3,5-difluorophenyl)-1-(1-oxazole-4-carbonyl)tetrahydro-3'H-spiro[piperidine-4,2'-pyrrolo[2,1-b]oxazol]-3'-one | Calc'd 404, found 404 |
| 5.31 | 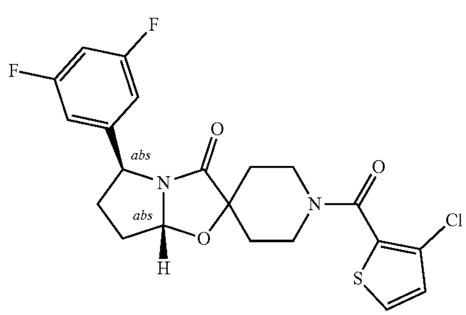 [SMILES: O=C(c1sccc1Cl)N1CCC2(CC1)O[C@@H]1CC[C@@H](c3cc(F)cc(F)c3)N1C2=O] | (5'S,7a'R)-1-(3-chlorothiophene-2-carbonyl)-5'-(3,5-difluorophenyl)tetrahydro-3'H-spiro[piperidine-4,2'-pyrrolo[2,1-b]oxazol]-3'-one | Calc'd 453, found 453 |

TABLE 14-continued

| Ex. No | Structure | Name | Exact Mass [M + H]+ |
|---|---|---|---|
| 5.32 | 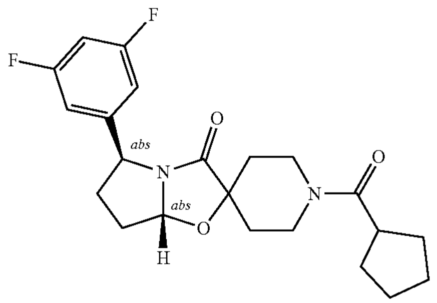 [SMILES: O=C(C1CCCC1)N1CCC2(CC1)O[C@@H]1CC[C@@H](c3cc(F)cc(F)c3)N1C2=O] | (5'S,7a'R)-1-(cyclopentane-carbonyl)-5'-(3,5-difluoro-phenyl)tetrahydro-3'H-spiro[piperidine-4,2'-pyrrolo[2,1-b]oxazol]-3'-one | Calc'd 405, found 405 |
| 5.33 | 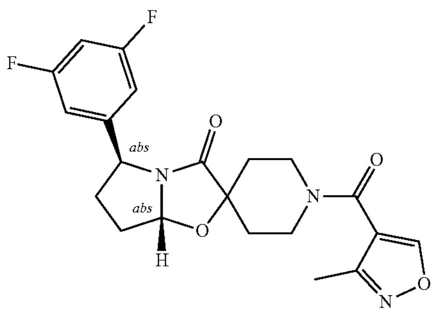 [SMILES: Cc1nocc1C(=O)N1CCC2(CC1)O[C@@H]1CC[C@@H](c3cc(F)cc(F)c3)N1C2=O] | (5'S,7a'R)-5'-(3,5-difluoro-phenyl)-1-(3-methylisoxa-zole-4-carbonyl)tetrahydro-3'H-spiro[piperidine-4,2'-pyrrolo[2,1-b]oxazol]-3'-one | Calc'd 418, found 418 |
| 5.34 | 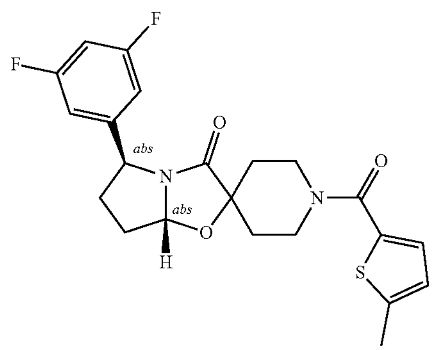 [SMILES: Cc1ccc(C(=O)N2CCC3(CC2)O[C@@H]2CC[C@@H](c4cc(F)cc(F)c4)N2C3=O)s1] | (5'S,7a'R)-5'-(3,5-difluoro-phenyl)-1-(5-methylthio-phene-2-carbonyl)tetra-hydro-3'H-spiro[piperidine-4,2'-pyrrolo[2,1-b]oxazol]-3'-one | Calc'd 433, found 433 |
| 5.35 | 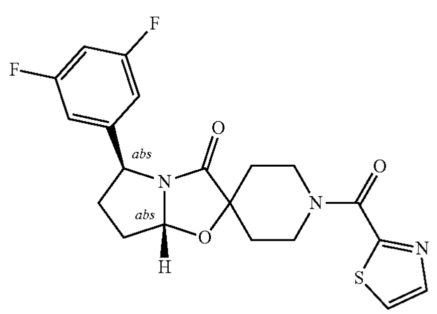 [SMILES: O=C(c1nccs1)N1CCC2(CC1)O[C@@H]1CC[C@@H](c3cc(F)cc(F)c3)N1C2=O] | (5'S,7a'R)-5'-(3,5-difluoro-phenyl)-1-(thiazole-2-carbonyl)tetrahydro-3'H-spiro[piperidine-4,2'-pyrrolo[2,1-b]oxazol]-3'-one | Calc'd 420, found 420 |
| 5.36 | 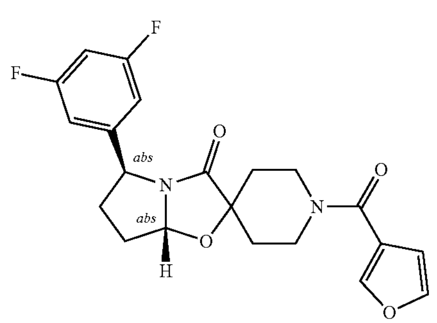 [SMILES: O=C(c1ccoc1)N1CCC2(CC1)O[C@@H]1CC[C@@H](c3cc(F)cc(F)c3)N1C2=O] | (5'S,7a'R)-5'-(3,5-difluoro-phenyl)-1-(furan-3-carbon-yl)tetrahydro-3'H-spiro[piperidine-4,2'-pyrrolo-[2,1-b]oxazol]-3'-one | Calc'd 403, found 403 |

TABLE 14-continued

| Ex. No | Structure | Name | Exact Mass [M + H]+ |
|---|---|---|---|
| 5.37 | 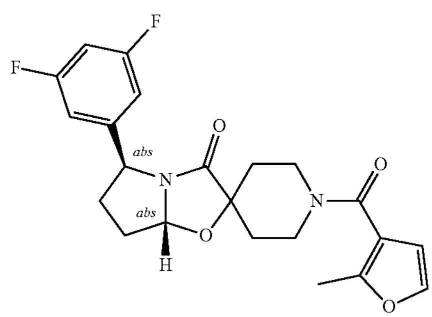 [SMILES: Cc1occc1C(=O)N1CCC2(CC1)O[C@@H]1CC[C@@H](c3cc(F)cc(F)c3)N1C2=O] | (5'S,7a'R)-5'-(3,5-difluorophenyl)-1-(2-methylfuran-3-carbonyl)tetrahydro-3'H-spiro[piperidine-4,2'-pyrrolo[2,1-b]oxazol]-3'-one | Calc'd 417, found 417 |
| 5.38 | 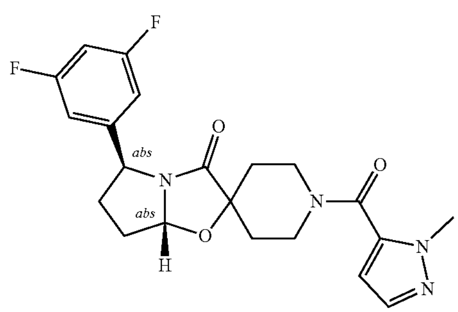 [SMILES: Cn1nccc1C(=O)N1CCC2(CC1)O[C@@H]1CC[C@@H](c3cc(F)cc(F)c3)N1C2=O] | (5'S,7a'R)-5'-(3,5-difluorophenyl)-1-(1-methyl-1H-pyrazole-5-carbonyl)tetrahydro-3'H-spiro[piperidine-4,2'-pyrrolo[2,1-b]oxazol]-3'-one | Calc'd 417, found 417 |
| 5.39 | 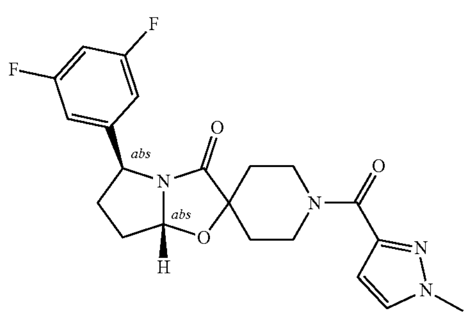 [SMILES: Cn1ccc(C(=O)N2CCC3(CC2)O[C@@H]2CC[C@@H](c4cc(F)cc(F)c4)N2C3=O)n1] | (5'S,7a'R)-5'-(3,5-difluorophenyl)-1-(1-methyl-1H-pyrazole-3-carbonyl)tetrahydro-3'H-spiro[piperidine-4,2'-pyrrolo[2,1-b]oxazol]-3'-one | Calc'd 417, found 417 |
| 5.40 | 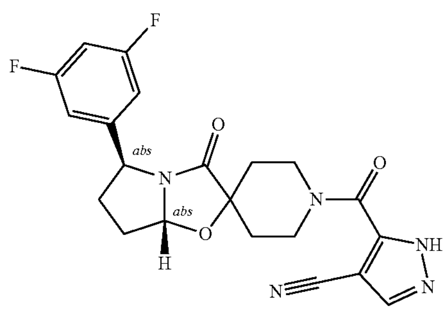 [SMILES: N#Cc1cn[nH]c1C(=O)N1CCC2(CC1)O[C@@H]1CC[C@@H](c3cc(F)cc(F)c3)N1C2=O] | 5-((5'S,7a'R)-5'-(3,5-difluorophenyl)-3'-oxo-tetrahydro-3'H-spiro[piperidine-4,2'-pyrrolo[2,1-b]oxazole]-1-carbonyl)-1H-pyrazole-4-carbonitrile | Calc'd 428, found 428 |

TABLE 14-continued

| Ex. No | Structure | Name | Exact Mass [M + H]+ |
|---|---|---|---|
| 5.41 | 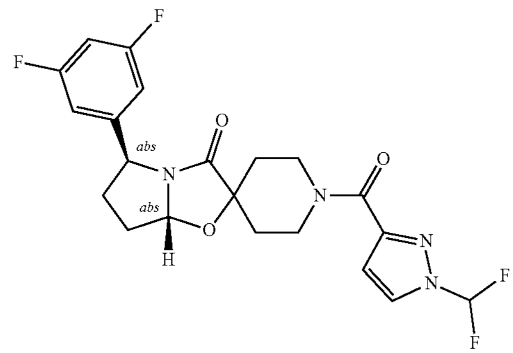 [SMILES: O=C(c1ccn(C(F)F)n1)N1CCC2(CC1)O[C@@H]1CC[C@@H](c3cc(F)cc(F)c3)N1C2=O] | (5'S,7a'R)-1-(1-(difluoromethyl)-1H-pyrazole-3-carbonyl)-5'-(3,5-difluorophenyl)tetrahydro-3'H-spiro[piperidine-4,2'-pyrrolo-[2,1-b]oxazol]-3'-one | Calc'd 453, found 453 |
| 5.42 | 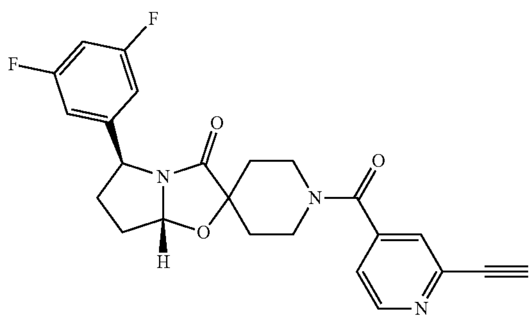 [SMILES: C#Cc1cc(C(=O)N2CCC3(CC2)O[C@@H]2CC[C@@H](c4cc(F)cc(F)c4)N2C3=O)ccn1] | (5'S,7a'R)-5'-(3,5-difluorophenyl)-1-(2-ethynylpyridine-4-carbonyl)tetrahydro-3'H-spiro[piperidine-4,2'-pyrrolo-[2,1-b][1,3]oxazol]-3'-one | Calc'd 438, found 438 |
| 5.43 | 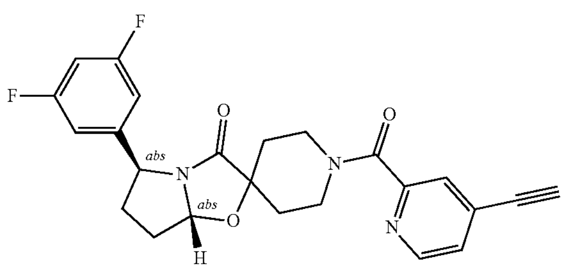 [SMILES: C#Cc1ccnc(C(=O)N2CCC3(CC2)O[C@@H]2CC[C@@H](c4cc(F)cc(F)c4)N2C3=O)c1] | (5'S,7a'R)-5'-(3,5-difluorophenyl)-1-(4-ethynylpicolinoyl)tetrahydro-3'H-spiro[piperidine-4,2'-pyrrolo[2,1-b]oxazol]-3'-one | Calc'd 438, found 438 |
| 5.44 | 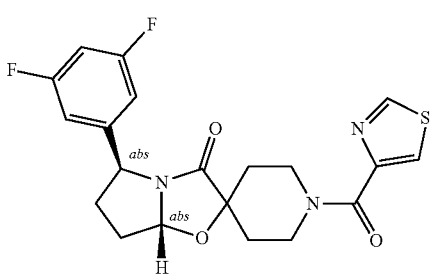 [SMILES: O=C(c1cscn1)N1CCC2(CC1)O[C@@H]1CC[C@@H](c3cc(F)cc(F)c3)N1C2=O] | (5'S,7a'R)-5'-(3,5-(difluorophenyl)-1-(thiazole-4-carbonyl)tetrahydro-3'H-spiro[piperidine-4,2'-pyrrolo[2,1-b]oxazol]-3'-one | Calc'd 420, found 420 |
| 5.45 | 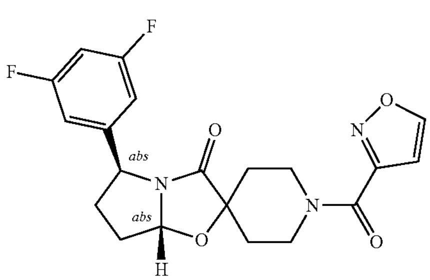 [SMILES: O=C(c1ccon1)N1CCC2(CC1)O[C@@H]1CC[C@@H](c3cc(F)cc(F)c3)N1C2=O] | (5'S,7a'R)-5'-(3,5-(difluorophenyl)-1-(isoxazole-3-carbonyl)tetrahydro-3'H-spiro[piperidine-4,2'-pyrrolo[2,1-b]oxazol]-3'-one | Calc'd 404, found 404 |

TABLE 14-continued

| Ex. No | Structure | Name | Exact Mass [M + H]+ |
|---|---|---|---|
| 5.46 | 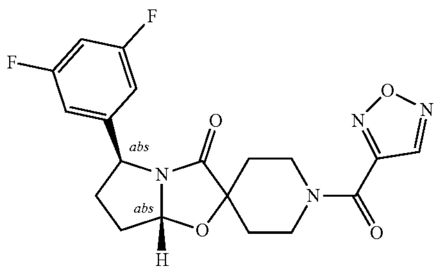 [SMILES: O=C(c1cnon1)N1CCC2(CC1)O[C@@H]1CC[C@@H](c3cc(F)cc(F)c3)N1C2=O] | (5'S,7a'R)-5'-(3,5-difluorophenyl)-1-(1,2,5-oxazole-3-carbonyl)tetrahydro-3'H-spiro[piperidine-4,2'-pyrrolo-[2,1-b]oxazol]-3'-one | Calc'd 405, found 405 |
| 5.47 | 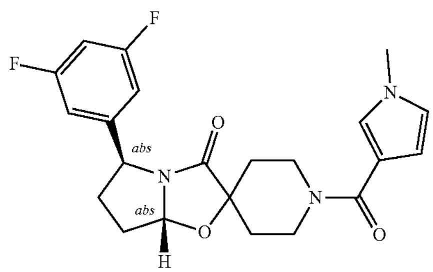 [SMILES: Cn1ccc(C(=O)N2CCC3(CC2)O[C@@H]2CC[C@@H](c4cc(F)cc(F)c4)N2C3=O)c1] | (5'S,7a'R)-5'-(3,5-difluorophenyl)-1-(1-methyl-1H-pyrrole-3-carbonyl)tetrahydro-3'H-spiro[piperidine-4,2'-pyrrolo[2,1-b]oxazol]-3'-one | Calc'd 416, found 416 |
| 5.48 | 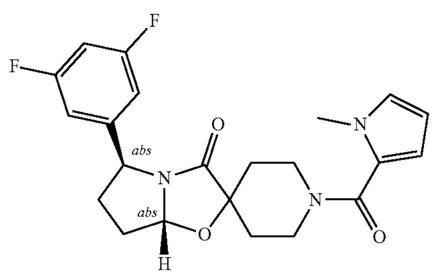 [SMILES: Cn1cccc1C(=O)N1CCC2(CC1)O[C@@H]1CC[C@@H](c3cc(F)cc(F)c3)N1C2=O] | (5'S,7a'R)-5'-(3,5-difluorophenyl)-1-(1-methyl-1H-pyrrole-2-carbonyl)tetrahydro-3'H-spiro[piperidine-4,2'-pyrrolo[2,1-b]oxazol]-3'-one | Calc'd 416, found 416 |
| 5.49 | 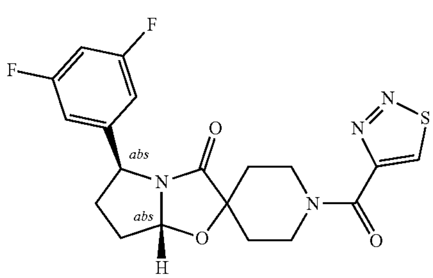 [SMILES: O=C(c1csnn1)N1CCC2(CC1)O[C@@H]1CC[C@@H](c3cc(F)cc(F)c3)N1C2=O] | (5'S,7a'R)-5'-(3,5-difluorophenyl)-1-(1,2,3-thiadiazole-4-carbonyl)tetrahydro-3'H-spiro[piperidine-4,2'-pyrrolo[2,1-b]oxazol]-3'-one | Calc'd 421, found 421 |
| 5.50 | 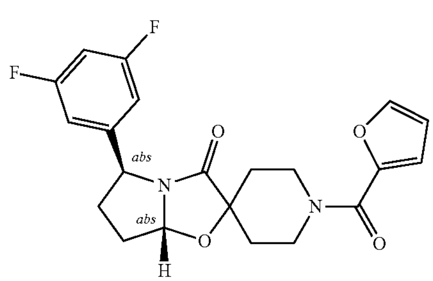 [SMILES: O=C(c1ccco1)N1CCC2(CC1)O[C@@H]1CC[C@@H](c3cc(F)cc(F)c3)N1C2=O] | (5'S,7a'R)-5'-(3,5-difluorophenyl)-1-(furan-2-carbonyl)tetrahydro-3'H-spiro[piperidine-4,2'-pyrrolo-[2,1-b]oxazol]-3'-one | Calc'd 403, found 403 |

TABLE 14-continued

| Ex. No | Structure | Name | Exact Mass [M + H]+ |
|---|---|---|---|
| 5.51 | 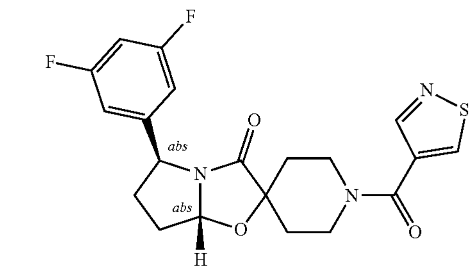 [SMILES: O=C(c1cnsc1)N1CCC2(CC1)O[C@@H]1CC[C@@H](c3cc(F)cc(F)c3)N1C2=O] | (5'S,7a'R)-5'-(3,5-difluorophenyl)-1-(isothiazole-4-carbonyl)tetrahydro-3'H-spiro[piperidine-4,2'-pyrrolo[2,1-b]oxazol]-3'-one | Calc'd 420, found 420 |
| 5.52 | 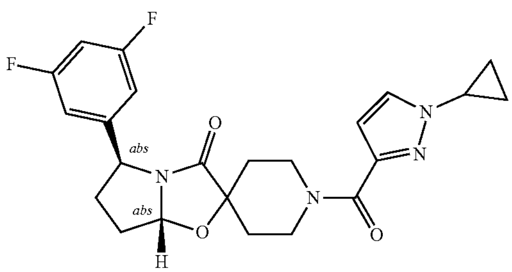 [SMILES: O=C(c1ccn(C2CC2)n1)N1CCC2(CC1)O[C@@H]1CC[C@@H](c3cc(F)cc(F)c3)N1C2=O] | (5'S,7a'R)-1-(1-cyclopropyl-1H-pyrazole-3-carbonyl)-5'-(3,5-difluorophenyl)tetrahydro-3'H-spiro[piperidine-4,2'-pyrrolo[2,1-b]oxazol]-3'-one | Calc'd 443, found 443 |
| 5.53 | 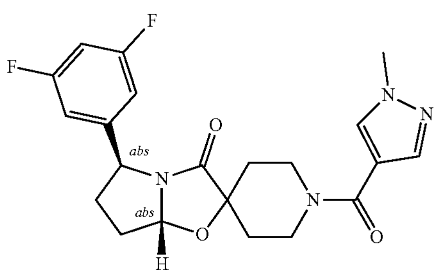 [SMILES: Cn1cc(C(=O)N2CCC3(CC2)O[C@@H]2CC[C@@H](c4cc(F)cc(F)c4)N2C3=O)cn1] | (5'S,7a'R)-5'-(3,5-difluorophenyl)-1-(1-methyl-1H-pyrazole-4-carbonyl)tetrahydro-3'H-spiro[piperidine-4,2'-pyrrolo[2,1-b]oxazol]-3'-one | Calc'd 417, found 417 |
| 5.54 | 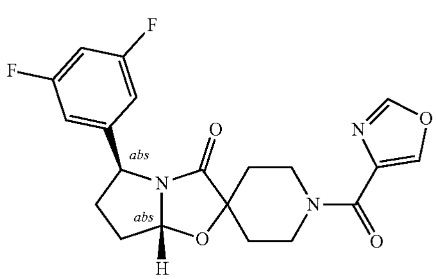 [SMILES: O=C(c1cocn1)N1CCC2(CC1)O[C@@H]1CC[C@@H](c3cc(F)cc(F)c3)N1C2=O] | (5'S,7a'R)-5'-(3,5-difluorophenyl)-1-(oxazole-4-carbonyl)tetrahydro-3'H-spiro[piperidine-4,2'-pyrrolo[2,1-b]oxazol]-3'-one | Calc'd 404, found 404 |
| 5.55 | 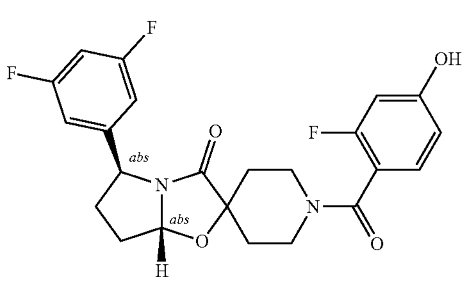 [SMILES: O=C(c1ccc(O)cc1F)N1CCC2(CC1)O[C@@H]1CC[C@@H](c3cc(F)cc(F)c3)N1C2=O] | (5'S,7a'R)-5'-(3,5-difluorophenyl)-1-(2-fluoro-4-hydroxybenzoyl)tetrahydro-3'H-spiro[piperidine-4,2'-pyrrolo[2,1-b]oxazol]-3'-one | Calc'd 447, found 447 |

TABLE 14-continued

| Ex. No | Structure | Name | Exact Mass [M + H]+ |
|---|---|---|---|
| 5.56 | 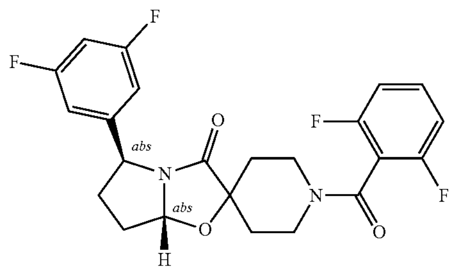 [SMILES: O=C(c1c(F)cccc1F)N1CCC2(CC1)O[C@@H]1CC[C@@H](c3cc(F)cc(F)c3)N1C2=O] | (5'S,7a'R)-1-(2,6-difluorobenzoyl)-5'-(3,5-difluorophenyl)tetrahydro-3'H-spiro[piperidine-4,2'-pyrrolo[2,1-b]oxazol]-3'-one | Calc'd 449, found 449 |
| 5.57 | 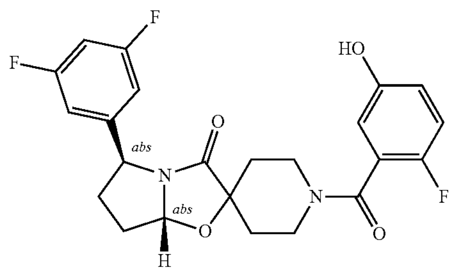 [SMILES: O=C(c1cc(O)ccc1F)N1CCC2(CC1)O[C@@H]1CC[C@@H](c3cc(F)cc(F)c3)N1C2=O] | (5'S,7a'R)-5'-(3,5-difluorophenyl)-1-(2-fluoro-5-hydroxybenzoyl)tetrahydro-3'H-spiro[piperidine-4,2'-pyrrolo[2,1-b]oxazol]-3'-one | Calc'd 447, found 447 |
| 5.58 | 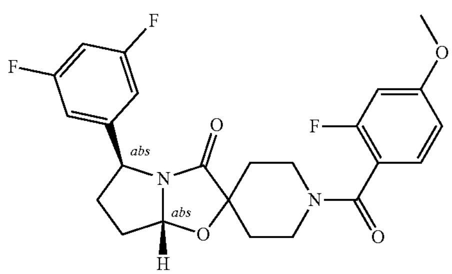 [SMILES: COc1ccc(C(=O)N2CCC3(CC2)O[C@@H]2CC[C@@H](c4cc(F)cc(F)c4)N2C3=O)c(F)c1] | (5'S,7a'R)-5'-(3,5-difluorophenyl)-1-(2-fluoro-4-methoxybenzoyl)tetrahydro-3'H-spiro[piperidine-4,2'-pyrrolo[2,1-b]oxazol]-3'-one | Calc'd 461, found 461 |
| 5.59 | 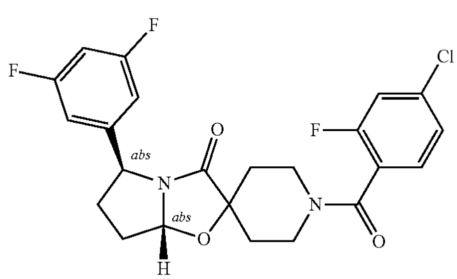 [SMILES: O=C(c1ccc(Cl)cc1F)N1CCC2(CC1)O[C@@H]1CC[C@@H](c3cc(F)cc(F)c3)N1C2=O] | (5'S,7a'R)-1-(4-chloro-2-fluorobenzoyl)-5'-(3,5-difluorophenyl)tetrahydro-3'H-spiro[piperidine-4,2'-pyrrolo[2,1-b]oxazol]-3'-one | Calc'd 465, found 465 |
| 5.60 | 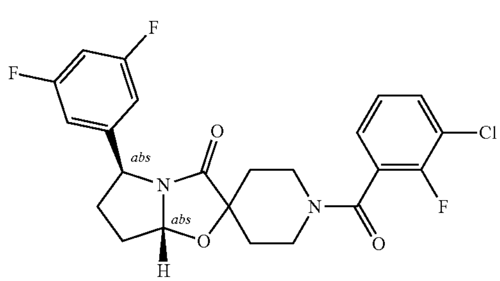 [SMILES: O=C(c1cccc(Cl)c1F)N1CCC2(CC1)O[C@@H]1CC[C@@H](c3cc(F)cc(F)c3)N1C2=O] | (5'S,7a'R)-1-(3-chloro-2-fluorobenzoyl)-5'-(3,5-difluorophenyl)tetrahydro-3'H-spiro[piperidine-4,2'-pyrrolo[2,1-b]oxazol]-3'-one | Calc'd 465, found 465 |

TABLE 14-continued

| Ex. No | Structure | Name | Exact Mass [M + H]+ |
|---|---|---|---|
| 5.61 | 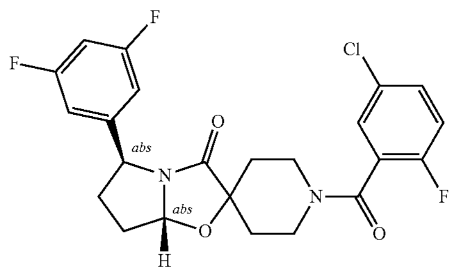 [SMILES: O=C(c1cc(Cl)ccc1F)N1CCC2(CC1)O[C@@H]1CC[C@@H](c3cc(F)cc(F)c3)N1C2=O] | (5'S,7a'R)-1-(5-chloro-2-fluorobenzoyl)-5'-(3,5-difluorophenyl)tetrahydro-3'H-spiro[piperidine-4,2'-pyrrolo[2,1-b]oxazol]-3'-one | Calc'd 465, found 465 |
| 5.62 | 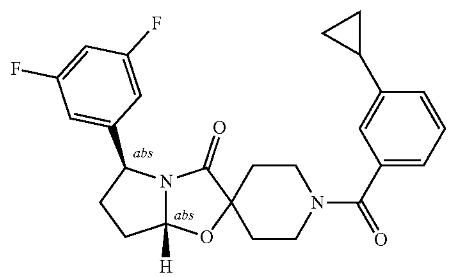 [SMILES: O=C(c1cccc(C2CC2)c1)N1CCC2(CC1)O[C@@H]1CC[C@@H](c3cc(F)cc(F)c3)N1C2=O] | (5'S,7a'R)-1-(3-cyclopropylbenzoyl)-5'-(3,5-difluorophenyl)tetrahydro-3'H-spiro[piperidine-4,2'-pyrrolo[2,1-b]oxazol]-3'-one | Calc'd 453, found 453 |
| 5.63 | 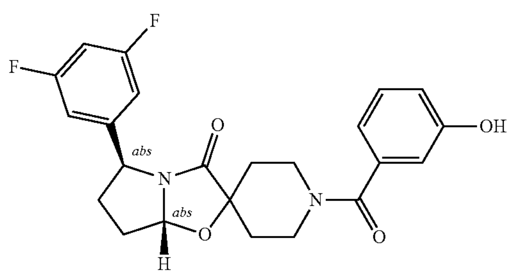 [SMILES: O=C(c1cccc(O)c1)N1CCC2(CC1)O[C@@H]1CC[C@@H](c3cc(F)cc(F)c3)N1C2=O] | (5'S,7a'R)-5'-(3,5-difluorophenyl)-1-(3-hydroxybenzoyl)tetrahydro-3'H-spiro[piperidine-4,2'-pyrrolo[2,1-b]oxazol]-3'-one | Calc'd 429, found 429 |
| 5.64 | 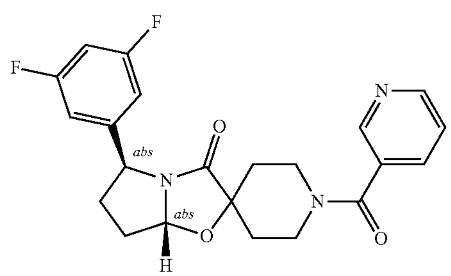 [SMILES: O=C(c1cccnc1)N1CCC2(CC1)O[C@@H]1CC[C@@H](c3cc(F)cc(F)c3)N1C2=O] | (5'S,7a'R)-5'-(3,5-difluorophenyl)-1-nicotinoyltetrahydro-3'H-spiro[piperidine-4,2'-pyrrolo[2,1-b]oxazol]-3'-one | Calc'd 414, found 414 |
| 5.65 | 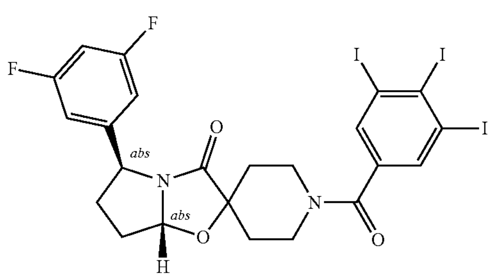 [SMILES: O=C(c1cc(I)c(I)c(I)c1)N1CCC2(CC1)O[C@@H]1CC[C@@H](c3cc(F)cc(F)c3)N1C2=O] | (5'S,7a'R)-5'-(3,5-difluorophenyl)-1-(3,4,5-triiodobenzoyl)tetrahydro-3'H-spiro[piperidine-4,2'-pyrrolo[2,1-b]oxazol]-3'-one | Calc'd 791, found 791 |

TABLE 14-continued

| Ex. No | Structure | Name | Exact Mass [M + H]+ |
|---|---|---|---|
| 5.66 | 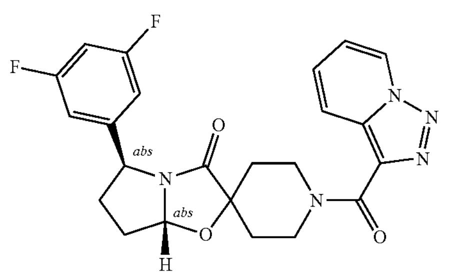 [SMILES: O=C(c1nnn2ccccc12)N1CCC2(CC1)O[C@@H]1CC[C@@H](c3cc(F)cc(F)c3)N1C2=O] | (5'S,7a'R)-1-([1,2,3]-triazolo-[1,5-a]pyridine-3-carbonyl)-5'-(3,5-difluorophenyl)tetrahydro-3'H-spiro[piperidine-4,2'-pyrrolo[2,1-b]oxazol]-3'-one | Calc'd 454, found 454 |
| 5.67 | 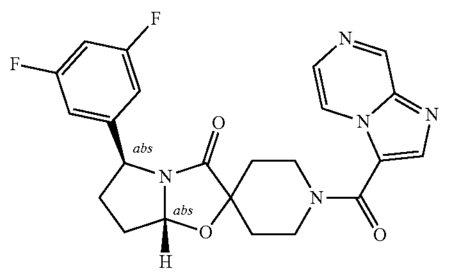 [SMILES: O=C(c1cnc2cnccn12)N1CCC2(CC1)O[C@@H]1CC[C@@H](c3cc(F)cc(F)c3)N1C2=O] | (5'S,7a'R)-5'-(3,5-difluorophenyl)-1-(imidazo[1,2-a]pyrazine-3-carbonyl)-tetrahydro-3'H-spiro[piperidine-4,2'-pyrrolo-[2,1-b]oxazol]-3'-one | Calc'd 454, found 454 |
| 5.68 | 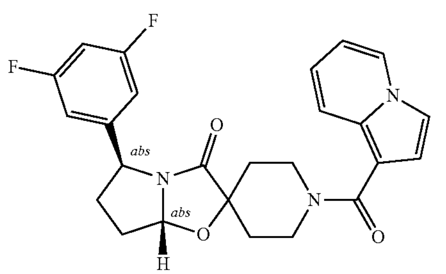 [SMILES: O=C(c1ccn2ccccc12)N1CCC2(CC1)O[C@@H]1CC[C@@H](c3cc(F)cc(F)c3)N1C2=O] | (5'S,7a'R)-5'-(3,5-difluorophenyl)-1-(indolizine-1-carbonyl)tetrahydro-3'H-spiro[piperidine-4,2'-pyrrolo[2,1-b]oxazol]-3'-one | Calc'd 452, found 452 |
| 5.69 | 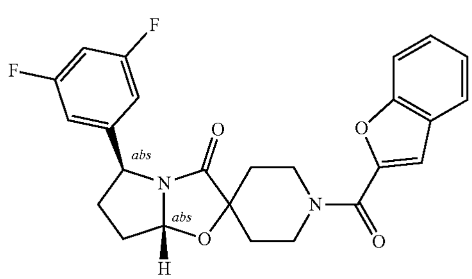 [SMILES: O=C(c1cc2ccccc2o1)N1CCC2(CC1)O[C@@H]1CC[C@@H](c3cc(F)cc(F)c3)N1C2=O] | (5'S,7a'R)-1-(benzofuran-2-carbonyl-5'-(3,5-difluorophenyl)tetrahydro-3'H-spiro[piperidine-4,2'-pyrrolo[2,1-b]oxazol]-3'-one | Calc'd 453, found 453 |
| 5.70 | 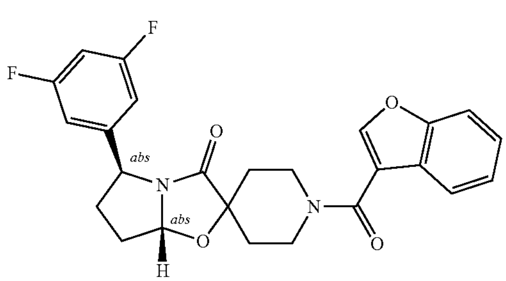 [SMILES: O=C(c1coc2ccccc12)N1CCC2(CC1)O[C@@H]1CC[C@@H](c3cc(F)cc(F)c3)N1C2=O] | (5'S,7a'R)-1-(benzofuran-3-carbonyl-5'-(3,5-difluorophenyl)tetrahydro-3'H-spiro[piperidine-4,2'-pyrrolo[2,1-b]oxazol]-3'-one | Calc'd 453, found 453 |

TABLE 14-continued

| Ex. No | Structure | Name | Exact Mass [M + H]+ |
|---|---|---|---|
| 5.71 | 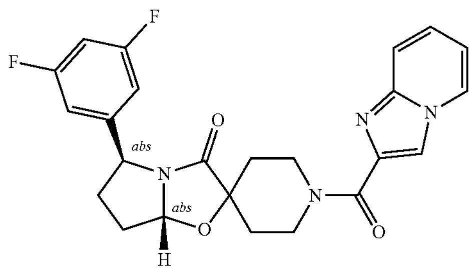 [SMILES: O=C(c1cn2ccccc2n1)N1CCC2(CC1)O[C@@H]1CC[C@@H](c3cc(F)cc(F)c3)N1C2=O] | (5'S,7a'R)-5'-(3,5-difluorophenyl)-1-(imidazo[1,2-a]-pyridine-2-carbonyl)tetrahydro-3'H-spiro[piperidine-4,2'-pyrrolo[2,1-b]oxazol]-3'-one | Calc'd 453, found 453 |
| 5.72 | 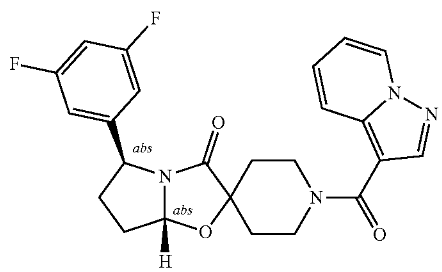 [SMILES: O=C(c1cnn2ccccc12)N1CCC2(CC1)O[C@@H]1CC[C@@H](c3cc(F)cc(F)c3)N1C2=O] | (5'S,7a'R)-5'-(3,5-difluorophenyl)-1-(pyrazolo[1,5-a]-pyridine-3-carbonyl)tetrahydro-3'H-spiro[piperidine-4,2'-pyrrolo[2,1-b]oxazol]-3'-one | Calc'd 453, found 453 |
| 5.73 | 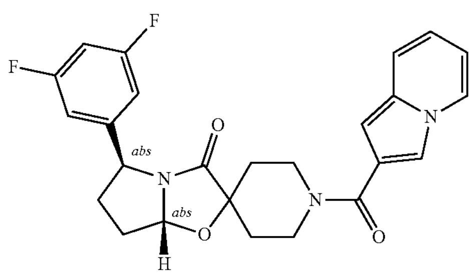 [SMILES: O=C(c1cc2ccccn2c1)N1CCC2(CC1)O[C@@H]1CC[C@@H](c3cc(F)cc(F)c3)N1C2=O] | (5'S,7a'R)-5'-(3,5-difluorophenyl)-1-(indolizine-2-carbonyl)tetrahydro-3'H-spiro[piperidine-4,2'-pyrrolo[2,1-b]oxazol]-3'-one | Calc'd 452, found 452 |
| 5.74 | 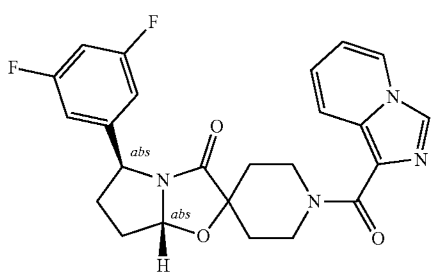 [SMILES: O=C(c1ncn2ccccc12)N1CCC2(CC1)O[C@@H]1CC[C@@H](c3cc(F)cc(F)c3)N1C2=O] | (5'S,7a'R)-5'-(3,5-difluorophenyl)-1-(imidazo[1,5-a]-pyridine-1-carbonyl)tetrahydro-3'H-spiro[piperidine-4,2'-pyrrolo[2,1-b]oxazol]-3'-one | Calc'd 453, found 453 |
| 5.75 | 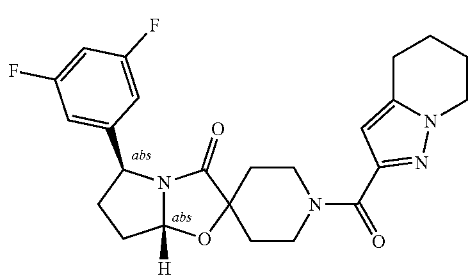 [SMILES: O=C(c1cc2n(n1)CCCC2)N1CCC2(CC1)O[C@@H]1CC[C@@H](c3cc(F)cc(F)c3)N1C2=O] | (5'S,7a'R)-5'-(3,5-difluorophenyl)-1-(4,5,6,7-tetrahydropyrazolo[1,5-a]-pyridine-2-carbonyl)tetrahydro-3'H-spiro[piperidine-4,2'-pyrrolo[2,1-b]oxazol]-3'-one | Calc'd 457, found 457 |

TABLE 14-continued

| Ex. No | Structure | Name | Exact Mass [M + H]+ |
|---|---|---|---|
| 5.76 | 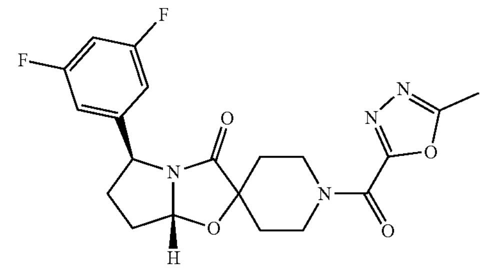 [SMILES: Cc1nnc(C(=O)N2CCC3(CC2)O[C@@H]2CC[C@@H](c4cc(F)cc(F)c4)N2C3=O)o1] | (5'S,7a'R)-5'-(3,5-difluorophenyl)-1-(5-methyl-1,3,4-oxadiazole-2-carbonyl)-tetrahydro-3'H-spiro[piperidine-4,2'-pyrrolo[2,1-b][1,3]oxazol]-3'-one | Calc'd 419, found 419 |

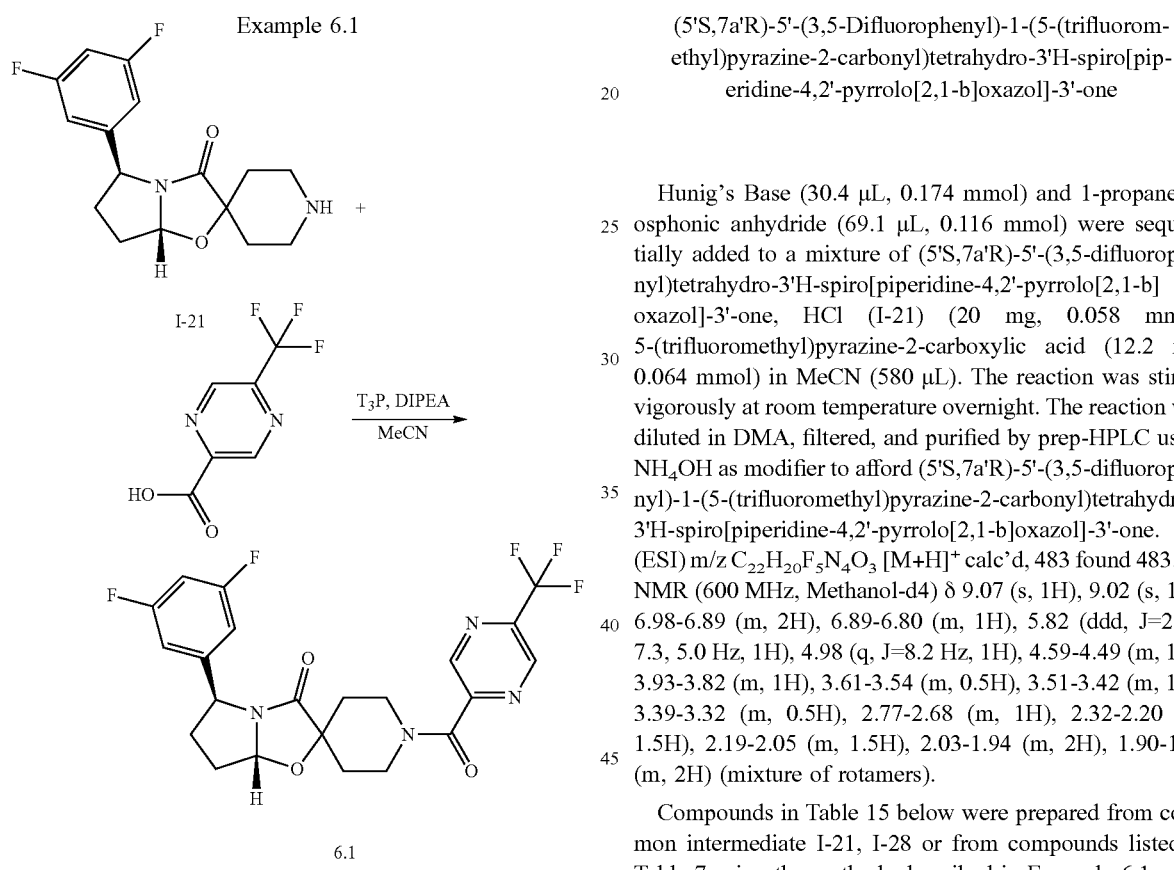

Example 6.1

(5'S,7a'R)-5'-(3,5-Difluorophenyl)-1-(5-(trifluoromethyl)pyrazine-2-carbonyl)tetrahydro-3'H-spiro[piperidine-4,2'-pyrrolo[2,1-b]oxazol]-3'-one Hunig's Base (30.4 μL, 0.174 mmol) and 1-propanephosphonic anhydride (69.1 μL, 0.116 mmol) were sequentially added to a mixture of (5'S,7a'R)-5'-(3,5-difluorophenyl)tetrahydro-3'H-spiro[piperidine-4,2'-pyrrolo[2,1-b]oxazol]-3'-one, HCl (I-21) (20 mg, 0.058 mmol) 5-(trifluoromethyl)pyrazine-2-carboxylic acid (12.2 mg, 0.064 mmol) in MeCN (580 μL). The reaction was stirred vigorously at room temperature overnight. The reaction was diluted in DMA, filtered, and purified by prep-HPLC using NH$_4$OH as modifier to afford (5'S,7a'R)-5'-(3,5-difluorophenyl)-1-(5-(trifluoromethyl)pyrazine-2-carbonyl)tetrahydro-3'H-spiro[piperidine-4,2'-pyrrolo[2,1-b]oxazol]-3'-one. MS (ESI) m/z C$_{22}$H$_{20}$F$_5$N$_4$O$_3$ [M+H]$^+$ calc'd, 483 found 483. $^1$H NMR (600 MHz, Methanol-d4) δ 9.07 (s, 1H), 9.02 (s, 1H), 6.98-6.89 (m, 2H), 6.89-6.80 (m, 1H), 5.82 (ddd, J=29.7, 7.3, 5.0 Hz, 1H), 4.98 (q, J=8.2 Hz, 1H), 4.59-4.49 (m, 1H), 3.93-3.82 (m, 1H), 3.61-3.54 (m, 0.5H), 3.51-3.42 (m, 1H), 3.39-3.32 (m, 0.5H), 2.77-2.68 (m, 1H), 2.32-2.20 (m, 1.5H), 2.19-2.05 (m, 1.5H), 2.03-1.94 (m, 2H), 1.90-1.68 (m, 2H) (mixture of rotamers).

Compounds in Table 15 below were prepared from common intermediate I-21, I-28 or from compounds listed in Table 7 using the methods described in Example 6.1.

TABLE 15

| Ex. No. | Structure | Name | Exact Mass [M + H]+ |
|---|---|---|---|
| 6.2 | 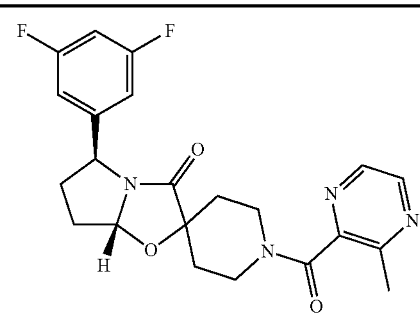 | (5'S,7a'R)-5'-(3,5-difluorophenyl)-1-(3-methylpyrazine-2-carbonyl)tetrahydro-3'H-spiro[piperidine-4,2'-pyrrolo[2,1-b][1,3]oxazol]-3'-one | Calc'd 429, found 429 |

TABLE 15-continued

| Ex. No. | Structure | Name | Exact Mass [M + H]+ |
|---|---|---|---|
| 6.3 | 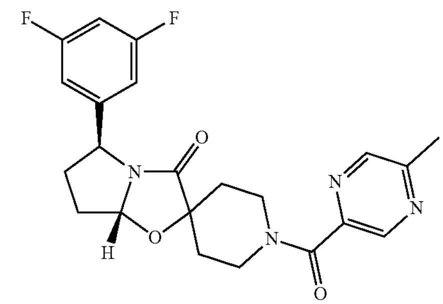 [SMILES: Cc1cnc(C(=O)N2CCC3(CC2)O[C@@H]2CC[C@@H](c4cc(F)cc(F)c4)N2C3=O)cn1] | (5'S,7a'R)-5'-(3,5-difluorophenyl)-1-(5-methylpyrazine-2-carbonyl)tetrahydro-3'H-spiro[piperidine-4,2'-pyrrolo[2,1-b][1,3]oxazol]-3'-one | Calc'd 429, found 429 |
| 6.4 | 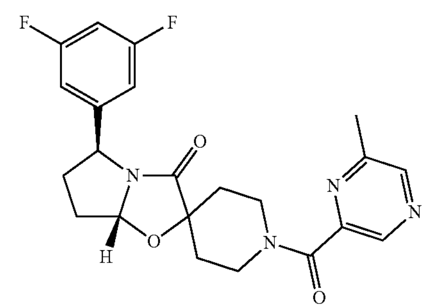 [SMILES: Cc1cncc(C(=O)N2CCC3(CC2)O[C@@H]2CC[C@@H](c4cc(F)cc(F)c4)N2C3=O)n1] | (5'S,7a'R)-5'-(3,5-difluorophenyl)-1-(6-methylpyrazine-2-carbonyl)tetrahydro-3'H-spiro[piperidine-4,2'-pyrrolo[2,1-b][1,3]oxazol]-3'-one | Calc'd 429, found 429 |
| 6.5 | 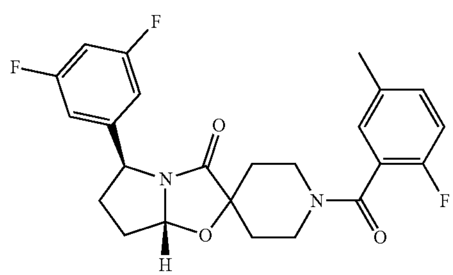 [SMILES: Cc1ccc(F)c(C(=O)N2CCC3(CC2)O[C@@H]2CC[C@@H](c4cc(F)cc(F)c4)N2C3=O)c1] | (5'S,7a'R)-5'-(3,5-difluorophenyl)-1-(2-fluoro-5-methyl-benzene-1-carbonyl)tetrahydro-3'H-spiro[piperidine-4,2'-pyrrolo[2,1-b][1,3]oxazol]-3'-one | Calc'd 445, found 445 |
| 6.6 | 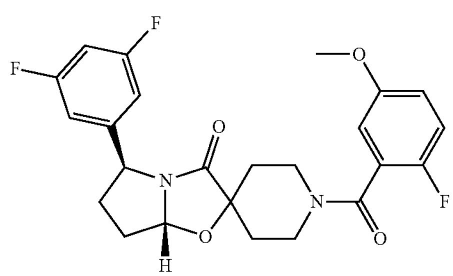 [SMILES: COc1ccc(F)c(C(=O)N2CCC3(CC2)O[C@@H]2CC[C@@H](c4cc(F)cc(F)c4)N2C3=O)c1] | (5'S,7a'R)-5'-(3,5-difluorophenyl)-1-(2-fluoro-5-methoxy-benzene-1-carbonyl)tetrahydro-3'H-spiro[piperidine-4,2'-pyrrolo[2,1-b][1,3]oxazol]-3'-one | Calc'd 461, found 461 |
| 6.7 | 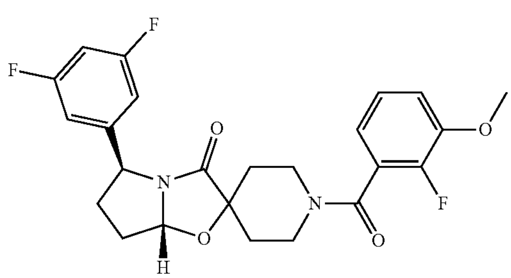 [SMILES: COc1cccc(C(=O)N2CCC3(CC2)O[C@@H]2CC[C@@H](c4cc(F)cc(F)c4)N2C3=O)c1F] | (5'S,7a'R)-5'-(3,5-difluorophenyl)-1-(2-fluoro-3-methoxy-benzene-1-carbonyl)tetrahydro-3'H-spiro[piperidine-4,2'-pyrrolo[2,1-b][1,3]oxazol]-3'-one | Calc'd 461, found 461 |

TABLE 15-continued

| Ex. No. | Structure | Name | Exact Mass [M + H]+ |
|---|---|---|---|
| 6.8 | 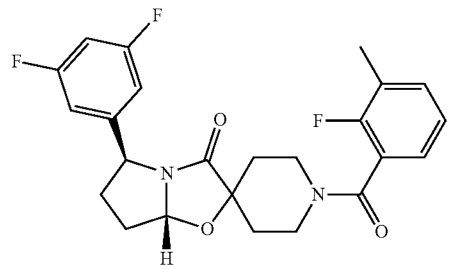 [SMILES: Cc1cccc(C(=O)N2CCC3(CC2)O[C@@H]2CC[C@@H](c4cc(F)cc(F)c4)N2C3=O)c1F] | (5'S,7a'R)-5'-(3,5-difluorophenyl)-1-(2-fluoro-3-methyl-benzene-1-carbonyl)tetrahydro-3'H-spiro[piperidine-4,2'-pyrrolo[2,1-b][1,3]oxazol]-3'-one | Calc'd 445, found 445 |
| 6.9 | 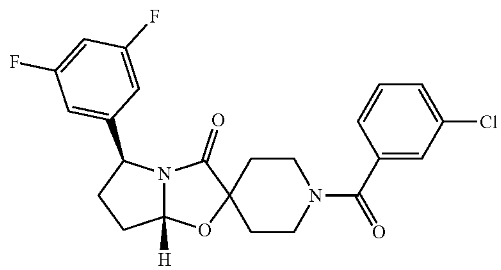 [SMILES: O=C(c1cccc(Cl)c1)N1CCC2(CC1)O[C@@H]1CC[C@@H](c3cc(F)cc(F)c3)N1C2=O] | (5'S,7a'R)-1-(3-chloro-benzene-1-carbonyl)-5'-(3,5-difluoro-phenyl)tetrahydro-3'H-spiro[piperidine-4,2'-pyrrolo[2,1-b][1,3]oxazol]-3'-one | Calc'd 447, found 447 |
| 6.10 | 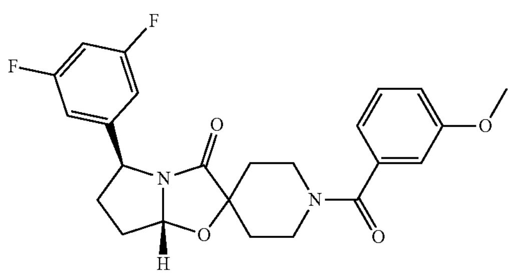 [SMILES: COc1cccc(C(=O)N2CCC3(CC2)O[C@@H]2CC[C@@H](c4cc(F)cc(F)c4)N2C3=O)c1] | (5'S,7a'R)-5'-(3,5-difluorophenyl)-1-(3-methoxybenzene-1-carbonyl)tetrahydro-3'H-spiro[piperidine-4,2'-pyrrolo[2,1-b][1,3]oxazol]-3'-one | Calc'd 443, found 443 |
| 6.11 | 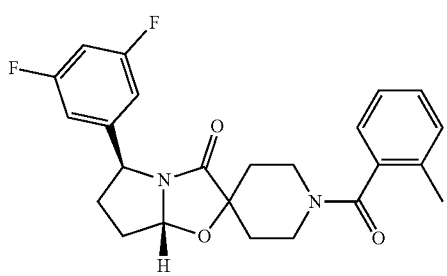 [SMILES: Cc1ccccc1C(=O)N1CCC2(CC1)O[C@@H]1CC[C@@H](c3cc(F)cc(F)c3)N1C2=O] | (5'S,7a'R)-5'-(3,5-difluorophenyl)-1-(2-methybenzene-1-carbonyl)tetrahydro-3'H-spiro[piperidine-4,2'-pyrrolo[2,1-b][1,3]oxazol]-3'-one | Calc'd 427, found 427 |
| 6.12 | 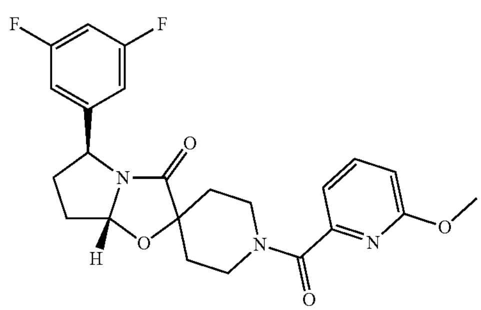 [SMILES: COc1cccc(C(=O)N2CCC3(CC2)O[C@@H]2CC[C@@H](c4cc(F)cc(F)c4)N2C3=O)n1] | (5'S,7a'R)-5'-(3,5-difluorophenyl)-1-(6-methoxypyridine-2-carbonyl)tetrahydro-3'H-spiro[piperidine-4,2'-pyrrolo[2,1-b][1,3]oxazol]-3'-one | Calc'd 444, found 444 |

TABLE 15-continued

| Ex. No. | Structure | Name | Exact Mass [M + H]+ |
|---|---|---|---|
| 6.13 | 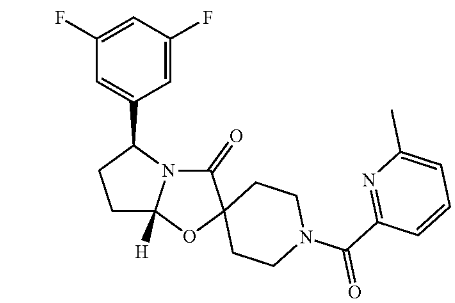 [SMILES: Cc1cccc(C(=O)N2CCC3(CC2)O[C@@H]2CC[C@@H](c4cc(F)cc(F)c4)N2C3=O)n1] | (5'S,7a'R)-5'-(3,5-difluorophenyl)-1-(6-methylpyridine-2-carbonyl)tetrahydro-3'H-spiro[piperidine-4,2'-pyrrolo[2,1-b][1,3]oxazol]-3'-one | Calc'd 428, found 428 |
| 6.14 | 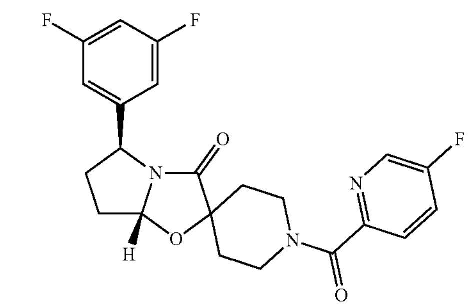 [SMILES: O=C(c1ccc(F)cn1)N1CCC2(CC1)O[C@@H]1CC[C@@H](c3cc(F)cc(F)c3)N1C2=O] | (5'S,7a'R)-5'-(3,5-difluorophenyl)-1-(5-fluoropyridine-2-carbonyl)tetrahydro-3'H-spiro[piperidine-4,2'-pyrrolo[2,1-b][1,3]oxazol]-3'-one | Calc'd 432, found 432 |
| 6.15 | 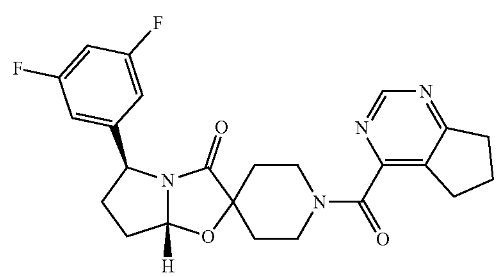 [SMILES: O=C(c1ncnc2c1CCC2)N1CCC2(CC1)O[C@@H]1CC[C@@H](c3cc(F)cc(F)c3)N1C2=O] | (5'S,7a'R)-5'-(3,5-difluorophenyl)-1-(6,7-dihydro-5H-cyclopenta[d]pyrimidine-4-carbonyl)-tetrahydro-3'H-spiro[piperidine-4,2'-pyrrolo-[2,1-b][1,3]oxazol]-3'-one | Calc'd 455, found 455 |
| 6.16 | 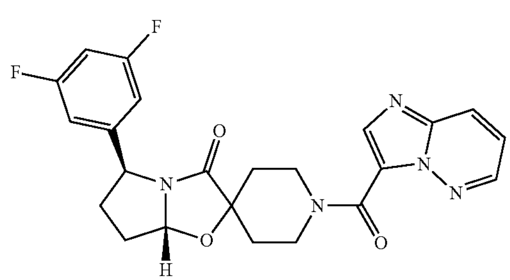 [SMILES: O=C(c1cnc2cccnn12)N1CCC2(CC1)O[C@@H]1CC[C@@H](c3cc(F)cc(F)c3)N1C2=O] | (5'S,7a'R)-5'-(3,5-difluorophenyl)-1-(imidazo[1,2-b]-pyridazine-3-carbonyl)tetrahydro-3'H-spiro[piperidine-4,2'-pyrrolo[2,1-b][1,3]oxazol]-3'-one | Calc'd 454, found 454 |
| 6.17 | 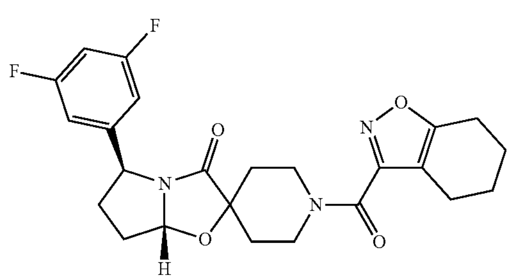 [SMILES: O=C(c1noc2c1CCCC2)N1CCC2(CC1)O[C@@H]1CC[C@@H](c3cc(F)cc(F)c3)N1C2=O] | (5'S,7a'R)-5'-(3,5-difluorophenyl)-1-(4,5,6,7-tetrahydro-1,2-benoxazole-3-carbonyl)tetrahydro-3'H-spiro[piperidine-4,2'-pyrrolo[2,1-b][1,3]oxazol]-3'-one | Calc'd 458, found 458 |

TABLE 15-continued

| Ex. No. | Structure | Name | Exact Mass [M + H]+ |
|---|---|---|---|
| 6.18 | 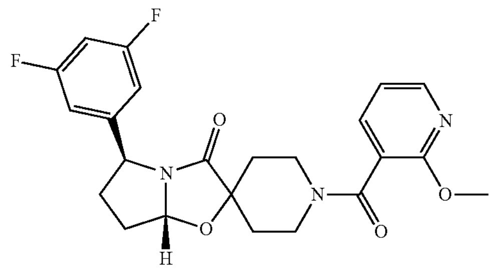 [SMILES: COc1ncccc1C(=O)N1CCC2(CC1)O[C@@H]1CC[C@@H](c3cc(F)cc(F)c3)N1C2=O] | (5'S,7a'R)-5'-(3,5-difluorophenyl)-1-(2-methoxypyridine-3-carbonyl)tetrahydro-3'H-spiro[piperidine-4,2'-pyrrolo[2,1-b][1,3]oxazol]-3'-one | Calc'd 444, found 444 |
| 6.19 | 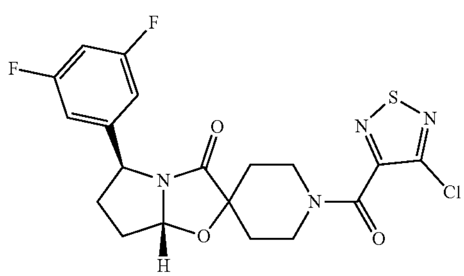 [SMILES: O=C(c1nsnc1Cl)N1CCC2(CC1)O[C@@H]1CC[C@@H](c3cc(F)cc(F)c3)N1C2=O] | (5'S,7a'R)-1-(4-chloro-1,2,5-thiadiazole-3-carbonyl)-5'-(3,5-difluorophenyl)-tetrahydro-3'H-spiro[piperidine-4,2'-pyrrolo[2,1-b][1,3]oxazol]-3'-one | Calc'd 455, found 455 |
| 6.20 | 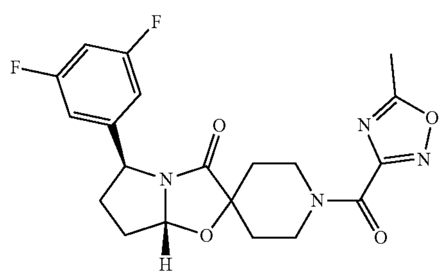 [SMILES: Cc1nc(C(=O)N2CCC3(CC2)O[C@@H]2CC[C@@H](c4cc(F)cc(F)c4)N2C3=O)no1] | (5'S,7a'R)-5'-(3,5-difluorophenyl)-1-(5-methyl-1,2,4-oxadiazole-3-carbonyl)-tetrahydro-3'H-spiro[piperidine-4,2'-pyrrolo[2,1-b][1,3]oxazol]-3'-one | Calc'd 419, found 419 |
| 6.21 | 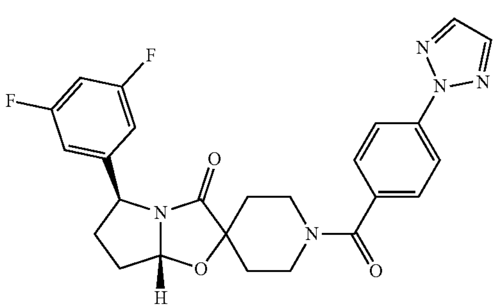 [SMILES: O=C(c1ccc(-n2nccn2)cc1)N1CCC2(CC1)O[C@@H]1CC[C@@H](c3cc(F)cc(F)c3)N1C2=O] | (5'S,7a'R)-5'-(3,5-difluorophenyl)-1-[4-(2H)-1,2,3-triazol-2-yl)benzene-1-carbonyl]tetrahydro-3'H-spiro[piperidine-4,2'-pyrrolo[2,1-b][1,3]oxazol]-3'-one | Calc'd 480, found 480 |
| 6.22 | 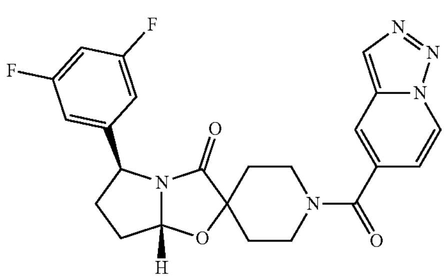 [SMILES: O=C(c1ccn2nncc2c1)N1CCC2(CC1)O[C@@H]1CC[C@@H](c3cc(F)cc(F)c3)N1C2=O] | (5'S,7a'R)-5'-(3,5-difluorophenyl)-1-([1,2,3]triazolo[1,5-a]pyridine-5-carbonyl)tetrahydro-3'H-spiro[piperidine-4,2'-pyrrolo[2,1-b][1,3]oxazol]-3'-one | Calc'd 454, found 454 |

TABLE 15-continued

| Ex. No. | Structure | Name | Exact Mass [M + H]+ |
|---|---|---|---|
| 6.23 | 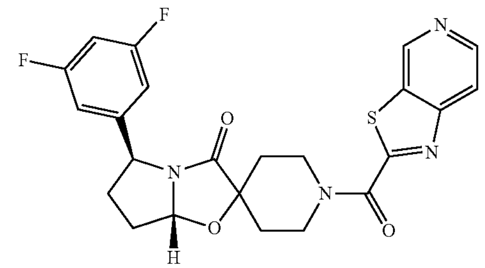 [SMILES: O=C(c1nc2ccncc2s1)N1CCC2(CC1)O[C@@H]1CC[C@@H](c3cc(F)cc(F)c3)N1C2=O] | (5'S,7a'R)-5'-(3,5-difluorophenyl)-1-([1,3]thiazolo[5,4-c]-pyridine-2-carbonyl)tetrahydro-3'H-spiro[piperidine-4,2'-pyrrolo[2,1-b][1,3]oxazol]-3'-one | Calc'd 471, found 471 |
| 6.24 | 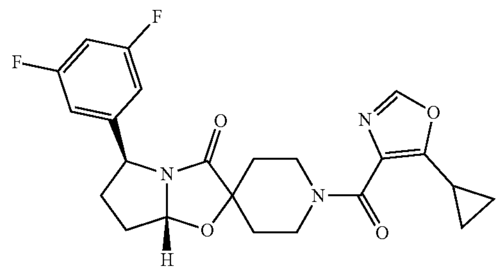 [SMILES: O=C(c1ncoc1C1CC1)N1CCC2(CC1)O[C@@H]1CC[C@@H](c3cc(F)cc(F)c3)N1C2=O] | (5'S,7a'R)-1-(5-cyclopropyl-1,3-oxazole-4-carbonyl)-5'-(3,5-difluorophenyl)tetrahydro-3'H-spiro[piperidine-4,2'-pyrrolo[2,1-b][1,3]oxazol]-3'-one | Calc'd 444, found 444 |
| 6.25 | 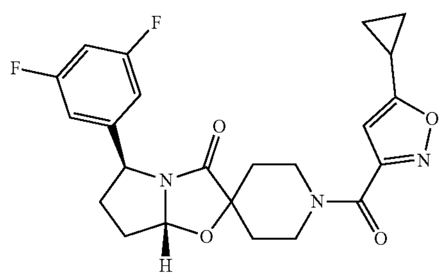 [SMILES: O=C(c1cc(C2CC2)on1)N1CCC2(CC1)O[C@@H]1CC[C@@H](c3cc(F)cc(F)c3)N1C2=O] | (5'S,7a'R)-1-(5-cyclopropyl-1,2-oxazole-3-carbonyl)-5'-(3,5-difluorophenyl)tetrahydro-3'H-spiro[piperidine-4,2'-pyrrolo[2,1-b][1,3]oxazol]-3'-one | Calc'd 444, found 444 |
| 6.26 | 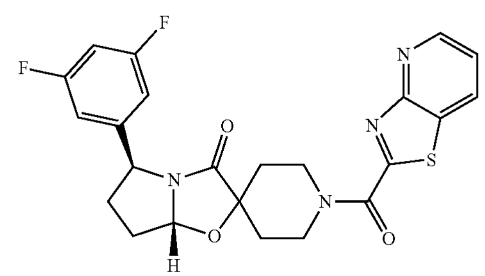 [SMILES: O=C(c1nc2ncccc2s1)N1CCC2(CC1)O[C@@H]1CC[C@@H](c3cc(F)cc(F)c3)N1C2=O] | (5'S,7a'R)-5'-(3,5-difluorophenyl)-1-[1,3]thiazolo[4,5-b]pyridine-2-carbonyl)-tetrahydro-3'H-spiro[piperidine-4,2'-pyrrolo[2,1-b][1,3]oxazol]-3'-one | Calc'd 471, found 471 |
| 6.27 | 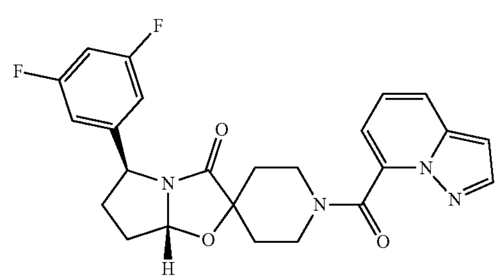 | (5'S,7a'R)-5'-(3,5-difluorophenyl)-1-(pyrazolo[1,5-a]pyridine-7-carbonyl)tetrahydro-3'H-spiro[piperidine-4,2'-pyrrolo[2,1-b][1,3]oxazol]-3'-one | Calc'd 453, found 453 |

TABLE 15-continued

| Ex. No. | Structure | Name | Exact Mass [M + H]+ |
|---|---|---|---|
| 6.28 | 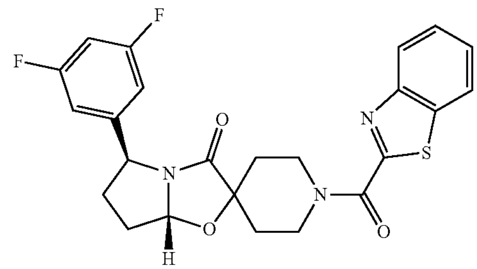 [SMILES: O=C(c1nc2ccccc2s1)N1CCC2(CC1)O[C@@H]1CC[C@@H](c3cc(F)cc(F)c3)N1C2=O] | (5'S,7a'R)-1-(1,3-benzothiazole-2-carbonyl)-5'-(3,5-difluorophenyl)tetrahydro-3'H-spiro[piperidine-4,2'-pyrrolo[2,1-b][1,3]oxazol]-3'-one | Calc'd 470, found 470 |
| 6.29 | 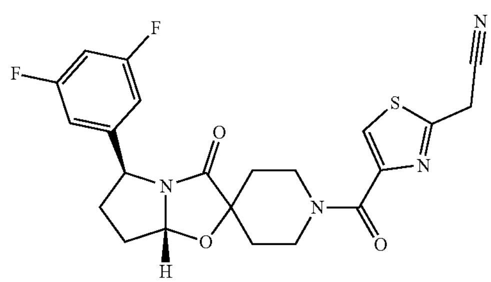 [SMILES: N#CCc1nc(C(=O)N2CCC3(CC2)O[C@@H]2CC[C@@H](c4cc(F)cc(F)c4)N2C3=O)cs1] | {4-[(5'S,7a'R)-5'-(3,5-difluorophenyl)-3-oxo-tetrahydro-1H,3'H-spiro[piperidine-4,2'-pyrrolo[2,1-b][1,3]oxazole]-1-carbonyl]-1,3-thiazol-2-yl}acetonitrile | Calc'd 459, found 459 |
| 6.30 | 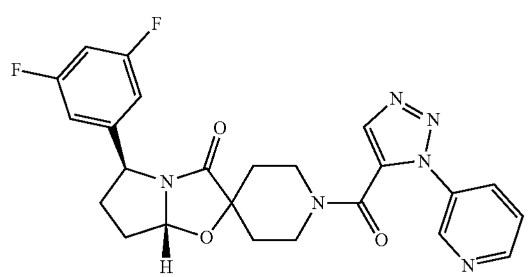 [SMILES: O=C(c1cnnn1-c1cccnc1)N1CCC2(CC1)O[C@@H]1CC[C@@H](c3cc(F)cc(F)c3)N1C2=O] | (5'S,7a'R)-5'-(3,5-difluorophenyl)-1-[1-(pyridin-3-yl)-1H-1,2,3-triazole-5-carbonyl]tetrahydro-3'H-spiro[piperidine-4,2'-pyrrolo[2,1-b][1,3]oxazol]-3'-one | Calc'd 481, found 481 |
| 6.31 | 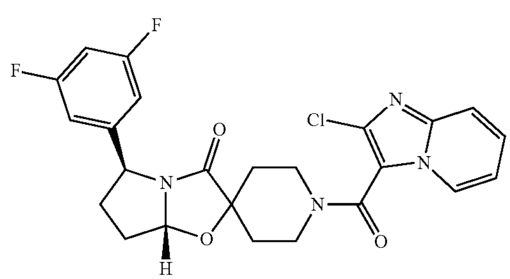 [SMILES: O=C(c1c(Cl)nc2ccccn12)N1CCC2(CC1)O[C@@H]1CC[C@@H](c3cc(F)cc(F)c3)N1C2=O] | (5'S,7a'R)-1-(2-chloroimidazo[1,2-a]pyridine-3-carbonyl)-5'-(3,5-difluorophenyl)tetrahydro-3'H-spiro[piperidine-4,2'-pyrrolo[2,1-b][1,3]oxazol]-3'-one | Calc'd 487, found 487 |
| 6.32 | 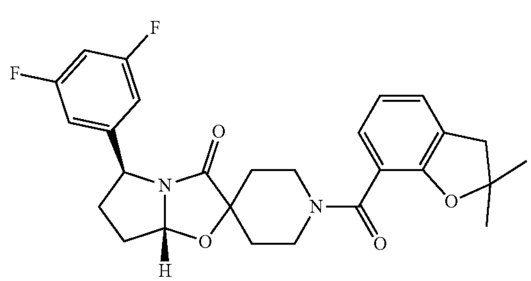 [SMILES: CC1(C)Cc2cccc(C(=O)N3CCC4(CC3)O[C@@H]3CC[C@@H](c5cc(F)cc(F)c5)N3C4=O)c2O1] | (5'S,7a'R)-5'-(3,5-difluorophenyl)-1-(2,2-dimethyl-2,3-dihydro-1-benzofuran-7-carbonyl)-tetrahydro-3'H-spiro[piperidine-4,2'-pyrrolo[2,1-b][1,3]oxazol]-3'-one | Calc'd 483, found 483 |

TABLE 15-continued

| Ex. No. | Structure | Name | Exact Mass [M + H]+ |
|---|---|---|---|
| 6.33 | 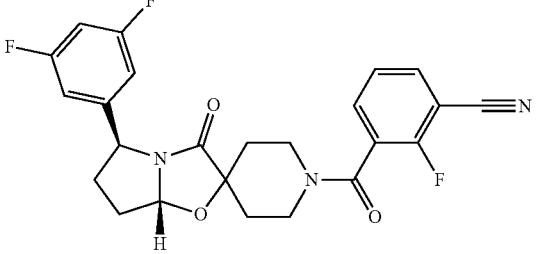 | 3-[(5'S,7a'R)-5'-(3,5-difluorophenyl)-3'-oxotetrahydro-1H,3'H-spiro[piperidine-4,2'-pyrrolo[2,1-b][1,3]oxazole]-1-carbonyl]-2-fluorobenzonitrile | Calc'd 456, found 456 |
| 6.34 | 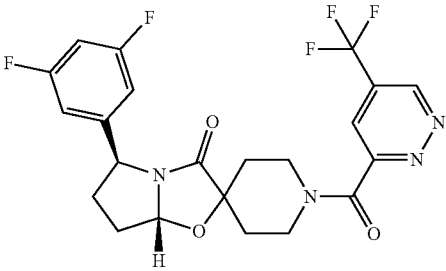 [SMILES: O=C(c1cc(C(F)(F)F)cnn1)N1CCC2(CC1)O[C@@H]1CC[C@@H](c3cc(F)cc(F)c3)N1C2=O] | (5'S,7a'R)-5'-(3,5-difluorophenyl)-1-[5-(trifluoromethyl)pyridazine-3-carbonyl]tetrahydro-3'H-spiro[piperidine-4,2'-pyrrolo[2,1-b][1,3]oxazol]-3'-one | Calc'd 483, found 483 |
| 6.35 | 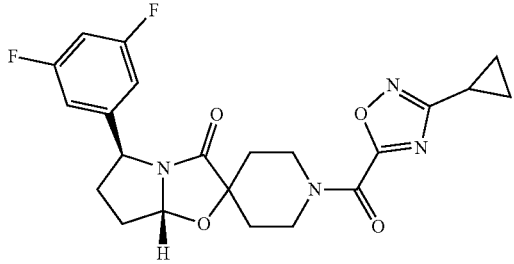 [SMILES: O=C(c1nc(C2CC2)no1)N1CCC2(CC1)O[C@@H]1CC[C@@H](c3cc(F)cc(F)c3)N1C2=O] | (5'S,7a'R)-1-(3-cyclopropyl-1,2,4-oxadiazole-5-carbonyl)-5'-(3,5-difluorophenyl)tetrahydro-3'H-spiro[piperidine-4,2'-pyrrolo[2,1-b][1,3]oxazol-3'-one | Calc'd 445, found 445 |
| 6.36 | 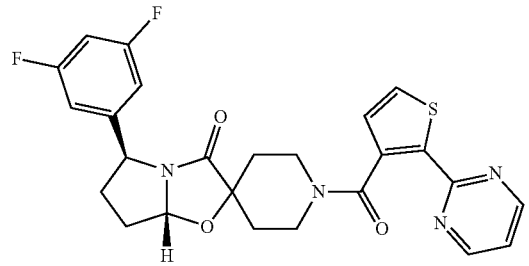 [SMILES: O=C(c1ccsc1-c1ncccn1)N1CCC2(CC1)O[C@@H]1CC[C@@H](c3cc(F)cc(F)c3)N1C2=O] | (5'S,7a'R)-5'-(3,5-difluorophenyl)-1-[2-(pyrimidin-2-yl)thiophene-3-carbonyl]tetrahydro-3'H-spiro[piperidine-4,2'-pyrrolo[2,1-b][1,3]oxazol]-3'-one | Calc'd 497, found 497 |
| 6.37 | 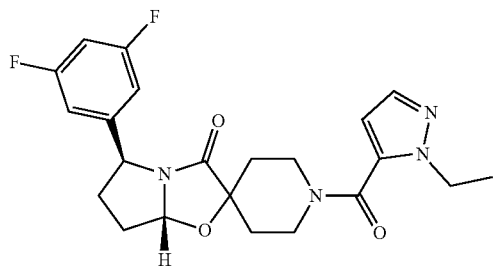 [SMILES: CCn1nccc1C(=O)N1CCC2(CC1)O[C@@H]1CC[C@@H](c3cc(F)cc(F)c3)N1C2=O] | (5'S,7a'R)-5'-(3,5-difluorophenyl)-1-(1-ethyl-1H-pyrazole-5-carbonyl)tetrahydro-3'H-spiro[piperidine-4,2'-pyrrolo[2,1-b][1,3]oxazol]-3'-one | Calc'd 431, found 431 |

TABLE 15-continued

| Ex. No. | Structure | Name | Exact Mass [M + H]+ |
|---|---|---|---|
| 6.38 | 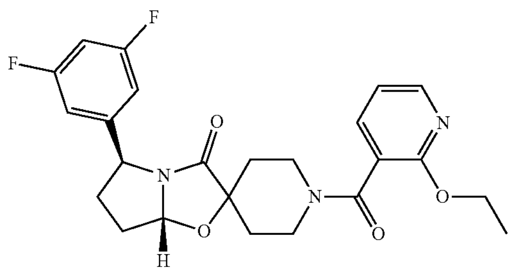 [SMILES: CCOc1ncccc1C(=O)N1CCC2(CC1)O[C@@H]1CC[C@@H](c3cc(F)cc(F)c3)N1C2=O] | (5'S,7a'R)-5'-(3,5-difluorophenyl)-1-(2-ethoxypyridine-3-carbonyl)tetrahydro-3'H-spiro[piperidine-4,2'-pyrrolo[2,1-b][1,3]oxazol]-3'-one | Calc'd 458, found 458 |
| 6.39 | 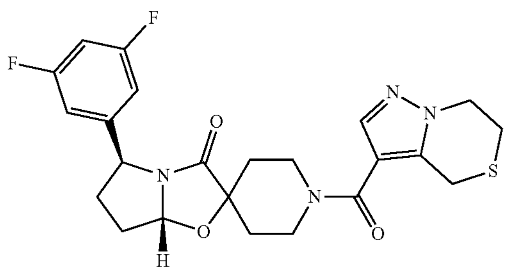 [SMILES: O=C(c1cnn2c1CSCC2)N1CCC2(CC1)O[C@@H]1CC[C@@H](c3cc(F)cc(F)c3)N1C2=O] | (5'S,7a'R)-5'-(3,5-difluorophenyl)-1-(6,7-dihydro-4H-pyrazolo[5,1-c][1,4]thiazine-3-carbonyl)tetrahydro-3'H-spiro[piperidine-4,2'-pyrrolo[2,1-b][1,3]oxazol]-3'-one | Calc'd 475, found 475 |
| 6.40 | 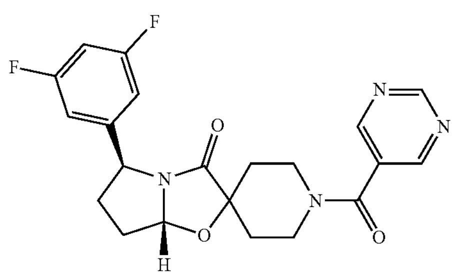 [SMILES: O=C(c1cncnc1)N1CCC2(CC1)O[C@@H]1CC[C@@H](c3cc(F)cc(F)c3)N1C2=O] | (5'S,7a'R)-5'-(3,5-difluorophenyl)-1-(pyrimidine-5-carbonyl)tetrahydro-3'H-spiro[piperidine-4,2'-pyrrolo[2,1-b][1,3]oxazol]-3'-one | Calc'd 415, found 415 |
| 6.41 | 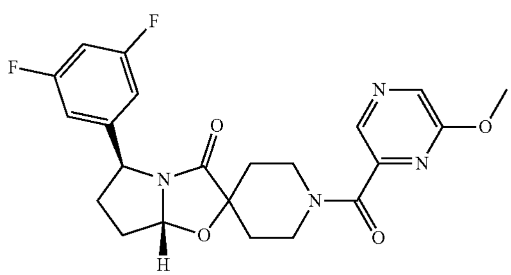 [SMILES: COc1cncc(C(=O)N2CCC3(CC2)O[C@@H]2CC[C@@H](c4cc(F)cc(F)c4)N2C3=O)n1] | (5'S,7a'R)-5'-(3,5-difluorophenyl)-1-(6-methoxypyrazine-2-carbonyl)tetrahydro-3'H-spiro[piperidine-4,2'-pyrrolo[2,1-b][1,3]-oxazol]-3'-one | Calc'd 445, found 445 |
| 6.42 | 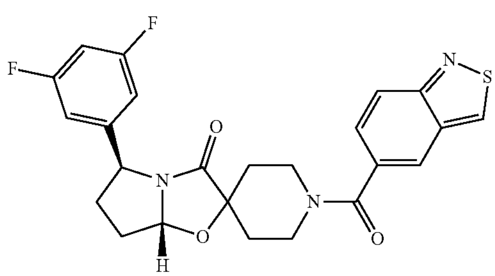 [SMILES: O=C(c1ccc2nscc2c1)N1CCC2(CC1)O[C@@H]1CC[C@@H](c3cc(F)cc(F)c3)N1C2=O] | (5'S,7a'R)-1-(2,1-benzothiazole-5-carbonyl)-5'-(3,5-difluorophenyl)tetrahydro-3'H-spiro[piperidine-4,2'-pyrrolo[2,1-b][1,3]oxazol]-3'-one | Calc'd 470, found 470 |

TABLE 15-continued

| Ex. No. | Structure | Name | Exact Mass [M + H]+ |
|---|---|---|---|
| 6.43 | 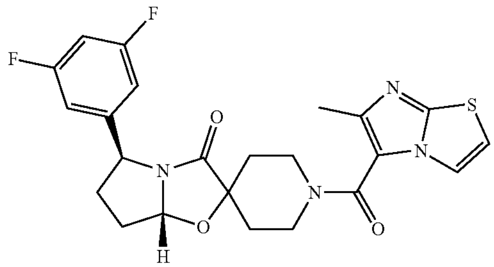 [SMILES: Cc1nc2sccn2c1C(=O)N1CCC2(CC1)O[C@@H]1CC[C@@H](c3cc(F)cc(F)c3)N1C2=O] | (5'S,7a'R)-5'-(3,5-difluorophenyl)-1-(6-methylimidazo[2,1-b][1,3]thiazole-5-carbonyl)tetrahydro-3'H-spiro[piperidine-4,2'-pyrrolo[2,1-b][1,3]oxazol]-3'-one | Calc'd 473, found 473 |
| 6.44 | 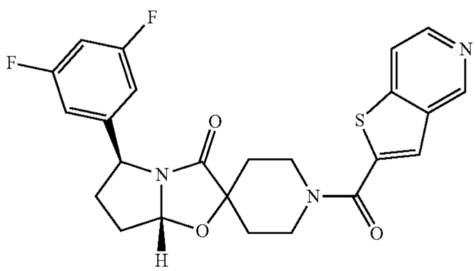 [SMILES: O=C(c1cc2cnccc2s1)N1CCC2(CC1)O[C@@H]1CC[C@@H](c3cc(F)cc(F)c3)N1C2=O] | (5'S,7a'R)-5'-(3,5-difluorophenyl)-1-([1,3]thiazolo[4,5-c]pyridine-2-carbonyl)tetrahydro-3'H-spiro[piperidine-4,2'-pyrrolo[2,1-b][1,3]oxazol]-3'-one | Calc'd 471, found 471 |
| 6.45 | 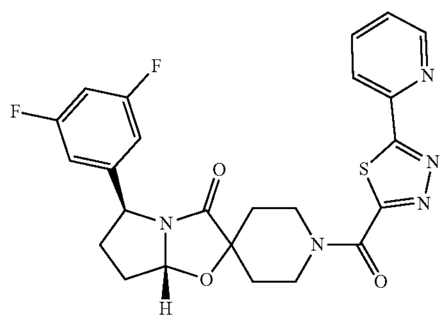 [SMILES: O=C(c1nnc(-c2ccccn2)s1)N1CCC2(CC1)O[C@@H]1CC[C@@H](c3cc(F)cc(F)c3)N1C2=O] | (5'S,7a'R)-5'-(3,5-difluorophenyl)-1-[5-(pyridin-2-yl)-1,3,4-thiadiazole-2-carbonyl]tetrahydro-3'H-spiro[piperidine-4,2'-pyrrolo[2,1-b][1,3]oxazol]-3'-one | Calc'd 498, found 498 |
| 6.46 | 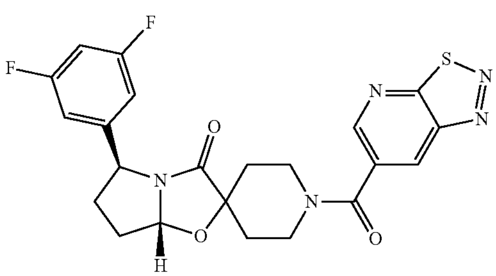 [SMILES: O=C(c1cnc2snnc2c1)N1CCC2(CC1)O[C@@H]1CC[C@@H](c3cc(F)cc(F)c3)N1C2=O] | (5'S,7a'R)-5'-(3,5-difluorophenyl)-1-([1,2,3]thiadiazolo-[5,4-b]pyridine-6-carbonyl)tetrahydro-3'H-spiro[piperidine-4,2'-pyrrolo[2,1-b][1,3]oxazol]-3'-one | Calc'd 472, found 472 |
| 6.47 | 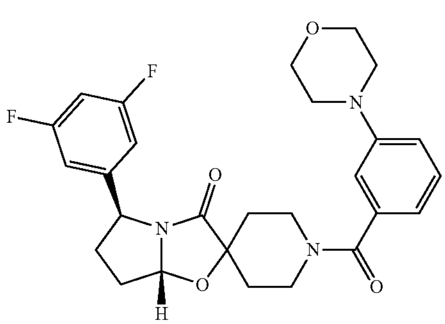 [SMILES: O=C(c1cccc(N2CCOCC2)c1)N1CCC2(CC1)O[C@@H]1CC[C@@H](c3cc(F)cc(F)c3)N1C2=O] | (5'S,7a'R)-5'-(3,5-difluorophenyl)-1-[3-(morpholin-4-yl)-benzene-1-carbonyl]-tetrahydro-3'H-spiro[piperidine-4,2'-pyrrolo[2,1-b][1,3]oxazol]-3'-one | Calc'd 498, found 498 |

TABLE 15-continued

| Ex. No. | Structure | Name | Exact Mass [M + H]+ |
|---|---|---|---|
| 6.48 | 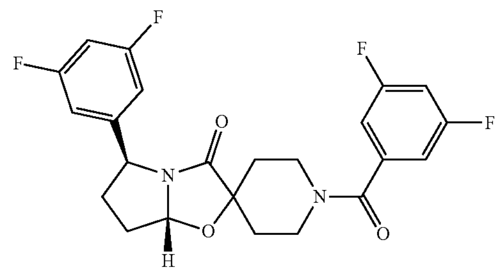 [SMILES: O=C(c1cc(F)cc(F)c1)N1CCC2(CC1)O[C@@H]1CC[C@@H](c3cc(F)cc(F)c3)N1C2=O] | (5'S,7a'R)-1-(3,5-difluorobenzene-1-carbonyl)-5'-(3,5-difluorophenyl)tetrahydro-3'H-spiro[piperidine-4,2'-pyrrolo[2,1-b][1,3]oxazol]-3'-one | Calc'd 449, found 449 |
| 6.49 | 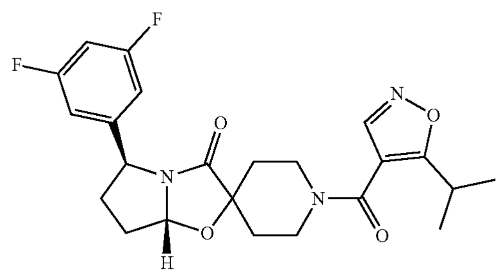 [SMILES: CC(C)c1oncc1C(=O)N1CCC2(CC1)O[C@@H]1CC[C@@H](c3cc(F)cc(F)c3)N1C2=O] | (5'S,7a'R)-5'-(3,5-difluorophenyl)-1-[5-(propan-2-yl)-1,2-oxazole-4-carbonyl]-tetrahydro-3'H-spiro[piperidine-4,2'-pyrrolo[2,1-b][1,3]-oxazol]-3'-one | Calc'd 446, found 446 |
| 6.50 | 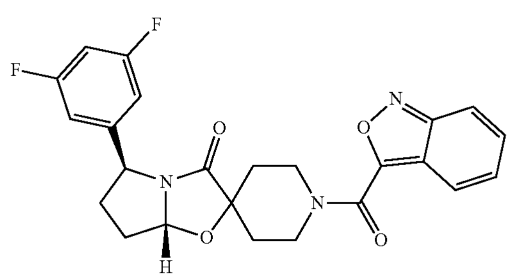 [SMILES: O=C(c1onc2ccccc12)N1CCC2(CC1)O[C@@H]1CC[C@@H](c3cc(F)cc(F)c3)N1C2=O] | (5'S,7a'R)-1-(2,1-benzoxazole-3-carbonyl)-5'-(3,5-difluorophenyl)tetrahydro-3'H-spiro[piperidine-4,2'-pyrrolo[2,1-b][1,3]oxazol]-3'-one | Calc'd 454, found 454 |
| 6.51 | 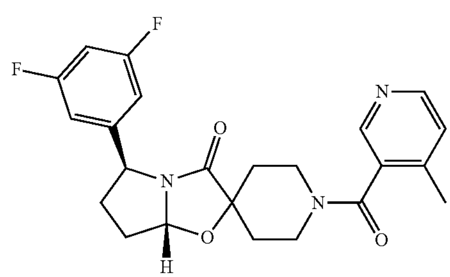 [SMILES: Cc1ccncc1C(=O)N1CCC2(CC1)O[C@@H]1CC[C@@H](c3cc(F)cc(F)c3)N1C2=O] | (5'S,7a'R)-5'-(3,5-difluorophenyl)-1-(4-methylpyridine-3-carbonyl)tetrahydro-3'H-spiro[piperidine-4,2'-pyrrolo[2,1-b][1,3]oxazol]-3'-one | Calc'd 428, found 428 |
| 6.52 | 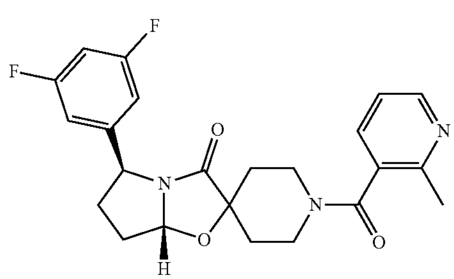 [SMILES: Cc1ncccc1C(=O)N1CCC2(CC1)O[C@@H]1CC[C@@H](c3cc(F)cc(F)c3)N1C2=O] | (5'S,7a'R)-5'-(3,5-difluorophenyl)-1-(2-methylpyridine-3-carbonyl)tetrahydro-3'H-spiro[piperidine-4,2'-pyrrolo[2,1-b][1,3]oxazol]-3'-one | Calc'd 428, found 428 |

TABLE 15-continued

| Ex. No. | Structure | Name | Exact Mass [M + H]+ |
|---|---|---|---|
| 6.53 | 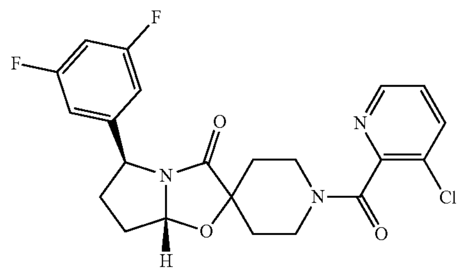 [SMILES: O=C(c1ncccc1Cl)N1CCC2(CC1)O[C@@H]1CC[C@@H](c3cc(F)cc(F)c3)N1C2=O] | (5'S,7a'R)-1-(3-chloropyridine-2-carbonyl)-5'-(3,5-difluorophenyl)tetrahydro-3'H-spiro[piperidine-4,2'-pyrrolo[2,1-b][1,3]-oxazol]-3'-one | Calc'd 448, found 448 |
| 6.54 | 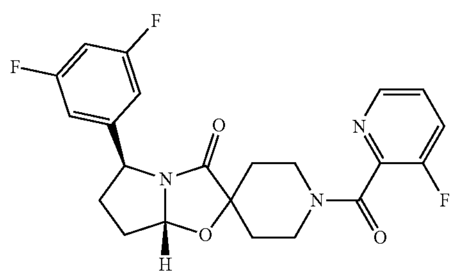 [SMILES: O=C(c1ncccc1F)N1CCC2(CC1)O[C@@H]1CC[C@@H](c3cc(F)cc(F)c3)N1C2=O] | (5'S,7a'R)-5'-(3,5-difluorophenyl)-1-(3-fluoropyridine-2-carbonyl)tetrahydro-3'H-spiro[piperidine-4,2'-pyrrolo[2,1-b][1,3]oxazol]-3-one | Calc'd 432, found 432 |
| 6.55 | 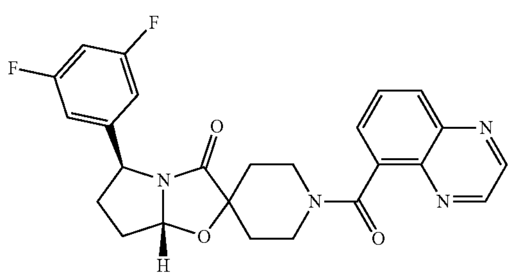 [SMILES: O=C(c1cccc2nccnc12)N1CCC2(CC1)O[C@@H]1CC[C@@H](c3cc(F)cc(F)c3)N1C2=O] | (5'S,7a'R)-5'-(3,5-difluorophenyl)-1-(quinoxaline-5-carbonyl)tetrahydro-3'H-spiro[piperidine-4,2'-pyrrolo[2,1-b][1,3]-oxazol]-3'-one | Calc'd 465, found 465 |
| 6.56 | 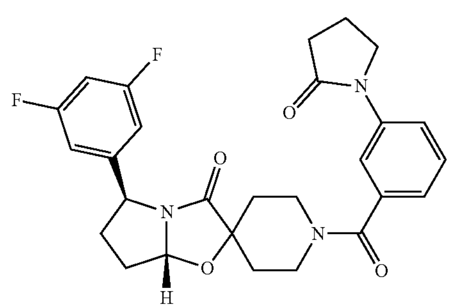 [SMILES: O=C(c1cccc(N2CCCC2=O)c1)N1CCC2(CC1)O[C@@H]1CC[C@@H](c3cc(F)cc(F)c3)N1C2=O] | (5'S,7a'R)-5'-(3,5-difluorophenyl)-1-[3-(2-oxopyrrolidin-1-yl)benzene-1-carbonyl]tetrahydro-3'H-spiro[piperidine-4,2'-pyrrolo[2,1-b][1,3]-oxazol]-3'-one | Calc'd 496, found 496 |
| 6.57 | 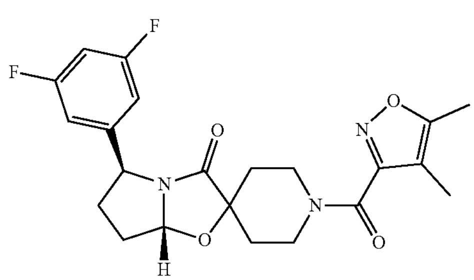 [SMILES: Cc1onc(C(=O)N2CCC3(CC2)O[C@@H]2CC[C@@H](c4cc(F)cc(F)c4)N2C3=O)c1C] | (5'S,7a'R)-5'-(3,5-difluorophenyl)-1-(4,5-dimethyl-1,2-oxazole-3-carbonyl)tetrahydro-3'H-spiro[piperidine-4,2'-pyrrolo[2,1-b][1,3]-oxazol]-3'-one | Calc'd 432, found 432 |

TABLE 15-continued

| Ex. No. | Structure | Name | Exact Mass [M + H]+ |
|---|---|---|---|
| 6.58 | 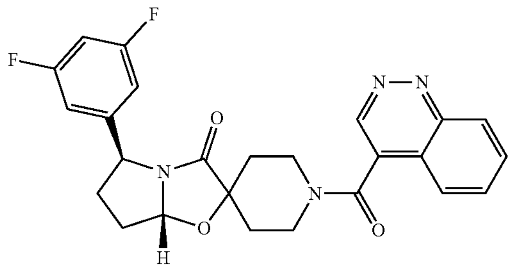 [SMILES: O=C(c1cnnc2ccccc12)N1CCC2(CC1)O[C@@H]1CC[C@@H](c3cc(F)cc(F)c3)N1C2=O] | (5'S,7a'R)-1-(cinnoline-4-carbonyl)-5'-(3,5-difluorophenyl)tetrahydro-3'H-spiro[piperidine-4,2'-pyrrolo[2,1-b][1,3]-oxazol]-3'-one | Calc'd 465, found 465 |
| 6.59 | 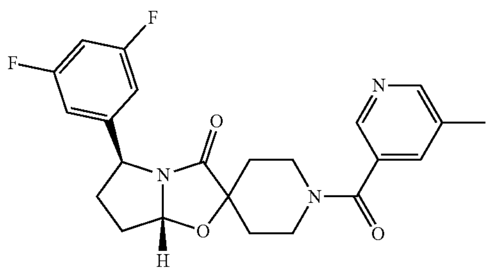 [SMILES: Cc1cncc(C(=O)N2CCC3(CC2)O[C@@H]2CC[C@@H](c4cc(F)cc(F)c4)N2C3=O)c1] | (5'S,7a'R)-5'-(3,5-difluorophenyl)-1-(5-methylpyridine-3-carbonyl)tetrahydro-3'H-spiro[piperidine-4,2'-pyrrolo[2,1-b][1,3]oxazol]-3'-one | Calc'd 428, found 428 |
| 6.60 | 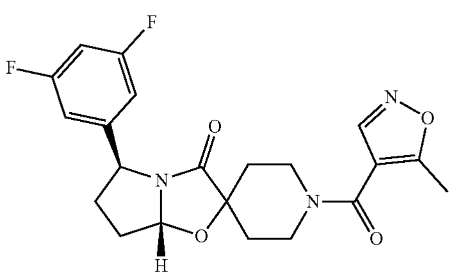 [SMILES: Cc1oncc1C(=O)N1CCC2(CC1)O[C@@H]1CC[C@@H](c3cc(F)cc(F)c3)N1C2=O] | (5'S,7a'R)-5'-(3,5-difluorophenyl)-1-(5-methyl-1,2-oxazole-4-carbonyl)tetrahydro-3'H-spiro[piperidine-4,2'-pyrrolo[2,1-b][1,3]oxazol]-3'-one | Calc'd 418, found 418 |
| 6.61 | 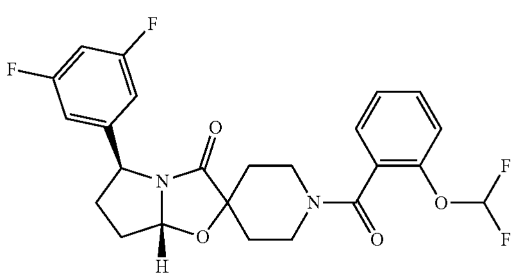 [SMILES: O=C(c1ccccc1OC(F)F)N1CCC2(CC1)O[C@@H]1CC[C@@H](c3cc(F)cc(F)c3)N1C2=O] | (5'S,7a'R)-1-[2-(difluoromethoxy)-benzene-1-carbonyl]-5'-(3,5-difluorophenyl)tetrahydro-3'H-spiro[piperidine-4,2'-pyrrolo[2,1-b][1,3]-oxazol]-3'-one | Calc'd 479, found 479 |
| 6.62 | 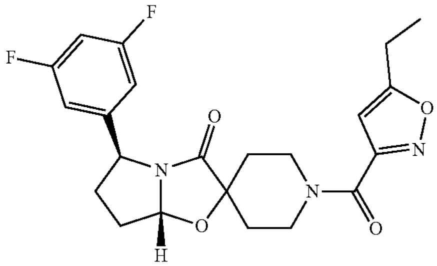 [SMILES: CCc1cc(C(=O)N2CCC3(CC2)O[C@@H]2CC[C@@H](c4cc(F)cc(F)c4)N2C3=O)no1] | (5'S,7a'R)-5'-(3,5-difluorophenyl)-1-(5-ethyl-1,2-oxazole-3-carbonyl)tetrahydro-3'H-spiro[piperidine-4,2'-pyrrolo[2,1-b][1,3]oxazol]-3'-one | Calc'd 432, found 432 |

TABLE 15-continued

| Ex. No. | Structure | Name | Exact Mass [M + H]+ |
|---|---|---|---|
| 6.63 | 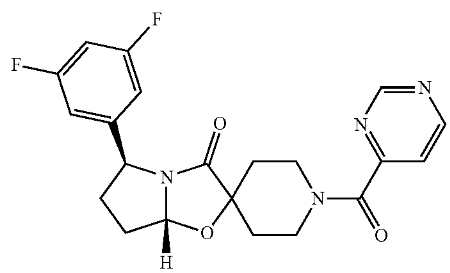 [SMILES: O=C(c1ccncn1)N1CCC2(CC1)O[C@@H]1CC[C@@H](c3cc(F)cc(F)c3)N1C2=O] | (5'S,7a'R)-5'-(3,5-difluorophenyl)-1-(pyrimidine-4-carbonyl)tetrahydro-3'H-spiro[piperidine-4,2'-pyrrolo[2,1-b][1,3]-oxazol]-3'-one | Calc'd 415, found 415 |
| 6.64 | 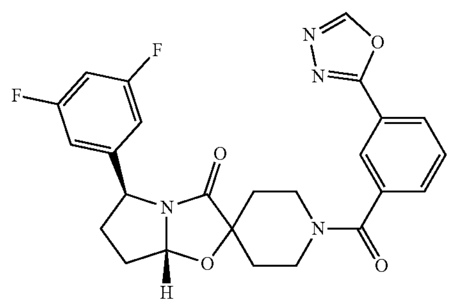 [SMILES: O=C(c1cccc(-c2nnco2)c1)N1CCC2(CC1)O[C@@H]1CC[C@@H](c3cc(F)cc(F)c3)N1C2=O] | (5'S,7a'R)-5'-(3,5-difluorophenyl)-1-[3-(1,3,4-oxadiazol-2-yl)benzene-1-carbonyl]tetrahydro-3'H-spiro[piperidine-4,2'-pyrrolo[2,1-b][1,3]-oxazol]-3'-one | Calc'd 481, found 481 |
| 6.65 | 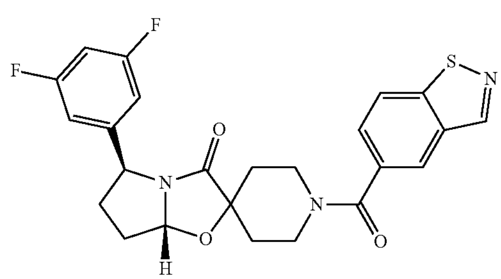 [SMILES: O=C(c1ccc2sncc2c1)N1CCC2(CC1)O[C@@H]1CC[C@@H](c3cc(F)cc(F)c3)N1C2=O] | (5'S,7a'R)-1-(1,2-benzothiazole-5-carbonyl)-5'-(3,5-difluorophenyl)tetrahydro-3'H-spiro[piperidine-4,2'-pyrrolo[2,1-b][1,3]-oxazol]-3'-one | Calc'd 470, found 470 |
| 6.66 | 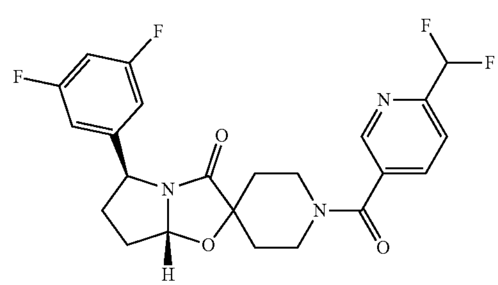 [SMILES: O=C(c1ccc(C(F)F)nc1)N1CCC2(CC1)O[C@@H]1CC[C@@H](c3cc(F)cc(F)c3)N1C2=O] | (5'S,7a'R)-1-[6-(difluoromethyl)pyridine-3-carbonyl]-5'-(3,5-difluorophenyl)-tetrahydro-3'H-spiro[piperidine-4,2'-pyrrolo[2,1-b][1,3]-oxazol]-3'-one | Calc'd 464, found 464 |
| 6.67 | 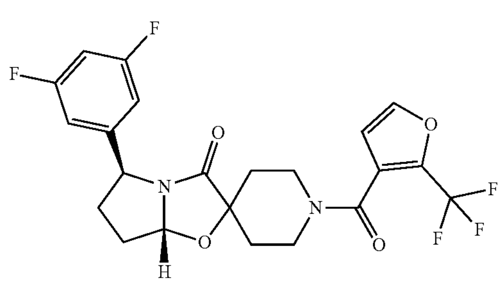 [SMILES: O=C(c1ccoc1C(F)(F)F)N1CCC2(CC1)O[C@@H]1CC[C@@H](c3cc(F)cc(F)c3)N1C2=O] | (5'S,7a'R)-5'-(3,5-difluorophenyl)-1-[2-(trifluoromethyl)-furan-3-carbonyl]-tetrahydro-3'H-spiro[piperidine-4,2'-pyrrolo[2,1-b][1,3]-oxazol]-3'-one | Calc'd 471, found 471 |

TABLE 15-continued

| Ex. No. | Structure | Name | Exact Mass [M + H]+ |
|---|---|---|---|
| 6.68 | 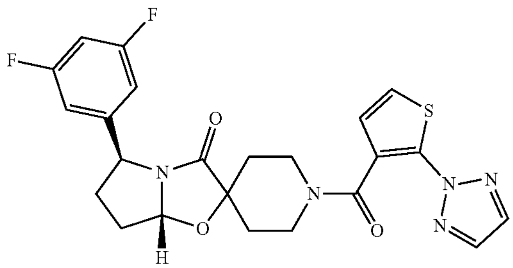 [SMILES: O=C(c1ccsc1-n1nccn1)N1CCC2(CC1)O[C@@H]1CC[C@@H](c3cc(F)cc(F)c3)N1C2=O] | (5'S,7a'R)-5'-(3,5-difluorophenyl)-1-[2-(2H-1,2,3-triazol-2-yl)thiophene-3-carbonyl]tetrahydro-3'H-spiro[piperidine-4,2'-pyrrolo[2,1-b][1,3]oxazol]-3'-one | Calc'd 486, found 486 |
| 6.69 | 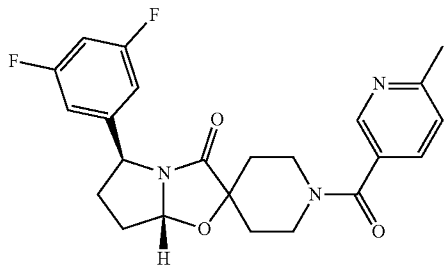 [SMILES: Cc1ccc(C(=O)N2CCC3(CC2)O[C@@H]2CC[C@@H](c4cc(F)cc(F)c4)N2C3=O)cn1] | (5'S,7a'R)-5'-(3,5-difluorophenyl)-1-(6-methylpyridine-3-carbonyl)tetrahydro-3'H-spiro[piperidine-4,2'-pyrrolo[2,1-b][1,3]oxazol]-3'-one | Calc'd 428, found 428 |
| 6.70 | 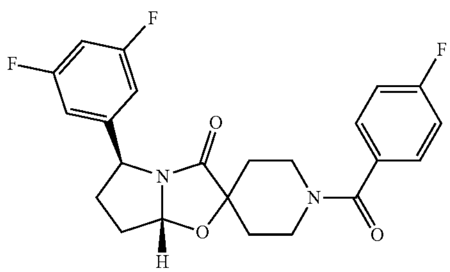 [SMILES: O=C(c1ccc(F)cc1)N1CCC2(CC1)O[C@@H]1CC[C@@H](c3cc(F)cc(F)c3)N1C2=O] | (5'S,7a'R)-5'-(3,5-difluorophenyl)-1-(4-fluorobenzene-1-carbonyl)tetrahydro-3'H-spiro[piperidine-4,2'-pyrrolo[2,1-b][1,3]oxazol]-3'-one | Calc'd 431, found 431 |
| 6.71 | 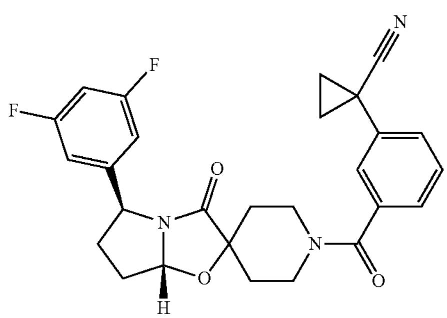 [SMILES: N#CC1(c2cccc(C(=O)N3CCC4(CC3)O[C@@H]3CC[C@@H](c5cc(F)cc(F)c5)N3C4=O)c2)CC1] | 1-{3-[(5'S,7a'R)-5'-(3,5-difluorophenyl)-3'-oxotetrahydro-1H,3'H-spiro[piperidine-4,2'-pyrrolo-[2,1-b][1,3]oxazole]-1-carbonyl]phenyl}cyclopropane-1-carbonitrile | Calc'd 478, found 478 |
| 6.72 | 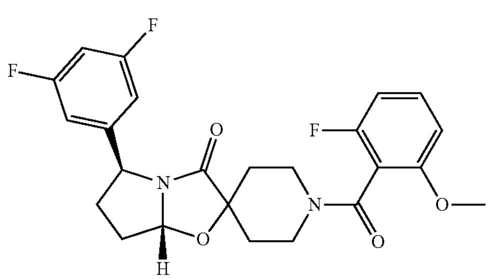 [SMILES: COc1cccc(F)c1C(=O)N1CCC2(CC1)O[C@@H]1CC[C@@H](c3cc(F)cc(F)c3)N1C2=O] | (5'S,7a'R)-5'-(3,5-difluorophenyl)-1-(2-fluoro-6-methoxybenzene-1-carbonyl)tetrahydro-3'H-spiro[piperidine-4,2'-pyrrolo[2,1-b][1,3]-oxazol]-3'-one | Calc'd 461, found 461 |

TABLE 15-continued

| Ex. No. | Structure | Name | Exact Mass [M + H]+ |
|---|---|---|---|
| 6.73 | 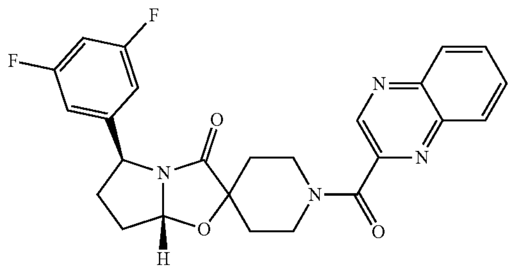 [SMILES: O=C(c1cnc2ccccc2n1)N1CCC2(CC1)O[C@@H]1CC[C@@H](c3cc(F)cc(F)c3)N1C2=O] | (5'S,7a'R)-5'-(3,5-difluorophenyl)-1-(quinoxaline-2-carbonyl)tetrahydro-3'H-spiro[piperidine-4,2'-pyrrolo[2,1-b][1,3]-oxazol]-3'-one | Calc'd 465, found 465 |
| 6.74 | 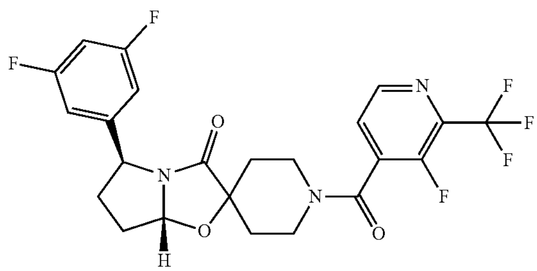 [SMILES: O=C(c1ccnc(C(F)(F)F)c1F)N1CCC2(CC1)O[C@@H]1CC[C@@H](c3cc(F)cc(F)c3)N1C2=O] | (5'S,7a'R)-5'-(3,5-difluorophenyl)-1-[3-fluoro-2-(trifluoromethyl)pyridine-4-carbonyl]tetrahydro-3'H-spiro[piperidine-4,2'-pyrrolo[2,1-b][1,3]oxazol]-3'-one | Calc'd 500, found 500 |
| 6.75 | 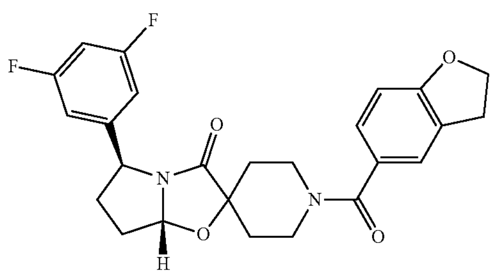 [SMILES: O=C(c1ccc2c(c1)CCO2)N1CCC2(CC1)O[C@@H]1CC[C@@H](c3cc(F)cc(F)c3)N1C2=O] | (5'S,7a'R)-5'-(3,5-difluorophenyl)-1-(2,3-dihydro-1-benzofuran-5-carbonyl)-tetrahydro-3'H-spiro[piperidine-4,2'-pyrrolo[2,1-b][1,3]-oxazol]-3'-one | Calc'd 455, found 455 |
| 6.76 | 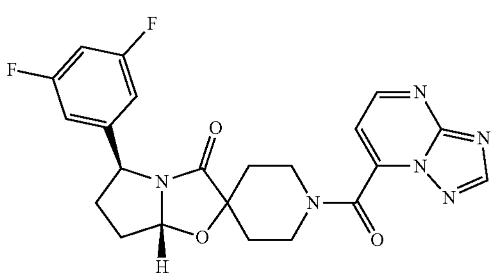 [SMILES: O=C(c1ccnc2ncnn12)N1CCC2(CC1)O[C@@H]1CC[C@@H](c3cc(F)cc(F)c3)N1C2=O] | (5'S,7a'R)-5'-(3,5-difluorophenyl)-1-([1,2,4]triazolo[1,5-a]pyrimidine-7-carbonyl)tetrahydro-3'H-spiro[piperidine-4,2'-pyrrolo[2,1-b][1,3]oxazol]-3'-one | Calc'd 455, found 455 |
| 6.77 | 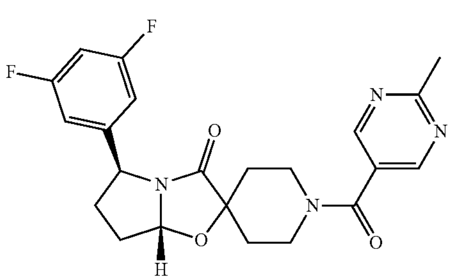 [SMILES: Cc1ncc(C(=O)N2CCC3(CC2)O[C@@H]2CC[C@@H](c4cc(F)cc(F)c4)N2C3=O)cn1] | (5'S,7a'R)-5'-(3,5-difluorophenyl)-1-(2-methylpyrimidine-5-carbonyl)tetrahydro-3'H-spiro[piperidine-4,2'-pyrrolo[2,1-b][1,3]oxazol]-3'-one | Calc'd 429, found 429 |

TABLE 15-continued

| Ex. No. | Structure | Name | Exact Mass [M + H]+ |
|---|---|---|---|
| 6.78 | 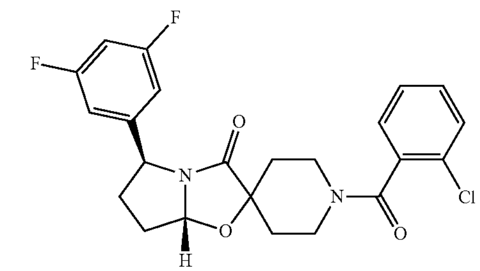 | (5'S,7a'R)-1-(2-chlorobenzene-1-carbonyl)-5'-(3,5-difluorophenyl)tetrahydro-3'H-spiro[piperidine-4,2'-pyrrolo[2,1-b][1,3]-oxazol]-3'-one | Calc'd 447, found 447 |
| 6.79 | 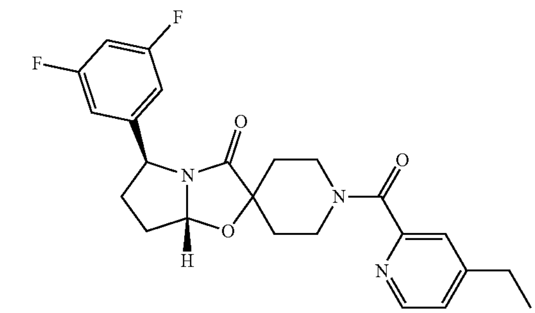 [SMILES: CCc1ccnc(C(=O)N2CCC3(CC2)O[C@@H]2CC[C@@H](c4cc(F)cc(F)c4)N2C3=O)c1] | (5'S,7a'R)-5'-(3,5-difluorophenyl)-1-(4-ethylpyridine-2-carbonyl)tetrahydro-3'H-spiro[piperidine-4,2'-pyrrolo[2,1-b][1,3]oxazol]-3'-one | Calc'd 442, found 442 |
| 6.80 | 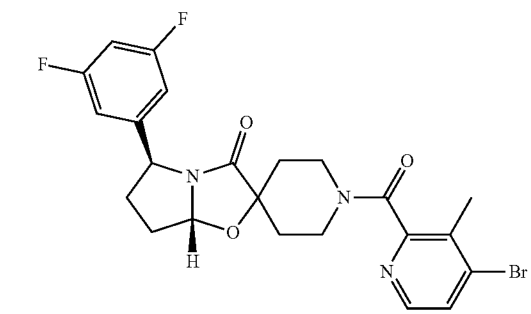 [SMILES: Cc1c(Br)ccnc1C(=O)N1CCC2(CC1)O[C@@H]1CC[C@@H](c3cc(F)cc(F)c3)N1C2=O] | (5'S,7a'R)-1-(4-bromo-3-methylpyridine-2-carbonyl)-5'-(3,5-difluorophenyl)tetrahydro-3'H-spiro[piperidine-4,2'-pyrrolo[2,1-b][1,3]-oxazol]-3'-one | Calc'd 506, found 506 |
| 6.81 | 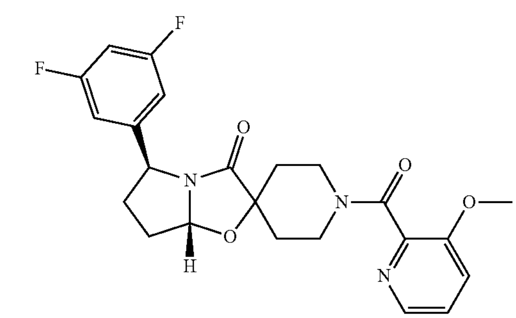 [SMILES: COc1cccnc1C(=O)N1CCC2(CC1)O[C@@H]1CC[C@@H](c3cc(F)cc(F)c3)N1C2=O] | (5'S,7a'R)-5'-(3,5-difluorophenyl)-1-(3-methoxypyridine-2-carbonyl)tetrahydro-3'H-spiro[piperidine-4,2'-pyrrolo[2,1-b][1,3]oxazol]-3'-one | Calc'd 444, found 444 |
| 6.82 | 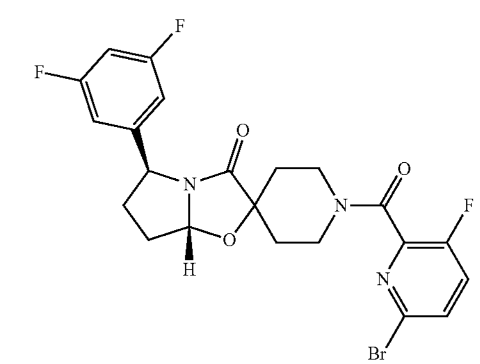 [SMILES: O=C(c1nc(Br)ccc1F)N1CCC2(CC1)O[C@@H]1CC[C@@H](c3cc(F)cc(F)c3)N1C2=O] | (5'S,7a'R)-1-(6-bromo-3-fluoropyridine-2-carbonyl)-5'-(3,5-difluorophenyl)tetrahydro-3'H-spiro[piperidine-4,2'-pyrrolo[2,1-b][1,3]-[oxazol]-3'-one | Calc'd 510, found 510 |

TABLE 15-continued

| Ex. No. | Structure | Name | Exact Mass [M + H]+ |
|---|---|---|---|
| 6.83 | 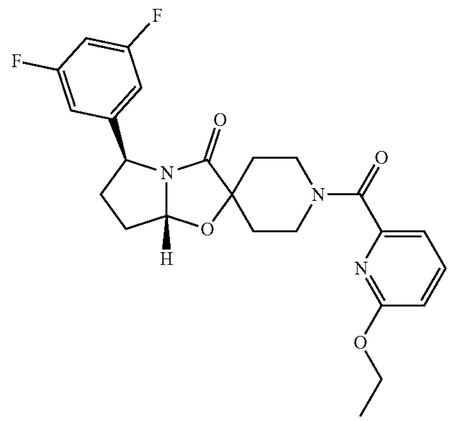 [SMILES: CCOc1cccc(C(=O)N2CCC3(CC2)O[C@@H]2CC[C@@H](c4cc(F)cc(F)c4)N2C3=O)n1] | (5'S,7a'R)-5'-(3,5-difluorophenyl)-1-(6-ethoxypyridine-2-carbonyl)tetrahydro-3'H-spiro[piperidine-4,2'-pyrrolo[2,1-b][1,3]oxazol]-3'-one | Calc'd 458, found 458 |
| 6.84 | 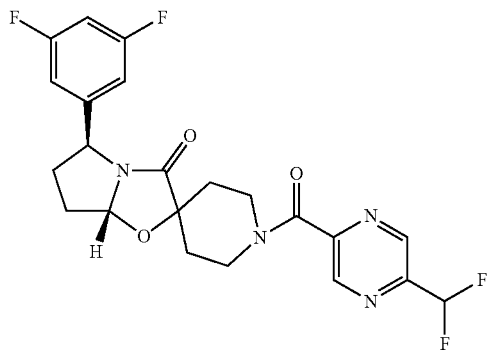 [SMILES: O=C(c1cnc(C(F)F)cn1)N1CCC2(CC1)O[C@@H]1CC[C@@H](c3cc(F)cc(F)c3)N1C2=O] | (5'S,7a'R)-1-[5-(difluoromethyl)pyrazine-2-carbonyl]-5'-(3,5-difluorophenyl)-tetrahydro-3'H-spiro[piperidine-4,2'-pyrrolo[2,1-b][1,3]-oxazol]-3'-one | Calc'd 465, found 465 |
| 6.85 | 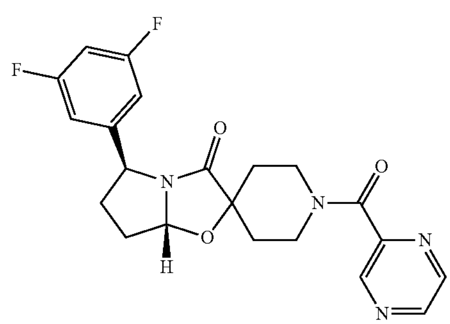 [SMILES: O=C(c1cnccn1)N1CCC2(CC1)O[C@@H]1CC[C@@H](c3cc(F)cc(F)c3)N1C2=O] | (5'S,7a'R)-5'-(3,5-difluorophenyl)-1-(pyrazine-2-carbonyl)tetrahydro-3'H-spiro[piperidine-4,2'-pyrrolo[2,1-b][1,3]-oxazol]-3'-one | Calc'd 415, found 415 |
| 6.86 | 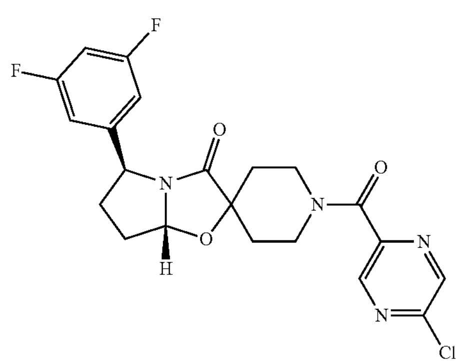 [SMILES: O=C(c1cnc(Cl)cn1)N1CCC2(CC1)O[C@@H]1CC[C@@H](c3cc(F)cc(F)c3)N1C2=O] | (5'S,7a'R)-1-(5-chloropyrazine-2-carbonyl)-5'-(3,5-difluorophenyl)tetrahydro-3'H-spiro[piperidine-4,2'-pyrrolo[2,1-b][1,3]-oxazol]-3'-one | Calc'd 449, found 449 |

TABLE 15-continued

| Ex. No. | Structure | Name | Exact Mass [M + H]+ |
|---|---|---|---|
| 6.87 | 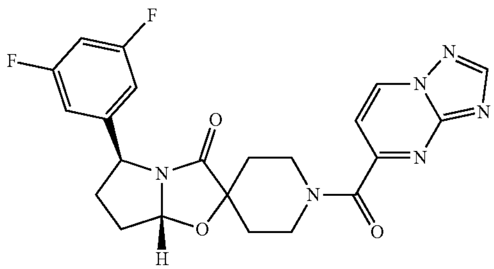 [SMILES: O=C(c1ccn2ncnc2n1)N1CCC2(CC1)O[C@@H]1CC[C@@H](c3cc(F)cc(F)c3)N1C2=O] | (5'S,7a'R)-5'-(3,5-difluorophenyl)-1-([1,2,4]triazolo[1,5-a]pyrimidine-5-carbonyl)tetrahydro-3'H-spiro[piperidine-4,2'-pyrrolo[2,1-b][1,3]oxazol]-3'-one | Calc'd 455, found 455 |
| 6.88 | 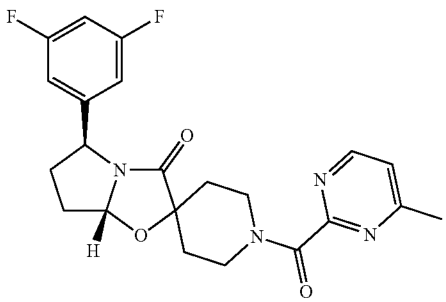 [SMILES: Cc1ccnc(C(=O)N2CCC3(CC2)O[C@@H]2CC[C@@H](c4cc(F)cc(F)c4)N2C3=O)n1] | (5'S,7a'R)-5'-(3,5-difluorophenyl)-1-(4-methylpyrimidine-2-carbonyl)tetrahydro-3'H-spiro[piperidine-4,2'-pyrrolo[2,1-b][1,3]oxazol]-3'-one | Calc'd 429, found 429 |
| 6.89 | 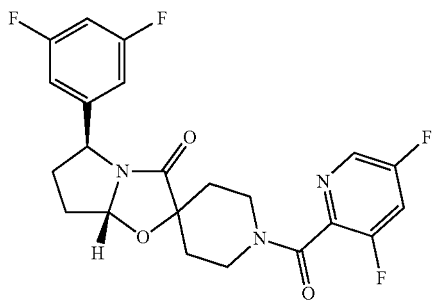 [SMILES: O=C(c1ncc(F)cc1F)N1CCC2(CC1)O[C@@H]1CC[C@@H](c3cc(F)cc(F)c3)N1C2=O] | (5'S,7a'R)-5'-(3,5-difluorophenyl)-1-(3,5-difluoropyridine-2-carbonyl)tetrahydro-3'H-spiro[piperidine-4,2'-pyrrolo[2,1-b][1,3]oxazol]-3'-one | Calc'd 450, found 450 |
| 6.90 | 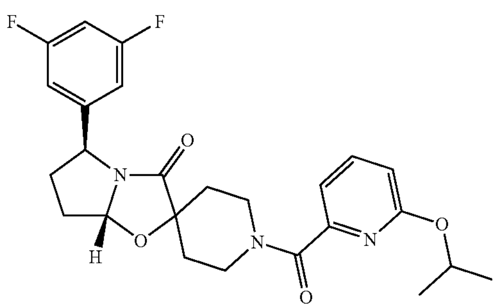 [SMILES: CC(C)Oc1cccc(C(=O)N2CCC3(CC2)O[C@@H]2CC[C@@H](c4cc(F)cc(F)c4)N2C3=O)n1] | (5'S,7a'R)-5'-(3,5-difluorophenyl)-1-{6-[(propan-2-yl)oxy]-pyridine-2-carbonyl}tetrahydro-3'H-spiro[piperidine-4,2'-pyrrolo[2,1-b][1,3]-oxazol]-3'-one | Calc'd 472, found 472 |
| 6.91 | 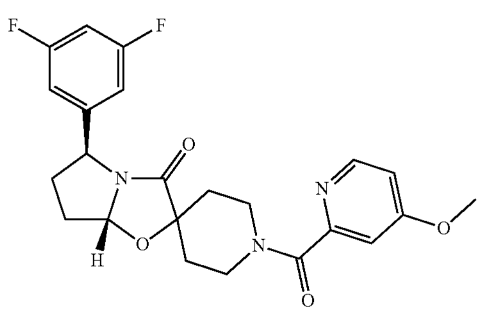 [SMILES: COc1ccnc(C(=O)N2CCC3(CC2)O[C@@H]2CC[C@@H](c4cc(F)cc(F)c4)N2C3=O)c1] | (5'S,7a'R)-5'-(3,5-difluorophenyl)-1-(4-methoxypyridine-2-carbonyl)tetrahydro-3'H-spiro[piperidine-4,2'-pyrrolo[2,1-b][1,3]oxazol]-3'-one | Calc'd 444, found 444 |

TABLE 15-continued

| Ex. No. | Structure | Name | Exact Mass [M + H]+ |
|---|---|---|---|
| 6.92 | 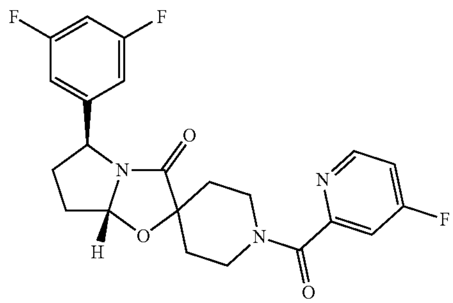 [SMILES: O=C(c1cc(F)ccn1)N1CCC2(CC1)O[C@@H]1CC[C@@H](c3cc(F)cc(F)c3)N1C2=O] | (5'S,7a'R)-5'-(3,5-difluorophenyl)-1-(4-fluoropyridine-2-carbonyl)tetrahydro-3'H-spiro[piperidine-4,2'-pyrrolo[2,1-b][1,3]oxazol]-3'-one | Calc'd 432, found 432 |
| 6.93 | 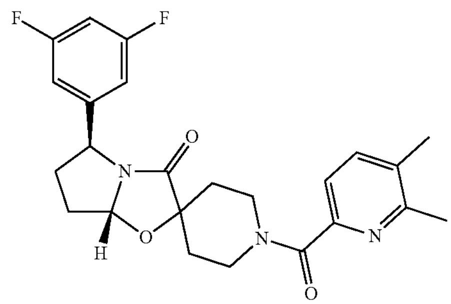 [SMILES: Cc1ccc(C(=O)N2CCC3(CC2)O[C@@H]2CC[C@@H](c4cc(F)cc(F)c4)N2C3=O)nc1C] | (5'S,7a'R)-5'-(3,5-difluorophenyl)-1-(5,6-dimethylpyridine-2-carbonyl)tetrahydro-3'H-spiro[piperidine-4,2'-pyrrolo[2,1-b][1,3]oxazol]-3'-one | Calc'd 442, found 442 |
| 6.94 | 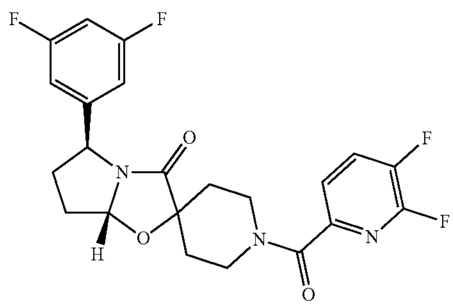 [SMILES: O=C(c1ccc(F)c(F)n1)N1CCC2(CC1)O[C@@H]1CC[C@@H](c3cc(F)cc(F)c3)N1C2=O] | (5'S,7a'R)-5'-(3,5-difluorophenyl)-1-(5,6-difluoropyridine-2-carbonyl)tetrahydro-3'H-spiro[piperidine-4,2'-pyrrolo[2,1-b][1,3]oxazol]-3'-one | Calc'd 450, found 450 |
| 6.95 | 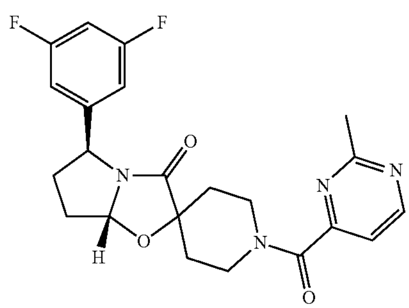 [SMILES: Cc1nccc(C(=O)N2CCC3(CC2)O[C@@H]2CC[C@@H](c4cc(F)cc(F)c4)N2C3=O)n1] | (5'S,7a'R)-5'-(3,5-(difluorophenyl)-1-(2-methylpyrimidine-4-carbonyl)tetrahydro-3'H-spiro[piperidine-4,2'-pyrrolo[2,1-b][1,3]oxazol]-3'-one | Calc'd 429, found 429 |
| 6.96 | 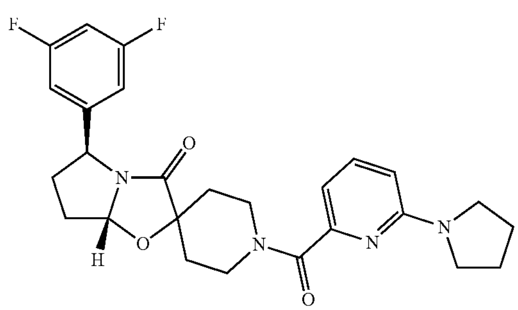 [SMILES: O=C(c1cccc(N2CCCC2)n1)N1CCC2(CC1)O[C@@H]1CC[C@@H](c3cc(F)cc(F)c3)N1C2=O] | (5'S,7a'R)-5'-(3,5-difluorophenyl)-1-[6-(pyrrolidin-1-yl)pyridine-2-carbonyl]tetrahydro-3'H-spiro[piperidine-4,2'-pyrrolo[2,1-b][1,3]oxazol]-3'-one | Calc'd 483, found 483 |

TABLE 15-continued

| Ex. No. | Structure | Name | Exact Mass [M + H]+ |
|---|---|---|---|
| 6.97 | 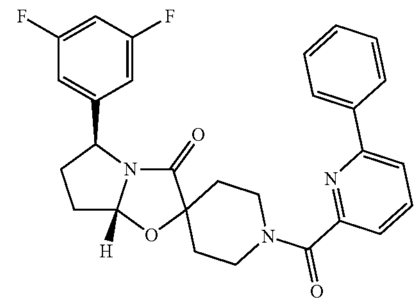 [SMILES: O=C(c1cccc(-c2ccccc2)n1)N1CCC2(CC1)O[C@@H]1CC[C@@H](c3cc(F)cc(F)c3)N1C2=O] | (5'S,7a'R)-5'-(3,5-difluorophenyl)-1-(6-phenylpyridine-2-carbonyl)tetrahydro-3'H-spiro[piperidine-4,2'-pyrrolo[2,1-b][1,3]oxazol]-3'-one | Calc'd 490, found 490 |
| 6.98 | 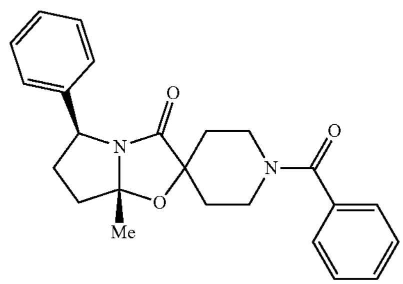 [SMILES: C[C@@]12CC[C@@H](c3ccccc3)N1C(=O)C1(CCN(C(=O)c3ccccc3)CC1)O2] | (5'S,7a'R)-1-(benzenecarbonyl)-7a'-methyl-5'-phenyltetrahydro-3'H-spiro[piperidine-4,2'-pyrrolo[2,1-b][1,3]oxazol]-3'-one | Calc'd 391, found 391 |
| 6.99 | 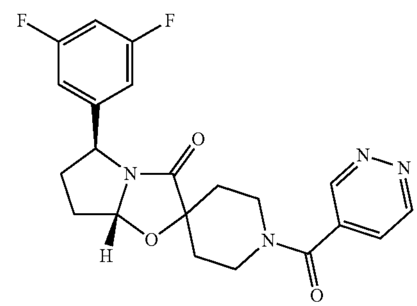 [SMILES: O=C(c1ccnnc1)N1CCC2(CC1)O[C@@H]1CC[C@@H](c3cc(F)cc(F)c3)N1C2=O] | (5'S,7a'R)-5'-(3,5-difluorophenyl)-1-(pyridazine-4-carbonyl)tetrahydro-3'H-spiro[piperidine-4,2'-pyrrolo[2,1-b][1,3]-oxazol]-3'-one | Calc'd 415, found 415 |
| 6.100 | 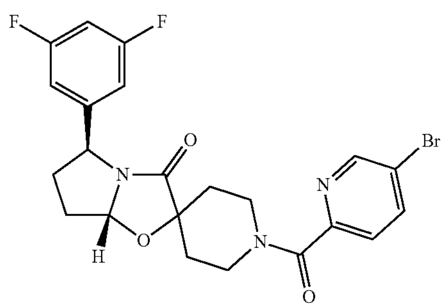 [SMILES: O=C(c1ccc(Br)cn1)N1CCC2(CC1)O[C@@H]1CC[C@@H](c3cc(F)cc(F)c3)N1C2=O] | (5'S,7a'R)-1-(5-bromopyridine-2-carbonyl)-5'-(3,5-difluorophenyl)tetrahydro-3'H-spiro[piperidine-4,2'-pyrrolo[2,1-b][1,3]-oxazol]-3'-one | Calc'd 492, found 492 |
| 6.101 | 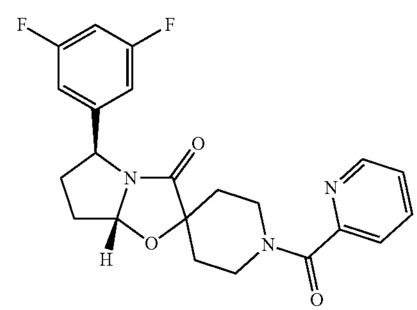 [SMILES: O=C(c1ccccn1)N1CCC2(CC1)O[C@@H]1CC[C@@H](c3cc(F)cc(F)c3)N1C2=O] | (5'S,7a'R)-5'-(3,5-difluorophenyl)-1-(pyridine-2-carbonyl)tetrahydro-3'H-spiro[piperidine-4,2'-pyrrolo[2,1-b][1,3]-oxazol]-3'-one | Calc'd 414, found 414 |

TABLE 15-continued

| Ex. No. | Structure | Name | Exact Mass [M + H]+ |
|---|---|---|---|
| 6.102 | 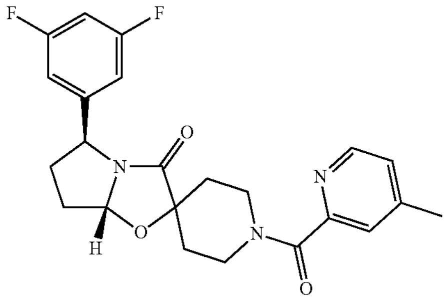 [SMILES: Cc1ccnc(C(=O)N2CCC3(CC2)O[C@@H]2CC[C@@H](c4cc(F)cc(F)c4)N2C3=O)c1] | (5'S,7a'R)-5'-(3,5-difluorophenyl)-1-(4-methylpyridine-2-carbonyl)tetrahydro-3'H-spiro[piperidine-4,2'-pyrrolo[2,1-b][1,3]oxazol]-3'-one | Calc'd 428, found 428 |
| 6.103 | 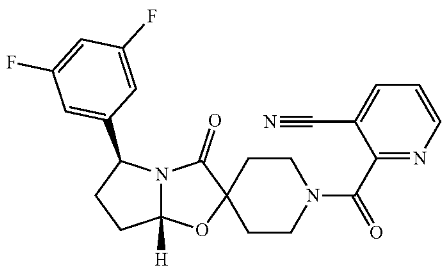 [SMILES: N#Cc1cccnc1C(=O)N1CCC2(CC1)O[C@@H]1CC[C@@H](c3cc(F)cc(F)c3)N1C2=O] | 2-[(5'S,7a'R)-5'-(3,5-difluorophenyl)-3 oxotetrahydro-1H,3'H-spiro[piperidine-4,2'-pyrrolo[2,1-b][1,3]-oxazole]-1-carbonyl]-pyridine-3-carbonitrile | Calc'd 439, found 439 |
| 6.104 | 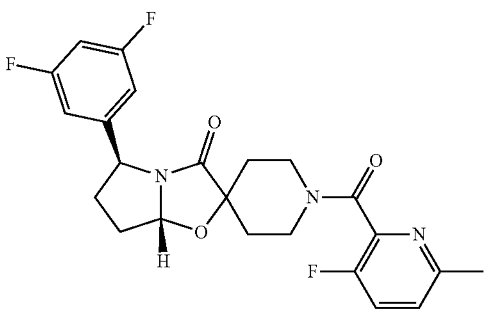 [SMILES: Cc1ccc(F)c(C(=O)N2CCC3(CC2)O[C@@H]2CC[C@@H](c4cc(F)cc(F)c4)N2C3=O)n1] | (5'S,7a'R)-5'-(3,5-difluorophenyl)-1-(3-fluoro-6-methylpyridine-2-carbonyl)tetrahydro-3'H-spiro[piperidine-4,2'-pyrrolo[2,1-b][1,3]oxazol]-3'-one | Calc'd 446, found 446 |
| 6.105 | 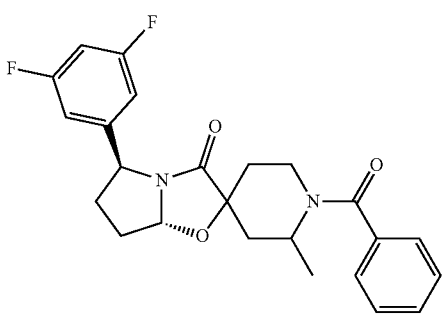 | (4R,5'S,7a'R)-1-(benzenecarbonyl)-5'-(3,5-difluorophenyl)-2-methyltetrahydro-3'H-spiro[piperidine-4,2'-pyrrolo[2,1-b][1,3]oxazol]-3'-one | Calc'd 427, found 427 |
| 6.106 | 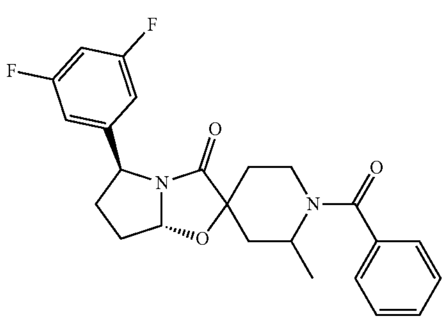 | (4R,5'S,7a'R)-1-(benzenecarbonyl)-5'-(3,5-difluorophenyl)-2-methyltetrahydro-3'H-spiro[piperidine-4,2'-pyrrolo[2,1-b][1,3]oxazol]-3'-one | Calc'd 427, found 427 |

TABLE 15-continued

| Ex. No. | Name | Exact Mass [M + H]+ |
|---|---|---|
| 6.107 | (4R,5'S,7a'R)-1-(benzenecarbonyl)-5'-(3,5-difluorophenyl)-2-methyltetrahydro-3'H-spiro[piperidine-4,2'-pyrrolo[2,1-b][1,3]oxazol]-3'-one | Calc'd 427, found 427 |
| 6.108 | (5'S,7'S,7a'R)-1-(benzenecarbonyl)-7'-fluoro-5'-phenyl-tetrahydro-3'H-spiro[piperidine-4,2'-pyrrolo[2,1-b][1,3]-oxazol]-3'-one | Calc'd 395, found 395 |
| 6.109 | (5'S,7a'R)-1-(benzenecarbonyl)-5'-(3,5-difluorophenyl)-3-methyltetrahydro-3'H-spiro[piperidine-4,2'-pyrrolo[2,1-b][1,3]-oxazol]-3'-one | Calc'd 427, found 427 |
| 6.110 | (5'S,7a'R)-1-(benzenecarbonyl)-5'-(3,5-difluorophenyl)-3-methyltetrahydro-3'H-spiro[piperidine-4,2'-pyrrolo[2,1-b][1,3]-oxazol]-3'-one | Calc'd 427, found 427 |
| 6.111 | (5'S,7a'R)-1-(2,5-difluorobenzene-1-carbonyl)-3-fluoro-5'-phenyltetrahydro-3'H-spiro[piperidine-4,2'-pyrrolo[2,1-b][1,3]-oxazol]-3'-one | Calc'd 431, found 431 |

TABLE 15-continued

| Ex. No. | Structure | Name | Exact Mass [M + H]+ |
|---|---|---|---|
| 6.112 | 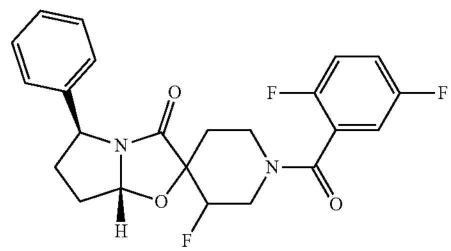 [SMILES: O=C(c1cc(F)ccc1F)N1CCC2(O[C@@H]3CC[C@@H](c4ccccc4)N3C2=O)C(F)C1] | (5'S,7a'R)-1-(2,5-difluorobenzene-1-carbonyl)-3-fluoro-5'-phenyltetrahydro-3'H-spiro[piperidine-4,2'-pyrrolo[2,1-b][1,3][oxazol]-3'-one | Calc'd 431, found 431 |
| 6.113 | 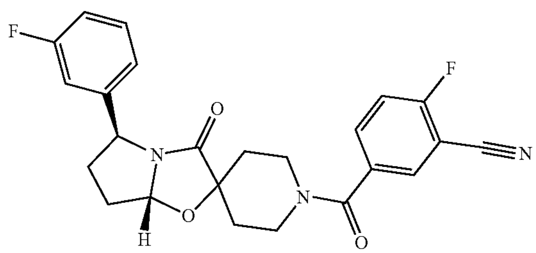 [SMILES: N#Cc1cc(C(=O)N2CCC3(CC2)O[C@@H]2CC[C@@H](c4cccc(F)c4)N2C3=O)ccc1F] | 2-fluoro-5-[(5'S,7a'R)-5'-(3-fluorophenyl)-3'-oxotetrahydro-1H,3'H-spiro[piperidine-4,2'-pyrrolo[2,1-b][1,3]oxazole]-1-carbonyl]benzonitrile | Calc'd 438, found 438 |
| 6.114 | 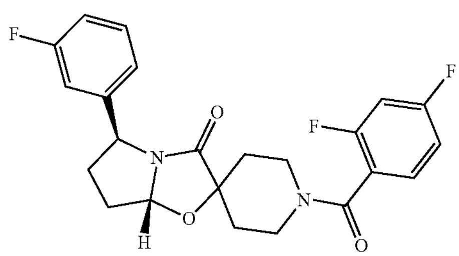 [SMILES: O=C(c1ccc(F)cc1F)N1CCC2(CC1)O[C@@H]1CC[C@@H](c3cccc(F)c3)N1C2=O] | (5'S,7a'R)-1-(2,4-difluorobenzene-1-carbonyl)-5'-(3-fluorophenyl)tetrahydro-3'H-spiro[piperidine-4,2'-pyrrolo[2,1-b][1,3]oxazol]-3'-one | Calc'd 431, found 431 |
| 6.115 | 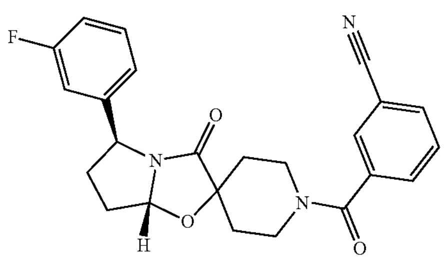 [SMILES: N#Cc1cccc(C(=O)N2CCC3(CC2)O[C@@H]2CC[C@@H](c4cccc(F)c4)N2C3=O)c1] | 3-[(5'S,7a'R)-5'-(3-fluorophenyl)-3'-oxotetrahydro-1H,3'H-spiro[piperidine-4,2'-pyrrolo[2,1-b][1,3]oxazole]-1-carbonyl]benzonitrile | Calc'd 420, found 420 |
| 6.116 | 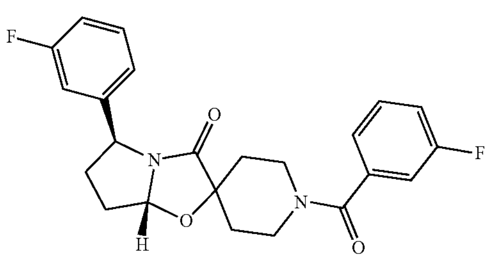 [SMILES: O=C(c1cccc(F)c1)N1CCC2(CC1)O[C@@H]1CC[C@@H](c3cccc(F)c3)N1C2=O] | (5'S,7a'R)-1-(3-fluorobenzene-1-carbonyl)-5'-(3-fluorophenyl)-tetrahydro-3'H-spiro[piperidine-4,2'-pyrrolo[2,1-b][1,3]oxazol]-3'-one | Calc'd 413, found 413 |
| 6.117 | 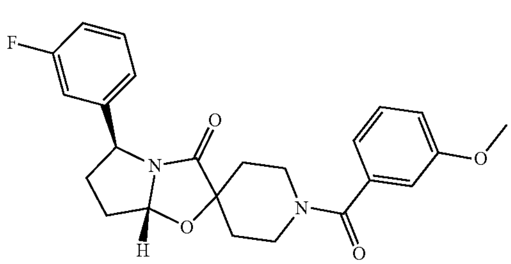 [SMILES: COc1cccc(C(=O)N2CCC3(CC2)O[C@@H]2CC[C@@H](c4cccc(F)c4)N2C3=O)c1] | (5'S,7a'R)-5'-(3-fluorophenyl)-1-(3-methoxybenzene-1-carbonyl)tetrahydro-3'H-spiro[piperidine-4,2'-pyrrolo[2,1-b][1,3]oxazol]-3'-one | Calc'd 425, found 425 |

TABLE 15-continued

| Ex. No. | Structure | Name | Exact Mass [M + H]+ |
|---|---|---|---|
| 6.118 | 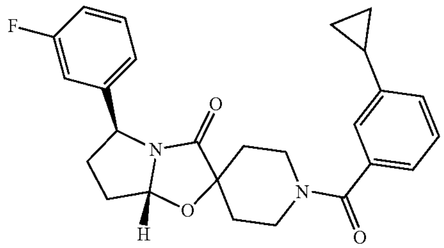 [SMILES: O=C(c1cccc(C2CC2)c1)N1CCC2(CC1)O[C@@H]1CC[C@@H](c3cccc(F)c3)N1C2=O] | (5'S,7a'R)-1-(3-cyclopropylbenzene-1-carbonyl)-5'-(3-fluorophenyl)tetrahydro-3'H-spiro[piperidine-4,2'-pyrrolo[2,1-b][1,3]oxazol]-3'-one | Calc'd 435, found 435 |
| 6.119 | 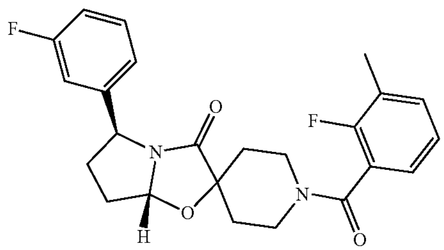 [SMILES: Cc1cccc(C(=O)N2CCC3(CC2)O[C@@H]2CC[C@@H](c4cccc(F)c4)N2C3=O)c1F] | (5'S,7a'R)-1-(2-fluoro-3-methylbenzene-1-carbonyl)-5'-(3-fluorophenyl)tetrahydro-3'H-spiro[piperidine-4,2'-pyrrolo[2,1-b][1,3]oxazol]-3'-one | Calc'd 427, found 427 |
| 6.120 | 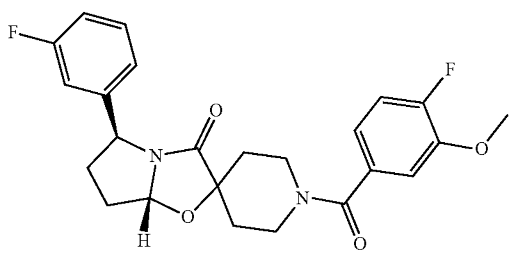 [SMILES: COc1cc(C(=O)N2CCC3(CC2)O[C@@H]2CC[C@@H](c4cccc(F)c4)N2C3=O)ccc1F] | (5'S,7a'R)-1-(4-fluoro-3-methoxybenzene-1-carbonyl)-5'-(3-fluorophenyl)tetrahydro-3'H-spiro[piperidine-4,2'-pyrrolo[2,1-b][1,3]oxazol]-3'-one | Calc'd 443, found 443 |
| 6.121 | 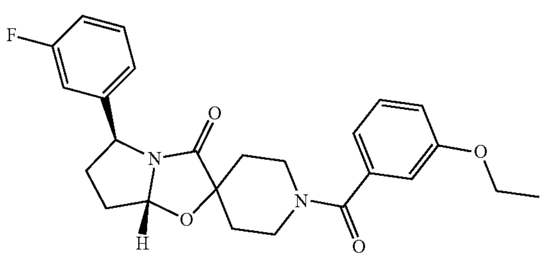 [SMILES: CCOc1cccc(C(=O)N2CCC3(CC2)O[C@@H]2CC[C@@H](c4cccc(F)c4)N2C3=O)c1] | (5'S,7a'R)-1-(3-ethoxybenzene-1-carbonyl)-5'-(3-fluorophenyl)tetrahydro-3'H-spiro[piperidine-4,2'-pyrrolo[2,1-b][1,3]oxazol]-3'-one | Calc'd 439, found 439 |
| 6.122 | 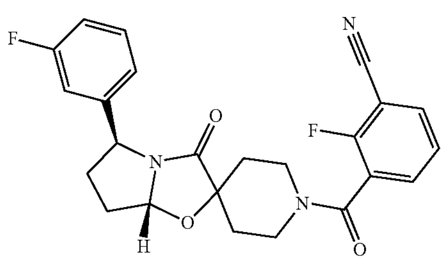 [SMILES: N#Cc1cccc(C(=O)N2CCC3(CC2)O[C@@H]2CC[C@@H](c4cccc(F)c4)N2C3=O)c1F] | 2-fluoro-3-[(5'S,7a'R)-5'-(3-fluorophenyl)-3'-oxotetrahydro-1H,3'H-spiro[piperidine-4,2'-pyrrolo[2,1-b][1,3]oxazole]-1-carbonyl]benzonitrile | Calc'd 438, found 438 |
| 6.123 | 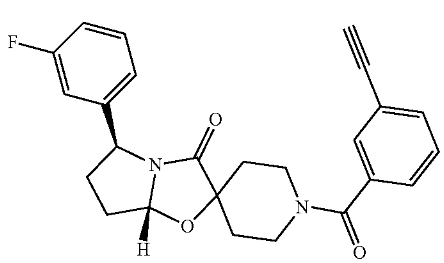 [SMILES: C#Cc1cccc(C(=O)N2CCC3(CC2)O[C@@H]2CC[C@@H](c4cccc(F)c4)N2C3=O)c1] | (5'S,7a'R)-1-(3-ethynylbenzene-1-carbonyl)-5'-(3-fluorophenyl)tetrahydro-3'H-spiro[piperidine-4,2'-pyrrolo[2,1-b][1,3]oxazol]-3-one | Calc'd 419, found 419 |

TABLE 15-continued

| Ex. No. | Structure | Name | Exact Mass [M + H]+ |
|---|---|---|---|
| 6.124 | 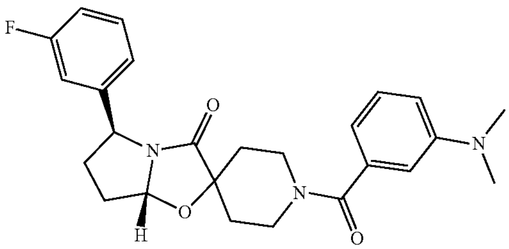 [SMILES: CN(C)c1cccc(C(=O)N2CCC3(CC2)O[C@@H]2CC[C@@H](c4cccc(F)c4)N2C3=O)c1] | (5'S,7a'R)-1-[3-(dimethylamino)-benzene-1-carbonyl]-5'-(3-fluorophenyl)tetrahydro-3'H-spiro[piperidine-4,2'-pyrrolo[2,1-b][1,3]-oxazol]-3'-one | Calc'd 438, found 438 |
| 6.125 | 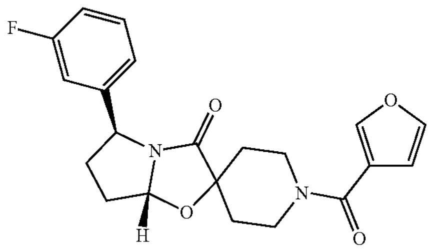 [SMILES: O=C(c1ccoc1)N1CCC2(CC1)O[C@@H]1CC[C@@H](c3cccc(F)c3)N1C2=O] | (5'S,7a'R)-5'-(3-fluorophenyl)-1-(furan-3-carbonyl)tetrahydro-3'H-spiro[piperidine-4,2'-pyrrolo[2,1-b][1,3]oxazol]-3'-one | Calc'd 385, found 385 |
| 6.126 | 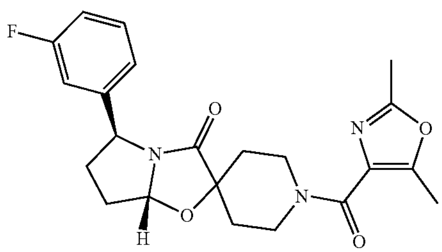 [SMILES: Cc1nc(C(=O)N2CCC3(CC2)O[C@@H]2CC[C@@H](c4cccc(F)c4)N2C3=O)c(C)o1] | (5'S,7a'R)-1-(2,5-dimethyl-1,3-oxazole-4-carbonyl)-5'-(3-fluorophenyl)tetrahydro-3'H-spiro[piperidine-4,2'-pyrrolo[2,1-b][1,3]oxazol]-3'-one | Calc'd 414, found 414 |
| 6.127 | 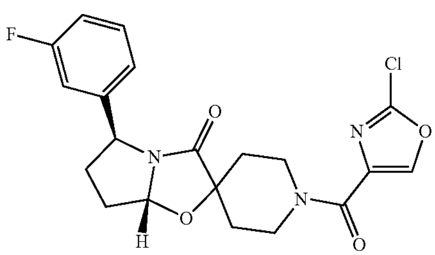 [SMILES: O=C(c1coc(Cl)n1)N1CCC2(CC1)O[C@@H]1CC[C@@H](c3cccc(F)c3)N1C2=O] | (5'S,7a'R)-1-(2-chloro-1,3-oxazole-4-carbonyl)-5'-(3-fluorophenyl)-tetrahydro-3'H-spiro[piperidine-4,2'-pyrrolo[2,1-b][1,3]oxazol]-3'-one | Calc'd 420, found 420 |
| 6.128 | 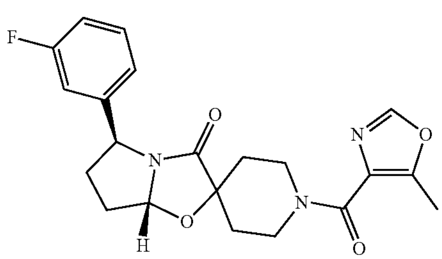 [SMILES: Cc1ocnc1C(=O)N1CCC2(CC1)O[C@@H]1CC[C@@H](c3cccc(F)c3)N1C2=O] | (5'S,7a'R)-5'-(3-fluorophenyl)-1-(5-methyl-1,3-oxazole-4-carbonyl)tetrahydro-3'H-spiro[piperidine-4,2'-pyrrolo[2,1-b][1,3]oxazol]-3'-one | Calc'd 400, found 400 |
| 6.129 | 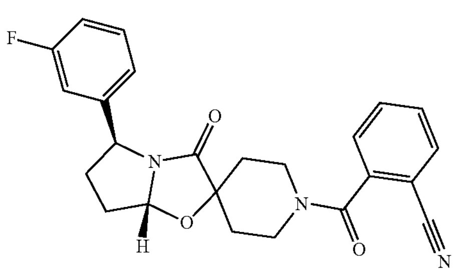 [SMILES: N#Cc1ccccc1C(=O)N1CCC2(CC1)O[C@@H]1CC[C@@H](c3cccc(F)c3)N1C2=O] | 2-[(5'S,7a'R)-5'-(3-fluorophenyl)-3'-oxotetrahydro-1H,3'H-spiro[piperidine-4,2'-pyrrolo[2,1-b][1,3]-oxazole]-1-carbonyl]benzonitrile | Calc'd 420, found 420 |

TABLE 15-continued

| Ex. No. | Structure | Name | Exact Mass [M + H]+ |
|---|---|---|---|
| 6.130 | 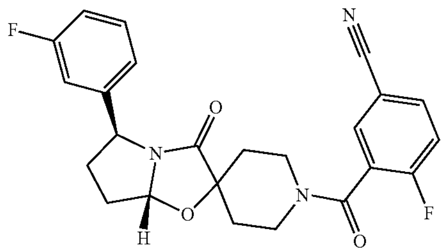 [SMILES: N#Cc1ccc(F)c(C(=O)N2CCC3(CC2)O[C@@H]2CC[C@@H](c4cccc(F)c4)N2C3=O)c1] | 4-fluoro-3-[(5'S,7a'R)-5'-(3-fluorophenyl)-3'-oxotetrahydro-1H,3'H-spiro[piperidine-4,2'-pyrrolo[2,1-b][1,3]-oxazole]-1-carbonyl]benzonitrile | Calc'd 438, found 438 |
| 6.131 | 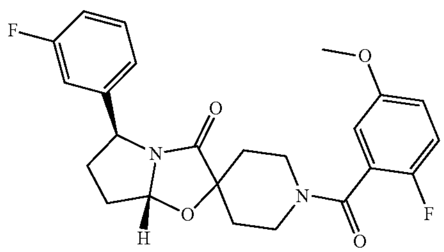 [SMILES: COc1ccc(F)c(C(=O)N2CCC3(CC2)O[C@@H]2CC[C@@H](c4cccc(F)c4)N2C3=O)c1] | (5'S,7a'R)-1-(2-fluoro-5-methoxybenzene-1-carbonyl)-5'-(3-fluorophenyl)tetrahydro-3'H-spiro[piperidine-4,2'-pyrrolo[2,1-b][1,3]oxazol]-3'-one | Calc'd 443, found 443 |
| 6.132 | 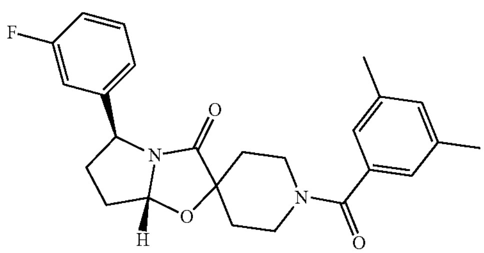 [SMILES: Cc1cc(C)cc(C(=O)N2CCC3(CC2)O[C@@H]2CC[C@@H](c4cccc(F)c4)N2C3=O)c1] | (5'S,7a'R)-1-(3,5-dimethylbenzene-1-carbonyl)-5'-(3-fluorophenyl)tetrahydro-3'H-spiro[piperidine-4,2'-pyrrolo[2,1-b][1,3]oxazol]-3'-one | Calc'd 423, found 423 |
| 6.133 | 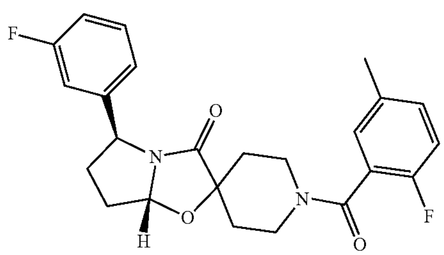 [SMILES: Cc1ccc(F)c(C(=O)N2CCC3(CC2)O[C@@H]2CC[C@@H](c4cccc(F)c4)N2C3=O)c1] | (5'S,7a'R)-1-(2-fluoro-5-methylbenzene-1-carbonyl)-5'-(3-fluorophenyl)tetrahydro-3'H-spiro[piperidine-4,2'-pyrrolo[2,1-b][1,3]oxazol]-3'-one | Calc'd 427, found 427 |
| 6.134 | 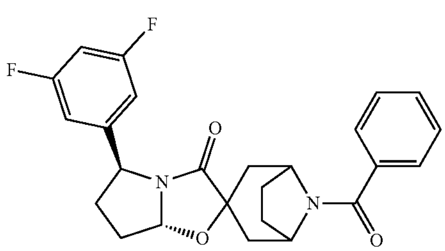 | (5'S,7a'R)-8-(benzenecarbonyl)-5'-(3,5-difluorophenyl)tetrahydro-3'H-spiro[8-azabicyclo[3.2.1]-octane-3,2'-pyrrolo-[2,1-b][1,3]oxazol]-3'-one | Calc'd 439, found 439 |
| 6.135 | 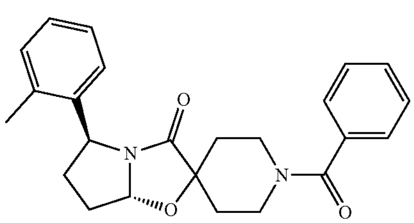 [SMILES: Cc1ccccc1[C@@H]1CC[C@H]2OC3(CCN(C(=O)c4ccccc4)CC3)C(=O)N21] | (5'S,7a'R)-1-(benzenecarbonyl)-5'-(2-methylphenyl)tetrahydro-3'H-spiro[piperidine-4,2'-pyrrolo[2,1-b][1,3]oxazol]-3'-one | Calc'd 391, found 391 |

TABLE 15-continued

| Ex. No. | Structure | Name | Exact Mass [M + H]+ |
|---|---|---|---|
| 6.136 | 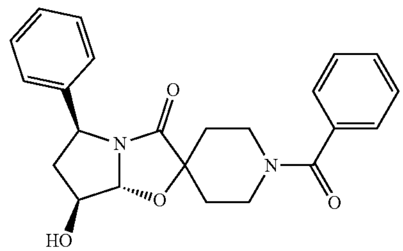 [SMILES: O=C(c1ccccc1)N1CCC2(CC1)O[C@@H]1[C@@H](O)C[C@@H](c3ccccc3)N1C2=O] | (5'S,7'S,7a'R)-1-(benzenecarbonyl)-7'-hydroxy-5'-phenyl-tetrahydro-3'H-spiro[piperidine-4,2'-pyrrolo[2,1-b][1,3]-[oxazol]-3'-one | Calc'd 393, found 393 |
| 6.137 | 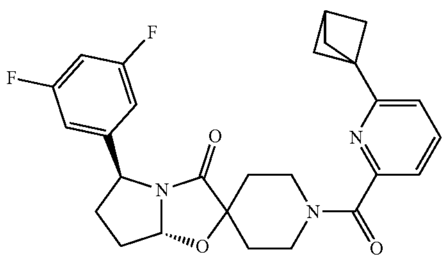 [SMILES: O=C(c1cccc(C23CC(C2)C3)n1)N1CCC2(CC1)O[C@@H]1CC[C@@H](c3cc(F)cc(F)c3)N1C2=O] | (5'S,7a'R)-1-[6-(bicyclo[1.1.1]pentan-1-yl)pyridine-2-carbonyl]-5-(3,5-difluoro-phenyl)tetrahydro-3'H-spiro[piperidine-4,2'-pyrrolo[2,1-b][1,3]oxazol]-3'-one | Calc'd 480, found 480 |
| 6.138 | 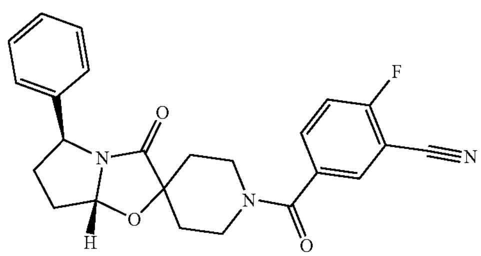 [SMILES: N#Cc1cc(C(=O)N2CCC3(CC2)O[C@@H]2CC[C@@H](c4ccccc4)N2C3=O)ccc1F] | 2-fluoro-5-[(5'S,7a'R)-3'-oxo-5'-phenyl-tetrahydro-1H,3'H-spiro[piperidine-4,2'-pyrrolo[2,1-b][1,3]-oxazole]-1-carbonyl]-benzonitrile | Calc'd 420, found 420 |
| 6.139 | 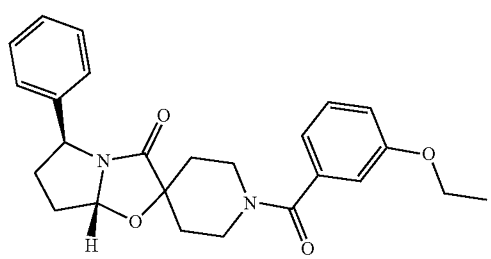 [SMILES: CCOc1cccc(C(=O)N2CCC3(CC2)O[C@@H]2CC[C@@H](c4ccccc4)N2C3=O)c1] | (5'S,7a'R)-1-(3-ethoxybenzene-1-carbonyl)-5'-phenyl-tetrahydro-3'H-spiro[piperidine-4,2'-pyrrolo[2,1-b][1,3]-oxazol]-3'-one | Calc'd 421, found 421 |
| 6.140 | 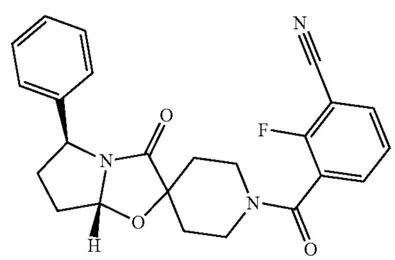 [SMILES: N#Cc1cccc(C(=O)N2CCC3(CC2)O[C@@H]2CC[C@@H](c4ccccc4)N2C3=O)c1F] | 2-fluoro-3-[(5'S,7a'R)-3'-oxo-5'-phenyltetra-hydro-1H,3'H-spiro[piperidine-4,2'-pyrrolo[2,1-b][1,3]oxazole]-1-carbonyl]benzonitrile | Calc'd 420, found 420 |
| 6.141 | 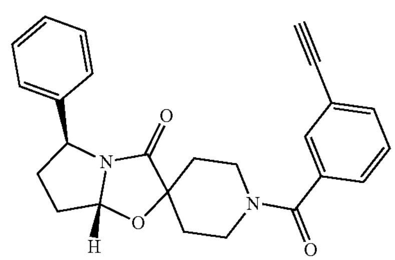 [SMILES: C#Cc1cccc(C(=O)N2CCC3(CC2)O[C@@H]2CC[C@@H](c4ccccc4)N2C3=O)c1] | (5'S,7a'R)-1-(3-ethynylbenzene-1-carbonyl)-5'-phenyl-tetrahydro-3'H-spiro[piperidine-4,2'-pyrrolo[2,1-b][1,3]oxazol]-3'-one | Calc'd 401, found 401 |

TABLE 15-continued

| Ex. No. | Structure | Name | Exact Mass [M + H]+ |
|---|---|---|---|
| 6.142 | 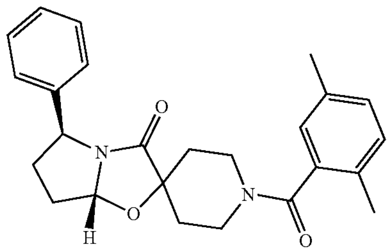 [SMILES: Cc1ccc(C)c(C(=O)N2CCC3(CC2)O[C@@H]2CC[C@@H](c4ccccc4)N2C3=O)c1] | (5'S,7a'R)-1-(2,5-dimethylbenzene-1-carbonyl)-5'-phenyl-tetrahydro-3'H-spiro[piperidine-4,2'-pyrrolo[2,1-b][1,3]oxazol]-3'-one | Calc'd 405, found 405 |
| 6.143 | 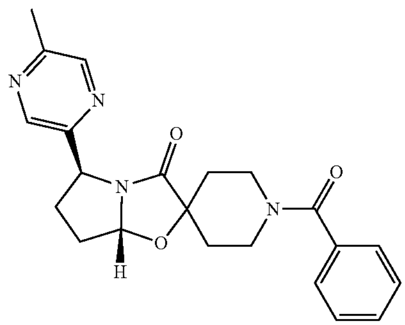 [SMILES: Cc1cnc([C@@H]2CC[C@H]3OC4(CCN(C(=O)c5ccccc5)CC4)C(=O)N32)cn1] | (5'S,7a'R)-1-(benzene-carbonyl)-5'-(5-methylpyrazin-2-yl)tetrahydro-3'H-spiro[piperidine-4,2'-pyrrolo[2,1-b][1,3]oxazol]-3'-one | Calc'd 393, found 393 |
| 6.144 | 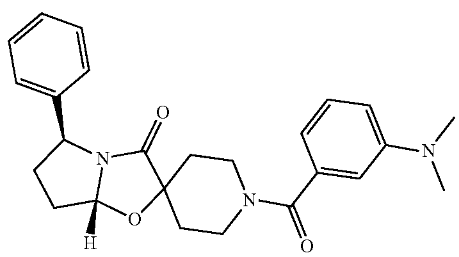 [SMILES: CN(C)c1cccc(C(=O)N2CCC3(CC2)O[C@@H]2CC[C@@H](c4ccccc4)N2C3=O)c1] | (5'S,7a'R)-1-[3-(dimethylamino)benzene-1-carbonyl]-5'-phenyltetrahydro-3'H-spiro[piperidine-4,2'-pyrrolo[2,1-b][1,3]oxazol]-3'-one | Calc'd 420, found 420 |
| 6.145 | 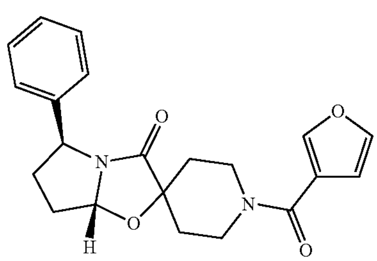 [SMILES: O=C(c1ccoc1)N1CCC2(CC1)O[C@@H]1CC[C@@H](c3ccccc3)N1C2=O] | (5'S,7a'R)-1-(furan-3-carbonyl)-5'-phenyl-tetrahydro-3'H-spiro[piperidine-4,2'-pyrrolo[2,1-b][1,3]oxazol]-3'-one | Calc'd 367, found 367 |
| 6.146 | 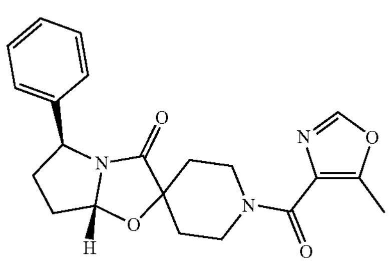 [SMILES: Cc1ocnc1C(=O)N1CCC2(CC1)O[C@@H]1CC[C@@H](c3ccccc3)N1C2=O] | (5'S,7a'R)-1-(5-methyl-1,3-oxazole-4-carbonyl)-5'-phenyl-tetrahydro-3'H-spiro[piperidine-4,2'-pyrrolo[2,1-b][1,3]oxazol]-3'-one | Calc'd 382, found 382 |

TABLE 15-continued

| Ex. No. | Structure | Name | Exact Mass [M + H]+ |
|---|---|---|---|
| 6.147 | 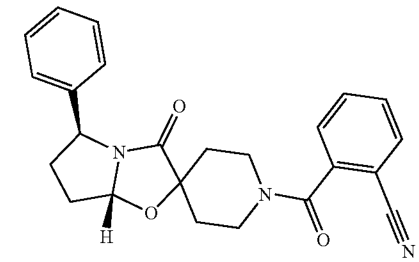 [SMILES: N#Cc1ccccc1C(=O)N1CCC2(CC1)O[C@@H]1CC[C@@H](c3ccccc3)N1C2=O] | 2-[(5'S,7a'R)-3'-oxo-5'-phenyltetrahydro-1H,3'H-spiro[piperidine-4,2'-pyrrolo[2,1-b][1,3]oxazole]-1-carbonyl]benzonitrile | Calc'd 402, found 402 |
| 6.148 | 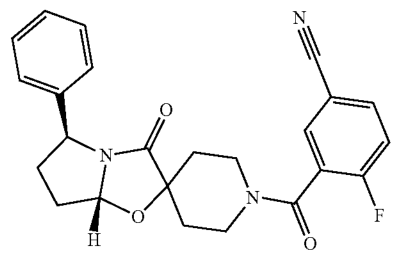 [SMILES: N#Cc1ccc(F)c(C(=O)N2CCC3(CC2)O[C@@H]2CC[C@@H](c4ccccc4)N2C3=O)c1] | 4-fluoro-3-[(5'S,7a'R)-3'-oxo-5'-phenyltetrahydro-1H,3'H-spiro[piperidine-4,2'-pyrrolo[2,1-b][1,3]oxazole-1-carbonyl]benzonitrile | Calc'd 420, found 420 |
| 6.149 | 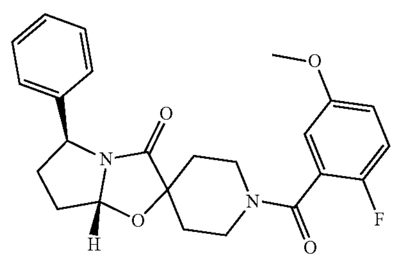 [SMILES: COc1ccc(F)c(C(=O)N2CCC3(CC2)O[C@@H]2CC[C@@H](c4ccccc4)N2C3=O)c1] | (5'S,7a'R)-1-(2-fluoro-5-methoxybenzene-1-carbonyl)-5'-phenyl-tetrahydro-3'H-spiro[piperidine-4,2'-pyrrolo[2,1-b][1,3]oxazol]-3'-one | Calc'd 425, found 425 |
| 6.150 | 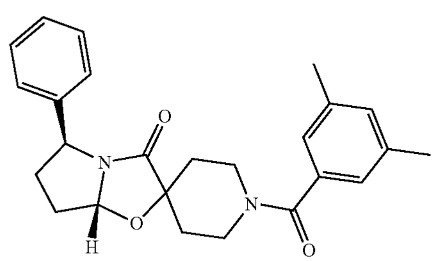 [SMILES: Cc1cc(C)cc(C(=O)N2CCC3(CC2)O[C@@H]2CC[C@@H](c4ccccc4)N2C3=O)c1] | (5'S,7a'R)-1-(3,5-dimethylbenzene-1-carbonyl)-5'-phenyl-tetrahydro-3'H-spiro[piperidine-4,2'-pyrrolo[2,1-b][1,3]oxazol]-3'-one | Calc'd 405, found 405 |
| 6.151 | 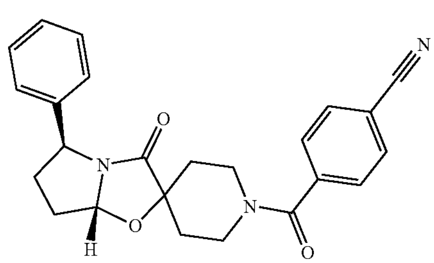 [SMILES: N#Cc1ccc(C(=O)N2CCC3(CC2)O[C@@H]2CC[C@@H](c4ccccc4)N2C3=O)cc1] | 4-[(5'S,7a'R)-3'-oxo-5'-phenyltetrahydro-1H,3'H-spiro[piperidine-4,2'-pyrrolo[2,1-b][1,3]oxazole]-1-carbonyl]benzonitrile | Calc'd 402, found 402 |
| 6.152 | 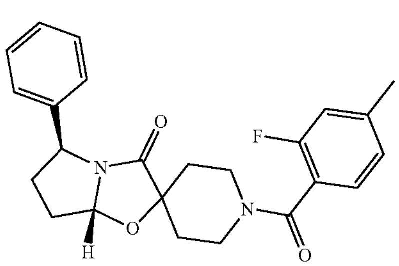 [SMILES: Cc1ccc(C(=O)N2CCC3(CC2)O[C@@H]2CC[C@@H](c4ccccc4)N2C3=O)c(F)c1] | (5'S,7a'R)-1-(2-fluoro-4-methylbenzene-1-carbonyl)-5'-phenyl-tetrahydro-3'H-spiro[piperidine-4,2'-pyrrolo[2,1-b][1,3]oxazol]-3'-one | Calc'd 409, found 409 |

TABLE 15-continued

| Ex. No. | Structure | Name | Exact Mass [M + H]+ |
|---|---|---|---|
| 6.153 | 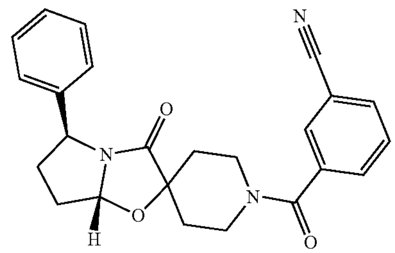 [SMILES: N#Cc1cccc(C(=O)N2CCC3(CC2)O[C@@H]2CC[C@@H](c4ccccc4)N2C3=O)c1] | 3-[(5'S,7a'R)-3'-oxo-5'-phenyltetrahydro-1H,3'H-spiro[piperidine-4,2'-pyrrolo[2,1-b][1,3]oxazole]-1-carbonyl]benzonitrile | Calc'd 402, found 402 |
| 6.154 | 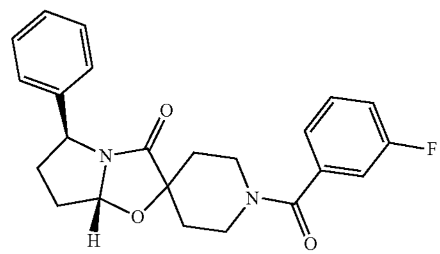 [SMILES: O=C(c1cccc(F)c1)N1CCC2(CC1)O[C@@H]1CC[C@@H](c3ccccc3)N1C2=O] | (5'S,7a'R)-1-(3-fluorobenzene-1-carbonyl)-5'-phenyltetrahydro-3'H-spiro[piperidine-4,2'-pyrrolo[2,1-b][1,3]oxazol]-3'-one | Calc'd 395, found 395 |
| 6.155 | 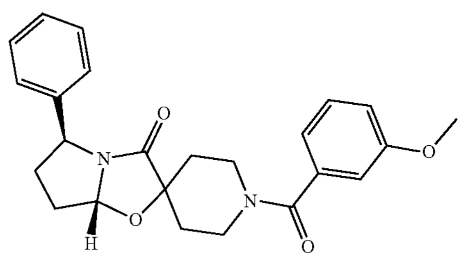 [SMILES: COc1cccc(C(=O)N2CCC3(CC2)O[C@@H]2CC[C@@H](c4ccccc4)N2C3=O)c1] | (5'S,7a'R)-1-(3-methoxybenzene-1-carbonyl)-5'-phenyltetrahydro-3'H-spiro[piperidine-4,2'-pyrrolo[2,1-b][1,3]oxazol]-3'-one | Calc'd 407, found 407 |
| 6.156 | 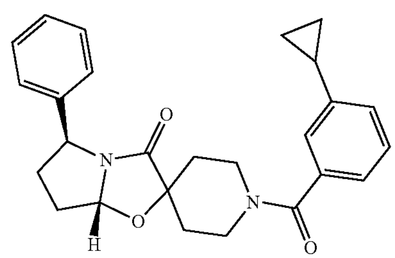 [SMILES: O=C(c1cccc(C2CC2)c1)N1CCC2(CC1)O[C@@H]1CC[C@@H](c3ccccc3)N1C2=O] | (5'S,7a'R)-1-(3-cyclopropylbenzene-1-carbonyl)-5'-phenyltetrahydro-3'H-spiro[piperidine-4,2'-pyrrolo[2,1-b][1,3]oxazol]-3'-one | Calc'd 417, found 417 |
| 6.157 | 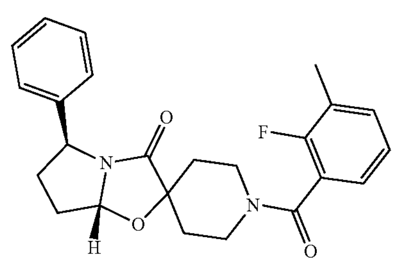 [SMILES: Cc1cccc(C(=O)N2CCC3(CC2)O[C@@H]2CC[C@@H](c4ccccc4)N2C3=O)c1F] | (5'S,7a'R)-1-(2-fluoro-3-methylbenzene-1-carbonyl)-5'-phenyltetrahydro-3'H-spiro[piperidine-4,2'-pyrrolo[2,1-b][1,3]oxazol]-3'-one | Calc'd 409, found 409 |
| 6.158 | 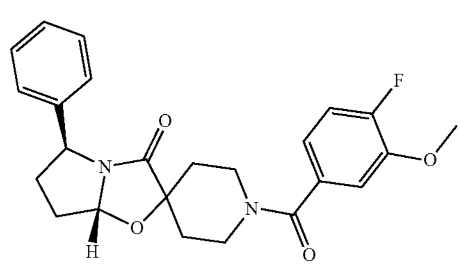 [SMILES: COc1cc(C(=O)N2CCC3(CC2)O[C@@H]2CC[C@@H](c4ccccc4)N2C3=O)ccc1F] | (5'S,7a'R)-1-(4-fluoro-3-methoxybenzene-1-carbonyl)-5'-phenyltetrahydro-3'H-spiro[piperidine-4,2'-pyrrolo[2,1-b][1,3]oxazol]-3'-one | Calc'd 425, found 425 |

TABLE 15-continued

| Ex. No. | Structure | Name | Exact Mass [M + H]+ |
|---|---|---|---|
| 6.159 | 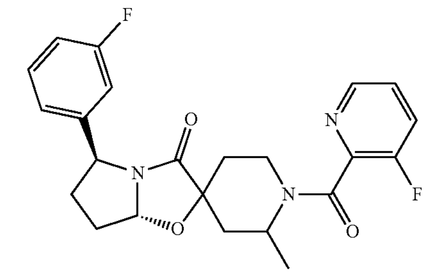 | (4R,5'S,7a'R)-5'-(3-fluorophenyl)-1-(3-fluoropyridine-2-carbonyl)-2-methyl-tetrahydro-3'H-spiro[piperidine-4,2'-pyrrolo[2,1-b][1,3]oxazol]-3'-one | Calc'd 428, found 428 |
| 6.160 | 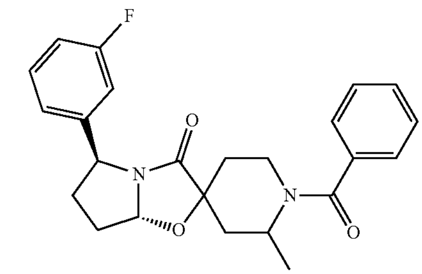 | (4R,5'S,7a'R)-1-(benzenecarbonyl)-5'-(3-fluorophenyl)-2-methyltetrahydro-3'H-spiro[piperidine-4,2'-pyrrolo[2,1-b][1,3]oxazol]-3'-one | Calc'd 409, found 409 |
| 6.161 | 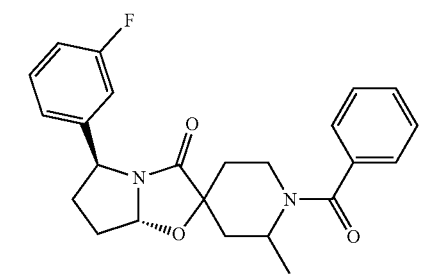 | (4R,5'S,7a'R)-1-(benzenecarbonyl)-5'-(3-fluorophenyl)-2-methyltetrahydro-3'H-spiro[piperidine-4,2'-pyrrolo[2,1-b][1,3]-oxazol]-3'-one | Calc'd 409, found 409 |
| 6.162 | 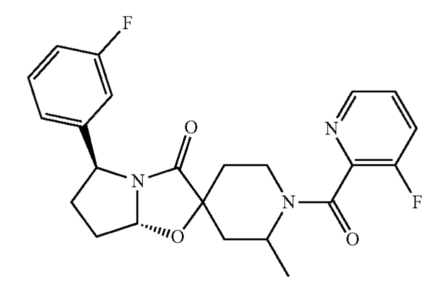 | (4R,5'S,7a'R)-5'-(3-fluorophenyl)-1-(3-fluoropyridine-2-carbonyl)-2-methyl-tetrahydro-3'H-spiro[piperidine-4,2'-pyrrolo[2,1-b][1,3]oxazol]-3'-one | Calc'd 428, found 428 |
| 6.163 | 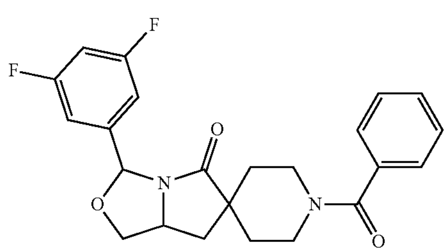 [SMILES: O=C(c1ccccc1)N1CCC2(CC1)CC1COC(c3cc(F)cc(F)c3)N1C2=O] | 1-(benzenecarbonyl)-3'-(3,5-difluorophenyl)dihydro-1'H,3'H,5'H-spiro[piperidine-4,6'-pyrrolo[1,2-c][1,3]oxazol]-5'-one | Calc'd 413, found 413 |

Example 7.1

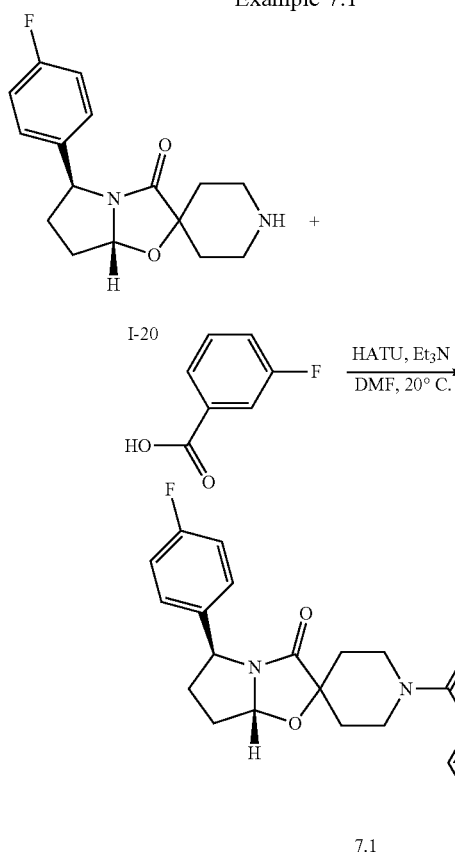

(5'S,7a'R)-1-(3-Fluorobenzoyl)-5'-(4-fluorophenyl)tetrahydro-3'H-spiro[piperidine-4,2'-pyrrolo[2,1-b]oxazol]-3'-one A mixture of (5'S,7a'R)-5'-(4-fluorophenyl)tetrahydro-3'H-spiro[piperidine-4,2'-pyrrolo[2,1-b]oxazol]-3'-one (40 mg, 0.13 mmol), 3-fluorobenzoic acid (23 mg, 0.165 mmol) and triethylamine (96 µL, 0.69 mmol) in DMF (1.5 mL) was treated with HATU (79 mg, 0.207 mmol). The resulting reaction mixture was stirred at 20° C. for 16 h. The reaction mixture was directly purified via reversed phase HPLC [TFA method]. This provided (5'S,7a'R)-1-(3-fluorobenzoyl)-5'-(4-fluorophenyl)tetrahydro-3'H-spiro[piperidine-4,2'-pyrrolo[2,1-b]oxazol]-3'-one. MS (ESI) m/z $C_{23}H_{23}F_2N_2O_3$ [M+H]$^+$ calc'd 413, found 413. $^1$H NMR (400 MHz, MeOD-d$_4$) δ 7.61-7.44 (m, 1H), 7.39-7.16 (m, 5H), 7.07 (br t, J=8.4 Hz, 2H), 5.81 (br s, 1H), 5.06-4.93 (m, 1H), 4.63-4.34 (m, 1H), 3.69 (br s, 1H), 3.46-3.36 (m, 2H), 2.69 (br d, J=12.2 Hz, 1H), 2.40-2.22 (m, 1H), 2.17-1.54 (m, 6H).

Compounds in Table 16 below were prepared from common Intermediate I-28, I-20A, I-23B, or I-17 using the methods described in Example 7.1.

TABLE 16

| Ex. No | Structure | Name | Exact Mass [M + H]+ |
|---|---|---|---|
| 7.2 | 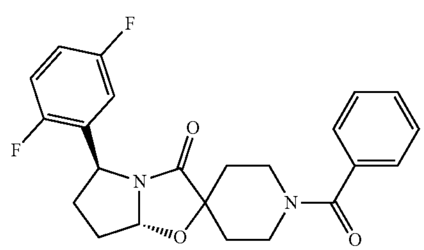 [SMILES: O=C(c1ccccc1)N1CCC2(CC1)O[C@@H]1CC[C@@H](c3cc(F)ccc3F)N1C2=O] | (5'S,7a'R)-1-(benzenecarbonyl)-5'-(2,5-difluorophenyl)tetrahydro-3'H-spiro[piperidine-4,2'-pyrrolo[2,1-b][1,3]oxazol]-3'-one | Calc'd 413, found 413 |
| 7.3 | 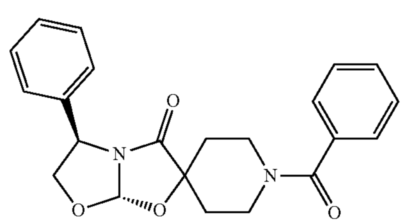 [SMILES: O=C(c1ccccc1)N1CCC2(CC1)O[C@@H]1OC[C@@H](c3ccccc3)N1C2=O] | (3'R,7a'S)-1-(benzenecarbonyl)-3'-phenyltetrahydro-5'H-spiro[piperidine-4,6'-pyrrolo[2,1-b][1,3]oxazol]-5'-one | Calc'd 377, found 377 |

TABLE 16-continued

| Ex. No | Structure | Name | Exact Mass [M + H]+ |
|---|---|---|---|
| 7.4 | 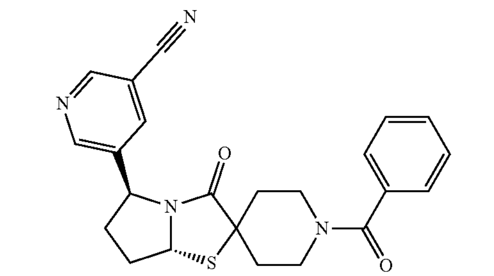 [SMILES: N#Cc1cncc([C@@H]2CC[C@H]3SC4(CCN(C(=O)c5ccccc5)CC4)C(=O)N32)c1] | 5-[(5'S,7a'R)-1-(benzenecarbonyl)-3'-oxotetrahydro-3'H-spiro[piperidine-4,2'-pyrrolo[2,1-b][1,3]thiazol]-5'-yl]pyridine-3-carbonitrile | Calc'd 419, found 419 |
| 7.5 | 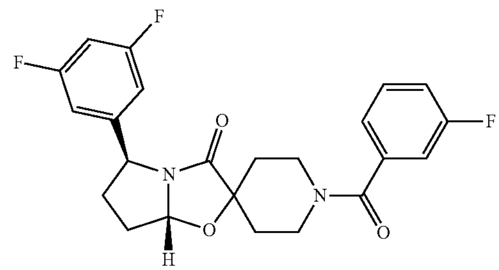 [SMILES: O=C(c1cccc(F)c1)N1CCC2(CC1)O[C@@H]1CC[C@@H](c3cc(F)cc(F)c3)N1C2=O] | (5'S,7a'R)-5'-(3,5-difluorophenyl)-1-(3-fluorobenzene-1-carbonyl)tetrahydro-3'H-spiro[piperidine-4,2'-pyrrolo[2,1-b][1,3]oxazol]-3'-one | Calc'd 431, found 431 |
| 7.6 | 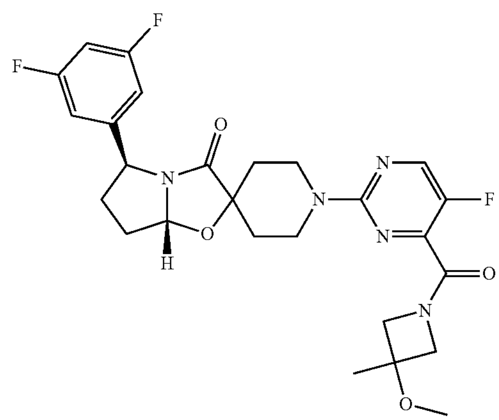 [SMILES: COC1(C)CN(C(=O)c2nc(N3CCC4(CC3)O[C@@H]3CC[C@@H](c5cc(F)cc(F)c5)N3C4=O)ncc2F)C1] | (5'S,7a'R)-5'-(3,5-difluorophenyl)-1-[5-fluoro-4-(3-methoxy-3-methylazetidine-1-carbonyl)pyrimidin-2-yl]tetrahydro-3'H-spiro[piperidine-4,2'-pyrrolo[2,1-b][1,3]oxazol]-3'-one | Calc'd 532, found 532 |
| 7.7 | 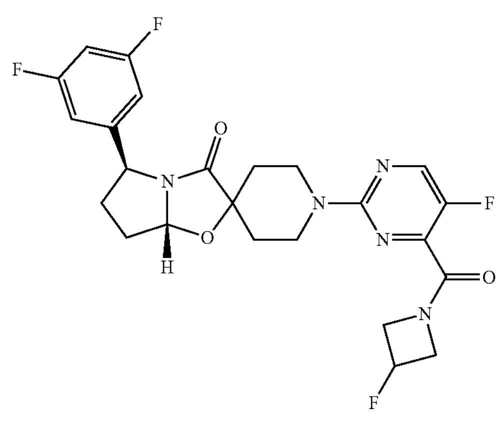 [SMILES: O=C(c1nc(N2CCC3(CC2)O[C@@H]2CC[C@@H](c4cc(F)cc(F)c4)N2C3=O)ncc1F)N1CC(F)C1] | (5'S,7a'R)-5'-(3,5-difluorophenyl)-1-[5-fluoro-4-(3-fluoroazetidine-1-carbonyl)pyrimidin-2-yl]tetrahydro-3'H-spiro[piperidine-4,2'-pyrrolo[2,1-b][1,3]oxazol]-3'-one | Calc'd 506, found 506 |

TABLE 16-continued

| Ex. No | Structure | Name | Exact Mass [M + H]+ |
|---|---|---|---|
| 7.8 | 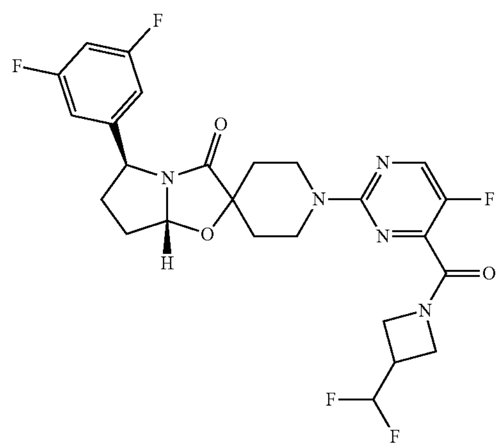 [SMILES: O=C(c1nc(N2CCC3(CC2)O[C@@H]2CC[C@@H](c4cc(F)cc(F)c4)N2C3=O)ncc1F)N1CC(C(F)F)C1] | (5'S,7a'R)-1-{4-[3-(difluoromethyl)azetidine-1-carbonyl]-5-fluoropyrimidin-2-yl}-5'-(3,5-difluorophenyl)tetrahydro-3'H-spiro[piperidine-4,2'-pyrrolo[2,1-b][1,3]oxazol]-3'-one | Calc'd 538, found 538 |
| 7.9 | 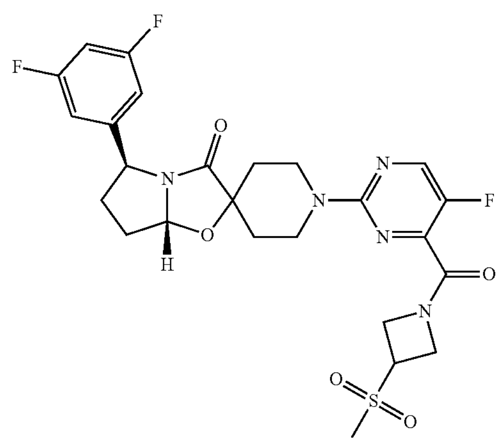 [SMILES: CS(=O)(=O)C1CN(C(=O)c2nc(N3CCC4(CC3)O[C@@H]3CC[C@@H](c5cc(F)cc(F)c5)N3C4=O)ncc2F)C1] | (5'S,7a'R)-5'-(3,5-difluorophenyl)-1-{5-fluoro-4-[3-(methylsulfonyl)azetidine-1-carbonyl]pyrimidin-2-yl}tetrahydro-3'H-spiro[piperidine-4,2'-pyrrolo[2,1-b][1,3]oxazol]-3'-one | Calc'd 566, found 566 |
| 7.10 | 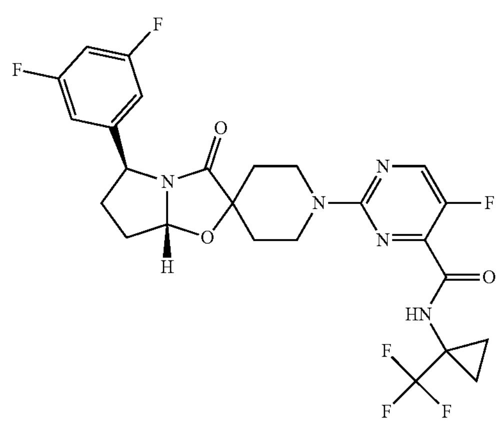 [SMILES: O=C(NC1(C(F)(F)F)CC1)c1nc(N2CCC3(CC2)O[C@@H]2CC[C@@H](c4cc(F)cc(F)c4)N2C3=O)ncc1F] | 2-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-5-fluoro-N-[1-(trifluoromethyl)cyclopropyl]pyrimidine-4-carboxamide | Calc'd 556, found 556 |

TABLE 16-continued

| Ex. No | Structure | Name | Exact Mass [M + H]+ |
|---|---|---|---|
| 7.11 | 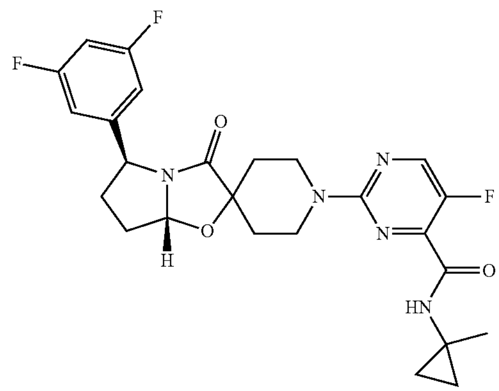 [SMILES: CC1(NC(=O)c2nc(N3CCC4(CC3)O[C@@H]3CC[C@@H](c5cc(F)cc(F)c5)N3C4=O)ncc2F)CC1] | 2-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-5-fluoro-N-(1-methylcyclopropyl)pyrimidine-4-carboxamide | Calc'd 502, found 502 |
| 7.12 | 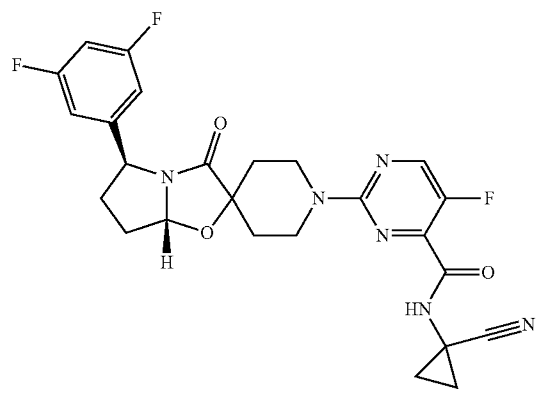 [SMILES: N#CC1(NC(=O)c2nc(N3CCC4(CC3)O[C@@H]3CC[C@@H](c5cc(F)cc(F)c5)N3C4=O)ncc2F)CC1] | N-(1-cyanocyclopropyl)-2-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-5-fluoropyrimidine-4-carboxamide | Calc'd 513, found 513 |
| 7.13 | 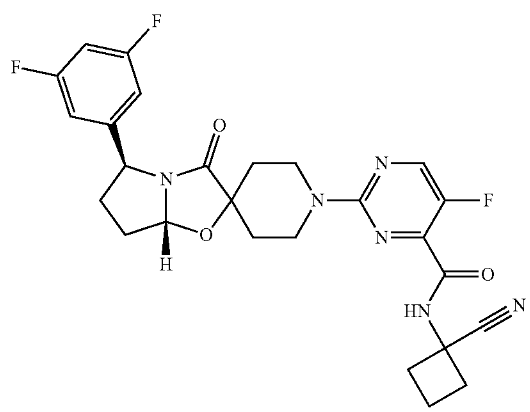 [SMILES: N#CC1(NC(=O)c2nc(N3CCC4(CC3)O[C@@H]3CC[C@@H](c5cc(F)cc(F)c5)N3C4=O)ncc2F)CCC1] | N-(1-cyanocyclobutyl)-2-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-5-fluoropyrimidine-4-carboxamide | Calc'd 527, found 527 |
| 7.14 | 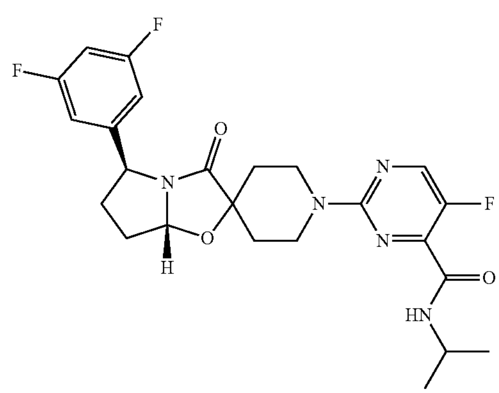 [SMILES: CC(C)NC(=O)c1nc(N2CCC3(CC2)O[C@@H]2CC[C@@H](c4cc(F)cc(F)c4)N2C3=O)ncc1F] | 2-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-5-fluoro-N-(propan-2-yl)pyrimidine-4-carboxamide | Calc'd 490, found 490 |

TABLE 16-continued

| Ex. No | Structure | Name | Exact Mass [M + H]+ |
|---|---|---|---|
| 7.15 | 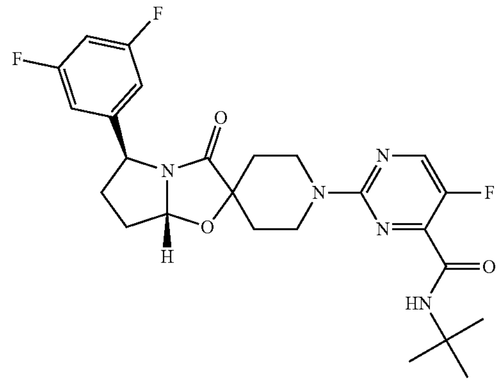 [SMILES: CC(C)(C)NC(=O)c1nc(N2CCC3(CC2)O[C@@H]2CC[C@@H](c4cc(F)cc(F)c4)N2C3=O)ncc1F] | N-tert-butyl-2-[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]-5-fluoropyrimidine-4-carboxamide | Calc'd 504, found 504 |

Example 8.1

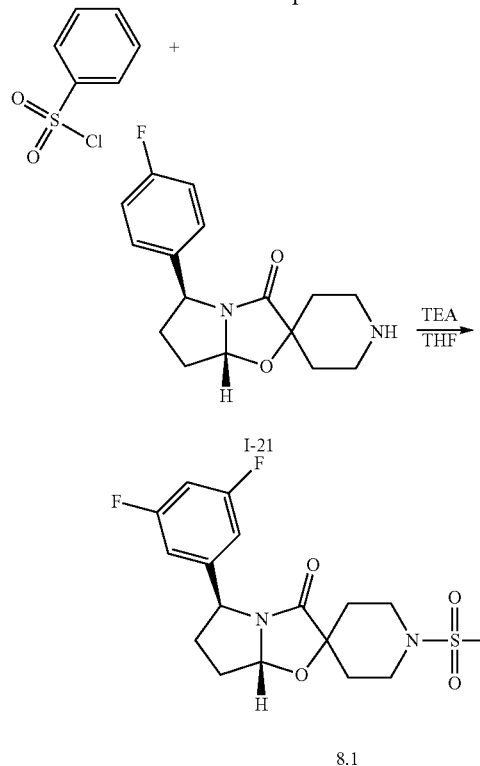

8.1

(5'S,7a'R)-5'-(3,5-Difluorophenyl)-1-(phenylsulfonyl)tetrahydro-3'H-spiro[piperidine-4,2'-pyrrolo[2,1-b]oxazol]-3'-one (5'S,7a'R)-5'-(3,5-Difluorophenyl)tetrahydro-3'H-spiro[piperidine-4,2'-pyrrolo[2,1-b]oxazol]-3'-one (14 mg, 0.040 mmol) and benzenesulfonyl chloride (8.8 mg, 0.05 mmol) in THF (450 μL) were added to a vial at room temperature. Triethylamine (11 μL, 0.12 mmol) was added in one portion and the mixture stirred at room temperature overnight. The mixture was concentrated and taken up in DMA and residue was purified by preparative HPLC Reverse phase (C-18), eluting with acetonitrile/water+0.05% $NH_3$, to give (5'S,7a'R)-5'-(3,5-difluorophenyl)-1-(phenylsulfonyl)tetrahydro-3'H-spiro[piperidine-4,2'-pyrrolo[2,1-b]oxazol]-3'-one. MS (ESI) m/z $C_{22}H_{23}F_2N_2O_4S$ [M+H]+ calc'd 449, found 449. $^1$H NMR (499 MHz, DMSO-d6) δ 7.78-7.73 (m, 3H), 7.69-7.66 (m, 2H), 7.13-7.02 (m, 1H), 7.03 (t, J=8 Hz, 2H), 5.67-5.64 (m, 1H), 4.86 (t, 1H), 2.59-2.56 (m, 3H), 2.48-2.47 (m, 2H), 2.10-2.07 (m, 2H), 1.93-1.89 (m, 1H), 1.81-1.52 (m, 4H).

Compounds in Table 17 below were prepared from common Intermediate I-21 or from compounds listed in Table 7 using the methods described in Example 8.1.

TABLE 17

| Ex. No. | Structure | Name | Exact Mass [M + H]+ |
|---|---|---|---|
| 8.2 | 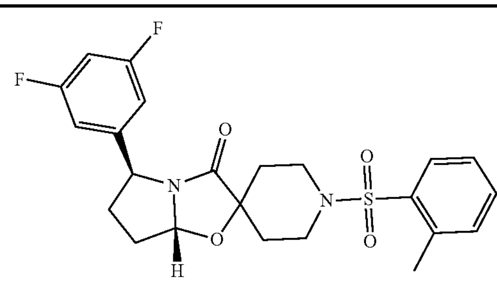 | (5'S,7a'R)-5'-(3,5-difluorophenyl)-1-[(2-methylphenyl)sulfonyl]tetrahydro-3'H-spiro[piperidine-4,2'-pyrrolo[2,1-b][1,3]oxazol]-3'-one | Calc'd 463, found 463 |

TABLE 17-continued

| Ex. No. | Structure | Name | Exact Mass [M + H]+ |
|---|---|---|---|
| 8.3 | 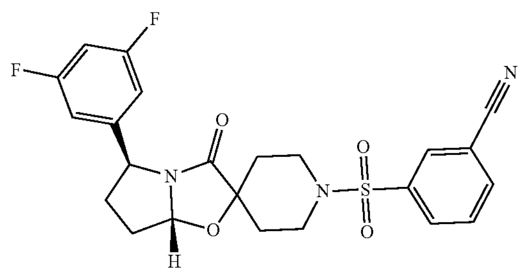 [SMILES: N#Cc1cccc(S(=O)(=O)N2CCC3(CC2)O[C@@H]2CC[C@@H](c4cc(F)cc(F)c4)N2C3=O)c1] | 3-{[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]sulfonyl}benzonitrile | Calc'd 474, found 474 |
| 8.4 | 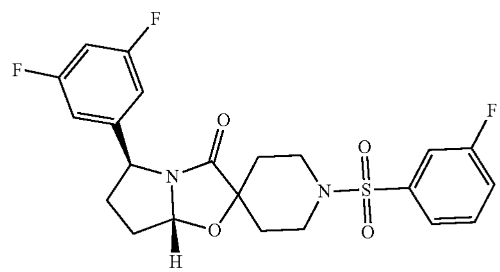 [SMILES: O=C1N2[C@@H](CC[C@H]2c2cc(F)cc(F)c2)OC12CCN(S(=O)(=O)c1cccc(F)c1)CC2] | (5'S,7a'R)-5'-(3,5-difluorophenyl)-1-[(3-fluorophenyl)sulfonyl]tetrahydro-3'H-spiro[piperidine-4,2'-pyrrolo[2,1-b][1,3]oxazol]-3'-one | Calc'd 467, found 467 |
| 8.5 | 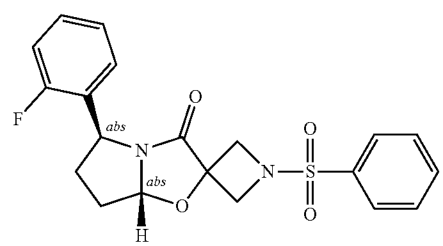 [SMILES: O=C1N2[C@@H](CC[C@H]2c2ccccc2F)OC12CN(S(=O)(=O)c1ccccc1)C2] | (5'S,7a'R)-5'-(2-fluorophenyl)-1-(phenylsulfonyl)tetrahydro-3'H-spiro[azetidine-3,2'-pyrrolo[2,1-b]oxazol]-3'-one | Calc'd 403, found 403 |
| 8.6 | 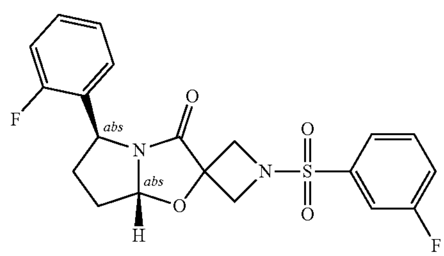 [SMILES: O=C1N2[C@@H](CC[C@H]2c2ccccc2F)OC12CN(S(=O)(=O)c1cccc(F)c1)C2] | (5'S,7a'R)-5'-(2-fluorophenyl)-1-((3-fluorophenyl)sulfonyl)tetrahydro-3'H-spiro[azetidine-3,2'-pyrrolo[2,1-b]oxazol]-3'-one | Calc'd 421, found 421 |
| 8.7 | 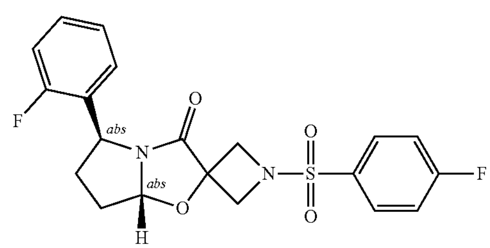 [SMILES: O=C1N2[C@@H](CC[C@H]2c2ccccc2F)OC12CN(S(=O)(=O)c1ccc(F)cc1)C2] | (5'S,7a'R)-5'-(2-fluorophenyl)-1-((4-fluorophenyl)sulfonyl)tetrahydro-3'H-spiro[azetidine-3,2'-pyrrolo[2,1-b]oxazol]-3'-one | Calc'd 421, found 421 |
| 8.8 | 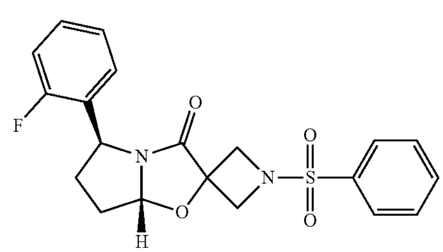 [SMILES: O=C1N2[C@@H](CC[C@H]2c2ccccc2F)OC12CN(S(=O)(=O)c1ccccc1)C2] | (5'S,7a'R)-5'-(2-fluorophenyl)-1-(phenylsulfonyl)tetrahydro-3'H-spiro[azetidine-3,2'-pyrrolo[2,1-b][1,3]oxazol]-3'-one | Calc'd 403, found 403 |

TABLE 17-continued

| Ex. No. | Structure | Name | Exact Mass [M + H]+ |
|---|---|---|---|
| 8.9 | 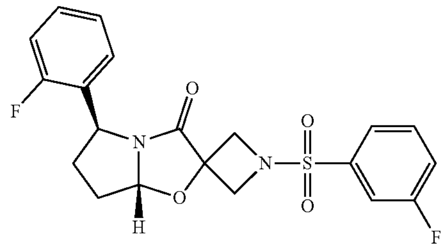 [SMILES: O=C1N2[C@@H](CC[C@H]2c2ccccc2F)OC12CN(S(=O)(=O)c1cccc(F)c1)C2] | (5'S,7a'R)-5'-(2-fluorophenyl)-1-[(3-fluorophenyl)sulfonyl]tetrahydro-3'H-spiro[azetidine-3,2'-pyrrolo[2,1-b][1,3]oxazol]-3'-one | Calc'd 421, found 421 |
| 8.10 | 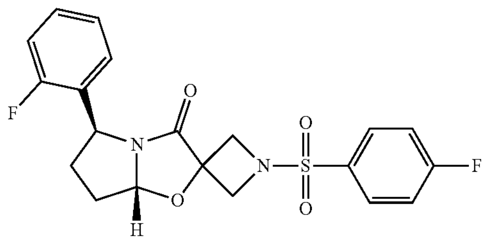 [SMILES: O=C1N2[C@@H](CC[C@H]2c2ccccc2F)OC12CN(S(=O)(=O)c1ccc(F)cc1)C2] | (5'S,7a'R)-5'-(2-fluorophenyl)-1-[(4-fluorophenyl)sulfonyl]tetrahydro-3'H-spiro[azetidine-3,2'-pyrrolo[2,1-b][1,3]oxazol]-3'-one | Calc'd 421, found 421 |

Example 9.1

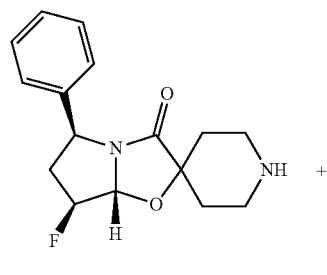

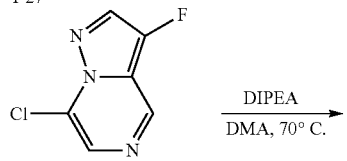

(5'S,7'S,7a'R)-7'-Fluoro-1-(3-fluoropyrazolo[1,5-a]pyrimidin-7-yl)-5'-phenyltetrahydro-3'H-spiro[piperidine-4,2'-pyrrolo[2,1-b]oxazol]-3'-one (5'S)-7'-Fluoro-5'-phenyltetrahydro-3'H-spiro[piperidine-4,2'-pyrrolo[2,1-b]oxazol]-3'-one (25 mg, 0.086 mmol, I-27) and 7-chloro-3-fluoropyrazolo[1,5-a]pyrimidine I-13 (17.7 mg, 0.103 mmol) in DMA (1076 μL) were added to a vial. TEA (36 μL, 0.26 mmol) was added in one portion and the mixture was capped and heated to 70° C. for 90 min. The reaction mixture was cooled, diluted with MeOH (2 ml) and filtered. The mixture was purified by preparative HPLC Reverse phase (C-18), eluting with acetonitrile/water+ 0.05% NH$_3$, to give (5'S,7'S,7a'R)-7'-fluoro-1-(3-fluoropyrazolo[1,5-a]pyrimidin-7-yl)-5'-phenyltetrahydro-3'H-spiro [piperidine-4,2'-pyrrolo[2,1-b]oxazol]-3'-one. MS (ESI) m/z C$_{22}$H$_{22}$F$_2$N$_5$O$_2$[M+H]$^+$ calc'd 425, found 425. $^1$H NMR (499 MHz, DMSO-d6) δ 8.29 (dd, J=12.2, 4.2 Hz, 2H), 7.39 (d, J=4.4 Hz, 4H), 7.30 (dt, J=8.7, 4.1 Hz, 1H), 6.49 (d, J=5.0 Hz, 1H), 5.91 (dd, J=11.8, 4.1 Hz, 1H), 5.21-5.08 (m, 2H), 4.38 (d, J=12.7 Hz, 1H), 4.30 (d, J=12.8 Hz, 1H), 3.51 (t, J=10.9 Hz, 1H), 3.40 (t, J=11.0 Hz, 1H), 3.08-2.94 (m, 1H), 2.15 (ddt, J=23.4, 17.4, 8.4 Hz, 3H), 2.02-1.80 (m, 2H).

Example 10.1

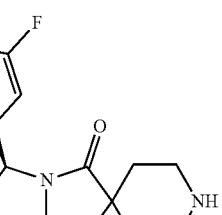

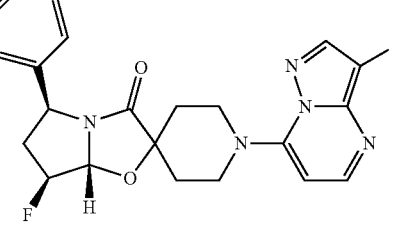

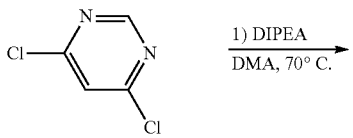

455

-continued

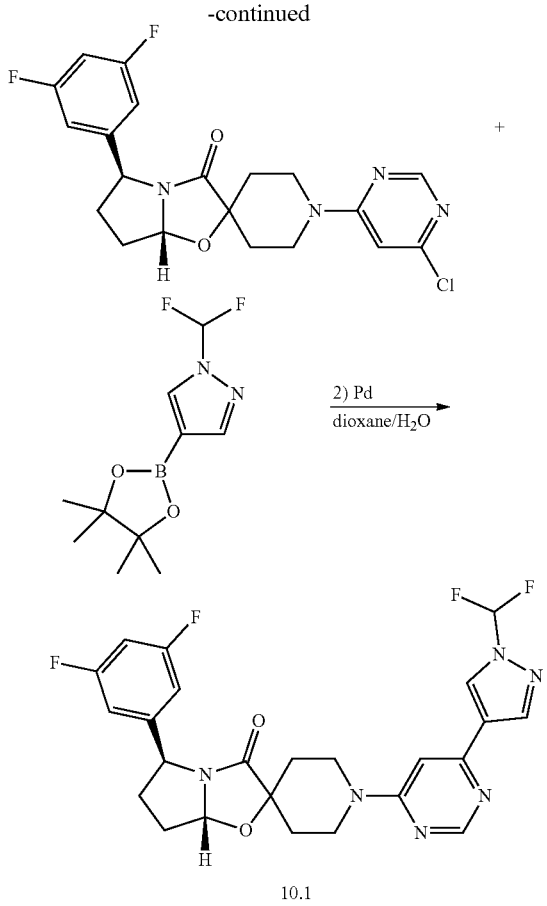

Step 1. (5'S,7a'R)-1-(6-Chloropyrimidin-4-yl)-5'-(3,5-difluorophenyl)tetrahydro-3'H-spiro [piperidine-4,2'-pyrrolo[2,1-b]oxazol]-3'-one (5'S,7a'R)-5'-(3,5-Difluorophenyl)tetrahydro-3'H-spiro [piperidine-4,2'-pyrrolo[2,1-b]oxazol]-3'-one (40 mg, 0.13 mmol) was combined with 4,6-dichloropyrimidine (19.3 mg, 0.130 mmol) in DMA (1297 μL) along with N-ethyl-N-isopropylpropan-2-amine (69.9 μL, 0.389 mmol). The mixture was capped and heated to 60° C. for 60 min. The mixture was cooled and the solvent was removed to afford crude (5'S,7a'R)-1-(6-chloropyrimidin-4-yl)-5'-(3,5-difluorophenyl)tetrahydro-3'H-spiro[piperidine-4,2'-pyrrolo[2,1-b]oxazol]-3'-one. The material was carried on without further purification. MS (ESI) m/z $C_{20}H_{20}ClF_2N_4O_2$ [M+H]$^+$ calc'd 421, found 421.

Step 2. (5'S,7a'R)-1-(6-(1-(difluoromethyl)-1H-pyrazol-4-yl)pyrimidin-4-yl)-5'-(3,5-difluorophenyl) tetrahydro-3'H-spiro[piperidine-4,2'-pyrrolo[2,1-b] oxazol]-3'-one A mixture of (5'S)-1-(6-chloropyrimidin-4-yl)-5'-(3,5-difluorophenyl)tetrahydro-3'H-spiro[piperidine-4,2'-pyrrolo [2,1-b]oxazol]-3'-one (45 mg, 0.107 mmol), 1-(difluoromethyl)-4-(4,4,5,5-tetramethyl-1,3,2-dioxaborolan-2-yl)-1H-pyrazole (26 mg, 0.107 mmol), XPHOS Pd G3 (4.53 mg, 5.35 μmol), and potassium phosphate tribasic (68 mg, 0.32 mmol) were dissolved in dioxane (1141 μL)/water (285 μL). The mixture was degassed under $N_2$ for 5 min, sealed, and stirred for 2 h at 80° C. The reaction mixture was cooled, diluted with DMA, filtered, and purified by preparative HPLC Reverse phase (C-18), eluting with Acetonitrile/Water+0.1% $NH_4$, to give (5'S,7a'R)-1-(6-(1-(difluoromethyl)-1H-pyrazol-4-yl)pyrimidin-4-yl)-5'-(3,5-difluorophenyl) tetrahydro-3'H-spiro[piperidine-4,2'-pyrrolo[2,1-b] oxazol]-3'-one. MS (ESI) m/z $C_{24}H_{23}F_4N_6O_2$[M+H]$^+$ calc'd 503, found 503. $^1$H NMR (499 MHz, DMSO-d6) δ 8.91 (s, 1H), 8.51 (s, 1H), 8.43 (s, 1H), 7.88 (t, J=59.1 Hz, 1H), 7.31 (s, 1H), 7.22-7.05 (m, 3H), 5.84 (dd, J=7.0, 5.1 Hz, 1H), 4.94 (t, J=7.8 Hz, 1H), 3.44-3.34 (m, 4H), 2.65 (dq, J=13.0, 7.6, 6.5 Hz, 1H), 2.27-2.17 (m, 1H), 2.10 (d, J=13.0 Hz, 1H), 1.95-1.79 (m, 2H), 1.71 (tq, J=11.8, 7.5, 6.0 Hz, 3H).

Compounds in Table 18 below were prepared from common Intermediate I-21C or I-18 using the methods described in Example 10.1.

TABLE 18

| Ex. No. | Structure | Name | Exact Mass [M + H]+ |
|---|---|---|---|
| 10.2 | 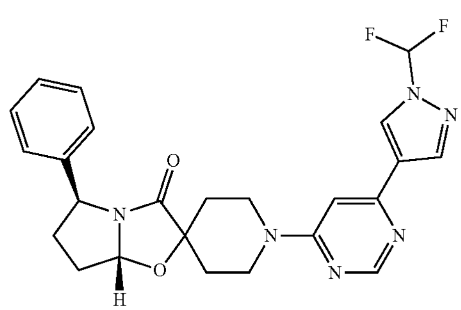 [SMILES: O=C1N2[C@@H](CC[C@H]2c2ccccc2)OC12CCN(c1cc(-c3cnn(C(F)F)c3)ncn1)CC2] | (5'S,7a'R)-1-{6-[1-(difluoromethyl)-1H-pyrazol-4-yl]pyrimidin-4-yl}-5'-phenyltetrahydro-3'H-spiro[piperidine-4,2'-pyrrolo[2,1-b][1,3]oxazol]-3'-one | Calc'd 467, found 467 |

TABLE 18-continued

| Ex. No. | Structure | Name | Exact Mass [M + H]+ |
|---|---|---|---|
| 10.3 | 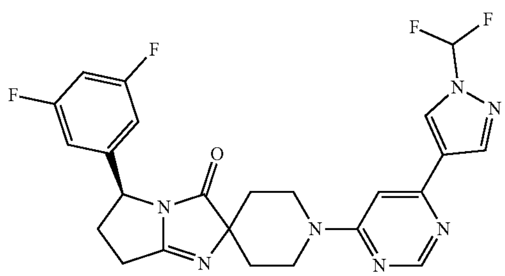 [SMILES: O=C1N2C(=NC13CCN(c1cc(-c4cnn(C(F)F)c4)ncn1)CC3)CC[C@H]2c1cc(F)cc(F)c1] | (S)-1-(6-(1-(difluoromethyl)-1H-pyrazol-4-yl)pyrimidin-4-yl)-5'-(3,5-difluorophenyl)-6',7'-dihydro-3'H,5'H-spiro[piperidine-4,2'-pyrrolo[1,2-a]imidazol]-3'-one | Calc'd 500, found 500 |
| 10.4 | 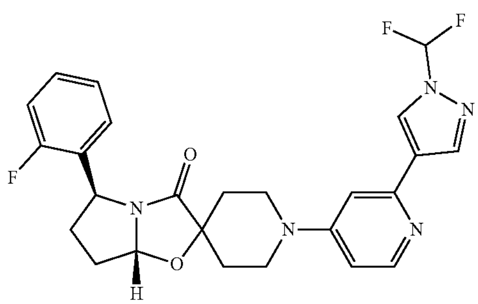 [SMILES: O=C1N2[C@@H](CC[C@H]2c2ccccc2F)OC12CCN(c1ccnc(-c3cnn(C(F)F)c3)c1)CC2] | (5'S,7a'R)-1-{2-[1-(difluoromethyl)-1H-pyrazol-4-yl]pyridin-4-yl}-5'-(2-fluorophenyl)tetrahydro-3'H-spiro[piperidine-4,2'-pyrrolo[2,1-b][1,3]oxazol]-3'-one | Calc'd 484, found 484 |

Example 11.1

5'-(3,5-Difluorophenyl)-1-(4-fluoropyridin-2-yl)-6' (7'-dihydro-3'H,5'H-Spiro[piperidine-4,2'-pyrrolo[1, 2-a]imidazol]-3'-one

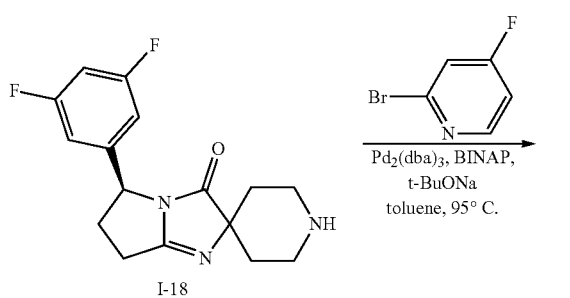

2-Bromo-4-fluoropyridine (36.9 mg, 0.210 mmol), Pd₂(dba)₃ (4.8 mg, 5.2 μmol), sodium 2-methylpropan-2-olate (42.3 mg, 0.440 mmol) and (2,2'-bis(diphenylphosphino)-1, 1'-binaphthyl) (BINAP) (3.26 mg, 5.24 μmol) were added to a solution of 5'-(3,5-difluorophenyl)-6',7'-dihydro-3'H,5'H-spiro[piperidine-4,2'-pyrrolo[1,2-a]imidazol]-3'-one (I-18) (40 mg, 0.105 mmol) in toluene (1 mL) at 20'° C. The mixture was stirred at 95° C. for 30 h under N₂. The mixture was filtered and the filtrate was purified by prep-HPLC (Column Boston Prime C18 150 mm×30 mm×5 pam; Condition water (0.05% NH₃/H₂O+10 mM NH₄HCO₃)-ACN (Gradient Time 10 min); 100% B Hold Time (min) 2 FlowRate (25 mL/min)) to provide 1-(6-(1-(difluoromethyl)-1H-pyrazol-4-yl)pyrimidin-4-yl)-5'-(3,5-difluorophenyl)-6',7'-dihydro-3'H,5'H-spiro[piperidine-4,2'-pyrrolo[1, 2-a]imidazol]-3'-one. MS (ESI) m/z C₂₁H₂F₃N₄O [M+H]⁺ calc'd 401, found 401. ¹H NMR (400 MHz, METHANOL-d₄) δ 8.08 (dd, J 6.0, 9.6 Hz, 1H), 6.86-7.00 (m, 3H), 6.62 (dd, J=2.0, 12.8 Hz, 1H), 6.45 (ddd, J=2.0, 6.0, 8.4 Hz, 1H), 5.07 (dd, J 5.2, 8.0 Hz, 1H), 4.22 (br d, J=13.6 Hz, 2H), 3.48 (ddd, J=3.2, 11.2, 14.0 Hz, 2H), 2.70-3.05 (m, 3H), 2.29-2.42 (m, 1H), 1.95 (ddd, J=4.0, 11.2, 13.2 Hz, 2H), 1.63-1.80 (m, 2H).

Compounds in Table 18 below were prepared from common Intermediate I-20A using the methods described in Example 11.1.

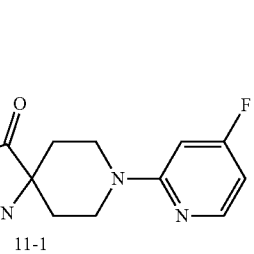

TABLE 19

| Ex. No. | Name | Exact Mass [M + H]+ |
|---|---|---|
| 11.2 | (3'R,7a'S)-1-(4-fluoropyridin-2-yl)-3'-phenyltetrahydro-5'H-spiro[piperidine-4,6'-pyrrolo[2,1-b][1,3]oxazol]-5'-one | Calc'd 368, found 368 |
| 11.3 | 3-fluoro-4-[(3'R,7a'S)-5'-oxo-3'-phenyltetrahydro-1H,5'H-spiro[piperidine-4,6'-pyrrolo[2,1-b][1,3]oxazol]-1-yl]benzonitrile | Calc'd 392, found 392 |
| 11.4 | (5'S,7a'R)-5'-phenyl-1-[4-(pyridin-2-yl)-1,3-thiazol-2-yl]tetrahydro-3'H-spiro[piperidine-4,2'-pyrrolo[2,1-b][1,3]oxazol]-3'-one | Calc'd 433, found 433 |
| 11.5 | (5'S,7a'R)-5'-phenyl-1-[1-(pyrazin-2-yl)-1H-pyrazol-3-yl]tetrahydro-3'H-spiro[piperidine-4,2'-pyrrolo[2,1-b][1,3]oxazol]-3'-one | Calc'd 417, found 417 |
| 11.6 | (5'S,7a'R)-1-[1-(2-methoxypyridin-4-yl)-1H-pyrazol-3-yl]-5'-phenyltetrahydro-3'H-spiro[piperidine-4,2'-pyrrolo[2,1-b][1,3]oxazol]-3'-one | Calc'd 446, found 446 |
| 11.7 | (5'S,7a'R)-1-(1-methyl-6-oxo-1,6-dihydropyridazin-3-yl)-5'-phenyltetrahydro-3'H-spiro[piperidine-4,2'-pyrrolo[2,1-b][1,3]oxazol]-3'-one | Calc'd 381, found 381 |

TABLE 19-continued

| Ex. No. | Structure | Name | Exact Mass [M + H]+ |
|---|---|---|---|
| 11.8 | 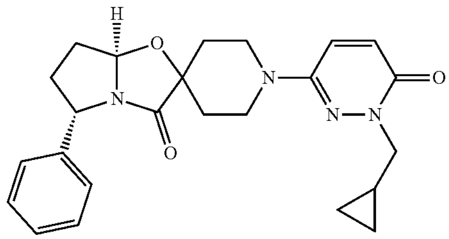 [SMILES: O=C1N2[C@@H](CC[C@H]2c2ccccc2)OC12CCN(c1ccc(=O)n(CC3CC3)n1)CC2] | (5'S,7a'R)-1-[1-(cyclopropylmethyl)-6-oxo-1,6-dihydropyridazin-3-yl]-5'-phenyltetrahydro-3'H-spiro[piperidine-4,2'-pyrrolo[2,1-b][1,3]oxazol]-3'-one | Calc'd 421, found 421 |
| 11.9 | 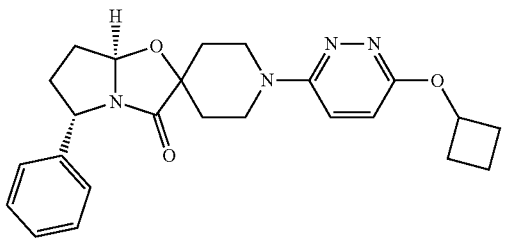 [SMILES: O=C1N2[C@@H](CC[C@H]2c2ccccc2)OC12CCN(c1ccc(OC3CCC3)nn1)CC2] | (5'S,7a'R)-1-[6-(cyclobutyloxy)pyridazin-3-yl]-5'-phenyltetrahydro-3'H-spiro[piperidine-4,2'-pyrrolo[2,1-b][1,3]oxazol]-3'-one | Calc'd 421, found 421 |
| 11.10 | 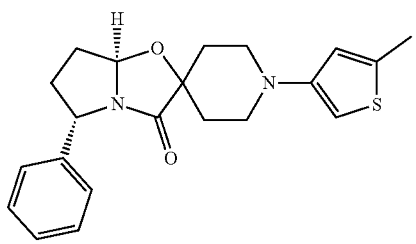 [SMILES: Cc1cc(N2CCC3(CC2)O[C@@H]2CC[C@@H](c4ccccc4)N2C3=O)cs1] | (5'S,7a'R)-1-(5-methylthiophen-3-yl)-5'-phenyltetrahydro-3'H-spiro[piperidine-4,2'-pyrrolo[2,1-b][1,3]oxazol]-3'-one | Calc'd 369, found 369 |
| 11.11 | 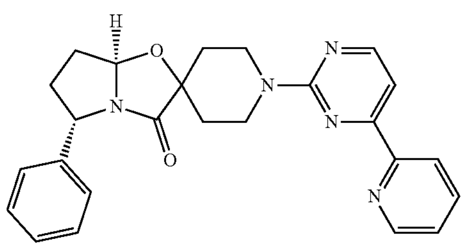 [SMILES: O=C1N2[C@@H](CC[C@H]2c2ccccc2)OC12CCN(c1nccc(-c3ccccn3)n1)CC2] | (5'S,7a'R)-5'-phenyl-1-[4-(pyridin-2-yl)pyrimidin-2-yl]tetrahydro-3'H-spiro[piperidine-4,2'-pyrrolo[2,1-b][1,3]oxazol]-3'-one | Calc'd 428, found 428 |
| 11.12 | 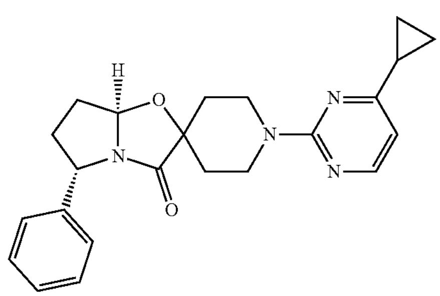 [SMILES: O=C1N2[C@@H](CC[C@H]2c2ccccc2)OC12CCN(c1nccc(C3CC3)n1)CC2] | (5'S,7a'R)-1-(4-cyclopropylpyrimidin-2-yl)-5'-phenyltetrahydro-3'H-spiro[piperidine-4,2'-pyrrolo[2,1-b][1,3]oxazol]-3'-one | Calc'd 391, found 391 |
| 11.13 | 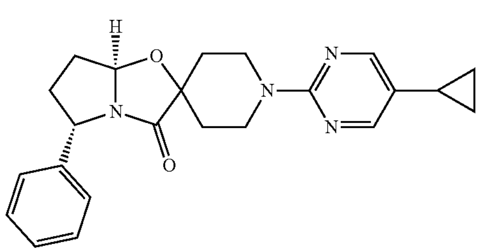 [SMILES: O=C1N2[C@@H](CC[C@H]2c2ccccc2)OC12CCN(c1ncc(C3CC3)cn1)CC2] | (5'S,7a'R)-1-(5-cyclopropylpyrimidin-2-yl)-5'-phenyltetrahydro-3'H-spiro[piperidine-4,2'-pyrrolo[2,1-b][1,3]oxazol]-3'-one | Calc'd 391, found 391 |

TABLE 19-continued

| Ex. No. | Structure | Name | Exact Mass [M + H]+ |
|---|---|---|---|
| 11.14 | 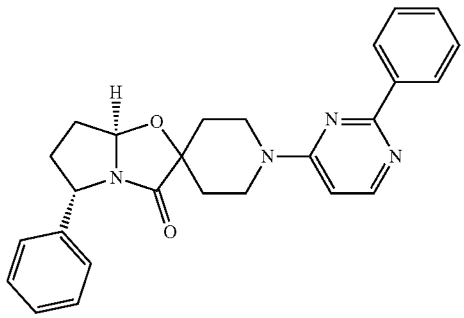 [SMILES: O=C1N2[C@@H](CC[C@H]2c2ccccc2)OC12CCN(c1ccnc(-c3ccccc3)n1)CC2] | (5'S,7a'R)-5'-phenyl-1-(2-phenylpyrimidin-4-yl)tetrahydro-3'H-spiro[piperidine-4,2'-pyrrolo[2,1-b][1,3]oxazol]-3'-one | Calc'd 427, found 427 |
| 11.15 | 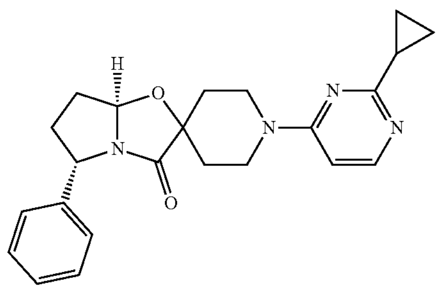 [SMILES: O=C1N2[C@@H](CC[C@H]2c2ccccc2)OC12CCN(c1ccnc(C3CC3)n1)CC2] | (5'S,7a'R)-1-(2-cyclopropylpyrimidin-4-yl)-5'-phenyltetrahydro-3'H-spiro[piperidine-4,2'-pyrrolo[2,1-b][1,3]oxazol]-3'-one | Calc'd 391, found 391 |
| 11.16 | 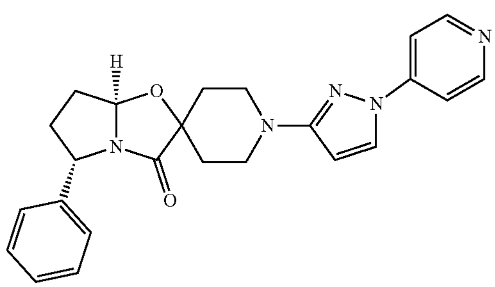 [SMILES: O=C1N2[C@@H](CC[C@H]2c2ccccc2)OC12CCN(c1ccn(-c3ccncc3)n1)CC2] | (5'S,7a'R)-5'-phenyl-1-[1-(pyridin-4-yl)-1H-pyrazol-3-yl]tetrahydro-3'H-spiro[piperidine-4,2'-pyrrolo[2,1-b][1,3]oxazol]-3'-one | Calc'd 416, found 416 |
| 11.17 | 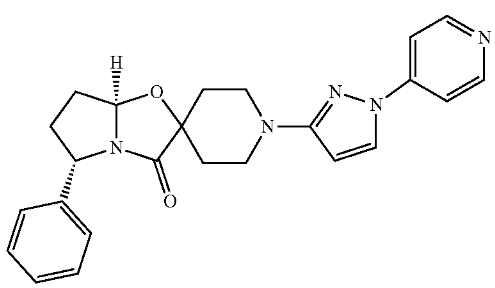 [SMILES: O=C1N2[C@@H](CC[C@H]2c2ccccc2)OC12CCN(c1ccn(-c3ccncc3)n1)CC2] | (5'S,7a'R)-5'-phenyl-1-[1-(pyridin-4-yl)-1H-pyrazol-3-yl]tetrahydro-3'H-spiro[piperidine-4,2'-pyrrolo[2,1-b][1,3]oxazol]-3'-one | Calc'd 416, found 416 |
| 11.18 | 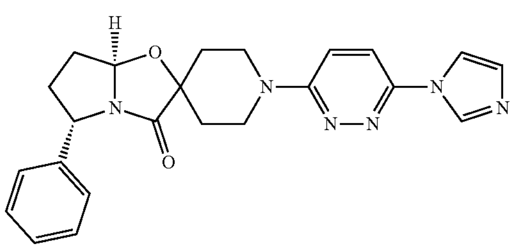 [SMILES: O=C1N2[C@@H](CC[C@H]2c2ccccc2)OC12CCN(c1ccc(-n3ccnc3)nn1)CC2] | (5'S,7a'R)-1-[6-(1H-imidazol-1-yl)pyridazin-3-yl]-5'-phenyltetrahydro-3'H-spiro[piperidine-4,2'-pyrrolo[2,1-b][1,3]oxazol]-3'-one | Calc'd 417, found 417 |

TABLE 19-continued

| Ex. No. | Structure | Name | Exact Mass [M + H]+ |
|---|---|---|---|
| 11.19 | 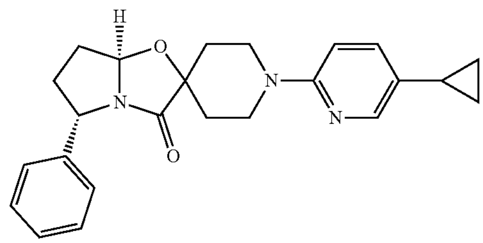 [SMILES: O=C1N2[C@@H](CC[C@H]2c2ccccc2)OC12CCN(c1ccc(C3CC3)cn1)CC2] | (5'S,7a'R)-1-(5-cyclopropylpyridin-2-yl)-5'-phenyltetrahydro-3'H-spiro[piperidine-4,2'-pyrrolo[2,1-b][1,3]oxazol]-3'-one | Calc'd 390, found 390 |
| 11.20 | 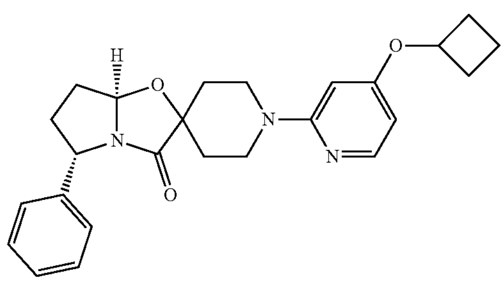 [SMILES: O=C1N2[C@@H](CC[C@H]2c2ccccc2)OC12CCN(c1cc(OC3CCC3)ccn1)CC2] | (5'S,7a'R)-1-[4-(cyclobutyloxy)pyridin-2-yl]-5'-phenyltetrahydro-3'H-spiro[piperidine-4,2'-pyrrolo[2,1-b][1,3]oxazol]-3'-one | Calc'd 420, found 420 |
| 11.21 | 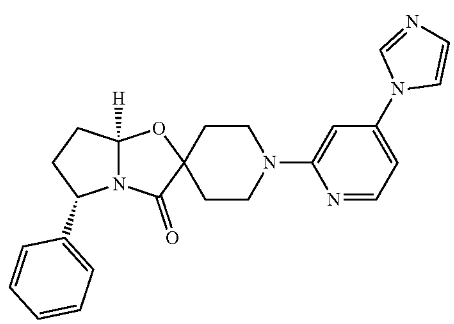 [SMILES: O=C1N2[C@@H](CC[C@H]2c2ccccc2)OC12CCN(c1cc(-n3ccnc3)ccn1)CC2] | (5'S,7a'R)-1-[4-(1H-imidazol-1-yl)pyridin-2-yl]-5'-phenyltetrahydro-3'H-spiro[piperidine-4,2'-pyrrolo[2,1-b][1,3]oxazol]-3'-one | Calc'd 416, found 416 |
| 11.22 | 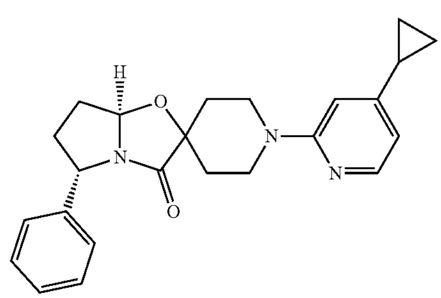 [SMILES: O=C1N2[C@@H](CC[C@H]2c2ccccc2)OC12CCN(c1cc(C3CC3)ccn1)CC2] | (5'S,7a'R)-1-(4-cyclopropylpyridin-2-yl)-5'-phenyltetrahydro-3'H-spiro[piperidine-4,2'-pyrrolo[2,1-b][1,3]oxazol]-3'-one | Calc'd 390, found 390 |
| 11.23 | 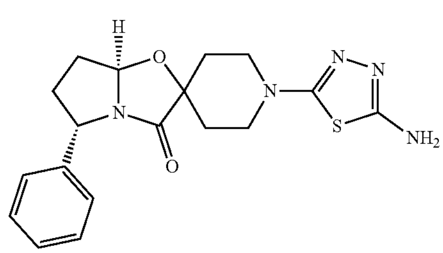 [SMILES: Nc1nnc(N2CCC3(CC2)O[C@@H]2CC[C@@H](c4ccccc4)N2C3=O)s1] | (5'S,7a'R)-1-(5-amino-1,3,4-thiadiazol-2-yl)-5'-phenyltetrahydro-3'H-spiro[piperidine-4,2'-pyrrolo[2,1-b][1,3]oxazol]-3'-one | Calc'd 372, found 372 |

TABLE 19-continued

| Ex. No. | Structure | Name | Exact Mass [M + H]+ |
|---|---|---|---|
| 11.24 | 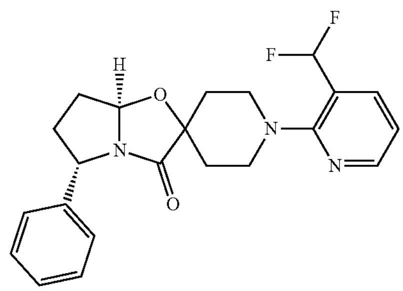 [SMILES: O=C1N2[C@@H](CC[C@H]2c2ccccc2)OC12CCN(c1ncccc1C(F)F)CC2] | (5'S,7a'R)-1-[3-(difluoromethyl)pyridin-2-yl]-5'-phenyltetrahydro-3'H-spiro[piperidine-4,2'-pyrrolo[2,1-b][1,3]oxazol]-3'-one | Calc'd 400, found 400 |
| 11.25 | 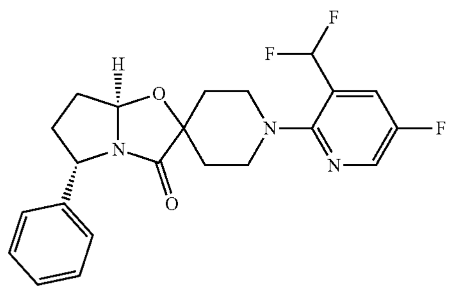 [SMILES: O=C1N2[C@@H](CC[C@H]2c2ccccc2)OC12CCN(c1ncc(F)cc1C(F)F)CC2] | (5'S,7a'R)-1-[3-(difluoromethyl)-5-fluoropyridin-2-yl]-5'-phenyltetrahydro-3'H-spiro[piperidine-4,2'-pyrrolo[2,1-b][1,3]oxazol]-3'-one | Calc'd 418, found 418 |
| 11.26 | 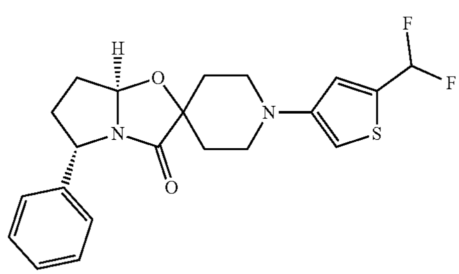 [SMILES: O=C1N2[C@@H](CC[C@H]2c2ccccc2)OC12CCN(c1csc(C(F)F)c1)CC2] | (5'S,7a'R)-1-[5-(difluoromethyl)thiophen-3-yl]-5'-phenyltetrahydro-3'H-spiro[piperidine-4,2'-pyrrolo[2,1-b][1,3]oxazol]-3'-one | Calc'd 405, found 405 |
| 11.27 | 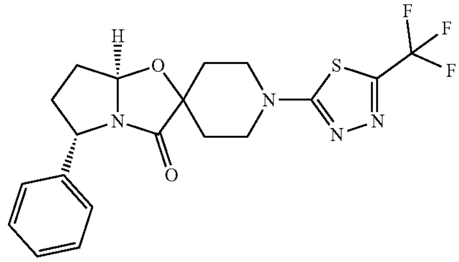 [SMILES: O=C1N2[C@@H](CC[C@H]2c2ccccc2)OC12CCN(c1nnc(C(F)(F)F)s1)CC2] | (5'S,7a'R)-5'-phenyl-1-[5-(trifluoromethyl)-1,3,4-thiadiazol-2-yl]tetrahydro-3'H-spiro[piperidine-4,2'-pyrrolo[2,1-b][1,3]oxazol]-3'-one | Calc'd 425, found 425 |
| 11.28 | 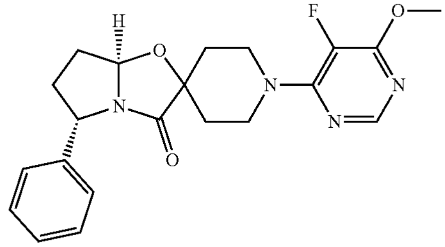 [SMILES: COc1ncnc(N2CCC3(CC2)O[C@@H]2CC[C@@H](c4ccccc4)N2C3=O)c1F] | (5'S,7a'R)-1-(5-fluoro-6-methoxypyrimidin-4-yl)-5'-phenyltetrahydro-3'H-spiro[piperidine-4,2'-pyrrolo[2,1-b][1,3]oxazol]-3'-one | Calc'd 399, found 399 |

TABLE 19-continued

| Ex. No. | Structure | Name | Exact Mass [M + H]+ |
|---|---|---|---|
| 11.29 | 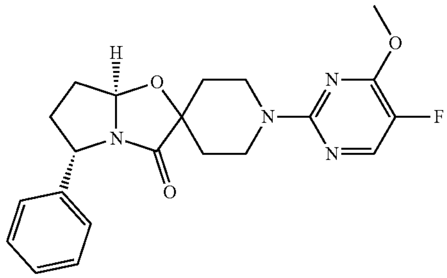 [SMILES: COc1nc(N2CCC3(CC2)O[C@@H]2CC[C@@H](c4ccccc4)N2C3=O)ncc1F] | (5'S,7a'R)-1-(5-fluoro-4-methoxypyrimidin-2-yl)-5'-phenyltetrahydro-3'H-spiro[piperidine-4,2'-pyrrolo[2,1-b][1,3]oxazol]-3'-one | Calc'd 399, found 399 |
| 11.30 | 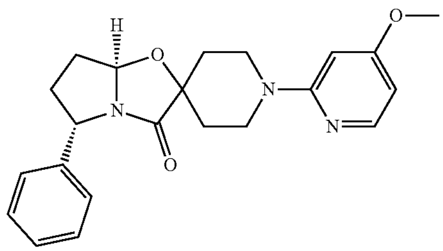 [SMILES: COc1ccnc(N2CCC3(CC2)O[C@@H]2CC[C@@H](c4ccccc4)N2C3=O)c1] | (5'S,7a'R)-1-(4-methoxypyridin-2-yl)-5'-phenyltetrahydro-3'H-spiro[piperidine-4,2'-pyrrolo[2,1-b][1,3]oxazol]-3'-one | Calc'd 380, found 380 |
| 11.31 | 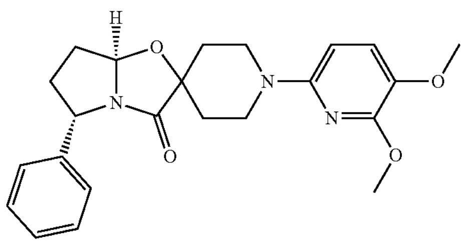 [SMILES: COc1ccc(N2CCC3(CC2)O[C@@H]2CC[C@@H](c4ccccc4)N2C3=O)nc1OC] | (5'S,7a'R)-1-(5,6-dimethoxypyridin-2-yl)-5'-phenyltetrahydro-3'H-spiro[piperidine-4,2'-pyrrolo[2,1-b][1,3]oxazol]-3'-one | Calc'd 410, found 410 |
| 11.32 | 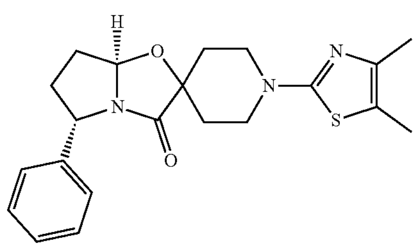 [SMILES: Cc1nc(N2CCC3(CC2)O[C@@H]2CC[C@@H](c4ccccc4)N2C3=O)sc1C] | (5'S,7a'R)-1-(4,5-dimethyl-1,3-thiazol-2-yl)-5'-phenyltetrahydro-3'H-spiro[piperidine-4,2'-pyrrolo[2,1-b][1,3]oxazol]-3'-one | Calc'd 384, found 384 |
| 11.33 | 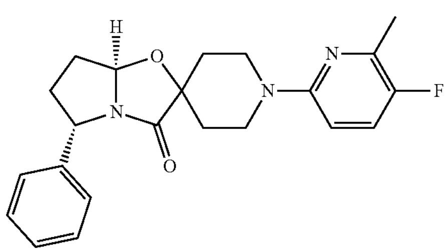 [SMILES: Cc1nc(N2CCC3(CC2)O[C@@H]2CC[C@@H](c4ccccc4)N2C3=O)ccc1F] | (5'S,7a'R)-1-(5-fluoro-6-methylpyridin-2-yl)-5'-phenyltetrahydro-3'H-spiro[piperidine-4,2'-pyrrolo[2,1-b][1,3]oxazol]-3'-one | Calc'd 382, found 382 |
| 11.34 | 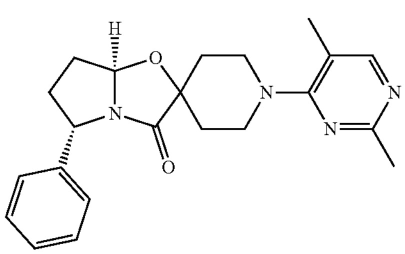 [SMILES: Cc1ncc(C)c(N2CCC3(CC2)O[C@@H]2CC[C@@H](c4ccccc4)N2C3=O)n1] | (5'S,7a'R)-1-(2,5-dimethylpyrimidin-4-yl)-5'-phenyltetrahydro-3'H-spiro[piperidine-4,2'-pyrrolo[2,1-b][1,3]oxazol]-3'-one | Calc'd 379, found 379 |

TABLE 19-continued

| Ex. No. | Structure | Name | Exact Mass [M + H]+ |
|---|---|---|---|
| 11.35 | 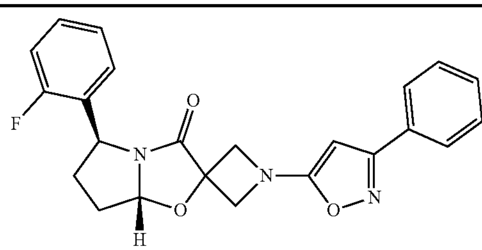 | (5'S,7a'R)-5'-(2-fluorophenyl)-1-(3-phenyl-1,2-oxazol-5-yl)tetrahydro-3'H-spiro[azetidine-3,2'-pyrrolo[2,1-b][1,3]oxazol]-3'-one | Calc'd 406, found 406 |

Example 12.1

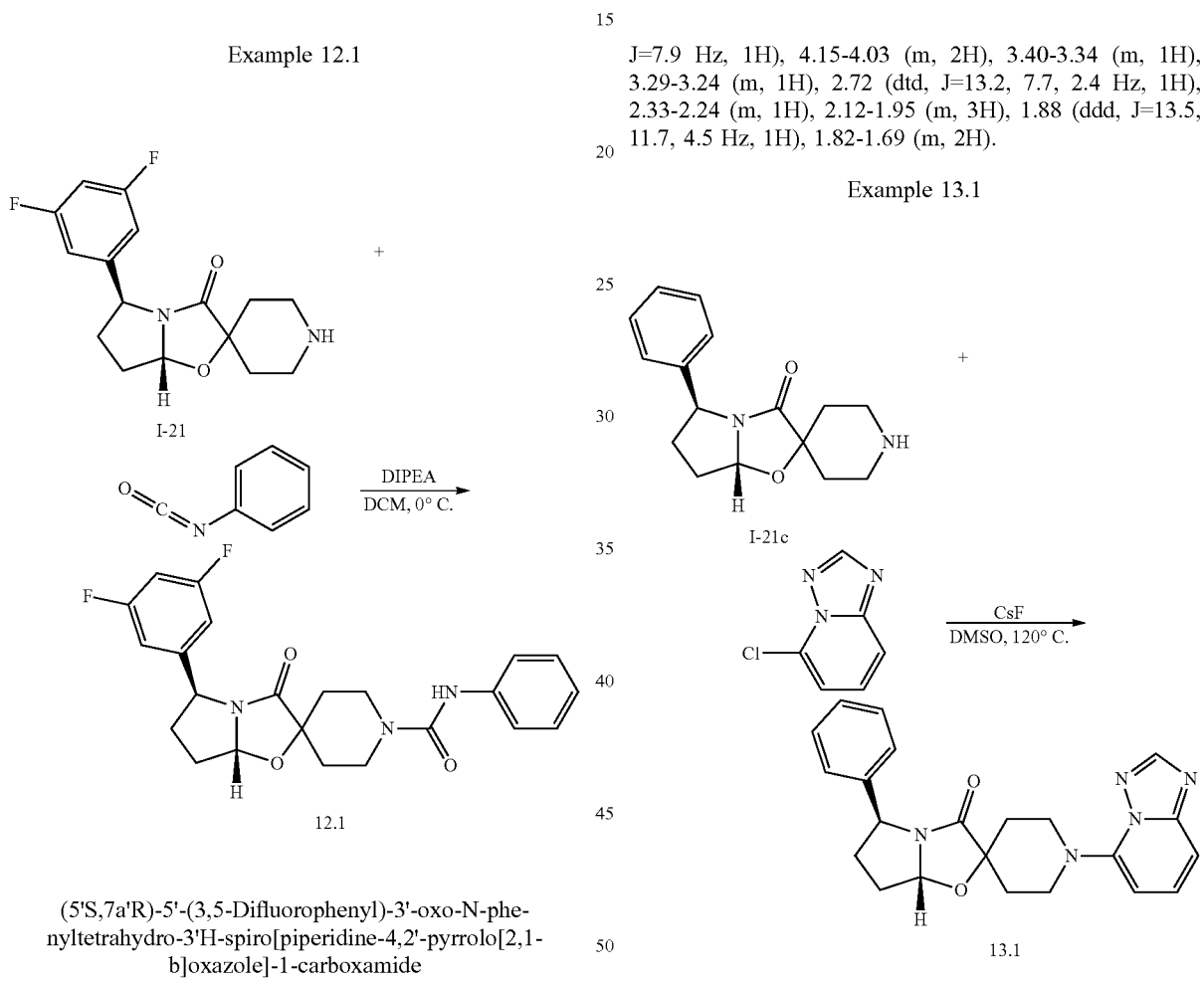

(5'S,7a'R)-5'-(3,5-Difluorophenyl)-3'-oxo-N-phenyltetrahydro-3'H-spiro[piperidine-4,2'-pyrrolo[2,1-b]oxazole]-1-carboxamide A mixture of (5'S,7a'R)-5'-(3,5-difluorophenyl)tetrahydro-3'H-spiro[piperidine-4,2'-pyrrolo[2,1-b]oxazol]-3'-one hydrochloride I-21 (30 mg, 0.087 mmol) and DIEA (46 µL, 0.261 mmol) in DCM (1 ml) was cooled to 0° C. and treated with isocyanatobenzene (10 mg, 0.084 mmol). The resulting mixture was stirred at 0° C. for 2 h. The reaction mixture was directly concentrated under reduced pressure and the residue was purified via reversed phase HPLC [TFA method]. This provided (5'S,7a'R)-5'-(3,5-difluorophenyl)-3'-oxo-N-phenyltetrahydro-3'H-spiro[piperidine-4,2'-pyrrolo [2,1-b]oxazole]-1-carboxamide. MS (ESI) m/z $C_{23}H_{24}F_2N_3O_3$ [M+H]$^+$ calc'd 428, found 428. $^1$H NMR (500 MHz, MeOD-d$_4$) δ 7.38-7.32 (m, 2H), 7.29-7.23 (m, 2H), 7.02 (t, J=7.4 Hz, 1H), 6.97-6.90 (m, 2H), 6.85 (tt, J=9.1, 2.3 Hz, 1H), 5.81 (dd, J=7.3, 4.9 Hz, 1H), 4.98 (t, J=7.9 Hz, 1H), 4.15-4.03 (m, 2H), 3.40-3.34 (m, 1H), 3.29-3.24 (m, 1H), 2.72 (dtd, J=13.2, 7.7, 2.4 Hz, 1H), 2.33-2.24 (m, 1H), 2.12-1.95 (m, 3H), 1.88 (ddd, J=13.5, 11.7, 4.5 Hz, 1H), 1.82-1.69 (m, 2H).

Example 13.1

(5'S,7a'R)-1-([1,2,4]Triazolo[1,5-a]pyridin-5-yl)-5'-phenyltetrahydro-3'H-spiro[piperidine-4,2'-pyrrolo [2,1-b]oxazol]-3'-one, TFA A scintillation vial containing (5'S,7a'R)-5'-phenyltetrahydro-3'H-spiro[piperidine-4,2'-pyrrolo[2,1-b]oxazol]-3'-one, HCl (40 mg, 0.130 mmol), 5-chloro-[1,2,4]triazolo[1,5-a]pyridine (30 mg, 0.194 mmol) and CsF (59 mg, 0.389 mmol) was taken up in DMSO (1.3 mL), and the resulting mixture was stirred for 16 h at 120° C. After cooling, the reaction mixture was directly filtered and purified via reversed phase HPLC [TFA method]. This provided (5'S, 7a'R)-1-([1,2,4]triazolo[1,5-a]pyridin-5-yl)-5'-phenyltetrahydro-3'H-spiro[piperidine-4,2'-pyrrolo[2,1-b]oxazol]-3'- one, TFA salt. MS (ESI) m/z $C_{22}H_{24}N_5O_2$ [M+H]+ calc'd 390, found 390. ¹H NMR (600 MHz, CD₃CN) δ 8.70 (s, 1H), 7.89 (t, J=8.3 Hz, 1H), 7.54 (d, J=8.5 Hz, 1H), 7.36 (t, J=7.5 Hz, 2H), 7.32 (d, J=7.3 Hz, 2H), 7.28 (t, J=7.2 Hz, 1H), 6.86 (d, J=8.0 Hz, 1H), 5.79 (dd, J=7.3, 5.0 Hz, 1H), 4.94 (t, J=7.9 Hz, 1H), 4.03 (dt, J=12.1, 4.1 Hz, 1H), 3.98 (dt, J=12.4, 3.5 Hz, 1H), 3.46 (td, J=12.1, 2.9 Hz, 1H), 3.37 (td, J=12.0, 3.0 Hz, 1H), 2.67 (dtd, J=13.3, 7.7, 2.2 Hz, 1H), 2.28-2.20 (m, 2H), 2.17 (d, J=13.8 Hz, 1H), 2.10-2.01 (m, 1H), 2.00-1.91 (m, 1H), 1.89-1.83 (m, 1H), 1.74 (tt, J=11.7, 7.6 Hz, 1H).

Compounds in Table 20 below were prepared from common Intermediates I-16, I-21 or from compounds listed in Table 5 and 7 described above using the methods described in Example 13-1.

TABLE 20

| Ex. No. | Structure | Name | Exact Mass [M + H]+ |
|---|---|---|---|
| 13.2 | 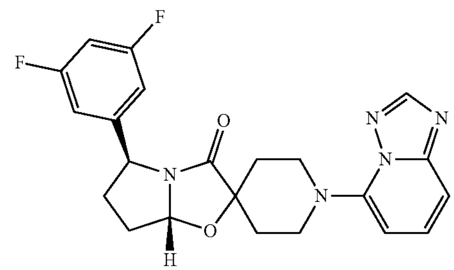 [SMILES: O=C1N2[C@@H](CC[C@H]2c2cc(F)cc(F)c2)OC12CCN(c1cccc3ncnn13)CC2] | (5'S,7a'R)-1-([1,2,4]triazolo[1,5-a]pyridin-5-yl)-5'-(3,5-difluorophenyl)tetrahydro-3'H-spiro[piperidine-4,2'-pyrrolo[2,1-b]oxazol]-3'-one, TFA salt | Calc'd 426, found 426 |
| 13.3 | 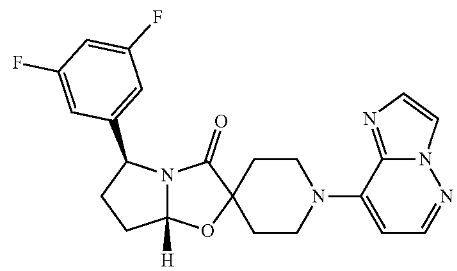 [SMILES: O=C1N2[C@@H](CC[C@H]2c2cc(F)cc(F)c2)OC12CCN(c1ccnn3ccnc13)CC2] | (5'S,7a'R)-5'-(3,5-difluorophenyl)-1-(imidazo[1,2-b]pyridazin-8-yl)tetrahydro-3'H-spiro[piperidine-4,2'-pyrrolo[2,1-b]oxazol]-3'-one, TFA salt | Calc'd 426, found 426 |
| 13.4 | 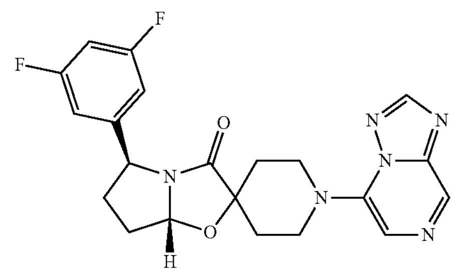 [SMILES: O=C1N2[C@@H](CC[C@H]2c2cc(F)cc(F)c2)OC12CCN(c1cncc3ncnn13)CC2] | (5'S,7a'R)-1-([1,2,4]triazolo[1,5-a]pyrazin-5-yl)-5'-(3,5-difluorophenyl)tetrahydro-3'H-spiro[piperidine-4,2'-pyrrolo[2,1-b]oxazol]-3'-one, TFA salt | Calc'd 427, found 427 |
| 13.5 | 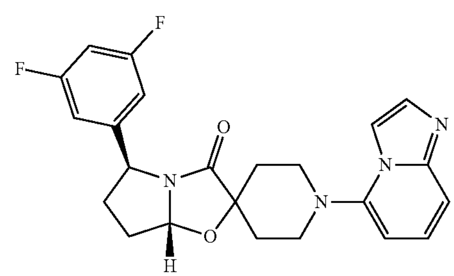 [SMILES: O=C1N2[C@@H](CC[C@H]2c2cc(F)cc(F)c2)OC12CCN(c1cccc3nccn13)CC2] | (5'S,7a'R)-5'-(3,5-difluorophenyl)-1-(imidazo[1,2-a]pyridin-5-yl)tetrahydro-3'H-spiro[piperidine-4,2'-pyrrolo[2,1-b]oxazol]-3'-one, TFA salt | Calc'd 425, found 425 |
| 13.6 | 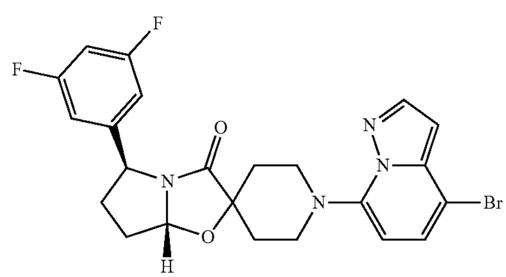 [SMILES: O=C1N2[C@@H](CC[C@H]2c2cc(F)cc(F)c2)OC12CCN(c1ccc(Br)c3ccnn13)CC2] | (5'S,7a'R)-1-(4-bromopyrazolo[1,5-a]pyridin-7-yl)-5'-(3,5-difluorophenyl)tetrahydro-3'H-spiro[piperidine-4,2'-pyrrolo[2,1-b]oxazol]-3'-one, TFA salt | Calc'd 503, found 503, 505 |

TABLE 20-continued

| Ex. No. | Structure | Name | Exact Mass [M + H]+ |
|---|---|---|---|
| 13.7 | 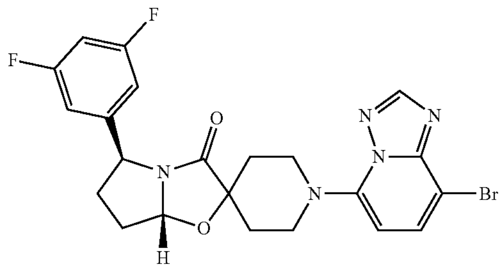 [SMILES: O=C1N2[C@@H](CC[C@H]2c2cc(F)cc(F)c2)OC12CCN(c1ccc(Br)c3ncnn13)CC2] | (5'S,7a'R)-1-(8-bromo-[1,2,4]triazolo[1,5-a]pyridin-5-yl)-5'-(3,5-difluorophenyl)tetrahydro-3'H-spiro[piperidine-4,2'-pyrrolo[2,1-b]oxazol]-3'-one | Calc'd 504, found 504, 506 |
| 13.8 | 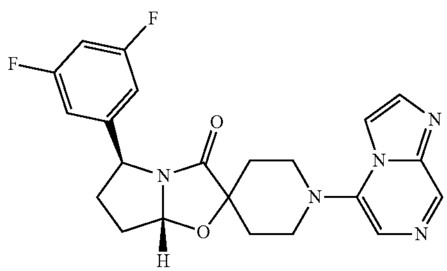 [SMILES: O=C1N2[C@@H](CC[C@H]2c2cc(F)cc(F)c2)OC12CCN(c1cncc3nccn13)CC2] | (5'S,7a'R)-5'-(3,5-difluorophenyl)-1-(imidazo[1,2-a]pyrazin-5-yl)tetrahydro-3'H-spiro[piperidine-4,2'-pyrrolo[2,1-b]oxazol]-3'-one, TFA salt | Calc'd 426, found 426 |
| 13.9 | 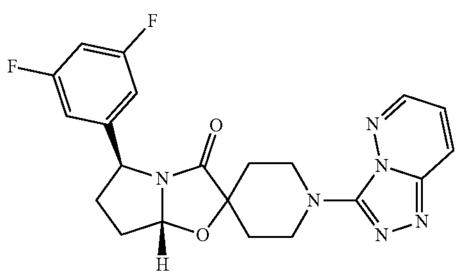 [SMILES: O=C1N2[C@@H](CC[C@H]2c2cc(F)cc(F)c2)OC12CCN(c1nnc3cccnn13)CC2] | (5'S,7a'R)-1-([1,2,4]triazolo[4,3-b]pyridazin-3-yl)-5'-(3,5-difluorophenyl)tetrahydro-3'H-spiro[piperidine-4,2'-pyrrolo[2,1-b]oxazol]-3'-one, TFA salt | Calc'd 427, found 427 |
| 13.10 | 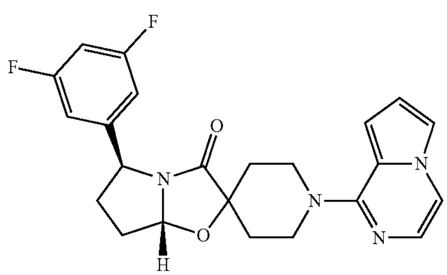 [SMILES: O=C1N2[C@@H](CC[C@H]2c2cc(F)cc(F)c2)OC12CCN(c1nccn3cccc13)CC2] | (5'S,7a'R)-5'-(3,5-difluorophenyl)-1-(pyrrolo[1,2-a]pyrazin-1-yl)tetrahydro-3'H-spiro[piperidine-4,2'-pyrrolo[2,1-b]oxazol]-3'-one | Calc'd 425, found 425 |
| 13.11 | 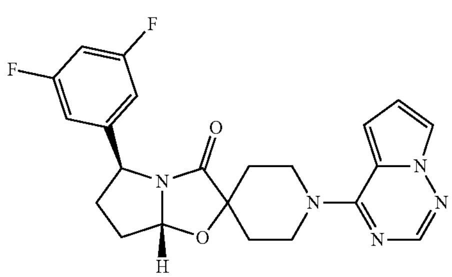 [SMILES: O=C1N2[C@@H](CC[C@H]2c2cc(F)cc(F)c2)OC12CCN(c1ncnn3cccc13)CC2] | (5'S,7a'R)-5'-(3,5-difluorophenyl)-1-(pyrrolo[2,1-f][1,2,4]triazin-4-yl)tetrahydro-3'H-spiro[piperidine-4,2'-pyrrolo[2,1-b]oxazol]-3'-one, TFA salt | Calc'd 426, found 426 |

TABLE 20-continued

| Ex. No. | Structure | Name | Exact Mass [M + H]+ |
|---|---|---|---|
| 13.12 | 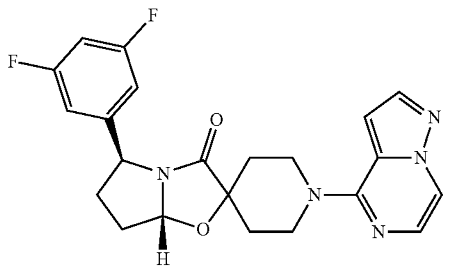 [SMILES: O=C1N2[C@@H](CC[C@H]2c2cc(F)cc(F)c2)OC12CCN(c1nccn3nccc13)CC2] | (5'S,7a'R)-5'-(3,5-difluorophenyl)-1-(pyrazolo[1,5-a]pyrazin-4-yl)tetrahydro-3'H-spiro[piperidine-4,2'-pyrrolo[2,1-b]oxazol]-3'-one, TFA salt | Calc'd 426, found 426 |
| 13.13 | 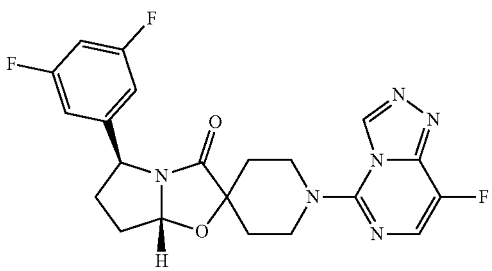 [SMILES: O=C1N2[C@@H](CC[C@H]2c2cc(F)cc(F)c2)OC12CCN(c1ncc(F)c3nncn13)CC2] | (5'S,7a'R)-5'-(3,5-difluorophenyl)-1-(8-fluoro-[1,2,4]triazolo[4,3-c]pyrimidin-5-yl)tetrahydro-3'H-spiro[piperidine-4,2'-pyrrolo[2,1-b]oxazol]-3'-one, TFA salt | Calc'd 445, found 445 |
| 13.14 | 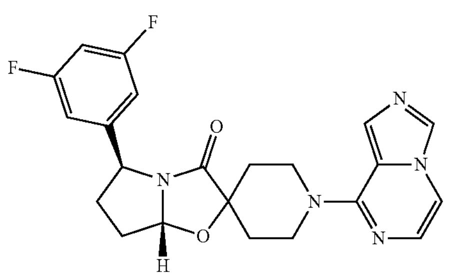 [SMILES: O=C1N2[C@@H](CC[C@H]2c2cc(F)cc(F)c2)OC12CCN(c1nccn3cncc13)CC2] | (5'S,7a'R)-5'-(3,5-difluorophenyl)-1-(imidazo[1,5-a]pyrazin-8-yl)tetrahydro-3'H-spiro[piperidine-4,2'-pyrrolo[2,1-b]oxazol]-3'-one, TFA salt | Calc'd 426, found 426 |
| 13.15 | 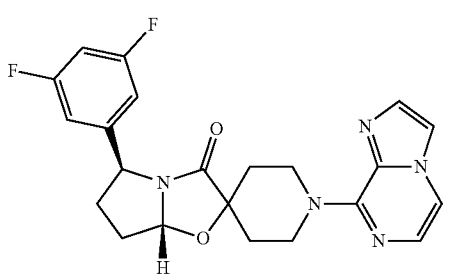 [SMILES: O=C1N2[C@@H](CC[C@H]2c2cc(F)cc(F)c2)OC12CCN(c1nccn3ccnc13)CC2] | (5'S,7a'R)-5'-(3,5-difluorophenyl)-1-(imidazo[1,2-a]pyrazin-8-yl)tetrahydro-3'H-spiro[piperidine-4,2'-pyrrolo[2,1-b]oxazol]-3'-one, TFA salt | Calc'd 426, found 426 |
| 13.16 | 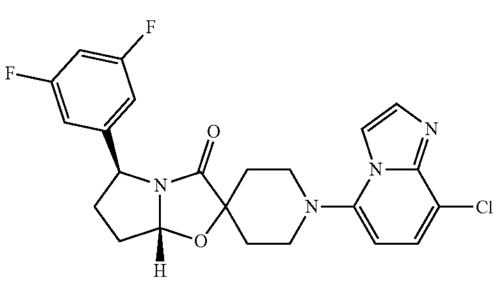 [SMILES: O=C1N2[C@@H](CC[C@H]2c2cc(F)cc(F)c2)OC12CCN(c1ccc(Cl)c3nccn13)CC2] | (5'S,7a'R)-1-(8-chloroimidazo[1,2-a]pyridin-5-yl)-5'-(3,5-difluorophenyl)tetrahydro-3'H-spiro[piperidine-4,2'-pyrrolo[2,1-b]oxazol]-3'-one, TFA salt | Calc'd 459, found 459 |

TABLE 20-continued

| Ex. No. | Structure | Name | Exact Mass [M + H]+ |
|---|---|---|---|
| 13.17 | 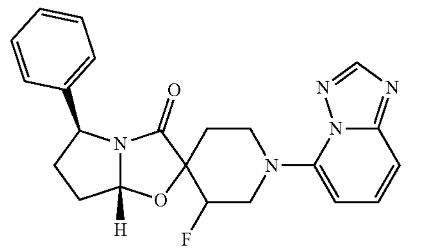 [SMILES: O=C1N2[C@@H](CC[C@H]2c2ccccc2)OC12CCN(c1cccc3ncnn13)CC2F] | (3[R or S], 4[S or R], 5'S,7a'R)-1-([1,2,4]triazolo[1,5-a]pyridin-5-yl)-3-fluoro-5'-phenyltetrahydro-3'H-spiro[piperidine-4,2'-pyrrolo[2,1-b]oxazol]-3'-one, TFA salt | Calc'd 408, found 408 |
| 13.18 | 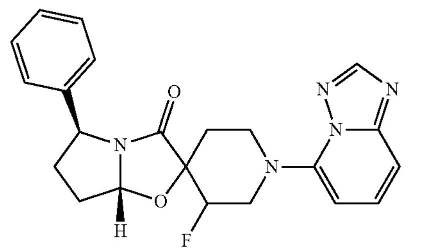 [SMILES: O=C1N2[C@@H](CC[C@H]2c2ccccc2)OC12CCN(c1cccc3ncnn13)CC2F] | (3[S or R], 4 [R or S], 5'S,7a'R)-1-([1,2,4]triazolo[1,5-a]pyridin-5-yl)-3-fluoro-5'-phenyltetrahydro-3'H-spiro[piperidine-4,2'-pyrrolo[2,1-b]oxazol]-3'-one, TFA salt | Calc'd 408, found 408 |
| 13.19 | 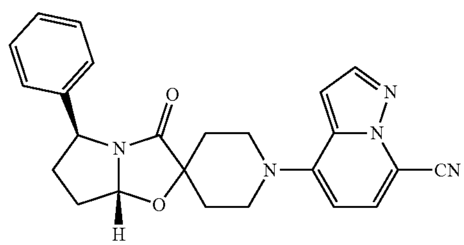 [SMILES: N#Cc1ccc(N2CCC3(CC2)O[C@@H]2CC[C@@H](c4ccccc4)N2C3=O)c2ccnn12] | 4-((5'S,7a'R)-3'-oxo-5'-phenyltetrahydro-3'H-spiro[piperidine-4,2'-pyrrolo[2,1-b]oxazol]-1-yl)pyrazolo[1,5-a]pyridine-7-carbonitrile, TFA salt | Calc'd 414, found 414 |
| 13.20 | 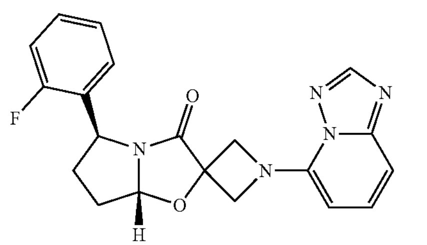 [SMILES: O=C1N2[C@@H](CC[C@H]2c2ccccc2F)OC12CN(c1cccc3ncnn13)C2] | (5'S,7a'R)-1-([1,2,4]triazolo[1,5-a]pyridin-5-yl)-5'-(2-fluorophenyl)tetrahydro-3'H-spiro[azetidine-3,2'-pyrrolo[2,1-b]oxazol]-3'-one, TFA salt | Calc'd 380, found 380 |
| 13.21 | 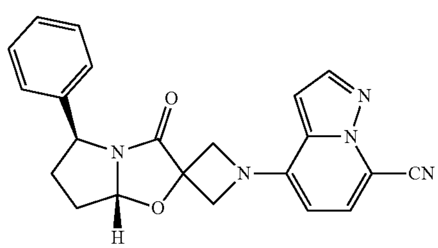 [SMILES: N#Cc1ccc(N2CC3(C2)O[C@@H]2CC[C@@H](c4ccccc4)N2C3=O)c2ccnn12] | 4-((5'S,7a'R)-3'-oxo-5'-phenyltetrahydro-3'H-spiro[azetidine-3,2'-pyrrolo[2,1-b]oxazol]-1-yl)pyrazolo[1,5-a]pyridine-7-carbonitrile, TFA salt | Calc'd 386, found 386 |
| 13.22 | 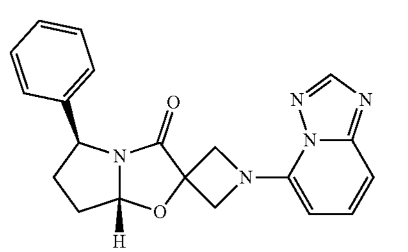 [SMILES: O=C1N2[C@@H](CC[C@H]2c2ccccc2)OC12CN(c1cccc3ncnn13)C2] | (5'S,7a'R)-1-([1,2,4]triazolo[1,5-a]pyridin-5-yl)-5'-phenyltetrahydro-3'H-spiro[azetidine-3,2'-pyrrolo[2,1-b]oxazol]-3'-one, TFA salt | Calc'd 362, found 362 |

TABLE 20-continued

| Ex. No. | Structure | Name | Exact Mass [M + H]+ |
|---|---|---|---|
| 13.23 | 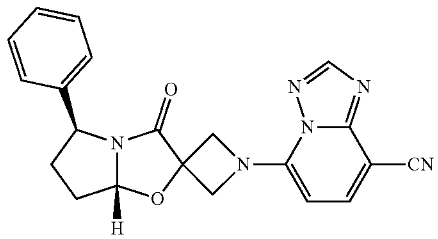 [SMILES: N#Cc1ccc(N2CC3(C2)O[C@@H]2CC[C@@H](c4ccccc4)N2C3=O)n2ncnc12] | 5-((5'S,7a'R)-3'-oxo-5'-phenyltetrahydro-3'H-spiro[azetidine-3,2'-pyrrolo[2,1-b]oxazol]-1-yl)-[1,2,4]triazolo[1,5-a]pyridine-8-carbonitrile, TFA salt | Calc'd 387, found 387 |
| 13.24 | 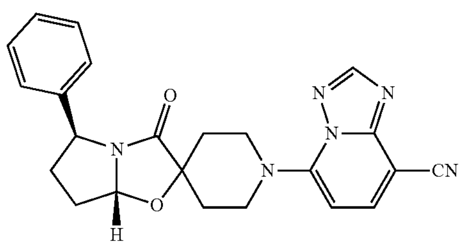 [SMILES: N#Cc1ccc(N2CCC3(CC2)O[C@@H]2CC[C@@H](c4ccccc4)N2C3=O)n2ncnc12] | 5-((5'S,7a'R)-3'-oxo-5'-phenyltetrahydro-3'H-spiro[piperidine-4,2'-pyrrolo[2,1-b]oxazol]-1-yl)-[1,2,4]triazolo[1,5-a]pyridine-8-carbonitrile, TFA salt | Calc'd 415, found 415 |

Example 14.1

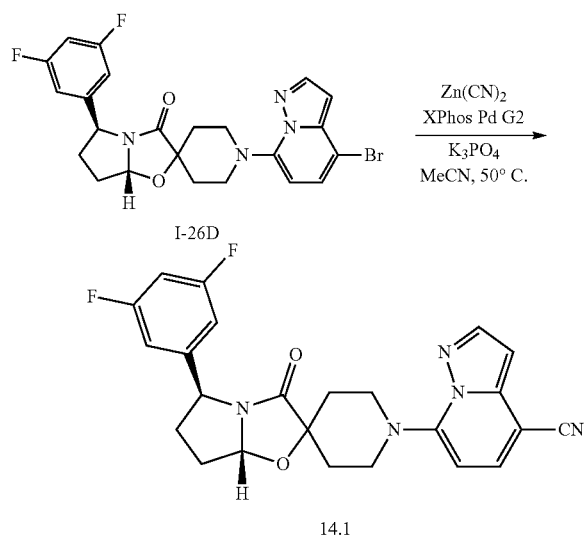

7-((5'S,7a'R)-5'-(3,5-difluorophenyl)-3'-oxotetrahydro-3'H-spiro [piperidine-4,2'-pyrrolo [2,1-b]oxazol]-1-yl)pyrazolo[1,5-a]pyridine-4-carbonitrile, TFA A 2 mL Biotage® microwave vial equipped with a stir bar was charged with (5'S,7a'R)-1-(4-bromopyrazolo [1,5-a]pyridin-7-yl)-5'-(3,5-difluorophenyl)tetrahydro-3'H-spiro [piperidine-4,2'-pyrrolo[2,1-b]oxazol]-3'-one I-26D (25 mg, 0.050 mmol), 2nd generation Xphos Pd precatalyst (3.9 mg, 0.005 mmol), Zn(CN)$_2$ (8.8 mg, 0.075 mmol) and K$_3$PO$_4$ (15.8 mg, 0.075 mmol). The vial was evacuated and backfilled with nitrogen (3×). A sample of MeCN (0.5 mL) was purged with argon for 15 min with sonication, then added to the reaction vial. The resulting suspension was then stirred at 50° C. for 16 h. After cooling, the reaction was quenched with 1 M NaOH (3 mL) and DCM (3 mL). The layers were separated, and the aqueous layer was extracted with DCM (3 mL, ×3). The combined organic layers were dried (MgSO4), filtered and concentrated under reduced pressure. The crude residue was taken up in DMSO (2 mL), filtered and purified via reversed phase HPLC [TFA method]. This provided 7-((5'S,7a'R)-5'-(3,5-difluorophenyl)-3'-oxotetrahydro-3'H-spiro[piperidine-4,2'-pyrrolo[2,1-b]oxazol]-1-yl)pyrazolo [1,5-a]pyridine-4-carbonitrile, TFA salt. MS (ESI) m/z C$_{24}$H$_{22}$F$_2$N$_5$O$_2$[M+1]$^+$ calc'd 450, found 450. $^1$H NMR (600 MHz, DMSO-d$_6$) δ 8.22 (d, J=2.3 Hz, 1H), 7.87 (d, J=8.0 Hz, 1H), 7.16-7.11 (m, 1H), 7.09 (d, J=6.5 Hz, 2H), 6.75 (d, J=2.3 Hz, 1H), 6.49 (d, J=8.0 Hz, 1H), 5.84 (dd, J=7.2, 5.0 Hz, 1H), 4.96 (t, J=7.8 Hz, 1H), 4.21 (d, J=12.6 Hz, 1H), 4.11 (d, J=12.0 Hz, 1H), 3.41 (t, J=10.6 Hz, 1H), 3.32-3.25 (m, 1H), 2.70-2.60 (m, 1H), 2.24-2.11 (m, 3H), 2.02-1.94 (m, 1H), 1.88 (ddd, J=19.8, 12.4, 7.1 Hz, 1H), 1.81 (d, J=13.5 Hz, 1H), 1.74-1.64 (m, 1H).

Compounds in Table 21 below were prepared from common Intermediates listed in Table 10 using the methods described in Example 14.1. Example 14.3 was prepared using a modified procedure wherein the reaction was stirred at 70° C. for 3 days.

TABLE 21
| Ex. No. | Structure | Name | Exact Mass [M + H]+ |
|---|---|---|---|
| 14.2 | 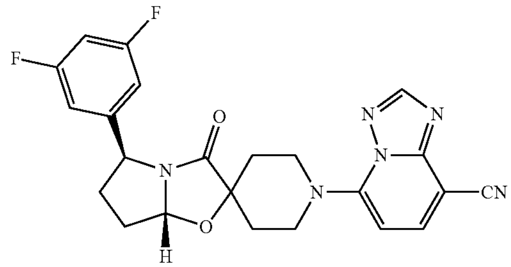 [SMILES: N#Cc1ccc(N2CCC3(CC2)O[C@@H]2CC[C@@H](c4cc(F)cc(F)c4)N2C3=O)n2ncnc12] | 5-((5'S,7a'R)-5'-(3,5-difluorophenyl)-3'-oxotetrahydro-3'H-spiro[piperidine-4,2'-pyrrolo[2,1-b]oxazol]-1-yl)-[1,2,4]triazolo[1,5-a]pyridine-8-carbonitrile, TFA salt | Calc'd 451, found 451 |
| 14.3 | 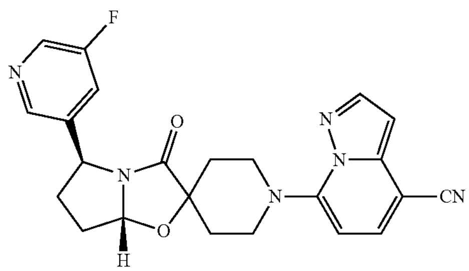 [SMILES: N#Cc1ccc(N2CCC3(CC2)O[C@@H]2CC[C@@H](c4cncc(F)c4)N2C3=O)n2nccc12] | 7-((5'S,7a'R)-5'-(5-fluoropyridin-3-yl)-3'-oxotetrahydro-3'H-spiro[piperidine-4,2'-pyrrolo[2,1-b]oxazol]-1-yl)pyrazolo[1,5-a]pyridine-4-carbonitrile | Calc'd 433, found 433 |
Example 15.1, 15.2
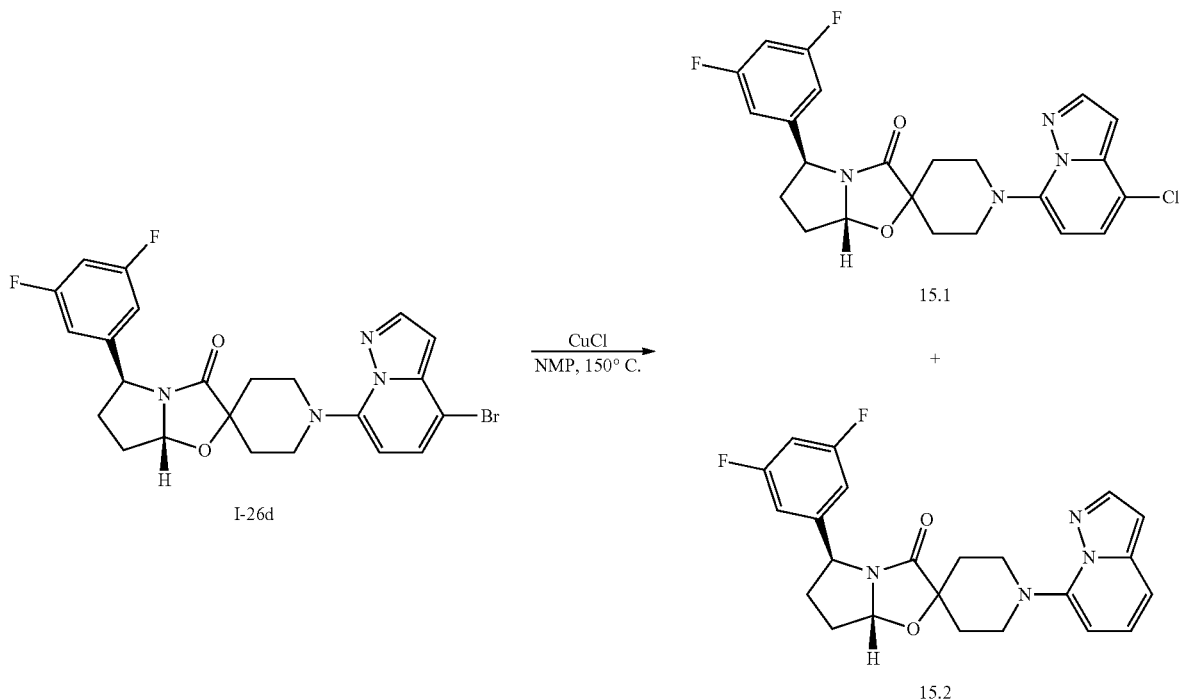 [SMILES: O=C1N2[C@@H](CC[C@H]2c2cc(F)cc(F)c2)OC12CCN(c1ccc(Br)c3ccnn13)CC2 ; "CuCl" ; O=C1N2[C@@H](CC[C@H]2c2cc(F)cc(F)c2)OC12CCN(c1ccc(Cl)c3ccnn13)CC2 ; O=C1N2[C@@H](CC[C@H]2c2cc(F)cc(F)c2)OC12CCN(c1cccc3ccnn13)CC2]

(5'S,7a'R)-1-(4-chloropyrazolo[1,5-a]pyridin-7-yl)-5'-(3,5-difluorophenyl)tetrahydro-3'H-spiro[piperidine-4,2'-pyrrolo[2,1-b]oxazol]-3'-one, TFA (Ex. 15.1) and (5'S,7a'R)-5'-(3,5-difluorophenyl)-1-(pyrazolo[1,5-a]pyridin-7-yl)tetrahydro-3'H-spiro[piperidine-4,2'-pyrrolo[2,1-b]oxazol]-3'-one, TFA (Ex. 15.2)

A 2 mL Biotage® microwave vial equipped with a stir bar was charged with (5'S,7a'R)-1-(4-bromopyrazolo[1,5-a]pyridin-7-yl)-5'-(3,5-difluorophenyl)tetrahydro-3'H-spiro[piperidine-4,2'-pyrrolo[2,1-b]oxazol]-3'-one I-26d (20 mg, 0.040 mmol), CuCl (11.8 mg, 0.119 mmol), and NMP (0.5 mL). The resulting reaction mixture was then stirred at 150° C. under microwave irradiation for 90 min. The reaction was quenched with water (3 mL) and DCM (3 mL). The layers were separated, and the aqueous layer was extracted (3 mL, ×2). The combined organic layers were dried (MgSO4), filtered through Celite®, and concentrated under reduced pressure. The crude residue was taken up in DMSO (2 mL), filtered and purified via reversed phase HPLC [TFA method]. This provided (5'S,7a'R)-1-(4-chloropyrazolo[1,5-a]pyridin-7-yl)-5'-(3,5-difluorophenyl)tetrahydro-3'H-spiro[piperidine-4,2'-pyrrolo[2,1-b]oxazol]-3'-one, TFA salt and (5'S,7a'R)-5'-(3,5-difluorophenyl)-1-(pyrazolo[1,5-a]pyridin-7-yl)tetrahydro-3'H-spiro[piperidine-4,2'-pyrrolo[2,1-b]oxazol]-3'-one, TFA salt. Ex 15.1: MS (ESI) m/z $C_{23}H_{22}ClF_2N_4O_2$ [M+1]+ calc'd 459, found 459. $^1$H NMR (600 MHz, DMSO-$d_6$) δ 8.12 (d, J=2.1 Hz, 1H), 7.35 (d, J=8.0 Hz, 1H), 7.14 (t, J=9.2 Hz, 1H), 7.09 (d, J=6.6 Hz, 2H), 6.69 (d, J=2.2 Hz, 1H), 6.38 (d, J=8.0 Hz, 1H), 5.83 (dd, J=7.0, 5.2 Hz, 1H), 4.96 (app t, J=7.8 Hz, 1H), 3.89 (d, J=11.5 Hz, 1H), 3.81 (d, J=11.6 Hz, 1H), 3.19 (app, J=10.2 Hz, 1H), 3.07 (app t, J=10.5 Hz, 1H), 2.67-2.59 (m, 1H), 2.23-2.11 (m, 3H), 2.01-1.93 (m, 1H), 1.87 (td, J=13.2, 12.6, 6.6 Hz, 1H), 1.79 (d, J=12.9 Hz, 1H), 1.73-1.64 (m, 1H). Ex. 15.2: MS (ESI) m/z $C_{23}H_{23}F_2N_4O_2$ [M+1]+ calc'd 425, found 425. $^1$H NMR (600 MHz, DMSO-$d_6$) δ 8.01 (d, J=2.2 Hz, 1H), 7.35 (d, J=8.0 Hz, 1H), 7.19-7.16 (m, 1H), 7.16-7.11 (m, 1H), 7.09 (d, J=6.7 Hz, 2H), 6.60 (d, J=2.2 Hz, 1H), 6.36 (d, J=6.8 Hz, 1H), 5.83 (dd, J=7.1, 5.1 Hz, 1H), 4.96 (t, J=7.6 Hz, 1H), 3.94-3.88 (m, 1H), 3.86-3.79 (m, 1H), 3.20-3.13 (m, 1H), 3.07-3.01 (m, 1H), 2.68-2.61 (m, 1H), 2.25-2.13 (m, 3H), 2.01-1.95 (m, 1H), 1.91-1.84 (m, 1H), 1.79 (d, J=15.4 Hz, 1H), 1.74-1.64 (m, 1H).

Compounds in Table 22 below were prepared from common Intermediates listed in Table 10 using the methods described in Example 15.1

TABLE 22

| Ex. No. | Structure | Name | Exact Mass [M + H]+ |
| --- | --- | --- | --- |
| 15.3 | 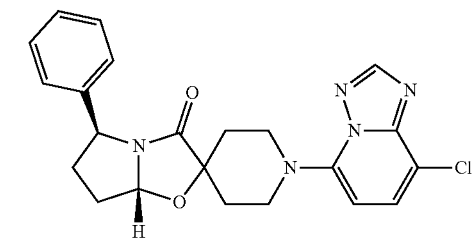 | (5'S,7a'R)-1-(8-chloro-[1,2,4]triazolo[1,5-a]pyridin-5-yl)-5'-phenyltetrahydro-3'H-spiro[piperidine-4,2'-pyrrolo[2,1-b]oxazol]-3'-one, TFA salt | Calc'd 424, found 424 |
| 15.4 | 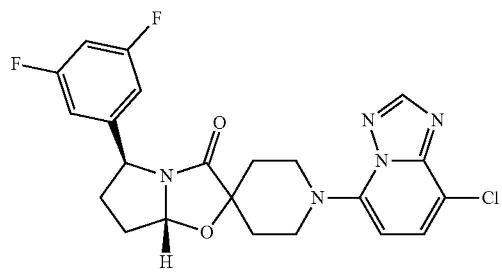 [SMILES: O=C1N2[C@@H](CC[C@H]2c2cc(F)cc(F)c2)OC12CCN(c1ccc(Cl)c3ncnn13)CC2] | (5'S,7a'R)-1-(8-chloro-[1,2,4]triazolo[1,5-a]pyridin-5-yl)-5'-(3,5-difluorophenyl)tetrahydro-3'H-spiro[piperidine-4,2'-pyrrolo[2,1-b]oxazol]-3'-one, TFA salt | Calc'd 460, found 460 |

Example 16.1

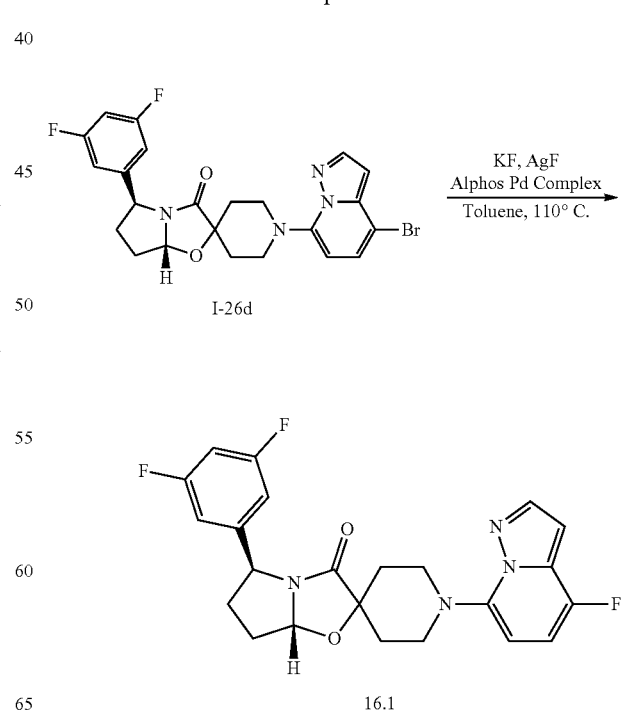

(5'S,7a'R)-5'-(3,5-difluorophenyl)-1-(4-fluoropyrazolo[1,5-a]pyridin-7-yl)tetrahydro-3'H-spiro[piperidine-4,2'-pyrrolo[2,1-b]oxazol]-3'-one, TFA salt A 2 mL Biotage® microwave vial equipped with a stir bar was charged with (5'S,7a'R)-1-(4-bromopyrazolo[1,5-a]pyridin-7-yl)-5'-(3,5-difluorophenyl)tetrahydro-3'H-spiro[piperidine-4,2'-pyrrolo[2,1-b]oxazol]-3'-one I-26d (10 mg, 0.020 mmol) and Alphos Pd Complex (2.3 mg, 0.001 mmol). The vial was then taken into a glovebox, KF (0.6 mg, 0.010 mmol) and silver(I) fluoride (5 mg, 0.040 mmol) were added to the vial. Toluene (0.3 mL) was then added and the reaction vial was sealed, removed from the glovebox, and stirred at 110° C. for 16 h. After cooling, the reaction was partitioned with DCM (3 mL), saturated aqueous $NaHCO_3$ (2 mL) and water (2 mL), then extracted with DCM (4 mL, ×2). The combined organic layers were dried ($MgSO_4$), filtered and concentrated under reduced pressure. The crude residue was taken up in DMSO (2 mL), filtered and purified via reversed phase HPLC [TFA method]. This provided (5'S,7a'R)-5'-(3,5-difluorophenyl)-1-(4-fluoropyrazolo[1,5-a]pyridin-7-yl)tetrahydro-3'H-spiro[piperidine-4,2'-pyrrolo[2,1-b]oxazol]-3'-one, TFA salt. MS (ESI) m/z $C_{23}H_{22}F_3N_4O_2$ [M+1]+ calc'd 443, found 443. $^1$H NMR (600 MHz, DMSO-$d_6$) δ 8.10 (d, J=2.2 Hz, 1H), 7.18-7.05 (m, 4H), 6.77 (d, J=2.2 Hz, 1H), 6.31 (dd, J=8.2, 4.5 Hz, 1H), 5.83 (dd, J=7.0, 5.1 Hz, 1H), 4.96 (app t, J=7.8 Hz, 2H), 3.80 (d, J=11.5 Hz, 1H), 3.72 (d, J=11.4 Hz, 1H), 3.17-3.10 (m, 1H), 3.05-2.98 (m, 1H), 2.68-2.60 (m, 1H), 2.23-2.12 (m, 3H), 2.01-1.94 (m, 1H), 1.87 (dt, J=13.4, 6.6 Hz, 1H), 1.79 (d, J=12.4 Hz, 1H), 1.72-1.63 (m, 1H).

Example 17.1

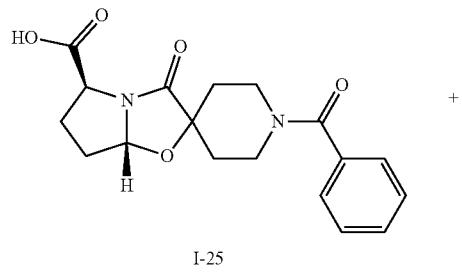

I-25

+

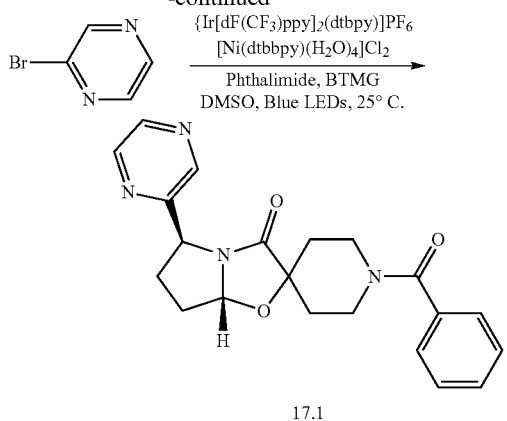

(5'S,7a'R)-1-benzoyl-5'-(pyrazin-2-yl)tetrahydro-3'H-spiro[piperidine-4,2'-pyrrolo[2,1-b]oxazol]-3'-one, TFA A scintillation vial was charged with (5'S,7a'R)-1-benzoyl-3'-oxotetrahydro-3'H-spiro[piperidine-4,2'-pyrrolo[2,1-b]oxazole]-5'-carboxylic acid I-25 (15 mg, 0.044 mmol), 2-bromopyrazine (10.4 mg, 0.065 mmol), phthalimide (6.4 mg, 0.044 mmol), [Ni(dtbbpy)(H$_2$O)$_4$]Cl$_2$ (3.5 mg, 0.009 mmol), 2-tert-Butyl-1,1,3,3-tetramethylguanidine (BTMG) (14.9 mg, 0.087 mmol) and {Ir[dF(CF$_3$)ppy]$_2$(dtbpy)}PF$_6$ (1.0 mg, 0.009 mmol). The vial was evacuated and back-filled with nitrogen (3×), DMSO (1.1 mL) was added, and the reaction mixture was purged with argon for 15 min. The reaction was then irradiated with 450 nm LED light in a PennOC/Merck photoreactor (500 rpm stirring, 1000 rpm fan speed, 100% LED power) at 25° C. for 14 h. The reaction mixture was directly filtered and purified via reversed phase HPLC [TFA method]. This provided (5'S,7a'R)-1-benzoyl-5'-(pyrazin-2-yl)tetrahydro-3'H-spiro[piperidine-4,2'-pyrrolo[2,1-b]oxazol]-3'-one, TFA salt. MS (ESI) m/z $C_{21}H_{23}N_4O_3$ [M+1]+ calc'd 379, found 379. $^1$H NMR (600 MHz, DMSO-$d_6$) δ 8.70 (s, 1H), 8.63 (s, 1H), 8.60 (s, 1H), 7.48-7.38 (m, 5H), 5.84-5.71 (m, 1H), 5.06 (app t, J=7.6 Hz, 1H), 4.42-4.19 (m, 2H), 3.68-3.43 (m, 2H), 3.26-3.16 (m, 1H), 2.64-2.44 (m, 2H), 2.30-2.22 (m, 1H), 2.15-2.04 (m, 1H), 1.98-1.83 (m, 1H), 1.80-1.65 (m, 2H).

Compounds in Table 23 below were prepared from common intermediate I-25, using the methods described in Example 17.1.

TABLE 23

| Ex. No. | Structure | Name | Exact Mass [M + H]+ |
|---|---|---|---|
| 17.2 | ![structure] | (5'S,7a'R)-5'-(benzo[b]thiophen-5-yl)-1-benzoyltetrahydro-3'H-spiro[piperidine-4,2'-pyrrolo[2,1-b]oxazol]-3'-one | Calc'd 433, found 433 |

TABLE 23-continued

| Ex. No. | Structure | Name | Exact Mass [M + H]+ |
|---|---|---|---|
| 17.3 | 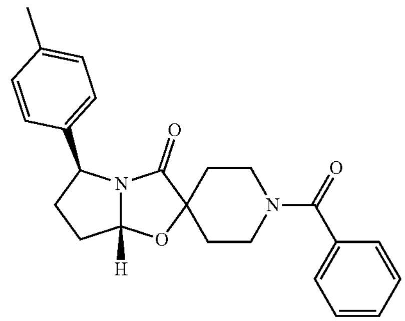 [SMILES: Cc1ccc([C@@H]2CC[C@H]3OC4(CCN(C(=O)c5ccccc5)CC4)C(=O)N32)cc1] | (5'S,7a'R)-1-benzoyl-5'-(p-tolyl)tetrahydro-3'H-spiro[piperidine-4,2'-pyrrolo[2,1-b]oxazol]-3'-one | Calc'd 391, found 391 |
| 17.4 | 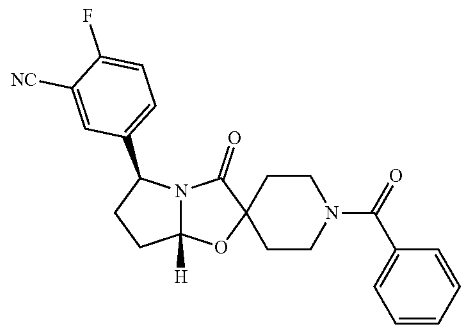 [SMILES: N#Cc1cc([C@@H]2CC[C@H]3OC4(CCN(C(=O)c5ccccc5)CC4)C(=O)N32)ccc1F] | 5-((5'S,7a'R)-1-benzoyl-3'-oxotetrahydro-3'H-spiro[piperidine-4,2'-pyrrolo[2,1-b]oxazol]-5'-yl)-2-fluorobenzonitrile | Calc'd 420, found 420 |
| 17.5 | 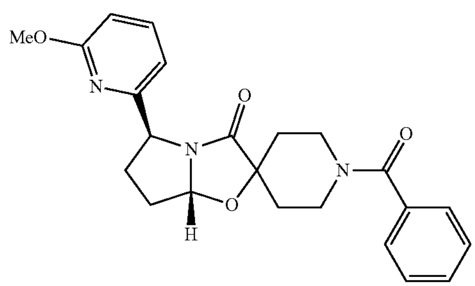 [SMILES: COc1cccc([C@@H]2CC[C@H]3OC4(CCN(C(=O)c5ccccc5)CC4)C(=O)N32)n1] | (5'S,7a'R)-1-benzoyl-5'-(6-methoxypyridin-2-yl)tetrahydro-3'H-spiro[piperidine-4,2'-pyrrolo[2,1-b]oxazol]-3'-one, TFA salt | Calc'd 408, found 408 |
| 17.6 | 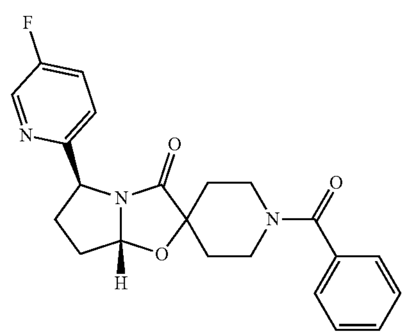 [SMILES: O=C(c1ccccc1)N1CCC2(CC1)O[C@@H]1CC[C@@H](c3ccc(F)cn3)N1C2=O] | (5'S,7a'R)-1-benzoyl-5'-(5-fluoropyridin-2-yl)tetrahydro-3'H-spiro[piperidine-4,2'-pyrrolo[2,1-b]oxazol]-40'-one, TFA salt | Calc'd 396, found 396 |
| 17.7 | 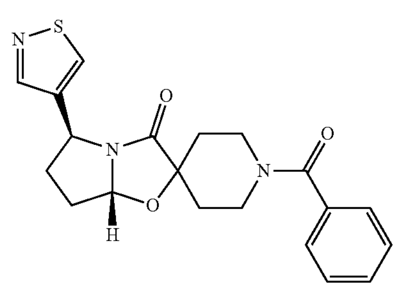 [SMILES: O=C(c1ccccc1)N1CCC2(CC1)O[C@@H]1CC[C@@H](c3cnsc3)N1C2=O] | (5'S,7a'R)-1-benzoyl-5'-(isothiazol-4-yl)tetrahydro-3'H-spiro[piperidine-4,2'-pyrrolo[2,1-b]oxazol]-3'-one | Calc'd 384, found 384 |

TABLE 23-continued

| Ex. No. | Structure | Name | Exact Mass [M + H]+ |
| --- | --- | --- | --- |
| 17.8 | 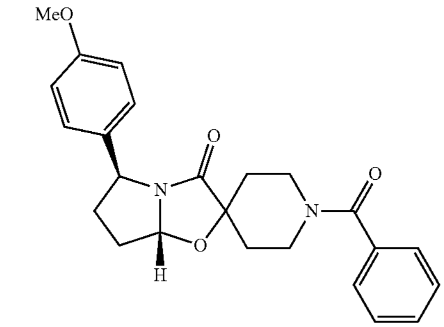 [SMILES: COc1ccc([C@@H]2CC[C@H]3OC4(CCN(C(=O)c5ccccc5)CC4)C(=O)N32)cc1] | (5'S,7a'R)-1-benzoyl-5'-(4-methoxyphenyl)tetrahydro-3'H-spiro[piperidine-4,2'-pyrrolo[2,1-b]oxazol]-3'-one | Calc'd 407, found 407 |
| 17.9 | 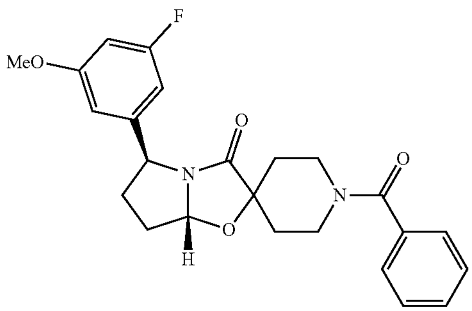 [SMILES: COc1cc(F)cc([C@@H]2CC[C@H]3OC4(CCN(C(=O)c5ccccc5)CC4)C(=O)N32)c1] | (5'S,7a'R)-1-benzoyl-5'-(3-fluoro-5-methoxyphenyl)tetrahydro-3'H-spiro[piperidine-4,2'-pyrrolo[2,1-b]oxazol]-3'-one | Calc'd 425, found 425 |
| 17.10 | 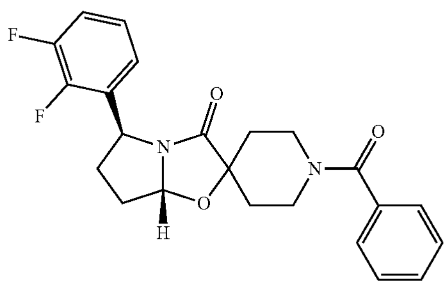 [SMILES: O=C(c1ccccc1)N1CCC2(CC1)O[C@@H]1CC[C@@H](c3cccc(F)c3F)N1C2=O] | (5'S,7a'R)-1-benzoyl-5'-(2,3-difluorophenyl)tetrahydro-3'H-spiro[piperidine-4,2'-pyrrolo[2,1-b]oxazol]-3'-one | Calc'd 413, found 413 |
| 17.11 | 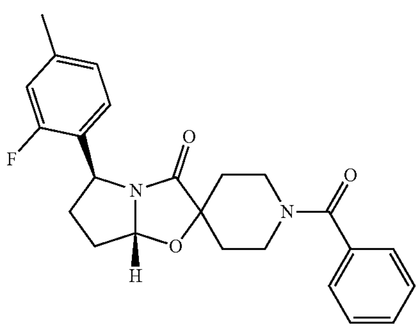 [SMILES: Cc1ccc([C@@H]2CC[C@H]3OC4(CCN(C(=O)c5ccccc5)CC4)C(=O)N32)c(F)c1] | (5'S,7a'R)-1-benzoyl-5'-(2-fluoro-4-methylphenyl)tetrahydro-3'H-spiro[piperidine-4,2'-pyrrolo[2,1-b]oxazol]-3'-one | Calc'd 409, found 409 |
| 17.12 | 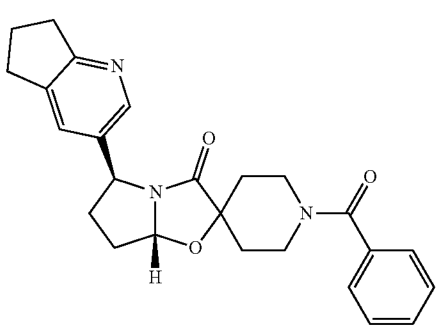 [SMILES: O=C(c1ccccc1)N1CCC2(CC1)O[C@@H]1CC[C@@H](c3cnc4c(c3)CCC4)N1C2=O] | (5'S,7a'R)-1-benzoyl-5'-(6,7-dihydro-5H-cyclopenta[b]pyridin-3-yl)tetrahydro-3'H-spiro[piperidine-4,2'-pyrrolo[2,1-b]oxazol]-3'-one | Calc'd 418, found 418 |

TABLE 23-continued

| Ex. No. | Structure | Name | Exact Mass [M + H]+ |
|---|---|---|---|
| 17.13 | 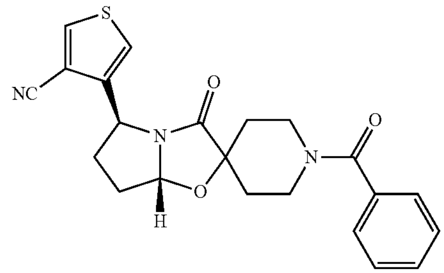 [SMILES: N#Cc1cscc1[C@@H]1CC[C@H]2OC3(CCN(C(=O)c4ccccc4)CC3)C(=O)N21] | 4-((5'S,7a'R)-1-benzoyl-3'-oxotetrahydro-3'H-spiro[piperidine-4,2'-pyrrolo[2,1-b]oxazol]-5'-yl)thiophene-3-carbonitrile | Calc'd 408, found 408 |
| 17.14 | 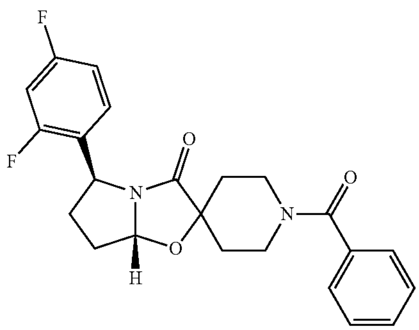 [SMILES: O=C(c1ccccc1)N1CCC2(CC1)O[C@@H]1CC[C@@H](c3ccc(F)cc3F)N1C2=O] | (5'S,7a'R)-1-(benzenecarbonyl)-5'-(2,4-difluorophenyl)tetrahydro-3'H-spiro[piperidine-4,2'-pyrrolo[2,1-b][1,3]oxazol]-3'-one | Calc'd 413, found 413 |
| 17.15 | 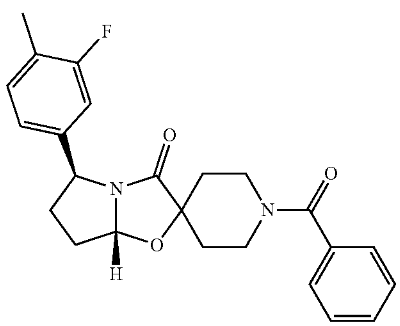 [SMILES: Cc1ccc([C@@H]2CC[C@H]3OC4(CCN(C(=O)c5ccccc5)CC4)C(=O)N32)cc1F] | (5'S,7a'R)-1-(benzenecarbonyl)-5'-(3-fluoro-4-methylphenyl)tetrahydro-3'H-spiro[piperidine-4,2'-pyrrolo[2,1-b][1,3]oxazol]-3'-one | Calc'd 409, found 409 |

Example 18.1

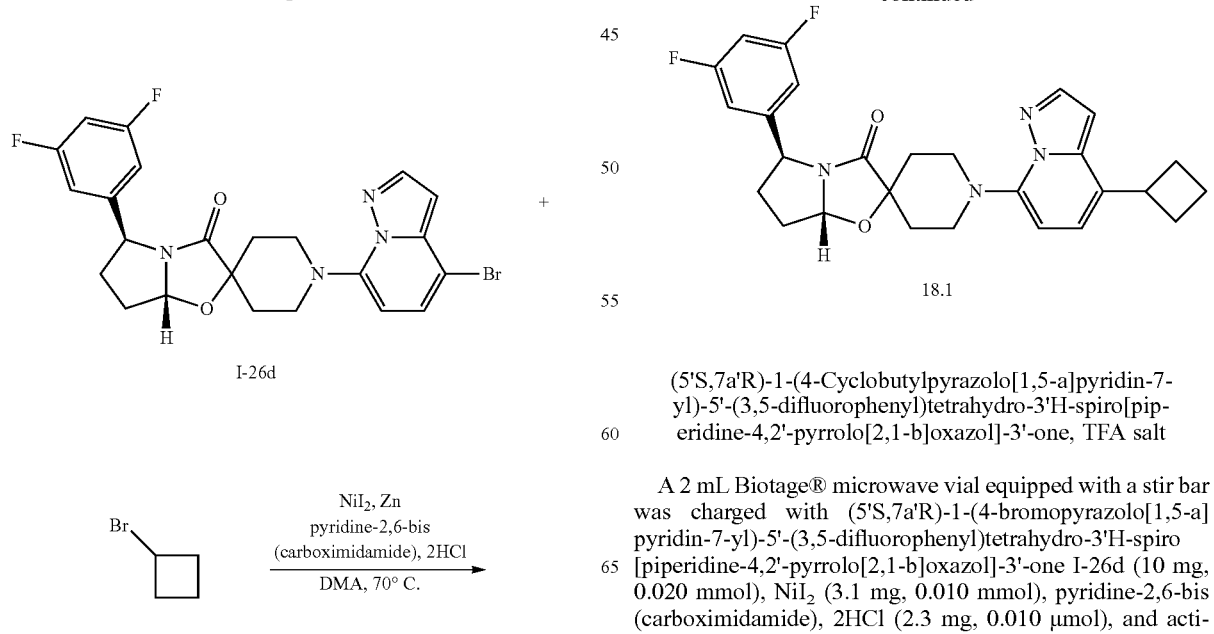

(5'S,7a'R)-1-(4-Cyclobutylpyrazolo[1,5-a]pyridin-7-yl)-5'-(3,5-difluorophenyl)tetrahydro-3'H-spiro[piperidine-4,2'-pyrrolo[2,1-b]oxazol]-3'-one, TFA salt A 2 mL Biotage® microwave vial equipped with a stir bar was charged with (5'S,7a'R)-1-(4-bromopyrazolo[1,5-a]pyridin-7-yl)-5'-(3,5-difluorophenyl)tetrahydro-3'H-spiro[piperidine-4,2'-pyrrolo[2,1-b]oxazol]-3'-one I-26d (10 mg, 0.020 mmol), NiI$_2$ (3.1 mg, 0.010 mmol), pyridine-2,6-bis(carboximidamide), 2HCl (2.3 mg, 0.010 μmol), and activated Zn powder (6.5 mg, 0.099 mmol) and bromocyclobutane (5.4 mg, 0.040 mmol). The vial was evacuated and backfilled with nitrogen (3×), DMA (0.25 mL) was added, and the reaction was stirred at 70° C. for 16 h. After cooling, the reaction was partitioned with DCM (3 mL) and water (3 mL), and then extracted with DCM (5 mL, ×2). The combined organic layers were dried (MgSO$_4$), filtered through Celite®, and concentrated under reduced pressure. The crude residue was taken up in DMSO (2 mL), filtered and purified via reversed phase HPLC [TFA method]. This provided (5'S,7a'R)-1-(4-cyclobutylpyrazolo[1,5-a]pyridin-7-yl)-5'-(3,5-difluorophenyl)tetrahydro-3'H-spiro[piperidine-4,2'-pyrrolo[2,1-b]oxazol]-3'-one, TFA salt. MS (ESI) m/z C$_{27}$H$_{29}$F$_2$N$_4$O$_2$ [M+1]$^+$ calc'd 479, found 479. $^1$H NMR (600 MHz, DMSO-d$_6$) δ 7.98 (d, J=2.1 Hz, 1H), 7.14 (t, J=9.2 Hz, 1H), 7.09 (d, J=6.6 Hz, 2H), 6.98 (d, J=7.6 Hz, 1H), 6.56 (d, J=2.1 Hz, 1H), 6.34 (d, J=7.5 Hz, 1H), 5.85-5.79 (m, 1H), 4.96 (app t, J=7.9 Hz, 2H), 3.84 (d, J=12.3 Hz, 1H), 3.75 (d, J=11.9 Hz, 1H), 3.74-3.67 (m, 1H), 3.13 (app t, J=10.2 Hz, 1H), 3.00 (app t, J=10.4 Hz, 1H), 2.68-2.59 (m, 1H), 2.43-2.34 (m, 2H), 2.24-2.10 (m, 5H), 2.10-2.00 (m, 1H), 2.00-1.94 (m, 1H), 1.92-1.83 (m, 2H), 1.78 (d, J=14.1 Hz, 1H), 1.68 (ddd, J=18.9, 11.6, 7.6 Hz, 1H).

Compounds in Table 24 below were prepared from intermediates listed in Table 10 using the methods described in Example 18.1.

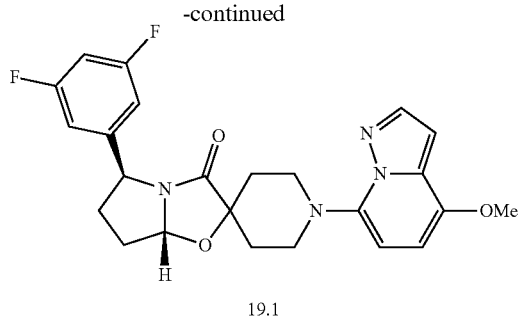

19.1

(5'S,7a'R)-5'-(3,5-Difluorophenyl)-1-(4-methoxypyrazolo[1,5-a]pyridin-7-yl)tetrahydro-3'H-spiro[piperidine-4,2'-pyrrolo[2,1-b]oxazol]-3'-one, TFA A 2 mL microwave vial equipped with a stir bar was charged with (5'S,7a'R)-1-(4-bromopyrazolo[1,5-a]pyridin-7-yl)-5'-(3,5-difluorophenyl)tetrahydro-3'H-spiro[piperidine-4,2'-pyrrolo[2,1-b]oxazol]-3'-one (10 mg, 0.020 mmol), t-BuBrettPhos (0.2 mg, 0.0004 mmol) and NaOt-Bu (2.7 mg, 0.03 mmol). The vial was evacuated and backfilled with nitrogen (3×), MeOH (4.0 μL, 0.099 mmol) was added, and the vial was again evacuated and backfilled with N$_2$

TABLE 24

| Ex. No. | Structure | Name | Exact Mass [M + H]+ |
|---|---|---|---|
| 18.2 | 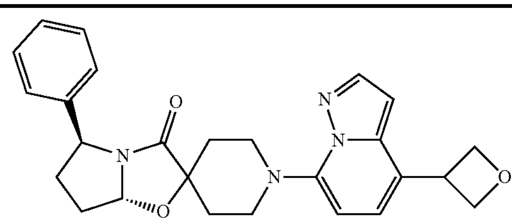 | (5'S,7a'R)-1-[4-(oxetan-3-yl)pyrazolo[1,5-a]pyridin-7-yl]-5'-phenyltetrahydro-3'H-spiro[piperidine-4,2'-pyrrolo[2,1-b][1,3]oxazol]-3'-one | Calc'd 445, found 445 |
| 18.3 | 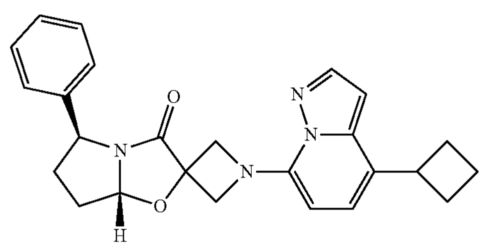 [SMILES: O=C1N2[C@@H](CC[C@H]2c2ccccc2)OC12CN(c1ccc(C3CCC3)c3ccnn13)C2] | (5'S,7a'R)-1-(4-cyclobutylpyrazolo[1,5-a]pyridin-7-yl)-5'-phenyltetrahydro-3'H-spiro[azetidine-3,2'-pyrrolo[2,1-b][1,3]oxazol]-3'-one | Calc'd 415, found 415 |

Example 19.1

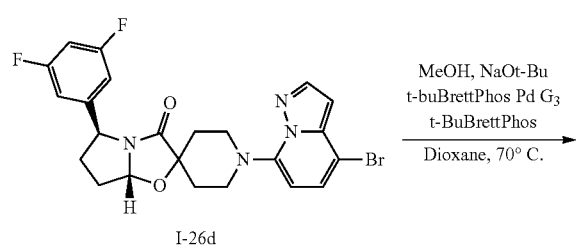

(3×). A sample of dioxane (0.3 mL) was purged with argon for 15 min with sonication, then added to a vial containing 3$^{rd}$ generation t-BuBrettPhos Pd precatalyst (0.3 mg, 0.004 mmol) under N$_2$. This solution of precatalyst was stirred at 25° C. for 1 min, then added to the reaction vial. The reaction mixture was then stirred at 70° C. for 3 days. After cooling, the reaction was partitioned with DCM (3 mL) and water (3 mL), then extracted with DCM (5 mL, ×2). The combined organic layers were dried (MgSO$_4$), filtered and concentrated under reduced pressure. The crude residue was taken up in DMSO (2 mL), filtered and purified via reversed phase HPLC [TFA method]. This provided (5'S,7a'R)-5'-(3,5-difluorophenyl)-1-(4-methoxypyrazolo[1,5-a]pyridin-7-yl)tetrahydro-3'H-spiro[piperidine-4,2'-pyrrolo[2,1-b]oxazol]-3'-one, TFA. MS (ESI) m/z C$_{24}$H$_{25}$F$_2$N$_4$O$_3$[M+1]$^+$ calc'd 455, found 455. ¹H NMR (600 MHz, DMSO-d₆) δ 7.96 (d, J=2.2 Hz, 1H), 7.16-7.11 (m, 1H), 7.11-7.06 (m, 2H), 6.62 (d, J=2.2 Hz, 1H), 6.61 (d, J=8.1 Hz, 1H), 6.28 (d, J=8.0 Hz, 1H), 5.82 (dd, J=7.1, 5.0 Hz, 1H), 4.95 (app t, J=7.8 Hz, 1H), 3.88 (s, 3H), 3.74-3.68 (m, 1H), 3.66-3.60 (m, 1H), 3.07 (app t, J=10.1 Hz, 1H), 2.99-2.91 (m, 1H), 2.64 (ddd, J=13.0, 7.7, 5.2 Hz, 1H), 2.23-2.11 (m, 3H), 2.00-1.93 (m, 1H), 1.87 (td, J=14.4, 13.5, 5.6 Hz, 1H), 1.77 (d, J=11.4 Hz, 1H), 1.68 (tt, J=11.6, 7.6 Hz, 1H).

Compounds in Table 25 below were prepared from intermediates listed in Table 10 using the methods described in Example 19.1. Example 19.3, Example 19.4, and Example 19.5 were prepared using a modified procedure wherein the reaction was stirred at 100° C. for 1.5 days.

TABLE 25

| Ex. No. | Structure | Name | Exact Mass [M + H]+ |
|---|---|---|---|
| 19.2 | 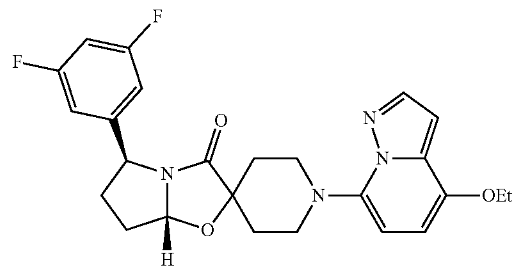 [SMILES: CCOc1ccc(N2CCC3(CC2)O[C@@H]2CC[C@@H](c4cc(F)cc(F)c4)N2C3=O)n2nccc12] | (5'S,7a'R)-5'-(3,5-difluorophenyl)-1-(4-ethoxypyrazolo[1,5-a]pyridin-7-yl)tetrahydro-3'H-spiro[piperidine-4,2'-pyrrolo[2,1-b]oxazol]-3'-one, TFA salt | Calc'd 469, found 469 |
| 19.3 | 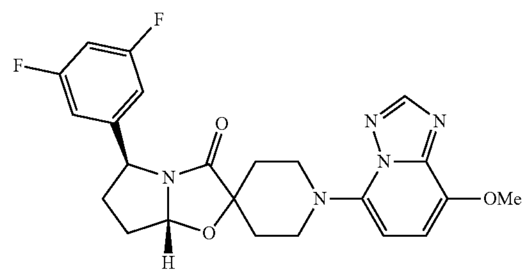 [SMILES: COc1ccc(N2CCC3(CC2)O[C@@H]2CC[C@@H](c4cc(F)cc(F)c4)N2C3=O)n2ncnc12] | (5'S,7a'R)-5'-(3,5-difluorophenyl)-1-(8-methoxy-[1,2,4]triazolo[1,5-a]pyridin-5-yl)tetrahydro-3'H-spiro[piperidine-4,2'pyrrolo[2,1-b]oxazol]-3'-one, TFA salt | Calc'd 456, found 456 |
| 19.4 | 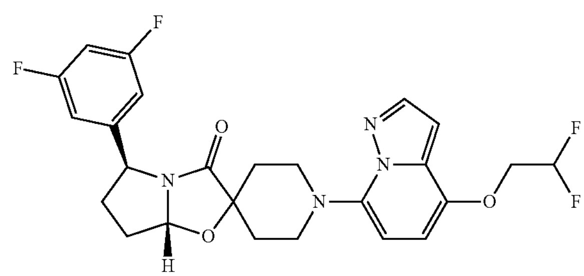 [SMILES: O=C1N2[C@@H](CC[C@H]2c2cc(F)cc(F)c2)OC12CCN(c1ccc(OCC(F)F)c3ccnn13)CC2] | (5'S,7a'R)-1-(4-(2,2-difluoroethoxy)pyrazolo[1,5-a]pyridin-7-yl)-5'-(3,5-difluorophenyl)tetrahydro-3'H-spiro[piperidine-4,2'-pyrrolo[2,1-b]oxazol]-3'-one, TFA salt | Calc'd 505, found 505 |
| 19.5 | 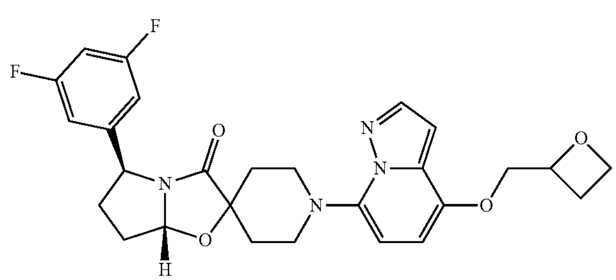 [SMILES: O=C1N2[C@@H](CC[C@H]2c2cc(F)cc(F)c2)OC12CCN(c1ccc(OCC3CCO3)c3ccnn13)CC2] | (5'S,7a'R)-5'-(3,5-difluorophenyl)-1-(4-(((R and S)-oxetan-2-yl)methoxy)pyrazolo[1,5-a]pyridin-7-yl)tetrahydro-3'H-spiro[piperidine-4,2'-pyrrolo[2,1-b]oxazol]-3'-one, TFA salt | Calc'd 511, found 511 |
| 19.6 | 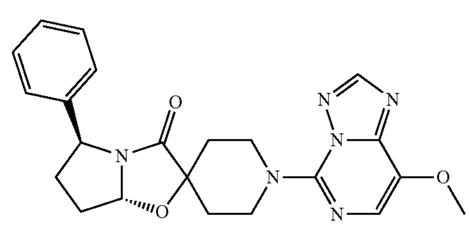 [SMILES: COc1cnc(N2CCC3(CC2)O[C@@H]2CC[C@@H](c4ccccc4)N2C3=O)n2ncnc12] | (5'S,7a'R)-1-(8-methoxy[1,2,4]triazolo[1,5-c]pyrimidin-5-yl)-5'-phenyltetrahydro-3'H-spiro[piperidine-4,2'-pyrrolo[2,1-b][1,3]oxazol]-3'-one | Calc'd 421, found |

TABLE 25-continued

| Ex. No. | Structure | Name | Exact Mass [M + H]+ |
|---|---|---|---|
| 19.7 | 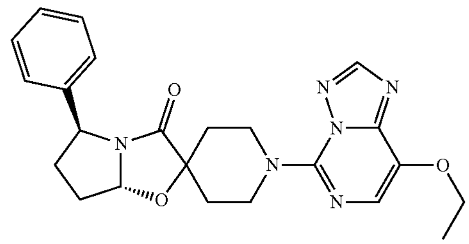 [SMILES: CCOc1cnc(N2CCC3(CC2)O[C@@H]2CC[C@@H](c4ccccc4)N2C3=O)n2ncnc12] | (5'S,7a'R)-1-(8-ethoxy[1,2,4]triazolo[1,5-c]pyrimidin-5-yl)-5'-phenyltetrahydro-3'H-spiro[piperidine-4,2'-pyrrolo[2,1-b][1,3]oxazol]-3'-one | Calc'd 435, found 435 |
| 19.8 | 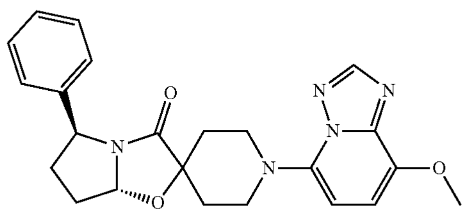 [SMILES: COc1ccc(N2CCC3(CC2)O[C@@H]2CC[C@@H](c4ccccc4)N2C3=O)n2ncnc12] | (5'S,7a'R)-1-(8-methoxy[1,2,4]triazolo[1,5-a]pyridin-5-yl)-5'-phenyltetrahydro-3'H-spiro[piperidine-4,2'-pyrrolo[2,1-b][1,3]oxazol]-3'-one | Calc'd 420, found 420 |

Example 20.1

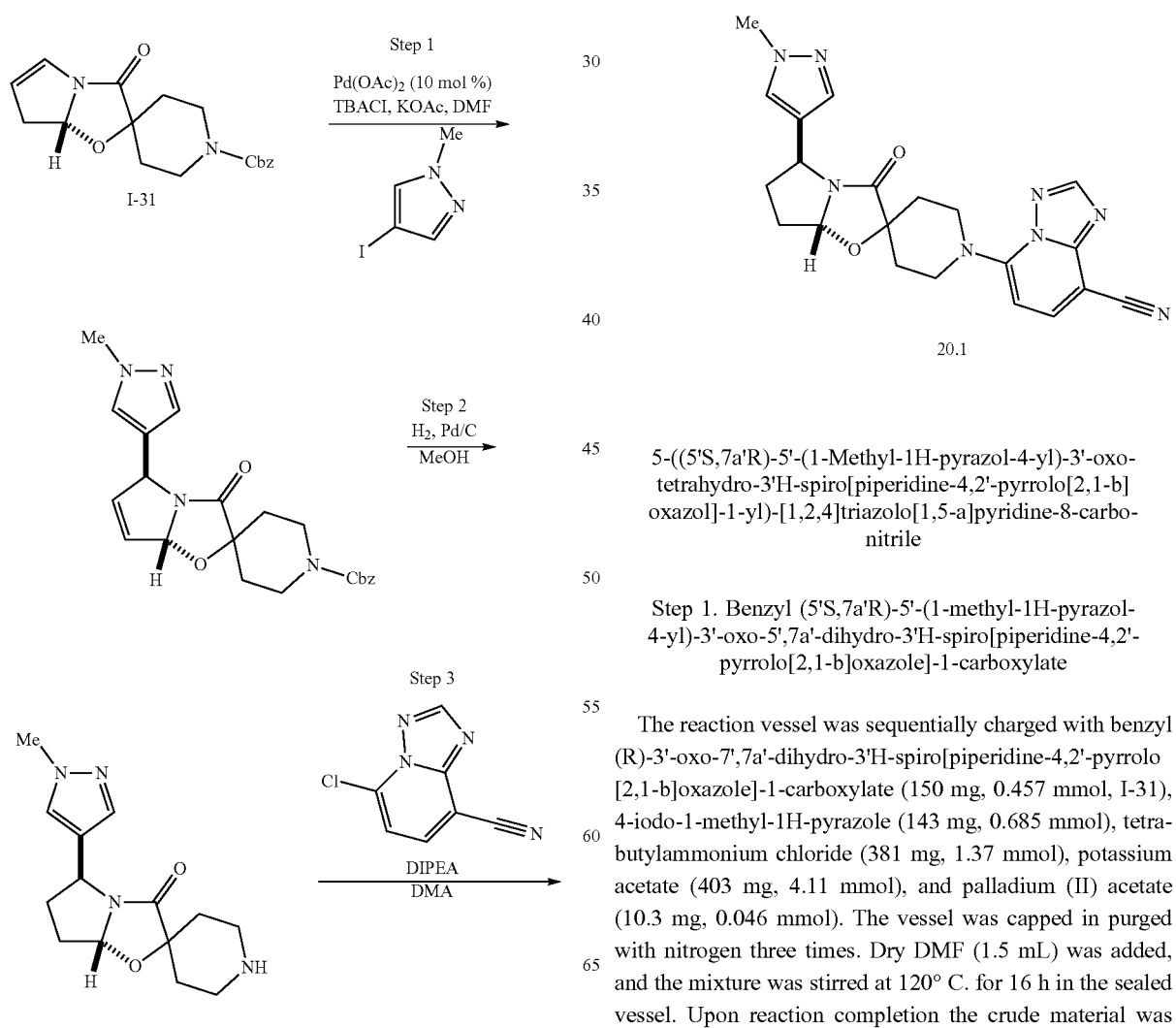

5-((5'S,7a'R)-5'-(1-Methyl-1H-pyrazol-4-yl)-3'-oxotetrahydro-3'H-spiro[piperidine-4,2'-pyrrolo[2,1-b]oxazol]-1-yl)-[1,2,4]triazolo[1,5-a]pyridine-8-carbonitrile Step 1. Benzyl (5'S,7a'R)-5'-(1-methyl-1H-pyrazol-4-yl)-3'-oxo-5',7a'-dihydro-3'H-spiro[piperidine-4,2'-pyrrolo[2,1-b]oxazole]-1-carboxylate The reaction vessel was sequentially charged with benzyl (R)-3'-oxo-7',7a'-dihydro-3'H-spiro[piperidine-4,2'-pyrrolo[2,1-b]oxazole]-1-carboxylate (150 mg, 0.457 mmol, I-31), 4-iodo-1-methyl-1H-pyrazole (143 mg, 0.685 mmol), tetrabutylammonium chloride (381 mg, 1.37 mmol), potassium acetate (403 mg, 4.11 mmol), and palladium (II) acetate (10.3 mg, 0.046 mmol). The vessel was capped in purged with nitrogen three times. Dry DMF (1.5 mL) was added, and the mixture was stirred at 120° C. for 16 h in the sealed vessel. Upon reaction completion the crude material was directly purified by reverse phase flash chromatography using C18-modified silica gel (ISCO®; 12 g SepaFlash® Silica Flash Column, eluent of 10-75% acetonitrile/water gradient). Benzyl (5'S,7a'R)-5'-(1-methyl-1H-pyrazol-4-yl)-3'-oxo-5',7a'-dihydro-3'H-spiro[piperidine-4,2'-pyrrolo[2,1-b]oxazole]-1-carboxylate (143 mg, 0.350 mmol) was isolated as yellow oil. MS (ESI) m/z $C_{22}H_{25}N_4O_4$ [M+H]$^+$ calc'd 409, found 409.

Step 2. (5'S,7a'R)-5'-(1-Methyl-1H-pyrazol-4-yl) tetrahydro-3'H-spiro[piperidine-4,2'-pyrrolo[2,1-b]oxazol]-3'-one 10 w/w % Palladium on carbon (37.3 mg, 0.035 mmol) was added to the solution of benzyl (5'S,7a'R)-5'-(1-methyl-1H-pyrazol-4-yl)-3'-oxo-5',7a'-dihydro-3'H-spiro[piperidine-4,2'-pyrrolo[2,1-b]oxazole]-1-carboxylate (143 mg, 0.350 mmol) in anhydrous methanol (3.5 mL). The resulting suspension was aged under 1 atm of hydrogen for 17 hours at 22° C. Upon completion the reaction mixture was filtered through celite and concentrated. The resulting crude (5'S,7a'R)-5'-(1-methyl-1H-pyrazol-4-yl)tetrahydro-3'H-spiro[piperidine-4,2'-pyrrolo[2,1-b]oxazol]-3'-one was used without further purification. MS (ESI) m/z $C_{14}H_{21}N_4O_2$ [M+H]$^+$ calc'd 277, found 277.

Step 3. 5-((5'S,7a'R)-5'-(1-methyl-1H-pyrazol-4-yl)-3'-oxotetrahydro-3'H-spiro[piperidine-4,2'-pyrrolo[2,1-b]oxazol]-1'-yl)-[1,2,4]triazolo[1,5-a]pyridine-8-carbonitrile (20.1)

(5'S,7a'R)-5'-(1-Methyl-1H-pyrazol-4-yl)tetrahydro-3'H-spiro[piperidine-4,2'-pyrrolo[2,1-b]oxazol]-3'-one (4.0 mg, 0.014 mmol) and 5-chloro-[1,2,4]triazolo[1,5-a]pyridine-8-carbonitrile (3.9 mg, 0.022 mmol) was dissolved in dry DMA (0.3 mL). The resulting solution was treated with diisopropylethylamine (5.61 mg, 0.043 mmol) under inert atmosphere. The reaction was heated to 60° C. for 2 h then cooled and diluted with DMA. The mixture was purified by reverse phase HPLC (C18, 150×30 mm×5 um; Water (TFA)-CAN 25-100 Gradient; FlowRate (mL/min) 40) to give 5-((5'S,7a'R)-5'-(1-methyl-1H-pyrazol-4-yl)-3'-oxotetrahydro-3'H-spiro[piperidine-4,2'-pyrrolo[2,1-b]oxazol]-1-yl)-[1,2,4]triazolo[1,5-a]pyridine-8-carbonitrile as a solid. $^1$H NMR (400 MHz, DMSO): δ 8.61 (s, 1H), 8.18 (d, J=4.0 Hz, 1H), 7.64 (s 1H), 7.38 (s, 1H), 6.72 (d, J=4.0 Hz, 1H), 4.89-4.86 (m, 1H), 4.31-4.21 (m, 2H), 3.80 (s, 3H), 3.52-3.38 (m, 2H), 2.44 (br s, 1H), 2.20-1.68 (m, 7H).

Compounds in Table 26 below were prepared using the methods and sequence described in Example 20.1, using intermediate(s) I-31.

TABLE 26

| Ex. No. | Structure | Name | Exact Mass [M + H]+ |
|---|---|---|---|
| 20.2 | 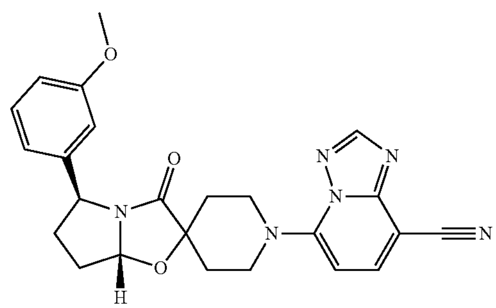 [SMILES: COc1cccc([C@@H]2CC[C@H]3OC4(CCN(c5ccc(C#N)c6ncnn56)CC4)C(=O)N32)c1] | 5-[(5'S,7a'R)-5'-(3-methoxyphenyl)-3'-oxotetrahydro-1H,3'H-spiro[piperidine-4,2'-pyrrolo[2,1-b][1,3]oxazol]-1-yl]-1,2,4]triazolo[1,5-a]pyridine-8-carbonitrile | Calc'd 445, found 445 |
| 20.3 | 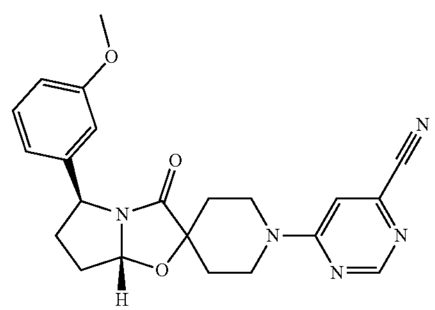 [SMILES: COc1cccc([C@@H]2CC[C@H]3OC4(CCN(c5cc(C#N)ncn5)CC4)C(=O)N32)c1] | 6-[(5'S,7a'R)-5'-(3-methoxyphenyl)-3'-oxotetrahydro-1H,3'H-spiro[piperidine-4,2'-pyrrolo[2,1-b][1,3]oxazol]-1-yl]pyrimidine-4-carbonitrile | Calc'd 406, found 406 |
| 20.4 | 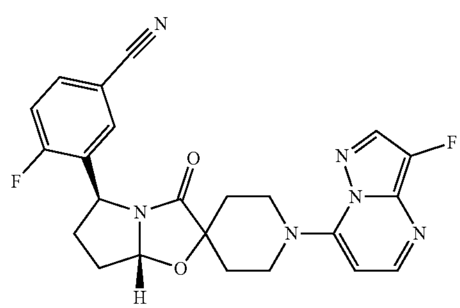 [SMILES: N#Cc1ccc(F)c([C@@H]2CC[C@H]3OC4(CCN(c5ccnc6c(F)cnn56)CC4)C(=O)N32)c1] | 4-fluoro-3-[(5'S,7a'R)-1-(3-fluoropyrazolo[1,5-a]pyrimidin-7-yl)-3'-oxotetrahydro-3'H-spiro[piperidine-4,2'-pyrrolo[2,1-b][1,3]oxazol]-5'-yl]benzonitrile | Calc'd 451, found 451 |

TABLE 26-continued

| Ex. No. | Structure | Name | Exact Mass [M + H]+ |
| --- | --- | --- | --- |
| 20.5 | 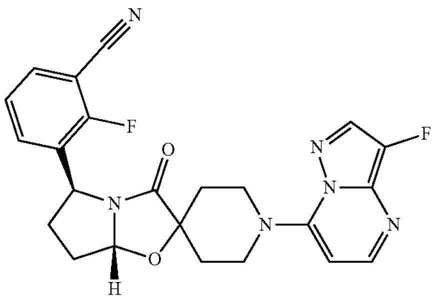 [SMILES: N#Cc1cccc([C@@H]2CC[C@H]3OC4(CCN(c5ccnc6c(F)cnn56)CC4)C(=O)N32)c1F] | 2-fluoro-3-[(5'S,7a'R)-1-(3-fluoropyrazolo[1,5-a]pyrimidin-7-yl)-3'-oxotetrahydro-3'H-spiro[piperidine-4,2'-pyrrolo[2,1-b][1,3]oxazol]-5'-yl]benzonitrile | Calc'd 451, found 451 |
| 20.6 | 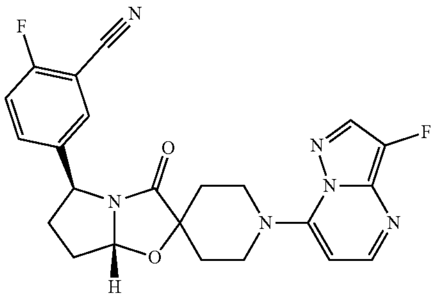 [SMILES: N#Cc1cc([C@@H]2CC[C@H]3OC4(CCN(c5ccnc6c(F)cnn56)CC4)C(=O)N32)ccc1F] | 2-fluoro-5-[(5'S,7a'R)-1-(3-fluoropyrazolo[1,5-a]pyrimidin-7-yl)-3'-oxotetrahydro-3'H-spiro[piperidine-4,2'-pyrrolo[2,1-b][1,3]oxazol]-5'-yl]benzonitrile | Calc'd 451, found 451 |
| 20.7 | 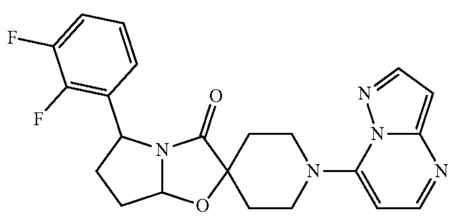 [SMILES: O=C1N2C(CCC2c2cccc(F)c2F)OC12CCN(c1ccnc3ccnn13)CC2] | 5'-(2,3-difluorophenyl)-1-(pyrazolo[1,5-a]pyrimidin-7-yl)tetrahydro-3'H-spiro[piperidine-4,2'-pyrrolo[2,1-b][1,3]oxazol]-3'-one | Calc'd 426, found 426 |
| 20.8 | 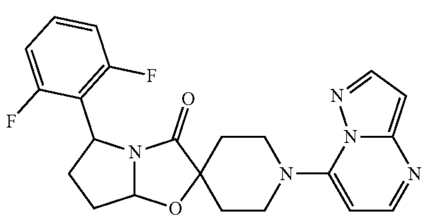 [SMILES: O=C1N2C(CCC2c2c(F)cccc2F)OC12CCN(c1ccnc3ccnn13)CC2] | 5'-(2,6-difluorophenyl)-1-(pyrazolo[1,5-a]pyrimidin-7-yl)tetrahydro-3'H-spiro[piperidine-4,2'-pyrrolo[2,1-b][1,3]oxazol]-3'-one | Calc'd 426, found 426 |

Example 21.1

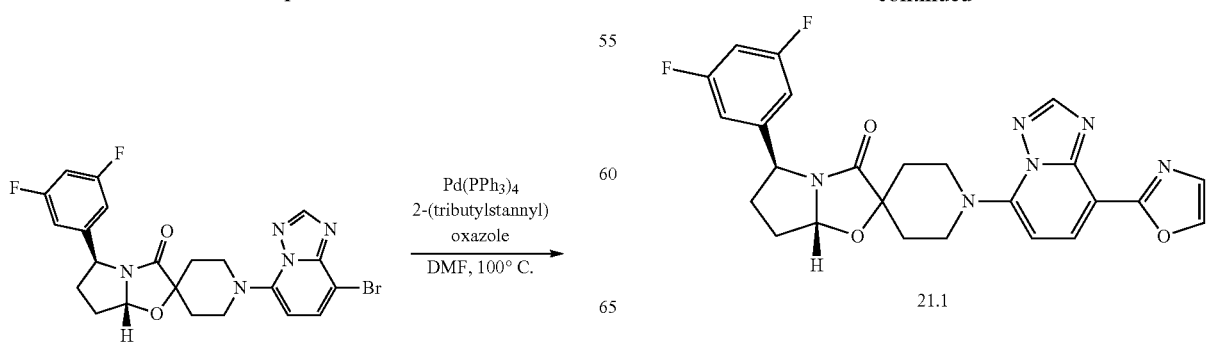

(5'S,7a'R)-5'-(3,5-Difluorophenyl)-1-(8-(oxazol-2-yl)-[1,2,4]triazolo[1,5-a]pyridin-5-yl)tetrahydro-3'H-spiro[piperidine-4,2'-pyrrolo[2,1-b]oxazol]-3'-one To a vial was added (5'S,7a'R)-1-(8-bromo-[1,2,4]triazolo[1,5-a]pyridin-5-yl)-5'-(3,5-difluorophenyl)tetrahydro-3'H-spiro[piperidine-4,2'-pyrrolo[2,1-b]oxazol]-3'-one (20 mg, 0.040 mmol), Pd(Ph3P)4 (4.58 mg, 3.97 Fmol) with stirbar in DMF (500 uL). 2-(tributylstannyl) oxazole (18.2 μl, 0.059 mmol) was added in one portion and the mixture was purged under N2 for 5 min then heated to 100° C. for 1 h. The mixture was cooled, the Pd-scavenger polymer was added and stirred for 15 min at RT. The mixture was diluted in DMF, MeOH, and filtered. The residue was purified by preparative HPLC Reverse phase (C-18), eluting with Acetonitrile/Water+0.05% NH3, to give (5'S,7a'R)-5'-(3,5-difluorophenyl)-1-(8-(oxazol-2-yl)-[1,2,4]triazolo[1,5-a]pyridin-5-yl)tetrahydro-3'H-spiro[piperidine-4,2'-pyrrolo[2,1-b]oxazol]-3'-one as a colorless solid. MS (ESI) m/z $C_{25}H_{23}F_2N_6O_3$[M+H]t calc'd 493, found 493.

Compounds in Table 27 below were prepared from intermediates listed in Table 10 using the methods described in Example 21.1.

TABLE 27

| Ex. No. | Structure | Name | Exact Mass [M + H]+ |
|---|---|---|---|
| 21.2 | 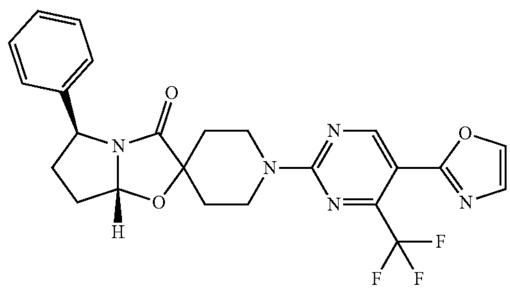 [SMILES: O=C1N2[C@@H](CC[C@H]2c2ccccc2)OC12CCN(c1ncc(-c3ncco3)c(C(F)(F)F)n1)CC2] | (5'S,7a'R)-1-[5-(1,3-oxazol-2-yl)-4-(trifluoromethyl)pyrimidin-2-yl]-5'-phenyltetrahydro-3'H-spiro[piperidine-4,2'-pyrrolo[2,1-b][1,3]oxazol]-3'-one | Calc'd 486, found 486 |
| 21.3 | 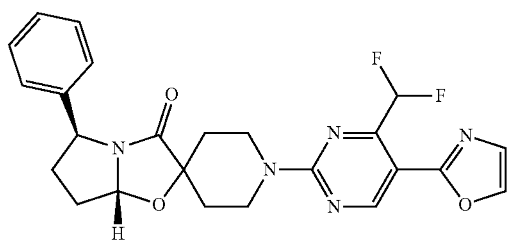 [SMILES: O=C1N2[C@@H](CC[C@H]2c2ccccc2)OC12CCN(c1ncc(-c3ncco3)c(C(F)F)n1)CC2] | (5'S,7a'R)-1-[4-(difluoromethyl)-5-(1,3-oxazol-2-yl)pyrimidin-2-yl]-5'-phenyltetrahydro-3'H-spiro[piperidine-4,2'-pyrrolo[2,1-b][1,3]oxazol]-3'-one | Calc'd 468, found 468 |
| 21.4 | 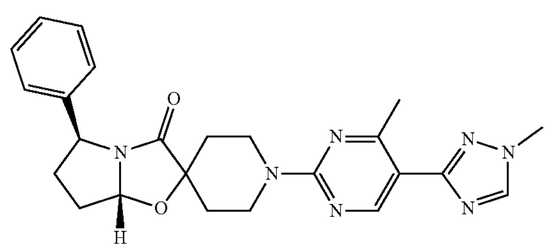 [SMILES: Cc1nc(N2CCC3(CC2)O[C@@H]2CC[C@@H](c4ccccc4)N2C3=O)ncc1-c1ncn(C)n1] | (5'S,7a'R)-1-[4-methyl-5-(1-methyl-1H-1,2,4-triazol-3-yl)pyrimidin-2-yl]-5'-phenyltetrahydro-3'H-spiro[piperidine-4,2'-pyrrolo[2,1-b][1,3]oxazol]-3'-one | Calc'd 446, found 446 |
| 21.5 | 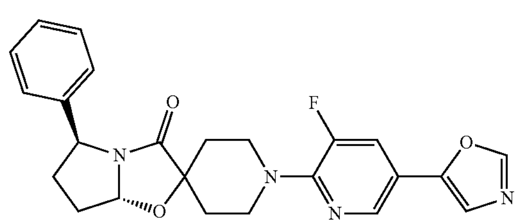 [SMILES: O=C1N2[C@@H](CC[C@H]2c2ccccc2)OC12CCN(c1ncc(-c3cnco3)cc1F)CC2] | (5'S,7a'R)-1-[3-fluoro-5-(1,3-oxazol-5-yl)pyridin-2-yl]-5'-phenyltetrahydro-3'H-spiro[piperidine-4,2'-pyrrolo[2,1-b][1,3]oxazol]-3'-one | Calc'd 435, found 435 |
| 21.6 | 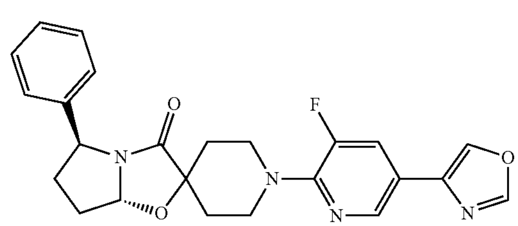 [SMILES: O=C1N2[C@@H](CC[C@H]2c2ccccc2)OC12CCN(c1ncc(-c3cocn3)cc1F)CC2] | (5'S,7a'R)-1-[3-fluoro-5-(1,3-oxazol-4-yl)pyridin-2-yl]-5'-phenyltetrahydro-3'H-spiro[piperidine-4,2'-pyrrolo[2,1-b][1,3]oxazol]-3'-one | Calc'd 435, found 435 |

TABLE 27-continued

| Ex. No. | Structure | Name | Exact Mass [M + H]+ |
|---|---|---|---|
| 21.7 | 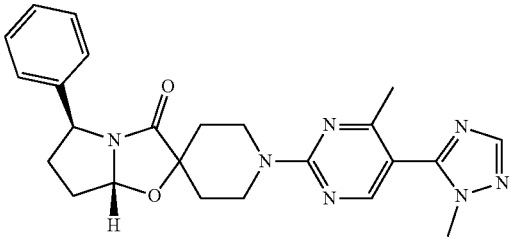 [SMILES: Cc1nc(N2CCC3(CC2)O[C@@H]2CC[C@@H](c4ccccc4)N2C3=O)ncc1-c1ncnn1C] | (5'S,7a'R)-1-[4-methyl-5-(1-methyl-1H-1,2,4-triazol-5-yl)pyrimidin-2-yl]-5'-phenyltetrahydro-3'H-spiro[piperidine-4,2'-pyrrolo[2,1-b][1,3]oxazol]-3'-one | Calc'd 446, found 446 |
| 21.8 | 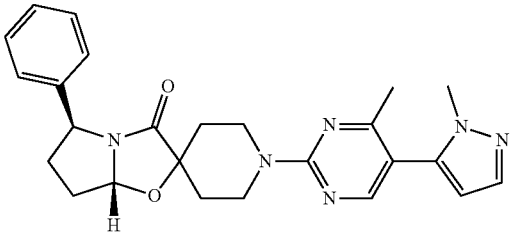 [SMILES: Cc1nc(N2CCC3(CC2)O[C@@H]2CC[C@@H](c4ccccc4)N2C3=O)ncc1-c1ccnn1C] | (5'S,7a'R)-1-[4-methyl-5-(1-methyl-1H-pyrazol-5-yl)pyrimidin-2-yl]-5'-phenyltetrahydro-3'H-spiro[piperidine-4,2'-pyrrolo[2,1-b][1,3]oxazol]-3'-one | Calc'd 445, found 445 |
| 21.9 | 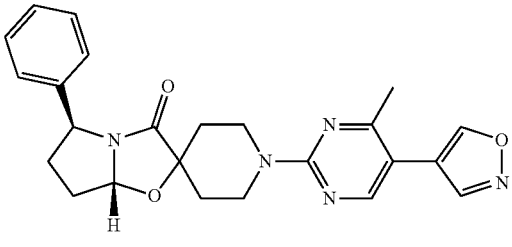 [SMILES: Cc1nc(N2CCC3(CC2)O[C@@H]2CC[C@@H](c4ccccc4)N2C3=O)ncc1-c1cnoc1] | (5'S,7a'R)-1-[4-methyl-5-(1,2-oxazol-4-yl)pyrimidin-2-yl]-5'-phenyltetrahydro-3'H-spiro[piperidine-4,2'-pyrrolo[2,1-b][1,3]oxazol]-3'-one | Calc'd 432, found 432 |
| 21.10 | 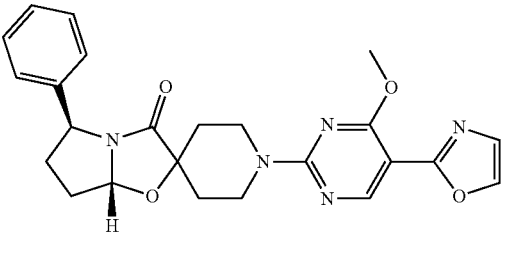 | (5'S,7a'R)-1-[4-methoxy-5-(1,3-oxazol-2-yl)pyrimidin-2-yl]-5'-phenyltetrahydro-3'H-spiro[piperidine-4,2'-pyrrolo[2,1-b][1,3]oxazol]-3'-one | Calc'd 448, found 448 |
| 21.11 | 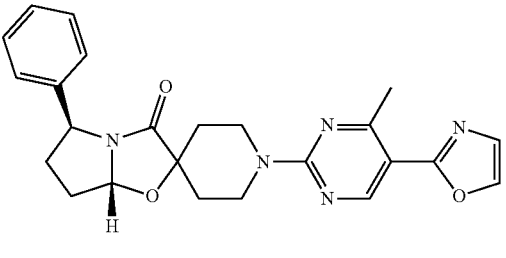 [SMILES: Cc1nc(N2CCC3(CC2)O[C@@H]2CC[C@@H](c4ccccc4)N2C3=O)ncc1-c1ncco1] | (5'S,7a'R)-1-[4-methyl-5-(1,3-oxazol-2-yl)pyrimidin-2-yl]-5'-phenyltetrahydro-3'H-spiro[piperidine-4,2'-pyrrolo[2,1-b][1,3]oxazol]-3'-one | Calc'd 432, found 432 |
| 21.12 | 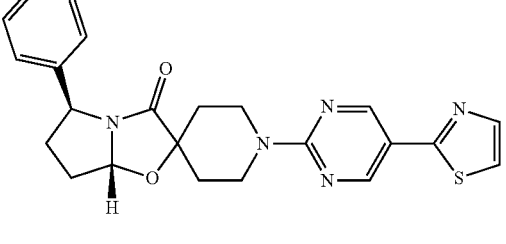 | (5'S,7a'R)-5'-phenyl-1-[5-(1,3-thiazol-2-yl)pyrimidin-2-yl]tetrahydro-3'H-spiro[piperidine-4,2'-pyrrolo[2,1-b][1,3]oxazol]-3'-one | Calc'd 434, found 434 |

TABLE 27-continued

| Ex. No. | Structure | Name | Exact Mass [M + H]+ |
|---|---|---|---|
| 21.13 | 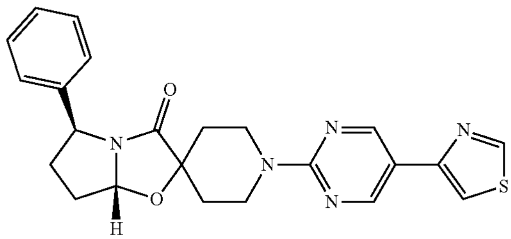 [SMILES: O=C1N2[C@@H](CC[C@H]2c2ccccc2)OC12CCN(c1ncc(-c3cscn3)cn1)CC2] | (5'S,7a'R)-5'-phenyl-1-[5-(1,3-thiazol-4-yl)pyrimidin-2-yl]tetrahydro-3'H-spiro[piperidine-4,2'-pyrrolo[2,1-b][1,3]oxazol]-3'-one | Calc'd 434, found 434 |
| 21.14 | 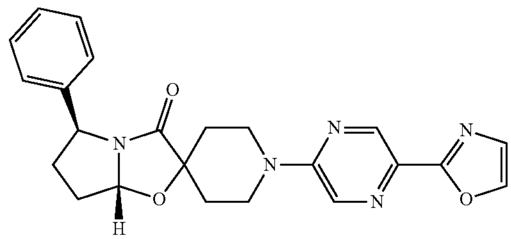 [SMILES: O=C1N2[C@@H](CC[C@H]2c2ccccc2)OC12CCN(c1cnc(-c3ncco3)cn1)CC2] | (5'S,7a'R)-1-[5-(1,3-oxazol-2-yl)pyrazin-2-yl]-5'-phenyltetrahydro-3'H-spiro[piperidine-4,2'-pyrrolo[2,1-b][1,3]oxazol]-3'-one | Calc'd 418, found 418 |
| 21.15 | 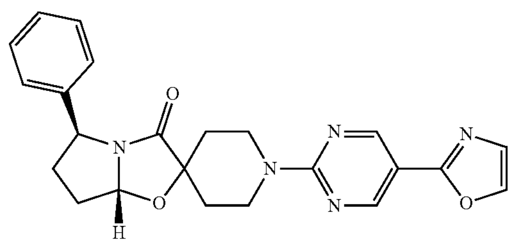 | (5'S,7a'R)-1-[5-(1,3-oxazol-2-yl)pyrimidin-2-yl]-5'-phenyltetrahydro-3'H-spiro[piperidine-4,2'-pyrrolo[2,1-b][1,3]oxazol]-3'-one | Calc'd 418, found 418 |
| 21.16 | 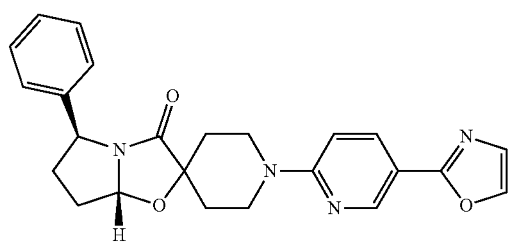 | (5'S,7a'R)-1-[5-(1,3-oxazol-2-yl)pyridin-2-yl]-5'-phenyltetrahydro-3'H-spiro[piperidine-4,2'-pyrrolo[2,1-b][1,3]oxazol]-3'-one | Calc'd 417, found 417 |
| 21.17 | 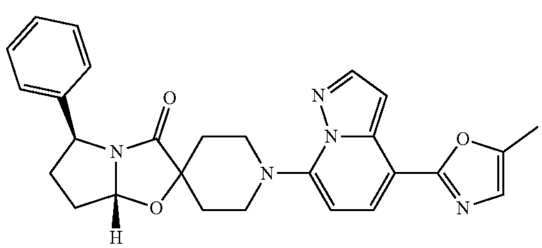 [SMILES: Cc1cnc(-c2ccc(N3CCC4(CC3)O[C@@H]3CC[C@@H](c5ccccc5)N3C4=O)n3nccc23)o1] | (5'S,7a'R)-1-[4-(5-methyl-1,3-oxazol-2-yl)pyrazolo[1,5-a]pyridin-7-yl]-5'-phenyltetrahydro-3'H-spiro[piperidine-4,2'-pyrrolo[2,1-b][1,3]oxazol]-3'-one | Calc'd 470, found 470 |
| 21.18 | 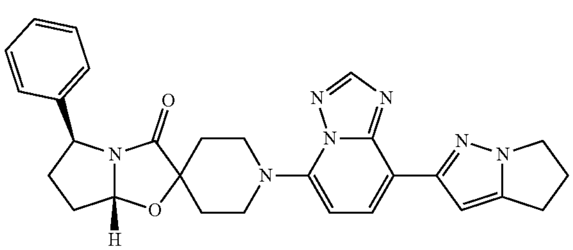 [SMILES: O=C1N2[C@@H](CC[C@H]2c2ccccc2)OC12CCN(c1ccc(-c3cc4n(n3)CCC4)c3ncnn13)CC2] | (5'S,7a'R)-1-[8-(5,6-dihydro-4H-pyrrolo[1,2-b]pyrazol-2-yl)[1,2,4]triazolo[1,5-a]pyridin-5-yl]-5'-phenyltetrahydro-3'H-spiro[piperidine-4,2'-pyrrolo[2,1-b][1,3]oxazol]-3'-one | Calc'd 496, found 496 |

TABLE 27-continued

| Ex. No. | Structure | Name | Exact Mass [M + H]+ |
|---|---|---|---|
| 21.19 | 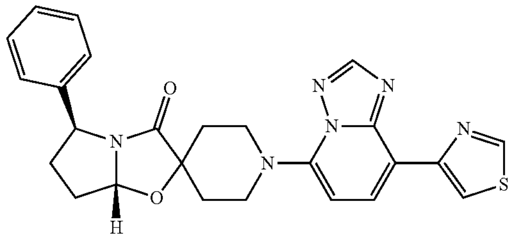 [SMILES: O=C1N2[C@@H](CC[C@H]2c2ccccc2)OC12CCN(c1ccc(-c3cscn3)c3ncnn13)CC2] | (5'S,7a'R)-5'-phenyl-1-[8-(1,3-thiazol-4-yl)[1,2,4]triazolo[1,5-a]pyridin-5-yl]tetrahydro-3'H-spiro[piperidine-4,2'-pyrrolo[2,1-b][1,3]oxazol]-3'-one | Calc'd 473, found 473 |
| 21.20 | 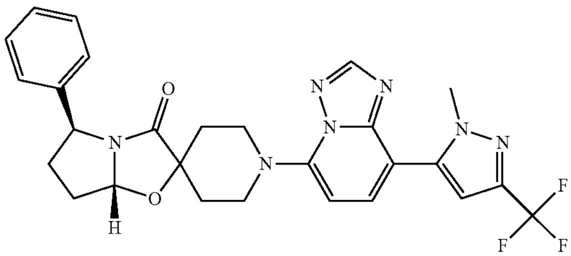 [SMILES: Cn1nc(C(F)(F)F)cc1-c1ccc(N2CCC3(CC2)O[C@@H]2CC[C@@H](c4ccccc4)N2C3=O)n2ncnc12] | (5'S,7a'R)-1-{8-[1-methyl-3-(trifluoromethyl)-1H-pyrazol-5-yl][1,2,4]triazolo[1,5-a]pyridin-5-yl}-5'-phenyltetrahydro-3'H-spiro[piperidine-4,2'-pyrrolo[2,1-b][1,3]oxazol]-3'-one | Calc'd 538, found 538 |
| 21.21 | 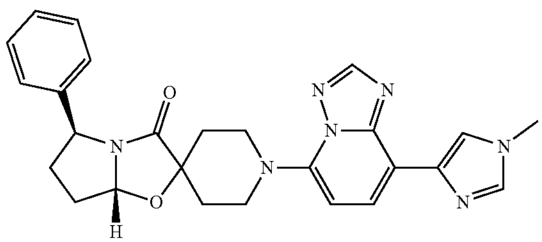 [SMILES: Cn1cnc(-c2ccc(N3CCC4(CC3)O[C@@H]3CC[C@@H](c5ccccc5)N3C4=O)n3ncnc23)c1] | (5'S,7a'R)-1-[8-(1-methyl-1H-imidazol-4-yl)[1,2,4]triazolo[1,5-a]pyridin-5-yl]-5'-phenyltetrahydro-3'H-spiro[piperidine-4,2'-pyrrolo[2,1-b][1,3]oxazol]-3'-one | Calc'd 470, found 470 |
| 21.22 | 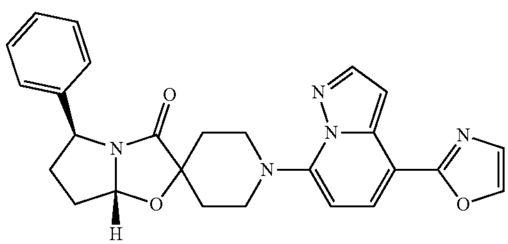 [SMILES: O=C1N2[C@@H](CC[C@H]2c2ccccc2)OC12CCN(c1ccc(-c3ncco3)c3ccnn13)CC2] | (5'S,7a'R)-1-[4-(1,3-oxazol-2-yl)pyrazolo[1,5-a]pyridin-7-yl]-5'-phenyltetrahydro-3'H-spiro[piperidine-4,2'-pyrrolo[2,1-b][1,3]oxazol]-3'-one | Calc'd 456, found 456 |
| 21.23 | 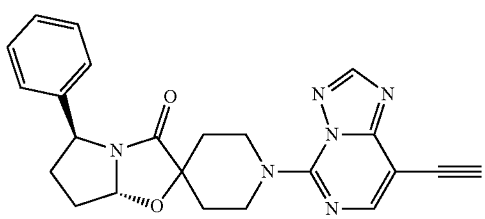 [SMILES: C#Cc1cnc(N2CCC3(CC2)O[C@@H]2CC[C@@H](c4ccccc4)N2C3=O)n2ncnc12] | (5'S,7a'R)-1-(8-ethynyl[1,2,4]triazolo[1,5-c]pyrimidin-5-yl)-5'-phenyltetrahydro-3'H-spiro[piperidine-4,2'-pyrrolo[2,1-b][1,3]oxazol]-3'-one | Calc'd 415, found 415 |
| 21.24 | 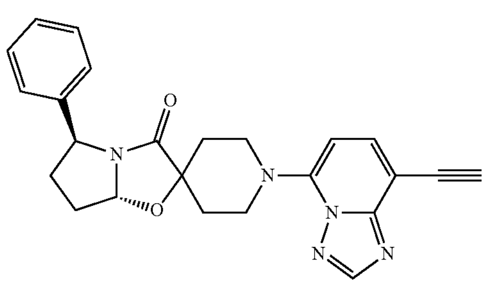 [SMILES: C#Cc1ccc(N2CCC3(CC2)O[C@@H]2CC[C@@H](c4ccccc4)N2C3=O)n2ncnc12] | (5'S,7a'R)-1-(8-ethynyl[1,2,4]triazolo[1,5-a]pyridin-5-yl)-5'-phenyltetrahydro-3'H-spiro[piperidine-4,2'-pyrrolo[2,1-b][1,3]oxazol]-3'-one | Calc'd 414, found 414 |

Example 22.1

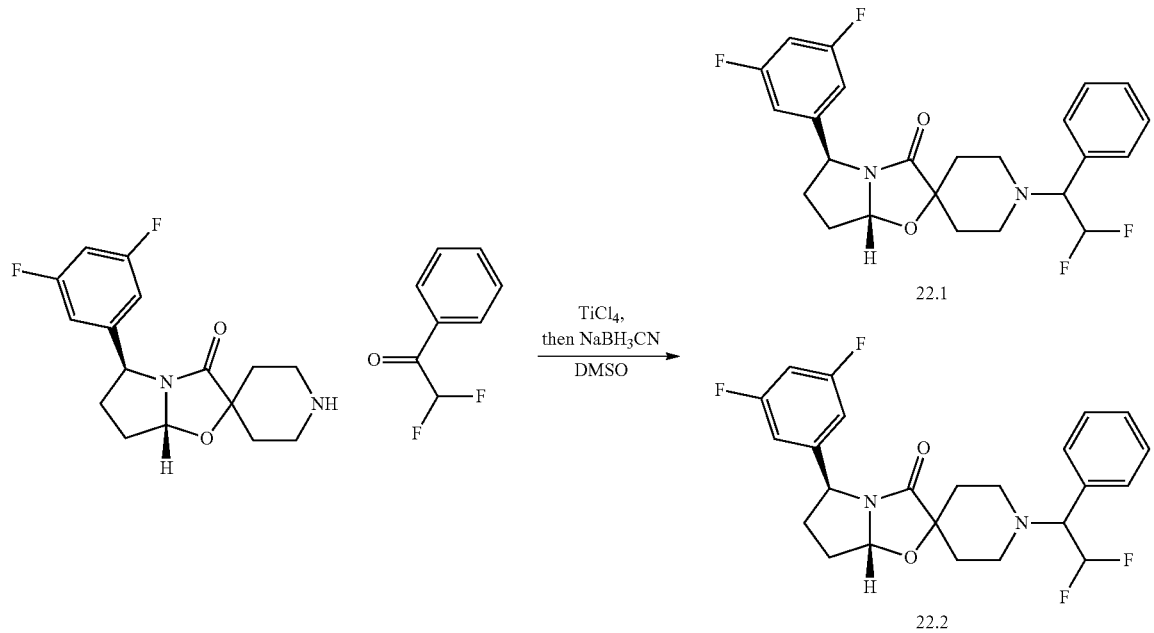 [SMILES: O=C1N2[C@@H](CC[C@H]2c2cc(F)cc(F)c2)OC12CCNCC2 ; O=C(c1ccccc1)C(F)F ; O=C1N2[C@@H](CC[C@H]2c2cc(F)cc(F)c2)OC12CCN(C(c1ccccc1)C(F)F)CC2 ; O=C1N2[C@@H](CC[C@H]2c2cc(F)cc(F)c2)OC12CCN(C(c1ccccc1)C(F)F)CC2]

(5'S,7a'R)-1-(2,2-Difluoro-1-phenylethyl)-5'-(3,5-difluorophenyl)tetrahydro-3'H-spiro[piperidine-4,2'-pyrrolo[2,1-b]oxazol]-3'-one To a solution of 2,2-difluoro-1-phenylethan-1-one (50.6 mg, 0.324 mmol), (5'S,7a'R)-5'-(3,5-difluorophenyl)tetrahydro-3'H-spiro[piperidine-4,2'-pyrrolo[2,1-b]oxazol]-3'-one (50 mg, 0.162 mmol) in DMSO (1 ml) was added titanium(IV) chloride (6.15 mg, 0.032 mmol), followed by dropwise addition of TEA (0.068 ml, 0.486 mmol). The mixture was stirred at 25° C. for 12 h, then NaBH$_3$CN (40.8 mg, 0.649 mmol) in 1 mL of MeOH was added. The mixture was stirred at 25° C. for another 2 h. The reaction mixture was quenched by adding 5 mL of 1N HCl at 0° C., and then extracted with DCM (15 mL×3). The combined organic layers were dried (Na$_2$SO$_4$), filtered and concentrated under reduced pressure and purified by Pre-HPLC (EJ Column) eluting with Acetonitrile/Water+0.05% NH$_3$, to give (5'S,7a'R)-1-(2,2-difluoro-1-phenylethyl)-5'-(3,5-difluorophenyl)tetrahydro-3'H-spiro[piperidine-4,2'-pyrrolo[2,1-b]oxazol]-3'-one as a solid. MS (ESI) m/z C$_{24}$H$_{25}$F$_4$N$_2$O$_2$[M+H]$^+$ calc'd 449, found 449. $^1$H NMR (500 MHz, METHANOL-d4) δ 7.54 (s, 5H), 6.90-6.96 (m, 2H), 6.82-6.89 (m, 1H), 5.69-5.79 (m, 1H), 4.97 (dt, J=3.43, 7.97 Hz, 2H), 4.64 (br s, 1H), 3.46-3.64 (m, 1H), 2.93-3.27 (m, 3H), 2.67-2.76 (m, 1H), 2.20-2.39 (m, 3H), 1.83-2.15 (m, 3H), 1.67-1.78 (m, 1H). The two diastereomers were further separated by chiral SFC, Column: DAICEL CHIRALPAK AD (250 mm×30 mm×10 um); 0.1% NH$_3$H$_2$O in IPA, 40-100% IPA; 80 ml/min to afford two compounds.

Compounds in Table 28 below were prepared from intermediates using the methods described in Example 22.1. Examples 22.3-22.8 were prepared using the same conditions using DCE as the solvent and without employing the Lewis Acid, TiCl$_4$.

TABLE 28

| Ex. No. | Structure | Name | Exact Mass [M + H]+ |
|---|---|---|---|
| 22.3 | 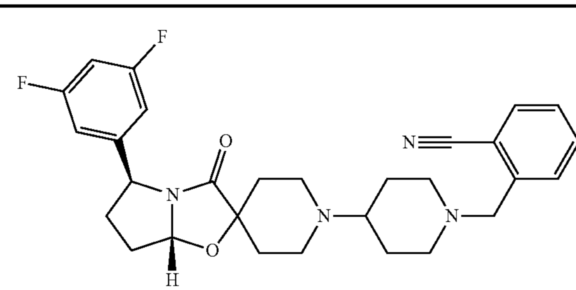 | 2-{[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]methyl}benzonitrile | Calc'd 424, found 424 |

TABLE 28-continued

| Ex. No. | Structure | Name | Exact Mass [M + H]+ |
|---|---|---|---|
| 22.4 | 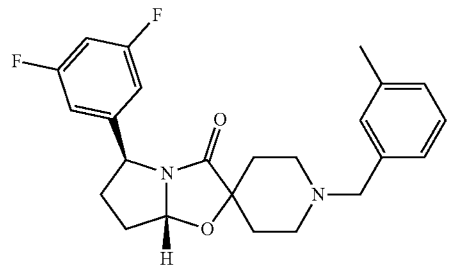 [SMILES: Cc1cccc(CN2CCC3(CC2)O[C@@H]2CC[C@@H](c4cc(F)cc(F)c4)N2C3=O)c1] | (5'S,7a'R)-5'-(3,5-difluorophenyl)-1-[(3-methylphenyl)methyl]tetrahydro-3'H-spiro[piperidine-4,2'-pyrrolo[2,1-b][1,3]oxazol]-3'-one | Calc'd 413, found 413 |
| 22.5 | 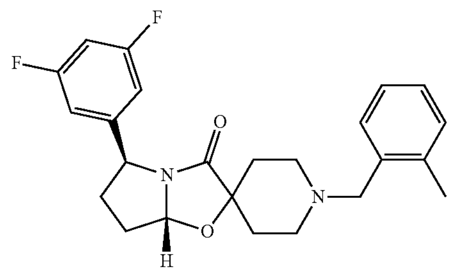 [SMILES: Cc1ccccc1CN1CCC2(CC1)O[C@@H]1CC[C@@H](c3cc(F)cc(F)c3)N1C2=O] | (5'S,7a'R)-5'-(3,5-difluorophenyl)-1-[(2-methylphenyl)methyl]tetrahydro-3'H-spiro[piperidine-4,2'-pyrrolo[2,1-b][1,3]oxazol]-3'-one | Calc'd 413, found 413 |
| 22.6 | 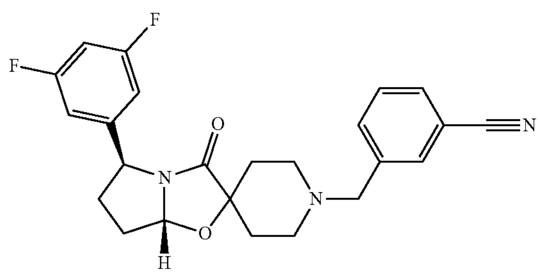 [SMILES: N#Cc1cccc(CN2CCC3(CC2)O[C@@H]2CC[C@@H](c4cc(F)cc(F)c4)N2C3=O)c1] | 3-{[(5'S,7a'R)-5'-(3,5-difluorophenyl)-3'-oxotetrahydro-1H,3'H-spiro[piperidine-4,2'-pyrrolo[2,1-b][1,3]oxazol]-1-yl]methyl}benzonitrile | Calc'd 424, found 424 |
| 22.7 | 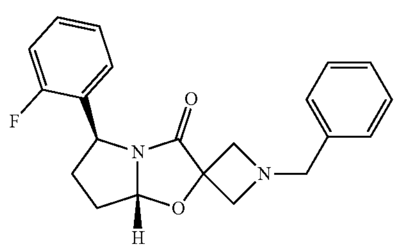 [SMILES: O=C1N2[C@@H](CC[C@H]2c2ccccc2F)OC12CN(Cc1ccccc1)C2] | (5'S,7a'R)-1-benzyl-5'-(2-fluorophenyl)tetrahydro-3'H-spiro[azetidine-3,2'-pyrrolo[2,1-b][1,3]oxazol]-3'-one | Calc'd 353, found 353 |
| 22.8 | 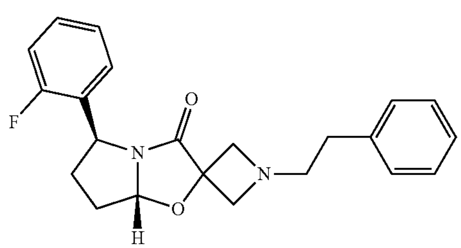 [SMILES: O=C1N2[C@@H](CC[C@H]2c2ccccc2F)OC12CN(CCc1ccccc1)C2] | (5'S,7a'R)-5'-(2-fluorophenyl)-1-(2-phenylethyl)tetrahydro-3'H-spiro[azetidine-3,2'-pyrrolo[2,1-b][1,3]oxazol]-3'-one | Calc'd 367, found 367 |

Example 23.1

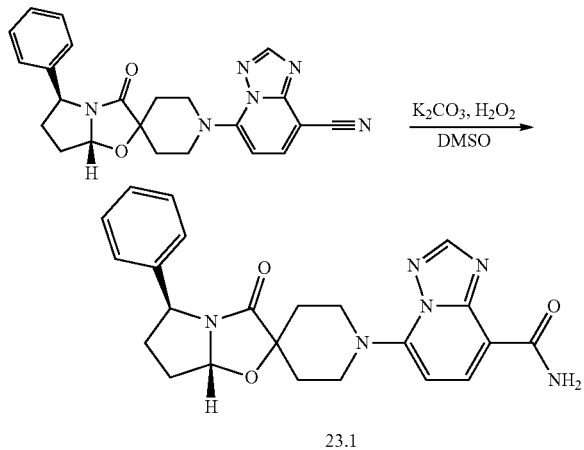

23.1

5-((5'S,7a'R)-3'-oxo-5'-phenyltetrahydro-3'H-spiro [piperidine-4,2'-pyrrolo[2,1-b]oxazol]-1-yl)-[1,2,4] triazolo[1,5-a]pyridine-8-carboxamide A vial was charged with 5-((5'S,7a'R)-3'-oxo-5'-phenyltetrahydro-3'H-spiro[piperidine-4,2'-pyrrolo[2,1-b]oxazol]-1-yl)-[1,2,4]triazolo[1,5-a]pyridine-8-carbonitrile (40 mg, 0.097 mmol) and $K_2CO_3$ (40.0 mg, 0.290 mmol) then $H_2O_2$ (42.2 μl, 0.483 mmol) in DMSO (965 μl). The mixture was stirred at RT and left overnight. The mixture was diluted with DMA (2 mL), filtered, and the residue was purified directly by preparative HPLC Reverse phase (C-18), eluting with Acetonitrile/Water+0.05% $NH_3$, to give 5-((5'S,7a'R)-3'-oxo-5'-phenyltetrahydro-3'H-spiro[piperidine-4,2'-pyrrolo[2,1-b]oxazol]-1-yl)-[1,2,4]triazolo[1,5-a]pyridine-8-carboxamide as a colorless solid after dry down. MS (ESI) m/z $C_{23}H_{25}N_6O_3$ [M+H]$^+$ calc'd 433, found 433. $^1$H NMR (499 MHz, DMSO-d6) δ 8.77 (s, 1H), 8.64 (s, 1H), 8.25 (d, J=8.2 Hz, 1H), 7.85 (s, 1H), 7.33 (ddd, J=25.8, 16.6, 7.2 Hz, 4H), 6.80 (d, J=8.2 Hz, 1H), 5.84 (t, J=5.6 Hz, 1H), 4.95 (t, J=7.7 Hz, 1H), 4.20 (d, J=12.7 Hz, 1H), 4.12 (d, J=12.2 Hz, 1H), 3.45 (d, J=11.4 Hz, 1H), 3.31 (s, 2H), 2.24-2.16 (m, 2H), 2.15 (s, 1H), 1.98 (t, J=10.6 Hz, 1H), 1.89 (dd, J=11.9, 5.8 Hz, 1H), 1.82 (d, J=14.1 Hz, 1H), 1.75-1.68 (m, 1H).

Assay

RIPK1-ADP-Glo Enzymatic Assay

The enzymatic activity of RIPK1 is measured using an assay derived from ADP-Glo kit (TMPromega), which provides a luminescent-based ADP detection system. Specifically, the ADP generated by RIPK1 kinase is proportionally detected as luminescent signals in a homogenous fashion. In this context, the assessment of the inhibitory effect of small molecules (EC50) is measured by the effectiveness of the compounds to inhibit the ATP to ADP conversion by RIPK1.

In this assay, the potency (EC50) of each compound was determined from a ten-point (1:3 serial dilution; top compound concentration of 100000 nM) titration curve using the following outlined procedure. The assay bottom or lower limit of confidence is ~25 nM. To each well of a white ProxiPlus 384 well-plate, 30 nL of compound (1% DMSO in final assay volume of 3 μL) was dispensed, followed by the addition of 2 μL of 1×assay buffer (25 mM Hepes 7.3, 20 mM MgCl2, 50 mM NaCl, 1 mM DTT, 0.005% Tween20, and 0.02% BSA) containing 37.5 nM of GST-RIPK1 (recombinant GST-RIPK1 kinase domain (residues 1-327) enzyme produced from baculovirus-transfected Sf21 cells: MW=62 kDa). Plates were placed in an ambient temperature humidified chamber for a 30-minute pre-incubation with compound. Subsequently, each reaction was initiated by the addition of 1 μL 1×assay buffer containing 900 μM ATP and 3 μM dephosphorylated-MBP substrate. The final reaction in each well of 3 μL consists of 25 nM of GST-RIPK1, 300 μM ATP, and 3 μM dephosphorylated-MBP. Kinase reactions were allowed to proceed for 150 minutes prior to adding ADP-Glo reagents per Promega's outlined kit protocol. Dose-response curves were generated by plotting percent effect (% product conversion; Y-axis) vs. Log10 compound concentrations (X-axis). EC50 values were calculated using a non-linear regression, four-parameters sigmoidal dose-response model.

POTENCY TABLE

| Ex. No. | RIPK1 V0 $Ec_{50}$ |
|---|---|
| 1.1 | <25 |
| 1.2 | 115 |
| 1.3 | <25 |
| 1.4 | 121 |
| 1.5 | <25 |
| 1.6 | <25 |
| 1.7 | <25 |
| 1.8 | 256 |
| 1.9 | <25 |
| 1.10 | <25 |
| 1.11 | <25 |
| 1.12 | <25 |
| 1.13 | <25 |
| 1.14 | <25 |
| 1.15 | 33.4 |
| 1.16 | <25 |
| 1.17 | <25 |
| 1.18 | 39.0 |
| 1.19 | 82.9 |
| 1.20 | 41.7 |
| 1.21 | 501 |
| 1.22 | <25 |
| 1.23 | 26.1 |
| 1.24 | 23.0 |
| 1.25 | 98.3 |
| 2.1 | 76.5 |
| 2.2 | <25 |
| 2.3 | <25 |
| 2.4 | <25 |
| 2.5 | 40.7 |
| 2.6 | <25 |
| 2.7 | 43.1 |
| 2.8 | 36.8 |
| 2.9 | 106 |
| 2.10 | 136 |
| 3.1 | <25 |
| 4.1 | <25 |
| 4.2 | <25 |
| 4.3 | <25 |
| 4.4 | <25 |
| 4.5 | <25 |
| 4.6 | <25 |
| 4.7 | 113 |
| 4.8 | <25 |
| 4.9 | <25 |
| 4.10 | 35.5 |
| 4.11 | <25 |
| 4.12 | <25 |
| 4.13 | <25 |
| 4.14 | <25 |
| 4.15 | <25 |
| 4.16 | <25 |
| 4.17 | <25 |

POTENCY TABLE

| Ex. No. | RIPK1 V0 Ec$_{50}$ |
|---|---|
| 4.18 | <25 |
| 4.19 | 477 |
| 4.20 | <25 |
| 4.21 | <25 |
| 4.22 | 26.9 |
| 4.23 | 52.8 |
| 4.24 | <25 |
| 4.25 | <25 |
| 4.26 | 24.6 |
| 4.27 | 18.0 |
| 4.28 | <25 |
| 4.29 | <25 |
| 4.30 | <25 |
| 4.31 | <25 |
| 4.32 | <25 |
| 4.33 | 50 |
| 4.34 | 83.0 |
| 4.35 | <25 |
| 4.36 | 37.4 |
| 4.37 | <25 |
| 4.38 | 12.0 |
| 4.39 | 22.3 |
| 4.40 | 32.2 |
| 4.41 | <25 |
| 4.42 | <25 |
| 4.43 | <25 |
| 4.44 | <25 |
| 4.45 | 250 |
| 4.46 | 46.9 |
| 4.47 | <25 |
| 4.48 | 150 |
| 4.49 | <25 |
| 4.50 | 30.7 |
| 4.51 | 41.2 |
| 4.52 | 69 |
| 4.53 | <25 |
| 4.54 | 31.1 |
| 4.55 | 246 |
| 4.56 | 565 |
| 4.57 | 243 |
| 4.58 | 45.9 |
| 4.59 | 149 |
| 4.60 | 452 |
| 4.61 | 53.4 |
| 4.62 | 39.2 |
| 4.63 | 48.6 |
| 4.64 | 80.7 |
| 4.65 | 164 |
| 4.66 | 38.4 |
| 4.67 | 89.2 |
| 4.68 | <25 |
| 4.69 | 114 |
| 4.70 | 54.3 |
| 4.71 | 30.3 |
| 4.72 | 29.8 |
| 4.73 | <25 |
| 4.74 | <25 |
| 4.75 | <25 |
| 4.76 | 38.2 |
| 4.77 | <25 |
| 4.78 | 58.7 |
| 4.79 | <25 |
| 4.80 | 494 |
| 4.81 | 51.2 |
| 4.82 | 25 |
| 4.83 | 363 |
| 4.84 | 29.3 |
| 4.85 | 63.4 |
| 4.86 | 269 |
| 4.87 | <25 |
| 4.88 | <25 |
| 4.89 | 29.4 |
| 4.90 | 380 |
| 4.91 | <25 |
| 4.92 | <25 |
| 4.93 | <25 |
| 4.94 | 154 |
| 4.95 | 58.3 |
| 4.96 | <25 |
| 4.97 | <25 |
| 4.98 | 36.3 |
| 4.99 | <25 |
| 4.100 | 240 |
| 4.101 | 40.4 |
| 4.102 | <25 |
| 4.103 | <25 |
| 4.104 | 33.9 |
| 4.105 | <25 |
| 4.106 | 30.5 |
| 4.107 | 101 |
| 4.108 | 26.9 |
| 4.109 | 37.8 |
| 4.110 | <25 |
| 4.111 | 38.1 |
| 4.112 | <25 |
| 4.113 | 309 |
| 4.114 | <25 |
| 4.115 | 180 |
| 4.116 | <25 |
| 4.117 | <25 |
| 4.118 | 228 |
| 4.119 | 537 |
| 4.120 | <25 |
| 4.121 | <25 |
| 4.122 | 35.6 |
| 4.123 | <25 |
| 4.124 | <25 |
| 4.125 | <25 |
| 4.126 | 46.7 |
| 4.127 | <25 |
| 4.128 | <25 |
| 4.129 | <25 |
| 4.130 | <25 |
| 4.131 | 30.6 |
| 4.132 | <25 |
| 4.133 | 48.8 |
| 4.134 | 27.3 |
| 4.135 | 63.7 |
| 4.136 | <25 |
| 4.137 | 235 |
| 4.138 | 145 |
| 4.139 | <25 |
| 4.140 | 25.6 |
| 4.141 | <25 |
| 4.142 | <25 |
| 4.143 | <25 |
| 4.144 | 41.7 |
| 4.145 | <25 |
| 4.146 | <25 |
| 4.147 | <25 |
| 4.148 | <25 |
| 4.149 | <25 |
| 4.150 | 34.4 |
| 4.151 | <25 |
| 4.152 | <25 |
| 4.153 | <25 |
| 4.154 | 35.7 |
| 4.155 | <25 |
| 4.156 | <25 |
| 4.157 | <25 |
| 4.158 | 50.8 |
| 4.159 | 62.6 |
| 4.160 | 76.8 |
| 4.161 | <25 |
| 4.162 | 361 |
| 4.163 | 30.3 |
| 4.164 | 28.8 |
| 4.165 | 144 |

POTENCY TABLE

| Ex. No. | RIPK1 V0 Ec$_{50}$ |
|---|---|
| 4.166 | 56.4 |
| 4.167 | 259 |
| 4.168 | 42.9 |
| 4.169 | 26.4 |
| 4.170 | <25 |
| 4.171 | <25 |
| 4.172 | 25.2 |
| 4.173 | 69.2 |
| 4.174 | <25 |
| 4.175 | <25 |
| 4.176 | 48.8 |
| 4.177 | <25 |
| 4.178 | <25 |
| 4.179 | <25 |
| 4.180 | <25 |
| 4.181 | 110 |
| 4.182 | <25 |
| 4.183 | <25 |
| 4.184 | <25 |
| 4.185 | 83.0 |
| 4.186 | <25 |
| 4.187 | 357 |
| 4.188 | 540 |
| 4.189 | 25.4 |
| 4.190 | 92.6 |
| 4.191 | 53.0 |
| 4.192 | 54.4 |
| 4.193 | <25 |
| 4.194 | 699 |
| 4.195 | 48.4 |
| 4.196 | 31.7 |
| 4.197 | 25.1 |
| 4.198 | 249 |
| 4.199 | 36.2 |
| 4.200 | 52.5 |
| 4.201 | <25 |
| 4.202 | 38.5 |
| 4.203 | 48.0 |
| 4.204 | <25 |
| 4.205 | 63.3 |
| 4.206 | <25 |
| 4.207 | <25 |
| 4.208 | 56.0 |
| 4.209 | 166 |
| 4.210 | 76.0 |
| 4.211 | <25 |
| 4.212 | <25 |
| 4.213 | <25 |
| 4.214 | 128 |
| 4.215 | 552 |
| 4.216 | <25 |
| 4.217 | 25.8 |
| 4.218 | <25 |
| 4.219 | <25 |
| 4.220 | <25 |
| 4.221 | <25 |
| 4.222 | 57.3 |
| 4.223 | <25 |
| 4.224 | <25 |
| 4.225 | 31.8 |
| 4.226 | <25 |
| 4.227 | 27.3 |
| 4.228 | 78.9 |
| 4.229 | <25 |
| 4.230 | <25 |
| 4.231 | <25 |
| 4.232 | 1 |
| 4.233 | <25 |
| 4.234 | 56.5 |
| 4.235 | <25 |
| 4.236 | 50.0 |
| 4.237 | <25 |
| 4.238 | <25 |
| 4.239 | <25 |
| 4.240 | <25 |
| 4.241 | <25 |
| 4.242 | <25 |
| 4.243 | 26.31 |
| 4.244 | <25 |
| 4.245 | <25 |
| 4.246 | <25 |
| 4.247 | 86.5 |
| 4.248 | 33.7 |
| 4.249 | <25 |
| 4.250 | <25 |
| 4.251 | <25 |
| 4.252 | <25 |
| 4.253 | <25 |
| 4.254 | 126 |
| 4.255 | 40.3 |
| 4.256 | 25 |
| 4.257 | <25 |
| 4.258 | <25 |
| 4.259 | <25 |
| 4.260 | <25 |
| 4.261 | <25 |
| 4.262 | 256 |
| 4.263 | 26.2 |
| 4.264 | <25 |
| 4.265 | 28.4 |
| 4.266 | <25 |
| 4.267 | <25 |
| 4.268 | <25 |
| 4.269 | <25 |
| 4.270 | <25 |
| 4.271 | <25 |
| 4.272 | 931 |
| 4.273 | 566 |
| 5.1 | <25 |
| 5.2 | <25 |
| 5.3 | <25 |
| 5.4 | <25 |
| 5.5 | <25 |
| 5.6 | <25 |
| 5.7 | 236 |
| 5.8 | <25 |
| 5.9 | <25 |
| 5.10 | <25 |
| 5.11 | <25 |
| 5.12 | <25 |
| 5.13 | 277 |
| 5.14 | <25 |
| 5.15 | 96.8 |
| 5.16 | <25 |
| 5.17 | 25.0 |
| 5.18 | 138 |
| 5.19 | 333 |
| 5.20 | 212 |
| 5.21 | 342 |
| 5.22 | 392 |
| 5.23 | 143 |
| 5.24 | <25 |
| 5.25 | <25 |
| 5.26 | 737 |
| 5.27 | 170 |
| 5.28 | 208 |
| 5.29 | 62.2 |
| 5.30 | 28.4 |
| 5.31 | <25 |
| 5.32 | 409 |
| 5.33 | 189 |
| 5.34 | <25 |
| 5.35 | 25.0 |
| 5.36 | <25 |
| 5.37 | <25 |
| 5.38 | 103. |
| 5.39 | 172 |
| 5.40 | 459 |

POTENCY TABLE

| Ex. No. | RIPK1 V0 $Ec_{50}$ |
|---|---|
| 5.41 | 129 |
| 5.42 | 39.2 |
| 5.43 | <25 |
| 5.44 | 33.1 |
| 5.45 | 31.0 |
| 5.46 | 444 |
| 5.47 | 26.9 |
| 5.48 | 42.2 |
| 5.49 | 78.1 |
| 5.50 | <25 |
| 5.51 | 48.3 |
| 5.52 | 88.8 |
| 5.53 | 509 |
| 5.54 | 27.2 |
| 5.55 | 26.2 |
| 5.56 | <25 |
| 5.57 | <25 |
| 5.58 | 24.8 |
| 5.59 | <25 |
| 5.60 | <25 |
| 5.61 | <25 |
| 5.62 | <25 |
| 5.63 | <25 |
| 5.64 | 38.8 |
| 5.65 | 244 |
| 5.66 | 81.1 |
| 5.67 | 135 |
| 5.68 | <25 |
| 5.69 | 45.3 |
| 5.70 | <25 |
| 5.71 | 155 |
| 5.72 | 30.8 |
| 5.73 | <25 |
| 5.74 | 42.4 |
| 5.75 | 524 |
| 5.76 | 924 |
| 6.1 | 388 |
| 6.2 | 493 |
| 6.3 | 60.1 |
| 6.4 | 760 |
| 6.5 | <25 |
| 6.6 | <25 |
| 6.7 | <25 |
| 6.8 | <25 |
| 6.9 | <25 |
| 6.10 | <25 |
| 6.11 | 69.2 |
| 6.12 | 25.1 |
| 6.13 | 60.0 |
| 6.14 | 30.0 |
| 6.15 | 547 |
| 6.16 | 276 |
| 6.17 | 173 |
| 6.18 | 154 |
| 6.19 | <25 |
| 6.20 | 136 |
| 6.21 | 881 |
| 6.22 | 30.5 |
| 6.23 | 96.4 |
| 6.24 | 32.3 |
| 6.25 | 82.4 |
| 6.26 | 321 |
| 6.27 | 47.6 |
| 6.28 | 30.2 |
| 6.29 | 413 |
| 6.30 | 208 |
| 6.31 | 36.5 |
| 6.32 | 228 |
| 6.33 | 40.2 |
| 6.34 | 550 |
| 6.35 | 89.7 |
| 6.36 | 851 |
| 6.37 | 230 |
| 6.38 | 867 |
| 6.39 | 738 |
| 6.40 | 436 |
| 6.41 | 131 |
| 6.42 | <25 |
| 6.43 | 151 |
| 6.44 | 67.1 |
| 6.45 | 451 |
| 6.46 | 211 |
| 6.47 | <25 |
| 6.48 | 34.2 |
| 6.49 | 989 |
| 6.50 | <25 |
| 6.51 | 600 |
| 6.52 | 528 |
| 6.53 | 147 |
| 6.54 | 45.1 |
| 6.55 | 280 |
| 6.56 | <25 |
| 6.57 | 426 |
| 6.58 | 263 |
| 6.59 | 281 |
| 6.60 | 95.0 |
| 6.61 | 261 |
| 6.62 | 64.8 |
| 6.63 | 57.9 |
| 6.64 | <25 |
| 6.65 | <25 |
| 6.66 | 311 |
| 6.67 | 50. |
| 6.68 | 212 |
| 6.69 | 46.8 |
| 6.70 | <25 |
| 6.71 | <25 |
| 6.72 | 41.3 |
| 6.73 | 48.6 |
| 6.74 | 31.9 |
| 6.75 | 24.7 |
| 6.76 | 182 |
| 6.77 | 572 |
| 6.78 | 36.9 |
| 6.79 | 38.3 |
| 6.80 | 153 |
| 6.81 | 935 |
| 6.82 | <25 |
| 6.83 | 31.8 |
| 6.84 | 405 |
| 6.85 | 36.9 |
| 6.86 | 86.0 |
| 6.87 | 43.8 |
| 6.88 | 136 |
| 6.89 | 35.4 |
| 6.90 | 36.1 |
| 6.91 | 706 |
| 6.92 | 40.6 |
| 6.93 | 192 |
| 6.94 | 30.5 |
| 6.95 | 245 |
| 6.96 | 31.6 |
| 6.97 | <25 |
| 6.98 | 523 |
| 6.99 | 146 |
| 6.100 | 66.7 |
| 6.101 | 56.9 |
| 6.102 | 48.6 |
| 6.103 | 934 |
| 6.104 | 32.2 |
| 6.105 | 841 |
| 6.106 | 202 |
| 6.107 | <25 |
| 6.108 | 43.8 |
| 6.109 | <25 |
| 6.110 | <25 |
| 6.111 | <25 |
| 6.112 | <25 |

POTENCY TABLE

| Ex. No. | RIPK1 V0 Ec$_{50}$ |
|---|---|
| 6.113 | <25 |
| 6.114 | <25 |
| 6.115 | <25 |
| 6.116 | <25 |
| 6.117 | <25 |
| 6.118 | <25 |
| 6.119 | <25 |
| 6.120 | <25 |
| 6.121 | <25 |
| 6.122 | 47.5 |
| 6.123 | <25 |
| 6.124 | <25 |
| 6.125 | <25 |
| 6.126 | 619 |
| 6.127 | 60.8 |
| 6.128 | 42.7 |
| 6.129 | 188 |
| 6.130 | <25 |
| 6.131 | <25 |
| 6.132 | 71.7 |
| 6.133 | <25 |
| 6.134 | 92.4 |
| 6.135 | 457 |
| 6.136 | 136 |
| 6.137 | 78.7 |
| 6.138 | <25 |
| 6.139 | <25 |
| 6.140 | 47.1 |
| 6.141 | <25 |
| 6.142 | 75.1 |
| 6.143 | 56.8 |
| 6.144 | <25 |
| 6.145 | <25 |
| 6.146 | 34.9 |
| 6.147 | 328 |
| 6.148 | <25 |
| 6.149 | <25 |
| 6.150 | 118 |
| 6.151 | 349 |
| 6.152 | <25 |
| 6.153 | <25 |
| 6.154 | <25 |
| 6.155 | <25 |
| 6.156 | <25 |
| 6.157 | <25 |
| 6.158 | <25 |
| 6.159 | 826 |
| 6.160 | <25 |
| 6.161 | 275 |
| 6.162 | 38.0 |
| 6.163 | 29.1 |
| 7.1 | 121 |
| 7.2 | <25 |
| 7.3 | 102 |
| 7.4 | 108 |
| 7.5 | <25 |
| 7.6 | 271 |
| 7.7 | <25 |
| 7.8 | <25 |
| 7.9 | 72.6 |
| 7.10 | 147 |
| 7.11 | 92.2 |
| 7.12 | 165 |
| 7.13 | 191 |
| 7.14 | 69.8 |
| 7.15 | 171 |
| 8.1 | 728 |
| 8.2 | 685 |
| 8.3 | 213 |
| 8.4 | 672 |
| 8.5 | 429 |
| 8.6 | 421 |
| 8.7 | 345 |
| 8.8 | 429 |
| 8.9 | 421 |
| 8.10 | 345 |
| 9.1 | <25 |
| 10.1 | <25 |
| 10.2 | <25 |
| 10.3 | 355 |
| 10.4 | <25 |
| 11.1 | 885 |
| 11.2 | 295 |
| 11.3 | 66.88 |
| 11.4 | 61.1 |
| 11.5 | 67.7 |
| 11.6 | 31.4 |
| 11.7 | 91.3 |
| 11.8 | 215 |
| 11.9 | 907 |
| 11.10 | 253 |
| 11.11 | 42.0 |
| 11.12 | 97.7 |
| 11.13 | 266 |
| 11.14 | 33.7 |
| 11.15 | 81.7 |
| 11.16 | 35.4 |
| 11.17 | 204 |
| 11.18 | 93.0 |
| 11.19 | 624 |
| 11.20 | 26.85 |
| 11.21 | 229 |
| 11.22 | 761 |
| 11.23 | 306 |
| 11.24 | 366 |
| 11.25 | 61.1 |
| 11.26 | 132 |
| 11.27 | 757 |
| 11.28 | <25 |
| 11.29 | <25 |
| 11.30 | 191 |
| 11.31 | <25 |
| 11.32 | 319 |
| 11.33 | <25 |
| 11.34 | 601 |
| 11.35 | 34.5 |
| 12.1 | 537 |
| 13.1 | 26.8 |
| 13.2 | <25 |
| 13.3 | <25 |
| 13.4 | 56.0 |
| 13.5 | 98.4 |
| 13.6 | <25 |
| 13.7 | <25 |
| 13.8 | 664 |
| 13.9 | 339 |
| 13.10 | 36.8 |
| 13.11 | <25 |
| 13.12 | <25 |
| 13.13 | 366 |
| 13.14 | 487 |
| 13.15 | 188 |
| 13.16 | 32.0 |
| 13.17 | <25 |
| 13.18 | <25 |
| 13.19 | <25 |
| 13.20 | 24.9 |
| 13.21 | 25.3 |
| 13.22 | 37.6 |
| 13.23 | 54.3 |
| 13.24 | <25 |
| 14.1 | <25 |
| 14.2 | <25 |
| 14.3 | <25 |
| 15.1 | <25 |
| 15.2 | <25 |
| 15.3 | <25 |
| 15.4 | <25 |

-continued

POTENCY TABLE

| Ex. No. | RIPK1 V0 Ec$_{50}$ |
|---|---|
| 16.1 | <25 |
| 17.1 | 34.4 |
| 17.2 | 26.1 |
| 17.3 | <25 |
| 17.4 | 196 |
| 17.5 | 344 |
| 17.6 | 94.4 |
| 17.7 | 558 |
| 17.8 | 49.0 |
| 17.9 | 40.7 |
| 17.10 | <25 |
| 17.11 | <25 |
| 17.12 | 342 |
| 17.13 | 208 |
| 17.14 | <25 |
| 17.15 | <25 |
| 18.1 | 159 |
| 18.2 | 27.6 |
| 18.3 | <25 |
| 19.1 | <25 |
| 19.2 | <25 |
| 19.3 | <25 |
| 19.4 | 32.0 |
| 19.5 | 208 |
| 19.6 | 45.4 |
| 19.7 | 25.0 |
| 19.8 | 394 |
| 20.1 | 45.4 |
| 20.2 | 25.0 |
| 20.3 | 394 |
| 20.4 | <25 |
| 20.5 | <25 |
| 20.6 | <25 |
| 20.7 | <25 |
| 20.8 | <25 |
| 21.1 | <25 |
| 21.2 | <25 |
| 21.3 | <25 |
| 21.4 | 117 |
| 21.5 | <25 |
| 21.6 | <25 |
| 21.7 | 181 |
| 21.8 | 36.6 |
| 21.9 | 37.8 |
| 21.10 | <25 |
| 21.11 | <25 |
| 21.12 | 25.2 |
| 21.13 | 40.3 |
| 21.14 | 57.8 |
| 21.15 | <25 |
| 21.16 | <25 |
| 21.17 | <25 |
| 21.18 | <25 |
| 21.19 | <25 |
| 21.20 | <25 |
| 21.21 | <25 |
| 21.22 | <25 |
| 21.23 | <25 |
| 21.24 | <25 |
| 22.1 | 221 |
| 22.2 | 243 |
| 22.3 | 807 |
| 22.4 | 701 |
| 22.5 | 213 |
| 22.6 | 234 |
| 22.7 | 103 |
| 22.8 | 348 |
| 23.1 | <25 |

What is claimed is:

1. A compound of Formula I:

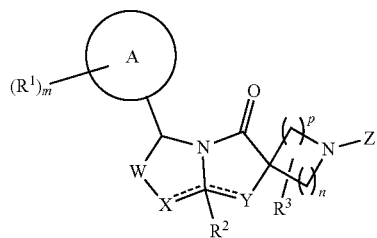

I or a pharmaceutically acceptable salt thereof, wherein:
A is aryl, heteroaryl, heterocycloalkyl or $C_3$-$C_6$cycloalkyl;
each occurrence of $R^1$ is independently selected from the group consisting of: —OH, $C_1$-$C_6$alkylOH, —CN, $C_1$-$C_6$alkylCN, $C_1$-$C_6$alkyl, halo$C_1$-$C_6$alkyl, halogen, —NH$_2$, —N($C_1$-$C_6$alkyl)$_2$, —NH($C_1$-$C_6$alkyl) and $C_1$-$C_6$alkoxy;
W is CH$_2$;
X is CH$_2$;
Y O;
$R^2$ is hydrogen, OH, $C_1$-$C_6$alkylOH, CN, $C_1$-$C_6$alkylCN, $C_1$-$C_6$alkyl, halo$C_1$-$C_6$alkyl, halogen, —NH$_2$, —N($C_1$-$C_6$alkyl)$_2$, —NH($C_1$-$C_6$alkyl) or $C_1$-$C_6$alkoxy, or when X or Y is N, $R^2$ is absent;
$R^3$ is hydrogen, —OH, $C_1$-$C_6$alkylOH, —CN, $C_1$-$C_6$alkylCN, $C_1$-$C_6$alkyl, halo$C_1$-$C_6$alkyl, halogen, —NH$_2$, —N($C_1$-$C_6$alkyl)$_2$, —NH($C_1$-$C_6$alkyl) or $C_1$-$C_6$alkoxy;
Z is —CN, aryl, $C_1$-$C_6$alkylaryl, —COaryl, —CONHaryl, —SO$_2$aryl, $C_3$-$C_{10}$cycloalkyl, $C_1$-$C_6$alkyl$C_3$-$C_{10}$cycloalkyl, —COC$_3$-$C_{10}$cycloalkyl, —CONHC$_3$-$C_{10}$cycloalkyl, —SO$_2$C$_3$-$C_{10}$cycloalkyl, heteroaryl, $C_1$-$C_6$alkylheteroaryl, —COheteroaryl, —CONHheteroaryl, —SO$_2$heteroaryl, heterocycloalkyl, $C_1$-$C_6$alkylheterocycloalkyl, —COheterocycloalkyl, —CONHheterocycloalkyl, —SO$_2$heterocycloalkyl, —COOC$_1$-$C_6$alkyl, or —COOC$_3$-$C_6$cycloalkyl, wherein the aryl, $C_1$-$C_6$alkylaryl, —COaryl, —CONHaryl, —SO$_2$aryl, $C_3$-$C_{10}$cycloalkyl, $C_1$-$C_6$alkyl$C_3$-$C_{10}$cycloalkyl, —COC$_3$-$C_{10}$cycloalkyl, —CONHC$_3$-$C_{10}$cycloalkyl, —SO$_2$C$_3$-$C_{10}$cycloalkyl, heteroaryl, $C_1$-$C_6$alkylheteroaryl, —COheteroaryl, —CONHheteroaryl, —SO$_2$heteroaryl, heterocycloalkyl, $C_1$-$C_6$alkylheterocycloalkyl, —COheterocycloalkyl, —CONHheterocycloalkyl or —SO$_2$heterocycloalkyl, is unsubstituted or substituted with one to three substituents independently selected from the group consisting of halogen, —CN, $C_1$-$C_6$alkylCN, $C_1$-$C_6$alkyl, $C_2$-$C_6$ alkynyl, $C_1$-$C_6$haloalkyl, $C_1$-$C_6$alkoxy, $C_1$-$C_6$haloalkoxy, —COOC$_1$-$C_6$alkyl, —SC$_1$-$C_6$alkyl, oxo, $C_3$-$C_6$cycloalkyl, aryl, heteroaryl and heterocycloalkyl, wherein said substituent heteroaryl, heterocycloalkyl, $C_3$-$C_6$cycloalkyl, $C_2$-$C_6$ alkynyl and $C_1$-$C_6$alkoxy, is unsubstituted or further substituted with one to two substituents independently selected Prom the group consisting of halogen, —CN, $C_1$-$C_6$alkyl, $C_1$-$C_6$haloalkyl, $C_1$-$C_6$alkoxy, —OH and heterocycloalkyl;
m is 0, 1, 2 or 3;
n is 1 or 2; and
p is 1 or 2.

2. The compound of claim 1, or a pharmaceutically acceptable salt thereof, wherein A is aryl, $C_3$-$C_6$cycloalkyl or heteroaryl.

3. The compound of claim 2, or a pharmaceutically acceptable salt thereof, wherein A is aryl, wherein the aryl is phenyl.

4. The compound of claim 2, or a pharmaceutically acceptable salt thereof, wherein A is heteroaryl, wherein the heteroaryl is

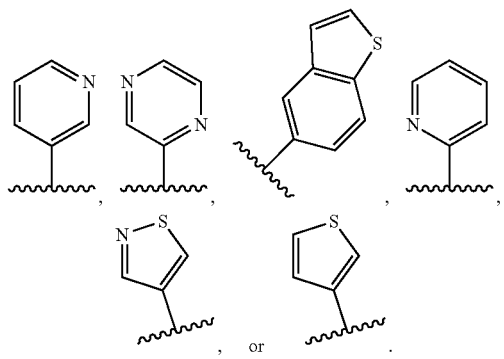

5. The compound of claim 2, or a pharmaceutically acceptable salt thereof, wherein A is $C_3$-$C_6$cycloalkyl, wherein the $C_3$-$C_6$cycloalkyl is cyclohexyl or cyclopentyl.

6. The compound of claim 1, or a pharmaceutically acceptable salt thereof, wherein each occurrence of $R^1$ is independently selected from the group consisting of halogen, —CN, $C_1$-$C_6$alkoxy and $C_1$-$C_6$alkyl.

7. The compound of claim 1, or a pharmaceutically acceptable salt thereof, wherein each occurrence of $R^1$ is independently selected from the group consisting of —CN, fluorine, methoxy, and methyl and m is 1 or 2.

8. The compound of claim 1, or a pharmaceutically acceptable salt thereof, wherein n and p are both 2.

9. The compound of claim 1, or a pharmaceutically acceptable salt thereof, wherein n and p are both 1.

10. The compound of claim 1, or a pharmaceutically acceptable salt thereof, wherein $R^2$ is hydrogen or methyl.

11. The compound of claim 1, or a pharmaceutically acceptable salt thereof, wherein Z is aryl, wherein the aryl is unsubstituted or substituted with one, two or three substituents independently selected from the group consisting of halogen, —CN, $C_1$-$C_6$alkyl, heterocycloalkyl, $C_3$-$C_6$cycloalkyl, $C_1$-$C_6$alkoxy, $C_2$-$C_6$ alkynyl, heteroaryl or $C_1$-$C_6$haloalkoxy, wherein the heterocycloalkyl, $C_2$-$C_6$ alkynyl or $C_3$-$C_6$cycloalkyl is unsubstituted or substituted with an oxo group, —CN or —OH.

12. A compound of Formula I

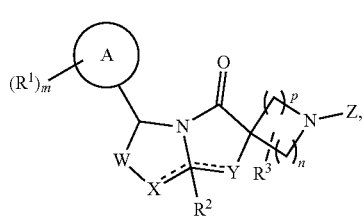

I or a pharmaceutically acceptable salt thereof, wherein:
A is aryl, heteroaryl, heterocycloalkyl or $C_3$-$C_6$cycloalkyl;
W is $CH_2$;
X is $CH_2$;
Y is O;

$R^2$ is hydrogen, OH, $C_1$-$C_6$alkylOH, CN, $C_1$-$C_6$alkylCN, $C_1$-$C_6$alkyl, halo$C_1$-$C_6$alkyl, halogen, —$NH_2$, —N($C_1$-$C_6$alkyl)$_2$, —NH($C_1$-$C_6$alkyl) or $C_1$-$C_6$alkoxy, or when X or Y is N, $R^2$ is absent;

$R^3$ is hydrogen, —OH, $C_1$-$C_6$alkylOH, —CN, $C_1$-$C_6$alkylCN, $C_1$-$C_6$alkyl, halo$C_1$-$C_6$alkyl, halogen, —$NH_2$, —N($C_1$-$C_6$alkyl)$_2$, —NH($C_1$-$C_6$alkyl) or $C_1$-$C_6$alkoxy;

each occurrence of $R^4$ is independently selected from the group consisting of hydrogen, —OH, $C_1$-$C_6$alkylOH, —CN, $C_1$-$C_6$alkylCN, $C_1$-$C_6$alkyl, halo$C_1$-$C_6$alkyl, halogen, —$NH_2$, —N($C_1$-$C_6$alkyl)$_2$, —NH($C_1$-$C_6$alkyl) and $C_1$-$C_6$alkoxy;

Z is heteroaryl, wherein the heteroaryl is unsubstituted or substituted with one to three substituents independently selected from the group consisting of —CN, —OH, phenyl, halogen, $C_1$-$C_6$alkylOH, $C_1$-$C_6$alkylCN, $C_1$-$C_6$alkyl, $C_1$-$C_6$haloalkyl, $C_1$-$C_6$alkoxy, $C_1$-$C_6$haloalkoxy, —CO$C_1$-$C_6$alkyl, —COO$C_1$-$C_6$alkyl, —S$C_1$-$C_6$alkyl, oxo, $C_3$-$C_6$cycloalkyl, heterocycloalkyl, CONH($C_1$-$C_6$alkyl), $CONH_2$, CON($C_1$-$C_6$alkyl)$_2$ or heteroaryl, wherein the phenyl, $C_1$-$C_6$alkoxy or heteroaryl is unsubstituted or substituted with halogen, $C_1$-$C_6$haloalkyl, heterocycloalkyl or $C_1$-$C_6$alkyl;

m is 0, 1, 2 or 3;
n is 1 or 2; and
p is 1 or 2.

13. The compound of claim 12, or a pharmaceutically acceptable salt thereof, wherein Z is heteroaryl, wherein the heteroaryl is:

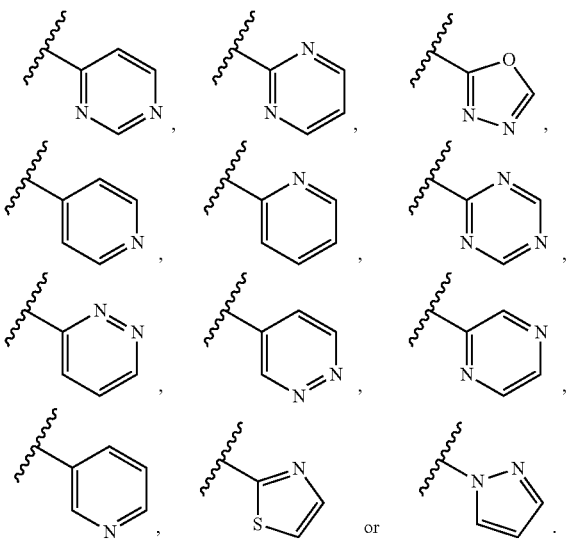

14. The compound of claim 12, or a pharmaceutically acceptable salt thereof, wherein Z is heteroaryl, wherein the heteroaryl is

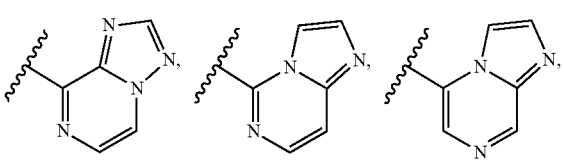

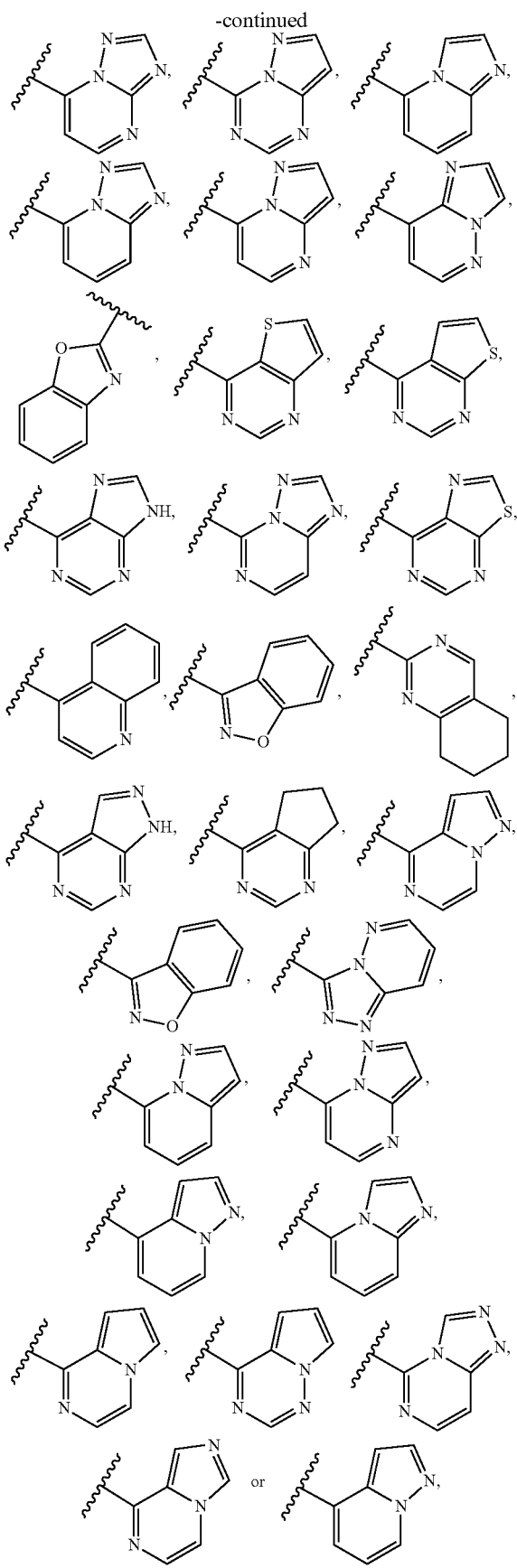

15. The compound of claim 1, or a pharmaceutically acceptable salt thereof, wherein Z is SO$_2$aryl, wherein the SO$_2$aryl is unsubstituted or substituted with halogen, —CN or C$_1$-C$_6$alkyl.

16. The compound of claim 1, or a pharmaceutically acceptable salt thereof, wherein Z is —COaryl, wherein the —COaryl is unsubstituted or substituted with one, two b or three substituents independently selected from the group consisting of halogen, —CN, C$_1$-C$_6$alkyl, heterocycloalkyl, C$_3$-C$_6$cycloalkyl, C$_1$-C$_6$alkoxy, C$_2$-C$_6$ alkynyl, heteroaryl and C$_1$-C$_6$haloalkoxy, wherein the heterocycloalkyl, C$_2$-C$_6$ alkynyl or C$_3$-C$_6$cycloalkyl is unsubstituted or b substituted with —CN or —OH.

17. The compound of claim 1, or a pharmaceutically acceptable salt thereof, wherein Z is —COheteroaryl, wherein the —COheteroaryl is 533
-continued
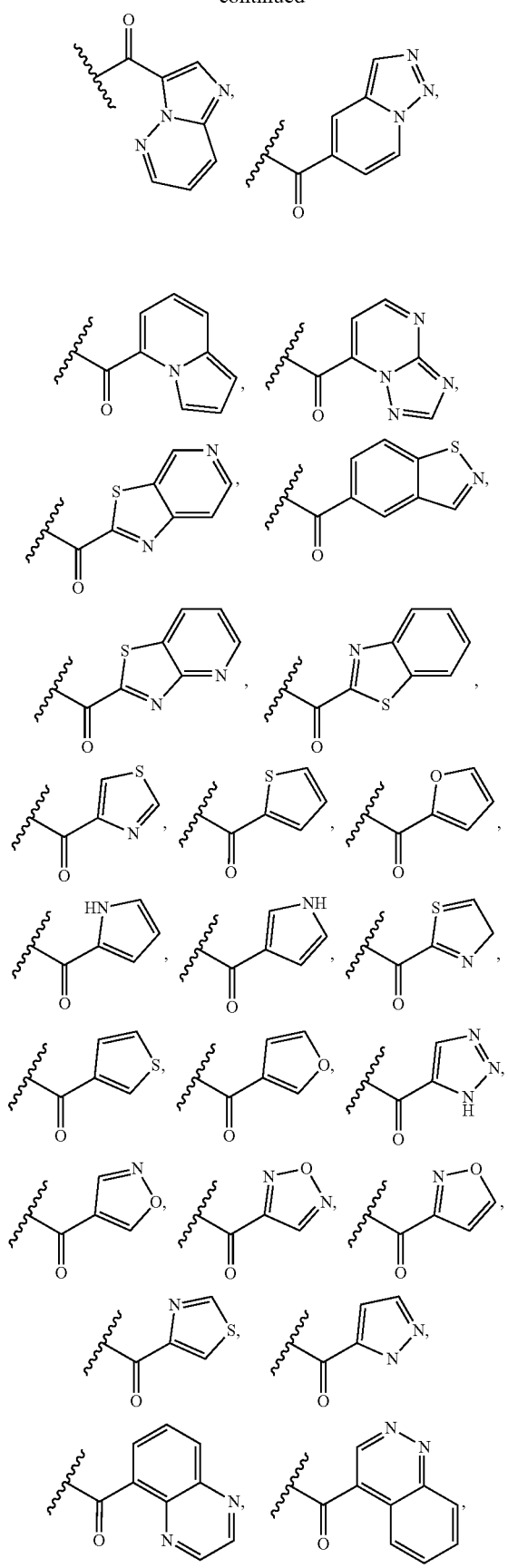
534
-continued
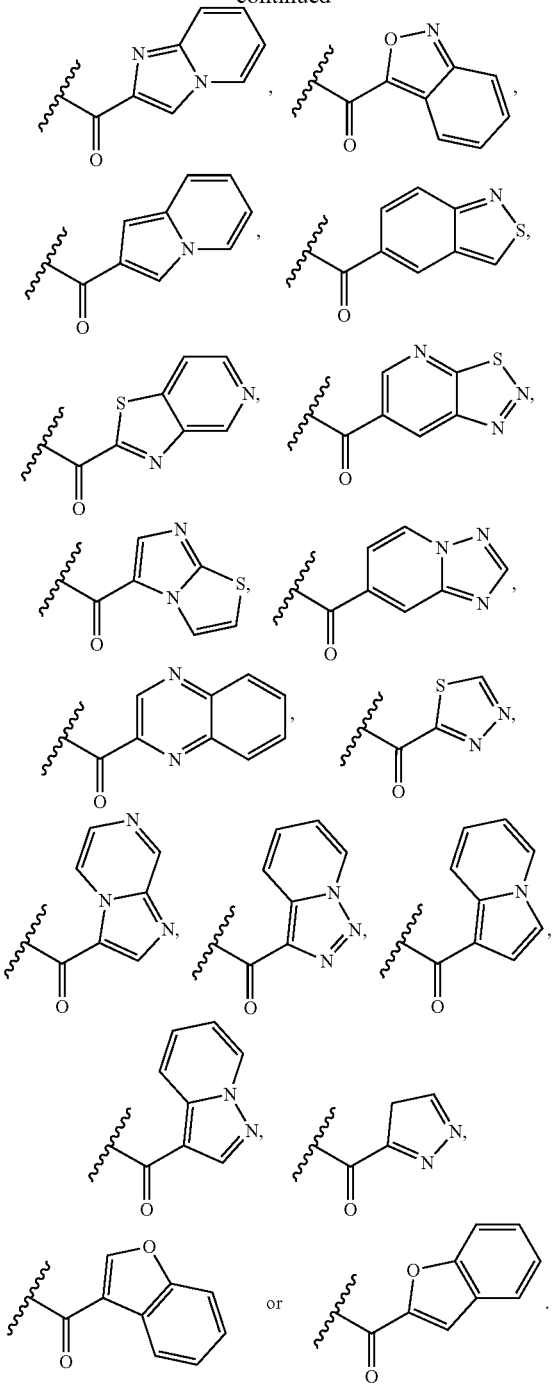
18. The compound of claim 1, or a pharmaceutically acceptable salt thereof, wherein Z is
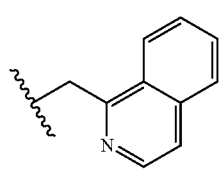

19. The compound of claim 1, or a pharmaceutically acceptable salt thereof, wherein Z is —COOCH$_3$, —COOcyclobutyl, —COcyclohexane, —COcyclopentane, or

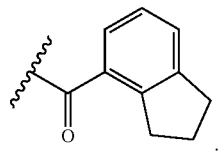 [SMILES: *C(=O)c1cccc2c1CCC2]

20. The compound of claim 1, or a pharmaceutically acceptable salt thereof, wherein Z is —CONHaryl.

21. The compound of claim 1, or a pharmaceutically acceptable salt thereof, wherein Z is —COheterocycloalkyl, wherein the —COheterocycloalkyl is

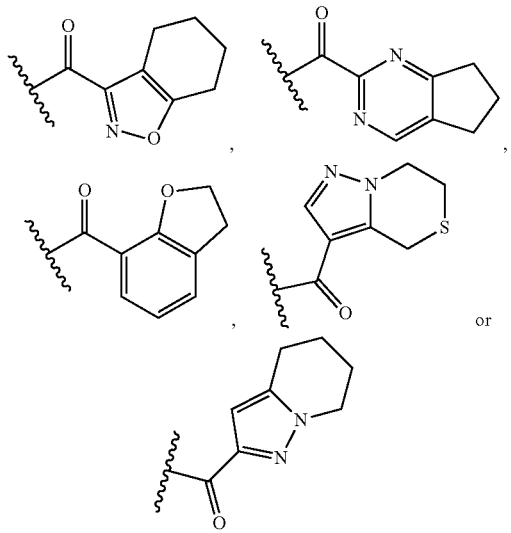

22. A compound of Formula I

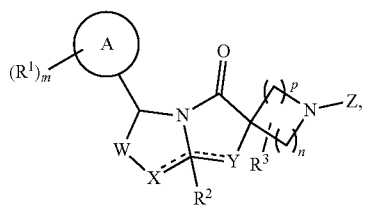

or a pharmaceutically acceptable salt thereof, wherein:
A is aryl, heteroaryl, heterocycloalkyl or C$_3$-C$_6$cycloalkyl;
W is CH$_2$;
X is CH$_2$;
Y is O;
R$^2$ is hydrogen, OH, C$_1$-C$_6$alkylOH, CN, C$_1$-C$_6$alkylCN, C$_1$-C$_6$alkyl, haloC$_1$-C$_6$alkyl, halogen, —NH$_2$, —N(C$_1$-C$_6$alkyl)$_2$, —NH(C$_1$-C$_6$alkyl) or C$_1$-C$_6$alkoxy, or when X or Y is N, R$^2$ is absent;
R$^3$ is hydrogen, —OH, C$_1$-C$_6$alkylOH, —CN, C$_1$-C$_6$alkylCN, C$_1$-C$_6$alkyl, haloC$_1$-C$_6$alkyl, halogen, —NH$_2$, —N(C$_1$-C$_6$alkyl)$_2$, —NH(C$_1$-C$_6$alkyl) or C$_1$-C$_6$alkoxy;

each occurrence of R$^4$ is independently selected from the group consisting of hydrogen, —OH, C$_1$-C$_6$alkylOH, —CN, C$_1$-C$_6$alkylCN, C$_1$-C$_6$alkyl, haloC$_1$-C$_6$alkyl, halogen, —NH$_2$, —N(C$_1$-C$_6$alkyl)$_2$, —NH(C$_1$-C$_6$alkyl) and C$_1$-C$_6$alkoxy;
Z is aryl, C$_1$-C$_6$alkylaryl, —COaryl, —CONHaryl, —SO$_2$aryl, C$_3$-C$_{10}$cycloalkyl, C$_1$-C$_6$alkylC$_3$-C$_{10}$cycloalkyl, —COC$_3$-C$_{10}$cycloalkyl, —CONHC$_3$-C$_{10}$cycloalkyl, —SO$_2$C$_3$-C$_{10}$cycloalkyl, heteroaryl, C$_1$-C$_6$alkylheteroaryl, —COheteroaryl, —CONHheteroaryl, —SO$_2$heteroaryl, heterocycloalkyl, C$_1$-C$_6$alkylheterocycloalkyl, —COheterocycloalkyl, —CONHheterocycloalkyl or —SO$_2$heterocycloalkyl, wherein the aryl, C$_1$-C$_6$alkylaryl, —COaryl, —CONHaryl, —SO$_2$aryl, C$_3$-C$_{10}$cycloalkyl, C$_1$-C$_6$alkylC$_3$-C$_{10}$cycloalkyl, —COC$_3$-C$_{10}$cycloalkyl, —CONHC$_3$-C$_{10}$cycloalkyl, —SO$_2$C$_3$-C$_{10}$cycloalkyl, heteroaryl, C$_1$-C$_6$alkylheteroaryl, —COheteroaryl, —CONHheteroaryl, —SO$_2$heteroaryl, heterocycloalkyl, C$_1$-C$_6$alkylheterocycloalkyl, —COheterocycloalkyl, —CONHheterocycloalkyl or —SO$_2$heterocycloalkyl is unsubstituted or substituted with one to three substituents independently selected from the group consisting of: —CN, —OH, phenyl, halogen, C$_1$-C$_6$alkylOH, C$_1$-C$_6$alkylCN, C$_1$-C$_6$alkyl, C$_1$-C$_6$haloalkyl, C$_1$-C$_6$alkoxy, C$_1$-C$_6$haloalkoxy, —COC$_1$-C$_6$alkyl, C$_1$-C$_6$alkynyl, —COOC$_1$-C$_6$alkyl, —SC$_1$-C$_6$alkyl, oxo, C$_3$-C$_6$cycloalkyl, heterocycloalkyl, —CONH(C$_1$-C$_6$alkyl), —CONH$_2$, —CON(C$_1$-C$_6$alkyl)$_2$ and heteroaryl, wherein said substituent phenyl, heterocycloalkyl, C$_1$-C$_6$alkynyl, C$_3$-C$_6$cycloalkyl, C$_1$-C$_6$alkoxy or heteroaryl is unsubstituted or further substituted with an oxo group, —CN —OH, halogen, C$_1$-C$_6$haloalkyl, heterocycloalkyl or C$_1$-C$_6$alkyl;
m is 0, 1, 2 or 3;
n is 1 or 2; and
p is 1 or 2.

23. A compound of Formula IV:

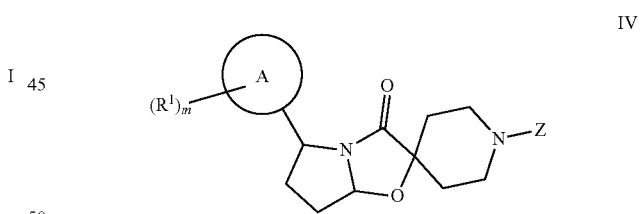

or a pharmaceutically acceptable salt thereof, wherein:
A is aryl, heteroaryl, heterocycloalkyl or C$_3$-C$_6$cycloalkyl;
each occurrence of R$^1$ is independently selected from the group consisting of —OH, C$_1$-C$_6$alkylOH, —CN, C$_1$-C$_6$alkylCN, C$_1$-C$_6$alkyl, haloC$_1$-C$_6$alkyl, halogen, —NH$_2$, —N(C$_1$-C$_6$alkyl)$_2$, —NH(C$_1$-C$_6$alkyl) and C$_1$-C$_6$alkoxy;
Z is —CN, aryl, C$_1$-C$_6$alkylaryl, —COaryl, —CONHaryl, —SO$_2$aryl, C$_3$-C$_{10}$cycloalkyl, C$_1$-C$_6$alkylC$_3$-C$_{10}$cycloalkyl, —COC$_3$-C$_{10}$cycloalkyl, —CONHC$_3$-C$_{10}$cycloalkyl, —SO$_2$C$_3$-C$_{10}$cycloalkyl, heteroaryl, C$_1$-C$_6$alkylheteroaryl, —COheteroaryl, —CONHheteroaryl, —SO$_2$heteroaryl, heterocycloalkyl, C$_1$-C$_6$alkylheterocycloalkyl, —COheterocycloalkyl, —CONHheterocycloalkyl, —SO$_2$heterocycloalkyl, —COOC$_1$-C$_6$alkyl or —COOC$_3$-C$_6$cycloalkyl, wherein the aryl, C$_1$-C$_6$alkylaryl, —COaryl, —CONHaryl, —SO$_2$aryl, C$_3$-C$_{10}$cycloalkyl, C$_1$-C$_6$alkylC$_3$-C$_{10}$cycloalkyl, —COC$_3$-C$_{10}$cycloalkyl, —CONHC$_3$-C$_{10}$cycloalkyl, —SO$_2$C$_3$-C$_{10}$cycloalkyl, heteroaryl, C$_1$-C$_6$alkylheteroaryl, —COheteroaryl, —CONHheteroaryl, —SO$_2$heteroaryl, heterocycloalkyl, C$_1$-C$_6$alkylheterocycloalkyl, —COheterocycloalkyl, —CONHheterocycloalkyl or —SO$_2$heterocycloalkyl, is unsubstituted or substituted with one to four substituents independently selected from the group consisting of: CN, OH, halogen, C$_1$-C$_6$alkylCN, C$_1$-C$_6$alkylOH, C$_1$-C$_6$alkyl, C$_1$-C$_6$alkynyl, C$_1$-C$_6$haloalkyl, C$_1$-C$_6$alkoxy, C$_1$-C$_6$haloalkoxy, —COOC$_1$-C$_6$alkyl, —COC$_1$-C$_6$alkyl, —SC$_1$-C$_6$alkyl, oxo, C$_3$-C$_6$cycloalkyl, aryl, heteroaryl, heterocycloalkyl, —CONH(C$_1$-C$_6$alkyl), —CONH$_2$, and —CON(C$_1$-C$_6$alkyl)$_2$, wherein said substituent heteroaryl, heterocycloalkyl, C$_3$-C$_6$cycloalkyl, C$_1$-C$_6$alkynyl, or C$_1$-C$_6$alkoxy, is unsubstituted or further substituted with one to two substituents independently selected from the group consisting of: halogen, CN, C$_1$-C$_6$alkyl, C$_1$-C$_6$haloalkyl, C$_1$-C$_6$alkoxy, OH and heterocycloalkyl; and m is 0, 1, 2 or 3.

24. The compound of Formula V:

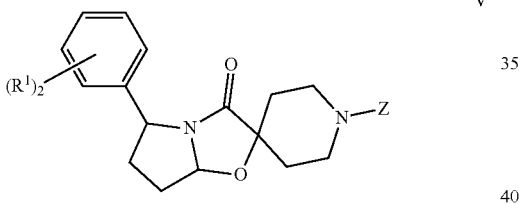

V or a pharmaceutically acceptable salt thereof, wherein:
each occurrence of R$^1$ is independently selected from the group consisting of —OH, C$_1$-C$_6$alkylOH, —CN, C$_1$-C$_6$alkylCN, C$_1$-C$_6$alkyl, haloC$_1$-C$_6$alkyl, halogen and C$_1$-C$_6$alkoxy;

Z is —CN, aryl, C$_1$-C$_6$alkylaryl, —COaryl, —CONHaryl, —SO$_2$aryl, C$_3$-C$_{10}$cycloalkyl, C$_1$-C$_6$alkylC$_3$-C$_{10}$cycloalkyl, —COC$_3$-C$_{10}$cycloalkyl, —CONHC$_3$-C$_{10}$cycloalkyl, —SO$_2$C$_3$-C$_{10}$cycloalkyl, heteroaryl, C$_1$-C$_6$alkylheteroaryl, —COheteroaryl, —CONHheteroaryl, —SO$_2$heteroaryl, heterocycloalkyl, C$_1$-C$_6$alkylheterocycloalkyl, —COheterocycloalkyl, —CONHheterocycloalkyl, —SO$_2$heterocycloalkyl, —COOC$_1$-C$_6$alkyl or —COOC$_3$-C$_6$cycloalkyl, wherein the aryl, C$_1$-C$_6$alkylaryl, —COaryl, —CONHaryl, —SO$_2$aryl, C$_3$-C$_{10}$cycloalkyl, C$_1$-C$_6$alkylC$_3$-C$_{10}$cycloalkyl, —COC$_3$-C$_{10}$cycloalkyl, —CONHC$_3$-C$_{10}$cycloalkyl, —SO$_2$C$_3$-C$_{10}$cycloalkyl, heteroaryl, C$_1$-C$_6$alkylheteroaryl, —COheteroaryl, —CONHheteroaryl, —SO$_2$heteroaryl, heterocycloalkyl, C$_1$-C$_6$alkylheterocycloalkyl, —COheterocycloalkyl, —CONHheterocycloalkyl or —SO$_2$heterocycloalkyl, is unsubstituted or substituted with one to four substituents independently selected from the group consisting of —CN, —OH, halogen, C$_1$-C$_6$alkylCN, C$_1$-C$_6$alkylOH, C$_1$-C$_6$alkyl, C$_1$-C$_6$alkynyl, C$_1$-C$_6$haloalkyl, C$_1$-C$_6$alkoxy, C$_1$-C$_6$haloalkoxy, —COOC$_1$-C$_6$alkyl, —COC$_1$-C$_6$alkyl, —SC$_1$-C$_6$alkyl, oxo, C$_3$-C$_6$cycloalkyl, aryl, heteroaryl, heterocycloalkyl, —CONH(C$_1$-C$_6$alkyl), —CONH$_2$, CON(C$_1$-C$_6$alkyl)$_2$, wherein the heteroaryl, heterocycloalkyl, C$_3$-C$_6$cycloalkyl, C$_1$-C$_6$alkynyl, or C$_1$-C$_6$alkoxy, is unsubstituted or substituted with one to two substituents independently selected from the group consisting of halogen, CN, C$_1$-C$_6$alkyl, C$_1$-C$_6$haloalkyl, C$_1$-C$_6$alkoxy, OH and heterocycloalkyl.

25. A compound selected from the following structures:

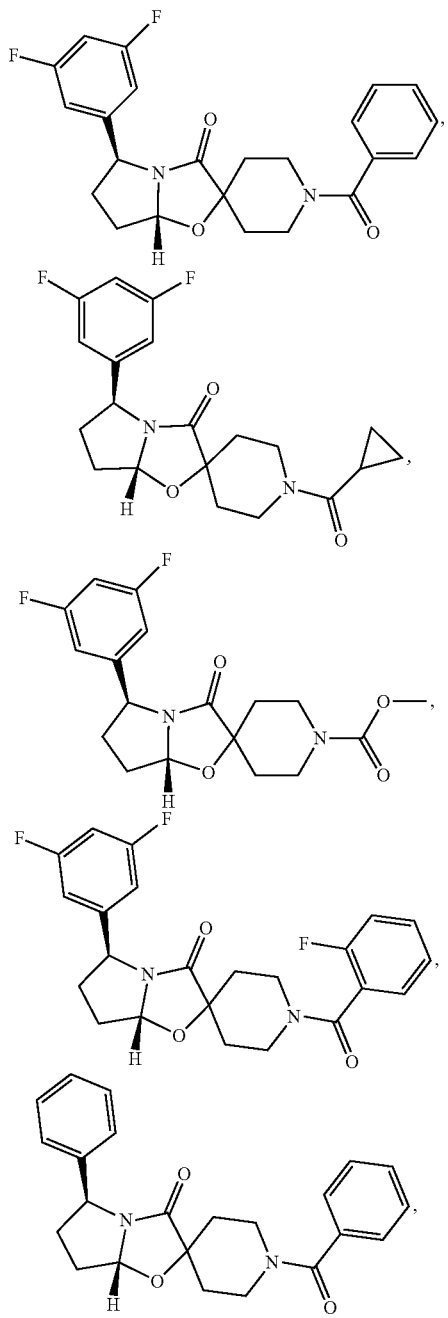

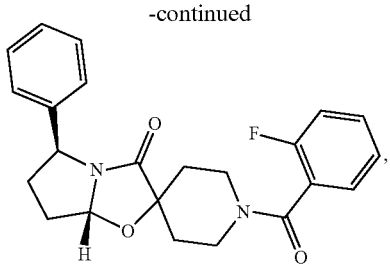
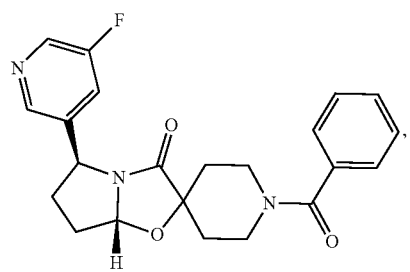
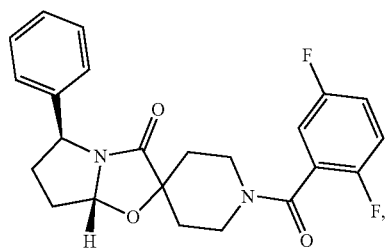
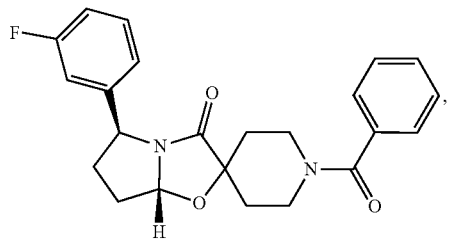
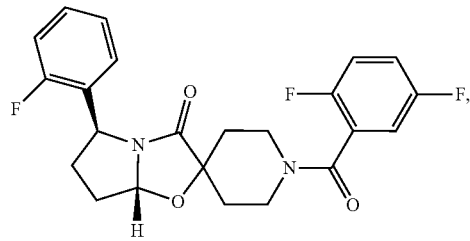
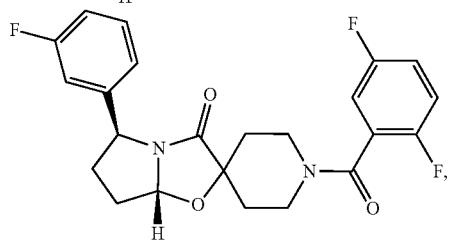
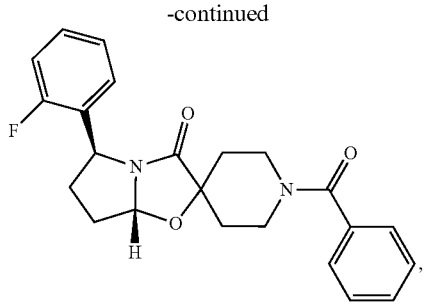
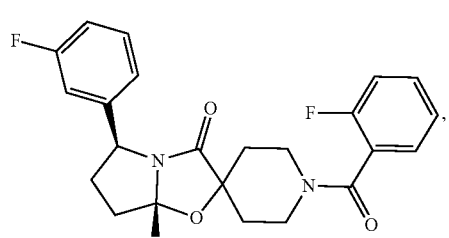
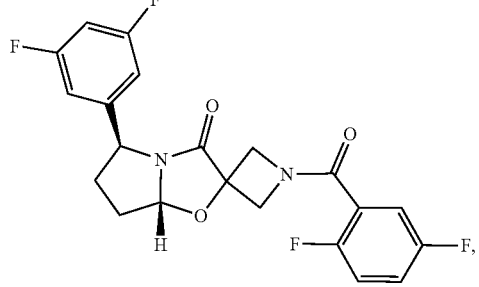
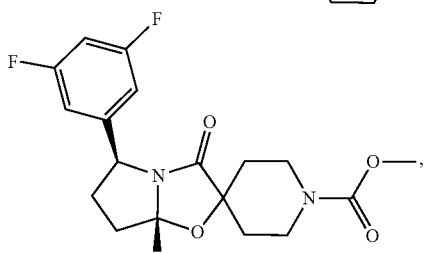
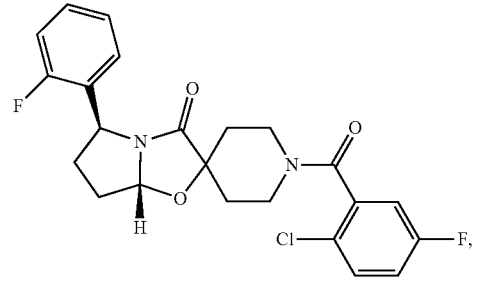
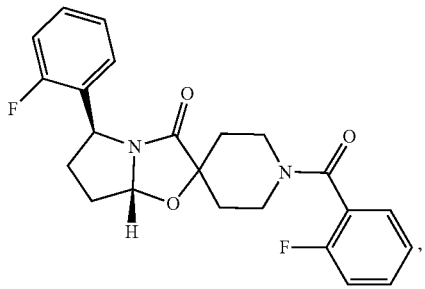

541
-continued
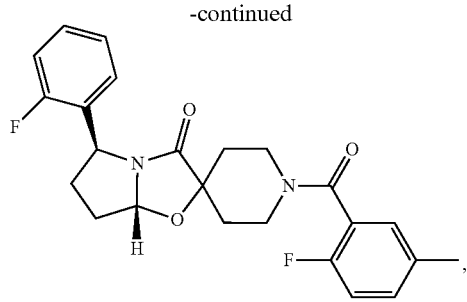
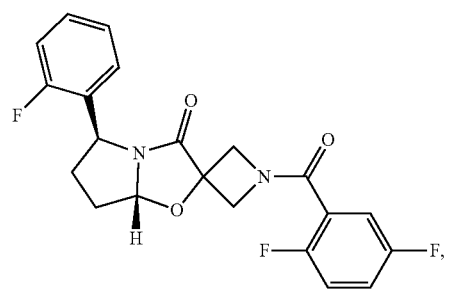
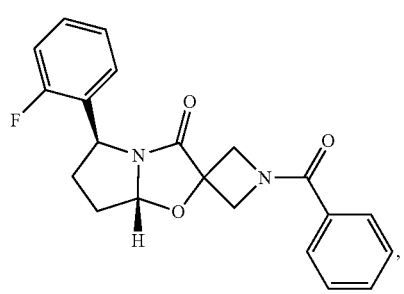
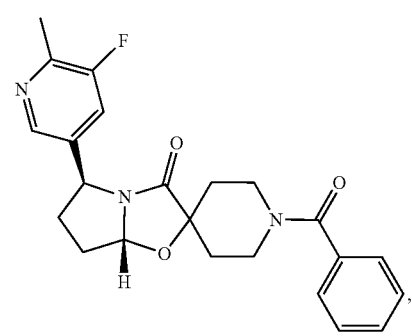
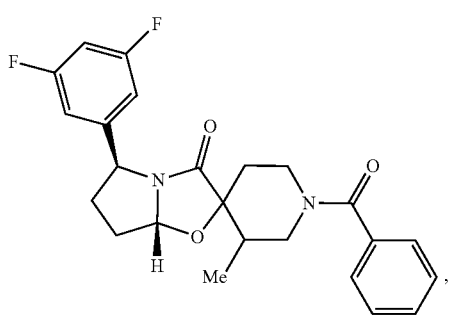
542
-continued
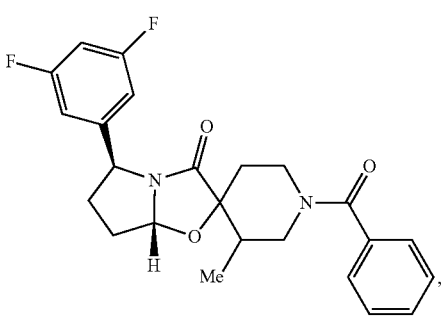
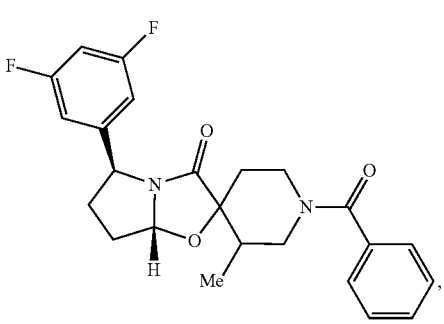
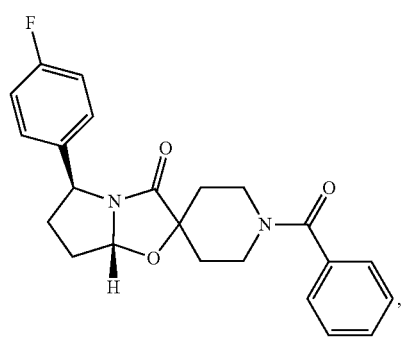
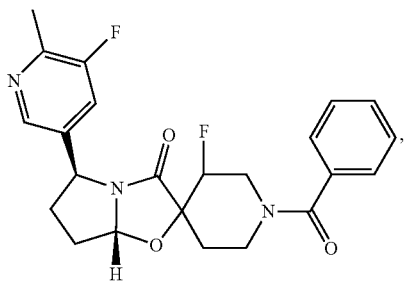

543
-continued
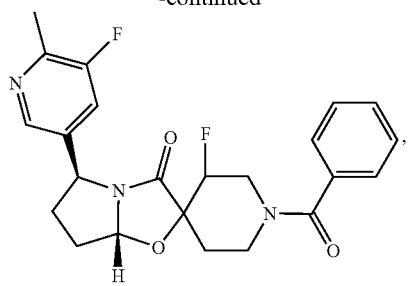
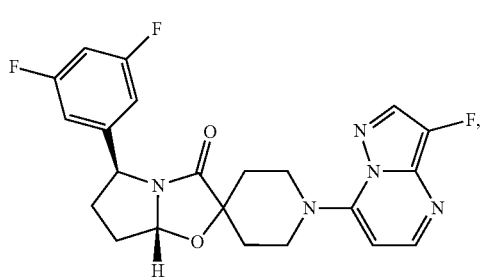
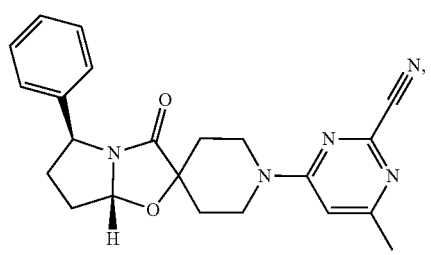
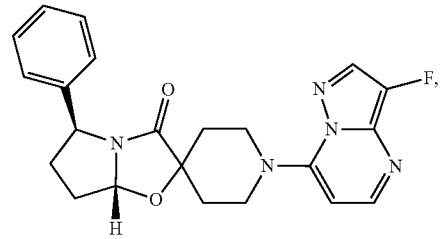
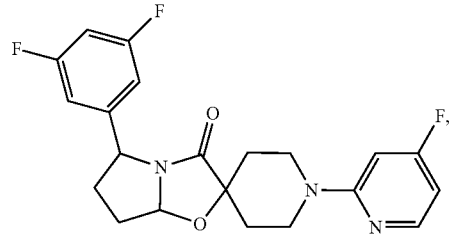
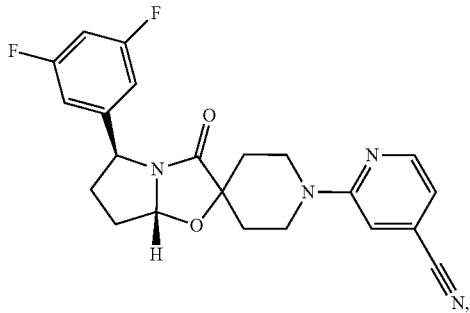
544
-continued
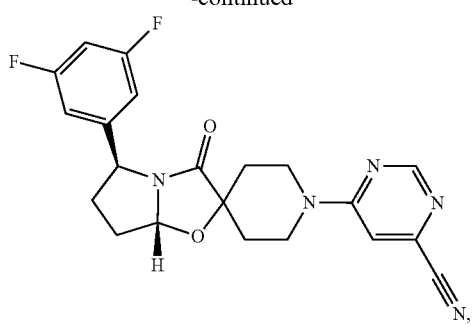
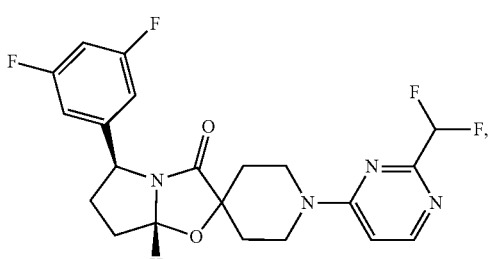
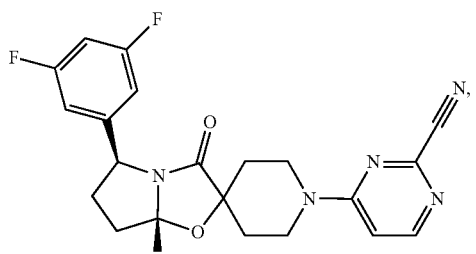
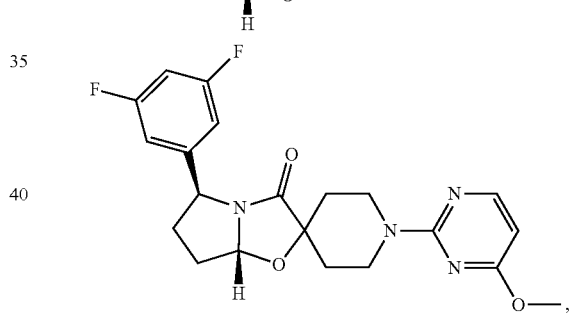
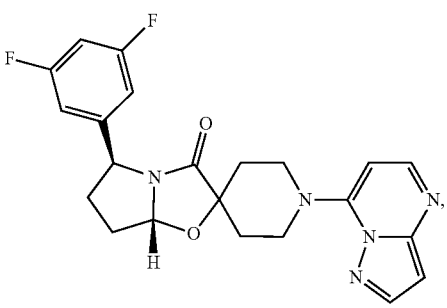
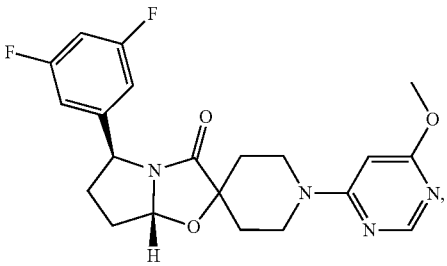

545
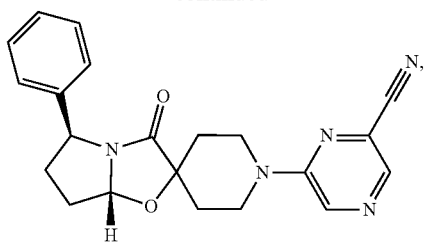
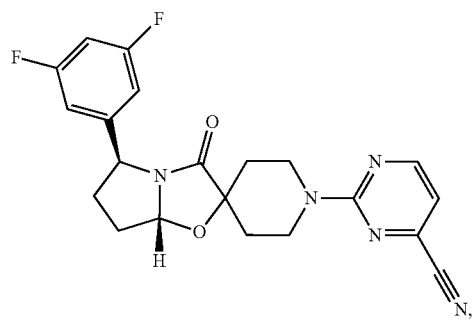
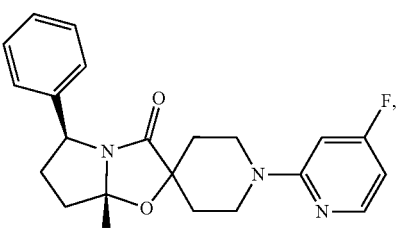
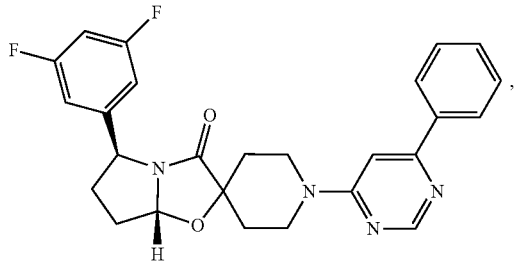
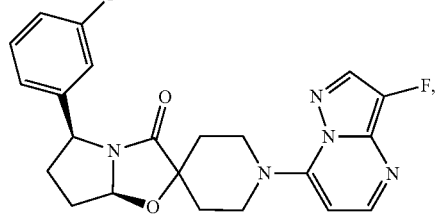
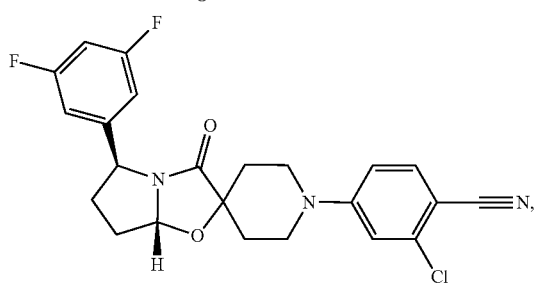
546
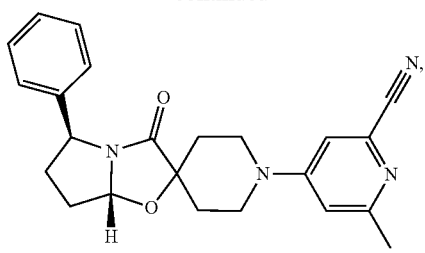
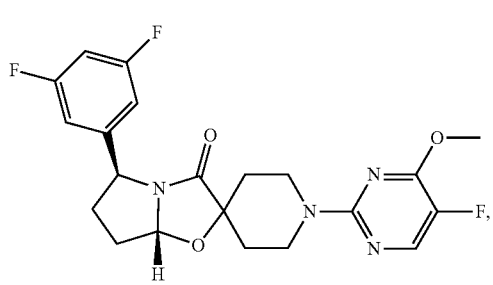
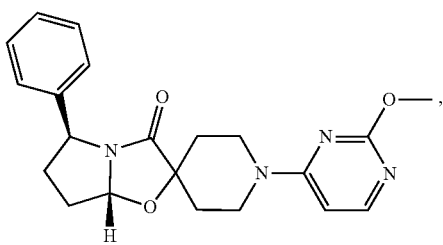
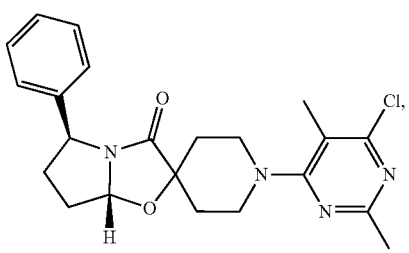
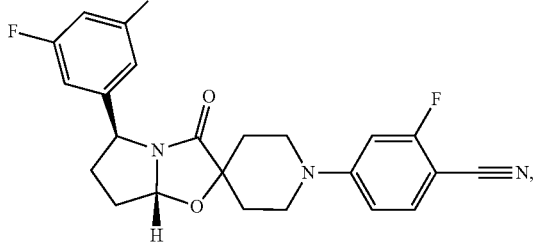
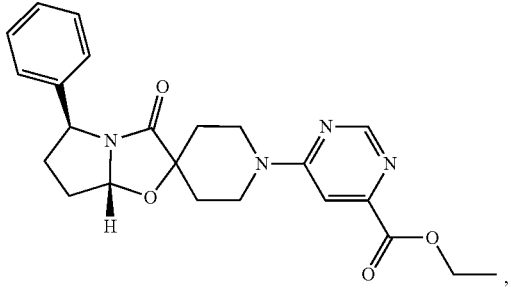

547
-continued
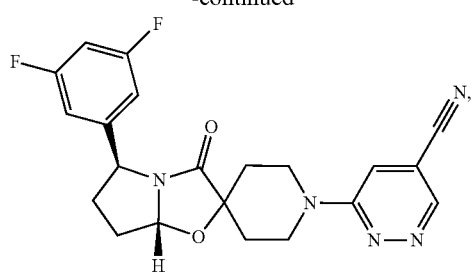
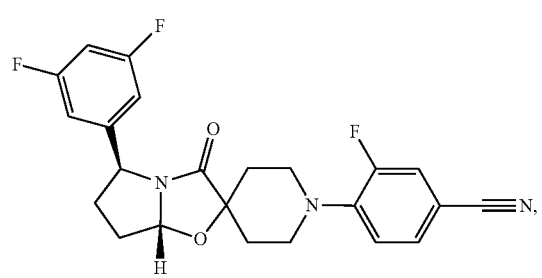
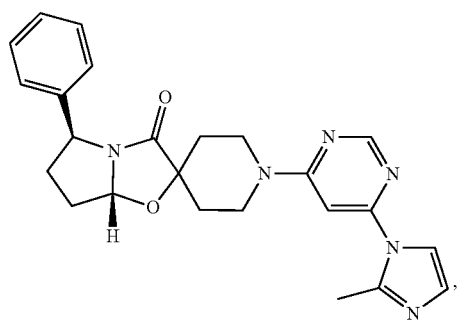
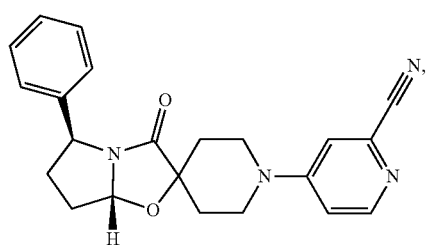
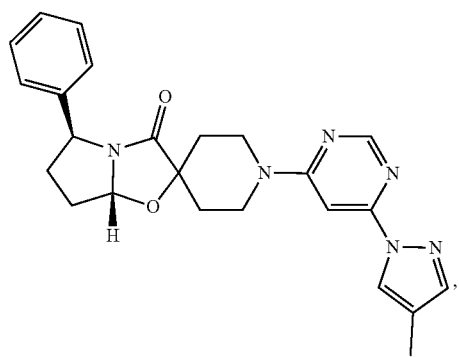
548
-continued
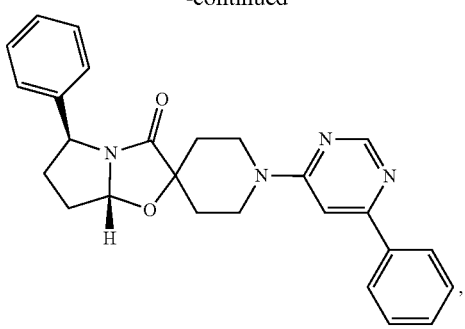
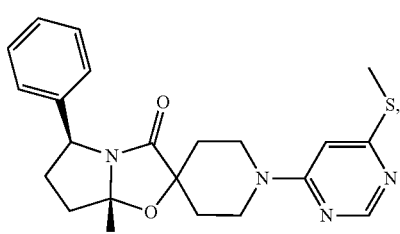
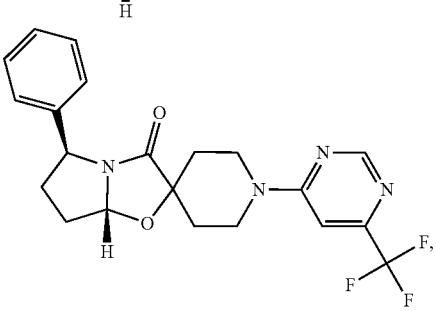
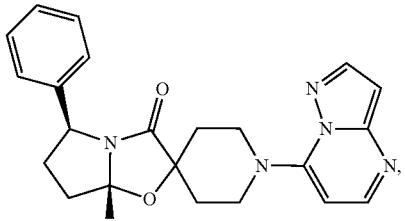
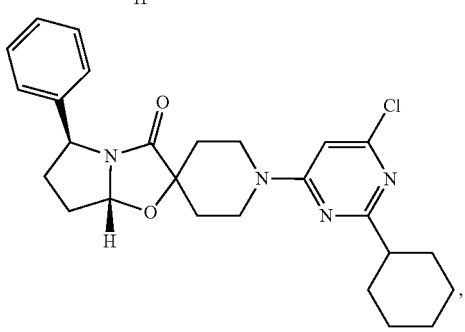
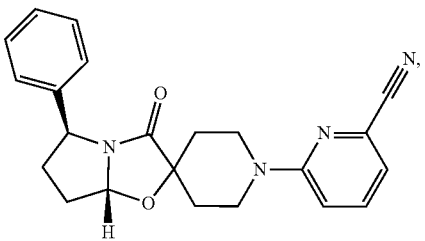

549
-continued
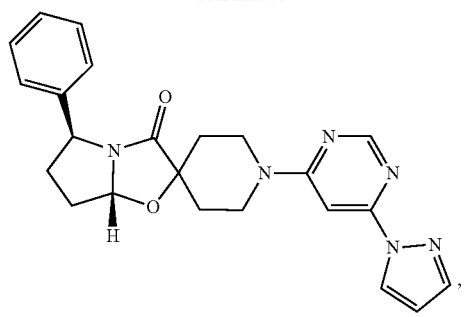
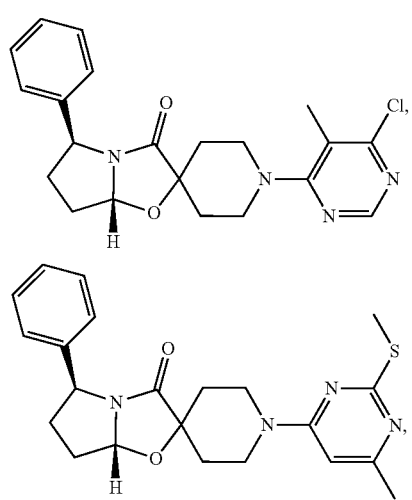
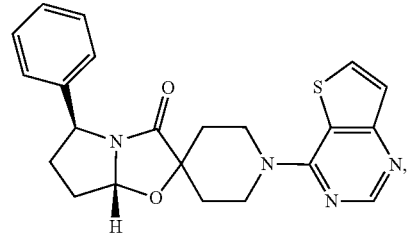
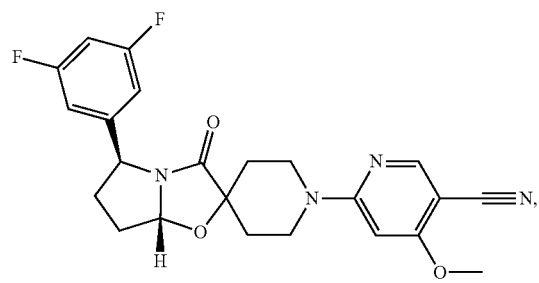
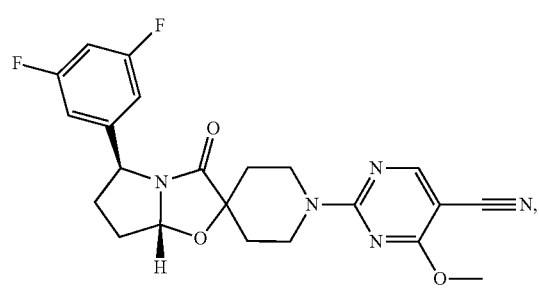
550
-continued
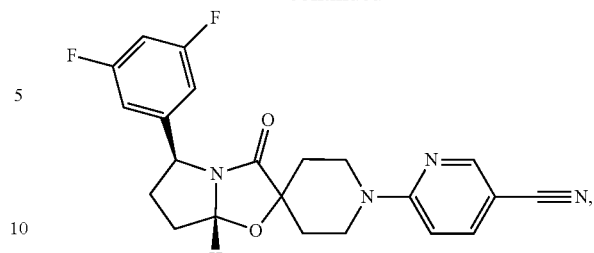
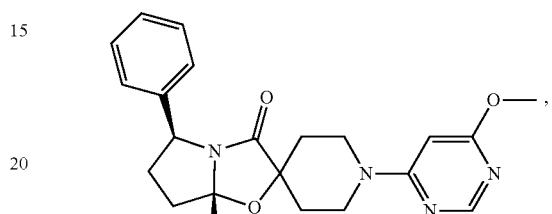
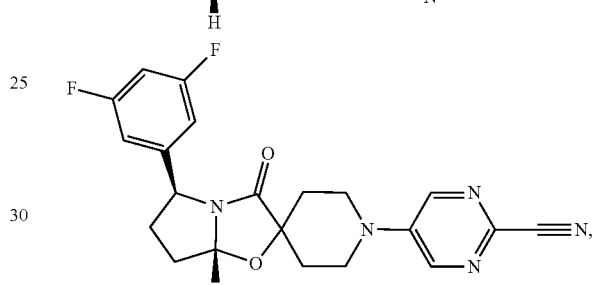
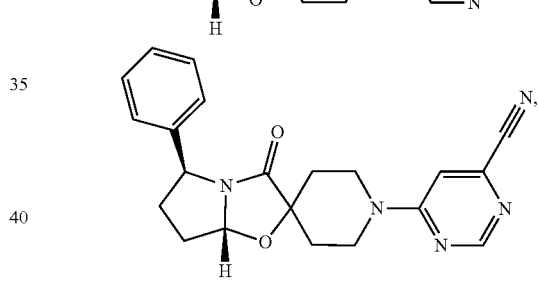
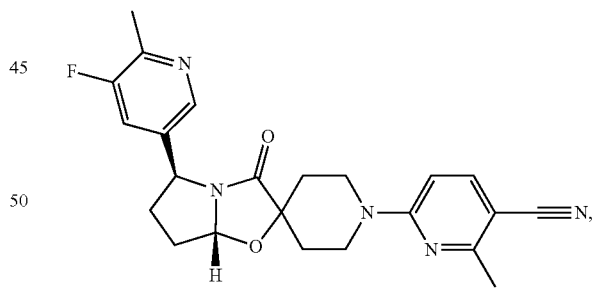
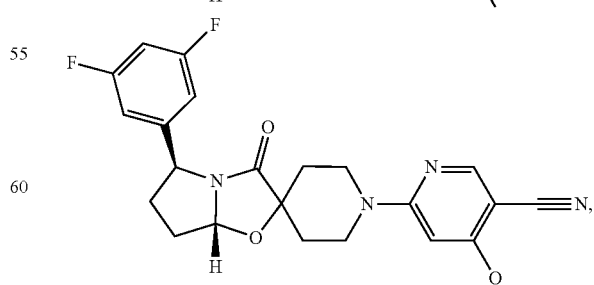

551
-continued
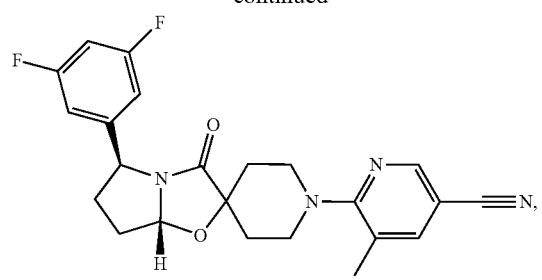
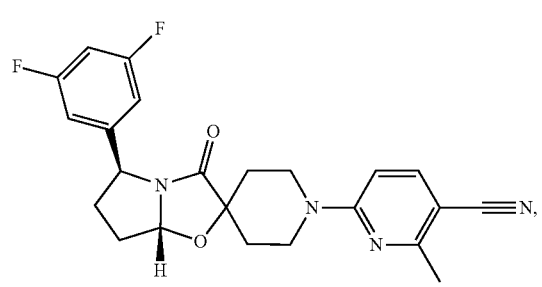
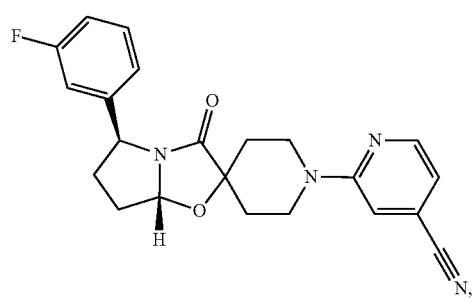
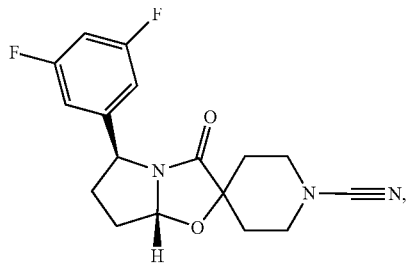
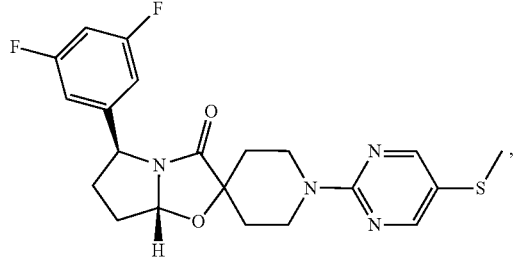
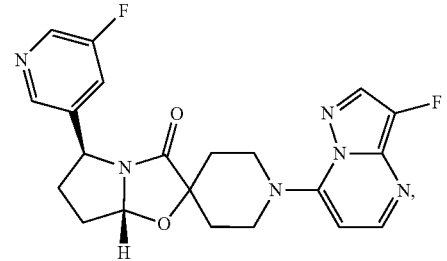
552
-continued
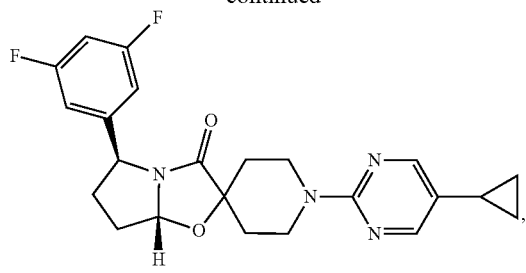
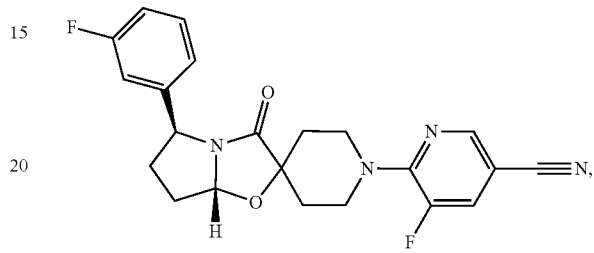
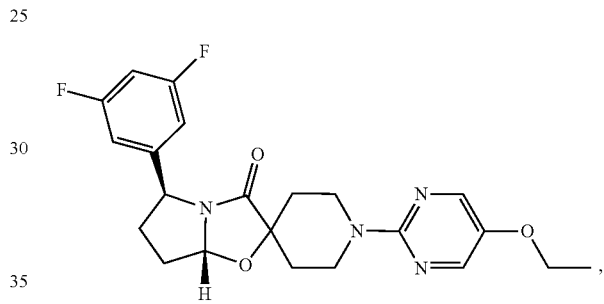
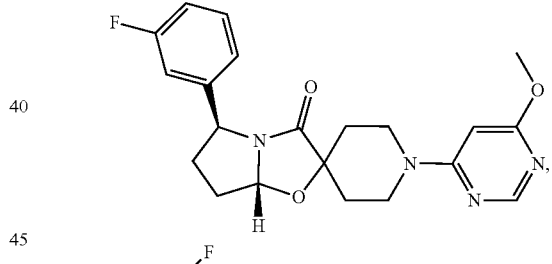
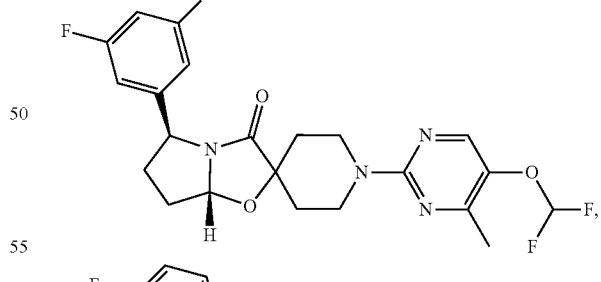
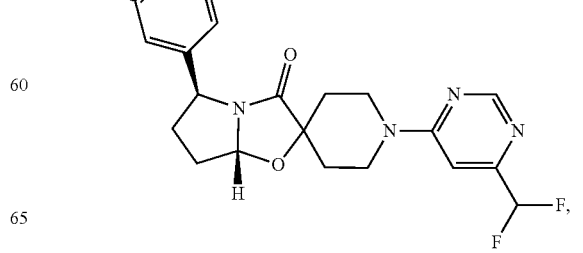

553
-continued
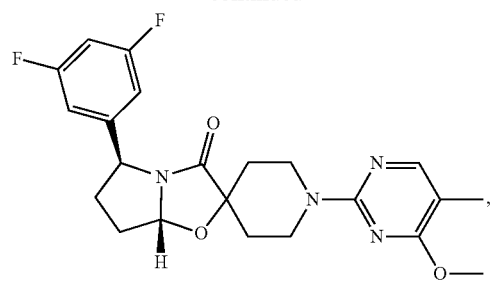
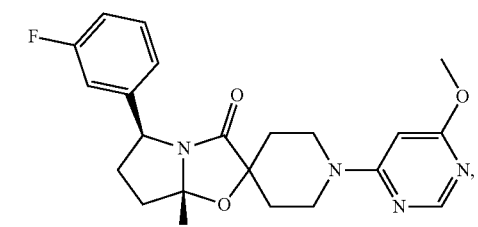
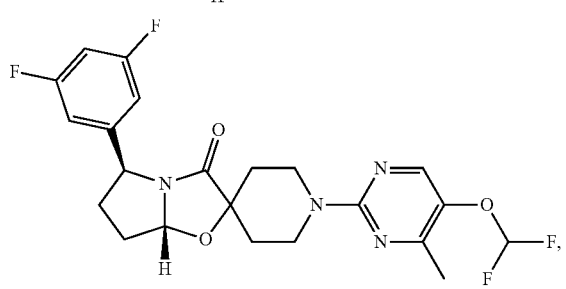
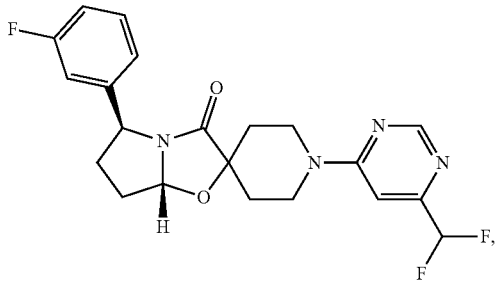
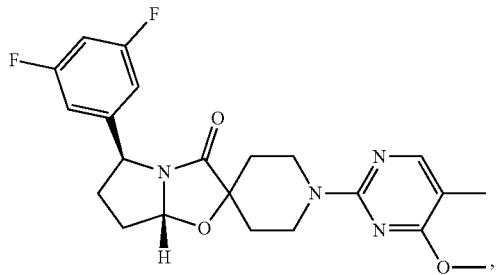
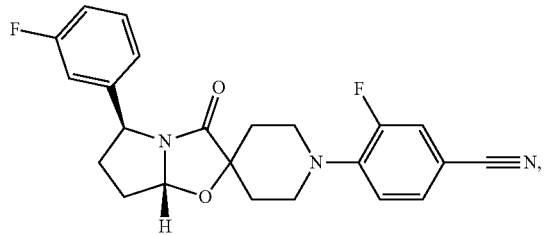
554
-continued
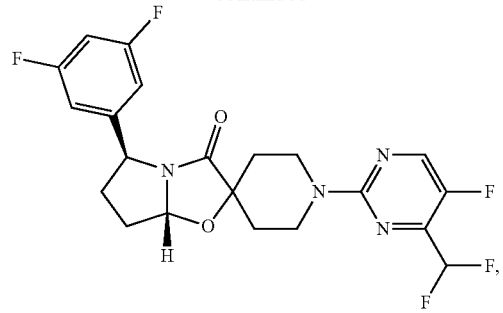
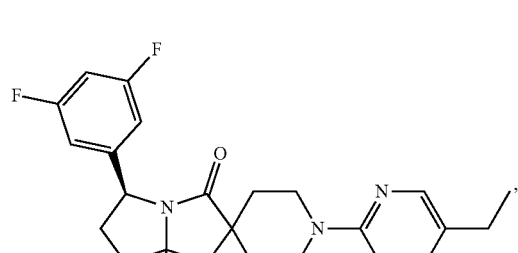
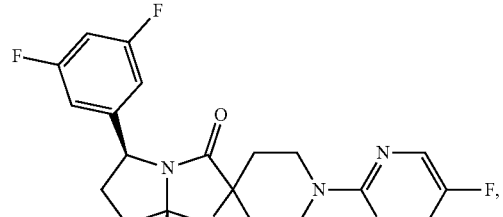
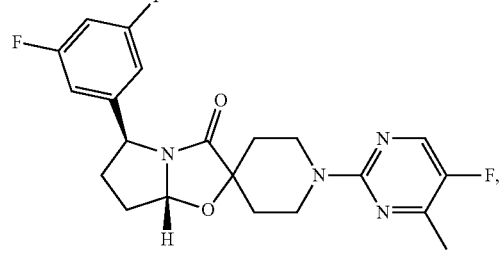
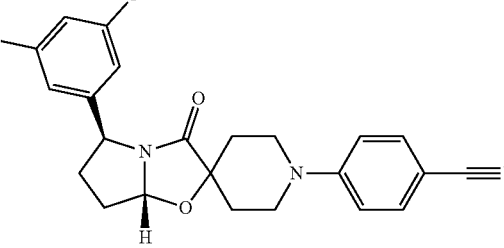
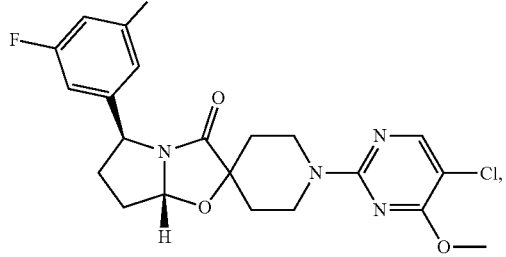

555
-continued
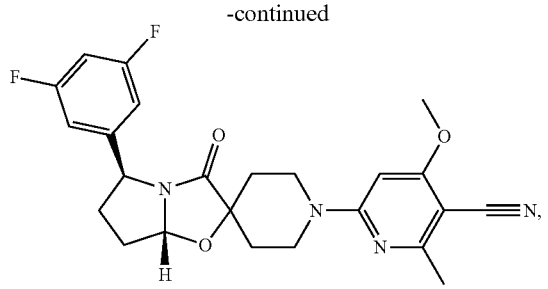
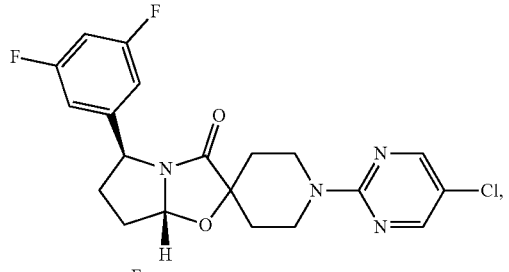
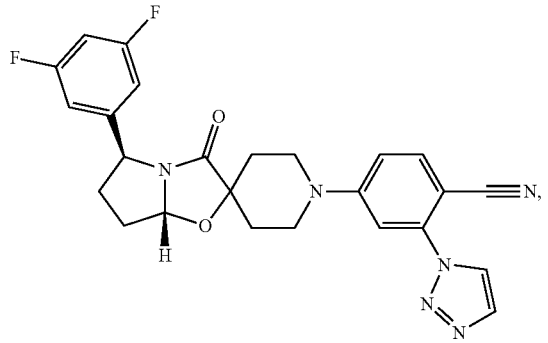
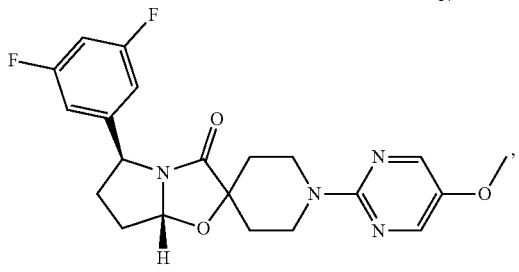
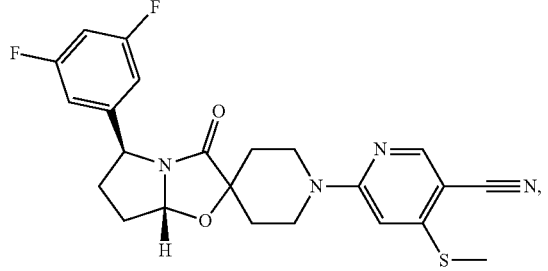
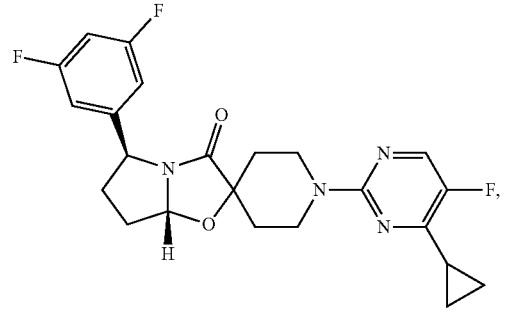
556
-continued
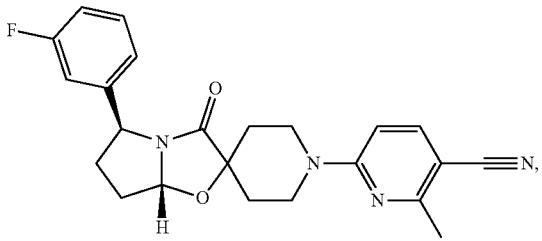
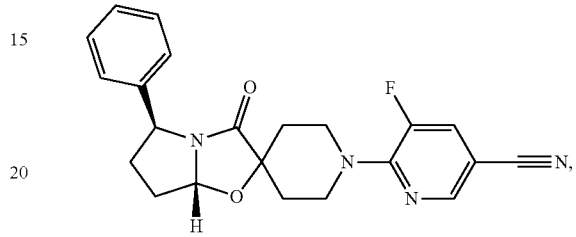
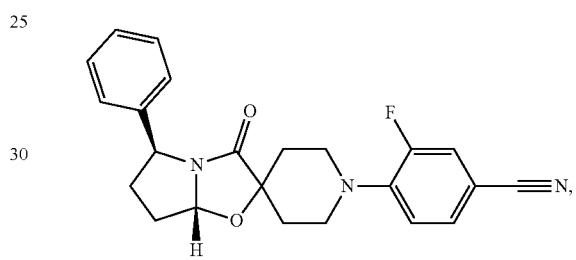
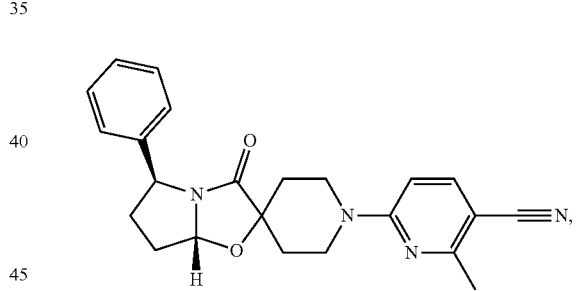
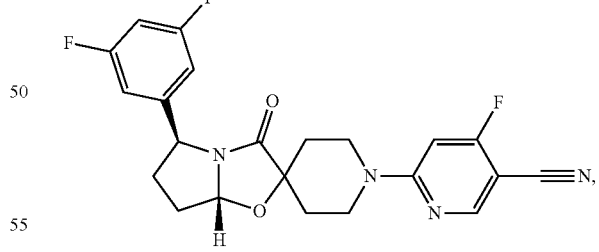
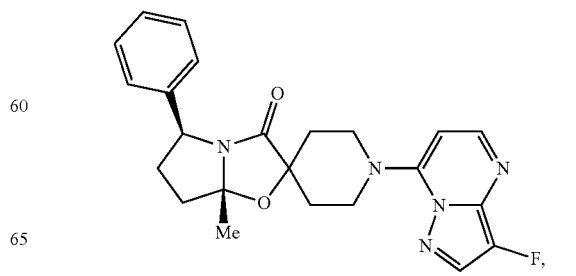

557
-continued
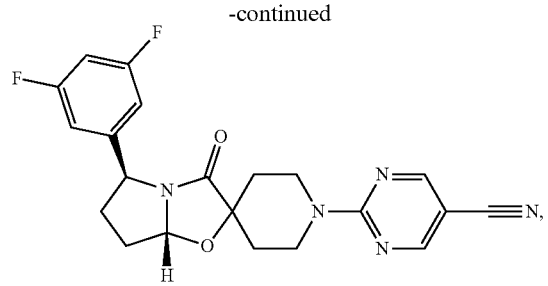
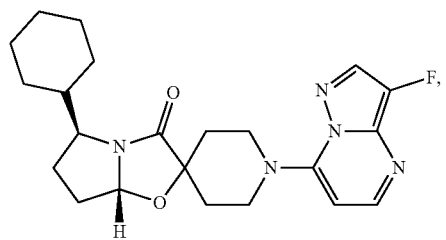
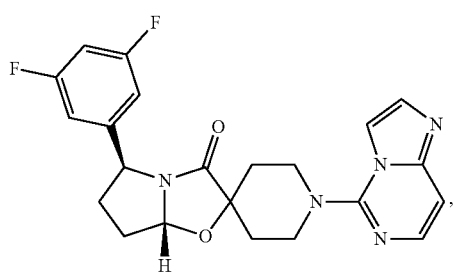
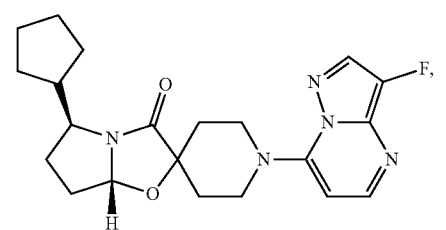
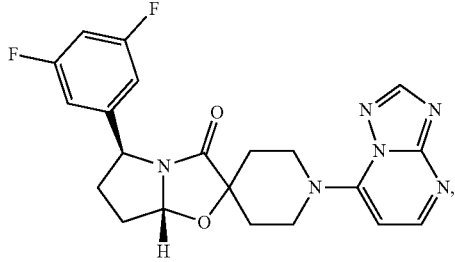
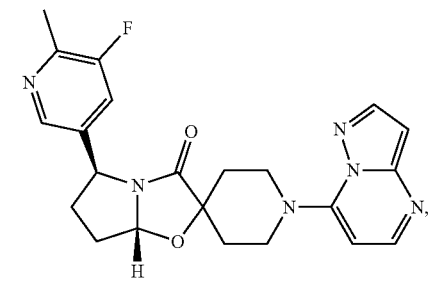
558
-continued
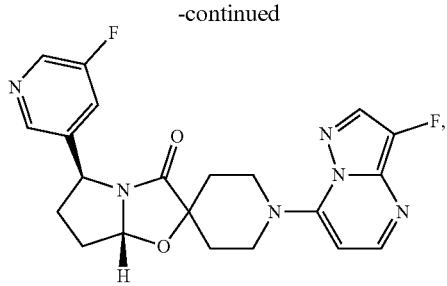
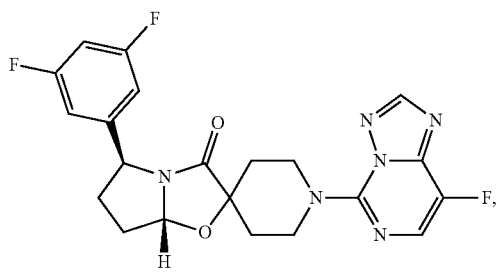
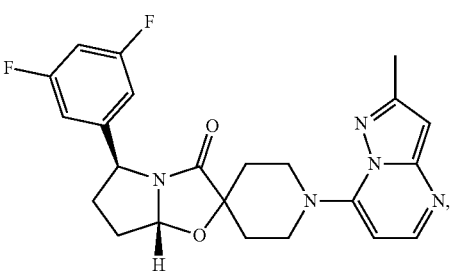
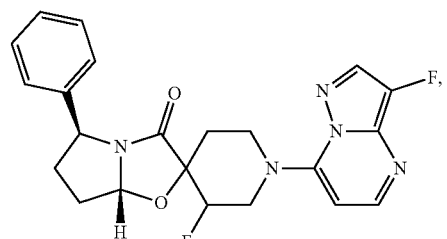
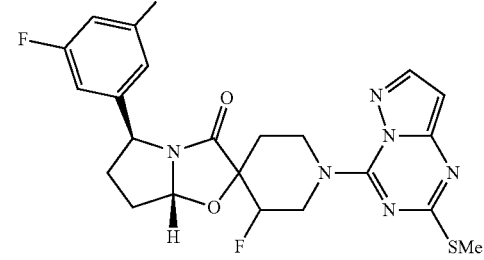
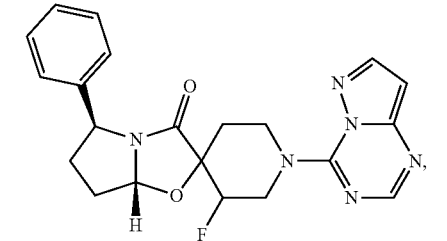

559
-continued
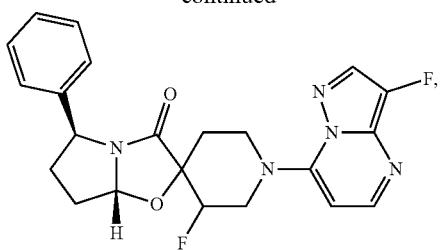
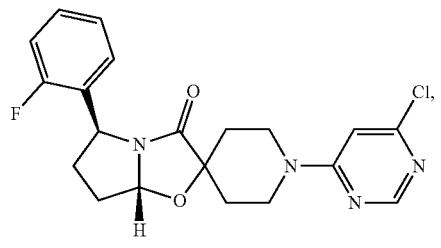
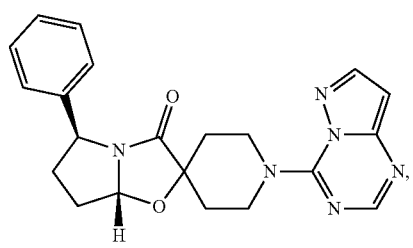
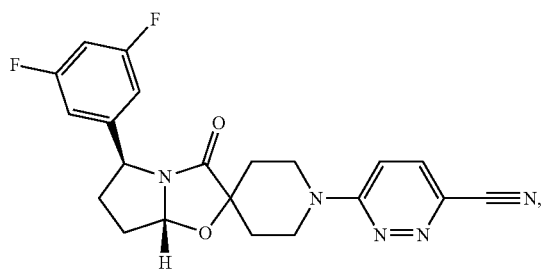
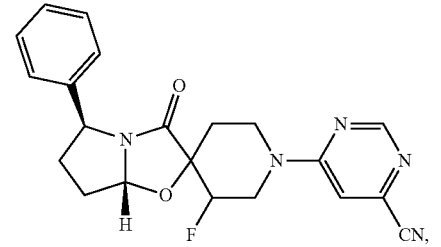
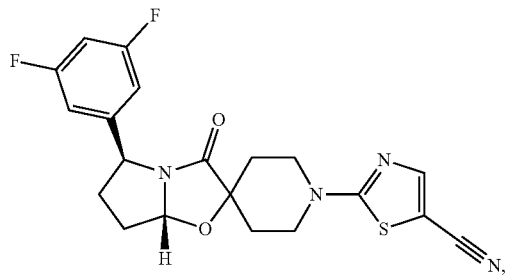
560
-continued
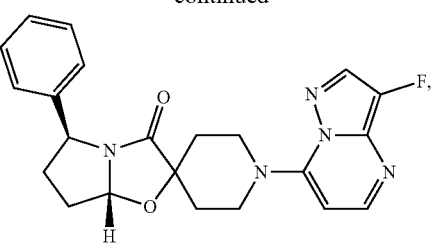
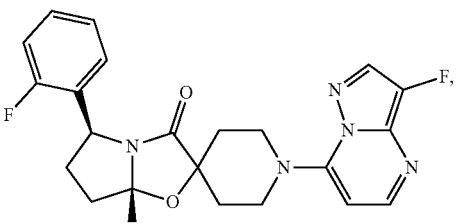
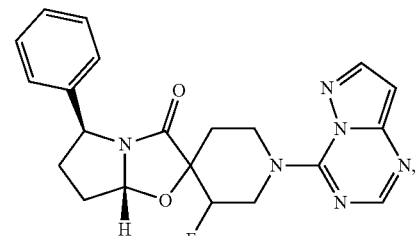
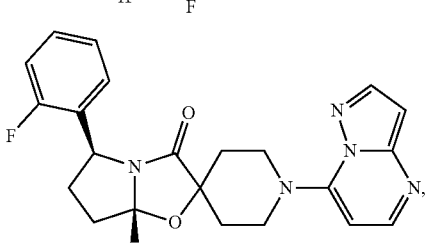
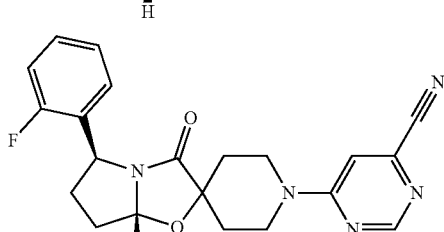
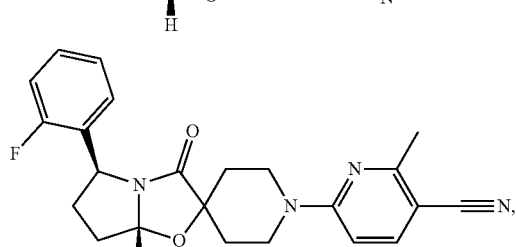
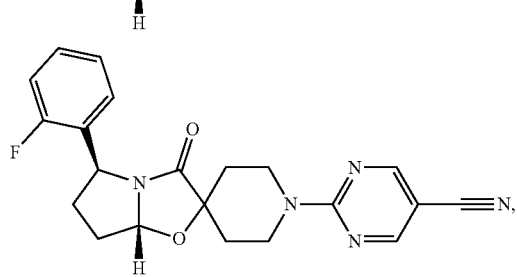

561
-continued
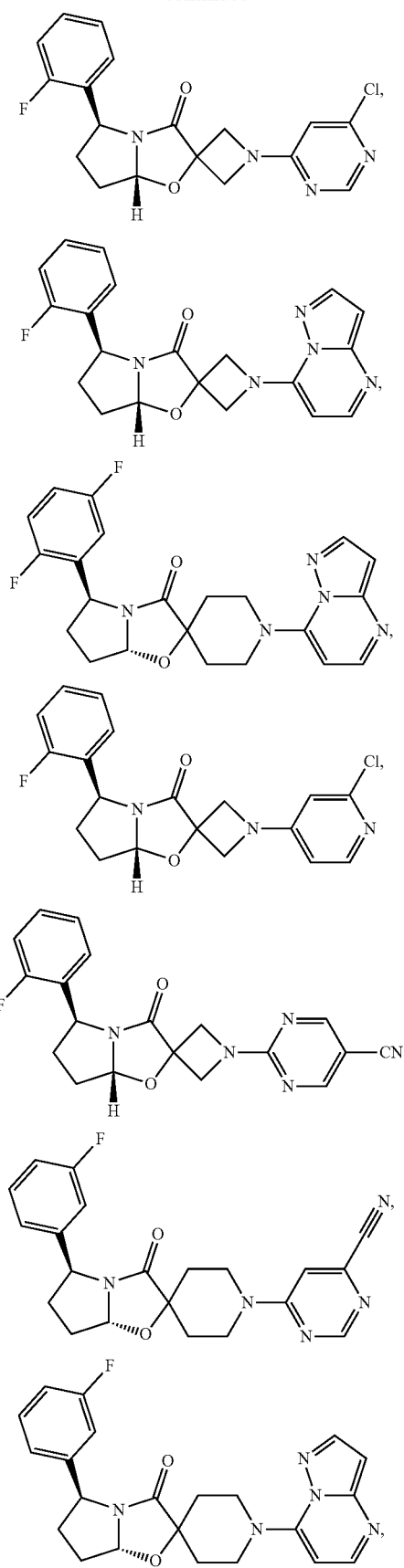
562
-continued
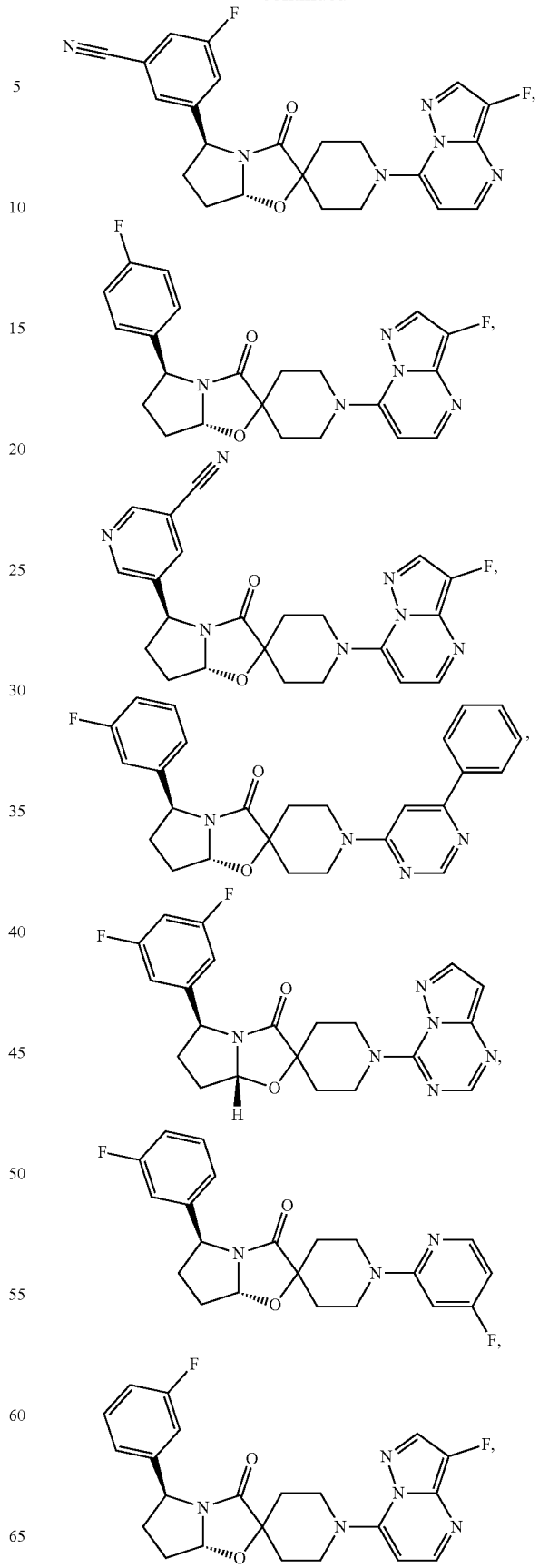

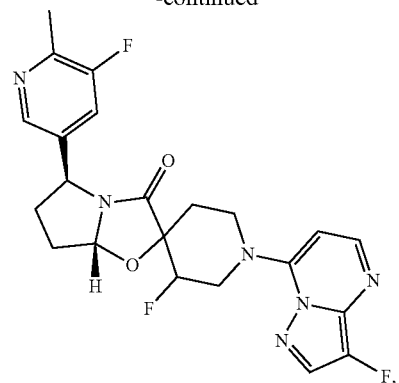
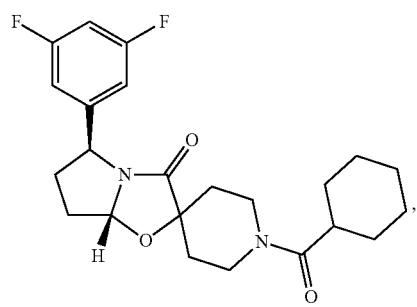
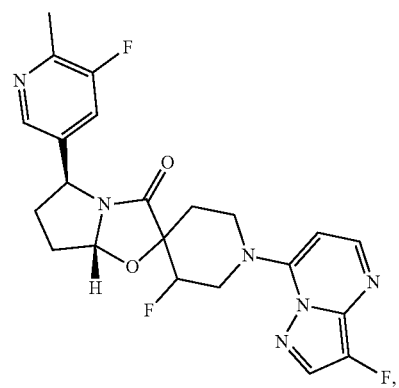
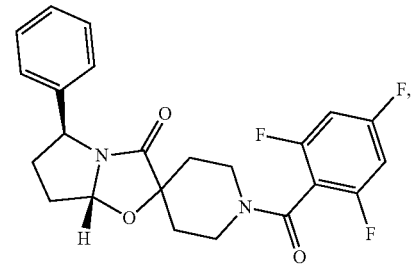
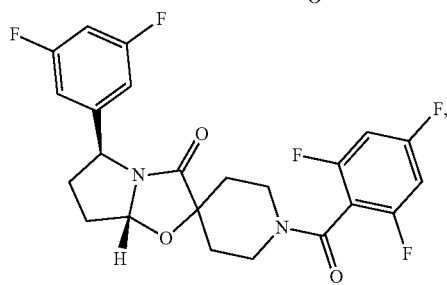
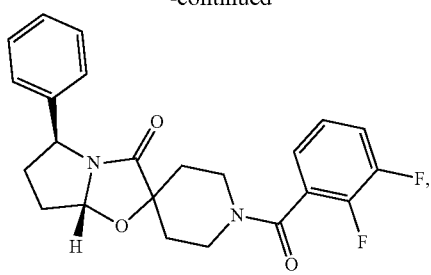
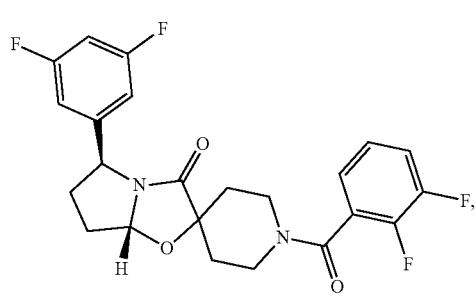
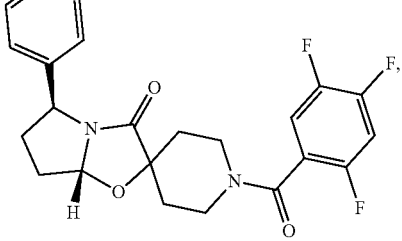
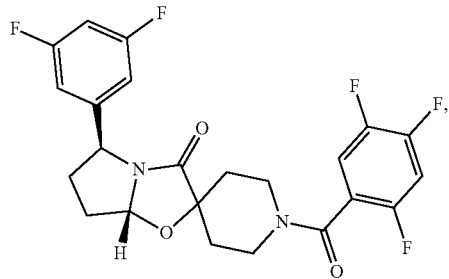
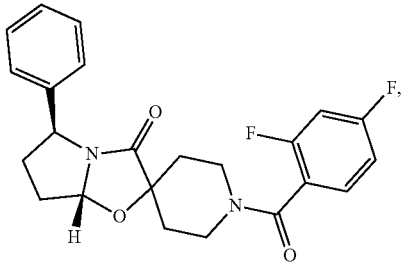
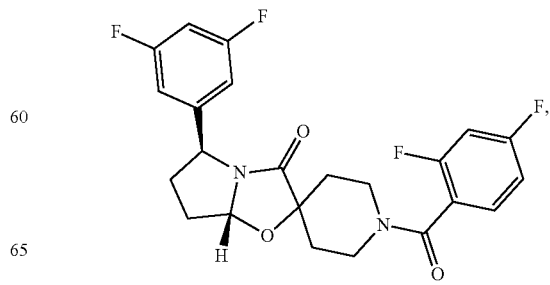

565
-continued
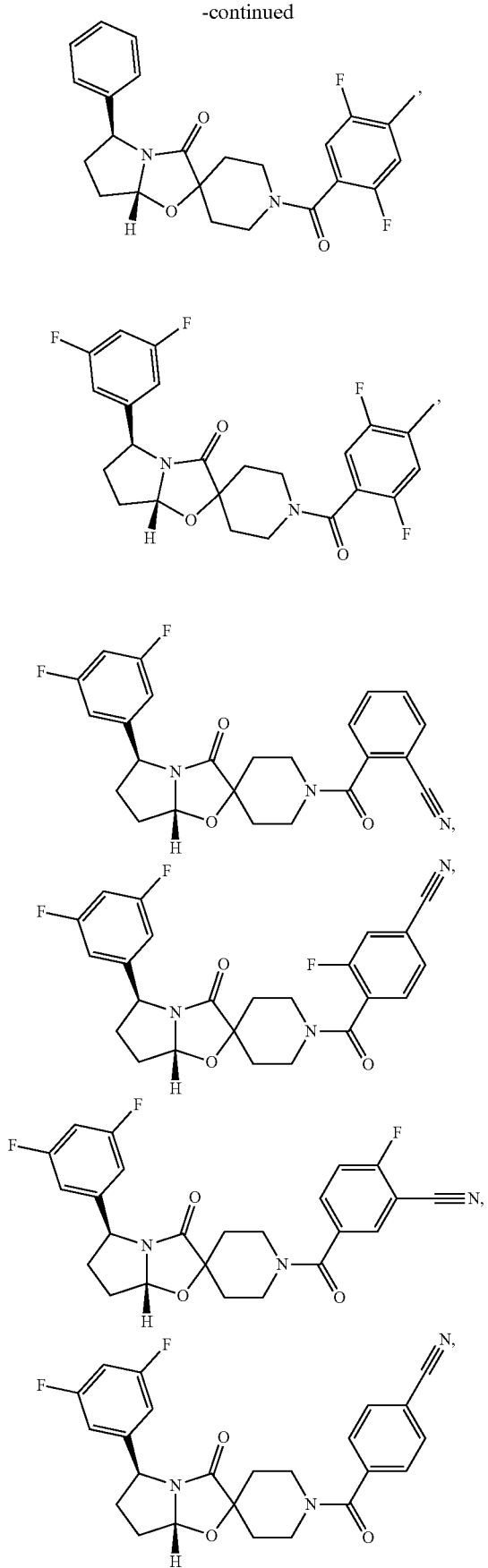
566
-continued
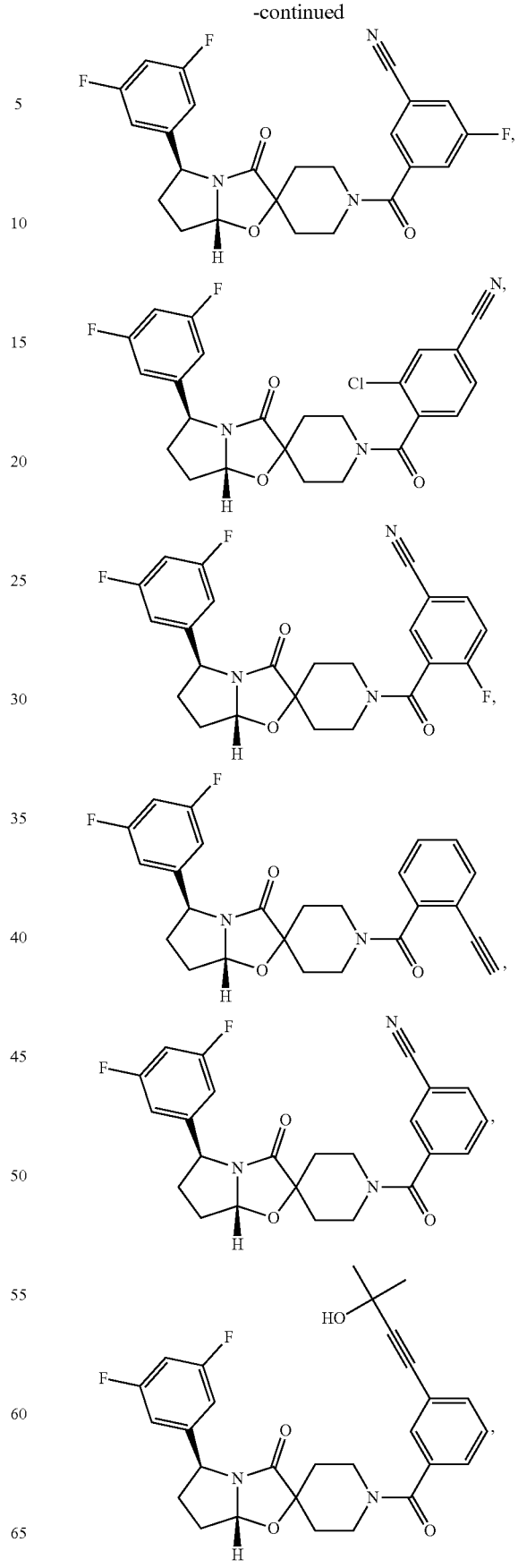

567
-continued
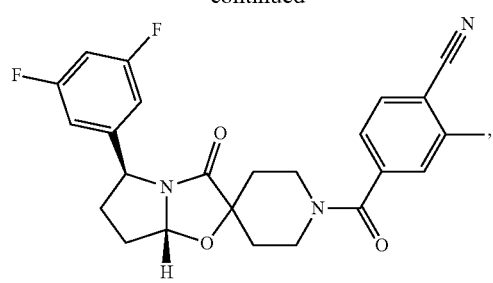
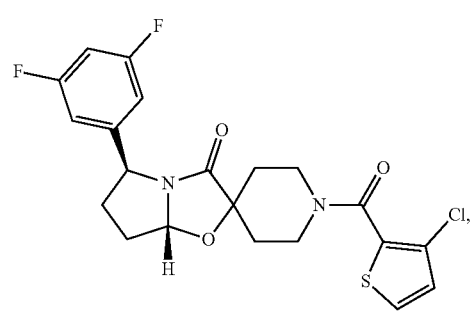
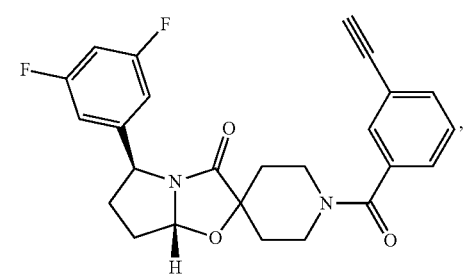
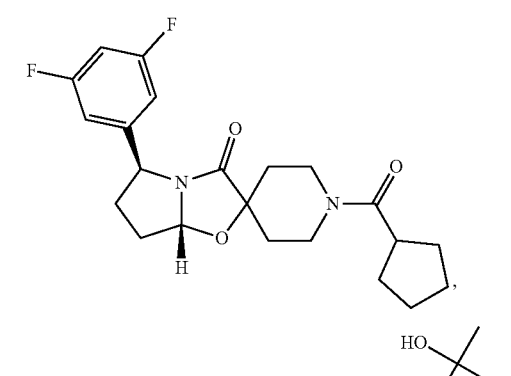
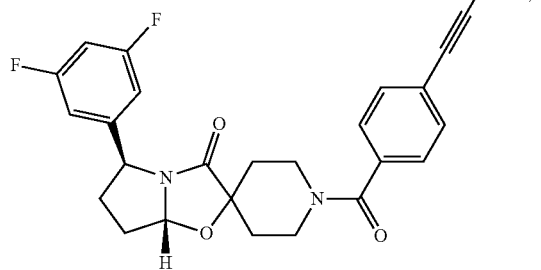
568
-continued
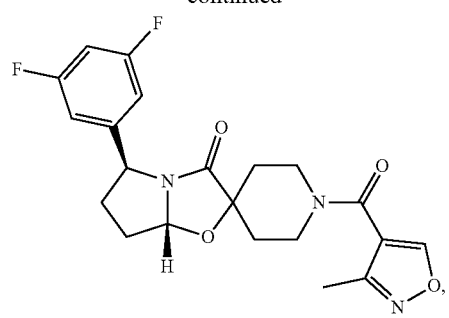
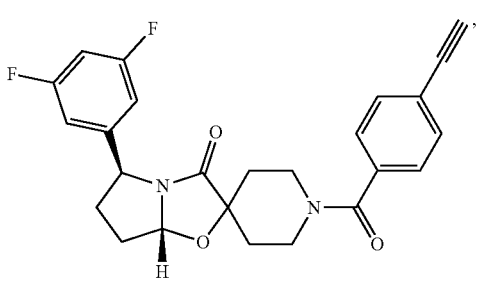
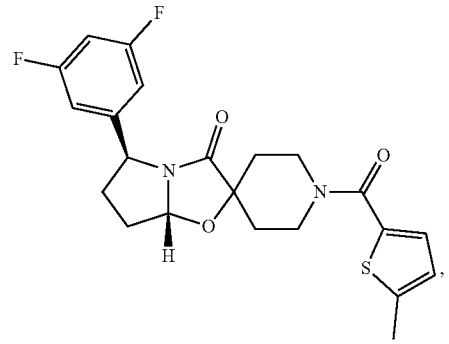
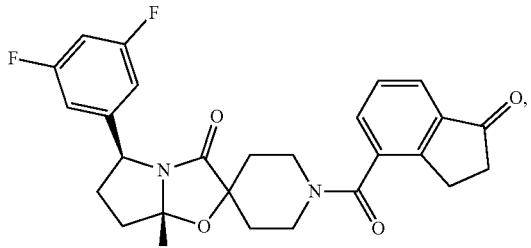
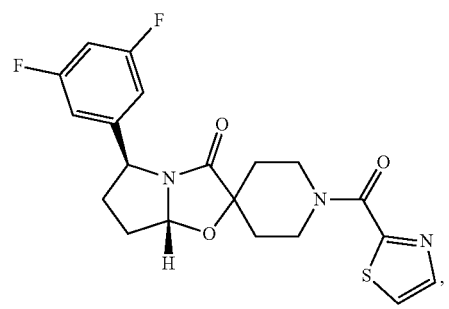

569
-continued
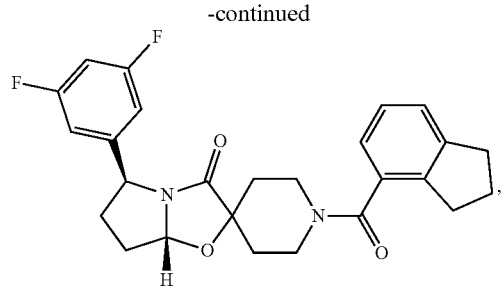
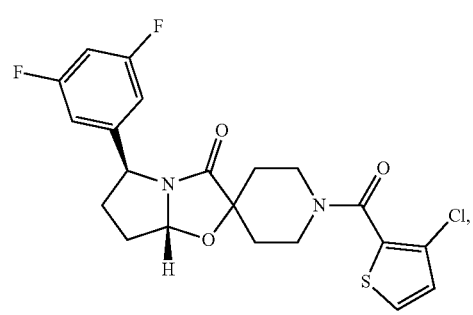
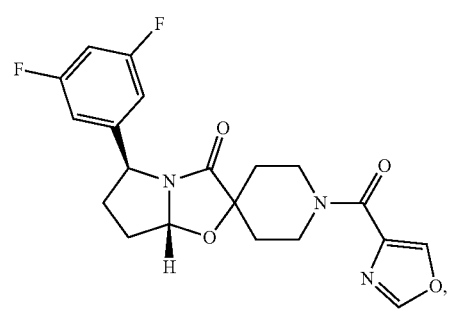
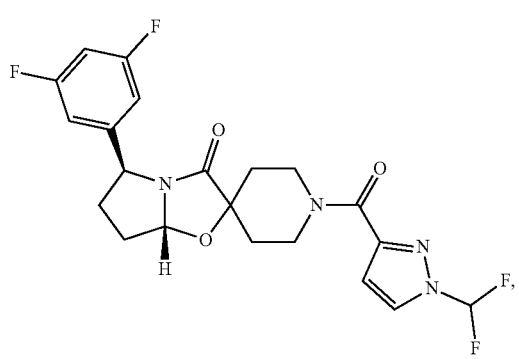
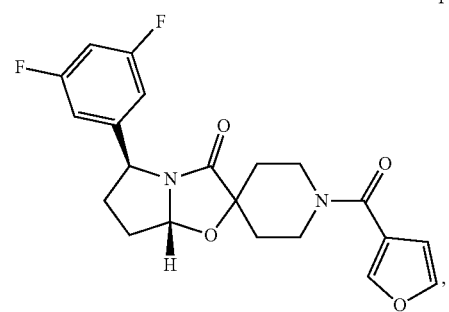
570
-continued
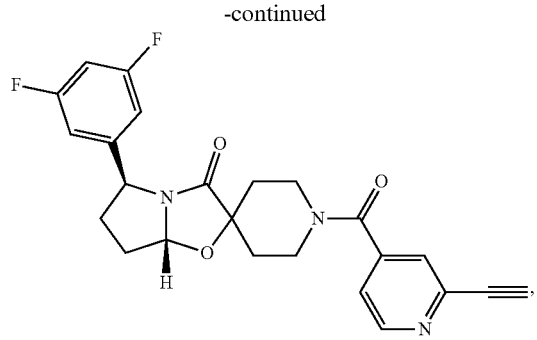
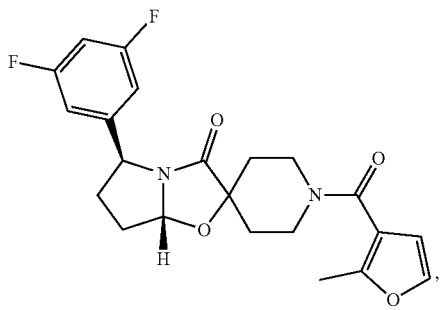
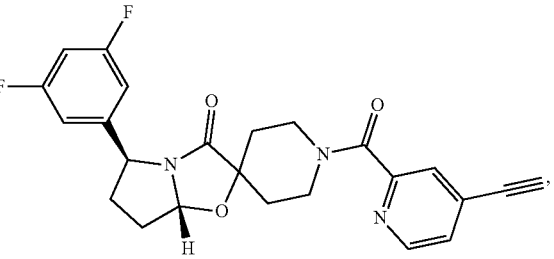
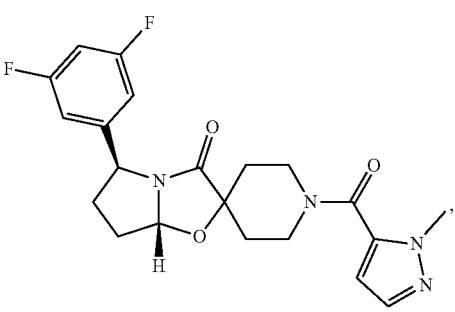
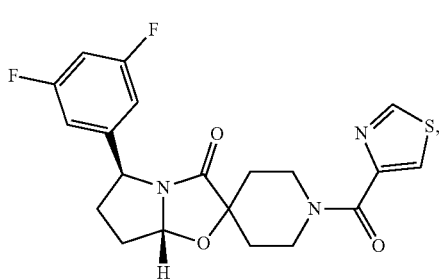

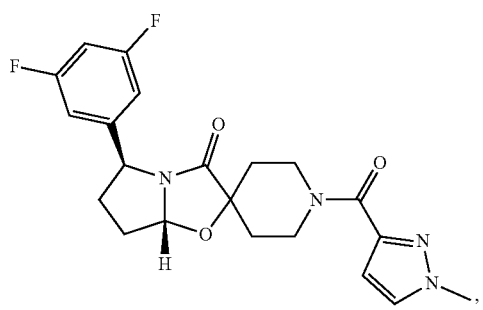
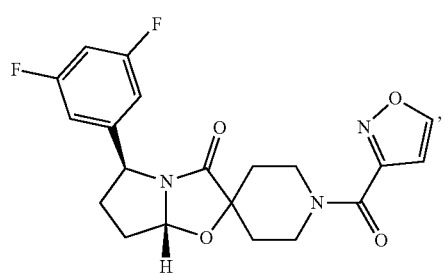
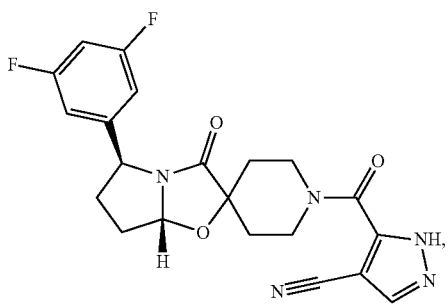
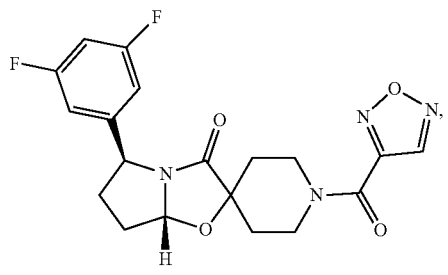
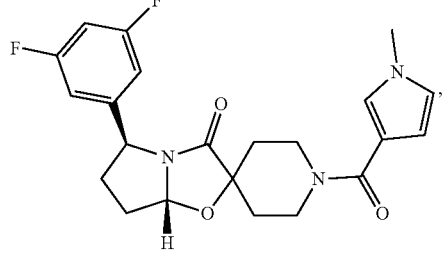
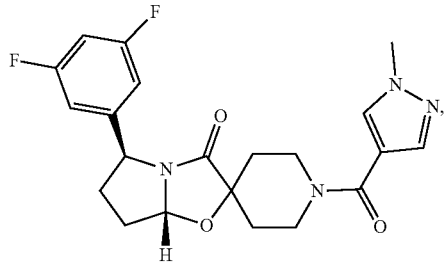
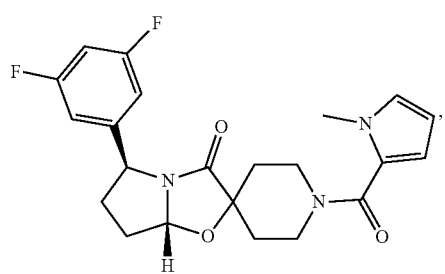
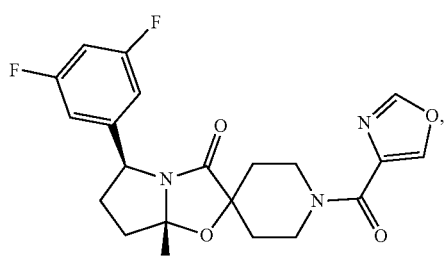
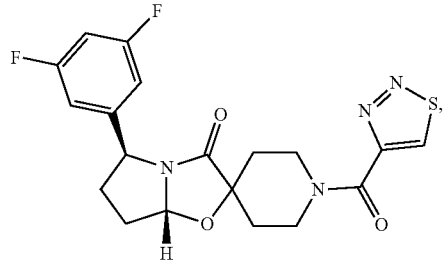
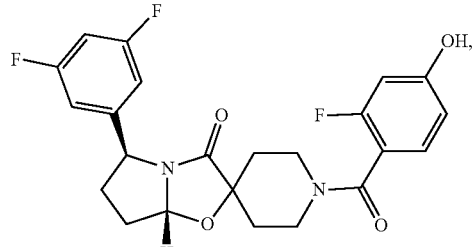
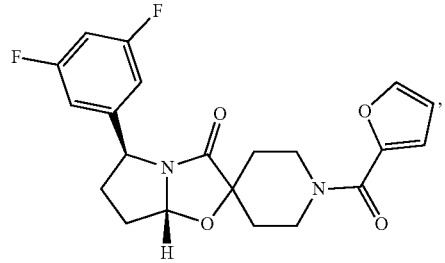

-continued
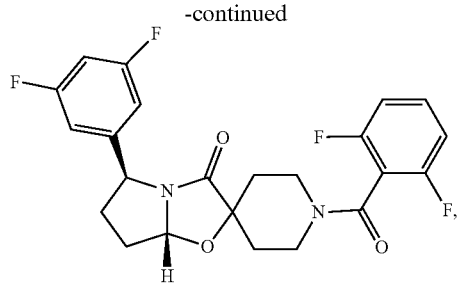
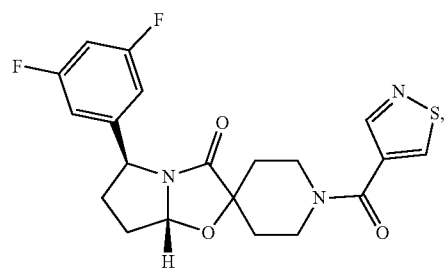
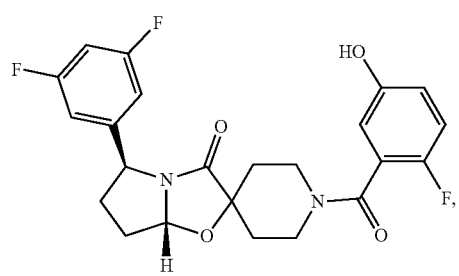
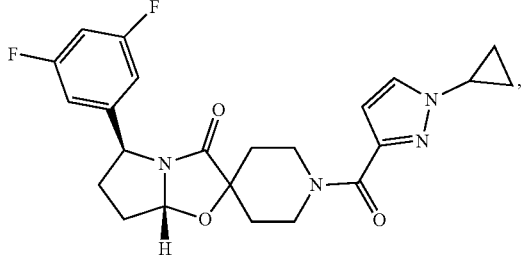
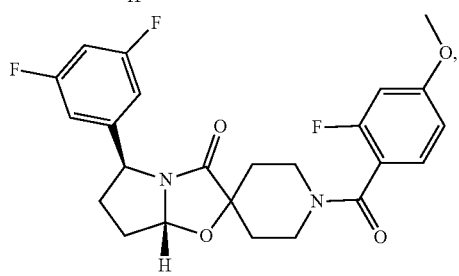
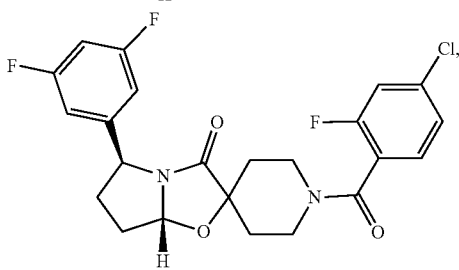
-continued
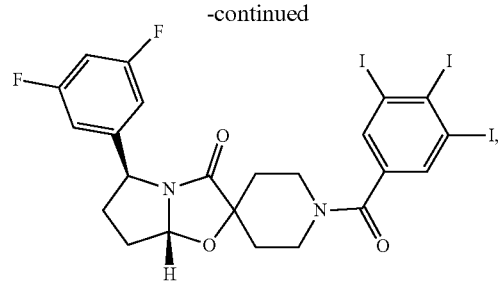
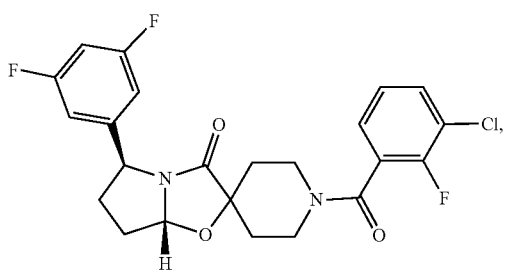
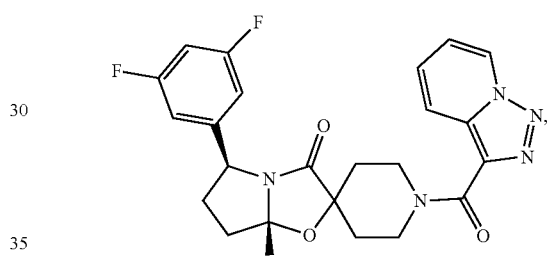
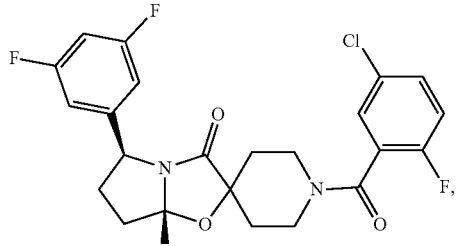
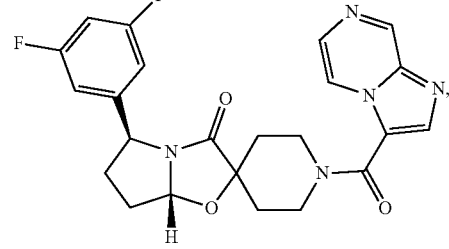
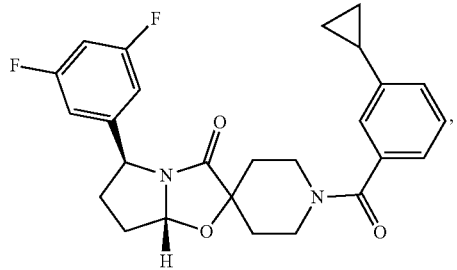

575
-continued
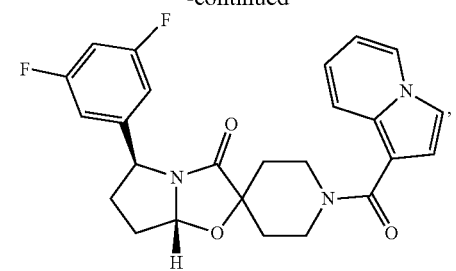
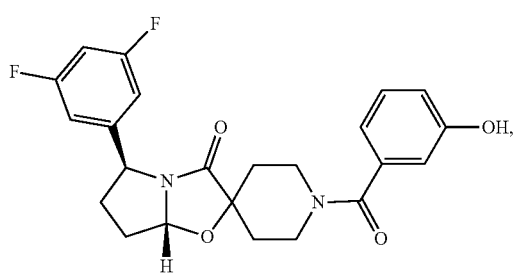
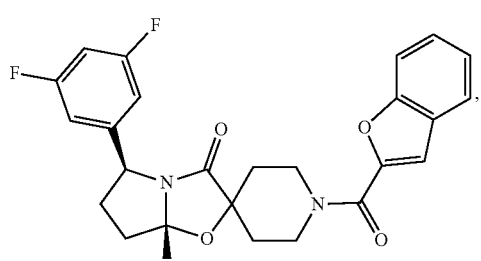
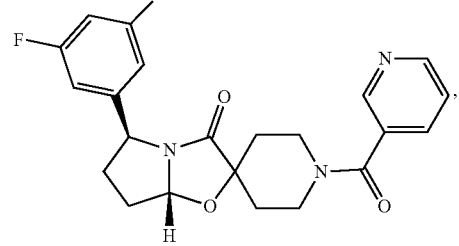
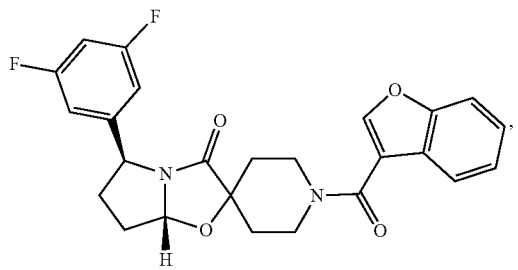
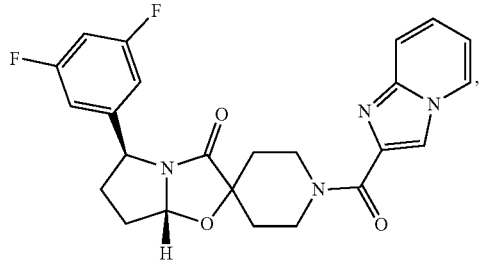
576
-continued
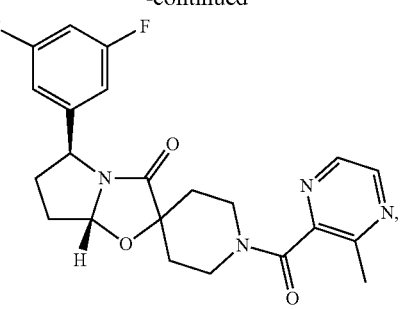
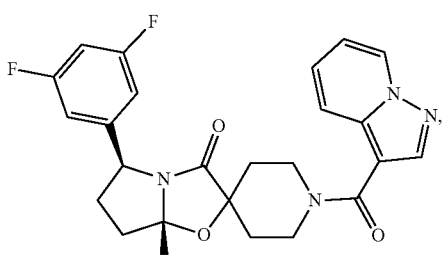
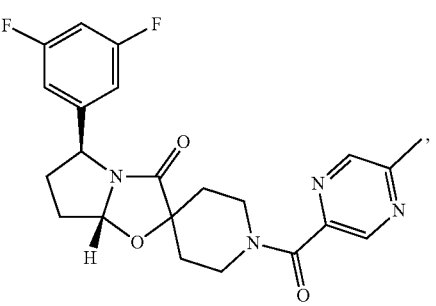
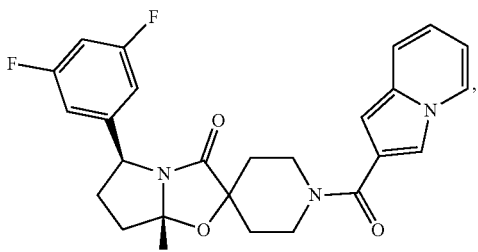
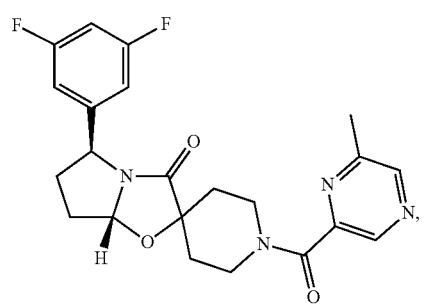
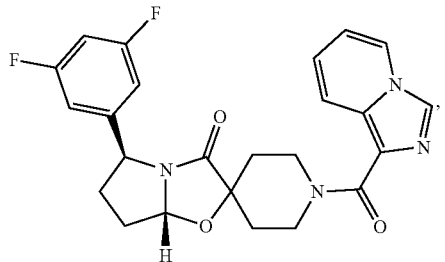

577
-continued
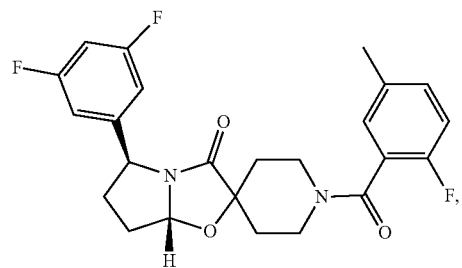
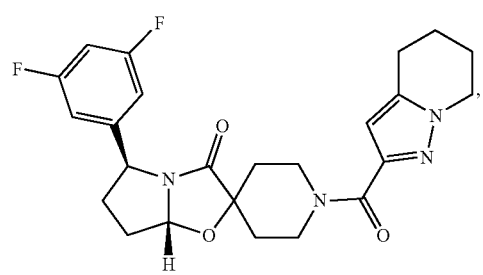
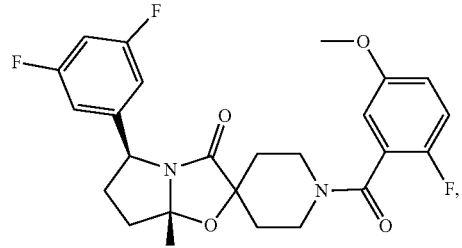
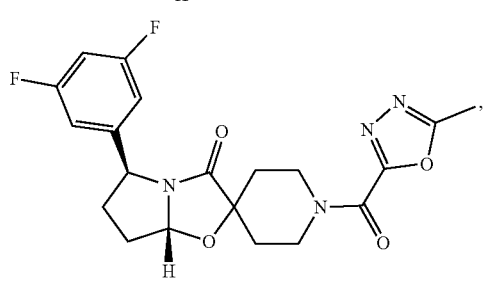
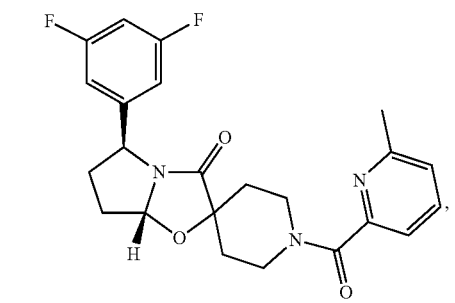
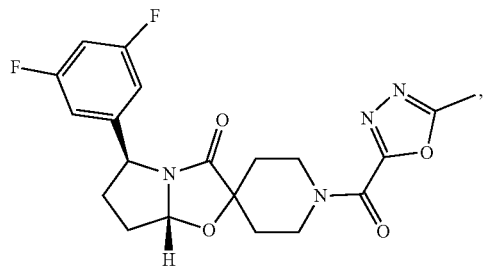
578
-continued
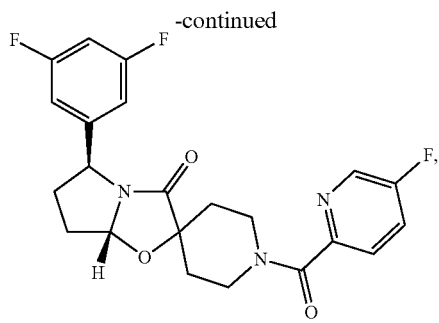
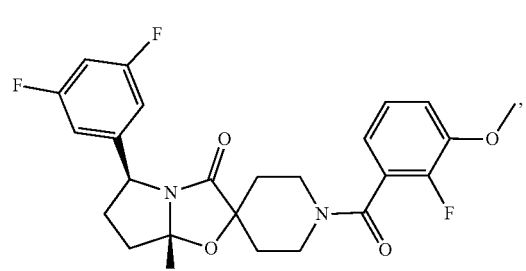
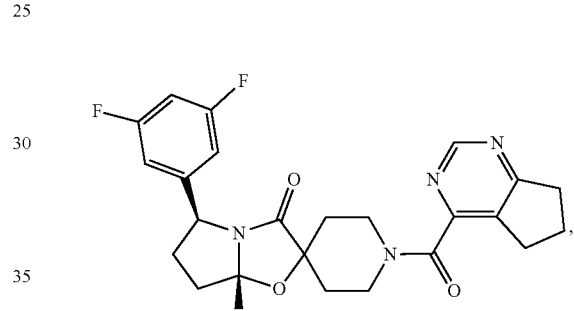
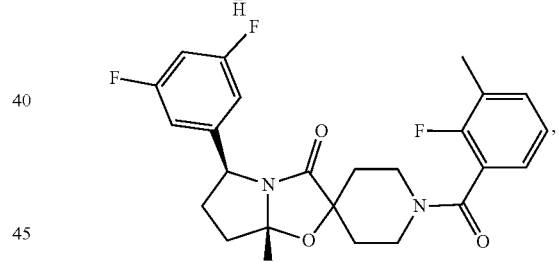
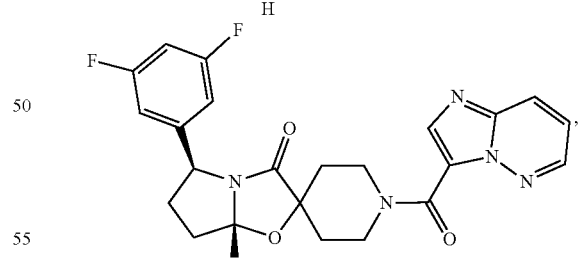
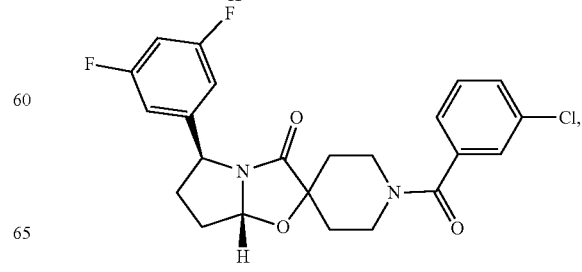

579
-continued
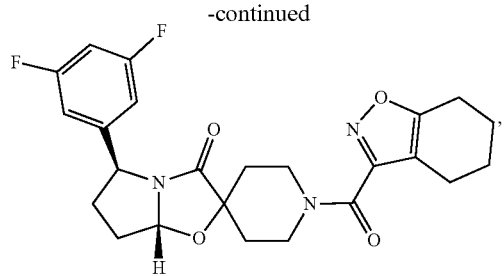
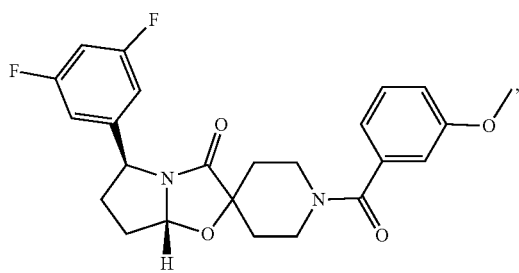
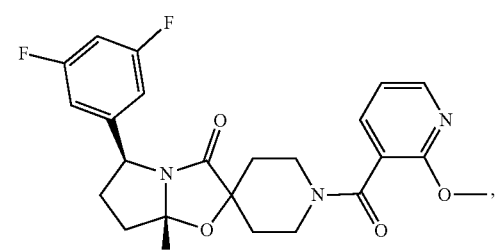
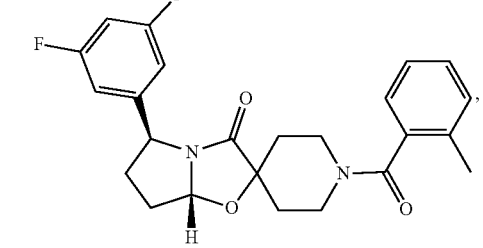
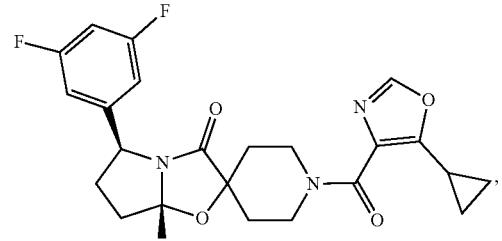
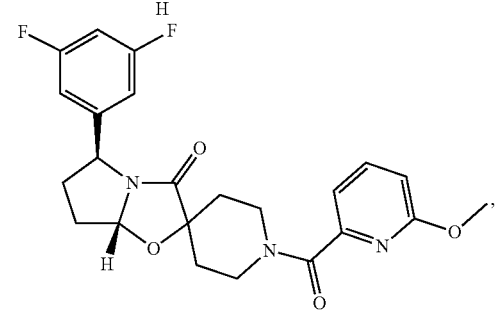
580
-continued
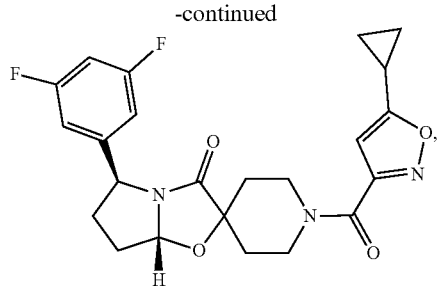
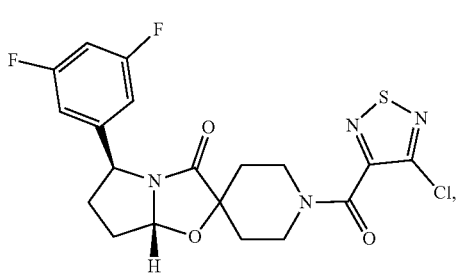
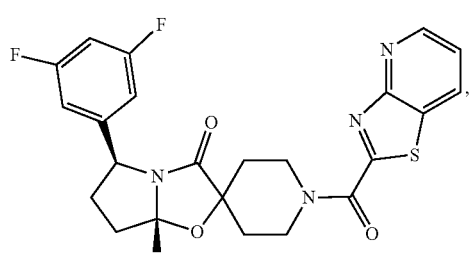
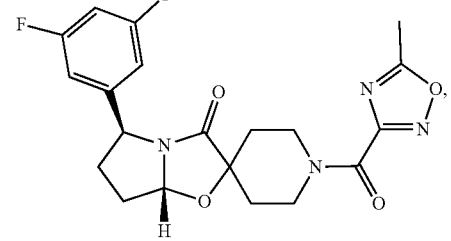
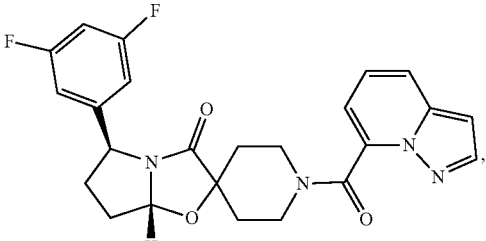
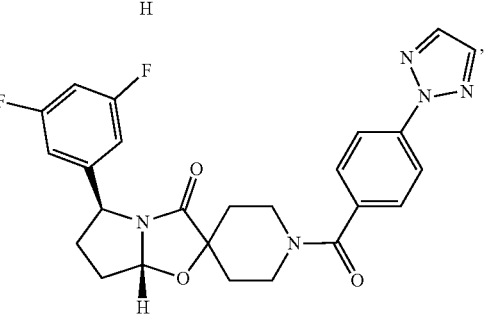

581
-continued
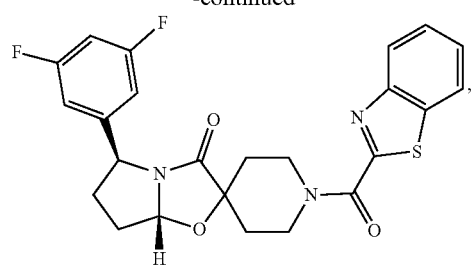
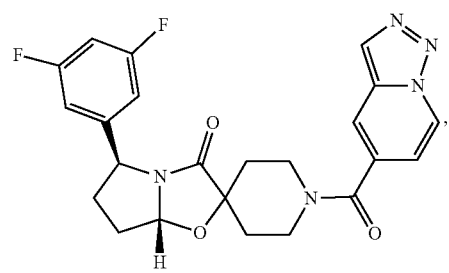
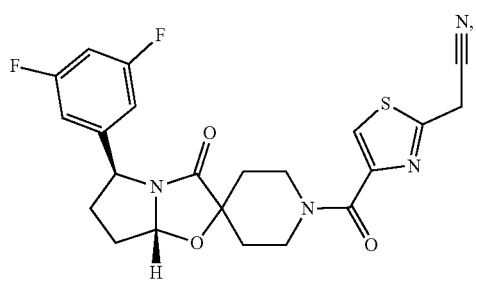
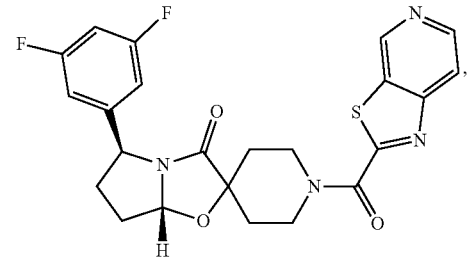
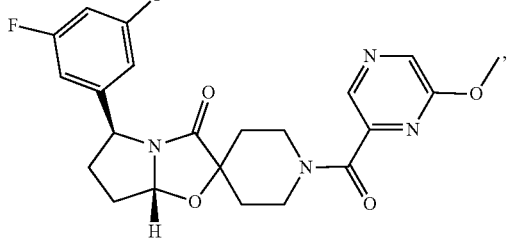
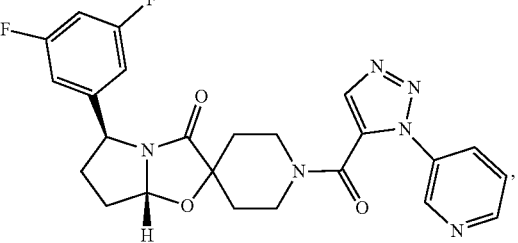
582
-continued
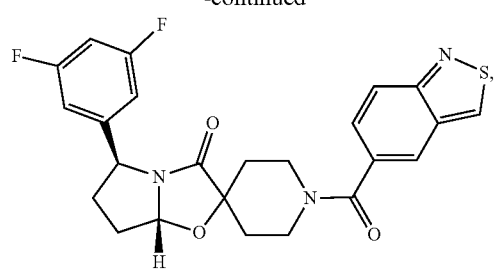
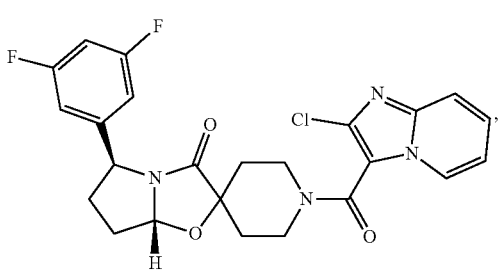
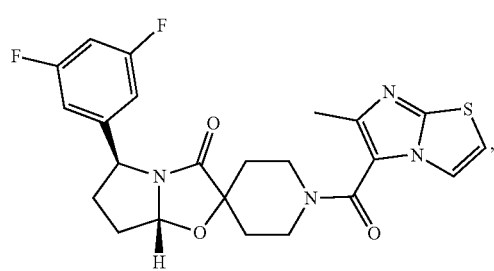
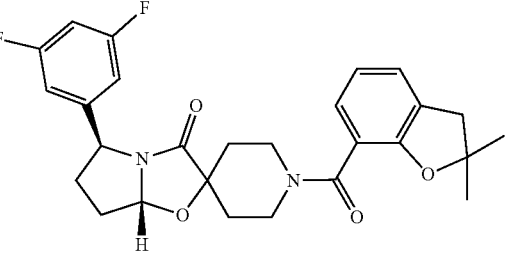
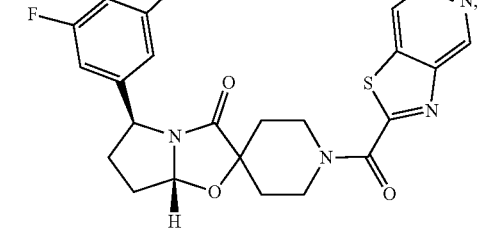
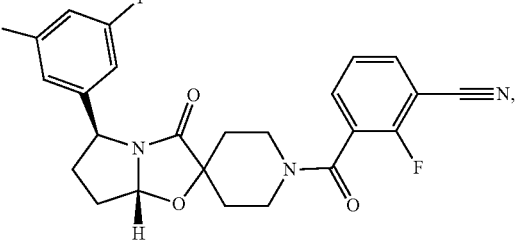

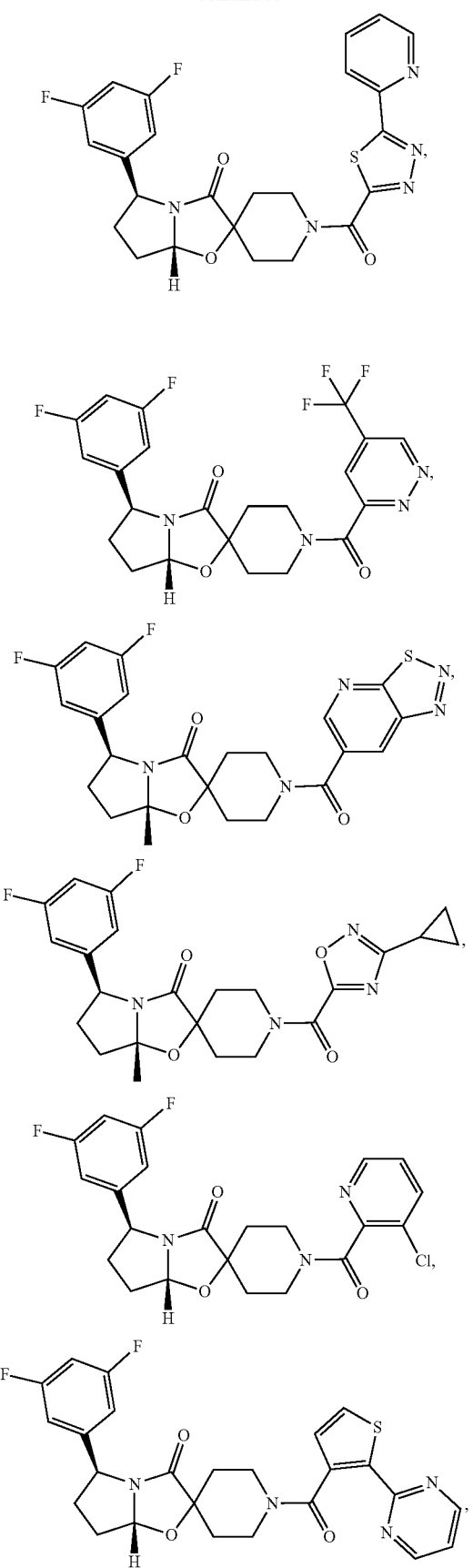
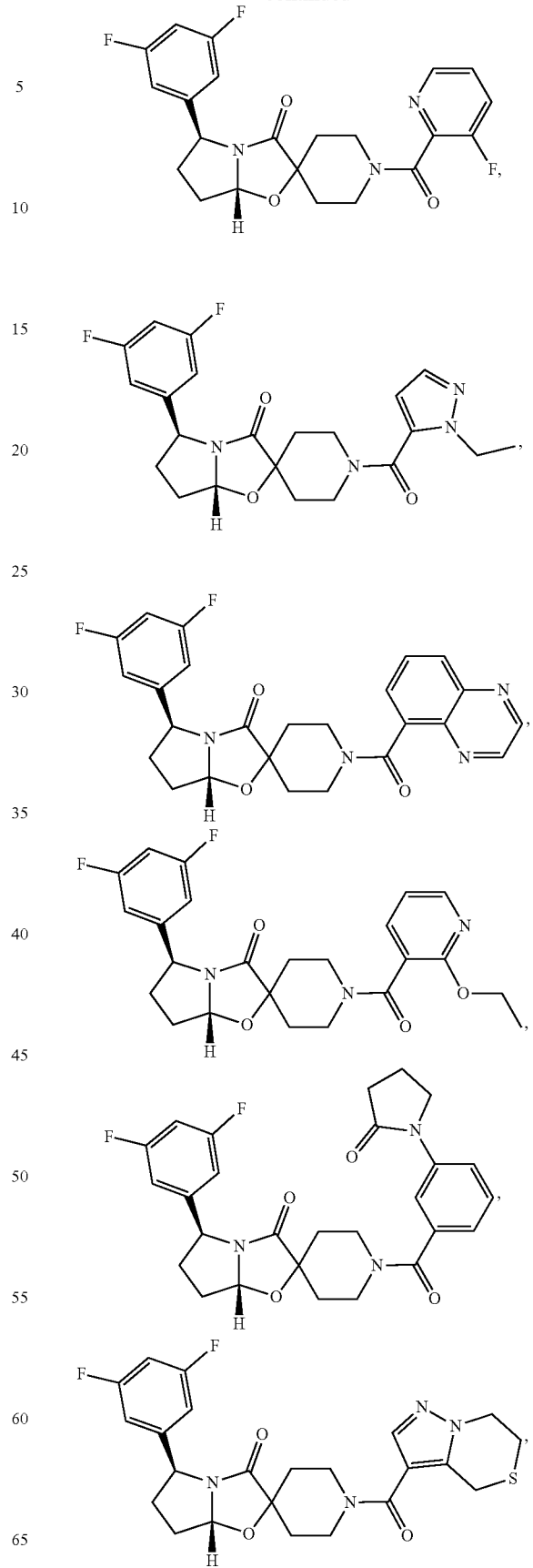

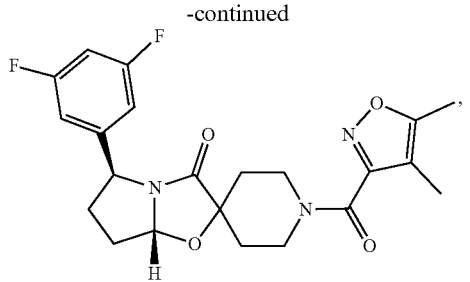
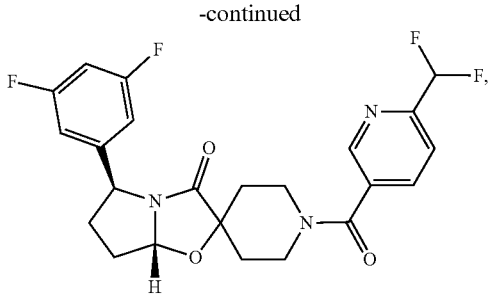
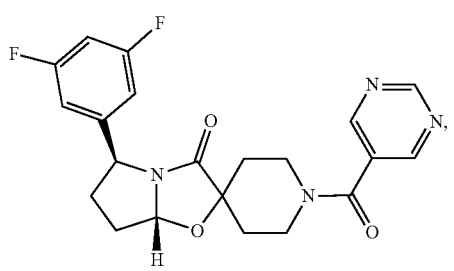
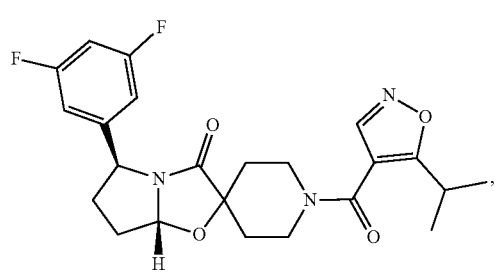
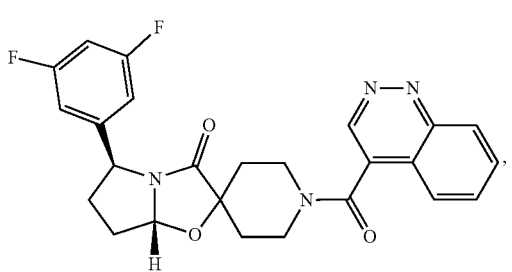
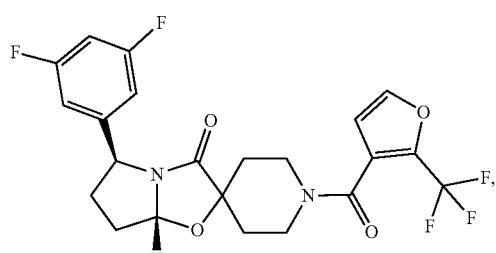
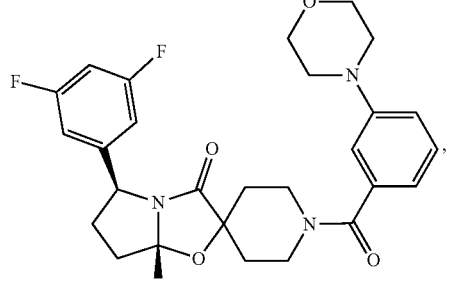
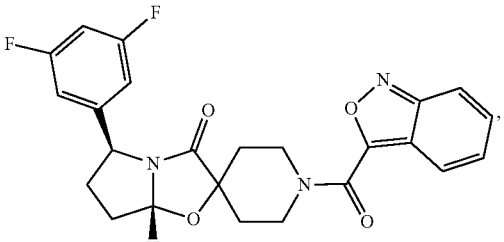
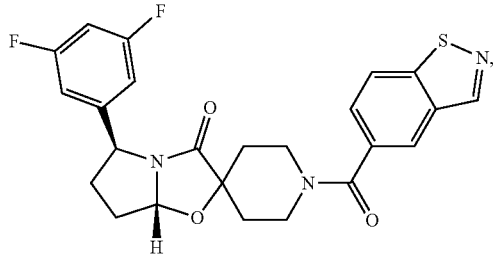
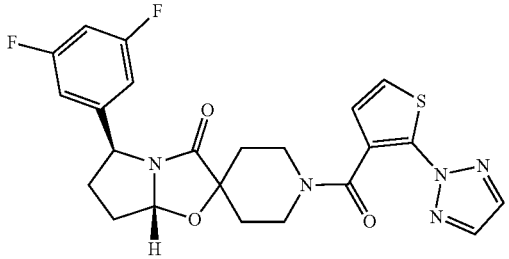
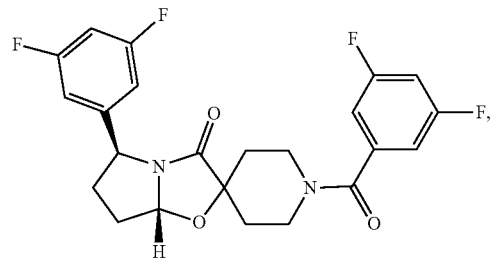

-continued
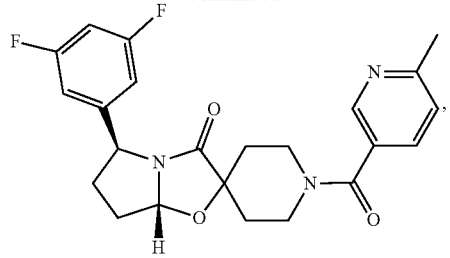
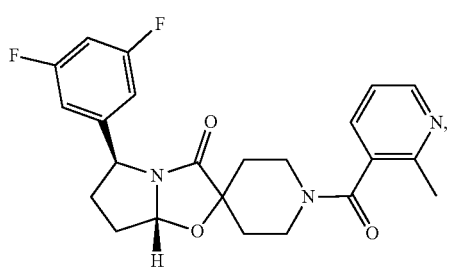
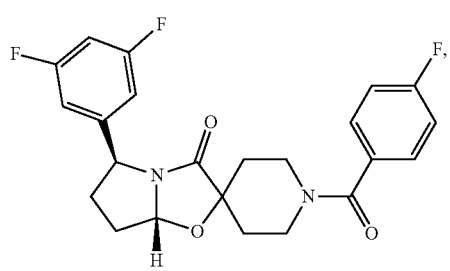
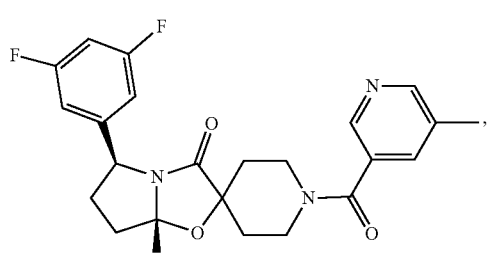
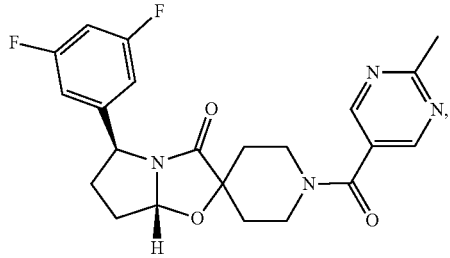
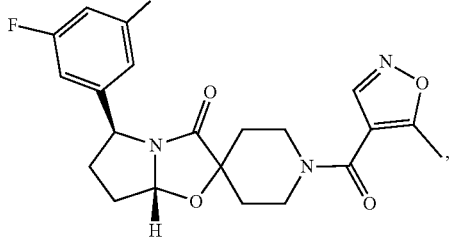
-continued
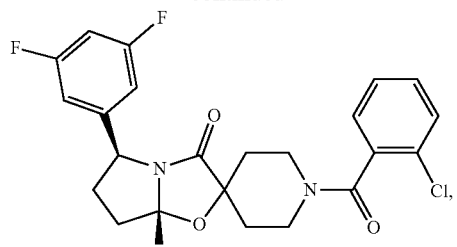
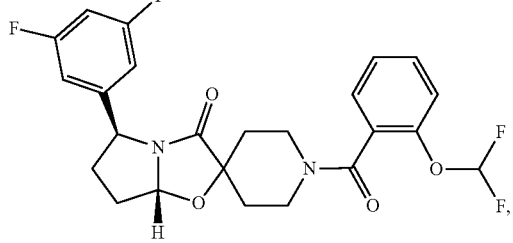
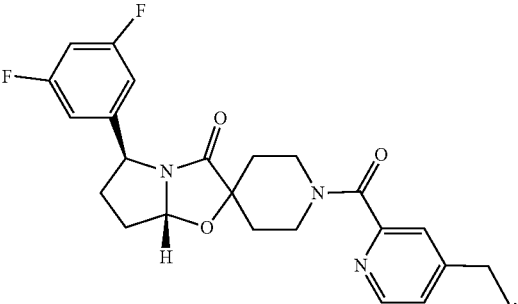
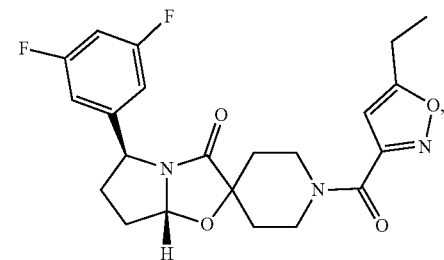
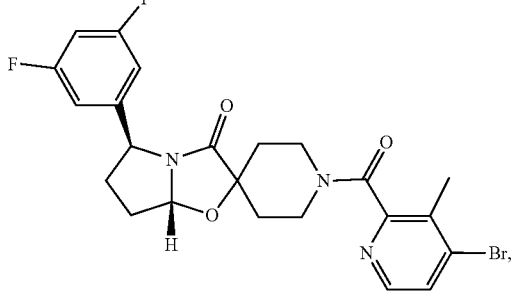
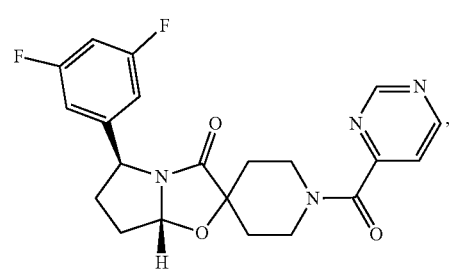

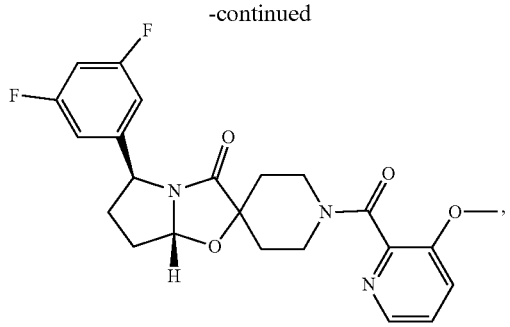
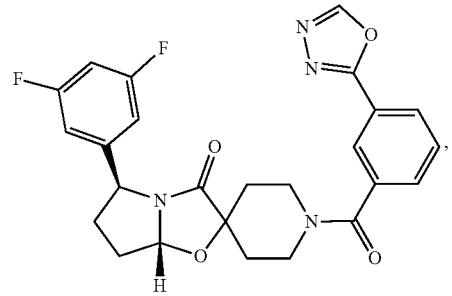
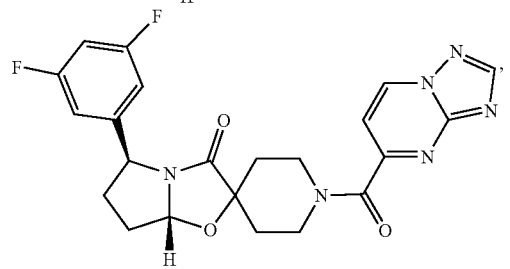
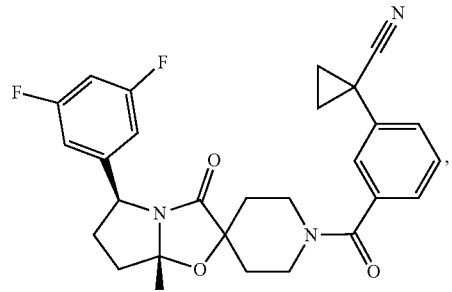
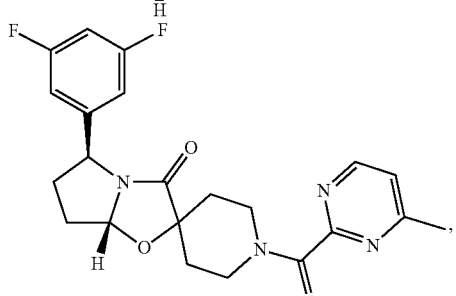
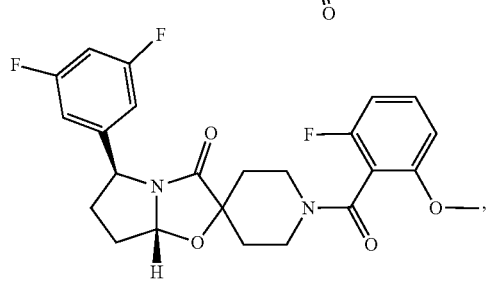
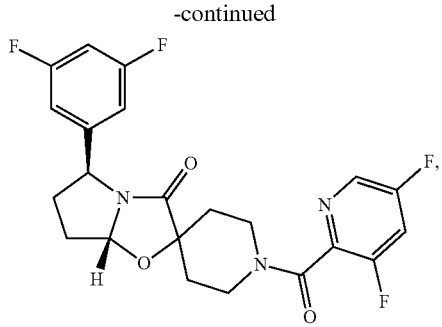
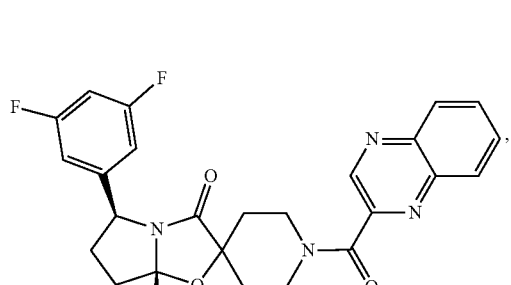
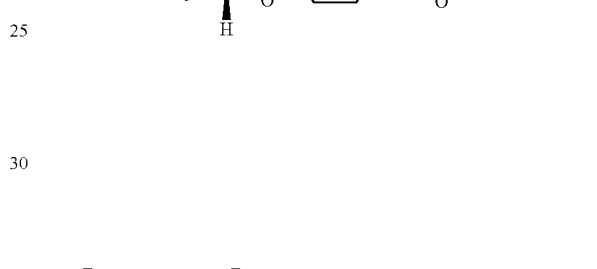
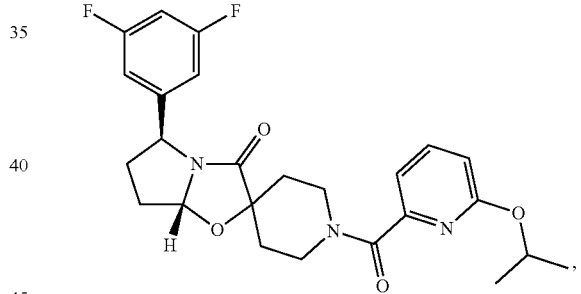
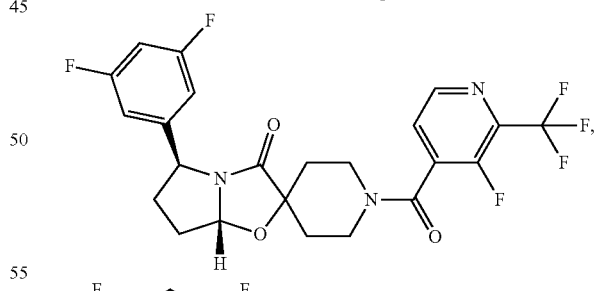
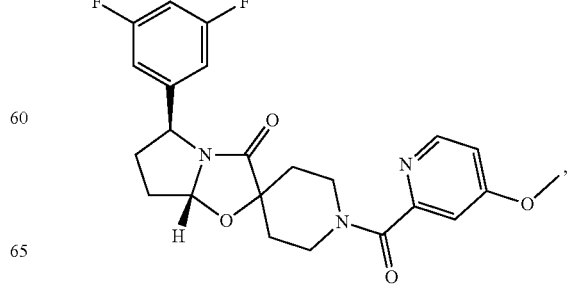

591
-continued
592
-continued
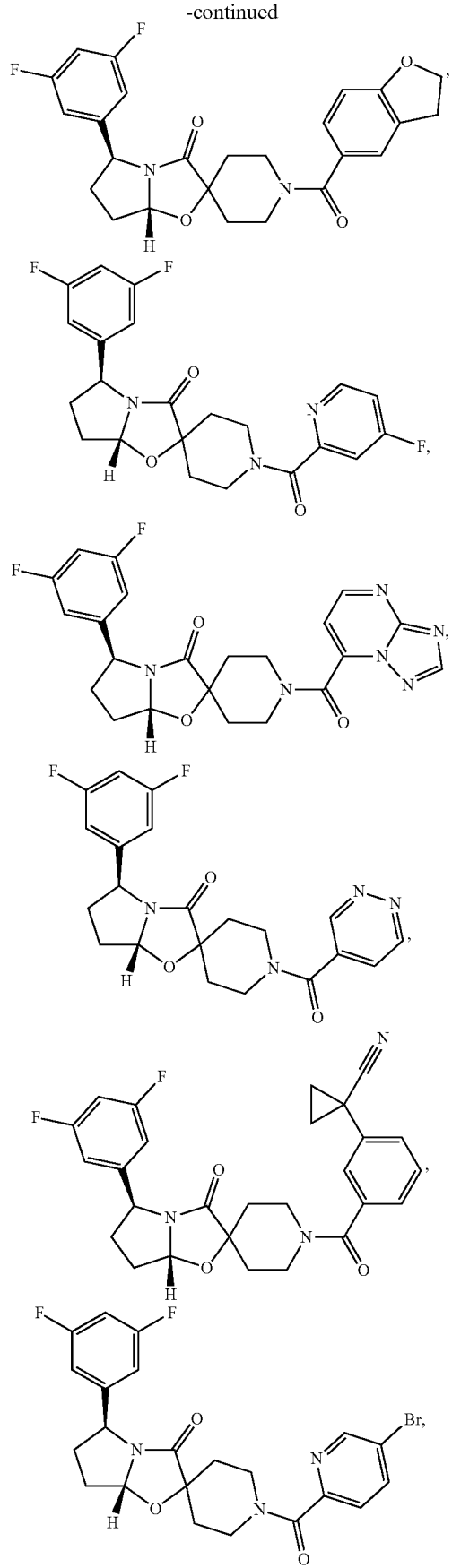
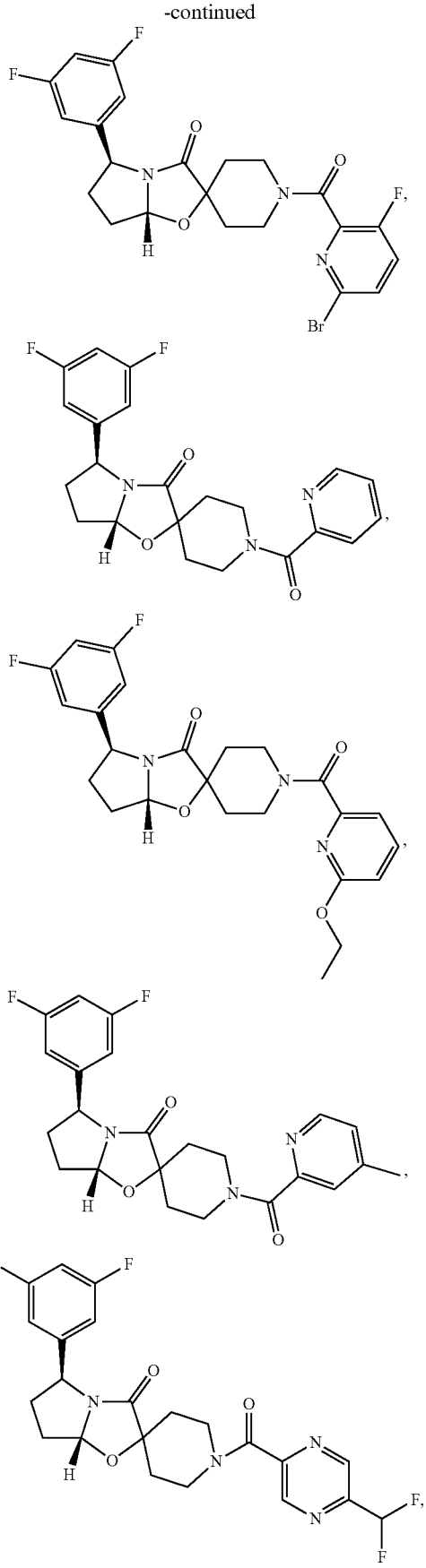

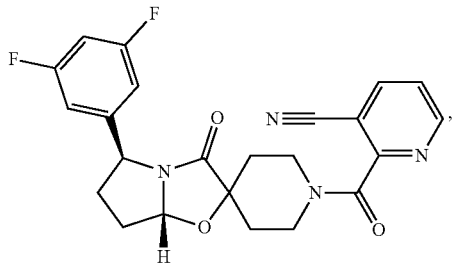
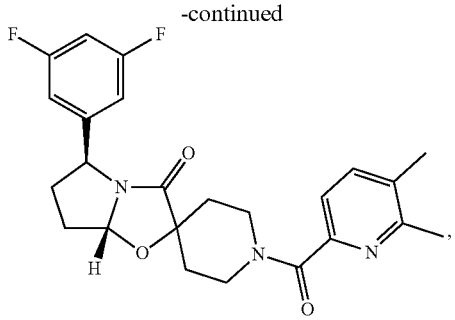
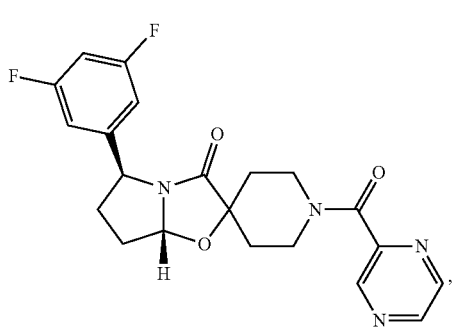
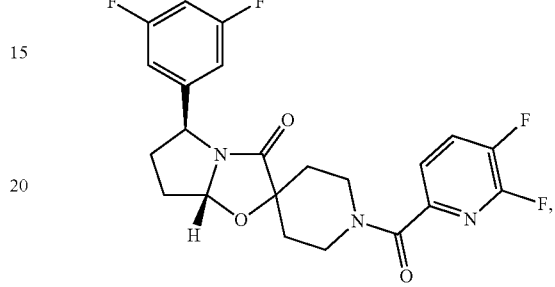
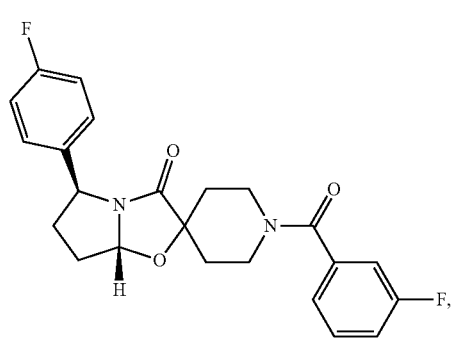
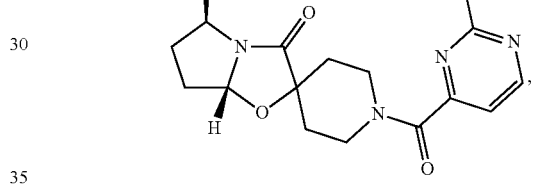
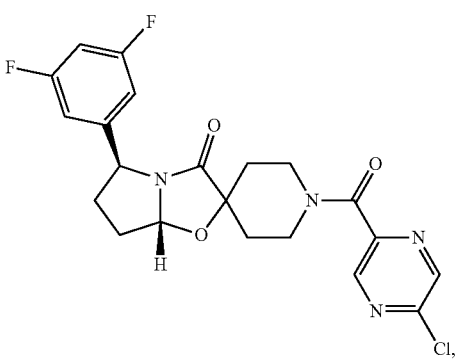
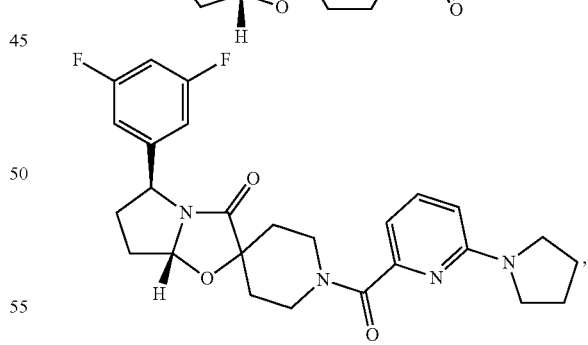
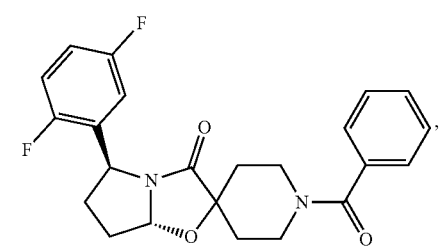
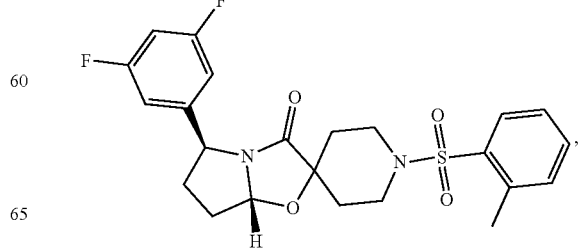

595
-continued
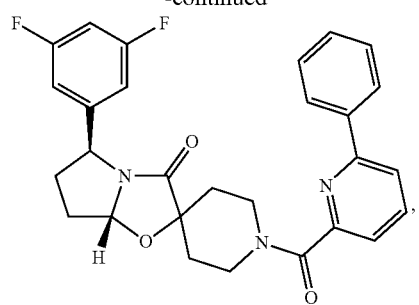
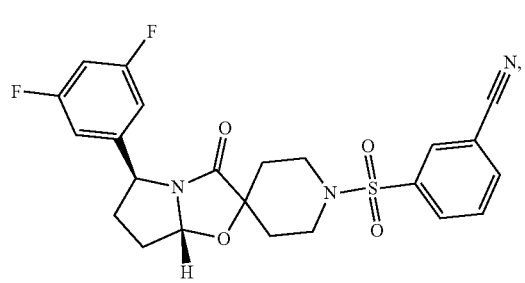
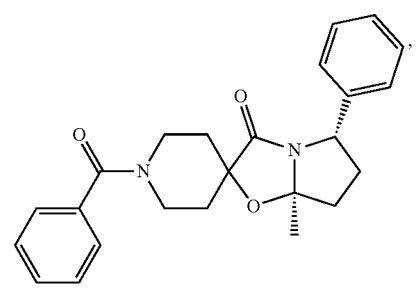
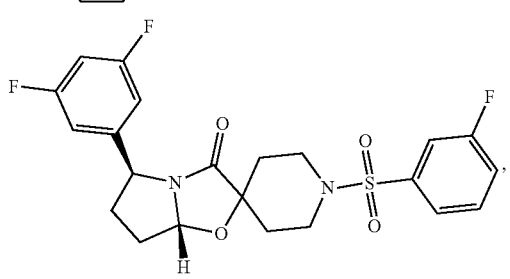
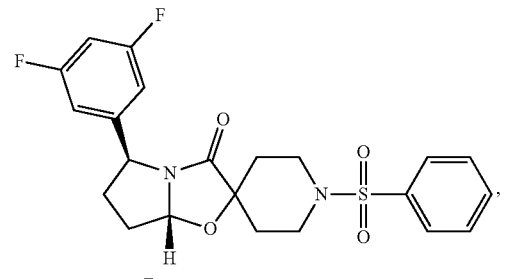
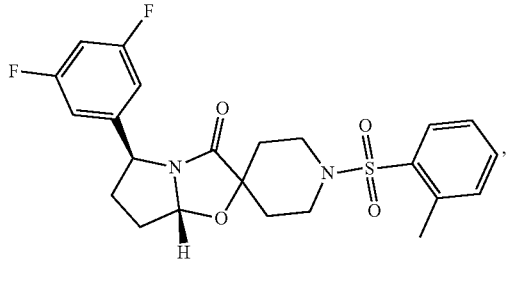
596
-continued
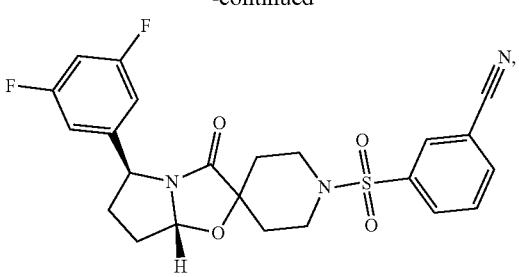
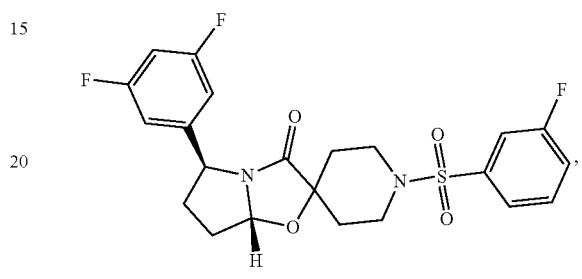
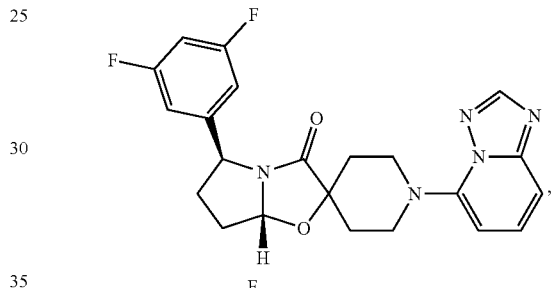
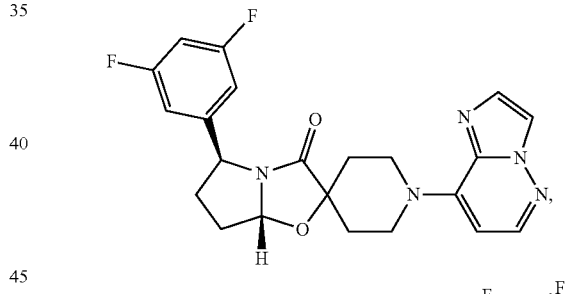
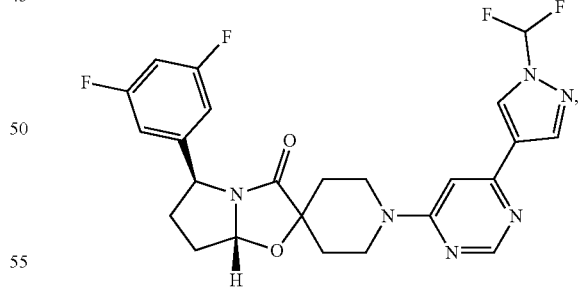
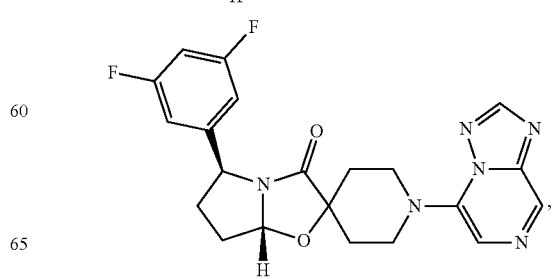

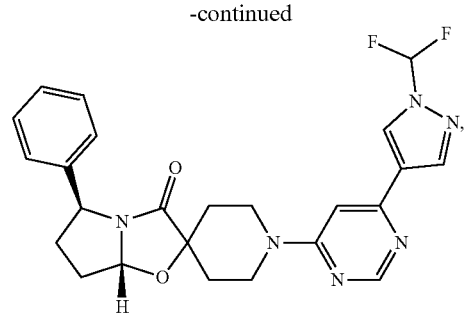
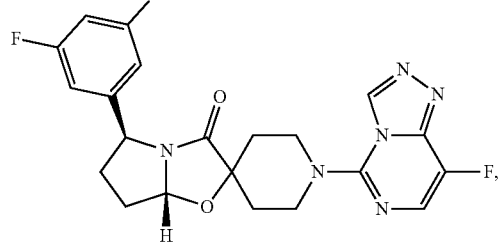
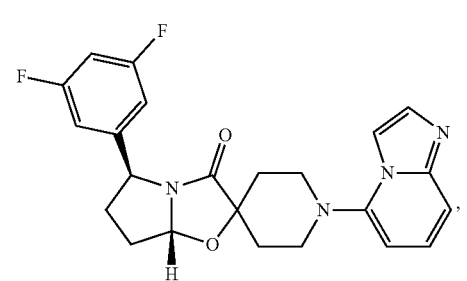
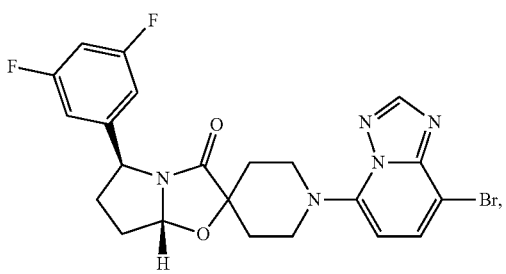
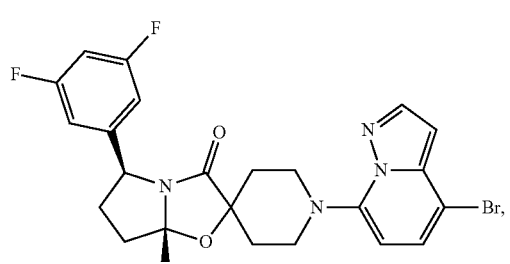
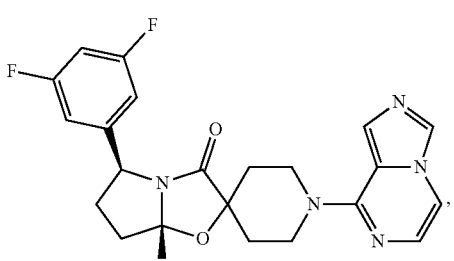
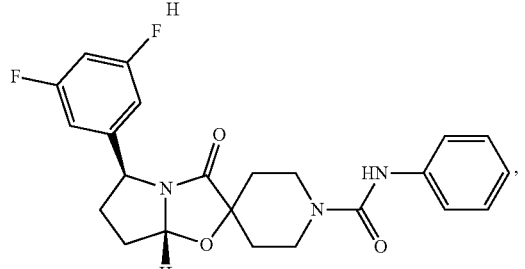
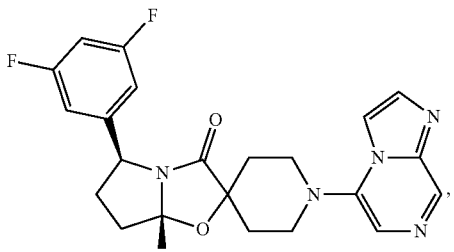
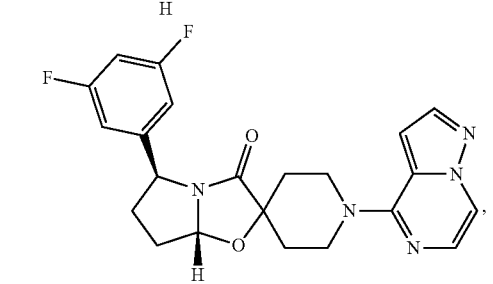
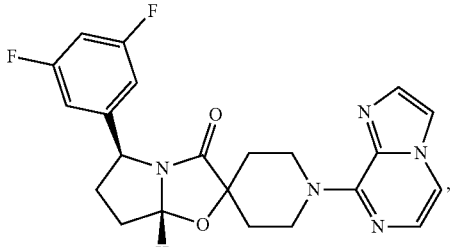
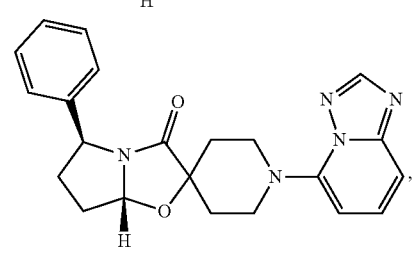
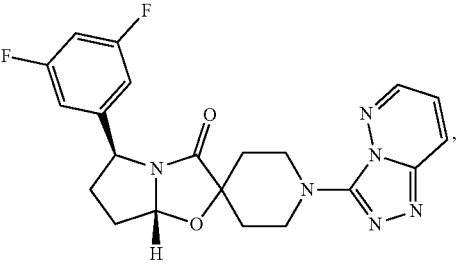

599
-continued
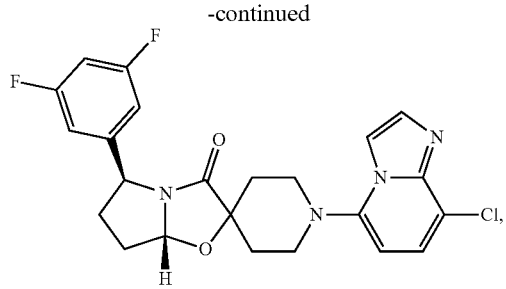
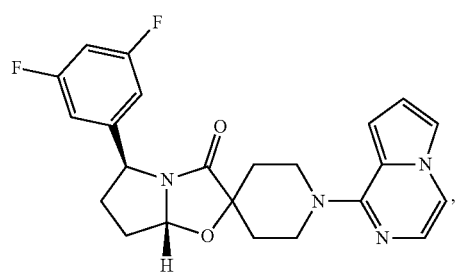
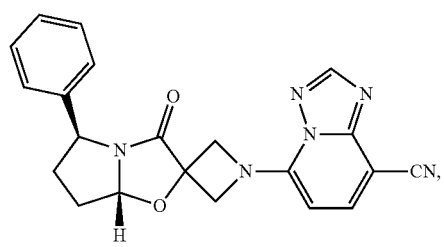
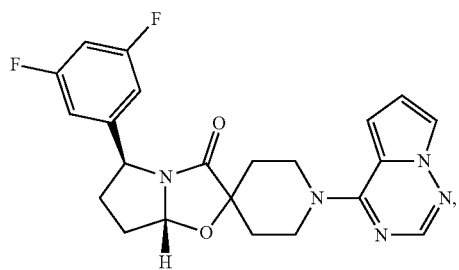
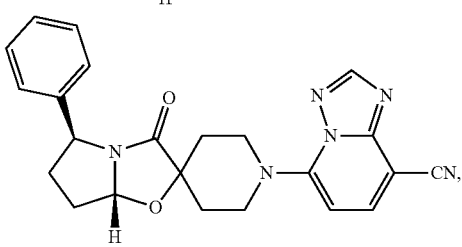
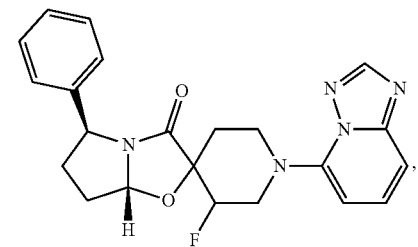
600
-continued
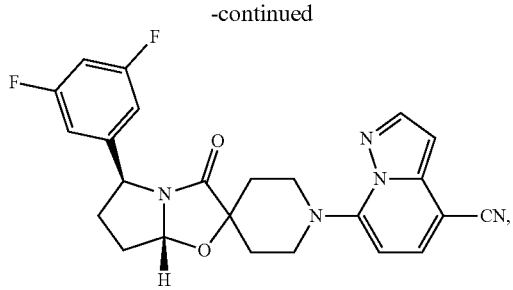
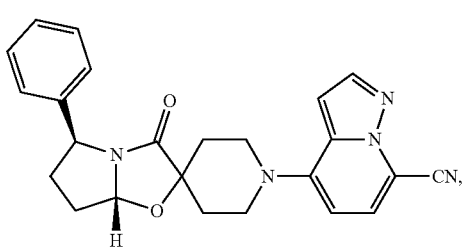
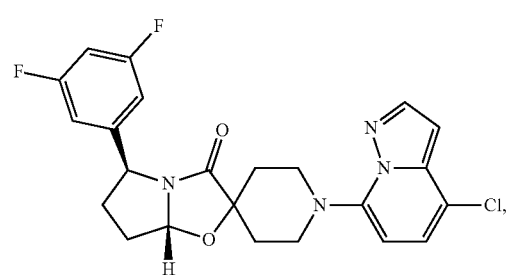
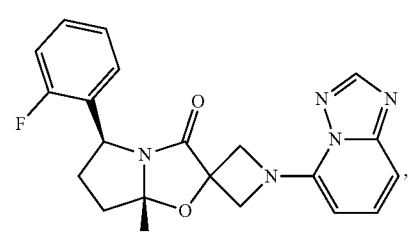
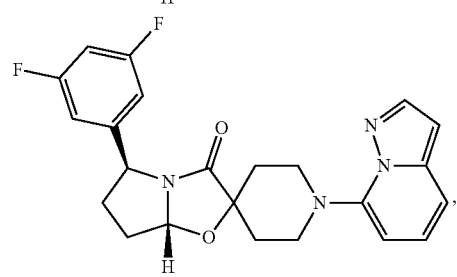
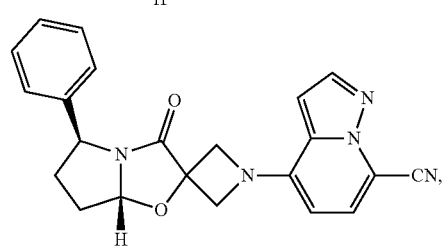

-continued
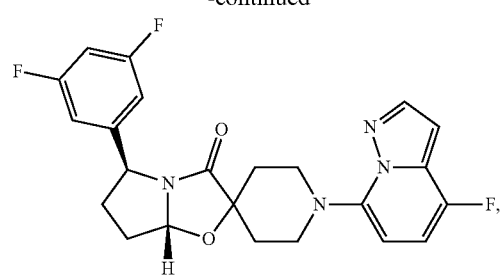
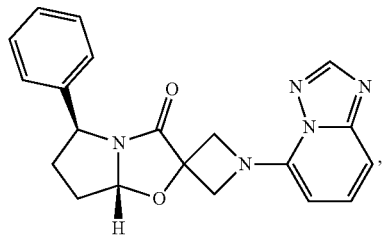
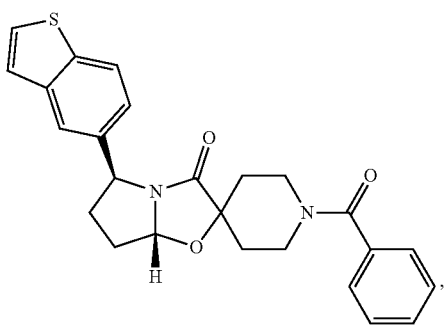
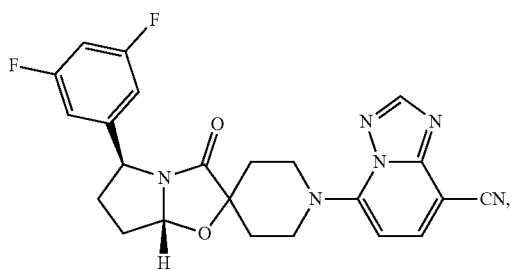
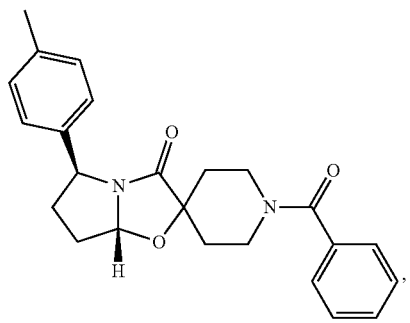
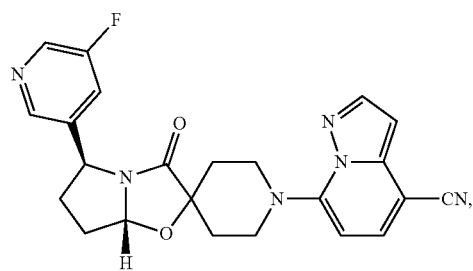
-continued
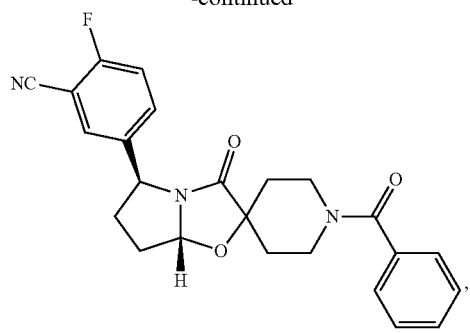
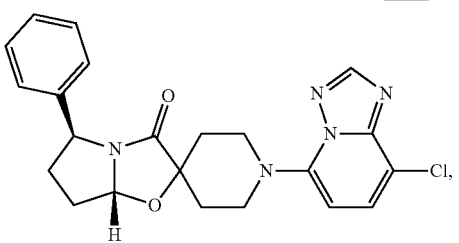
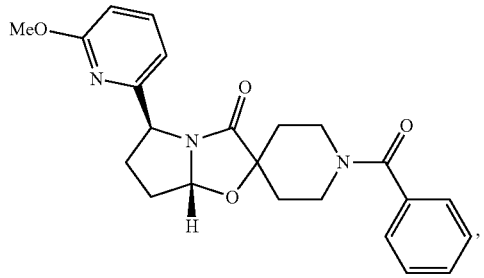
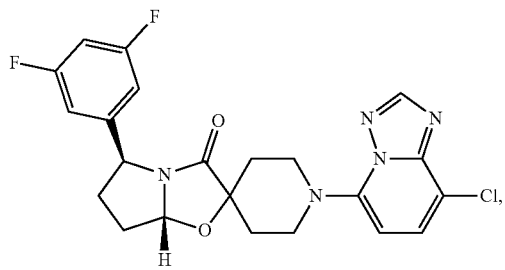
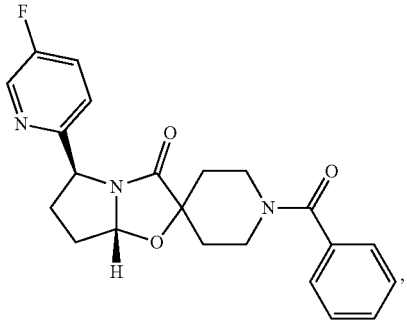
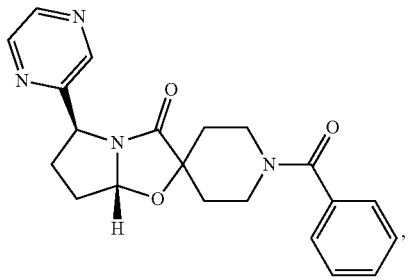

603
-continued
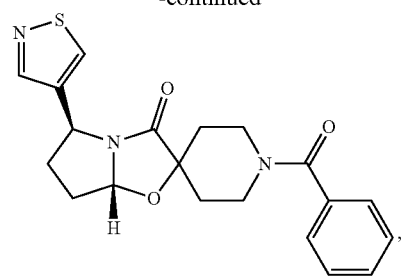
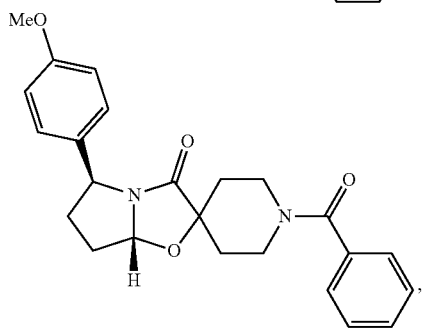
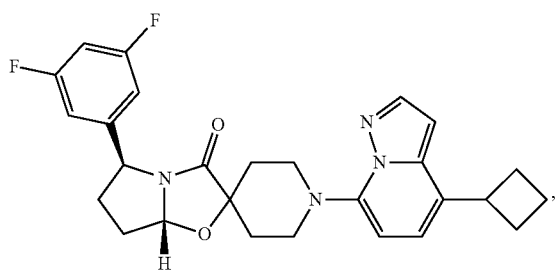
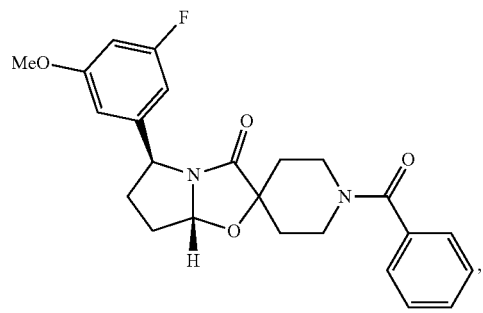
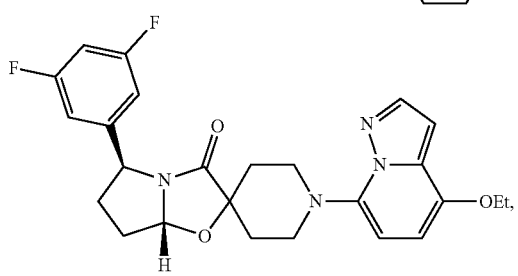
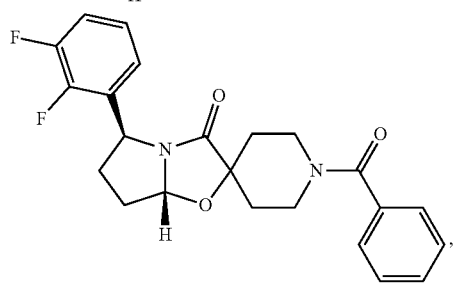
604
-continued
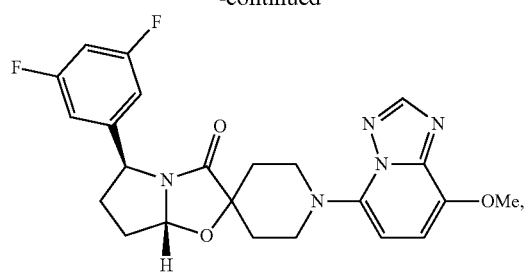
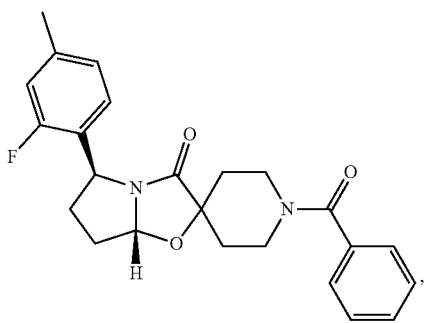
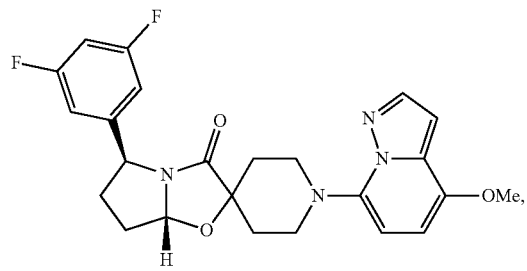
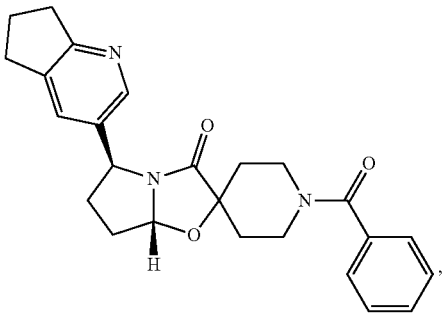
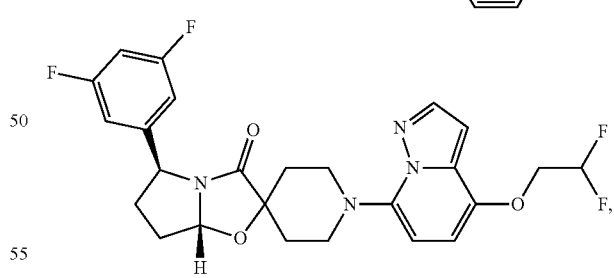
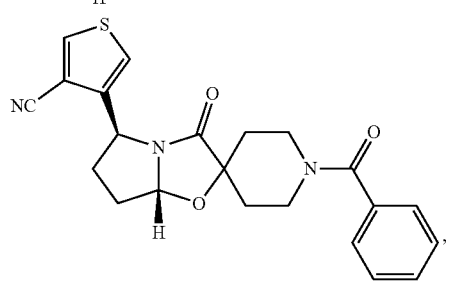

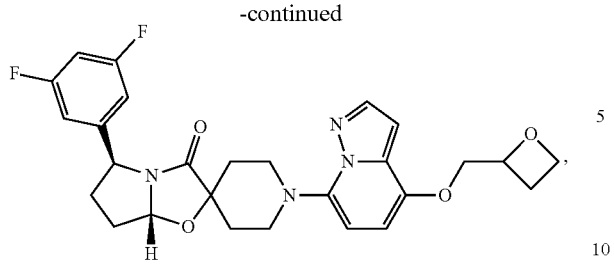
26. A pharmaceutical composition comprising a compound of claim 1, or a pharmaceutically acceptable salt thereof and a pharmaceutically acceptable carrier.
27. A pharmaceutical composition comprising a compound of claim 1 and a pharmaceutically acceptable carrier.
* * * * *

UNITED STATES PATENT AND TRADEMARK OFFICE
CERTIFICATE OF CORRECTION

PATENT NO. : 12,180,226 B2
APPLICATION NO. : 18/049344
DATED : October 25, 2022
INVENTOR(S) : Abdelghani Abe Achab et al.

It is certified that error appears in the above-identified patent and that said Letters Patent is hereby corrected as shown below:

In the Specification

Column 528, Line 25:
Please delete "Y O" and replace with "Y is O".

In the Claims

Claim 12, Column 530, Lines 9-13:
Please delete "each occurrence of R4 is independently selected from the group consisting of hydrogen, -OH, C1-C6alkylOH, -CN, C1-C6alkylCN, C1-C6alkyl, haloC1-C6alkyl, halogen, -NH2, -N(C1-C6alkyl)2, -NH(C1-C6alkyl) and C1-C6alkoxy;"

Claim 22, Column 536, Lines 1-5:
Please delete "each occurrence of R4 is independently selected from the group consisting of hydrogen, -OH, C1-C6alkylOH, -CN, C1-C6alkylCN, C1-C6alkyl, haloC1-C6alkyl, halogen, -NH2, -N(C1-C6alkyl)2, -NH(C1-C6alkyl) and C1-C6alkoxy;"

Signed and Sealed this
Twenty-fifth Day of February, 2025

Coke Morgan Stewart
*Acting Director of the United States Patent and Trademark Office*